US011660293B2

(12) United States Patent
Micheli et al.

(10) Patent No.: US 11,660,293 B2
(45) Date of Patent: May 30, 2023

(54) SUBSTITUTED 2-AZABICYCLO[3.1.1]HEPTANE AND 2-AZABICYCLO[3.2.1]OCTANE DERIVATIVES AS OREXIN RECEPTOR ANTAGONISTS

(71) Applicant: Chronos Therapeutics Limited, Oxford (GB)

(72) Inventors: Fabrizio Micheli, Verona (IT); Barbara Bertani, Verona (IT); Karl Richard Gibson, Kent (GB); Romano Di Fabio, Verona (IT); Luca Raveglia, Verona (IT); Riccardo Zanaletti, Montecchio Maggiore (IT); Susanna Cremonesi, Verona (IT); Alfonso Pozzan, Verona (IT); Teresa Semeraro, Verona (IT); Luca Tarsi, Verona (IT); Timothy Jon Luker, Nottinghamshire (GB)

(73) Assignee: CHRONOS THERAPEUTICS LIMITED, Oxford (GB)

( * ) Notice: Subject to any disclaimer, the term of this patent is extended or adjusted under 35 U.S.C. 154(b) by 274 days.

(21) Appl. No.: 16/643,420

(22) PCT Filed: Aug. 31, 2018

(86) PCT No.: PCT/GB2018/052479
§ 371 (c)(1),
(2) Date: Feb. 28, 2020

(87) PCT Pub. No.: WO2019/043407
PCT Pub. Date: Mar. 7, 2019

(65) Prior Publication Data
US 2022/0331299 A1     Oct. 20, 2022

(30) Foreign Application Priority Data

Sep. 1, 2017 (GB) .................................. 1714049
Mar. 23, 2018 (GB) .................................. 1804745

(51) Int. Cl.
| | | |
|---|---|---|
| *A61K 31/439* | (2006.01) | |
| *A61K 31/444* | (2006.01) | |
| *A61K 31/4709* | (2006.01) | |
| *A61K 31/4725* | (2006.01) | |
| *A61K 31/498* | (2006.01) | |
| *A61K 31/506* | (2006.01) | |
| *A61K 31/519* | (2006.01) | |
| *A61K 45/06* | (2006.01) | |
| *C07D 471/08* | (2006.01) | |
| *C07D 519/00* | (2006.01) | |

(52) U.S. Cl.
CPC .......... *A61K 31/439* (2013.01); *A61K 31/444* (2013.01); *A61K 31/4709* (2013.01); *A61K 31/4725* (2013.01); *A61K 31/498* (2013.01); *A61K 31/506* (2013.01); *A61K 31/519* (2013.01); *A61K 45/06* (2013.01); *C07D 471/08* (2013.01); *C07D 519/00* (2013.01)

(58) Field of Classification Search
None
See application file for complete search history.

(56) References Cited

U.S. PATENT DOCUMENTS

| | | | | |
|---|---|---|---|---|
| 8,653,071 | B2 * | 2/2014 | Nirogi | .................... A61P 25/16 546/276.7 |
| 2012/0245196 | A1 | 9/2012 | Stevens | |
| 2017/0204096 | A1 | 7/2017 | Gelin | |

FOREIGN PATENT DOCUMENTS

| | | |
|---|---|---|
| WO | 2009104155 | 8/2009 |
| WO | 2010122151 | 10/2010 |
| WO | 2011006960 | 1/2011 |
| WO | 2011023578 | 3/2011 |
| WO | 2012089606 | 7/2012 |
| WO | 2012089607 | 7/2012 |
| WO | 2013119639 | 8/2013 |
| WO | 2013139730 | 9/2013 |
| WO | 2014165070 | 10/2014 |
| WO | 2016040789 | 3/2016 |
| WO | 2017129829 | 8/2017 |
| WO | 2017139603 | 8/2017 |
| WO | 2002089800 | 11/2022 |

OTHER PUBLICATIONS

Wu et al., Toxicology, 236, pp. 1-6 (Year: 2007).*
Lei et al, Neuropharmacology, vol. 110, pp. 431-437, Aug. 2016.*
International Preliminary Report on Patentability corresponding PCT application PCT/GB2018/052479 dated Mar. 3, 2020.
Bonaventure, et al., "A Selective Orexin-1 Receptor Antagonist Attenuates Stress-Induced Hyperarousal without Hypnotic Effects", J. Pharmacol. Exp. Ther., 352:590-601 (2015).
Bonaventure, et al., "Evaluation of JNJ-54717793 a Novel Brain Penetrant Selective Orexin 1 Receptor Antagonist in Two Rat Models of Panic Attack Provocation" Frontiers in Pharmacology, 8(357):1-13 (2017).
Flores, et al., "Orexins and fear: implications for the treatment of anxiety disorders", Trends in Neurosciences, 38(9):550-559 (2015).
Futamura, et al., "Identification of highly selective and potent orexin receptor 1 antagonists derived from a dual orexin receptor 1/2 antagonist based on the structural framework of pyrazoylethylbenzamide", Bioorganic & Medicinal Chemistry, 25(20):5203-5215 (2017).

(Continued)

*Primary Examiner* — Zinna Northington Davis
(74) *Attorney, Agent, or Firm* — Pabst Patent Group LLP

(57) ABSTRACT

There is provided a compound of formula (I), wherein $L^1$ to $L^{3'}$, $R^1$ to $R^4$, X, A and B have meanings given in the description, and pharmaceutically acceptable salts, solvates and prodrugs thereof, which compounds are useful as antagonists of the orexin-1 and orexin-2 receptors or as selective antagonists of the orexin-1 receptor, and thus, in particular, in the treatment or prevention of inter alia substance dependence, addiction, anxiety disorders, panic disorders, binge eating, compulsive disorders, impulse control disorders, cognitive impairment and Alzheimer's disease.

20 Claims, No Drawings

(56) References Cited

OTHER PUBLICATIONS

Hollander, et al., "Insular hypocretin transmission regulates nicotine reward", PNAS, 105(49):19480-19485 (2008).
Hutcheson, et al., "Orexin-1 receptor antagonist SB-334867 reduces the acquisition and expression of cocaine-conditioned . . . ", Behavioural Pharmacology, 22(2):173-181 (2011).
Johnson, et al., "A key role for orexin in panic anxiety", Nature Medicine, 16(1):111-116 (2010).
Johnson, et al., "Orexin 1 and 2receptor involvement in CO2-induced panic-associated behavior and autonomic responses", Depression And Anxiety, 32:671-683 (2015).
Johnson, et al., "Orexin 1 receptors are a novel target to modulate panic responses and the panic brain network", Physiology & Behavior, 107:733-742, (2012).
Johnson, et al., "Orexin, stress, and anxiety/panic states", Progress in Brain Research, 9(198):133-161, (2012).
Kordi, et al., "SB-334867, an orexin receptor 1 antagonist, decreased seizure and anxiety in pentylenetrazol-kindled rats", Fundamental & Clinical Pharmacology, 31:201-207 (2017).
Lopez, et al., "The highly selective orexin/hypocretin 1 receptor antagonist GSK1059865 potently reduces ethanol drinking in ethanol dependent mice", Brain Res., 1636:74-80 (2016).
Narita, et al., "Direct Involvement of Orexinergic Systems in the Activation of the Mesolimbic Dopamine Pathway and Related Behaviors Induced by Morphine", J. Neurosci.,26(2): 398-405 (2006).

Olney, et al., "Binge-Like Consumption of Ethanol and Other Salient Reinforcers is Blocked by Orexin-1 Receptor Inhibition and Leads to a Reduction of Hypothalamic Orexin Immunoreactivity", Alcohol Clin. Exp. Res., 39(1):21-29 (2015).
Olney, et al., "The Role of Orexin Signaling in the Ventral Tegmental Area and Central Amygdala inModulating Binge-Like Ethanol Drinking Behavior", Alcohol Clin. Exp. Res., 41(3):551-561 (2017).
Piccoli, et al., "Role of Orexin-1 Receptor Mechanisms on Compulsive Food Consumption in a Model of Binge Eating in Female Rats", Neuropsychopharmacology, 37:1999-2011 (2012).
Pich, et al., "Orexin 1 receptor antagonists in compulsive behavior and anxiety: possible therapeutic use", Frontiers in Neuroscience, 8(26) (2014).
Plaza-Zabala, et al., "A Role for Hypocretin/Orexin Receptor-1 in Cue-Induced Reinstatement of Nicotine-Seeking Behavior", Neuropsychopharmacology, 38:1724-1736 (2013).
Smith, et al., "Orexin / hypocretin 1 receptor antagonist reduces heroin selfadministration and cue-induced heroin seeking", Eur. J. Neurosci., 35(5):798-804 (2012).
Smith, et al., "Orexin / hypocretin signaling at the OX1 receptor regulates cueelicited cocaine-seeking", Eur. J. Neurosci., 30(3):493-503 (2009).
Vanderhaven, et al., "The orexin-1 receptor antagonist SB-334867 decreases anxiety-like behavior and c-Fos expression in the hypothalamus of rats exposed to cat odor", Behavioural Brain Research, 278:563-568 (2015).
Vickers, et al., "Effects of lisdexamfetamine in a rat model of binge-eating", J. Psychopharmacology, 2015, 29(12):1290-1307.

* cited by examiner

SUBSTITUTED 2-AZABICYCLO[3.1.1]HEPTANE AND 2-AZABICYCLO[3.2.1]OCTANE DERIVATIVES AS OREXIN RECEPTOR ANTAGONISTS

CROSS-REFERENCE TO RELATED APPLICATIONS

This application is a National Phase application under 35 U.S.C. §371 of International Application No. PCT/GB2018/052479, filed Aug. 31, 2018, which claims the benefit of and priority to U.K. Application No. GB 1714049.2, filed Sep. 1, 2017 and U.K. Application No. GB 1804745.6, filed Mar. 23, 2018, which are hereby incorporated by reference in their entirety.

FIELD OF THE INVENTION

This invention relates to novel pharmaceutically-useful compounds, which compounds are useful as antagonists of the orexin-1 and orexin-2 receptors or as selective antagonists of the orexin-1 receptor. The compounds are of potential utility in the treatment of addictive diseases, such as binge eating, and behavioural disorders, such as obsessive-compulsive disorders and impulse control disorder. The invention also relates to the use of such compounds as medicaments, to pharmaceutical compositions containing them, and to synthetic routes for their production.

BACKGROUND OF THE INVENTION

There are a number of addictive behaviours that represent a significant unmet medical need requiring novel treatments. These include binge eating, alcohol use disorder and nicotine addiction.

Binge eating is an eating disorder where a person feels compelled to overeat on a regular basis through regular "binges" or consumption of very large quantities of food over a very short period of time, even when they are not hungry. The condition tends to develop first in young adults, although many people do not seek help until they are in their 30s or 40s. There is a 1 in 30 to 1 in 50 chance of a person developing binge eating disorder at some point during their life and it can lead to a variety of health problems that can, in extreme circumstances, be life-threatening. Whilst more women suffer from the condition than men, binge eating is not particularly uncommon in men with the prevalence ratio of approximately 1.5 women for every man with the disorder.

Binge eating disorder (BED), one of three formal eating-disorder diagnoses in the fifth edition of the Diagnostic and Statistical Manual of Mental Disorders (DSM-5, 2013), is defined by recurrent binge eating (i.e., eating unusually large quantities of food accompanied by subjective feelings of loss of control), marked distress about the binge eating, and the absence of inappropriate weight compensatory behaviours (e.g., purging, laxative misuse, excessive exercise, or extreme restraint) that characterize bulimia nervosa. BED is a common clinical problem, with an estimated lifetime prevalence rate of roughly 2.8% in adults, and common in both sexes and across minority groups. BED is associated strongly with obesity and is associated with elevated rates of medical and psychiatric co-morbidity. BED is frequently associated with increased depressive and body-image psychopathology and with psychosocial impairment. BED shares many features with, but is distinct from, the other eating disorders and obesity.

Since BED was first introduced as a research category in the fourth edition of the Diagnostic and Statistical Manual of Mental Disorders (DSM-IV), the treatment literature has grown considerably for this eating disorder. BED represents a clinical challenge and effective treatments need to address binge eating, weight loss, and associated eating-disorder (e.g., body image concerns) and depressive psychopathology.

In the USA, clinicians treat approximately 80% of both their adolescent and adult BED patients with pharmacotherapy (based on physician recall of their past 6 months' caseload). The remaining patients received only behavioural therapy. Although Vyvanse is considered 'a big step forward', there is still a desire for new treatments mainly driven by side-effect profile being the 'big issue' with Vyvanse (currently, the only drug treatment that has been recently approved by the regulatory agencies for managing BED—a stimulant pro-drug). Individuals seeking treatment may also have co-morbid mood and/or anxiety disorder, or substance abuse disorder which preclude the use of Vyvanse.

Nicotine and alcohol addiction involves repeated use of a psychoactive substance (nicotine or alcohol) causing a user to be intoxicated with a compulsion to take the preferred substance and often a determination to obtain the substance by almost any means. Addicts also have difficulty in modifying or stopping substance use. They build up tolerance to the addictive substance, sometimes requiring more and more for the same effect and develop withdrawal syndromes when use is interrupted.

Tobacco smoking results in greater than 5 million deaths each year. Even when using the most clinically efficacious smoking cessation agents available, approximately 80% of smokers attempting to quit will relapse within one year, highlighting the need to develop safe yet more clinically effective smoking cessation agents Addiction to nicotine via tobacco kills one person prematurely every six seconds and 50% of long-term smokers according to World Health Organisation (WHO) reports, with tobacco attributed deaths predicted to rise to 8 million globally a year by 2030. The US Centers for Disease Control and Prevention (CDC) also note that about 480,000 Americans die every year from smoking related causes involving cancers (chiefly lung cancer), stroke, heart disease and chronic obstructive pulmonary disease (COPD).

Excessive alcohol use (as caused by addiction or binging) has caused 10% of deaths among working-age adults aged 20-64 years in the USA with economic costs in 2010 in the USA alone of $249 billion. WHO also estimates that harmful alcohol use causes 3.3 million deaths a year, globally. Short-term health risks, most often the result of binge drinking, include accidents, injuries, alcohol poisoning and risky sexual behaviours. Over a longer time, excessive alcohol use can lead to chronic diseases including high blood pressure, cancers, mental health and social problems.

Dependence on illicit drugs accounted for 3.6 million years of life lost through premature death globally in 2010, as well as 16.4 million years of life lived with disability, mainly caused by cardiovascular and liver disease, infection with HIV, hepatitis B and C and a range of other conditions. Of the estimated 183,100 reported deaths from drug abuse related causes in 2012, 44,600 were in North America, where the drug related mortality rate was estimated to be 142 per million aged 15-64 (UNODC World Drug Report 2014 (available at unodc.org)). Data from 2012 estimate there to be 297 million drug abusers worldwide, of whom 17.24 million abuse cocaine. Currently there are no FDA approved drugs for the treatment of cocaine addiction and dependence, and the development of efficacious, safe therapies is a societal priority.

The orexin system has been demonstrated to play a key role in substance seeking and craving. When conditioned animals received cues for cocaine, morphine or food, orexigenic neurons in the lateral hypothalamus are activated; in addition, when the reward seeking behaviour is extinguished, it can be reinstated by administration of an orexin agonist, and blocked by a selective orexin 1 receptor (OX1R) antagonist tool compound.

The orexin neuropeptides (OxA and OxB) are 33- and 28-amino acid peptides, respectively, produced by proteolysis of a common precursor, prepro-orexin. Production takes place in neurons of the hypothalamus which project to areas of the brain involved in sleep-wake state, regulation of food intake, panic, anxiety, emotion, reward and addictive behaviours. The role in reward, feeding behaviour and anxiety is attributed to the orexin 1 receptor subtype, while the role in sleep has been attributed to the orexin 2 receptor (OX2R). The orexin 1 receptors are found in the brain, the enteric nervous system and the gut.

There has been extensive preclinical validation of this mechanism of action in animal models of addictive disorders using first generation OX1R antagonists.

Several OX1R antagonists have been tested in preclinical models relevant to BED such as unpredictable, intermittent access to highly palatable food (with or without stress), whereby animals are trained to binge eat. Selective OX1R antagonists have been shown to be highly efficacious in reducing binge behaviour.

Selective OX1R antagonists have also been shown to be highly efficacious in animal models of alcohol dependence and binge drinking. In a model of voluntary ethanol intake mice treated with a selective OX1R antagonist showed a significantly reduced ethanol consumption which decreased in a dose dependent manner, (Lopez M. F. et al., *Brain Res.*, 2016 Apr. 1, 1636, 74-80). In another publication utilising the drinking in the dark paradigm, which models binge-like drinking, central infusion of an OX1R antagonist blunted the early stages of binge drinking (Olney J. J., et al., *Alcohol Clin. Exp. Res.*, 2017, 41(3):551-561; Olney J. J., et al., *Alcohol Clin. Exp. Res.*, 2015; 39(1):21-29).

In smoking cessation efficacy has been demonstrated in rodent models of nicotine seeking behaviour whereby OX1R antagonists were shown to block stress induced reinstatement as well as nicotine induced anxiety response (Plaza-Zabala A., et al., *Neuropsychopharmacology*, 2013, 38, 1724-1736). In a separate study it was shown that OX1R antagonism blocked nicotine related reward as measured by reversal of nicotine-induced lowering of intracranial self-stimulation thresholds (Hollander J. A., et al., *PNAS*, 2008, 105(49), 19480-19485).

Supporting the likely utility of OX1R antagonism as a likely therapeutic for broad addictive disorders orexigenic signalling via the OX1 receptor has been implicated in several other addictive disorders and OX1R antagonists have demonstrated efficacy in several animal models of addiction including cocaine, heroin and amphetamine (Smith and Aston-Jones, *Eur. J. Neurosci.*, 2012; 35(5):798-804; Hutcheson D. M., et al., *Behavioural Pharmacology*, 2011, 22(2), 173-181; Smith R. et al., *Eur. J. Neurosci.*, 2009; 30(3):493-503).

The involvement of orexins in the modulation of fear has been demonstrated in rodent models. Mice lacking OX1R showed impaired freezing responses and reduced expression of zif268 (an IEG (immediate-early gene) that is considered a marker of neuronal activation) in the lateral amygdala in both cued and contextual fear-conditioning paradigms. The dual orexin antagonist almorexant has been shown to reduce fear-potentiated startle responses in rats. (Flores A. et al., *Trends in Neurosciences*, September 2015, Vo. 38, No. 9, 550-559). Orexins also modulate the extinction of acquired aversive memory. For example, OX1R blockade with a centrally active OX1R antagonist SB334867 facilitated the consolidation of fear extinction in both contextual and cued tests, while orexin A infusion impaired this response.

The role of orexin in panic disorder has also been confirmed. Panic-prone rats that were systematically pre-treated with SB334867 showed attenuated anxiety-like behaviour, locomotor and cardioexcitatory responses induced by the lactate challenge. SB408124 (another OX1R antagonist) also attenuated the sodium lactate-induced increases in locomotor activity and tachycardia responses in another group of panic-prone rats when compared to vehicle (Johnson P. L., et al., *Progress in Brain Research*, Vol. 198, Chapter 9, A. Shekhar Ed.).

While no proof of concept has been achieved with OX1R antagonists in the clinic, several dual orexin receptor antagonist (DORA) compounds (generally equipotent at OX1R and OX2R) have been extensively tested in large scale clinical trials. The only adverse events reported (sleep and dependence related) are attributable to OX2R antagonism. This emphasises the need for a selective OX1R antagonist and also indicates that such a compound would be safe and well tolerated.

With the elucidation of distinct roles for OX1R and OX2R, OX1R antagonists have received a great deal of attention for the treatment of addictive and anxiety related disorders. OX1R antagonists are believed to be particularly useful in treating addictive disorders, specifically binge eating disorder (BED), alcohol use disorder (AUD) and smoking due to the fact that reward stimuli are known to trigger dopamine release and orexins enhance this signalling while OX1R antagonism normalises it (Narita M. et al., *J. Neurosci.*, 2006, 26(2): 398-405).

Confirming the specificity of this response as an OX1R driven effect, OX2R antagonists were not efficacious in preclinical models relevant to BED and dual orexin receptor antagonists (DORAs), while having efficacy, were burdened by sedative effects like the OX2R antagonists (Piccoli L., et al., *Neuropsychopharmacology*, 2012, 37, 1999-2011; Vickers S. P. et al., *J. Psychopharmacology*, 2015, 29(12):1290-1307).

OX1R antagonists have also been shown to block binge eating without affecting normal food consumption. This is a potential highly differentiating factor for OX1R antagonists in BED as other potential mechanisms such as opioid antagonists are likely to cause anhedonia and stimulants are likely to affect appetite and result in sleep disturbance.

We have identified a number of OX1R antagonists, many of which are highly selective for OX1R over other targets and have favourable drug like qualities.

The listing or discussion of an apparently prior-published document in this specification should not necessarily be taken as an acknowledgement that the document is part of the state of the art or is common general knowledge.

DISCLOSURE OF THE INVENTION

According to the invention, there is provided a compound of formula I,

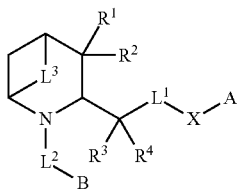

wherein:

$L^1$ represents a direct bond or —[$CR^5R^6$]—;

X represents a direct bond, —O—, —N($R^x$)—, —$CH_2$— or —S—;

A represents an aryl, heteroaryl, cycloalkyl or heterocycloalkyl group, each of which is optionally substituted with one or more $Q^1$ groups;

$L^2$ represents a direct bond or —C(=O)—;

B represents an aryl, heteroaryl, cycloalkyl or heterocycloalkyl group, each of which is optionally substituted with one or more $Q^2$ groups;

$L^3$ represents —$CH_2$— or —$CH_2CH_2$—;

$R^1$ and $R^2$ independently represent hydrogen, halogen, —$OR^7$, —$NR^8R^9$, $C_{1-12}$ alkyl, $C_{2-12}$ alkenyl, $C_{2-12}$ alkynyl or $C_{3-12}$ cycloalkyl (which latter four groups are optionally substituted by one or more $E^1$ substituents); or $R^1$ and $R^2$ together with the carbon atom to which they are bound form C=O, C=C($R^{10}$)$R^{11}$ or a $C_{3-6}$ cycloalkyl group optionally substituted by one or more $E^2$ substituents;

$R^3$, $R^4$, $R^5$ and $R^6$ independently represent hydrogen, halogen, $C_{1-12}$ alkyl, $C_{2-12}$ alkenyl, $C_{2-12}$ alkynyl or $C_{3-6}$ cycloalkyl (which latter four groups are optionally substituted by one or more $E^3$ substituents); or any relevant pair of $R^3$, $R^4$, $R^5$ and $R^6$ form, together with the carbon atom to which they are bound, C=O or a $C_{3-6}$ cycloalkyl group optionally substituted by one or more $E^4$ substituents;

$R^7$, $R^8$, $R^9$, $R^{10}$ and $R^{11}$ independently represent hydrogen or a $C_{1-6}$ alkyl group optionally substituted by one or more halo atoms;

$R^x$ represents hydrogen, $C_{1-6}$ alkyl, or $C_{3-6}$ cycloalkyl (which latter two groups are optionally substituted by one or more halo atoms);

$Q^1$ and $Q^2$ independently represent halogen, —CN, —$NHCOR^{12}$, $C_{1-6}$ alkyl, $C_{3-6}$ cycloalkyl, —O—$C_{1-6}$ alkyl, aryl or heteroaryl (which latter five groups are optionally substituted by one or more substituents selected from halogen, methyl and halomethyl (e.g. trifluoromethyl));

$E^1$, $E^2$, $E^3$ and $E^4$ independently represent halogen or a $C_{1-6}$ alkyl group optionally substituted by one or more halo atoms;

$R^{12}$ represents $C_{1-6}$ alkyl or phenyl;

or a pharmaceutically acceptable salt, solvate or prodrug thereof;

which compounds, salts, solvates and prodrugs are referred to hereinafter as "the compounds of the invention".

Pharmaceutically-acceptable salts include acid addition salts and base addition salts. Such salts may be formed by conventional means, for example by reaction of a free acid or a free base form of a compound of formula I with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of a compound of the invention in the form of a salt with another counter-ion, for example using a suitable ion exchange resin.

By "pharmaceutically acceptable salt, solvate or prodrug thereof", we include solvates of such salts.

For the purposes of this invention, prodrugs of compounds of the invention are also included within the scope of the invention. Prodrugs may include, for example, pharmaceutically acceptable esters and amides of the compounds of the invention (as well as salt or solvates of those pharmaceutically acceptable esters and amides). Pharmaceutically acceptable esters and amides of compounds of formula I may have an appropriate group, for example an acid group, an alcohol group or an amine group, converted to the appropriate ester or amide. For example, pharmaceutically acceptable esters (of carboxylic acids or alcohols) that may be mentioned include optionally substituted $C_{1-6}$ alkyl, $C_{5-10}$ aryl and/or $C_{5-10}$ aryl-$C_{1-6}$ alkyl-esters. Pharmaceutically acceptable amides (of carboxylic acids or amines) that may be mentioned include those of the formula —C(O)N($R^{z1}$)$R^{z2}$ or —N($R^{z3}$)C(O)$R^{z4}$, in which $R^{z1}$, $R^{z2}$, and $R^{z4}$ independently represent optionally substituted $C_{1-6}$ alkyl, $C_{5-10}$ aryl, or $C_{5-10}$ aryl-$C_{1-6}$ alkylene-. Preferably, $C_{1-6}$ alkyl groups that may be mentioned in the context of such pharmaceutically acceptable esters and amides are not cyclic, e.g. linear and/or branched.

Further prodrug compounds of the invention that may be mentioned include carbamate, carboxamido or ureido derivatives, e.g. such derivatives of existing amino functional groups.

More broadly, the term "prodrug" of a relevant compound of the invention includes any compound that, following oral or parenteral administration, is metabolised in vivo to form that compound in an experimentally-detectable amount, and within a predetermined time (e.g. within a dosing interval of between 6 and 24 hours (i.e. once to four times daily)).

For the avoidance of doubt, the term "parenteral" administration includes all forms of administration other than oral administration.

Prodrugs of compounds of the invention may be prepared by modifying functional groups present on the compound in such a way that the modifications are cleaved, in vivo when such prodrug is administered to a mammalian subject. The modifications typically are achieved by synthesising the parent compound with a prodrug substituent. Prodrugs include compounds of the invention wherein a hydroxyl, amino, sulfhydryl, carboxy or carbonyl group in a compound of the invention is bonded to any group that may be cleaved in vivo to regenerate the free hydroxyl, amino, sulfhydryl, carboxy or carbonyl group, respectively.

Examples of prodrugs include, but are not limited to, esters and carbamates of hydroxy functional groups, esters groups of carboxyl functional groups, N-acyl derivatives and N-Mannich bases. General information on prodrugs may be found e.g. in Bundegaard, H. "Design of Prodrugs" p. I-92, Elesevier, New York-Oxford (1985).

Compounds of the invention may contain double bonds and may thus exist as E (entgegen) and Z (zusammen) geometric isomers about each individual double bond. Positional isomers may also be embraced by the compounds of the invention. All such isomers (e.g. if a compound of the invention incorporates a double bond or a fused ring, the cis- and trans-forms, are embraced) and mixtures thereof are included within the scope of the invention (e.g. single positional isomers and mixtures of positional isomers may be included within the scope of the invention).

Compounds of the invention may also exhibit tautomerism. All tautomeric forms (or tautomers) and mixtures thereof are included within the scope of the invention. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerisations. Valence tautomers include interconversions by reorganisation of some of the bonding electrons.

Compounds of the invention may also contain one or more asymmetric carbon atoms and may therefore exhibit optical and/or diastereoisomerism. Diastereoisomers may be separated using conventional techniques, e.g. chromatography or fractional crystallisation. The various stereoisomers may be isolated by separation of a racemic or other mixture of the compounds using conventional, e.g. fractional crystallisation or HPLC, techniques. Alternatively the desired optical isomers may be made by reaction of the appropriate optically active starting materials under conditions which will not cause racemisation or epimerisation (i.e. a 'chiral pool' method), by reaction of the appropriate starting material with a 'chiral auxiliary' which can subsequently be removed at a suitable stage, by derivatisation (i.e. a resolution, including a dynamic resolution), for example with a homochiral acid followed by separation of the diastereomeric derivatives by conventional means such as chromatography, or by reaction with an appropriate chiral reagent or chiral catalyst all under conditions known to the skilled person.

All stereoisomers (including but not limited to diastereoisomers, enantiomers and atropisomers) and mixtures thereof (e.g. racemic mixtures) are included within the scope of the invention.

In the structures shown herein, where the stereochemistry of any particular chiral atom is not specified, then all stereoisomers are contemplated and included as the compounds of the invention. Where stereochemistry is specified by a solid wedge or dashed line representing a particular configuration, then that stereoisomer is so specified and defined.

The compounds of the present invention may exist in unsolvated as well as solvated forms with pharmaceutically acceptable solvents such as water, ethanol, and the like, and it is intended that the invention embrace both solvated and unsolvated forms.

The present invention also embraces isotopically-labelled compounds of the present invention which are identical to those recited herein, but for the fact that one or more atoms are replaced by an atom having an atomic mass or mass number different from the atomic mass or mass number usually found in nature (or the most abundant one found in nature). All isotopes of any particular atom or element as specified herein are contemplated within the scope of the compounds of the invention. Exemplary isotopes that can be incorporated into compounds of the invention include isotopes of hydrogen, carbon, nitrogen, oxygen, phosphorus, sulfur, fluorine, chlorine and iodine, such as $^{2}H$, $^{3}H$, $^{11}C$, $^{13}C$, $^{14}C$, $^{13}N$, $^{15}O$, $^{17}O$, $^{18}O$, $^{32}P$, $^{33}P$, $^{35}S$, $^{18}F$, $^{36}Cl$, $^{123}I$, and $^{125}I$. Certain isotopically-labelled compounds of the present invention (e.g., those labelled with $^{3}H$ and $^{14}C$) are useful in compound and for substrate tissue distribution assays. Tritiated ($^{3}H$) and carbon-14 ($^{14}C$) isotopes are useful for their ease of preparation and detectability. Further, substitution with heavier isotopes such as deuterium (i.e., $^{2}H$ may afford certain therapeutic advantages resulting from greater metabolic stability (e.g., increased in vivo half-life or reduced dosage requirements) and hence may be preferred in some circumstances. Positron emitting isotopes such as $^{15}O$, $^{13}N$, $^{11}C$ and $^{18}F$ are useful for positron emission tomography (PET) studies to examine substrate receptor occupancy. Isotopically labelled compounds of the present invention can generally be prepared by following procedures analogous to those disclosed in the Examples herein below, by substituting an isotopically labelled reagent for a non-isotopically labelled reagent.

Unless otherwise stated, the terms $C_{1-q}$ alkyl, and $C_{1-q}$ alkylene, groups (where q is the upper limit of the range) defined herein may be straight-chain or, when there is a sufficient number of carbon atoms, be branched-chain. Similarly, unless otherwise stated, the terms $C_{2-q}$ alkenyl, $C_{2-q}$ alkenylene, $C_{2-q}$ alkynyl, and $C_{2-q}$ alkynylene, groups (where q is the upper limit of the range) defined herein may be straight-chain or, when there is a sufficient number of carbon atoms, be branched-chain.

$C_{3-q}$ cycloalkyl groups (where q is the upper limit of the range) that may be mentioned may be monocyclic or bicyclic alkyl groups, which cycloalkyl groups may further be bridged (so forming, for example, fused ring systems such as three fused cycloalkyl groups). Such cycloalkyl groups may be saturated or unsaturated containing one or more double or triple bonds (forming for example a cycloalkenyl or cycloalkynyl group). Substituents may be attached at any point on the cycloalkyl group. Further, where there is a sufficient number (i.e. a minimum of four) such cycloalkyl groups may also be part cyclic, e.g. forming an alkyl-cycloalkyl group. For the avoidance of doubt, optional substituents may also be other cyclic groups, which may be attached via a single carbon atom common to both rings, so forming a spiro-cycle.

The term "halo", when used herein, includes fluoro, chloro, bromo and iodo.

Heterocycloalkyl groups that may be mentioned include non-aromatic monocyclic and bicyclic heterocycloalkyl groups in which at least one (e.g. one to four) of the atoms in the ring system is other than carbon (i.e. a heteroatom), and in which the total number of atoms in the ring system is from five to ten. Such heterocycloalkyl groups may also be bridged. Further, such heterocycloalkyl groups may be saturated or unsaturated containing one or more double and/or triple bonds, forming for example a $C_{2-q}$ heterocycloalkenyl (where q is the upper limit of the range) or a $C_{7-q}$ heterocycloalkynyl group. $C_{2-q}$ heterocycloalkyl groups that may be mentioned include 7-azabicyclo[2.2.1]heptanyl, 6-azabicyclo[3.1.1]heptanyl, 6-azabicyclo[3.2.1]-octanyl, 8-azabicyclo-[3.2.1]octanyl, aziridinyl, azetidinyl, dihydropyranyl, dihydropyridyl, dihydropyrrolyl (including 2,5-dihydropyrrolyl), dioxolanyl (including 1,3-dioxolanyl), dioxanyl (including 1,3-dioxanyl and 1,4-dioxanyl), dithianyl (including 1,4-dithianyl), dithiolanyl (including 1,3-dithiolanyl), imidazolidinyl, imidazolinyl, morpholinyl, 7-oxabicyclo[2.2.1]heptanyl, 6-oxabicyclo-[3.2.1]octanyl, oxetanyl, oxiranyl, piperazinyl, piperidinyl, pyranyl, pyrazolidinyl, pyrrolidinonyl, pyrrolidinyl, pyrrolinyl, quinuclidinyl, sulfolanyl, 3-sulfolenyl, tetrahydropyranyl, tetrahydrofuranyl, tetrahydropyridyl (such as 1,2,3,4-tetrahydropyridyl and 1,2,3,6-tetrahydropyridyl), thietanyl, thiiranyl, thiolanyl, thiomorpholinyl, trithianyl (including 1,3,5-trithianyl), tropanyl and the like. Substituents on heterocycloalkyl groups may, where appropriate, be located on any atom in the ring system including a heteroatom. The point of attachment of heterocycloalkyl groups may be via any atom in the ring system including (where appropriate) a heteroatom (such as a nitrogen atom), or an atom on any fused carbocyclic ring that may be present as part of the ring system. Heterocycloalkyl groups may also be in the N- or S-oxidised form (i.e. those heteroatoms may be substituted with one or two =O substituents, as appropriate). As stated herein other carbon atoms of the heterocycloalkyl groups mentioned herein may also be substituted by one or more =O substituents. For the avoidance of doubt, optional substituents may also be other cyclic groups, which may be attached via a single carbon atom common to both rings (so forming a spiro-cycle).

For the avoidance of doubt, the term "bicyclic" (e.g. when employed in the context of heterocycloalkyl groups) refers to groups in which the second ring of a two-ring system is formed between two adjacent atoms of the first ring. The term "bridged" (e.g. when employed in the context of cycloalkyl or heterocycloalkyl groups) refers to monocyclic or bicyclic groups in which two non-adjacent atoms are linked by either an alkylene or heteroalkylene chain (as appropriate).

Aryl groups that may be mentioned include $C_{6-10}$ aryl groups. Such groups may be monocyclic or bicyclic and have between 6 and 10 ring carbon atoms, in which at least one ring is aromatic. $C_{6-10}$ aryl groups include phenyl, naphthyl and the like, such as 1,2,3,4-tetrahydronaphthyl. The point of attachment of aryl groups may be via any atom of the ring system. However, when aryl groups are bicyclic, they are linked to the rest of the molecule via an aromatic ring. For the avoidance of doubt, optional substituents include those defined herein and also include =O substituents that may be attached to any non-aromatic rings of a polycyclic (e.g. bicyclic) aryl group (however, in an embodiment, =O substituents are not included). For the avoidance of doubt, optional substituents may also be other cyclic groups, which may be, when attached to a non-aromatic ring of an aryl group, attached via a single carbon atom common to both rings (so forming a spiro-cycle).

Unless otherwise specified, the term "heteroaryl" when used herein refers to an aromatic group containing one or more heteroatom(s) (e.g. one to four heteroatoms) preferably selected from N, O and S. Heteroaryl groups include those which have from 5 to 10 members and may be monocyclic or bicyclic, provided that at least one of the rings is aromatic (so forming, for example, a mono- or bicyclic heteroaromatic group). However, when heteroaryl groups are bicyclic, they are linked to the rest of the molecule via an aromatic ring. Heteroaryl groups that may be mentioned include acridinyl, benzimidazolyl, benzodioxanyl, benzodioxepinyl, benzodioxolyl (including 1,3-benzodioxolyl), benzofuranyl, benzofurazanyl, benzothiadiazolyl (including 2,1,3-benzothiadiazolyl), benzothiazolyl, benzoxadiazolyl (including 2,1,3-benzoxadiazolyl), benzoxazinyl (including 3,4-dihydro-2H-1,4-benzoxazinyl), benzoxazolyl, benzomorpholinyl, benzothienyl, carbazolyl, chromanyl, cinnolinyl, furanyl, imidazolyl, imidazo[1,2-a]pyridyl, indazolyl, indolinyl, indolyl, isobenzofuranyl, isochromanyl, isoindolinyl, isoindolyl, isoquinolinyl, isothiazolyl, isothiochromanyl, isoxazolyl, naphthyridinyl (including 1,6-naphthyridinyl or, preferably, 1,5-naphthyridinyl and 1,8-naphthyridinyl), oxadiazolyl (including 1,2,3-oxadiazolyl, 1,2,4-oxadiazolyl and 1,3,4-oxadiazolyl), oxazolyl, phenazinyl, phenothiazinyl, phthalazinyl, pteridinyl, purinyl, pyranyl, pyrazinyl, pyrazolyl, pyridazinyl, pyridyl, pyrimidinyl, pyrrolyl, quinazolinyl, quinolinyl, quinolizinyl, quinoxalinyl, tetrahydroisoquinolinyl (including 1,2,3,4-tetrahydroisoquinolinyl and 5,6,7,8-tetrahydroisoquinolinyl), tetrahydroquinolinyl (including 1,2,3,4-tetrahydroquinolinyl and 5,6,7,8-tetrahydroquinolinyl), tetrazolyl, thiadiazolyl (including 1,2,3-thiadiazolyl, 1,2,4-thiadiazolyl and 1,3,4-thiadiazolyl), thiazolyl, thiochromanyl, thiophenetyl, thienyl, triazolyl (including 1,2,3-triazolyl, 1,2,4-triazolyl and 1,3, 4-triazolyl) and the like. Substituents on heteroaryl groups may, where appropriate, be located on any atom in the ring system including a heteroatom. For the avoidance of doubt, optional substituents include those defined herein and also include =O substituents that may be attached to any non-aromatic rings of a bicyclic heteroaryl group (but, in an embodiment, =O substituents are not included). The point of attachment of heteroaryl groups may be via any atom in the ring system including (where appropriate) a heteroatom (such as a nitrogen atom), or an atom on any fused carbocyclic ring that may be present as part of the ring system.

In the case where it is specified that the heteroaryl is bicyclic, then it may consist of a five-, six- or seven-membered monocyclic ring (e.g. a monocyclic heteroaryl ring) fused with another a five-, six- or seven-membered ring (e.g. a monocyclic aryl or heteroaryl ring).

Heteroatoms that may be mentioned include phosphorus, silicon, boron and, preferably, oxygen, nitrogen and sulphur.

For the avoidance of doubt, in cases in which the identity of two or more substituents in a compound of the invention may be the same, the actual identities of the respective substituents are not in any way interdependent. For example, in the situation in which there is more than one $Q^2$ substituent present, then those $Q^2$ substituents may be the same or different. Further, in the case where there are two $R^7$ substituents present, in which one $R^7$ is present in the context of $R^1$ and the other is present in the context of $R^2$, then those $R^7$ groups may or may not be the same.

For the avoidance of doubt, in the instance where cyclic substituents (e.g. cycloalkyl or heterocycloalkyl groups) are present on groups (such as alkyl groups), then those cyclic substituents may be attached to the same carbon atom, so forming for example a spiro-cyclic group.

All individual features (e.g. preferred features) mentioned herein may be taken in isolation or in combination with any other feature (including preferred feature) mentioned herein (hence, preferred features may be taken in conjunction with other preferred features, or independently of them).

The skilled person will appreciate that compounds of the invention that are the subject of this invention include those that are stable. That is, compounds of the invention include those that are sufficiently robust to survive isolation from e.g. a reaction mixture to a useful degree of purity.

For the avoidance of doubt, when a term such as "$E^1$ to $E^4$" is employed herein, this will be understood by the skilled person to mean $E^1$, $E^2$, $E^3$ and $E^4$, inclusively.

Where a phrase such as "any relevant pair of $R^3$, $R^4$, $R^5$ and $R^6$" is used, this will be understood by the skilled person to refer to any pair of such groups where those groups are bonded to the same atom. Thus, the aforementioned phrase refers to either the pair $R^3$ and $R^4$ or the pair $R^5$ and $R^6$ (or both pairs simultaneously).

In an embodiment of the invention, there is provided compounds of the invention as hereinbefore defined but in which X represents —O—, —N($R^x$)— or —CH$_2$— (such as X represents —O— or —N($R^x$)—). In these and other embodiments, $R^x$ is preferably H. In another embodiment, there is provided compounds of the invention as hereinbefore defined but in which X does not represents —N($R^x$)—, preferably wherein X represents —O—.

In an embodiment of the invention, there is provided compounds of the invention as hereinbefore defined but in which X represents —N($R^x$)— (such as —NH—).

Compounds of the invention that may be mentioned include those in which —L$^1$-X— together represent —O—, —N(R$^x$)—, —CH$_2$— or —[CR$^5$R$^6$]—O—. In another embodiment, —L$^1$-X— together represent —O—, —N(R$^x$)— or —[CR$^5$R$^6$]—O— (e.g. —O—, —NH— or —CH$_2$—O—).

In an embodiment of the invention, R$^x$ represents hydrogen, methyl, ethyl, propyl, or methyl cyclopropyl (e.g. —CH$_2$—C$_3$H$_5$).

Further compounds of the invention that may be mentioned include those in which L$^2$ represents —C(=O)—.

Preferred compounds of the invention that may be mentioned include those in which L$^3$ represents —CH$_2$—.

In one embodiment, R$^1$ and R$^2$ independently represent hydrogen, halogen, —OR$^7$, —NR$^8$R$^9$, C$_{1-6}$ alkyl, or C$_{3-6}$ cycloalkyl (which latter two groups are optionally substituted by one or more E$^1$ substituents); or R$^1$ and R$^2$ together with the carbon atom to which they are bound form C=O.

In another embodiment, at least one of R$^1$ and R$^2$ represents hydrogen. Other particular compounds of the invention that may be mentioned include those in which at least one of R$^1$ and R$^2$ does not represent hydrogen.

In another embodiment, R$^1$ and R$^2$ independently represent hydrogen, halogen, —OR$^7$ or C$_{1-4}$ alkyl optionally substituted by one or more halo atoms. In a particular embodiment, R$^1$ represents hydrogen, halogen, —OR$^7$ or C$_{1-4}$ alkyl optionally substituted by one or more halo atoms, and R$^2$ represents hydrogen.

In yet another embodiment, R$^1$ and R$^2$ independently represent hydrogen, methyl or fluoro. In a particular embodiment, R$^1$ represents hydrogen, methyl or fluoro, and R$^2$ represents hydrogen. For the avoidance of doubt, when one of R$^1$ and R$^2$ represents a non-hydrogen group (e.g. methyl), said non-hydrogen group may be located either cis- or trans- to the fragment containing L$^1$-X-A. Compounds in which one of R$^1$ and R$^2$ represents a non-hydrogen group (e.g. methyl) and said non-hydrogen group at R$^1$/R$^2$ is oriented cis to the fragment containing L$^1$-X-A have been found to have increased activity levels compared to compounds in which said groups are oriented in the trans configuration. This difference is particularly evident for compounds in which X represents —N(R$^x$)—. Thus, in another embodiment, one of R$^1$ and R$^2$ represents a non-hydrogen group (e.g. methyl) which is oriented cis to the fragment containing L$^1$-X-A (e.g. cis to the fragment containing L$^1$-N(R$^x$)-A).

Preferred compounds of the invention that may be mentioned include those in which R$^3$, R$^4$, R$^5$ and R$^6$ (if present) independently represent hydrogen, fluoro, C$_{1-6}$ alkyl, or C$_{3-6}$ cycloalkyl (which latter two groups are optionally substituted by one or more E$^3$ substituents); or any relevant pair of R$^3$, R$^4$, R$^5$ and R$^6$ form, together with the carbon atom to which they are bound, C=O.

Further preferred compounds include those in which R$^3$, R$^4$, R$^5$ and R$^6$ independently represent hydrogen or a C$_{1-4}$ alkyl group optionally substituted by one or more halo atoms.

In a particular embodiment, each R$^3$, R$^4$, R$^5$ and R$^6$ independently represents hydrogen or methyl. Most preferably, R$^3$, R$^4$, R$^5$ and R$^6$ (if present) all represent hydrogen.

The linker between the core bridged ring system and A (i.e. the linker represented by —[CR$^3$R$^4$]-L$^1$-X—) preferably has one of the following structures:

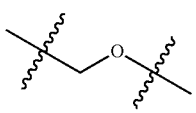 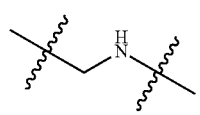

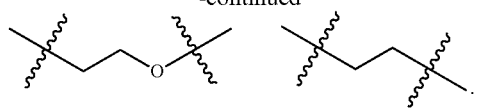

More preferably, the linker represented by —[CR$^3$R$^4$]-L$^1$-X— has one of the following structures:

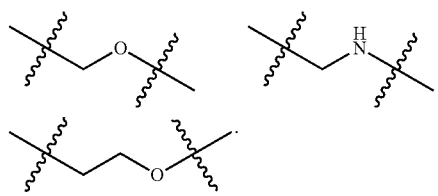

The most preferred of these linkers is —CH$_2$—O—. Another preferred linker is —CH$_2$—NH—.

Particular compounds of the invention that may be mentioned include compounds of formula IA:

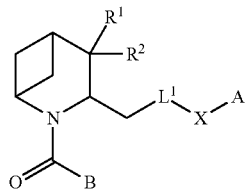

IA wherein R$^1$, R$^2$, L$^1$, A and B are as defined in respect of the compounds of formula I, and X represents —S—, —CH$_2$— or preferably —NH— or —O—, or a pharmaceutically acceptable salt, solvate or prodrug thereof.

Particular compounds of the invention that may be mentioned include compounds of formula IB:

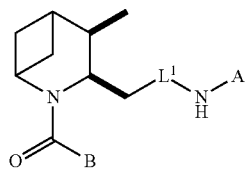

IB wherein L$^1$, A and B are as defined in respect of the compounds of formula I, or a pharmaceutically acceptable salt, solvate or prodrug thereof. In compounds of formula IB, the methyl group (at R$^2$ position) and the fragment containing —CH$_2$-L$^1$-NH-A are attached to the 2-azabicyclo[3.1.1]heptane core in the cis orientation.

Compounds of the invention that may be mentioned include those in which R$^7$ to R$^{11}$ independently represent hydrogen or methyl.

Other compounds of the invention that may be mentioned include those in which E$^1$ to E$^4$ independently represent a C$_{1-6}$ alkyl group or preferably a halogen.

In one embodiment (e.g. for compounds of formula I or IA), A represents an aryl, heteroaryl, cycloalkyl or heterocycloalkyl group (particularly an aromatic group (i.e. an aryl or heteroaryl group)), each of which is substituted with at least one Q$^1$ group.

In another embodiment, the heteroaryl and heterocycloalkyl groups represented by A are monocyclic or bicyclic groups each containing one or two heteroatoms selected from O, S and, most preferably, N. Said groups may be optionally substituted with one or more $Q^1$ groups as indicated above. Preferably A represents either a monocyclic heteroaryl or heterocyclyl group substituted with at least one $Q^1$ group, or a bicyclic heteroaryl or heterocyclyl group optionally substituted with one or more $Q^1$ groups.

In yet another embodiment, A represents a carbocyclic group, i.e. an aryl or cycloalkyl group, each of which is optionally substituted with one or more $Q^1$ groups.

In preferred embodiments, A represents an aryl or heteroaryl group, each of which is optionally substituted by one or more $Q^1$ groups. Particular aryl and heteroaryl groups that may be mentioned in this respect include naphthyl, benzimidazolyl, imidazolyl, thiazolyl, pyrazolyl, oxazolyl, pyridazinyl, pyrrolyl, indazolyl, indolyl, isoindolyl, isoxazolyl, pyranyl, thiazolyl, triazolyl (including 1,2,3-triazolyl, 1,2,4-triazolyl and 1,3,4-triazolyl), and most preferably phenyl, pyridyl, pyrimidinyl, pyrazinyl, quinolinyl, isoquinolinyl, quinoxalinyl, quinazolinyl, benzothiazolyl, pyridopyrazinyl, benzoxazolyl, oxazolopyridinyl and thiazolopyridinyl.

In one embodiment (e.g. for compounds of formula I or IA), B represents a monocyclic group. For example, B may represent phenyl or a monocyclic heteroaryl or heterocycloalkyl group containing one or two heteroatoms selected from O, S and N. For the avoidance of doubt, said monocyclic groups may be optionally substituted with one or more $Q^2$ groups as indicated above.

In another embodiment, B represents a heterocyclic group, i.e. a heteroaryl or heterocycloalkyl group, each of which is optionally substituted with one or more $Q^2$ groups.

In preferred embodiments, B represents an aryl or heteroaryl group (e.g. a monocyclic aromatic group), each of which is optionally substituted by one or more $Q^2$ substituents. Particular aryl and heteroaryl groups that may be mentioned in this respect include naphthyl, benzimidazolyl, imidazolyl, thiazolyl, oxazolyl, pyridazinyl, pyrrolyl, quinolinyl, isoquinolinyl, quinoxalinyl, indazolyl, indolyl, isoindolyl, isoxazolyl, pyranyl, quinazolinyl, triazolyl (including 1,2,3-triazolyl, 1,2,4-triazolyl and 1,3,4-triazolyl), and most preferably phenyl, pyrazolyl, pyridyl, thiazolyl, pyrimidinyl, pyrazinyl, imidazopyridinyl and imidazopyrazinyl.

In a yet further preferred embodiment (e.g. for compounds of formula I or IA), both A and B are aromatic groups. That is, A and B preferably independently represent an aryl or heteroaryl group, each of which is optionally substituted with one or more $Q^1$ or $Q^2$ groups, as appropriate.

In another preferred embodiment, A represents a carbocyclic group each of which is optionally substituted with one or more $Q^1$ groups, and B represents a heterocyclic group each of which is optionally substituted with one or more $Q^2$ groups. In one example of such an embodiment, at least one of $R^1$ and $R^2$ does not represent hydrogen, e.g. at least one of $R^1$ and $R^2$ represents methyl or fluoro.

Preferred compounds of the invention include those in which $Q^1$ represents halogen, —CN, $C_{1-4}$ alkyl, —O—$C_{1-4}$ alkyl, aryl or heteroaryl (which latter four groups are optionally substituted by one or more substituents selected from halogen, methyl and halomethyl (e.g. trifluoromethyl)). For example, $Q^1$ may represent halogen or $C_{1-4}$ alkyl optionally substituted by one or more halo atoms. In yet further preferred compounds, $Q^1$ represents halogen or a methyl group optionally substituted by one or more halo atoms.

Other preferred compounds of the invention include those in which $Q^2$ represents halogen, —CN, $C_{1-4}$ alkyl, O3-6 cycloalkyl, —O—$C_{1-4}$ alkyl, aryl or heteroaryl (which latter five groups are optionally substituted by one or more substituents selected from halogen, CN, methyl and halomethyl (e.g. trifluoromethyl)). For example, $Q^2$ may represent halogen, $C_{1-4}$ alkyl, $C_{3-6}$ cycloalkyl, —O—$C_{1-4}$ alkyl, phenyl or monocyclic heteroaryl (which latter five groups are optionally substituted by one or more substituents selected from halogen, methyl and halomethyl (e.g. trifluoromethyl)) wherein said monocyclic heteroaryl group contains from one to three heteroatoms selected from N, S and O. In further preferred compounds, $Q^2$ represents halogen, —CN, methyl, cyclopropyl, methoxy or ethoxy (which latter four groups are optionally substituted by one or more halo atoms), or phenyl, fluorophenyl, pyridinyl, pyrazinyl, pyrazolyl, pyrimidinyl, thiazolyl or triazolyl (which latter eight groups are optionally substituted by one or more substituents selected from halogen, methyl and halomethyl (e.g. trifluoromethyl)).

Further preferred compounds of the invention include those in which $Q^2$ represents halogen, —CN, $C_{1-4}$ alkyl, $C_{3-6}$ cycloalkyl, —O—$C_{1-4}$ alkyl, aryl or heteroaryl (which latter five groups are optionally substituted by one or more substituents selected from halogen, methyl and halomethyl (e.g. trifluoromethyl)). For example, $Q^2$ may represent halogen, $C_{1-4}$ alkyl, $C_{3-6}$ cycloalkyl, —O—$C_{1-4}$ alkyl, phenyl or monocyclic heteroaryl (which latter five groups are optionally substituted by one or more substituents selected from halogen, methyl and halomethyl (e.g. trifluoromethyl)) wherein said monocyclic heteroaryl group contains from one to three heteroatoms selected from N, S and O. In further preferred compounds, $Q^2$ represents halogen, methyl, cyclopropyl or methoxy (which latter three groups are optionally substituted by one or more halo atoms), or phenyl, fluorophenyl, pyridinyl, pyrazinyl, pyrazolyl, pyrimidinyl, thiazolyl or triazolyl (which latter eight groups are optionally substituted by one or more substituents selected from halogen, methyl and halomethyl (e.g. trifluoromethyl)).

Preferred compounds of the invention include those in which:

X represents —O—, —N($R^x$)— or —$CH_2$—;
$L^2$ represents —C(=O)—;
$L^3$ represents —$CH_2$—;
$R^1$ and $R^2$ independently represent hydrogen, halogen, —$OR^7$, —$NR^8R^9$, $C_{1-6}$ alkyl, or $C_{3-6}$ cycloalkyl (which latter two groups are optionally substituted by one or more $E^1$ substituents); or $R^1$ and $R^2$ together with the carbon atom to which they are bound form C=O;
$R^3$, $R^4$, $R^5$ and $R^6$ (if present) independently represent hydrogen, $C_{1-6}$ alkyl, or $C_{3-6}$ cycloalkyl (which latter two groups are optionally substituted by one or more $E^3$ substituents); or any relevant pair of $R^3$, $R^4$, $R^5$ and $R^6$ form, together with the carbon atom to which they are bound, C=O;
$R^7$ to $R^{11}$ and $R^x$ (if present) independently represent hydrogen or methyl;
$E^1$ to $E^4$ (if present) independently represent a $C_{1-6}$ alkyl group or preferably a halogen;
A represents an aryl, heteroaryl, cycloalkyl or heterocycloalkyl group (particularly an aryl or heteroaryl group), each of which is substituted with at least one $Q^1$ group;
B represents phenyl or a monocyclic heteroaryl or heterocycloalkyl group containing one or two heteroatoms selected from O, S and N, and which cyclic group is optionally substituted with at least one $Q^2$ group; and $Q^1$ and $Q^2$ independently represent halogen, —CN, $C_{1-4}$ alkyl, $C_{3-6}$ cycloalkyl, —O—$C_{1-4}$ alkyl, aryl or heteroaryl (which latter five groups are optionally substituted by one or more substituents selected from halogen, methyl and halomethyl (e.g. trifluoromethyl)).

More preferred compounds include those in which:
$L^2$ represents —C(=O)—;
$L^3$ represents —$CH_2$—;
$R^1$ and $R^2$ independently represent hydrogen, halogen, —$OR^7$ or $C_{1-4}$ alkyl optionally substituted by one or more halo atoms;
the linker between the core bridged ring system and A (i.e. the linker represented by —[$CR^3R^4$]-$L^1$-X—) has one of the following structures:

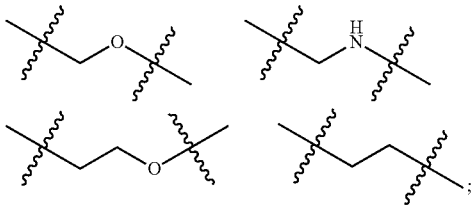

$R^7$ represents hydrogen or methyl;
A and B each independently represent an aryl or heteroaryl group, each of which is optionally substituted with one or more $Q^1$ or $Q^2$ groups, as appropriate;
$Q^1$ represents halogen or $C_{1-4}$ alkyl optionally substituted by one or more halo atoms; and
$Q^2$ represents halogen, —CN, $C_{1-4}$ alkyl, $C_{3-6}$ cycloalkyl, —O—$C_{1-4}$ alkyl, phenyl or monocyclic heteroaryl (which latter five groups are optionally substituted by one or more substituents selected from halogen, methyl and halomethyl (e.g. trifluoromethyl)) further wherein said monocyclic heteroaryl group contains from one to three heteroatoms selected from N, S and O.

Still more preferred compounds include those in which:
$L^1$ represents a direct bond or $CH_2$;
$L^2$ represents —C(=O)—;
$L^3$ represents —$CH_2$—;
$R^1$ and $R^2$ independently represent hydrogen, halogen or methyl;
$R^3$ and $R^4$ represent hydrogen;
X represents —O— or —NH— (preferably —O—);
A represents a monocyclic or bicyclic aromatic group which is optionally substituted with one or more $Q^1$ groups;
B represents a monocyclic aromatic group which is optionally substituted with one or more $Q^2$ groups;
$Q^1$ represents halogen or $C_{1-4}$ alkyl optionally substituted by one or more halo atoms; and
$Q^2$ represents halogen, —CN, $C_{1-4}$ alkyl, $C_{3-6}$ cycloalkyl, —O—$C_{1-4}$ alkyl, phenyl or monocyclic heteroaryl (which latter two groups are optionally substituted by one or more substituents selected from halogen, methyl and halomethyl (e.g. trifluoromethyl)) further wherein said monocyclic heteroaryl group contain from one to three heteroatoms selected from N, S and O.

Particularly preferred compounds of the invention include those of the examples described hereinafter, including:
3-[(4-fluorophenoxy)methyl]-2-(2-methyl-5-phenyl-1,3-thiazole-4-carbonyl)-2-azabicyclo[3.1.1]heptane;
(3R)-3-[(4-fluorophenoxy)methyl]-2-(2-methyl-5-phenyl-1,3-thiazole-4-carbonyl)-2-azabicyclo[3.1.1]heptane;
(3S)-3-[(4-fluorophenoxy)methyl]-2-(2-methyl-5-phenyl-1,3-thiazole-4-carbonyl)-2-azabicyclo[3.1.1]heptane;
3-(4-fluorophenoxymethyl)-2-{[6-methyl-3-(1,3-thiazol-2-yl)pyridin-2-yl]carbonyl}-2-azabicyclo[3.1.1]heptane;
(3R)-3-(4-fluorophenoxymethyl)-2-{[6-methyl-3-(1,3-thiazol-2-yl)pyridin-2-yl]carbonyl}-2-azabicyclo[3.1.1]heptane;
(3S)-3-(4-fluorophenoxymethyl)-2-{[6-methyl-3-(1,3-thiazol-2-yl)pyridin-2-yl]carbonyl}-2-azabicyclo[3.1.1]heptane;
3-(4-fluorophenoxymethyl)-2-{[5-methyl-2-(1,3-thiazol-2-yl)phenyl]carbonyl}-2-azabicyclo[3.1.1]heptane;
(3R)-3-(4-fluorophenoxymethyl)-2-{[5-methyl-2-(1,3-thiazol-2-yl)phenyl]carbonyl}-2-azabicyclo[3.1.1]heptane;
(3S)-3-(4-fluorophenoxymethyl)-2-{[5-methyl-2-(1,3-thiazol-2-yl)phenyl]carbonyl}-2-azabicyclo[3.1.1]heptane;
3-(4-fluorophenoxymethyl)-2-{[5-methyl-2-(2H-1,2,3-triazol-2-yl)phenyl]carbonyl}-2-azabicyclo[3.1.1]heptane;
(3R)-3-(4-fluorophenoxymethyl)-2-{[5-methyl-2-(2H-1,2,3-triazol-2-yl)phenyl]carbonyl}-2-azabicyclo[3.1.1]heptane;
(3S)-3-(4-fluorophenoxymethyl)-2-{[5-methyl-2-(2H-1,2,3-triazol-2-yl)phenyl]carbonyl}-2-azabicyclo[3.1.1]heptane;
3-(4-fluorophenoxymethyl)-2-{[6-methyl-3-(pyrimidin-2-yl)pyridin-2-yl]carbonyl}-2-azabicyclo[3.1.1]heptane;
(3R)-3-(4-fluorophenoxymethyl)-2-{[6-methyl-3-(pyrimidin-2-yl)pyridin-2-yl]carbonyl}-2-azabicyclo[3.1.1]heptane;
(3S)-3-(4-fluorophenoxymethyl)-2-{[6-methyl-3-(pyrimidin-2-yl)pyridin-2-yl]carbonyl}-2-azabicyclo[3.1.1]heptane;
3-(4-fluorophenoxymethyl)-2-{[5-methyl-2-(pyrimidin-2-yl)phenyl]carbonyl}-2-azabicyclo[3.1.1]heptane;
(3S)-3-(4-fluorophenoxymethyl)-2-{[5-methyl-2-(pyrimidin-2-yl)phenyl]carbonyl}-2-azabicyclo[3.1.1]heptane;
(3R)-3-(4-fluorophenoxymethyl)-2-{[5-methyl-2-(pyrimidin-2-yl)phenyl]carbonyl}-2-azabicyclo[3.1.1]heptane;
3-(4-chlorophenoxymethyl)-2-{[5-methyl-2-(pyrimidin-2-yl)phenyl]carbonyl}-2-azabicyclo[3.1.1]heptane;
3-(4-chlorophenoxymethyl)-2-{[5-methyl-2-(1,3-thiazol-2-yl)phenyl]carbonyl}-2-azabicyclo[3.1.1]heptane;
3-{[(5-fluoropyridin-2-yl)oxy]methyl}-2-{[6-methyl-3-(pyrimidin-2-yl)pyridin-2-yl]carbonyl}-2-azabicyclo[3.1.1]heptane;
(3S)-3-{[(5-fluoropyridin-2-yl)oxy]methyl}-2-{[6-methyl-3-(pyrimidin-2-yl)pyridin-2-yl]carbonyl}-2-azabicyclo[3.1.1]heptane;
(3R)-3-{[(5-fluoropyridin-2-yl)oxy]methyl}-2-{[6-methyl-3-(pyrimidin-2-yl)pyridin-2-yl]carbonyl}-2-azabicyclo[3.1.1]heptane;
3-{[(5-fluoropyridin-2-yl)oxy]methyl}-2-[(2-methyl-5-phenyl-1,3-thiazol-4-yl)carbonyl]-2-azabicyclo[3.1.1]heptane;
3-{[(5-fluoropyridin-2-yl)oxy]methyl}-2-{[5-methyl-2-(1,3-thiazol-2-yl)phenyl]carbonyl}-2-azabicyclo[3.1.1]heptane;
(3S)-3-{[(5-fluoropyridin-2-yl)oxy]methyl}-2-{[5-methyl-2-(1,3-thiazol-2-yl)phenyl]carbonyl}-2-azabicyclo[3.1.1]heptane;
(3R)-3-{[(5-fluoropyridin-2-yl)oxy]methyl}-2-{[5-methyl-2-(1,3-thiazol-2-yl)phenyl]carbonyl}-2-azabicyclo[3.1.1]heptane;

3-{[(5-fluoropyridin-2-yl)oxy]methyl}-2-{[5-methyl-2-(2H-1,2,3-triazol-2-yl)phenyl]carbonyl}-2-azabicyclo[3.1.1]heptane;
(3S)-3-{[(5-fluoropyridin-2-yl)oxy]methyl}-2-{[5-methyl-2-(2H-1,2,3-triazol-2-yl)phenyl]carbonyl}-2-azabicyclo[3.1.1]heptane;
(3R)-3-{[(5-fluoropyridin-2-yl)oxy]methyl}-2-{[5-methyl-2-(2H-1,2,3-triazol-2-yl)phenyl]carbonyl}-2-azabicyclo[3.1.1]heptane;
3-{[(5-fluoropyridin-2-yl)oxy]methyl}-2-{[6-methyl-3-(1,3-thiazol-2-yl)pyridin-2-yl]carbonyl}-2-azabicyclo[3.1.1]heptane;
3-{[(5-chloropyridin-2-yl)oxy]methyl}-2-{[5-methyl-2-(pyrimidin-2-yl)phenyl]carbonyl}-2-azabicyclo[3.1.1]heptane;
(3S)-3-{[(5-chloropyridin-2-yl)oxy]methyl}-2-{[5-methyl-2-(pyrimidin-2-yl)phenyl]carbonyl}-2-azabicyclo[3.1.1]heptane;
(3R)-3-{[(5-chloropyridin-2-yl)oxy]methyl}-2-{[5-methyl-2-(pyrimidin-2-yl)phenyl]carbonyl}-2-azabicyclo[3.1.1]heptane;
2-{[5-methyl-2-(pyrimidin-2-yl)phenyl]carbonyl}-3-({[5-(trifluoromethyl)pyridin-2-yl]oxy}methyl)-2-azabicyclo[3.1.1]heptane;
(3S)-2-{[5-methyl-2-(pyrimidin-2-yl)phenyl]carbonyl}-3-({[5-(trifluoromethyl)pyridin-2-yl]oxy}methyl)-2-azabicyclo[3.1.1]heptane;
(3R)-2-{[5-methyl-2-(pyrimidin-2-yl)phenyl]carbonyl}-3-({[5-(trifluoromethyl)pyridin-2-yl]oxy}methyl)-2-azabicyclo[3.1.1]heptane;
3-{[2-(2-methyl-5-phenyl-1,3-thiazole-4-carbonyl)-2-azabicyclo[3.1.1]heptan-3-yl]methoxy}isoquinoline;
3-[(4-fluorophenoxy)methyl]-2-[6-methyl-3-(2H-1,2,3-triazol-2-yl)pyridine-2-carbonyl]-2-azabicyclo[3.1.1]heptane;
3-[(4-fluorophenoxy)methyl]-2-[5-(2-fluorophenyl)-2-methyl-1,3-thiazole-4-carbonyl]-2-azabicyclo[3.1.1]heptane;
3-[2-(4-fluorophenoxy)ethyl]-2-[5-methyl-2-(pyrimidin-2-yl)benzoyl]-2-azabicyclo[3.1.1]heptane;
(3S)-3-[2-(4-fluorophenoxy)ethyl]-2-[5-methyl-2-(pyrimidin-2-yl)benzoyl]-2-azabicyclo[3.1.1]heptane;
(3R)-3-[2-(4-fluorophenoxy)ethyl]-2-[5-methyl-2-(pyrimidin-2-yl)benzoyl]-2-azabicyclo[3.1.1]heptane;
3-(3-fluorophenoxymethyl)-2-(2-methyl-5-phenyl-1,3-thiazole-4-carbonyl)-2-azabicyclo[3.1.1]heptane;
3-(2-fluorophenoxymethyl)-2-(2-methyl-5-phenyl-1,3-thiazole-4-carbonyl)-2-azabicyclo[3.1.1]heptane;
3-(4-bromophenoxymethyl)-2-(2-methyl-5-phenyl-1,3-thiazole-4-carbonyl)-2-azabicyclo[3.1.1]heptane;
3-(3,4-difluorophenoxymethyl)-2-(2-methyl-5-phenyl-1,3-thiazole-4-carbonyl)-2-azabicyclo[3.1.1]heptane;
2-(2-methyl-5-phenyl-1,3-thiazole-4-carbonyl)-3-(4-methylphenoxymethyl)-2-azabicyclo[3.1.1]heptane;
3-(4-chlorophenoxymethyl)-2-(2-methyl-5-phenyl-1,3-thiazole-4-carbonyl)-2-azabicyclo[3.1.1]heptane;
3-(4-fluorophenoxymethyl)-2-[5-(4-fluorophenyl)-2-methyl-1,3-thiazole-4-carbonyl]-2-azabicyclo[3.1.1]heptane;
2-(2-chloro-5-phenyl-1,3-thiazole-4-carbonyl)-3-[(4-fluorophenoxy)methyl]-2-azabicyclo[3.1.1]heptane;
3-[(4-fluorophenoxy)methyl]-2-(2-methoxy-5-phenyl-1,3-thiazole-4-carbonyl)-2-azabicyclo[3.1.1]heptane;
2-(2-cyclopropyl-5-phenyl-1,3-thiazole-4-carbonyl)-3-[(4-fluorophenoxy)methyl]-2-azabicyclo[3.1.1]heptane;
6-fluoro-2-{[2-(2-methyl-5-phenyl-1,3-thiazole-4-carbonyl)-2-azabicyclo[3.1.1]heptan-3-yl]methoxy}-1,3-benzothiazole;
2-(2-methyl-5-phenyl-1,3-thiazole-4-carbonyl)-3-({[5-(trifluoromethyl)pyridin-2-yl]oxy}methyl)-2-azabicyclo[3.1.1]heptane;
2-{[2-(2-methyl-5-phenyl-1,3-thiazole-4-carbonyl)-2-azabicyclo[3.1.1]heptan-3-yl]methoxy}quinoline;
2-(2-methyl-5-phenyl-1,3-thiazole-4-carbonyl)-3-[({7-methyl-7H-pyrrolo[2,3-d]pyrimidin-2-yl}oxy)methyl]-2-azabicyclo[3.1.1]heptane;
2-{[2-(2-methyl-5-phenyl-1,3-thiazole-4-carbonyl)-2-azabicyclo[3.1.1]heptan-3-yl]methoxy}quinoxaline;
N-{[2-{2-methyl-5-phenyl-1,3-thiazole-4-carbonyl)-2-azabicyclo[3.1.1]heptan-3-yl]methyl}isoquinolin-3-amine;
N-([2-{2-methyl-5-phenyl-1,3-thiazole-4-carbonyl)-2-azabicyclo[3.1.1]heptan-3-yl]methyl}quinolin-2-amine;
6-fluoro-N-{([2-(2-methyl-5-phenyl-1,3-thiazole-4-carbonyl)-2-azabicyclo[3.1.1]heptan-3-yl]methyl}-1,3-benzothiazol-2-amine;
(3S,4R)-4-fluoro-3-{[(5-fluoropyridin-2-yl)oxy]methyl}-2-(2-methyl-5-phenyl-1,3-thiazole-4-carbonyl)-2-azabicyclo[3.1.1]heptane;
(3R,4S)-4-fluoro-3-{[(5-fluoropyridin-2-yl)oxy]methyl}-2-(2-methyl-5-phenyl-1,3-thiazole-4-carbonyl)-2-azabicyclo[3.1.1]heptane;
3-(4-fluorophenoxymethyl)-4-methyl-2-(2-methyl-5-phenyl-1,3-thiazole-4-carbonyl)-2-azabicyclo[3.1.1]heptane;
(3R,4R)-3-(4-fluorophenoxymethyl)-4-methyl-2-(2-methyl-5-phenyl-1,3-thiazole-4-carbonyl)-2-azabicyclo[3.1.1]heptane;
(3R,4S)-3-(4-fluorophenoxymethyl)-4-methyl-2-(2-methyl-5-phenyl-1,3-thiazole-4-carbonyl)-2-azabicyclo[3.1.1]heptane;
(3S,4S)-3-(4-fluorophenoxymethyl)-4-methyl-2-(2-methyl-5-phenyl-1,3-thiazole-4-carbonyl)-2-azabicyclo[3.1.1]heptane;
(3S,4R)-3-(4-fluorophenoxymethyl)-4-methyl-2-(2-methyl-5-phenyl-1,3-thiazole-4-carbonyl)-2-azabicyclo[3.1.1]heptane;
3-(4-fluorophenoxymethyl)-4-methyl-2-[5-methyl-2-(pyrimidin-2-yl)benzoyl]-2-azabicyclo[3.1.1]heptane;
(3S,4S)-3-(4-fluorophenoxymethyl)-4-methyl-2-[5-methyl-2-(pyrimidin-2-yl)benzoyl]-2-azabicyclo[3.1.1]heptane;
(3R,4S)-3-(4-fluorophenoxymethyl)-4-methyl-2-[5-methyl-2-(pyrimidin-2-yl)benzoyl]-2-azabicyclo[3.1.1]heptane;
(3R,4R)-3-(4-fluorophenoxymethyl)-4-methyl-2-[5-methyl-2-(pyrimidin-2-yl)benzoyl]-2-azabicyclo[3.1.1]heptane;
(3S,4R)-3-(4-fluorophenoxymethyl)-4-methyl-2-[5-methyl-2-(pyrimidin-2-yl)benzoyl]-2-azabicyclo[3.1.1]heptane;
Racemic mixture of cis-3-{[(5-fluoropyridin-2-yl)oxy]methyl}-4-methyl-2-[5-methyl-2-(pyrimidin-2-yl)benzoyl]-2-azabicyclo[3.1.1]heptane;
(3S,4R)-3-{[(5-fluoropyridin-2-yl)oxy]methyl}-4-methyl-2-[5-methyl-2-(pyrimidin-2-yl)benzoyl]-2-azabicyclo[3.1.1]heptane;
(3R,4S)-3-{[(5-fluoropyridin-2-yl)oxy]methyl}-4-methyl-2-[5-methyl-2-(pyrimidin-2-yl)benzoyl]-2-azabicyclo[3.1.1]heptane;
3-{[(5-fluoropyridin-2-yl)oxy]methyl}-4-methyl-2-(2-methyl-5-phenyl-1,3-thiazole-4-carbonyl)-2-azabicyclo[3.1.1]heptane;
3-{[(5-fluoropyridin-2-yl)oxy]methyl}-4-methyl-2-[6-methyl-3-(pyrimidin-2-yl)pyridine-2-carbonyl]-2-azabicyclo[3.1.1]heptane;

(3R,4S)-3-{[(5-fluoropyridin-2-yl)oxy]methyl}-4-methyl-2-[6-methyl-3-(pyrimidin-2-yl)pyridine-2-carbonyl]-2-azabicyclo[3.1.1]heptane;

(3R,4R)-3-{[(5-fluoropyridin-2-yl)oxy]methyl}-4-methyl-2-[6-methyl-3-(pyrimidin-2-yl)pyridine-2-carbonyl]-2-azabicyclo[3.1.1]heptane;

(3S,4R)-3-{[(5-fluoropyridin-2-yl)oxy]methyl}-4-methyl-2-[6-methyl-3-(pyrimidin-2-yl)pyridine-2-carbonyl]-2-azabicyclo[3.1.1]heptane;

(3S,4S)-3-{[(5-fluoropyridin-2-yl)oxy]methyl}-4-methyl-2-[6-methyl-3-(pyrimidin-2-yl)pyridine-2-carbonyl]-2-azabicyclo[3.1.1]heptane;

1-{[4-methyl-2-(2-methyl-5-phenyl-1,3-thiazole-4-carbonyl)-2-azabicyclo[3.1.1]heptan-3-yl]methoxy}isoquinoline;

7-chloro-2-{[4-methyl-2-(2-methyl-5-phenyl-1,3-thiazole-4-carbonyl)-2-azabicyclo[3.1.1]heptan-3-yl]methoxy}quinoxaline;

3-{[4-methyl-2-(2-methyl-5-phenyl-1,3-thiazole-4-carbonyl)-2-azabicyclo[3.1.1]heptan-3-yl]methoxy}isoquinoline;

3-{[(3R,4R)-4-methyl-2-(2-methyl-5-phenyl-1,3-thiazole-4-carbonyl)-2-azabicyclo[3.1.1]heptan-3-yl]methoxy}isoquinoline;

3-{[(3R,4S)-4-methyl-2-(2-methyl-5-phenyl-1,3-thiazole-4-carbonyl)-2-azabicyclo[3.1.1]heptan-3-yl]methoxy}isoquinoline;

3-{[(3S,4S)-4-methyl-2-(2-methyl-5-phenyl-1,3-thiazole-4-carbonyl)-2-azabicyclo[3.1.1]heptan-3-yl]methoxy}isoquinoline;

3-{[(3S,4R)-4-methyl-2-(2-methyl-5-phenyl-1,3-thiazole-4-carbonyl)-2-azabicyclo[3.1.1]heptan-3-yl]methoxy}isoquinoline;

(3R,4S)-3-(4-fluorophenoxymethyl)-4-methyl-2-[6-methyl-3-(pyrimidin-2-yl)pyridine-2-carbonyl]-2-azabicyclo[3.1.1]heptane;

(3S,4R)-3-(4-fluorophenoxymethyl)-4-methyl-2-[6-methyl-3-(pyrimidin-2-yl)pyridine-2-carbonyl]-2-azabicyclo[3.1.1]heptane;

(3R,4R)-3-(4-fluorophenoxymethyl)-4-methyl-2-[6-methyl-3-(pyrimidin-2-yl)pyridine-2-carbonyl]-2-azabicyclo[3.1.1]heptane;

(3S,4S)-3-(4-fluorophenoxymethyl)-4-methyl-2-[6-methyl-3-(pyrimidin-2-yl)pyridine-2-carbonyl]-2-azabicyclo[3.1.1]heptane;

Racemic mixture of cis-3-[(4-fluorophenoxy)methyl]-4-methyl-2-[2-methyl-5-(pyrimidin-2-yl)-1,3-thiazole-4-carbonyl]-2-azabicyclo[3.1.1]heptane;

Racemic mixture of cis-3-[(4-fluorophenoxy)methyl]-4-methyl-2-[6-methyl-3-(2H-1,2,3-triazol-2-yl)pyridine-2-carbonyl]-2-azabicyclo[3.1.1]heptane;

Racemic mixture of cis-3-[(4-fluorophenoxy)methyl]-4-methyl-2-[6-methyl-3-(1,3-thiazol-2-yl)pyridine-2-carbonyl]-2-azabicyclo[3.1.1]heptane;

Racemic mixture of cis-3-[(4-fluorophenoxy)methyl]-4-methyl-2-[5-methyl-2-(2H-1,2,3-triazol-2-yl)benzoyl]-2-azabicyclo[3.1.1]heptane;

Racemic mixture of cis-3-[(4-fluorophenoxy)methyl]-4-methyl-2-[5-methyl-2-(1,3-thiazol-2-yl)benzoyl]-2-azabicyclo[3.1.1]heptane;

Racemic mixture of cis-3-{[(5-chloropyridin-2-yl)oxy]methyl}-4-methyl-2-[6-methyl-3-(2H-1,2,3-triazol-2-yl)pyridine-2-carbonyl]-2-azabicyclo[3.1.1]heptane;

Racemic mixture of cis-4-methyl-2-[6-methyl-3-(2H-1,2,3-triazol-2-yl)pyridine-2-carbonyl]-3-{[(5-methylpyridin-2-yl)oxy]methyl}-2-azabicyclo[3.1.1]heptane;

Racemic mixture of trans-3-[(4-fluorophenoxy)methyl]-4-methyl-2-[5-methyl-2-(1,3-thiazol-2-yl)benzoyl]-2-azabicyclo[3.1.1]heptane;

Racemic mixture of trans-3-{[(5-chloropyridin-2-yl)oxy]methyl}-4-methyl-2-[6-methyl-3-(2H-1,2,3-triazol-2-yl)pyridine-2-carbonyl]-2-azabicyclo[3.1.1]heptane;

Racemic mixture of trans-3-[(4-fluorophenoxy)methyl]-4-methyl-2-[6-methyl-3-(2H-1,2,3-triazol-2-yl)pyridine-2-carbonyl]-2-azabicyclo[3.1.1]heptane;

(3R,4R)-3-[(4-fluorophenoxy)methyl]-4-methyl-2-[6-methyl-3-(2H-1,2,3-triazol-2-yl)pyridine-2-carbonyl]-2-azabicyclo[3.1.1]heptane;

(3S,4S)-3-[(4-fluorophenoxy)methyl]-4-methyl-2-[6-methyl-3-(2H-1,2,3-triazol-2-yl)pyridine-2-carbonyl]-2-azabicyclo[3.1.1]heptane;

Racemic mixture of trans-3-[(4-fluorophenoxy)methyl]-4-methyl-2-[6-methyl-3-(1,3-thiazol-2-yl)pyridine-2-carbonyl]-2-azabicyclo[3.1.1]heptane;

(3R,4R)-3-[(4-fluorophenoxy)methyl]-4-methyl-2-[6-methyl-3-(1,3-thiazol-2-yl)pyridine-2-carbonyl]-2-azabicyclo[3.1.1]heptane;

(3S,4S)-3-[(4-fluorophenoxy)methyl]-4-methyl-2-[6-methyl-3-(1,3-thiazol-2-yl)pyridine-2-carbonyl]-2-azabicyclo[3.1.1]heptane;

Racemic mixture of trans-3-[(4-fluorophenoxy)methyl]-4-methyl-2-[5-methyl-2-(2H-1,2,3-triazol-2-yl)benzoyl]-2-azabicyclo[3.1.1]heptane;

Racemic mixture of trans-6-fluoro-2-({4-methyl-2-[6-methyl-3-(2H-1,2,3-triazol-2-yl)pyridine-2-carbonyl]-2-azabicyclo[3.1.1]heptan-3-yl}methoxy)-1,3-benzothiazole;

Racemic mixture of trans-3-[(3,4-difluorophenoxy)methyl]-4-methyl-2-[6-methyl-3-(2H-1,2,3-triazol-2-yl)pyridine-2-carbonyl]-2-azabicyclo[3.1.1]heptane;

Racemic mixture of trans-3-[(4-fluorophenoxy)methyl]-4-methyl-2-[2-methyl-5-(pyrimidin-2-yl)-1,3-thiazole-4-carbonyl]-2-azabicyclo[3.1.1]heptane;

Racemic mixture of trans-3-{[(5-fluoropyridin-2-yl)oxy]methyl}-4-methyl-2-[2-methyl-5-(pyrimidin-2-yl)-1,3-thiazole-4-carbonyl]-2-azabicyclo[3.1.1]heptane;

Racemic mixture of trans-3-{[(5-fluoropyridin-2-yl)oxy]methyl}-4-methyl-2-[2-methyl-5-(pyridin-2-yl)-1,3-thiazole-4-carbonyl]-2-azabicyclo[3.1.1]heptane;

Racemic mixture of cis-2'-(3-{[(5-fluoropyridin-2-yl)oxy]methyl}-4-methyl-2-azabicyclo[3.1.1]heptane-2-carbonyl)-6'-methyl-2,3'-bipyridine;

Racemic mixture of cis-3-[(4-fluorophenoxy)methyl]-4-methyl-2-[2-methyl-5-(pyridin-2-yl)-1,3-thiazole-4-carbonyl]-2-azabicyclo[3.1.1]heptane;

Racemic mixture of cis-3-[(4-fluorophenoxy)methyl]-4-methyl-2-{6-methyl-3-[5-(trifluoromethyl)pyrimidin-2-yl]pyridine-2-carbonyl}-2-azabicyclo[3.1.1]heptane;

Racemic mixture of trans-3-[(4-chlorophenoxy)methyl]-4-methyl-2-[6-methyl-3-(2H-1,2,3-triazol-2-yl)pyridine-2-carbonyl]-2-azabicyclo[3.1.1]heptane;

(3R,4R)-3-[(4-chlorophenoxy)methyl]-4-methyl-2-[6-methyl-3-(2H-1,2,3-triazol-2-yl)pyridine-2-carbonyl]-2-azabicyclo[3.1.1]heptane;

(3S,4S)-3-[(4-chlorophenoxy)methyl]-4-methyl-2-[6-methyl-3-(2H-1,2,3-triazol-2-yl)pyridine-2-carbonyl]-2-azabicyclo[3.1.1]heptane;

Racemic mixture of cis-3-[(4-fluorophenoxy)methyl]-2-[3-(5-fluoropyrimidin-2-yl)-6-methylpyridine-2-carbonyl]-4-methyl-2-azabicyclo[3.1.1]heptane;

(3S,4S)-3-[(4-fluorophenoxy)methyl]-4-methyl-2-[2-methyl-5-(pyrimidin-2-yl)-1,3-thiazole-4-carbonyl]-2-azabicyclo[3.1.1]heptane;

(3R,4R)-3-[(4-fluorophenoxy)methyl]-4-methyl-2-[2-methyl-5-(pyrimidin-2-yl)-1,3-thiazole-4-carbonyl]-2-azabicyclo[3.1.1]heptane;

Racemic mixture of trans-3-[(4-fluorophenoxy)methyl]-4-methyl-2-[2-methyl-5-(pyrazin-2-yl)-1,3-thiazole-4-carbonyl]-2-azabicyclo[3.1.1]heptane;

Racemic mixture of trans-3-[(4-fluorophenoxy)methyl]-4-methyl-2-[6-methyl-3-(1H-pyrazol-1-yl)pyridine-2-carbonyl]-2-azabicyclo[3.1.1]heptane;

Racemic mixture of cis-N-({4-methyl-2-[6-methyl-3-(2H-1,2,3-triazol-2-yl)pyridine-2-carbonyl]-2-azabicyclo[3.1.1]heptan-3-yl}methyl)isoquinolin-3-amine;

Racemic mixture of cis-6-fluoro-N-({4-methyl-2-[6-methyl-3-(2H-1,2,3-triazol-2-yl)pyridine-2-carbonyl]-2-azabicyclo[3.1.1]heptan-3-yl}methyl)-1,3-benzothiazol-2-amine;

Racemic mixture of cis-3-[(4-fluorophenoxy)methyl]-4-methyl-2-[6-methyl-3-(4-methyl-1H-pyrazol-1-yl)pyridine-2-carbonyl]-2-azabicyclo[3.1.1]heptane;

Racemic mixture of cis-3-[(4-fluorophenoxy)methyl]-4-methyl-2-[2-methyl-5-(pyrazin-2-yl)-1,3-thiazole-4-carbonyl]-2-azabicyclo[3.1.1]heptane;

Racemic mixture of cis-N-({4-methyl-2-[6-methyl-3-(2H-1,2,3-triazol-2-yl)pyridine-2-carbonyl]-2-azabicyclo[3.1.1]heptan-3-yl}methyl)quinazolin-2-amine;

Racemic mixture of cis-3-[(4-fluorophenoxy)methyl]-4-methyl-2-[2-methyl-5-(6-methylpyridin-2-yl)-1,3-thiazole-4-carbonyl]-2-azabicyclo[3.1.1]heptane;

Racemic mixture of cis-3-[(4-fluorophenoxy)methyl]-4-methyl-2-[6-methyl-3-(5-methylpyrimidin-2-yl)pyridine-2-carbonyl]-2-azabicyclo[3.1.1]heptane;

Racemic mixture of cis-2-[5-(5-chloropyridin-3-yl)-2-methyl-1,3-thiazole-4-carbonyl]-3-[(4-fluorophenoxy)methyl]-4-methyl-2-azabicyclo[3.1.1]heptane;

Racemic mixture of cis-3-[(4-fluorophenoxy)methyl]-4-methyl-2-[2-methyl-5-(2H-1,2,3-triazol-2-yl)-1,3-thiazole-4-carbonyl]-2-azabicyclo[3.1.1]heptane;

Racemic mixture of cis-3-[(4-fluorophenoxy)methyl]-4-methyl-2-[2-methyl-5-(1H-pyrazol-1-yl)-1,3-thiazole-4-carbonyl]-2-azabicyclo[3.1.1]heptane;

Racemic mixture of trans-3-{[(5-chloropyridin-2-yl)oxy]methyl}-4-methyl-2-[6-methyl-3-(pyrimidin-2-yl)pyridine-2-carbonyl]-2-azabicyclo[3.1.1]heptane;

Racemic mixture of trans-3-[(4-fluorophenoxy)methyl]-4-methyl-2-[2-methyl-5-(pyridin-2-yl)-1,3-thiazole-4-carbonyl]-2-azabicyclo[3.1.1]heptane;

(3S,4S)-3-[(4-fluorophenoxy)methyl]-4-methyl-2-[2-methyl-5-(pyridin-2-yl)-1,3-thiazole-4-carbonyl]-2-azabicyclo[3.1.1]heptane;

(3R,4R)-3-[(4-fluorophenoxy)methyl]-4-methyl-2-[2-methyl-5-(pyridin-2-yl)-1,3-thiazole-4-carbonyl]-2-azabicyclo[3.1.1]heptane;

Racemic mixture of trans-3-[(4-fluorophenoxy)methyl]-4-methyl-2-[2-methyl-5-(2H-1,2,3-triazol-2-yl)-1,3-thiazole-4-carbonyl]-2-azabicyclo[3.1.1]heptane;

Racemic mixture of trans-3-[(4-fluorophenoxy)methyl]-4-methyl-2-[6-methyl-3-(4-methyl-2H-1,2,3-triazol-2-yl)pyridine-2-carbonyl]-2-azabicyclo[3.1.1]heptane;

Racemic mixture of trans-2-[5-fluoro-2-(2H-1,2,3-triazol-2-yl)benzoyl]-3-[(4-fluorophenoxy)methyl]-4-methyl-2-azabicyclo[3.1.1]heptane;

Racemic mixture of cis-4-methyl-2-[6-methyl-3-(2H-1,2,3-triazol-2-yl)pyridine-2-carbonyl]-3-({[5-(trifluoromethyl)pyridin-2-yl]oxy}methyl)-2-azabicyclo[3.1.1]heptane;

Racemic mixture of cis-3-{[(5-fluoropyridin-2-yl)oxy]methyl}-4-methyl-2-[6-methyl-3-(2H-1,2,3-triazol-2-yl)pyridine-2-carbonyl]-2-azabicyclo[3.1.1]heptane;

Racemic mixture of cis-3-{3-[(4-fluorophenoxy)methyl]-4-methyl-2-azabicyclo[3.1.1]heptane-2-carbonyl}-4-(2H-1,2,3-triazol-2-yl)benzonitrile;

Racemic mixture of cis-3-[(4-fluorophenoxy)methyl]-4-methyl-2-[2-methyl-5-(6-methylpyridin-3-yl)-1,3-thiazole-4-carbonyl]-2-azabicyclo[3.1.1]heptane;

Racemic mixture of cis-3-[(4-fluorophenoxy)methyl]-4-methyl-2-[6-methyl-3-(4-methyl-2H-1,2,3-triazol-2-yl)pyridine-2-carbonyl]-2-azabicyclo[3.1.1]heptane;

Racemic mixture of cis-3-[(4-fluorophenoxy)methyl]-4-methyl-2-[6-methyl-3-(2H-1,2,3-triazol-2-yl)pyrazine-2-carbonyl]-2-azabicyclo[3.1.1]heptane;

Racemic mixture of cis-3-[(4-fluorophenoxy)methyl]-4-methyl-2-[6-methyl-3-(4-methyl-1H-1,2,3-triazol-1-yl)pyridine-2-carbonyl]-2-azabicyclo[3.1.1]heptane;

Racemic mixture of trans-6-fluoro-N-({4-methyl-2-[6-methyl-3-(2H-1,2,3-triazol-2-yl)pyridine-2-carbonyl]-2-azabicyclo[3.1.1]heptan-3-yl}methyl)-1,3-benzothiazol-2-amine;

Racemic mixture of trans-5-chloro-N-({4-methyl-2-[6-methyl-3-(2H-1,2,3-triazol-2-yl)pyridine-2-carbonyl]-2-azabicyclo[3.1.1]heptan-3-yl}methyl)pyridin-2-amine;

Racemic mixture of trans-N-({4-methyl-2-[6-methyl-3-(2H-1,2,3-triazol-2-yl)pyridine-2-carbonyl]-2-azabicyclo[3.1.1]heptan-3-yl}methyl)quinazolin-2-amine;

Racemic mixture of trans-N-({4-methyl-2-[6-methyl-3-(2H-1,2,3-triazol-2-yl)pyridine-2-carbonyl]-2-azabicyclo[3.1.1]heptan-3-yl}methyl)-1,3-benzothiazol-2-amine;

6-fluoro-N-{[(3R,4S)-4-methyl-2-[6-methyl-3-(2H-1,2,3-triazol-2-yl)pyridine-2-carbonyl]-2-azabicyclo[3.1.1]heptan-3-yl]methyl}-1,3-benzothiazol-2-amine;

6-fluoro-N-{[(3S,4R)-4-methyl-2-[6-methyl-3-(2H-1,2,3-triazol-2-yl)pyridine-2-carbonyl]-2-azabicyclo[3.1.1]heptan-3-yl]methyl}-1,3-benzothiazol-2-amine;

Racemic mixture of cis-5-chloro-N-({4-methyl-2-[6-methyl-3-(2H-1,2,3-triazol-2-yl)pyridine-2-carbonyl]-2-azabicyclo[3.1.1]heptan-3-yl}methyl)pyridin-2-amine;

Racemic mixture of cis-5-fluoro-N-({4-methyl-2-[6-methyl-3-(2H-1,2,3-triazol-2-yl)pyridine-2-carbonyl]-2-azabicyclo[3.1.1]heptan-3-yl}methyl)-1,3-benzothiazol-2-amine;

Racemic mixture of cis-N-({4-methyl-2-[6-methyl-3-(2H-1,2,3-triazol-2-yl)pyridine-2-carbonyl]-2-azabicyclo[3.1.1]heptan-3-yl}methyl)quinoxalin-2-amine;

N-{[(3S,4R)-4-methyl-2-[6-methyl-3-(2H-1,2,3-triazol-2-yl)pyridine-2-carbonyl]-2-azabicyclo[3.1.1]heptan-3-yl]methyl}quinoxalin-2-amine;

N-{[(3R,4S)-4-methyl-2-[6-methyl-3-(2H-1,2,3-triazol-2-yl)pyridine-2-carbonyl]-2-azabicyclo[3.1.1]heptan-3-yl]methyl}quinoxalin-2-amine;

Racemic mixture of cis-N-({4-methyl-2-[6-methyl-3-(2H-1,2,3-triazol-2-yl)pyridine-2-carbonyl]-2-azabicyclo[3.1.1]heptan-3-yl}methyl)quinolin-2-amine;

Racemic mixture of cis-6-fluoro-N-({4-methyl-2-[2-methyl-5-(pyrimidin-2-yl)-1,3-thiazole-4-carbonyl]-2-azabicyclo[3.1.1]heptan-3-yl}methyl)-1,3-benzothiazol-2-amine;

6-fluoro-N-({(3R,4S)-4-methyl-2-[2-methyl-5-(pyrimidin-2-yl)-1,3-thiazole-4-carbonyl]-2-azabicyclo[3.1.1]heptan-3-yl}methyl)-1,3-benzothiazol-2-amine;

6-fluoro-N-({(3S,4R)-4-methyl-2-[2-methyl-5-(pyrimidin-2-yl)-1,3-thiazole-4-carbonyl]-2-azabicyclo[3.1.1]heptan-3-yl}methyl)-1,3-benzothiazol-2-amine;

Racemic mixture of cis-N-({4-methyl-2-[6-methyl-3-(2H-1,2,3-triazol-2-yl)pyridine-2-carbonyl]-2-azabicyclo[3.1.1]heptan-3-yl}methyl)-5-(trifluoromethyl)pyrazin-2-amine;
N-{[(3S,4R)-4-methyl-2-[6-methyl-3-(2H-1,2,3-triazol-2-yl)pyridine-2-carbonyl]-2-azabicyclo[3.1.1]heptan-3-yl]methyl}-5-(trifluoromethyl)pyrazin-2-amine;
N-{[(3R,4S)-4-methyl-2-[6-methyl-3-(2H-1,2,3-triazol-2-yl)pyridine-2-carbonyl]-2-azabicyclo[3.1.1]heptan-3-yl]methyl}-5-(trifluoromethyl)pyrazin-2-amine;
Racemic mixture of cis-6-fluoro-N-({2-[5-fluoro-2-(2H-1,2,3-triazol-2-yl)benzoyl]-4-methyl-2-azabicyclo[3.1.1]heptan-3-yl}methyl)-1,3-benzothiazol-2-amine;
6-fluoro-N-({(3R,4S)-2-[5-fluoro-2-(2H-1,2,3-triazol-2-yl)benzoyl]-4-methyl-2-azabicyclo[3.1.1]heptan-3-yl}methyl)-1,3-benzothiazol-2-amine;
6-fluoro-N-({(3S,4R)-2-[5-fluoro-2-(2H-1,2,3-triazol-2-yl)benzoyl]-4-methyl-2-azabicyclo[3.1.1]heptan-3-yl}methyl)-1,3-benzothiazol-2-amine;
Racemic mixture of cis-N-({2-[5-chloro-2-(2H-1,2,3-triazol-2-yl)benzoyl]-4-methyl-2-azabicyclo[3.1.1]heptan-3-yl}methyl)-6-fluoro-1,3-benzothiazol-2-amine;
N-({(3S,4R)-2-[5-chloro-2-(2H-1,2,3-triazol-2-yl)benzoyl]-4-methyl-2-azabicyclo[3.1.1]heptan-3-yl}methyl)-6-fluoro-1,3-benzothiazol-2-amine;
N-({(3R,4S)-2-[5-chloro-2-(2H-1,2,3-triazol-2-yl)benzoyl]-4-methyl-2-azabicyclo[3.1.1]heptan-3-yl}methyl)-6-fluoro-1,3-benzothiazol-2-amine;
Racemic mixture of cis-N-{[2-(3-ethoxy-6-methylpyridine-2-carbonyl)-4-methyl-2-azabicyclo[3.1.1]heptan-3-yl]methyl}-6-fluoro-1,3-benzothiazol-2-amine;
Racemic mixture of cis-3-(3-{[(6-fluoro-1,3-benzothiazol-2-yl)amino]methyl}-4-methyl-2-azabicyclo[3.1.1]heptane-2-carbonyl)-4-(2H-1,2,3-triazol-2-yl)benzonitrile;
3-[(3S,4R)-3-{[(6-fluoro-1,3-benzothiazol-2-yl)amino]methyl}-4-methyl-2-azabicyclo[3.1.1]heptane-2-carbonyl]-4-(2H-1,2,3-triazol-2-yl)benzonitrile;
3-[(3R,4S)-3-{[(6-fluoro-1,3-benzothiazol-2-yl)amino]methyl}-4-methyl-2-azabicyclo[3.1.1]heptane-2-carbonyl]-4-(2H-1,2,3-triazol-2-yl)benzonitrile;
Racemic mixture of cis-N-({4-methyl-2-[6-methyl-3-(2H-1,2,3-triazol-2-yl)pyridine-2-carbonyl]-2-azabicyclo[3.1.1]heptan-3-yl}methyl)-1,3-benzothiazol-2-amine;
N-{[(3S,4R)-4-methyl-2-[6-methyl-3-(2H-1,2,3-triazol-2-yl)pyridine-2-carbonyl]-2-azabicyclo[3.1.1]heptan-3-yl]methyl}-1,3-benzothiazol-2-amine;
N-{[(3R,4S)-4-methyl-2-[6-methyl-3-(2H-1,2,3-triazol-2-yl)pyridine-2-carbonyl]-2-azabicyclo[3.1.1]heptan-3-yl]methyl}-1,3-benzothiazol-2-amine;
Racemic mixture of cis-N-({4-methyl-2-[6-methyl-3-(2H-1,2,3-triazol-2-yl)pyridine-2-carbonyl]-2-azabicyclo[3.1.1]heptan-3-yl}methyl)-5-(trifluoromethyl)pyridin-2-amine;
N-{[(3S,4R)-4-methyl-2-[6-methyl-3-(2H-1,2,3-triazol-2-yl)pyridine-2-carbonyl]-2-azabicyclo[3.1.1]heptan-3-yl]methyl}-5-(trifluoromethyl)pyridin-2-amine;
N-{[(3R,4S)-4-methyl-2-[6-methyl-3-(2H-1,2,3-triazol-2-yl)pyridine-2-carbonyl]-2-azabicyclo[3.1.1]heptan-3-yl]methyl}-5-(trifluoromethyl)pyridin-2-amine;
Racemic mixture of cis-N-({4-methyl-2-[6-methyl-3-(2H-1,2,3-triazol-2-yl)pyridine-2-carbonyl]-2-azabicyclo[3.1.1]heptan-3-yl}methyl)-[1,3]thiazolo[5,4-b]pyridin-2-amine;
N-({(3S,4R)-4-methyl-2-[6-methyl-3-(2H-1,2,3-triazol-2-yl)pyridine-2-carbonyl]-2-azabicyclo[3.1.1]heptan-3-yl}methyl)-[1,3]thiazolo[5,4-b]pyridin-2-amine;
N-({(3R,4S)-4-methyl-2-[6-methyl-3-(2H-1,2,3-triazol-2-yl)pyridine-2-carbonyl]-2-azabicyclo[3.1.1]heptan-3-yl}methyl)-[1,3]thiazolo[5,4-b]pyridin-2-amine;
Racemic mixture of cis-N-({2-[5-fluoro-2-(2H-1,2,3-triazol-2-yl)benzoyl]-4-methyl-2-azabicyclo[3.1.1]heptan-3-yl}methyl)quinoxalin-2-amine;
N-({(3S,4R)-2-[5-fluoro-2-(2H-1,2,3-triazol-2-yl)benzoyl]-4-methyl-2-azabicyclo[3.1.1]heptan-3-yl}methyl)quinoxalin-2-amine;
N-({(3R,4S)-2-[5-fluoro-2-(2H-1,2,3-triazol-2-yl)benzoyl]-4-methyl-2-azabicyclo[3.1.1]heptan-3-yl}methyl)quinoxalin-2-amine;
Racemic mixture of cis-N-({2-[5-fluoro-2-(2H-1,2,3-triazol-2-yl)benzoyl]-4-methyl-2-azabicyclo[3.1.1]heptan-3-yl}methyl)-5-(trifluoromethyl)pyridin-2-amine;
N-({(3S,4R)-2-[5-fluoro-2-(2H-1,2,3-triazol-2-yl)benzoyl]-4-methyl-2-azabicyclo[3.1.1]heptan-3-yl}methyl)-5-(trifluoromethyl)pyridin-2-amine;
N-({(3R,4S)-2-[5-fluoro-2-(2H-1,2,3-triazol-2-yl)benzoyl]-4-methyl-2-azabicyclo[3.1.1]heptan-3-yl}methyl)-5-(trifluoromethyl)pyridin-2-amine;
Racemic mixture of cis-N-({4-methyl-2-[6-methyl-3-(2H-1,2,3-triazol-2-yl)pyridine-2-carbonyl]-2-azabicyclo[3.1.1]heptan-3-yl}methyl)-5-(trifluoromethyl)pyrimidin-2-amine;
N-{[(3S,4R)-4-methyl-2-[6-methyl-3-(2H-1,2,3-triazol-2-yl)pyridine-2-carbonyl]-2-azabicyclo[3.1.1]heptan-3-yl]methyl}-5-(trifluoromethyl)pyrimidin-2-amine;
N-{[(3R,4S)-4-methyl-2-[6-methyl-3-(2H-1,2,3-triazol-2-yl)pyridine-2-carbonyl]-2-azabicyclo[3.1.1]heptan-3-yl]methyl}-5-(trifluoromethyl)pyrimidin-2-amine;
Racemic mixture of cis-5-fluoro-6-methyl-N-({4-methyl-2-[6-methyl-3-(2H-1,2,3-triazol-2-yl)pyridine-2-carbonyl]-2-azabicyclo[3.1.1]heptan-3-yl}methyl)pyridin-2-amine;
Racemic mixture of cis-N-({4-methyl-2-[6-methyl-3-(2H-1,2,3-triazol-2-yl)pyridine-2-carbonyl]-2-azabicyclo[3.1.1]heptan-3-yl}methyl)-6-(trifluoromethyl)pyridin-2-amine;
Racemic mixture of cis-6-fluoro-N-({4-methyl-2-[6-methyl-3-(2H-1,2,3-triazol-2-yl)pyridine-2-carbonyl]-2-azabicyclo[3.1.1]heptan-3-yl}methyl)quinoxalin-2-amine;
6-fluoro-N-{[(3S,4R)-4-methyl-2-[6-methyl-3-(2H-1,2,3-triazol-2-yl)pyridine-2-carbonyl]-2-azabicyclo[3.1.1]heptan-3-yl]methyl}quinoxalin-2-amine;
6-fluoro-N-{[(3R,4S)-4-methyl-2-[6-methyl-3-(2H-1,2,3-triazol-2-yl)pyridine-2-carbonyl]-2-azabicyclo[3.1.1]heptan-3-yl]methyl}quinoxalin-2-amine;
Racemic mixture of cis-6,7-difluoro-N-({4-methyl-2-[6-methyl-3-(2H-1,2,3-triazol-2-yl)pyridine-2-carbonyl]-2-azabicyclo[3.1.1]heptan-3-yl}methyl)quinoxalin-2-amine;
Racemic mixture of cis-4-fluoro-N-({4-methyl-2-[5-methyl-2-(1,3-thiazol-2-yl)benzoyl]-2-azabicyclo[3.1.1]heptan-3-yl}methyl)aniline;
Racemic mixture of cis-N-({2-[5-chloro-2-(2H-1,2,3-triazol-2-yl)benzoyl]-4-methyl-2-azabicyclo[3.1.1]heptan-3-yl}methyl)-5-(trifluoromethyl)pyrazin-2-amine;
N-({(3S,4R)-2-[5-chloro-2-(2H-1,2,3-triazol-2-yl)benzoyl]-4-methyl-2-azabicyclo[3.1.1]heptan-3-yl}methyl)-5-(trifluoromethyl)pyrazin-2-amine;
N-({(3R,4S)-2-[5-chloro-2-(2H-1,2,3-triazol-2-yl)benzoyl]-4-methyl-2-azabicyclo[3.1.1]heptan-3-yl}methyl)-5-(trifluoromethyl)pyrazin-2-amine;
Racemic mixture of cis-N-({2-[5-chloro-2-(2H-1,2,3-triazol-2-yl)benzoyl]-4-methyl-2-azabicyclo[3.1.1]heptan-3-yl}methyl)pyrido[2,3-b]pyrazin-2-amine;
Racemic mixture of cis-N-({2-[5-chloro-2-(2H-1,2,3-triazol-2-yl)benzoyl]-4-methyl-2-azabicyclo[3.1.1]heptan-3-yl}methyl)-6-fluoroquinoxalin-2-amine;

N-{[(3S,4R)-2-[5-chloro-2-(2H-1,2,3-triazol-2-yl)benzoyl]-4-methyl-2-azabicyclo[3.1.1]heptan-3-yl]methyl}-6-fluoroquinoxalin-2-amine;

N-{[(3R,4R)-2-[5-chloro-2-(2H-1,2,3-triazol-2-yl)benzoyl]-4-methyl-2-azabicyclo[3.1.1]heptan-3-yl]methyl}-6-fluoroquinoxalin-2-amine;

Racemic mixture of cis-N-{[4-methyl-2-(1-methyl-4-phenyl-1H-pyrazole-3-carbonyl)-2-azabicyclo[3.1.1]heptan-3-yl]methyl}-5-(trifluoromethyl)pyridin-2-amine;

N-{[(3S,4R)-4-methyl-2-(1-methyl-4-phenyl-1H-pyrazole-3-carbonyl)-2-azabicyclo[3.1.1]heptan-3-yl]methyl}-5-(trifluoromethyl)pyridin-2-amine;

N-{[(3R,4S)-4-methyl-2-(1-methyl-4-phenyl-1H-pyrazole-3-carbonyl)-2-azabicyclo[3.1.1]heptan-3-yl]methyl}-5-(trifluoromethyl)pyridin-2-amine;

Racemic mixture of cis-N-({4-methyl-2-[1-methyl-4-(pyrimidin-2-yl)-1H-pyrazole-3-carbonyl]-2-azabicyclo[3.1.1]heptan-3-yl}methyl)-5-(trifluoromethyl)pyridin-2-amine;

N-{[(3S,4R)-4-methyl-2-[1-methyl-4-(pyrimidin-2-yl)-1H-pyrazole-3-carbonyl]-2-azabicyclo[3.1.1]heptan-3-yl]methyl}-5-(trifluoromethyl)pyridin-2-amine;

N-{[(3R,4S)-4-methyl-2-[1-methyl-4-(pyrimidin-2-yl)-1H-pyrazole-3-carbonyl]-2-azabicyclo[3.1.1]heptan-3-yl]methyl}-5-(trifluoromethyl)pyridin-2-amine;

Racemic mixture of cis-5-methyl-N-({4-methyl-2-[6-methyl-3-(2H-1,2,3-triazol-2-yl)pyridine-2-carbonyl]-2-azabicyclo[3.1.1]heptan-3-yl}methyl)pyrazin-2-amine;

Racemic mixture of cis-N-({4-methyl-2-[6-methyl-3-(2H-1,2,3-triazol-2-yl)pyridine-2-carbonyl]-2-azabicyclo[3.1.1]heptan-3-yl}methyl)-6-(trifluoromethyl)pyrazin-2-amine;

Racemic mixture of cis-6-fluoro-N-({4-methyl-2-[6-methyl-3-(2H-1,2,3-triazol-2-yl)pyridine-2-carbonyl]-2-azabicyclo[3.1.1]heptan-3-yl}methyl)-1,3-benzoxazol-2-amine;

6-fluoro-N-{[(3S,4R)-4-methyl-2-[6-methyl-3-(2H-1,2,3-triazol-2-yl)pyridine-2-carbonyl]-2-azabicyclo[3.1.1]heptan-3-yl]methyl}-1,3-benzoxazol-2-amine;

6-fluoro-N-{[(3R,4S)-4-methyl-2-[6-methyl-3-(2H-1,2,3-triazol-2-yl)pyridine-2-carbonyl]-2-azabicyclo[3.1.1]heptan-3-yl]methyl}-1,3-benzoxazol-2-amine;

Racemic mixture of cis-N-({2-[5-fluoro-2-(2H-1,2,3-triazol-2-yl)benzoyl]-4-methyl-2-azabicyclo[3.1.1]heptan-3-yl}methyl)-5-(trifluoromethyl)pyrazin-2-amine;

N-{[(3S,4R)-2-[5-fluoro-2-(2H-1,2,3-triazol-2-yl)benzoyl]-4-methyl-2-azabicyclo[3.1.1]heptan-3-yl]methyl}-5-(trifluoromethyl)pyrazin-2-amine;

N-{[(3R,4S)-2-[5-fluoro-2-(2H-1,2,3-triazol-2-yl)benzoyl]-4-methyl-2-azabicyclo[3.1.1]heptan-3-yl]methyl}-5-(trifluoromethyl)pyrazin-2-amine;

Racemic mixture of cis-6-fluoro-N-({2-[5-fluoro-2-(2H-1,2,3-triazol-2-yl)benzoyl]-4-methyl-2-azabicyclo[3.1.1]heptan-3-yl}methyl)quinoxalin-2-amine;

Racemic mixture of cis-N-({4-methyl-2-[6-methyl-3-(2H-1,2,3-triazol-2-yl)pyridine-2-carbonyl]-2-azabicyclo[3.1.1]heptan-3-yl}methyl)-1,3-benzoxazol-2-amine;

N-{[(3S,4R)-4-methyl-2-[6-methyl-3-(2H-1,2,3-triazol-2-yl)pyridine-2-carbonyl]-2-azabicyclo[3.1.1]heptan-3-yl]methyl}-1,3-benzoxazol-2-amine;

N-{[(3R,4S)-4-methyl-2-[6-methyl-3-(2H-1,2,3-triazol-2-yl)pyridine-2-carbonyl]-2-azabicyclo[3.1.1]heptan-3-yl]methyl}-1,3-benzoxazol-2-amine;

Racemic mixture of cis-N-({2-[5-fluoro-2-(2H-1,2,3-triazol-2-yl)benzoyl]-4-methyl-2-azabicyclo[3.1.1]heptan-3-yl}methyl)-[1,3]thiazolo[5,4-b]pyridin-2-amine;

N-{[(3S,4R)-2-[5-fluoro-2-(2H-1,2,3-triazol-2-yl)benzoyl]-4-methyl-2-azabicyclo[3.1.1]heptan-3-yl]methyl}-[1,3]thiazolo[5,4-b]pyridin-2-amine;

N-{[(3R,4S)-2-[5-fluoro-2-(2H-1,2,3-triazol-2-yl)benzoyl]-4-methyl-2-azabicyclo[3.1.1]heptan-3-yl]methyl}-[1,3]thiazolo[5,4-b]pyridin-2-amine;

Racemic mixture of cis-3-{4-methyl-3-[({[1,3]thiazolo[5,4-b]pyridin-2-yl}amino)methyl]-2-azabicyclo[3.1.1]heptane-2-carbonyl}-4-(2H-1,2,3-triazol-2-yl)benzonitrile;

3-[(3S,4R)-4-methyl-3-[({[1,3]thiazolo[5,4-b]pyridin-2-yl}amino)methyl]-2-azabicyclo[3.1.1]heptane-2-carbonyl]-4-(2H-1,2,3-triazol-2-yl)benzonitrile;

3-[(3R,4S)-4-methyl-3-[({[1,3]thiazolo[5,4-b]pyridin-2-yl}amino)methyl]-2-azabicyclo[3.1.1]heptane-2-carbonyl]-4-(2H-1,2,3-triazol-2-yl)benzonitrile;

Racemic mixture of cis-N-({2-[5-chloro-2-(2H-1,2,3-triazol-2-yl)benzoyl]-4-methyl-2-azabicyclo[3.1.1]heptan-3-yl}methyl)-[1,3]thiazolo[5,4-b]pyridin-2-amine;

N-{[(3S,4R)-2-[5-chloro-2-(2H-1,2,3-triazol-2-yl)benzoyl]-4-methyl-2-azabicyclo[3.1.1]heptan-3-yl]methyl}-[1,3]thiazolo[5,4-b]pyridin-2-amine;

N-{[(3R,4S)-2-[5-chloro-2-(2H-1,2,3-triazol-2-yl)benzoyl]-4-methyl-2-azabicyclo[3.1.1]heptan-3-yl]methyl}-[1,3]thiazolo[5,4-b]pyridin-2-amine;

Racemic mixture of cis-3-[4-methyl-3-({[5-(trifluoromethyl)pyrazin-2-yl]amino}methyl)-2-azabicyclo[3.1.1]heptane-2-carbonyl]-4-(2H-1,2,3-triazol-2-yl)benzonitrile;

Racemic mixture of cis-3-(3-{[(6-fluoroquinoxalin-2-yl)amino]methyl}-4-methyl-2-azabicyclo[3.1.1]heptane-2-carbonyl)-4-(2H-1,2,3-triazol-2-yl)benzonitrile;

Racemic mixture of cis-N-({2-[5-chloro-2-(2H-1,2,3-triazol-2-yl)benzoyl]-4-methyl-2-azabicyclo[3.1.1]heptan-3-yl}methyl)-5-(trifluoromethyl)pyrimidin-2-amine;

N-{[(3S,4R)-2-[5-chloro-2-(2H-1,2,3-triazol-2-yl)benzoyl]-4-methyl-2-azabicyclo[3.1.1]heptan-3-yl]methyl}-5-(trifluoromethyl)pyrimidin-2-amine;

N-{[(3R,4S)-2-[5-chloro-2-(2H-1,2,3-triazol-2-yl)benzoyl]-4-methyl-2-azabicyclo[3.1.1]heptan-3-yl]methyl}-5-(trifluoromethyl)pyrimidin-2-amine;

Racemic mixture of cis-N-({2-[5-chloro-2-(2H-1,2,3-triazol-2-yl)benzoyl]-4-methyl-2-azabicyclo[3.1.1]heptan-3-yl}methyl)-[1,3]oxazolo[5,4-b]pyridin-2-amine;

N-{[(3S,4R)-2-[5-chloro-2-(2H-1,2,3-triazol-2-yl)benzoyl]-4-methyl-2-azabicyclo[3.1.1]heptan-3-yl]methyl}-[1,3]oxazolo[5,4-b]pyridin-2-amine;

N-{[(3R,4S)-2-[5-chloro-2-(2H-1,2,3-triazol-2-yl)benzoyl]-4-methyl-2-azabicyclo[3.1.1]heptan-3-yl]methyl}-[1,3]oxazolo[5,4-b]pyridin-2-amine;

Racemic mixture of cis-N-({4-methyl-2-[1-methyl-4-(pyrimidin-2-yl)-1H-pyrazole-3-carbonyl]-2-azabicyclo[3.1.1]heptan-3-yl}methyl)-5-(trifluoromethyl)pyrazin-2-amine;

Racemic mixture of cis-N-({2-[4-chloro-2-(2H-1,2,3-triazol-2-yl)benzoyl]-4-methyl-2-azabicyclo[3.1.1]heptan-3-yl}methyl)-5-(trifluoromethyl)pyrazin-2-amine;

Racemic mixture of cis-N-({2-[5-chloro-2-(2H-1,2,3-triazol-2-yl)benzoyl]-4-methyl-2-azabicyclo[3.1.1]heptan-3-yl}methyl)-6-(trifluoromethyl)pyridazin-3-amine;

Racemic mixture of cis-N-({4-methyl-2-[6-methyl-3-(pyrimidin-2-yl)pyridine-2-carbonyl]-2-azabicyclo[3.1.1]heptan-3-yl}methyl)-5-(trifluoromethyl)pyrazin-2-amine;

N-{[(3S,4R) or (3R,4S)-4-methyl-2-[6-methyl-3-(pyrimidin-2-yl)pyridine-2-carbonyl]-2-azabicyclo[3.1.1]heptan-3-yl]methyl}-5-(trifluoromethyl)pyrazin-2-amine;

N-{[(3R,4S) or (3S,4R)-4-methyl-2-[6-methyl-3-(pyrimidin-2-yl)pyridine-2-carbonyl]-2-azabicyclo[3.1.1]heptan-3-yl]methyl}-5-(trifluoromethyl)pyrazin-2-amine;
Racemic mixture of cis-N-({2-[4-fluoro-2-(2H-1,2,3-triazol-2-yl)benzoyl]-4-methyl-2-azabicyclo[3.1.1]heptan-3-yl}methyl)-5-(trifluoromethyl)pyrazin-2-amine;
Racemic mixture of cis-N-({2-[5-fluoro-2-(2H-1,2,3-triazol-2-yl)benzoyl]-4-methyl-2-azabicyclo[3.1.1]heptan-3-yl}methyl)-5-(trifluoromethyl)pyrimidin-2-amine;
Racemic mixture of cis-N-({2-[2-fluoro-6-(2H-1,2,3-triazol-2-yl)benzoyl]-4-methyl-2-azabicyclo[3.1.1]heptan-3-yl}methyl)-5-(trifluoromethyl)pyrazin-2-amine;
Racemic mixture of cis-N-({4-methyl-2-[5-methyl-2-(2H-1,2,3-triazol-2-yl)benzoyl]-2-azabicyclo[3.1.1]heptan-3-yl}methyl)-5-(trifluoromethyl)pyrazin-2-amine;
N-{[(3S,4R) or (3R,4S)-4-methyl-2-[5-methyl-2-(2H-1,2,3-triazol-2-yl)benzoyl]-2-azabicyclo[3.1.1]heptan-3-yl]methyl}-5-(trifluoromethyl)pyrazin-2-amine;
N-{[(3R,4S) or (3S,4R)-4-methyl-2-[5-methyl-2-(2H-1,2,3-triazol-2-yl)benzoyl]-2-azabicyclo[3.1.1]heptan-3-yl]methyl}-5-(trifluoromethyl)pyrazin-2-amine;
Racemic mixture of cis-N-({2-[5-chloro-2-(2H-1,2,3-triazol-2-yl)benzoyl]-4-methyl-2-azabicyclo[3.1.1]heptan-3-yl}methyl)-5-cyclopropylpyrazin-2-amine;
Racemic mixture of cis 5-cyclopropyl-N-({2-[5-fluoro-2-(2H-1,2,3-triazol-2-yl)benzoyl]-4-methyl-2-azabicyclo[3.1.1]heptan-3-yl}methyl)pyrazin-2-amine;
Racemic mixture of cis-N-({2-[5-chloro-2-(2H-1,2,3-triazol-2-yl)benzoyl]-4-methyl-2-azabicyclo[3.1.1]heptan-3-yl}methyl)-5-cyclopropylpyrimidin-2-amine; and
Racemic mixture of cis-5-cyclopropyl-N-({2-[5-fluoro-2-(2H-1,2,3-triazol-2-yl)benzoyl]-4-methyl-2-azabicyclo[3.1.1]heptan-3-yl}methyl)pyrimidin-2-amine.

Other compounds that may be mentioned include:
3-{[(5-fluoropyridin-2-yl)oxy]methyl}-2-[5-methyl-2-(1H-pyrazol-1-yl)benzoyl]-2-azabicyclo[3.1.1]heptane;
3-{[(5-fluoropyridin-2-yl)oxy]methyl}-2-[6-methyl-3-(pyrimidin-2-yl)pyridine-2-carbonyl]-2-azabicyclo[3.1.1]heptane;
6-({2-[5-methyl-2-(pyrimidin-2-yl)benzoyl]-2-azabicyclo[3.1.1]heptan-3-yl}methoxy)pyridine-2-carbonitrile;
3-[(4-fluorophenoxy)methyl]-2-[2-(pyrimidin-2-yl)benzoyl]-2-azabicyclo[3.1.1]heptane;
2-[5-methyl-2-(1,3-thiazol-2-yl)benzoyl]-3-{[4-(trifluoromethyl)phenoxy]methyl}-2-azabicyclo[3.1.1]heptane;
2-[5-fluoro-2-(pyrimidin-2-yl)benzoyl]-3-{[(5-fluoropyridin-2-yl)oxy]methyl}-2-azabicyclo[3.1.1]heptane;
3-{[(5-fluoropyridin-2-yl)oxy]methyl}-2-[5-methyl-2-(2H-1,2,3-triazol-2-yl)benzoyl]-2-azabicyclo[3.1.1]heptane;
2-[5-(4-fluorophenyl)-2-methyl-1,3-thiazole-4-carbonyl]-3-{[(5-fluoropyridin-2-yl)oxy]methyl}-2-azabicyclo[3.1.1]heptane;
3-{[(5-fluoropyridin-2-yl)oxy]methyl}-2-[5-methyl-2-(pyrimidin-2-yl)benzoyl]-2-azabicyclo[3.1.1]heptane;
Racemic mixture of cis-3-{[(5-fluoropyridin-2-yl)oxy]methyl}-2-[5-methyl-2-(pyrimidin-2-yl)benzoyl]-2-azabicyclo[3.2.1]octane;
Racemic mixture of cis-3-{[(5-fluoropyridin-2-yl)oxy]methyl}-2-(2-methyl-5-phenyl-1,3-thiazole-4-carbonyl)-2-azabicyclo[3.2.1]octane;
Racemic mixture of trans-3-[(4-fluorophenoxy)methyl]-4-methyl-2-[6-methyl-3-(3-methyl-1H-1,2,4-triazol-1-yl)pyridine-2-carbonyl]-2-azabicyclo[3.1.1]heptane;
Racemic mixture of cis-3-[(4-fluorophenoxy)methyl]-4-methyl-2-[2-methyl-5-(1H-1,2,3-triazol-1-yl)-1,3-thiazole-4-carbonyl]-2-azabicyclo[3.1.1]heptane;
Racemic mixture of cis-3-[(4-fluorophenoxy)methyl]-4-methyl-2-[6-methyl-3-(1H-1,2,4-triazol-1-yl)pyridine-2-carbonyl]-2-azabicyclo[3.1.1]heptane;
Racemic mixture of cis-6-fluoro-2-({4-methyl-2-[6-methyl-3-(2H-1,2,3-triazol-2-yl)pyridine-2-carbonyl]-2-azabicyclo[3.1.1]heptan-3-yl}methoxy)-1,3-benzothiazole;
Racemic mixture of cis-3-[(4-fluorophenoxy)methyl]-4-methyl-2-[6-methyl-3-(3-methyl-1H-1,2,4-triazol-1-yl)pyridine-2-carbonyl]-2-azabicyclo[3.1.1]heptane;
Racemic mixture of cis-3-[(4-fluorophenoxy)methyl]-4-methyl-2-[2-methyl-5-(1-methyl-1H-pyrazol-5-yl)-1,3-thiazole-4-carbonyl]-2-azabicyclo[3.1.1]heptane;
Racemic mixture of cis-3-[(4-fluorophenoxy)methyl]-4-methyl-2-[2-methyl-5-(2H-1,2,3-triazol-2-yl)pyrimidine-4-carbonyl]-2-azabicyclo[3.1.1]heptane;
Racemic mixture of cis-3-{[(5-fluoropyrimidin-2-yl)oxy]methyl}-4-methyl-2-[6-methyl-3-(2H-1,2,3-triazol-2-yl)pyridine-2-carbonyl]-2-azabicyclo[3.1.1]heptane;
Racemic mixture of cis-3-{[(5-fluoropyrimidin-2-yl)oxy]methyl}-4-methyl-2-(2-methyl-5-phenyl-1,3-thiazole-4-carbonyl)-2-azabicyclo[3.1.1]heptane;
Racemic mixture of cis-3-[(4-fluorophenoxy)methyl]-4-methyl-2-[5-methyl-2-(4H-1,2,4-triazol-4-yl)benzoyl]-2-azabicyclo[3.1.1]heptane;
Racemic mixture of cis-3-[(4-fluorophenoxy)methyl]-2-{imidazo[1,2-a]pyridine-8-carbonyl}-4-methyl-2-azabicyclo[3.1.1]heptane;
Racemic mixture of cis-3-[(4-fluorophenoxy)methyl]-2-[3-(1H-imidazol-1-yl)-6-methylpyridine-2-carbonyl]-4-methyl-2-azabicyclo[3.1.1]heptane;
Racemic mixture of cis-3-[(4-fluorophenoxy)methyl]-4-methyl-2-{6-methylimidazo[1,2-a]pyrazine-8-carbonyl}-2-azabicyclo[3.1.1]heptane;
Racemic mixture of cis-4-fluoro-N-{[4-methyl-2-[6-methyl-3-(2H-1,2,3-triazol-2-yl)pyridine-2-carbonyl]-2-azabicyclo[3.1.1]heptan-3-yl]methyl}aniline;
Racemic mixture of cis-N-({4-methyl-2-[6-methyl-3-(2H-1,2,3-triazol-2-yl)pyridine-2-carbonyl]-2-azabicyclo[3.1.1]heptan-3-yl}methyl)aniline;
Racemic mixture of cis-N-({4-methyl-2-[1-methyl-4-(pyridin-2-yl)-1H-pyrazole-3-carbonyl]-2-azabicyclo[3.1.1]heptan-3-yl}methyl)-5-(trifluoromethyl)pyrazin-2-amine;
Racemic mixture of cis-N-({4-methyl-2-[6-methyl-3-(2H-1,2,3-triazol-2-yl)pyridine-2-carbonyl]-2-azabicyclo[3.1.1]heptan-3-yl}methyl)-[1,3]thiazolo[4,5-b]pyridin-2-amine;
Racemic mixture of cis-N-({4-methyl-2-[6-methyl-3-(2H-1,2,3-triazol-2-yl)pyridine-2-carbonyl]-2-azabicyclo[3.1.1]heptan-3-yl}methyl)-[1,3]oxazolo[4,5-b]pyridin-2-amine;
Racemic mixture of cis-N-({4-methyl-2-[6-methyl-3-(2H-1,2,3-triazol-2-yl)pyridine-2-carbonyl]-2-azabicyclo[3.1.1]heptan-3-yl}methyl)-5-(trifluoromethyl)-[1,3]thiazolo[5,4-b]pyridin-2-amine;
Racemic mixture of cis-N-({4-methyl-2-[6-methyl-3-(2H-1,2,3-triazol-2-yl)pyridine-2-carbonyl]-2-azabicyclo[3.1.1]heptan-3-yl}methyl)-6-(trifluoromethyl)pyridazin-3-amine; and
Racemic mixture of cis-N-({2-[5-fluoro-2-(2H-1,2,3-triazol-2-yl)benzoyl]-4-methyl-2-azabicyclo[3.1.1]heptan-3-yl}methyl)-6-(trifluoromethyl)pyridazin-3-amine.

Particularly preferred compounds are those which are antagonists of OX1R and/or OX1R/OX2R, as defined herein.

In the case of a discrepancy between the names and structures of any of the compounds disclosed herein, the structures provided should prevail.

Compounds of the invention may be made in accordance with techniques that are well known to those skilled in the art, for example as described hereinafter. Moreover, by utilising the procedures described herein, one of ordinary skill in the art can readily prepare additional compounds that fall within the scope of the present invention claimed herein. The compounds illustrated in the examples are not, however, to be construed as forming the only genus that is considered as the invention. The examples further illustrate details for the preparation of the compounds of the present invention. Those skilled in the art will readily understand that known variations of the conditions and processes of the following preparative procedures can be used to prepare these compounds.

The compounds of the invention may be isolated in the form of their pharmaceutically acceptable salts, such as those described previously herein above.

According to a further aspect of the invention there is provided a process for the preparation of a compound of formula I which process comprises:

(i) for compounds of formula I in which $L^2$ represents —C(=O)—, reaction of a corresponding compound of formula II,

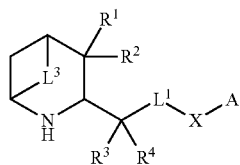

II wherein $L^1$, $L^3$, $R^1$, $R^2$, $R^3$, $R^4$, X and A are as hereinbefore defined, with a compound of formula III,

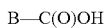   III wherein B is as hereinbefore defined, in the presence of a suitable coupling reagent (e.g. 1,1'-carbonyldiimidazole, N,N-dicyclohexylcarbodiimide, 1-hydroxy-benzotriazole (HOBt), 1-hydroxy-7-aza-benzotriazole (HOAt), (1-[Bis(dimethylamino)methylene]-1H-1,2,3-triazolo[4,5-b]pyridinium 3-oxid hexafluorophosphate (HATU), 2,4,6-Tripropyl-1,3,5,2,4,6-trioxatriphosphorinane-2,4,6-trioxide (T3P), or the like), or, alternatively the —C(O)OH group may first be activated to the corresponding acyl halide (e.g. —C(O)Cl, by treatment with oxalyl chloride, thionyl chloride, phosphorous pentachloride, phosphorous oxychloride, or the like), together with a suitable base such as, $Na_2CO_3$, $K_3PO_4$, $Cs_2CO_3$, NaOH, KOH, $K_2CO_3$, CsF, $Et_3N$, (i-Pr)$_2$NEt, t-BuONa or t-BuOK (or mixtures thereof) in a suitable solvent such as dioxane, toluene, ethanol, dimethylformamide, ethylene glycol dimethyl ether, water, dimethylsulfoxide, acetonitrile, dimethylacetamide, N-methylpyrrolidinone, tetrahydrofuran, dimethoxyethane (DME) or mixtures thereof (preferably a polar aprotic solvent is employed, e.g. dioxane or DME) under standard conditions known to those skilled in the art (e.g. optionally in an inert atmosphere);

(ii) for compounds of formula I in which X represents —O—, reaction of a corresponding compound of formula IVA,

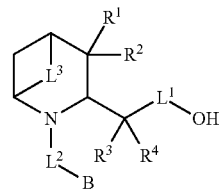

IVA wherein $L^1$, $L^2$, $L^3$, $R^1$, $R^2$, $R^3$, $R^4$ and B are as hereinbefore defined, with a compound of formula V,

   V wherein A is as hereinbefore defined, in the presence of a suitable coupling reagent (e.g. a dialkylazodicarboxylate (or another similar agent as is appropriate for the Mitsunobu reaction) and a triphenylphosphine) under standard conditions known to those skilled in the art (e.g. optionally in an inert atmosphere);

(iii) for compounds of formula I in which X represents —O—, reaction of a corresponding compound of formula IVA, as hereinbefore defined, with a compound of formula VI,

   VI wherein A is as hereinbefore defined and $L^x$ represents a suitable leaving group, such as iodo, bromo, chloro or a sulfonate group (e.g. —OS(O)$_2$CF$_3$, —OS(O)$_2$CH$_3$ or —OS(O)$_2$PhMe) (most preferably $L^x$ represents fluoro or chloro), in the presence of a suitable base such as, $Na_2CO_3$, $K_3PO_4$, $Cs_2CO_3$, NaH, NaOH, KOH, $K_2CO_3$, CsF, $Et_3N$, (i-Pr)$_2$NEt, t-BuONa or t-BuOK (or mixtures thereof) in a suitable solvent such as dioxane, toluene, ethanol, dimethylformamide, ethylene glycol dimethyl ether, water, dimethylsulfoxide, acetonitrile, dimethylacetamide, N-methylpyrrolidinone, tetrahydrofuran, dimethoxyethane (DME) or mixtures thereof (preferably a polar aprotic solvent is employed, e.g. dioxane or DME);

(iv) for compounds of formula I in which X represents —O—, reaction of a corresponding compound of formula VII,

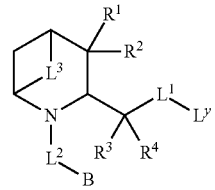

VII wherein $L^1$, $L^2$, $L^3$, $R^1$, $R^2$, $R^3$, $R^4$ and B are as hereinbefore defined and $L^y$ represents a suitable leaving group, e.g. as hereinabove defined in respect of $L^x$, with a compound of formula V as hereinbefore defined, and under conditions as defined above for step (iii);

(v) for compounds of formula I in which X represents —NH—, reaction of a corresponding compound of formula VIII,

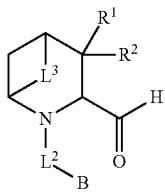

wherein $L^2$, $L^3$, $R^1$, $R^2$, and B are as hereinbefore defined, with a compound of formula IX,

A-NH$_2$   IX wherein A is as hereinbefore defined, under appropriate reaction conditions, for example in "one-pot" procedure in the presence of an appropriate reducing agent, such as a chemoselective reducing agent such as sodium cyanoborohydride or, preferably, sodium triacetoxyborohydride, or the like. Alternatively, such reactions may be performed in two steps, for example a condensation step (in the presence of e.g. a dehydrating agent such as trimethyl orthoformate or MgSO$_4$ or molecular sieves, etc) followed by a reduction step (e.g. by reaction in the presence of a reducing agent such as a chemoselective one mentioned above or NaBH$_4$, AlH$_4$, or the like); or (vi) for compounds of formula I in which X represents —NH—, reaction of a corresponding compound of formula IVB,

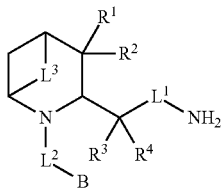

wherein $L^1$, $L^2$, $L^3$, $R^1$, $R^2$, $R^3$, $R^4$ and B are as hereinbefore defined, with a compound of formula VI as hereinbefore defined, in the presence of a suitable base such as, Na$_2$CO$_3$, K$_3$PO$_4$, Cs$_2$CO$_3$, NaH, NaOH, KOH, K$_2$CO$_3$, CsF, Et$_3$N, (i-Pr)$_2$NEt, t-BuONa or t-BuOK (or mixtures thereof) in a suitable solvent such as dioxane, toluene, ethanol, dimethylformamide, ethylene glycol dimethyl ether, water, dimethylsulfoxide, acetonitrile, dimethylacetamide, N-methylpyrrolidinone, tetrahydrofuran, dimethoxyethane (DME) or mixtures thereof (preferably a polar aprotic solvent is employed, e.g. dioxane or DME). This reaction may be performed, for example in the presence of a suitable catalyst system, e.g. a metal (or a salt or complex thereof) such as Pd$_2$(dba)$_3$, PdCl$_2$, Pd(OAc)$_2$, Pd(Ph$_3$P)$_2$Cl$_2$, or Pd(Ph$_3$P)$_4$ (i.e. palladium tetrakistriphenylphosphine), and a ligand such as t-Bu$_3$P, (C$_6$H$_{11}$)$_3$P, Ph$_3$P, AsPh$_3$, P(o-Tol)$_3$, 2-dicyclohexylphosphino-2'-(N,N-dimethylamino)biphenyl, 1,2-bis(diphenylphosphino)-ethane, 2,2'-bis(di-tert-butyl-phosphino)-1,1'-biphenyl, 2,2'-bis(diphenyl-phosphino)-1,1'-binaphthyl, 1,1'-bis(diphenyl-phosphino-ferrocene), 1,3-bis(diphenylphosphino)propane, xantphos, or a mixture thereof, under suitable conditions know to the person skilled in the art, e.g. for a Buchwald-Hartwig Cross Coupling Reaction.

Compounds of formulae II, IVA, IVB, VII and VIII may be prepared by reactions that are analogous to those described herein (particularly in the preparations and Examples), e.g. using one or more of the following specific transformations:

(i) reductions, for example of a carboxylic acid (or ester) to either an aldehyde or an alcohol, using appropriate reducing conditions (e.g. —C(O)OH (or an ester thereof), may be converted to a —C(O)H or —CH$_2$—OH group, using DIBAL and LiAlH$_4$, respectively (or similar chemoselective reducing agents));

(ii) reductions of an aldehyde (—C(O)H) group to an alcohol group (—CH$_2$OH), using appropriate reduction conditions such as those mentioned at point (i) above;

(iii) oxidations, for example of a moiety containing an alcohol group (e.g. —CH$_2$OH) to an aldehyde (e.g. —C(O)H) or of a —S— moiety to a —S(O)— or —S(O)$_2$— moiety (or the reverse reduction reaction), for example in the presence of a suitable oxidising agent, e.g. MnO$_2$ or mcpba or the like;

(iv) reductive amination of an aldehyde and an amine, under appropriate reaction conditions, for example in "one-pot" procedure in the presence of an appropriate reducing agent, such as a chemoselective reducing agent such as sodium cyanoborohydride or, preferably, sodium triacetoxyborohydride, or the like. Alternatively, such reactions may be performed in two steps, for example a condensation step (in the presence of e.g. a dehydrating agent such as trimethyl orthoformate or MgSO$_4$ or molecular sieves, etc.) followed by a reduction step (e.g. by reaction in the presence of a reducing agent such as a chemoselective one mentioned above or NaBH$_4$, AlH$_4$, or the like), for instance the conversion of —NH$_2$ to —N(H)-isopropyl by condensation in the presence of acetone (H$_3$C—C(O)—CH$_3$) followed by reduction in the presence of a reducing agent such as sodium cyanoborohydride (i.e. overall a reductive amination);

(v) formation of an amide or sulfonamide, for example by reaction of a sulfonyl chloride with an amine or by an amide coupling reaction, i.e. the formation of an amide from a carboxylic acid (or ester thereof), for example —C(O)OH (or an ester thereof), may be converted to —C(O)NR$^2$ group, and which reaction may (e.g. for —COOH) be performed in the presence of a suitable coupling reagent (e.g. 1,1'-carbonyldiimidazole, N,N-dicyclohexylcarbodiimide, or the like) or, in the case of an ester (e.g. —C(O)OCH$_3$ or —C(O)OCH$_2$CH$_3$), be performed in the presence of e.g. trimethylaluminium, or, alternatively the —C(O)OH group may first be activated to the corresponding acyl halide (e.g. —C(O)Cl, by treatment with oxalyl chloride, thionyl chloride, phosphorous pentachloride, phosphorous oxychloride, or the like), and, in all cases, the relevant compound is reacted with a compound of formula HNR$^2$, under standard conditions known to those skilled in the art (e.g. optionally in the presence of a suitable solvent, suitable base and/or in an inert atmosphere);

(vi) conversion of a primary amide to a nitrile functional group, for example under dehydration reaction conditions, e.g. in the presence of POCl$_3$, or the like;

(vii) nucleophilic substitution (e.g. aromatic nucleophilic substitution) reactions, where any nucleophile replaces a leaving group, e.g. an amine may replace a —S(O)CH$_3$ leaving group;

(viii) transformation of a methoxy group to a hydroxy group, by reaction in the presence of an appropriate reagent, such as boron fluoride-dimethyl sulfide complex or BBr₃ (e.g. in the presence of a suitable solvent such as dichloromethane);

(ix) alkylation, acylation or sulfonylation reactions, which may be performed in the presence of base and solvent (such as those described hereinbefore);

(x) specific deprotection steps, such as deprotection of an N-Boc protecting group by reaction in the presence of an acid, or, a hydroxy group protected as a silyl ether (e.g. a tert-butyl-dimethylsilyl protecting group) may be deprotected by reaction with a source of fluoride ions, e.g. by employing the reagent tetrabutylammonium fluoride (TBAF);

(xi) hydrogenation of an unsaturated system (e.g. a carbon-carbon double bond) by reduction in the presence of a source of hydrogen and a suitable catalyst (such as a palladium-based catalyst, e.g. Pd/C);

(xii) transformation of a hydroxyalkane into an alkene (a dehydration reaction), by reaction in the presence of an appropriate reagent, such as one which converts the alcohol into a suitable leaving group, optionally together with a base.

The compounds of formula I which contain a 2-azabicyclo[3.1.1]heptane core can be prepared using conventional synthetic methods for example, but not limited to, those which include the routes outlined in Scheme 1 below for the formation of 2-tert-butyl 3-methyl 4-oxo-2-azabicyclo[3.1.1]heptane-2,3-dicarboxylate moiety.

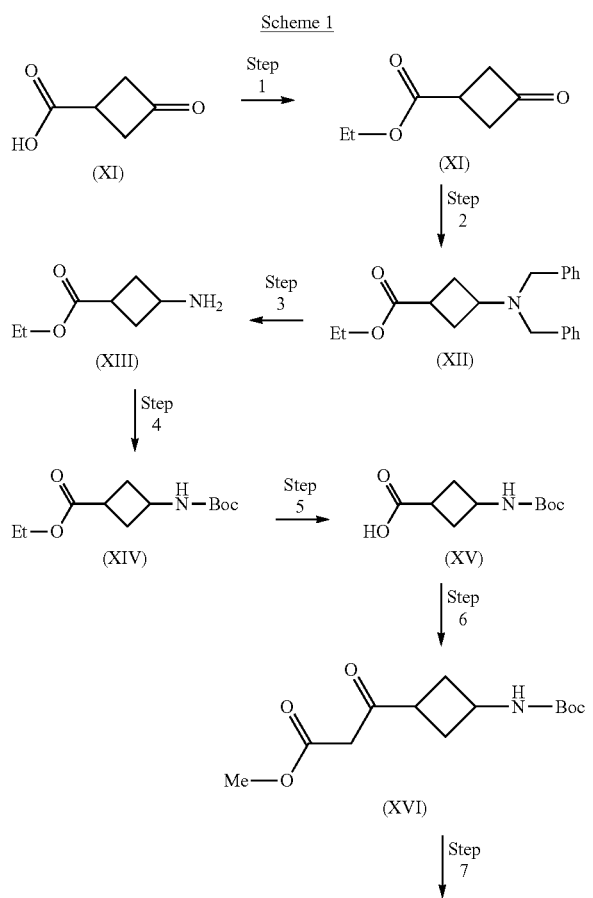

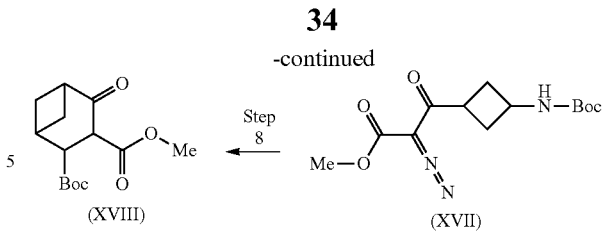

Step 1
Compound of formula XI may be obtained by esterification of a compound of formula X (commercially available from Sigma-Aldrich) under standard literature conditions such as by reaction with triethylorthoacetate in a suitable solvent, such as toluene, under reflux.

Step 2
Compound of formula XII may be obtained by reductive amination and of compound XI with a benzylamine, in a suitable solvent, such as THF, in presence of a reducing agent like Na(AcO)₃BH, Step 3
Compound of formula XIII may be obtained from compound XII by removing the benzyl groups by hydrogenolysis, e.g. using ammonium formate and palladium on carbon, in a suitable solvent such as methanol under reflux.

Step 4
Compound of formula XIV may be obtained by N-protection of compound XIII under standard literature conditions such as by reaction with Di-tert-butyl dicarbonate in a mixture of THF/water, in presence of a suitable base, such as Na₂CO₃, at a temperature around 0° C.

Step 5
Compound of formula XV may be obtained by hydrolysis of a compound of formula XIV in the presence of bases such as lithium or sodium hydroxide.

Step 6
Compound of formula XVI may be obtained by reaction of a compound of formula XV with an acetyl ester derivative, such as Meldrum's acid in the presence of a suitable base, such as DMAP.

Step 7
Compound of formula XVII may be obtained via a diazotransfer reaction starting from a compound of formula XVI in the presence of a suitable base, e.g. triethylamine, carrying out the reaction at a temperature between 0° C. and room temperature.

Step 8
Compound of formula XVIII (2-tert-butyl 3-methyl 4-oxo-2-azabicyclo[3.1.1]heptane-2,3-dicarboxylate) may be obtained by cyclisation of a compound of formula XVII using a suitable catalyst, such as a Rhodium II catalyst, in a suitable solvent, such as toluene, typically at reflux temperature.

The substituents $R^1$ to $R^6$, A and B (or substituents thereon, e.g. defined by $Q^1$ or $Q^2$) in final compounds of the invention or relevant intermediates may be modified one or more times, after or during the processes described above by way of methods that are well known to those skilled in the art. Examples of such methods include substitutions, reductions, oxidations, alkylations, acylations, hydrolyses, esterifications, etherifications, halogenations or nitrations. Such reactions may result in the formation of a symmetric or asymmetric final compound of the invention or intermediate. The precursor groups can be changed to a different such group, or to the groups defined in formula I, at any time during the reaction sequence. For example, in cases in which there is a —CO₂H present, the skilled person will appreciate that at any stage during the synthesis (e.g. the final step), the relevant ester group may be hydrolysed to form a carboxylic acid functional group.

Compounds of the invention may be isolated from their reaction mixtures using conventional techniques (e.g. recrystallisations).

It will be appreciated by those skilled in the art that, in the processes described above and hereinafter, the functional groups of intermediate compounds may need to be protected by protecting groups.

The protection and deprotection of functional groups may take place before or after a reaction in the above-mentioned schemes.

Protecting groups may be removed in accordance with techniques that are well known to those skilled in the art and as described hereinafter. For example, protected compounds/intermediates described herein may be converted chemically to unprotected compounds using standard deprotection techniques.

The type of chemistry involved will dictate the need, and type, of protecting groups as well as the sequence for accomplishing the synthesis.

The use of protecting groups is fully described in "*Protective Groups in Organic Synthesis*", $3^{rd}$ edition, T. W. Greene & P. G. M. Wutz, Wiley-Interscience (1999).

Medical and Pharmaceutical Uses

Compounds of the invention are indicated as pharmaceuticals. According to a further aspect of the invention there is provided a compound of the invention, for use as a pharmaceutical.

For the avoidance of doubt, although compounds of the invention may possess pharmacological activity as such, certain pharmaceutically-acceptable (e.g. "protected") derivatives of compounds of the invention may exist or be prepared which may not possess such activity, but may be administered parenterally or orally and thereafter be metabolised in the body to form compounds of the invention. Such compounds (which may possess some pharmacological activity, provided that such activity is appreciably lower than that of the "active" compounds to which they are metabolised) may therefore be described as "prodrugs" of compounds of the invention.

A "prodrug of a compound of the invention" is as hereinbefore defined, including compounds that form a compound of the invention, in an experimentally-detectable amount, within a predetermined time (e.g. about 1 hour), following oral or parenteral administration. All prodrugs of the compounds of the invention are included within the scope of the invention.

Furthermore, certain compounds of the invention may possess no or minimal pharmacological activity as such, but may be administered parenterally or orally, and thereafter be metabolised in the body to form compounds of the invention that possess pharmacological activity as such. Such compounds (which also includes compounds that may possess some pharmacological activity, but that activity is appreciably lower than that of the "active" compounds of the invention to which they are metabolised), may also be described as "prodrugs".

Thus, the compounds of the invention are useful because they possess pharmacological activity, and/or are metabolised in the body following oral or parenteral administration to form compounds which possess pharmacological activity.

Compounds of the invention may be antagonists of OX1R and/or OX1R/OX2R, for example as may be shown in the tests described below and/or in tests known to the skilled person. Thus, the compounds of the invention may be useful in the treatment of those disorders in an individual in which antagonism of the orexin-1 and/or both the orexin-1 and orexin-2 receptors is desired and/or required. Said antagonist compounds may be described herein as being "active". Compounds are typically considered to be effective as antagonists of OX1R and/or OX1R/OX2R if they exhibit a pKi of at least 6, e.g. when tested using the scintillation proximity assay (SPA) binding assay described herein. Similarly, compounds may be considered to be effective as antagonists of OX1R and/or OX1R/OX2R if they exhibit a fpKi of at least 6, e.g. when tested using the intracellular calcium measurement method described herein.

The term "antagonism" may refer to any measurable blocking or dampening of a biological response by binding to a particular receptor. The blocking or dampening of a biological response may be measured by the binding assays described herein (particularly the intracellular calcium measurement assay), as would be apparent to those skilled in the art. The measurable change may be objective (e.g. measurable by some test or marker, for example in an in vitro or in vivo assay or test, such as one described hereinafter, or otherwise another suitable assay or test known to those skilled in the art) or subjective (e.g. the subject gives an indication of or feels an effect).

The compounds of the invention may also be useful in the treatment of disorders in an individual in which selective antagonism of the orexin-1 receptor is desired and/or required. A compound may be considered to be selective for OX1R (e.g. preferentially selective for OX1R over OX2R) when the antagonistic effect with OX1R is at least 50 times (e.g. at least 100 times) greater than a that with second receptor (e.g. OX2R). Selectivity may similarly be determined using the binding assays described herein (particularly the intracellular calcium measurement assay) for the receptors under consideration. Compounds showing a high degree of selectivity may possess additional advantages in the clinic as their use would be less likely to give rise to biological effects that are associated with antagonism of the second receptor. In the case of compounds that are selective for OX1R over OX2R, such compounds would advantageously be less likely to induce sedation in a subject, which is an effect associated with OX2R antagonism.

Compounds of the invention are thus expected to be useful in the treatment or prevention of a disorder in which orexin-1 and/or orexin-2 receptors are known to play a role and which are characterised by or associated with an overall elevated activity of those receptors. The compounds of the invention are particularly expected to be useful in the treatment or prevention of disorders in which selective antagonism of the orexin-1 receptor is desired and/or required. Such conditions/disorders include substance dependence, addiction, an anxiety disorder, a panic disorder, binge eating, a compulsive disorder, an impulse control disorder, cognitive impairment and Alzheimer's disease.

The compounds of the invention are expected to be particularly effective in the treatment or prevention of substance dependence and addiction. Particular examples that may be mentioned include binge eating, binge drinking, alcohol addiction, nicotine addiction, gambling addiction, and cocaine addiction.

Anxiety disorders that may be treated or prevented using the compounds of the invention include generalized anxiety disorder, specific phobias, panic disorder, agoraphobia, social anxiety disorder, post-traumatic stress disorder, separation anxiety disorder, situational anxiety, obsessive-compulsive disorder, and selective mutism.

Compulsive disorders that may be treated or prevented using the compounds of the invention include obsessive-compulsive disorders, and disorders on the OCD spectrum, such as obsessive body dysmorphic disorder, delusional disorder, eating disorders (including anorexia nervosa, bulimia nervosa and binge eating disorder) hypochondriasis, impulse control disorders in general, olfactory reference syndrome, paraphilias, pathological gambling, pica, non-paraphilic sexual addictions, Tourette's syndrome, body-focused repetitive behaviours (such as trichotillomania), Asperger's syndrome (autism spectrum), social phobia and compulsive hoarding. The compounds of the invention may also be useful in treating or preventing the compulsive and/or impulsive behaviour associated with movement disorders such as Parkinson's disease and Alzheimer's disease.

Impulse control disorders that may be treated or prevented using the compounds of the invention include sexual compulsion (e.g. sex addiction), internet addiction, compulsive shopping, pyromania, intermittent explosive disorder, kleptomania (e.g. compulsive shop-lifting) and attention deficit hyperactivity disorder (ADHD).

Cognitive impairments that may be treated or prevented using the compounds of the invention include deficits in overall intelligence, deficits in cognitive abilities (such as learning disorders, dyslexia, dyscalculia, and the like), or neuropsychological deficits (such as in attention, working memory or executive function).

Particular patient groups that may be mentioned include those which have co-morbid mood and/or anxiety disorder, or substance abuse disorder which precludes the use of existing therapies, such as Vyvanse.

Compounds of the invention are indicated both in the therapeutic and/or prophylactic treatment of the above-mentioned conditions.

According to a further aspect of the present invention, there is provided a method of treating or preventing of a disease or condition (e.g. substance dependence or addiction) in which antagonism of the orexin-1 and/or orexin-2 receptors (e.g. selective antagonism of the orexin-1 receptor) is desired and/or required, which method comprises administration of a therapeutically effective amount of a compound of the invention, as hereinbefore defined to a patient suffering from, or susceptible to, such a condition.

"Patients" include mammalian (including human) patients. Hence, the method of treatment discussed above may include the treatment of a human or animal body.

The term "effective amount" refers to an amount of a compound, which confers a therapeutic effect on the treated patient. The effect may be objective (e.g. measurable by some test or marker) or subjective (e.g. the subject gives an indication of or feels an effect).

Compounds of the invention may be administered orally, intravenously, subcutaneously, buccally, rectally, dermally, nasally, tracheally, bronchially, sublingually, by any other parenteral route or via inhalation, in a pharmaceutically acceptable dosage form.

Compounds of the invention may be administered alone, but are preferably administered by way of known pharmaceutical formulations, including tablets, capsules or elixirs for oral administration, suppositories for rectal administration, sterile solutions or suspensions for parenteral or intramuscular administration, and the like. The type of pharmaceutical formulation may be selected with due regard to the intended route of administration and standard pharmaceutical practice. Such pharmaceutically acceptable carriers may be chemically inert to the active compounds and may have no detrimental side effects or toxicity under the conditions of use.

Such formulations may be prepared in accordance with standard and/or accepted pharmaceutical practice. Otherwise, the preparation of suitable formulations may be achieved non-inventively by the skilled person using routine techniques and/or in accordance with standard and/or accepted pharmaceutical practice.

According to a further aspect of the invention there is thus provided a pharmaceutical formulation including a compound of the invention, as hereinbefore defined, in admixture with a pharmaceutically acceptable adjuvant, diluent and/or carrier.

Depending on e.g. potency and physical characteristics of the compound of the invention (i.e. active ingredient), pharmaceutical formulations that may be mentioned include those in which the active ingredient is present in at least 1% (or at least 10%, at least 30% or at least 50%) by weight. That is, the ratio of active ingredient to the other components (i.e. the addition of adjuvant, diluent and carrier) of the pharmaceutical composition is at least 1:99 (or at least 10:90, at least 30:70 or at least 50:50) by weight.

The amount of compound of the invention in the formulation will depend on the severity of the condition, and on the patient, to be treated, as well as the compound(s) which is/are employed, but may be determined non-inventively by the skilled person.

The invention further provides a process for the preparation of a pharmaceutical formulation, as hereinbefore defined, which process comprises bringing into association a compound of the invention, as hereinbefore defined, or a pharmaceutically acceptable salt, solvate or prodrug thereof with a pharmaceutically-acceptable adjuvant, diluent or carrier.

Compounds of the invention may also be combined with other therapeutic agents that are antagonists of the orexin-1 and/or orexin-2 receptors (e.g. selective antagonism of the orexin-1 receptor) and/or useful in the treatment or prevention of substance dependence, addiction, an anxiety disorder, a panic disorder, binge eating, a compulsive disorder, an impulse control disorder, cognitive impairment or Alzheimer's disease. Compounds of the invention may also be combined with other therapies.

According to a further aspect of the invention, there is provided a combination product comprising:
(A) a compound of the invention, as hereinbefore defined; and
(B) another therapeutic agent that is useful in the treatment of a disease or disorder in which antagonism of the orexin-1 and/or orexin-2 receptors is desired and/or required,
wherein each of components (A) and (B) is formulated in admixture with a pharmaceutically-acceptable adjuvant, diluent or carrier.

Such combination products provide for the administration of a compound of the invention in conjunction with the other therapeutic agent, and may thus be presented either as separate formulations, wherein at least one of those formulations comprises a compound of the invention, and at least one comprises the other therapeutic agent, or may be presented (i.e. formulated) as a combined preparation (i.e. presented as a single formulation including a compound of the invention and the other therapeutic agent).

Thus, there is further provided:
(1) a pharmaceutical formulation including a compound of the invention, as hereinbefore defined, another therapeutic agent that is useful in the treatment of a disease or disorder in which antagonism of the orexin-1 and/or orexin-2 receptors is desired and/or required, and a pharmaceutically-acceptable adjuvant, diluent or carrier; and (2) a kit of parts comprising components:
  (a) a pharmaceutical formulation including a compound of the invention, as hereinbefore defined, in admixture with a pharmaceutically-acceptable adjuvant, diluent or carrier; and
  (b) a pharmaceutical formulation including another therapeutic that is useful in the treatment of a disease or disorder in which antagonism of the orexin-1 and/or orexin-2 receptors is desired and/or required in admixture with a pharmaceutically-acceptable adjuvant, diluent or carrier, which components (a) and (b) are each provided in a form that is suitable for administration in conjunction with the other.

The invention further provides a process for the preparation of a combination product as hereinbefore defined, which process comprises bringing into association a compound of the invention, as hereinbefore defined, or a pharmaceutically acceptable salt, solvate or prodrug thereof with the other therapeutic agent that is useful in the treatment of a disease or disorder in which antagonism of the orexin-1 and/or orexin-2 receptors is desired and/or required, and at least one pharmaceutically-acceptable adjuvant, diluent or carrier.

By "bringing into association", we mean that the two components are rendered suitable for administration in conjunction with each other.

Thus, in relation to the process for the preparation of a kit of parts as hereinbefore defined, by bringing the two components "into association with" each other, we include that the two components of the kit of parts may be:
(i) provided as separate formulations (i.e. independently of one another), which are subsequently brought together for use in conjunction with each other in combination therapy; or
(ii) packaged and presented together as separate components of a "combination pack" for use in conjunction with each other in combination therapy.

Depending on the disorder, and the patient, to be treated, as well as the route of administration, compounds of the invention may be administered at varying therapeutically effective doses to a patient in need thereof. However, the dose administered to a mammal, particularly a human, in the context of the present invention should be sufficient to effect a therapeutic response in the mammal over a reasonable timeframe. One skilled in the art will recognize that the selection of the exact dose and composition and the most appropriate delivery regimen will also be influenced by inter alia the pharmacological properties of the formulation, the nature and severity of the condition being treated, and the physical condition and mental acuity of the recipient, as well as the potency of the specific compound, the age, condition, body weight, sex and response of the patient to be treated, and the stage/severity of the disease.

Administration may be continuous or intermittent (e.g. by bolus injection). The dosage may also be determined by the timing and frequency of administration. In the case of oral or parenteral administration the dosage can vary from about 0.01 mg to about 2000 mg per day of a compound of the invention.

In any event, the medical practitioner, or other skilled person, will be able to determine routinely the actual dosage, which will be most suitable for an individual patient. The above-mentioned dosages are exemplary of the average case; there can, of course, be individual instances where higher or lower dosage ranges are merited, and such are within the scope of this invention.

Compounds of the invention may also have the advantage that they may be more efficacious than, be less toxic than, be longer acting than, be more potent than, produce fewer side effects than, be more easily absorbed than, and/or have a better pharmacokinetic profile (e.g. higher oral bioavailability and/or lower clearance) than, and/or have other useful pharmacological, physical, or chemical properties over, compounds known in the prior art, whether for use in the above-stated indications or otherwise.

It is also commonly accepted (free drug hypothesis) that unbound or free drug concentration at the site of action is responsible for pharmacological activity in vivo at steady state and, in the absence of active transport, the free drug concentration is the same in any biomembrane.

For drugs with an intended action in the central nervous system (CNS), the estimation of unbound fraction of drugs in brain has become essential for the evaluation and interpretation of the pharmacokinetics and pharmacodynamics of new central nervous system drug candidates.

For the above reasons, the total brain concentration (C brain) measured in vivo experiments, is corrected for the fraction of drug unbound determined by in vitro experiments to obtain an estimate of the brain unbound concentration (Cu, brain). Beside their activity as orexin antagonists, compounds of the present invention provide further advantageous pharmacokinetic properties such as adequate free fraction in brain, as is shown in the Examples.

Biological Test Methods
Scintillation Proximity Assay (SPA) Binding Assays

CHO cells stably transfected with human Orexin type 1 receptors (CHO-hOX$_1$) or HEK-293 cells transiently transfected with human Orexin type 2 receptors (HEK-hOX$_2$) were collected after 16 h induction with 5 mM sodium butyrate. The cell pellets were re-suspended, homogenized in 15 mM Tris/HCl pH=7.5, 1 mM EGTA, 0.3 mM EDTA, 2 mM MgCl$_2$, protease inhibitors and centrifuged at 40,000 g (20 min, 4° C.). After re-suspension, homogenization and centrifugation as above, the final pellets were re-suspended in 75 mM Tris/HCl pH=7.5, 1 mM EGTA, 0.3 mM EDTA, 12.5 mM MgCl$_2$, 250 mM Sucrose, protease inhibitors, divided into aliquots and frozen down at −80° C.

Compounds of invention were serially diluted in neat DMSO at 100-fold concentrations (1% DMSO final in the assay) and 2 µl/well were plated into 96-well Isoplates (Perkin Elmer).

CHO-hOX$_1$ cell membranes (6 µg ml$^{-1}$) or HEK-hOX$_2$ membranes (8 µg ml$^{-1}$) were pre-coupled with 1.0 mg ml$^{-1}$ of Wheatgerm Agglutinin-coated Yttrium Silicate (YSi-WGA) SPA beads (Perkin Elmer) in buffer containing 25 mM HEPES pH=7.4, 1 mM CaCl$_2$), 5 mM MgCl$_2$, 0.01% (w/v) BSA, 0.02% (w/v) Pluronic F-127 by shaking at room temperature for 2.5-3 h.

The binding was performed in a final volume of 200 µl. 100 µl of hOX$_1$ or hOX$_2$ beads-membranes suspension were added to 100 µl of [$^3$H]SB-674042 or [$^3$H]EMPA solutions (radioligand concentration 2 nM final in the assay), into the 96-well Isoplates containing the 2 µl/well of compounds to be tested. Nonspecific binding was measured in the presence of 1 µM Almorexant. Assay plates were then incubated at room temperature for 3 h before being counted in a Microbeta scintillation counter (PerkinElmer).

Data were analysed by non-linear regression analysis using XLfit Software. The pKi was calculated from the IC$_{50}$ using the Cheng-Prusoff correction: $pKi=IC_{50}/(1+([L]/K_D))$ where [L] is the radioligand concentration in the displacement assay, and $K_D$ is the dissociation constant of the radioligand as calculated from previous saturation binding experiments which were performed similarly to the competition binding experiments using increasing radioligand concentrations.

Intracellular Calcium Measurement

Intracellular calcium increase was measured by using FLIPR-384 (Molecular Devices). CHO-hOX$_1$ and CHO-hOX$_2$ cells were seeded into black walled clear-bottom 384-well plates at a density of 8,000 cells/well in F12K medium supplemented with 10% heat-inactivated foetal bovine serum and cultured overnight. Cells were then washed with assay buffer (20 mM HEPES, 145 mM NaCl, 5 mM KCl, 5.5 mM D-(+)-glucose, 1 mM MgCl$_2$ and 2 mM CaCl$_2$), pH 7.4) containing 2.5 mM probenecid and incubated at 37° C. for 60 min in assay buffer containing 2.5 mM probenecid, 0.01% (w/v) Pluronic F-127 and 1 μM of the calcium dye Fluo-4 AM. After a further washing step with assay buffer containing 2.5 mM probenecid plates were the placed into FLIPR to monitor cell fluorescence ($\lambda_{ex}$=488 nm, $\lambda_{em}$=510-570 nm).

Compounds of invention were serially diluted in neat DMSO at 200-fold concentrations (0.5% DMSO final in the assay), plated into 384-well plates and then diluted with assay buffer containing 0.05% Pluronic F-127 to reach 4 times the final assay concentration (4×, 2% DMSO).

A dual read-out FLIPR protocol was applied allowing for antagonist characterization. In the first, compound solution was added and the ability to increase intracellular calcium levels with respect to the agonist standard Orexin-A was monitored. After a 15 min compound incubation, a second addition containing Orexin-A at EC$_{80}$ concentration (concentration producing 80% of the maximal response) follows. Inhibition of the agonist evoked signal indicates antagonist activity of the compound and allows for the calculation of the compounds IC$_{50}$ (concentration of the antagonist required for 50% inhibition of the agonist effect).

A CRC (Concentration-response curves) of Orexin-A was tested in each experiment to estimate the EC$_{50}$ (concentration of the agonist needed to produce 50% of the maximum response) value to be used for functional pKi calculation and to calculate the EC$_{80}$ (EC$_{50}$×4).

Orexin-A CRCs were analysed by using GraphPad Prism5 Software to estimate EC$_{50}$ whereas antagonist inhibitory curves were analysed by using XLfit Software. Curve fitting and EC$_{50}$/IC$_{50}$ estimations were carried out using a four-parameter logistic model. In the case of antagonist activity, an estimation of the functional pKi ($-\log_{10}$Ki) can be calculated from the IC$_{50}$ using the Cheng-Prusoff correction: functional ki=$-\log$ (IC$_{50}$/1+([A]/EC$_{50}$)) where [A] is the Orexin-A concentration (EC$_{80}$) in the inhibition assay.

EXAMPLES

The invention is further illustrated by the following non-limiting examples.

In the procedures that follow, after each starting material, reference to a Preparation or Example by number is typically provided. This is provided merely for assistance to the skilled chemist. The starting material may not necessarily have been prepared from the batch referred to.

Where reference is made to the use of a "similar or analogous or as" procedure, as will be appreciated by those skilled in the art, such procedure may involve minor variation, for example reaction temperature, reagent/solvent amount, reaction time, work-up conditions or chromatographic purification conditions.

All temperatures refer to ° C.

Proton Magnetic Resonance (NMR) spectra may be typically recorded either on Varian instruments at 400 or 500 MHz, or on a Bruker instrument at 400 MHz. Chemical shifts are expressed in parts of million (ppm, δ units). Chemical shifts are reported in ppm downfield (δ) from Me$_4$Si, used as internal standard, and are typically assigned as singlets (s), broad singlets (br.s.), doublets (d), doublets of doublets (dd), doublets of doublets of doublets (ddd), doublets of triplets (dt), triplets (t), triplets of doublets (td), quartets (q), or multiplets (m).

LCMS may be recorded under the following conditions:

DAD chromatographic traces, mass chromatograms and mass spectra may be taken on UPLC/PDA/MS Acquity™ system coupled with Micromass ZQ™ or Waters SQD single quadrupole mass spectrometer operated in positive and/or negative ES ionisation mode. The QC methods used were two, one operated under low pH conditions and another one operated under high pH conditions. Details of the method operated under low pH conditions were: column, Acquity BEH C$_{18}$, 1.7 μm, 2.1×50 mm or Acquity CSH C$_{18}$, 1.7 μm, 2.1×50 mm, the temperature column was 40° C.; mobile phase solvent A was milliQ water+0.1% HCOOH, mobile phase solvent B MeCN+0.1% HCOOH. The flow rate was 1 ml/min. The gradient table was t=0 min 97% A-3% B, t=1.5 min 0.1% A-99.9% B, t=1.9 min 0.1% A-99.9% B and t=2 min 97% A-3% B. The UV detection range was 210-350 nm and the ES$^+$/ES$^-$ range was 100-1000 amu. Details of the method operated under high pH conditions were the same of those listed above for the low pH method apart from: column Acquity BEH C18, 1.7 μm, 2.1×50 mm; mobile phase solvent A was 10 mM aqueous solution of NH$_4$HCO$_3$ adjusted to pH=10 with ammonia, mobile phase solvent B MeCN.

Semipreparative mass directed autopurifications (MDAP) were carried out using Waters Fractionlynx™ systems operated under low or high pH chromatographic conditions. The stationary phases used were, XTerra C18, XBridge C18, Sunfire C18, XSelect C18, Gemini AXIA C18. The length of the columns was 5, 10 or 15 cm, while the internal diameter was 19, 21 or 30 mm. The particle size of the stationary phases was 5 or 10 μm. The purifications were carried out using low pH or high pH chromatographic conditions. The mobile phase solvent composition was the same used for QC analysis. The combinations stationary/mobile phases used were: XTerra, XBridge, Sunfire, XSelect—low pH mobile phases and XTerra, XBridge, Gemini AXIA—high pH mobile phases. All the purifications were carried out with the column kept at room T. The flow rate used was 17 or 20 ml/min for columns of internal diameter 19 or 21 mm and 40 or 43 ml/min for columns of internal diameter 30 mm. The trigger for the collection of the target species was the presence of the target m/z ratio value in the TIC MS signal. The gradient timetable was customised on the Rt behaviour of the target species.

Purification may also be performed using Biotage® Isolera or Biotage® SP1 flash chromatography systems, these instruments work with Biotage® KP-SIL cartridges, Biotage® KP-NH cartidges or Biotage® KP-C18 cartridges.

The order of compounds obtained from a chiral separation is given based on the order of elution from the chiral column. This means that when a racemate is resolved into single enantiomers, the terms "Enantiomer 1" or "Enantiomer 2", as reported in the descriptions, refer to "first eluted" or "second eluted" respectively. When a mixture of diastereoisomers is purified via chiral HPLC to separate single enantiomers for each diastereoisomer of the mixture, the order is given based on the order of elution. In this case the indication of relative stereochemistry is determined by NMR analyses and the terms "Enantiomer 1" or "Enantiomer 2", as reported in the descriptions, refer to "first eluted" or "second eluted" respectively for each diastereomer.

Relative stereochemistry "cis" is represented by using the bold highlight of the bonds, while the "trans" relative stereochemistry is represented by using bold and dotted highlight of the bonds.

Unless otherwise stated, all reactions are typically performed under inert atmosphere (for example under Nitrogen).

The following abbreviations are used in the text:
EtOAc, AcOEt, EA=ethyl acetate,
Et$_2$O=diethyl ether,
MeOH=methanol;
THF=tetrahydrofuran,
Tlc=thin layer chromatography on silica plates, and dried refers to a solution dried over anhydrous sodium sulphate,
r.t. (RT)=room temperature,
DMSO=dimethyl sulfoxide;
DMF=N,N'-dimethylformamide,
DCM=dichloromethane,
EtOH=ethanol,
RP=reverse phase
FA=formic acid
DCE=dichloroethane,
DME=1,2-Dimethoxyethane,
Cy, cHex=cyclohexane,
TEA=triethylamine,
DIPEA=N,N-Diisopropylethylamine,
Boc$_2$O=Di-tert-butyl dicarbonate;
TFA=trifluoroacetic acid,
DIAD=Diisopropyl azodicarboxylate,
HATU=1-[Bis(dimethylamino)methylene]-1H-1,2,3-triazolo[4,5-b]pyridinium 3-oxid hexafluorophosphate,
DAST=Diethylaminosulfur trifluoride,
TPP=triphenylphosphine,
AcOH=acetic acid,
LAH=Lithium aluminum hydride,
T3P=Propylphosphonic anhydride,
SCX Cartridge=Strong Cation Exchange Cartridge.
FC==Flash chromatography
O/N=overnight
TBTU=O-(Benzotriazol-1-yl)-N,N,N',N'-tetramethyluronium tetrafluoroborate
BINAP=(±)-2,2'-Bis(diphenylphosphino)-1,1'-binaphthalene
DavePhos=2-Dicyclohexylphosphino-2'-(N,N-dimethylamino)biphenyl
Pd$_2$(dba)$_3$=Tris(dibenzylideneacetone)dipalladium (0)
MTBE=tert-butyl methylether Preparation 1: ethyl 3-oxocyclobutane-1-carboxylate

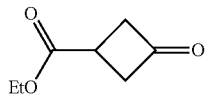

Triethyl orthoacetate (95 mL, 516 mmol) was added to a solution of 3-oxocyclobutane-1-carboxylic acid (20 g, 172 mmol) in toluene (400 mL) and the reaction was refluxed for 6 h. The reaction mixture was cooled down to RT, quenched with a 1 N solution of HCl (100 mL×2) and the layers were separated. The organic phase was washed with s.s. of NaHCO$_3$ (100 mL) and Brine (100 mL). HCl and NaHCO$_3$ aqueous phases were back-extracted several times with DCM until complete disappearance of the desired product (check by TLC, Cy/EtOAC 8/2, Ninhydrin). Combined organics were dried over Na$_2$SO$_4$, filtered and concentrated under vacuum affording ethyl 3-oxocyclobutane-1-carboxylate (p1, 23.3 g) as yellow oil that was used as crude without further purification.

NMR ($^1$H, Chloroform-d): δ 4.24 (q, 1H) 3.39-3.50 (m, 2H) 3.18-3.37 (m, 3H) 1.29-1.36 (m, 3H)

Preparation 2: ethyl 3-(dibenzylamino)cyclobutane-1-carboxylate

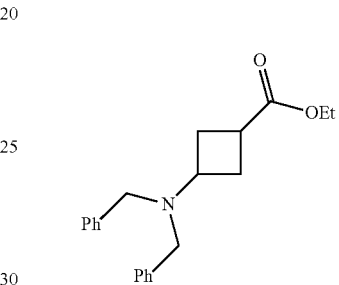

A mixture of ethyl 3-oxocyclobutane-1-carboxylate (p1, 23.3 g, 164 mmol), Dibenzylamine (35 mL, 180 mmol), Sodium triacetoxyborohydride (70 g, 328 mmol) and AcOH (18.8 mL, 328 mmol) in THF dry (230 mL) was stirred at RT under nitrogen overnight. THF was partially concentrated (until ~100 mL) and the residue was diluted with AcOEt; the resulting solution was washed with NaHCO$_3$ ss, and brine. Aqueous phase was basified to pH 7-8 with solid NaHCO$_3$ and extracted with EtOAC. Combined organics were dried over Na$_2$SO$_4$, filtered and evaporated to give ethyl 3-(dibenzylamino)cyclobutane-1-carboxylate (p2, 55 g), that was used as such in the next step.

MS (m/z): 324.3 [MH]+.

Preparation 3: ethyl 3-aminocyclobutane-1-carboxylate

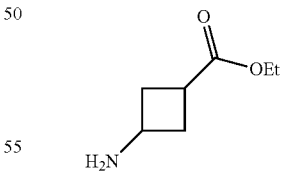

Ethyl 3-aminocyclobutane-1-carboxylate (p2, 55 g, 170 mmol), ammonium formate (54 g, 850 mmol) and Pd(OH)$_2$ (5.5 g) were suspended in MeOH (360 mL) and the reaction mixture was stirred at reflux for 1 h. The mixture was cooled down to RT, filtered through a pad of Celite and concentrated under reduced pressure to afford ethyl 3-aminocyclobutane-1-carboxylate (p3, 23.5 g) as white solid. Presence of ammonium formate detected, but material was used as such in the next step.

MS (m/z): 144.1 [MH]$^+$.

Preparation 4: ethyl 3-{[(tert-butoxy)carbonyl]amino}cyclobutane-1-carboxylate

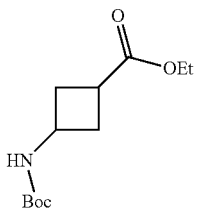 [SMILES: CCOC(=O)C1CC(NC(=O)OC(C)(C)C)C1]

Ditert-butyl dicarbonate (45 g, 197 mmol) was added portionwise to a solution of ethyl 3-aminocyclobutane-1-carboxylate (p3, 23.5 g, 164 mmol) and TEA (68.5 mL, 492 mmol) in THF dry (400 mL) at RT under nitrogen. The resulting mixture was stirred at RT overnight. The mixture was concentrated under vacuum, diluted with DCM and washed with s.s. of NaHCO$_3$. Then the organic phase was washed with 5% solution of KHSO$_4$, then dried, filtered and concentrated under vacuum affording ethyl 3-{[(tert-butoxy)carbonyl]amino}cyclobutane-1-carboxylate (p4, 45.5 g) as yellow oil that was used in the next step without further purification.

NMR ($^1$H, Chloroform-d): δ 4.11-4.18 (m, 1H) 4.04-4.23 (m, 4H) 2.72-2.82 (m, 1H) 2.57-2.68 (m, 2H) 2.04-2.15 (m, 2H) 1.42-1.50 (m, 9H) 1.24-1.30 (m, 2H).

Preparation 5: 3-{[(tert-butoxy)carbonyl]amino}cyclobutane-1-carboxylic acid

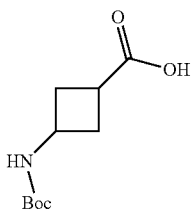 [SMILES: CC(C)(C)OC(=O)NC1CC(C(=O)O)C1]

A mixture of ethyl 3-{[(tert-butoxy)carbonyl]amino}cyclobutane-1-carboxylate (p4, 45.5 g, 164 mmol) and LiOH.H$_2$O (13.8 g, 328 mmol) in THF (350 mL) and water (350 mL) was stirred at RT overnight. Then the mixture was heated to 55° C. and stirred at that temperature for 24 hrs. Still presence of starting material detected, therefore volatiles were removed under reduced pressure, THF/MeOH (150 mL/50 mL) was added and the mixture stirred at 55° C. for further 3 hrs. Organic phase was evaporated, the aqueous phase was extracted with DCM and the DCM was discarded. The aqueous mixture was acidified with a 2 M solution of citric acid until pH 3 and was extracted with DCM (×3). Combined organics were dried and concentrated affording 3-{[(tert-butoxy)carbonyl]amino}cyclobutane-1-carboxylic acid (p5, 30.3 g)

NMR ($^1$H, DMSO-d6): δ ppm 12.04 (br. s., 1H) 7.18 (br. s., 1H) 7.13 (d, 1H) 3.84 (d, 1H) 2.59-2.67 (m, 1H) 2.33 (m, 2H) 2.18-2.18 (m, 1H) 1.95-2.07 (m, 2H) 1.33-1.40 (m, 2H)

Preparation 6: methyl 3-(3-{[(tert-butoxy)carbonyl]amino}cyclobutyl)-3-oxopropanoate

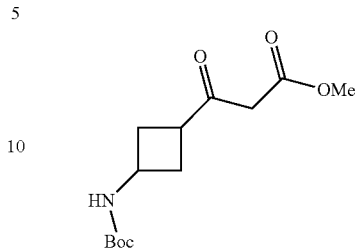

EDC.HCl (37.8 g, 197.4 mmol) was added slowly at 0° C. to a solution of 3-{[(tert-butoxy)carbonyl]amino}cyclobutane-1-carboxylic acid (p5, 30.3 g, 141 mmol), DMAP (25.8 g, 211.5 mmol) and Meldrum's acid (22.4 g, 155.1 mmol) in DCM dry (350 mL) under nitrogen. The mixture was stirred at RT for 2.5 h. The mixture was quenched with 5% solution of KHSO$_4$ until pH ~3. Phases were separated and the organic phase was washed with 5% solution of KHSO$_4$, then dried over Na$_2$SO$_4$, filtered and concentrated under vacuum to afford a dark brown solid. The crude was taken up with MeOH (350 mL) and stirred at reflux (70° C.) for 2 h. The reaction was cooled down to RT and concentrated under vacuum affording methyl 3-(3-{[(tert-butoxy)carbonyl]amino}cyclobutyl)-3-oxopropanoate (p6, 39 g) as brown solid.

NMR ($^1$H, Chloroform-d): δ 4.70 (br. s., 1H) 4.13 (br. s., 1H) 3.72-3.77 (m, 2H) 3.49-3.49 (m, 1H) 3.41-3.46 (m, 2H) 3.00-3.13 (m, 1H) 2.51-2.65 (m, 2H) 2.03-2.14 (m, 2H) 1.40-1.50 (m, 6H).

Preparation 7: methyl 3-(3-{[(tert-butoxy)carbonyl]amino}cyclobutyl)-2-diazo-3-oxopropanoate

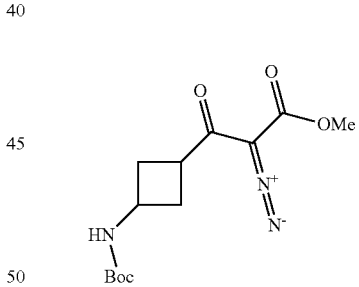

Methyl 3-(3-{[(tert-butoxy)carbonyl]amino}cyclobutyl)-3-oxopropanoate (p6, 39 g, 141 mmol) was dissolved in MeCN dry (500 mL) at 0° C. under nitrogen, then 4-acetamidobenzene-1-sulfonyl azide (37.2 g, 155 mmol) was added. TEA (59 mL, 423 mmol) was added dropwise and the solution turned into a suspension in 10 min. The resulting mixture was allowed to reach RT and stirred for 1.5 h. The mixture was filtered washing with MeCN and concentrated under vacuum. The residue was suspended in DCM, filtered and the filtrate was purified by a pad of silica using Cy/EtOAc 7:3 as eluent. The product was concentrated under vacuum to afford methyl 3-(3-{[(tert-butoxy)carbonyl]amino}cyclobutyl)-2-diazo-3-oxopropanoate (p7, 35.3 g) as yellow solid.

MS (m/z): 298.3 [MH]$^+$.

Preparation 8: 2-tert-butyl 3-methyl 4-oxo-2-azabicyclo[3.1.1]heptane-2,3-dicarboxylate

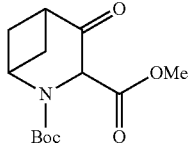 [SMILES: COC(=O)C1C(=O)C2CC(C2)N1C(=O)OC(C)(C)C]

Methyl 3-(3-{[(tert-butoxy)carbonyl]amino}cyclobutyl)-2-diazo-3-oxopropanoate (p7, 35.3 g, 118.7 mmol) was dissolved in toluene dry (400 mL) under nitrogen, and Rhodium(II)acetate dimer (681 mg, 1.54 mmol) was added, and the mixture was immediately stirred in a preheated bath at 90° C. The mixture immediately developed some bubbling, which stopped after 10 minutes. Therefore it was cooled down to RT and the catalyst was filtered off. The filtrate was evaporated affording a green oil that was purified by a pad of silica (eluent DCM/AcOEt 95:5) affording 2-tert-butyl 3-methyl 4-oxo-2-azabicyclo[3.1.1]heptane-2,3-dicarboxylate (p8, 21.5 g) as yellow solid.

NMR ($^1$H, Chloroform-d): δ 4.94-5.07 (m, 2H) 3.85 (s, 3H) 3.14 (q, 1H) 2.64-2.81 (m, 2H) 2.24-2.37 (m, 1H) 1.89 (dd, 1H) 1.40-1.52 (m, 9H)

Preparation 9: CIS/TRANS 3-(hydroxymethyl)-2-azabicyclo[3.1.1]heptan-4-ol

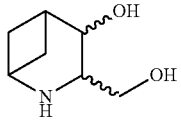

Step a:

2-tert-butyl 3-methyl 4-oxo-2-azabicyclo[3.1.1]heptane-2,3-dicarboxylate (p8, 3 g, 11.14 mmol) was dissolved in THF/MeOH (25/5 mL) and NaBH$_4$ (2.5 g, 66.84 mmol) was added portion wise and then the mixture was stirred at RT for 4 hrs. The reaction was quenched with H$_2$O and volatiles were removed under vacuum. pH was adjusted to 7 with 1N HCl, EtOAc was added and the product was extracted several times. The organic solvent was concentrated under vacuum affording CIS/TRANS tert-butyl 4-hydroxy-3-(hydroxymethyl)-2-azabicyclo[3.1.1]heptane-2-carboxylate (Int. a, 2.7 g) which was used as such in the next step Step b:

Int a (2.39 g, 9.82 mmol) was dissolved in DCM (16 mL) and TFA (4 mL) was added.

The mixture was stirred at RT for 3 hrs. Volatiles were removed under vacuum, the residue was charged on SCX, eluting with 1N NH$_3$ in MeOH affording CIS/TRANS 3-(hydroxymethyl)-2-azabicyclo[3.1.1]heptan-4-ol (p9, 1.4 g, mixture of cis and trans diastereoisomers) that was used as such in the next step.

MS (m/z): 143.9 [MH]$^+$.

Preparation 10: CIS/TRANS 2-tert-butyl 3-methyl 4-hydroxy-2-azabicyclo[3.1.1]heptane-2,3-dicarboxylate

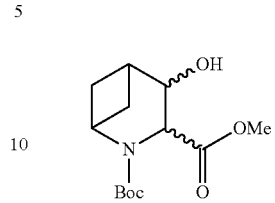

To a cooled solution of 2-tert-butyl 3-methyl 4-oxo-2-azabicyclo[3.1.1]heptane-2,3-dicarboxylate (p8, 5 g, 18.56 mmol) in MeOH (120 mL) at 0° C. NaBH$_4$ (1.4 g, 37.13 mmol) was added portionwise. The reaction was left to stir at RT for 2 h, cooled at 0° C. and HCl 1 N was added (50 mL). The mixture was diluted with water (200 mL) and extracted with DCM (5×50 mL). The organic phase was washed with Brine dried over Na$_2$SO$_4$, filtered and concentrated under vacuum affording CIS/TRANS 2-tert-butyl 3-methyl 4-hydroxy-2-azabicyclo[3.1.1]heptane-2,3-dicarboxylate (p10, 4.65 g, y=92%, mixture of cis and trans diastereoisomers) as colourless oil that was used in the next step as such.

NMR ($^1$H, Chloroform-d): δ 5.31-5.34 (m, 1H), 4.33-4.50 (m, 1H), 4.33-4.90 (m, 3H), 4.33-4.53 (m, 1H), 3.81 (s, 3H), 2.56-2.66 (m, 1H), 2.19-2.44 (m, 3H), 2.01-2.15 (m, 1H), 1.43 (br. s., 9H)

Preparation 11 and 12: CIS/TRANS 2-tert-butyl 3-methyl 4-[(1H-imidazol-1-yl)carbothioyloxy]-2-azabicyclo[3.1.1]heptane-2,3-dicarboxylate (p11) and 2-tert-butyl 3-methyl 2-azabicyclo[3.1.1]hept-3-ene-2,3-dicarboxylate (p12)

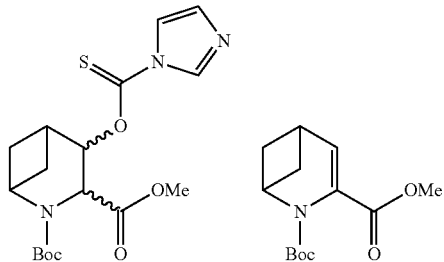 [SMILES: COC(=O)C1C(OC(=S)n2ccnc2)C2CC(C2)N1C(=O)OC(C)(C)C ; COC(=O)C1=CC2CC(C2)N1C(=O)OC(C)(C)C]

To a solution of CIS/TRANS 2-tert-butyl 3-methyl 4-hydroxy-2-azabicyclo[3.1.1]heptane-2,3-dicarboxylate (p10, 5.7 g, 21.00 mmol) in DCM dry (100 mL) at 0° C. DMAP (3.85 g, 31.5 mmol) and 1,1'-Thiocarbonyldiimidazole (10.29 g, 57.75 mmol) were added. The reaction was stirred at RT for 4 hrs and then concentrated under vacuum. The residue was purified by FC on silica gel (eluent: from DCM 100% to DCM/AcOEt 8:2) affording CIS/TRANS 2-tert-butyl 3-methyl 4-[(1H-imidazol-1-yl)carbothioyloxy]-2-azabicyclo[3.1.1]heptane-2,3-dicarboxylate (p11, 4 g, y=50%, mixture of cis and trans diastereoisomers) and 2-tert-butyl 3-methyl 2-azabicyclo[3.1.1]hept-3-ene-2,3-dicarboxylate (p12, 1.3 g, y=25%) as yellow solids.

p11: MS (m/z): 382.0 [MH]$^+$.
p12: MS (m/z): 276.0 [M+Na]$^+$.

Preparation 13: 2-tert-butyl 3-methyl 2-azabicyclo[3.1.1]heptane-2,3-dicarboxylate

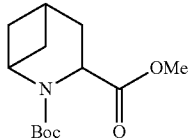 [SMILES: COC(=O)C1CC2CC(C2)N1C(=O)OC(C)(C)C]

Method A:

To a solution of CIS/TRANS 2-tert-butyl 3-methyl 4-[(1H-imidazol-1-yl)carbothioyloxy]-2-azabicyclo[3.1.1]heptane-2,3-dicarboxylate (p11, 3.7 g, 9.7 mmol) in toluene dry (80 mL) were added Tributyltin hydride (4.1 g, 13.97 mmol) and AIBN (0.350 g, 2.13 mmol). The reaction was stirred for 2 hrs at 90° C. Then it was cooled down to RT, the mixture was concentrated under vacuum and the residue was purified by pad of silica using as eluent a solution of DCM/AcOEt 95:5 affording 2-tert-butyl 3-methyl 2-azabicyclo[3.1.1]heptane-2,3-dicarboxylate (p13, 2.07 g, y=83%) as yellow oil.

Method B:

To a solution of 2-tert-butyl 3-methyl 2-azabicyclo[3.1.1]hept-3-ene-2,3-dicarboxylate (p12, 1.3 g, 5.13 mmol) in EtOH (60 mL) was added Pd/C 10% (1.0 g) and the reaction was stirred at RT O/N under H₂ atmosphere at 6 bar. The reaction was filtered over celite and concentrated under vacuum affording 2-tert-butyl 3-methyl 2-azabicyclo[3.1.1]heptane-2,3-dicarboxylate (p13, 1.10 g, y=84%) as colourless oil and used without further purifications MS (m/z): 256.0 [MH]⁺.

Preparation 14: tert-butyl 3-(hydroxymethyl)-2-azabicyclo[3.1.1]heptane-2-carboxylate

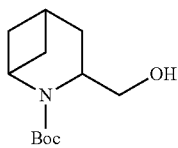 [SMILES: CC(C)(C)OC(=O)N1C(CO)CC2CC1C2]

2-tert-butyl 3-methyl 2-azabicyclo[3.1.1]heptane-2,3-dicarboxylate (p13, 0.100 g, 0.392 mmol) was dissolved in THF (5 mL) and cooled to −20° C. Lithium aluminium hydride 2M in THF (0.314 mL, 0.627 mmol) was added dropwise at −20° C., and then the mixture was stirred at same temperature for 2 h. The reaction was quenched with Na₂SO₄*10 H₂O. The mixture was filtered to remove the solid and concentrated under vacuum to afford tert-butyl 3-(hydroxymethyl)-2-azabicyclo[3.1.1]heptane-2-carboxylate (p14, 90 mg, 0.395 mmol), which was used without further purification.

MS (m/z): 228.2 [MH]⁺.

Preparation 15: tert-butyl 3-({[5-(trifluoromethyl)pyridin-2-yl]oxy}methyl)-2-azabicyclo[3.1.1]heptane-2-carboxylate

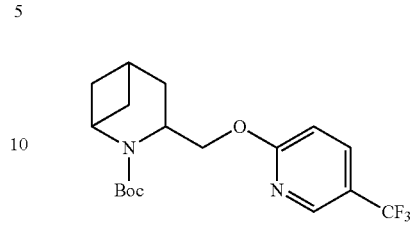

A mixture of tert-butyl 3-(hydroxymethyl)-2-azabicyclo[3.1.1]heptane-2-carboxylate (p14, 150 mg, 0.66 mmol), 2-fluoro-5-(trifluoromethyl)pyridine (120 mg, 0.72 mmol), and cesium carbonate (254 mg, 0.78 mmol) in DMF dry (5 mL) was stirred at RT under nitrogen for 3 h, then more 2-fluoro-5-(trifluoromethyl)pyridine (60 mg, 0.36 mmol) was added, and the mixture was stirred at RT for 3 h.

The mixture was combined with crude material from similar preparation and the combined crudes were diluted with AcOEt and washed several times with brine. The organic phase was dried over Na₂SO₄ and filtered, and the solvent was evaporated. Crude was purified by silica gel chromatography (eluent: Cy/AcOEt 80:20 to 60:40) affording tert-butyl 3-({[5-(trifluoromethyl)pyridin-2-yl]oxy}methyl)-2-azabicyclo[3.1.1]heptane-2-carboxylate (p15, 100 mg, 30% recovery on combined batches) as a colourless oil.

MS (m/z): 373.2 [MH]⁺.

Preparation 16: tert-butyl 3-[(isoquinolin-3-yloxy)methyl]-2-azabicyclo[3.1.1]heptane-2-carboxylate

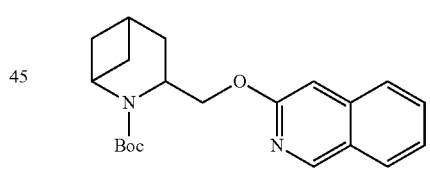

tert-butyl 3-(hydroxymethyl)-2-azabicyclo[3.1.1]heptane-2-carboxylate (p14, 100 mg, 0.44 mmol) was dissolved in THF (7 mL). PPh₃ (174 mg, 0.66 mmol) was added, followed by 3-hydroxyisoquinoline (96 mg, 0.66 mmol). The mixture was stirred at RT for 15', then cooled to 0° C. Di-tert-butyl azodicarboxylate (152 mg, 0.66 mmol) was added portionwise and, after 10', the ice bath was removed, allowing the mixture to stir at RT for 1.5 h. The mixture was concentrated under vacuum to obtain a crude that was combined with crude from a similar preparation. Combined crude material was purified by FC on silica gel (eluent from Cy to EtOAc 20%) to afford tert-butyl 3-[(isoquinolin-3-yloxy)methyl]-2-azabicyclo[3.1.1]heptane-2-carboxylate (p16, 72 mg, 30% recovery on combined batches) as colourless oil.

MS (m/z): 355.3 [MH]⁺.

Preparation 17: 3-({[5-(trifluoromethyl)pyridin-2-yl]oxy}methyl)-2-azabicyclo[3.1.1]heptane trifluoroacetate

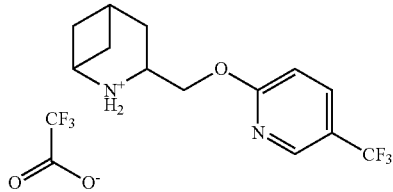

A mixture of tert-butyl 3-({[5-(trifluoromethyl)pyridin-2-yl]oxy}methyl)-2-azabicyclo[3.1.1]heptane-2-carboxylate (p15, 100 mg, 0.27 mmol) and TFA (0.75 mL) in DCM (5 mL) was stirred at RT for 1 h 30 minutes, then the solution was evaporated to give 3-({[5-(trifluoromethyl)pyridin-2-yl]oxy}methyl)-2-azabicyclo[3.1.1]heptane trifluoroacetate (p17, 104 mg, recovery assumed quantitative) as pale yellow oil.

MS (m/z): 273.1 [MH]$^+$.

Preparation 18: 3-{2-azabicyclo[3.1.1]heptan-3-ylmethoxy}isoquinoline

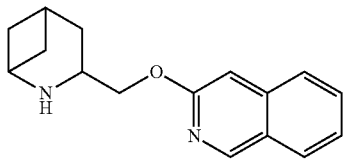 [SMILES: c1ccc2cc(OCC3CC4CC(C4)N3)ncc2c1]

To a solution of tert-butyl 3-[(isoquinolin-3-yloxy)methyl]-2-azabicyclo[3.1.1]heptane-2-carboxylate (p16, 72 mg, 0.20 mmol) in DCM (3 mL), TFA (1 mL) was added and the reaction was stirred at RT for 30'. It was concentrated under vacuum; the residue was purified by SCX washing with MeOH and eluting with NH$_3$ 1 M in MeOH to obtain 3-{2-azabicyclo[3.1.1]heptan-3-ylmethoxy}isoquinoline (p18, 44 mg, y=83%) as pale yellow oil.

MS (m/z): 255.2 [MH]$^+$.

Preparation 19: 2-azabicyclo[3.1.1]heptan-3-ylmethanol

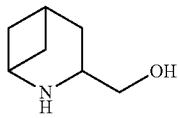

To a solution of tert-butyl 3-(hydroxymethyl)-2-azabicyclo[3.1.1]heptane-2-carboxylate (p14, 440 mg, 1.94 mmol) in DCM (21 mL), TFA (7 mL) was added and the reaction was stirred at RT for 1 h. Then it was concentrated under vacuum and the residue was purified by SCX washing with MeOH and eluting with NH$_3$ 1 M in MeOH to obtain 2-azabicyclo[3.1.1]heptan-3-ylmethanol (p19, 240 mg, 1.89 mmol, y=97%) as pale yellow oil.

MS (m/z): 128.1 [MH]$^+$.

Preparation 20: 2-azabicyclo[3.1.1]heptan-3-ylmethanol hydrochloride

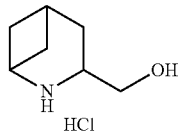

A 4N solution of HCl in dioxane (7 mL, 28 mmol) was added to tert-butyl 3-(hydroxymethyl)-2-azabicyclo[3.1.1]heptane-2-carboxylate (p14, 223 mg, 1 mmol) and the resulting reaction mixture was stirred at RT for 2 hrs. The reaction mixture was concentrated under reduced pressure affording 2-azabicyclo[3.1.1]heptan-3-ylmethanol hydrochloride (p20, 144 mg) as beige solid.

MS (m/z): 128.1 [MH]$^+$.

Preparation 21: 3-{[(5-fluoropyridin-2-yl)oxy]methyl}-2-azabicyclo[3.1.1]heptanes

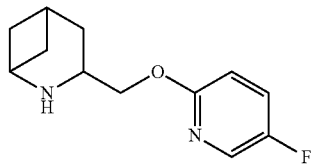 [SMILES: Fc1ccc(OCC2CC3CC(C3)N2)nc1]

NaH (60% in mineral oil, 53 mg, 1.32 mmol) was added to a solution of 2-azabicyclo[3.1.1]heptan-3-ylmethanol (p19, 152 mg, 1.1 mmol) in DMF dry (5 mL) at 0° C. under nitrogen, then the suspension was stirred at RT for 45 minutes. 2,5-difluoropyridine (0.14 mL, 1.21 mmol) was added, and the mixture was stirred at RT for 30 minutes, then at 60° C. for 1 h 30 minutes. The mixture was cooled to RT, then it was partitioned between AcOEt and brine. The aqueous phase was extracted with more AcOEt, then the combined organics were washed with brine, dried over Na$_2$SO$_4$, and filtered. The solvent was evaporated to give a crude yellow oil that was purified by FC on NH column (eluent: DCM:MeOH 100% to 98:2), to give 3-{[(5-fluoropyridin-2-yl)oxy]methyl}-2-azabicyclo[3.1.1]heptanes (p21, 95 mg, y=47%) as a yellow oil.

MS (m/z): 223.1 [MH]$^+$.

Preparation 22: 3-{[(5-chloropyridin-2-yl)oxy]methyl}-2-azabicyclo[3.1.1]heptane

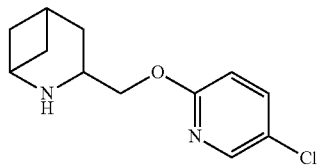 [SMILES: Clc1ccc(OCC2CC3CC(C3)N2)nc1]

NaH (60% in mineral oil, 81 mg, 2 mmol) was added to a solution of 2-azabicyclo[3.1.1]heptan-3-ylmethanol (p19, 215 mg, 1.69 mmol) in DMF dry (5 mL) at 0° C. under nitrogen, then the suspension was stirred at RT for 45 minutes. 5-Chloro-2-fluoropyridine (0.195 mL, 1.94 mmol) was added, and the mixture was stirred at 60° C. for 1 h. The mixture was cooled to RT, then it was partitioned between AcOEt and brine. The aqueous phase was extracted with more AcOEt, then the combined organics were washed with brine, dried over Na$_2$SO$_4$, and filtered. The solvent was evaporated to give a crude yellow oil that was purified by FC on NH column (eluent: Cy:AcOEt 90:10 to 70:30), to give 3-{[(5-fluoropyridin-2-yl)oxy]methyl}-2-azabicyclo[3.1.1] heptanes (p22, 254 mg, y=63%) as a colourless oil.

MS (m/z): 238.9 [MH]$^+$.

Preparation 23: methyl 2-azabicyclo[3.1.1]heptane-3-carboxylate

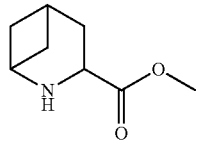

A mixture of 2-tert-butyl 3-methyl 2-azabicyclo[3.1.1] heptane-2,3-dicarboxylate (p13, 1.5 g, 5.9 mmol) and TFA (7.5 mL) in DCM (50 mL) was stirred at RT for 1 h, then the solution was concentrated, and the residue was purified by SCX cartridge (10 g, 0.9 meq/g), first eluting with MeOH, then with NH$_3$ 1 M in MeOH affording methyl 2-azabicyclo [3.1.1]heptane-3-carboxylate (p23, 816 mg, y=89%) as a yellow oil.

MS (m/z): 156.0 [MH]$^+$.

Preparation 24: methyl 2-[(4-methoxyphenyl) methyl]-2-azabicyclo[3.1.1]heptane-3-carboxylate

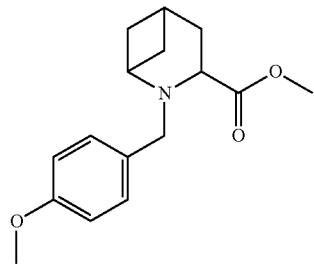 [SMILES: COC(=O)C1CC2CC(C2)N1Cc1ccc(OC)cc1]

A mixture of methyl 2-azabicyclo[3.1.1]heptane-3-carboxylate (p23, 816 mg, 5.26 mmol), potassium carbonate (1.09 g, 7.9 mmol), and 1-(chloromethyl)-4-methoxybenzene (0.85 mL, 6.3 mmol) in acetonitrile dry (35 mL) was stirred under nitrogen at 50° C. for 3 h. The mixture was filtered to remove the excess potassium carbonate, and the filtrate was evaporated. The crude material was purified by SCX cartridge (10 g, 0.9 meq/g), first eluting with MeOH, then with NH$_3$ 1 N in MeOH affording methyl 2-[(4-methoxyphenyl)methyl]-2-azabicyclo[3.1.1]heptane-3-carboxylate (p24, 1.29 g, y=89%) as a yellow oil.

MS (m/z): 276.1 [MH]$^+$.

Preparation 25: {2-[(4-methoxyphenyl)methyl]-2-azabicyclo[3.1.1]heptan-3-yl}methanol

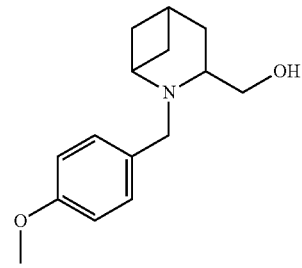 [SMILES: COc1ccc(CN2C(CO)CC3CC2C3)cc1]

LiAlH$_4$ (sol 2M in THF, 3.5 mL, 7 mmol) was added to a solution of methyl 2-[(4-methoxyphenyl)methyl]-2-azabicyclo[3.1.1]heptane-3-carboxylate (p24, 1.29 g, 4.7 mmol) in THF dry (40 mL) at 0° C. under nitrogen. The mixture was stirred for 45 minutes, then solid sodium sulphate decahydrate was added. The resulting mixture was stirred for 4 h, allowing temperature to reach RT. Solid was filtered off and the organic solution was evaporated to give {2-[(4-methoxyphenyl)methyl]-2-azabicyclo[3.1.1]heptan-3-yl}methanol (p25, 1.13 g, y=97%) as a colourless oil.

MS (m/z): 248.1 [MH]$^+$.

Preparation 26: 3-(4-fluorophenoxymethyl)-2-[(4-methoxyphenyl)methyl]-2-azabicyclo[3.1.1]heptane

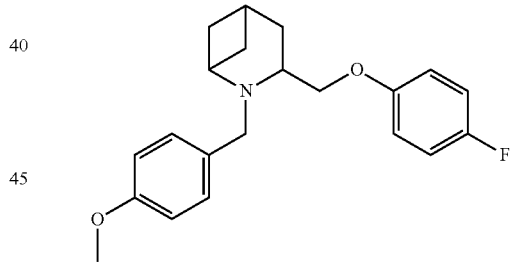

A solution of {2-[(4-methoxyphenyl)methyl]-2-azabicyclo[3.1.1]heptan-3-yl}methanol (p25, 1.13 g, 4.56 mmol), 4-fluorophenol (613 mg, 5.47 mmol), and Ph$_3$P (1.2 g, 4.56 mmol) in THF dry (35 mL) was prepared at 0° C. under nitrogen, then a solution of DIAD (1.35 mL, 6.84 mmol) in THF dry (5 mL) was added dropwise at 0° C. The mixture was allowed to reach RT, and stirred at RT overnight. The mixture was partitioned between AcOEt and aqueous NaHCO$_3$, then the organic phase was dried over Na$_2$SO$_4$ and filtered. The solvent was evaporated to give a yellow oil which was purified by FC on NH column (eluent: Cy/AcOEt 99:1 to 95:5) affording 3-(4-fluorophenoxymethyl)-2-[(4-methoxyphenyl)methyl]-2-azabicyclo[3.1.1]heptane (p26, 1.03 g, y=66%).

MS (m/z): 342.1 [MH]$^+$.

Preparation 27: 3-(4-chlorophenoxymethyl)-2-[(4-methoxyphenyl)methyl]-2-azabicyclo[3.1.1]heptane

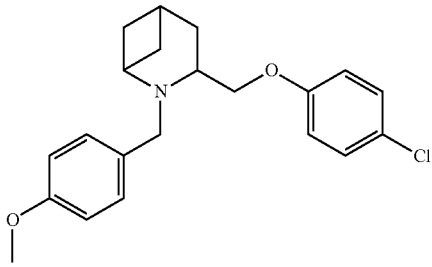 [SMILES: COc1ccc(CN2C(COc3ccc(Cl)cc3)CC3CC2C3)cc1]

A solution of {2-[(4-methoxyphenyl)methyl]-2-azabicyclo[3.1.1]heptan-3-yl}methanol (p25, 233 mg, 0.94 mmol), 4-chlorophenol (407 uL, 1.13 mmol), and Ph₃P (369 mg, 1.41 mmol) in THF dry (8 mL) was prepared at 0° C. under nitrogen, then a solution of DIAD (0.277 mL, 1.41 mmol) in THF dry (2 mL) was added dropwise at 0° C. The mixture was allowed to reach RT, and stirred at RT overnight. The solvent was evaporated and the crude material was purified by SCX cartridge first eluting with MeOH, then with NH₃ 1 N in MeOH then further purified by FC on silica gel (eluent: cyclohexane:ethyl acetate 100:0 to 85:15) affording 3-(4-chlorophenoxymethyl)-2-[(4-methoxyphenyl)methyl]-2-azabicyclo[3.1.1]heptane (p27, 185 mg, y=55%).

MS (m/z): 358.1 [MH]⁺.

Preparation 28: 3-(4-fluorophenoxymethyl)-2-azabicyclo[3.1.1]heptane

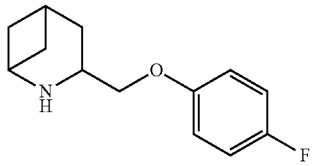 [SMILES: Fc1ccc(OCC2CC3CC(C3)N2)cc1]

To a solution of 3-(4-fluorophenoxymethyl)-2-[(4-methoxyphenyl)methyl]-2-azabicyclo[3.1.1]heptanes (p26, 420 mg, 1.23 mmol) in MeOH (30 mL) ammonium formate (775 mg, 12.3 mmol) and Pd(OH)₂ 20 wt. % (84 mg, 0.12 mmol) were added. The solution was stirred at 65° C. for 1 h, cooled to RT, filtered over celite and concentrated under vacuum. The crude was purified by SCX washing with MeOH and eluting with NH₃ 1 M in MeOH affording 3-(4-fluorophenoxymethyl)-2-azabicyclo[3.1.1]heptane (p28, 280 mg, y=50%) as yellow oil.

MS (m/z): 222.0 [MH]⁺.

Preparation 29: 3-(4-chlorophenoxymethyl)-2-azabicyclo[3.1.1]heptane

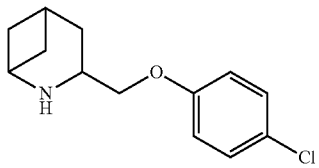 [SMILES: Clc1ccc(OCC2CC3CC(C3)N2)cc1]

To a solution of 3-(4-chlorophenoxymethyl)-2-[(4-methoxyphenyl)methyl]-2-azabicyclo[3.1.1]heptane (p27, 150 mg, 0.14 mmol) in DCE (5 mL), ACE-Cl (16 uL, 0.153 mmol) and DIPEA (73 uL, 0.42 mmol) were added. The reaction mixture was irradiated by MW (T=120° C., 25 min). Then solvent was removed under reduced pressure and the residue was dissolved in MeOH (2 mL). The solution was irradiated by MW (T=90° C., 20 min). Solvent was removed and crude was purified by SCX cartridge first eluting with MeOH, then with NH₃ 1 M in MeOH affording 3-(4-chlorophenoxymethyl)-2-azabicyclo[3.1.1]heptane (p29, 86 mg, y=85%) as a colourless oil.

NMR (¹H, Chloroform-d): δ 7.25 (d, 2H), 6.89 (d, 2H), 3.96-4.03 (m, 1H), 3.87-3.95 (m, 2H), 3.65-3.71 (m, 1H), 2.52-2.60 (m, 1H), 2.24-2.33 (m, 1H), 2.15-2.23 (m, 1H), 1.95-2.13 (m, 2H), 1.81-1.93 (m, 1H), 1.33-1.41 (t, 1H)

Preparation 30: tert-butyl 3-formyl-2-azabicyclo[3.1.1]heptane-2-carboxylate

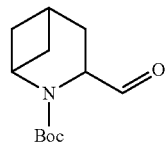 [SMILES: CC(C)(C)OC(=O)N1C(C=O)CC2CC1C2]

Dess-Martin periodinane (1.026 g, 2.42 mmol) was added portionwise to a stirred solution of tert-butyl 3-(hydroxymethyl)-2-azabicyclo[3.1.1]heptane-2-carboxylate (p14, 460 mg, 2.02 mmol) in DCM (10 mL) at 0° C. The reaction mixture was stirred for 2 hours at RT. The reaction mixture was diluted with DCM (10 mL) and quenched with 5% sodium thiosulphate in saturated NaHCO₃ aqueous solution (25 mL). The resulting biphasic mixture was stirred vigorously for 15 minutes then extracted with DCM (3×20 mL). The combined organic phases were evaporated under reduced pressure and the residue was purified by FC on silica gel (EtOAc/Cyclohexane 95:5 to 70:30) to give tert-butyl 3-formyl-2-azabicyclo[3.1.1]heptane-2-carboxylate (p30, 350 mg, y=77%) as colourless oil.

MS (m/z): 226.1 [MH]⁺.

Preparation 31: tert-butyl 3-[2-methoxyethenyl]-2-azabicyclo[3.1.1]heptane-2-carboxylate

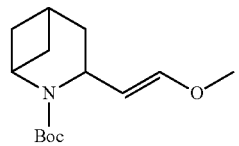 [SMILES: CO/C=C/C1CC2CC(C2)N1C(=O)OC(C)(C)C]

A solution of potassium tert-butoxide (278.3 mg, 2.48 mmol) in THF (3 mL) was added dropwise to a stirred suspension of the (methoxymethyl)triphenylphosphonium chloride (935.8 mg, 2.73 mmol) in THF (3 mL) cooled in an ice bath. After stirring the red solution at room temperature for 30 minutes, tert-butyl 3-formyl-2-azabicyclo[3.1.1]heptane-2-carboxylate (p30, 280 mg, 1.24 mmol) in THF (3 mL) was added and the reaction stirred at room temperature for 16 hours. The reaction was partitioned between saturated aqueous ammonium chloride solution and Ethyl Acetate.

Combined organic extracts were washed with water, dried and concentrated and the residue purified by FC on silica gel (Cyclohexane/EtOAc 10:0 to 7:3) affording tert-butyl 3-[2-methoxyethenyl]-2-azabicyclo[3.1.1]heptane-2-carboxylate (p31, 250 mg, y=80%) in a 80% purity due to presence of 20% of already deprotected homologated aldehyde.

MS (m/z): 254.1 [MH]$^+$.

Preparation 32: tert-butyl 3-(2-oxoethyl)-2-azabicyclo[3.1.1]heptane-2-carboxylate

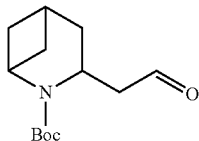 [SMILES: CC(C)(C)OC(=O)N1C(CC=O)CC2CC1C2]

tert-butyl 3-[2-methoxyethenyl]-2-azabicyclo[3.1.1]heptane-2-carboxylate (p31, 250 mg, 0.99 mmol) was dissolved in acetonitrile (10 mL) then 0.4 M trifluoroacetic acid in water (100 uL, 0.099 mmol) was added to the reaction mixture and the reaction was stirred at RT for 1 hour. After this period of time, the reaction was complete. A saturated solution of sodium bicarbonate (10 mL) was added to quench the reaction and then the solvent was evaporated. The resultant aqueous layer was then extracted with ethyl acetate (3×50 mL), and the combined organic layers dried with sodium sulfate, filtered and concentrated in vacuo to afford tert-butyl 3-(2-oxoethyl)-2-azabicyclo[3.1.1]heptane-2-carboxylate (p32, 190 mg, y=91%) as colorless oil, that was used as crude in the next step.

MS (m/z): 240.1 [MH]$^+$.

Preparation 33: tert-butyl 3-(2-hydroxyethyl)-2-azabicyclo[3.1.1]heptane-2-carboxylate

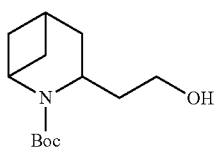

A mixture of tert-butyl 3-(2-oxoethyl)-2-azabicyclo[3.1.1]heptane-2-carboxylate (p32, 190 mg, 0.79 mmol) and sodium borohydride (32.8 mg, 0.87 mmol) in methanol (3 mL) were stirred at RT for 2 hours. Water was added and the mixture was extracted with ethyl acetate. The combined organic phases were washed with brine, dried, concentrated, and purified by FC on silica gel (Cyclohexane/EtOAc 90:10 to 60:40) affording tert-butyl 3-(2-hydroxyethyl)-2-azabicyclo[3.1.1]heptane-2-carboxylate (p33, 140 mg, y=73%).

MS (m/z): 242.1 [MH]$^+$.

Preparation 34: tert-butyl 3-[2-(4-fluorophenoxy)ethyl]-2-azabicyclo[3.1.1]heptane-2-carboxylate

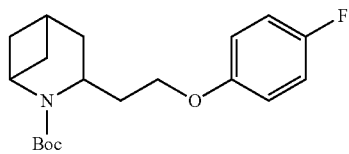 [SMILES: CC(C)(C)OC(=O)N1C(CCOc2ccc(F)cc2)CC2CC1C2]

To a solution of tert-butyl 3-(2-hydroxyethyl)-2-azabicyclo[3.1.1]heptane-2-carboxylate (p33, 140 mg, 0.58 mmol), 4-fluorphenol (90.8 mg, 0.81 mmol) and triphenylphosphine (212 mg, 0.81 mmol) in anhydrous tetrahydrofuran (5 mL) at 0° C. under an atmosphere of nitrogen was added diisopropyl azodicarboxylate (147.6 uL, 0.75 mmol) and the resulting mixture was stirred at ambient temperature for about 2 hours. The clear colourless solution was concentrated in vacuo. The crude liquid was purified by FC on silica gel (Cyclohexane/EtOAc 95:5 to 7:3) to give tert-butyl 3-[2-(4-fluorophenoxy)ethyl]-2-azabicyclo[3.1.1]heptane-2-carboxylate (p34, 170 mg, y=88%) as a white powder.

MS (m/z): 336.1 [MH]$^+$.

Preparation 35: 3-[2-(4-fluorophenoxy)ethyl]-2-azabicyclo[3.1.1]heptane

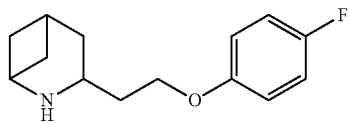 [SMILES: Fc1ccc(OCCC2CC3CC(C3)N2)cc1]

tert-butyl 3-[2-(4-fluorophenoxy)ethyl]-2-azabicyclo[3.1.1]heptane-2-carboxylate (p34, 170 mg, 0.51 mmol) was treated with TFA (1 mL) in DCM (3 mL) and stirred at RT for 1 hour. The solvent was evaporated and the crude was purified by SCX cartridge first washing with MeOH then eluting with NH$_3$ 1 M in MeOH affording 3-[2-(4-fluorophenoxy)ethyl]-2-azabicyclo[3.1.1]heptane (p35, 120 mg, y=quantitative).

MS (m/z): 236.0 [MH]$^+$.

Preparation 36: 2-tert-butyl 3-methyl 4-methylidene-2-azabicyclo[3.1.1]heptane-2,3-dicarboxylate

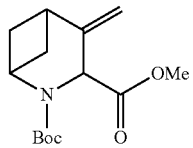 [SMILES: C=C1C2CC(C2)N(C(=O)OC(C)(C)C)C1C(=O)OC]

To an ice-bath cooled suspension of t-BuO$^-$K$^+$ (2.9 g, 25.98 mmol) in THF (35 mL) (methyl) triphenylphosphonium bromide (9.9 g, 27.85 mmol) was added. After 15 minutes the mixture was allowed to reach RT and stirred at that temperature for 45 minutes then cooled down again to 0° C. Then a solution of 2-tert-butyl 3-methyl 4-oxo-2-azabicyclo[3.1.1]heptane-2,3-dicarboxylate (p8, 5.0 g, 18.56 mmol) in THF (10 mL) was slowly added and the mixture was allowed to reach RT and stirred at that temperature for 1 h, then heated at 60° C. and stirred at that temperature for further 2 hours. The mixture was then cooled down to RT and quenched with water, extracted with AcOEt, dried and evaporated. The crude was purified by FC on silica gel (eluent: Cy:AcOEt 85:15) affording 2-tert-butyl 3-methyl 4-methylidene-2-azabicyclo[3.1.1]heptane-2,3-dicarboxylate (p36, 2.0 g, y=40%) as yellow oil.

MS (m/z): 268.0 [MH]+.

Preparation 37: CIS/TRANS 2-tert-butyl 3-methyl 4-methyl-2-azabicyclo[3.1.1]heptane-2,3-dicarboxylate

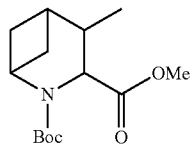 [SMILES: COC(=O)C1C(C)C2CC(C2)N1C(=O)OC(C)(C)C]

2-tert-butyl 3-methyl 4-methylidene-2-azabicyclo[3.1.1]heptane-2,3-dicarboxylate (p36, 1.75 g, 6.5 mmol) was dissolved in EtOH (60 mL). Then Pd/C [10%] (1.0 g) was added and the mixture was hydrogenated at 6 atm. After 4 h Pd/C 10% was added (1.0 g) and the reaction was stirred under H₂ atmosphere (6 atm) overnight. The day after further Pd/C 10% (1.0 g) was added and the reaction was stirred for additional 4 h at 6 atm. The catalyst was filtered off over a pad of celite and the reaction was concentrated under vacuum affording CIS/TRANS 2-tert-butyl 3-methyl 4-methyl-2-azabicyclo[3.1.1]heptane-2,3-dicarboxylate (p37, 1.66 g, y=95%, mixture of cis and trans diastereoisomers) as brown oil that was used as crude in the next step.

MS (m/z): 268.0 [MH]+.

Preparation 38: CIS/TRANS tert-butyl 3-(hydroxymethyl)-4-methyl-2-azabicyclo[3.1.1]heptane-2-carboxylate

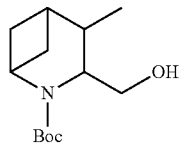 [SMILES: CC1C2CC(C2)N(C(=O)OC(C)(C)C)C1CO]

CIS/TRANS 2-tert-butyl 3-methyl 4-methyl-2-azabicyclo[3.1.1]heptane-2,3-dicarboxylate (p37, 0.3 g, 1.11 mmol) was dissolved in anhydrous THF (8.5 mL) and cooled to −20° C. LiAlH₄ 2 M in THF (0.9 mL, 1.78 mmol) was added dropwise and reaction was stirred at −20° for 4 h. The reaction was quenched with Na₂SO₄.10H₂O and warmed to RT. The reaction was filtered and concentrated under vacuum affording CIS/TRANS tert-butyl 3-(hydroxymethyl)-4-methyl-2-azabicyclo[3.1.1]heptane-2-carboxylate (p38, 0.25 g, y=93%, mixture of cis and trans diastereoisomers) as yellow solid, that was used as such in the next step.

MS (m/z): 236.0 [MH]+.

Preparation 39: CIS/TRANS {4-methyl-2-azabicyclo[3.1.1]heptan-3-yl}methanol

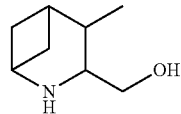

To a solution of CIS/TRANS tert-butyl 3-(hydroxymethyl)-4-methyl-2-azabicyclo[3.1.1]heptane-2-carboxylate (p38, 0.25 g, 1.03 mmol) in DCM (3 mL) TFA (0.5 mL) was added. The reaction was stirred at RT for 2 h. The mixture was concentrated under vacuum and the residue was purified by SCX, washing with MeOH and eluting with NH₃ 1 M in MeOH affording CIS/TRANS {4-methyl-2-azabicyclo[3.1.1]heptan-3-yl}methanol (p39, 0.15 g, y=99%, mixture of cis and trans diastereoisomers) as colourless oil.

MS (m/z): 141.9 [MH]+.

Preparation 40: CIS/TRANS 3-{[(5-fluoropyridin-2-yl)oxy]methyl}-2-azabicyclo[3.1.1]heptane

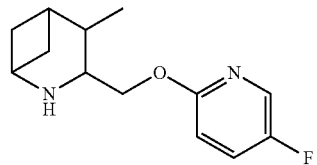 [SMILES: CC1C2CC(C2)NC1COc1ccc(F)cn1]

NaH (60% in mineral oil, 84 mg, 1.38 mmol) was added to a solution of CIS/TRANS {4-methyl-2-azabicyclo[3.1.1]heptan-3-yl}methanol (p39, 150 mg, 1.06 mmol) in DMF dry (3 mL) at 0° C. under nitrogen, then the suspension was stirred at RT for 45 minutes. 2,5-Difluoropyridine (0.126 mL, 1.38 mmol) was added, and the mixture was stirred at 70° C. for 3 hours. The reaction was then quenched with methanol. Solvents were removed under reduced pressure and crude was purified by SCX washing first with MeOH and then eluting with NH₃ 1 M in MeOH to give CIS/TRANS 3-{[(5-fluoropyridin-2-yl)oxy]methyl}-2-azabicyclo[3.1.1]heptane (p40, 0.11 g, mixture of cis and trans diastereoisomers) that was used as such in the next step.

MS (m/z): 237.0 [MH]+.

Preparation 41: CIS/TRANS 1-({4-methyl-2-azabicyclo[3.1.1]heptan-3-yl}methoxy)isoquinoline

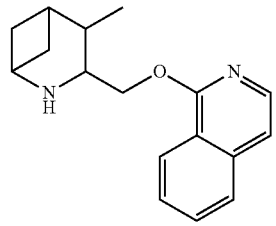 [SMILES: CC1C2CC(C2)NC1COc1nccc2ccccc12]

NaH (60% in mineral oil, 50 mg, 1.27 mmol) was added to a solution of CIS/TRANS {4-methyl-2-azabicyclo[3.1.1]heptan-3-yl}methanol (p39, 150 mg, 1.06 mmol) in DMF dry (4 mL) at 0° C. under nitrogen, then the suspension was stirred at RT for 45 minutes. 1-Chloroisoquinoline (0.85 mL, 1.27 mmol) was added, and the mixture was stirred at 80° C. for 6 h. The mixture was cooled to RT, then it was partitioned between AcOEt and brine. The aqueous phase was extracted again with AcOEt, then the combined organics were washed with brine, dried over Na₂SO₄, and filtered.

The solvent was evaporated and crude was purified by FC on silica gel (eluent: DCM/EtOH 100:0 to 9:1) affording CIS/TRANS 1-({4-methyl-2-azabicyclo[3.1.1]heptan-3-yl}methoxy)isoquinoline (p41, 0.1 g, y=42%, mixture of cis and trans diastereoisomers) as a yellow oil.

NMR (¹H, DMSO-d6): δ 8.26-8.32 (m, 1H), 7.99-8.05 (m, 1H), 7.88-7.93 (m, 1H), 7.75-7.82 (m, 1H), 7.62-7.69 (m, 1H), 7.37-7.43 (m, 1H), 4.35-4.47 (m., 2H), 4.00-4.11 (m, 1H), 3.50-3.61 (m, 1H), 2.44-2.51 (m, 1H), 2.32-2.42 (m, 1H), 2.10-2.21 (m, 1H), 1.99-2.07 (m, 1H), 1.84-1.96 (m, 1H), 1.51-1.61 (t, 1H), 1.01-1.07 (m, 3H)

Preparation 42: CIS/TRANS 7-chloro-2-({4-methyl-2-azabicyclo[3.1.1]heptan-3-yl}methoxy)quinoxaline

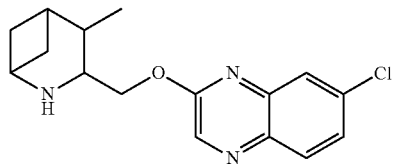 [SMILES: CC1C2CC(C2)NC1COc1cnc2ccc(Cl)cc2n1]

NaH (60% in mineral oil, 38 mg, 0.95 mmol) was added to a solution of CIS/TRANS {4-methyl-2-azabicyclo[3.1.1]heptan-3-yl}methanol (p39, 112 mg, 0.79 mmol) in DMF dry (4 mL) at 0° C. under nitrogen, then the suspension was stirred at RT for 45 minutes. 2,7-dichloroquinoxaline (173.2 mg, 0.87 mmol) was added, and the mixture was stirred at RT for 30 minutes, then at 60° C. for 1 h 30 minutes. The mixture was cooled to RT, then it was partitioned between AcOEt and brine. The aqueous phase was extracted with more AcOEt, and then the combined organics were washed with brine, dried over Na₂SO₄, and filtered. The solvent was evaporated and the crude was purified by FC on NH column (eluent: DCM/MeOH 100% to 98:2) affording CIS/TRANS 7-chloro-2-({4-methyl-2-azabicyclo[3.1.1]heptan-3-yl}methoxy)quinoxaline (p42, 194.4 mg, y=81%, mixture of cis and trans diastereoisomers).

MS (m/z): 303.93 [MH]⁺.

Preparation 43: CIS/TRANS methyl 4-methyl-2-azabicyclo[3.1.1]heptane-3-carboxylate

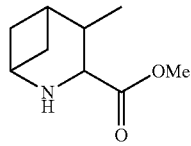

To a solution of CIS/TRANS 2-tert-butyl 3-methyl 4-methyl-2-azabicyclo[3.1.1]heptane-2,3-dicarboxylate (p37, 535 mg, 1.99 mmol) in DCM (10 mL), TFA (1 mL) was added and the mixture was stirred at RT overnight. The solvent was then removed and the crude mixture was purified by SCX first washing with MeOH then eluting with NH₃ 1 M in MeOH, affording CIS/TRANS methyl 4-methyl-2-azabicyclo[3.1.1]heptane-3-carboxylate (p43, 305 mg, y=91%, mixture of cis and trans diastereoisomers).

MS (m/z): 170.0 [MH]⁺.

Preparation 44: CIS/TRANS methyl 2-[(4-methoxyphenyl)methyl]-4-methyl-2-azabicyclo[3.1.1]heptane-3-carboxylate

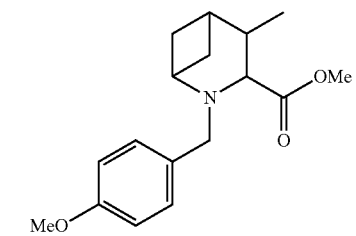 [SMILES: COC(=O)C1C(C)C2CC(C2)N1Cc1ccc(OC)cc1]

A mixture of CIS/TRANS methyl 4-methyl-2-azabicyclo[3.1.1]heptane-3-carboxylate (p43, 305 mg, 1.8 mmol), potassium carbonate (373 mg, 2.7 mmol), and 1-(chloromethyl)-4-methoxybenzene (0.292 mL, 2.16 mmol) in acetonitrile dry (11 mL) was stirred under nitrogen at 50° C. overnight. Then the mixture was filtered to remove the excess potassium carbonate, and the filtrate was evaporated.

The crude material was purified by SCX cartridge, first washing with MeOH, then eluting with NH₃ 1 N in MeOH, affording CIS/TRANS methyl 2-[(4-methoxyphenyl)methyl]-4-methyl-2-azabicyclo[3.1.1]heptane-3-carboxylate (p44, 457 mg, y=87%, mixture of cis and trans diastereoisomers) as colourless oil.

MS (m/z): 290.3 [MH]⁺.

Preparation 45: CIS/TRANS {2-[(4-methoxyphenyl)methyl]-4-methyl-2-azabicyclo[3.1.1]heptan-3-yl}methanol

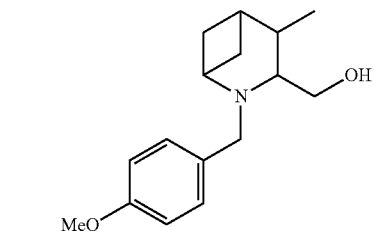 [SMILES: COc1ccc(CN2C3CC(C3)C(C)C2CO)cc1]

CIS/TRANS 2-[(4-methoxyphenyl)methyl]-4-methyl-2-azabicyclo[3.1.1]heptane-3-carboxylate (p44, 457 mg, 1.58 mmol) was dissolved in anhydrous THF (12 mL) and cooled at 0° C. LiAlH₄ 1M in THF (2.5 mL, 2.5 mmol) was added dropwise to the solution at 0° C., then the mixture was stirred at 0° C. for 2 hours and at RT for 1 hour. Then the reaction was quenched at 0° C. with Na₂SO₄*10 H₂O and left stirring overnight at RT. Then it was filtered and concentrated under reduced pressure. The residue was purified by SCX first washing with MeOH and then eluting with NH₃ 1 M in MeOH affording CIS/TRANS {2-[(4-methoxyphenyl)methyl]-4-methyl-2-azabicyclo[3.1.1]heptan-3-yl}methanol (p45, 400 mg, y=97%, mixture of cis and trans diastereoisomers) as colourless oil.

MS (m/z): 262.3 [MH]⁺.

Preparation 46 and Preparation 47: CIS-{2-[(4-methoxyphenyl)methyl]-4-methyl-2-azabicyclo[3.1.1]heptan-3-yl}methanol (p46) and TRANS-{2-[(4-methoxyphenyl)methyl]-4-methyl-2-azabicyclo[3.1.1]heptan-3-yl}methanol (p47)

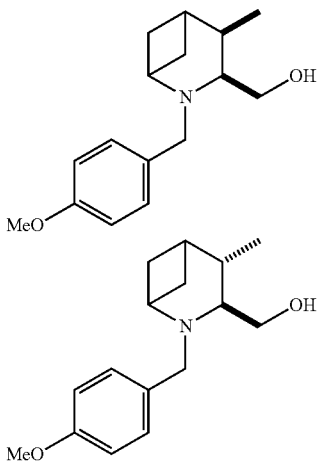

CIS/TRANS {2-[(4-methoxyphenyl)methyl]-4-methyl-2-azabicyclo[3.1.1]heptan-3-yl}methanol was synthesized following analogue procedure as in preparation 45 on a 19.7 g scale of CIS/TRANS 2-[(4-methoxyphenyl)methyl]-4-methyl-2-azabicyclo[3.1.1]heptane-3-carboxylate. Crude material was then purified by FC on RP using basic conditions (eluent: 100% ammonium bicarbonate aqueous solution adjusted to pH 10 with ammonia to $CH_3CN$ 100%) affording CIS-{2-[(4-methoxyphenyl)methyl]-4-methyl-2-azabicyclo[3.1.1]heptan-3-yl}methanol (p46, 11 g, y=62%) and TRANS-{2-[(4-methoxyphenyl)methyl]-4-methyl-2-azabicyclo[3.1.1]heptan-3-yl}methanol (p47, 2.6 g, y=15%)

p46:
NMR ($^1$H, Chloroform-d): δ 7.19 (d, 2H), 6.85 (d, 2H), 3.80 (s, 3H), 3.74-3.78 (m, 1H), 3.71 (d, 1H), 3.62 (dd, 1H), 3.54 (br. s, 1H), 3.42 (d, 1H), 3.29 (m, 1H), 2.96-3.11 (m, 1H), 2.43-2.58 (m, 1H), 2.20-2.28 (m, 1H), 1.45-2.01 (m, 4H), 1.12 (d, 3H).

p47:
NMR ($^1$H, Chloroform-d): δ 7.18 (d, 2H), 6.85 (d, 2H), 3.80 (s, 3H), 3.75 (dd, 1H), 3.70 (d, 1H), 3.41 (d, 1H), 3.32 (d, 1H), 3.23-3.31 (m, 1H), 2.32 (dd, 1H), 2.07-2.26 (m, 2H), 1.64-1.82 (m, 2H), 1.17-2.21 (m, 2H), 0.97 (d, 3H).

Preparation 48: CIS/TRANS 3-(4-fluorophenoxymethyl)-2-[(4-methoxyphenyl)methyl]-4-methyl-2-azabicyclo[3.1.1]heptane

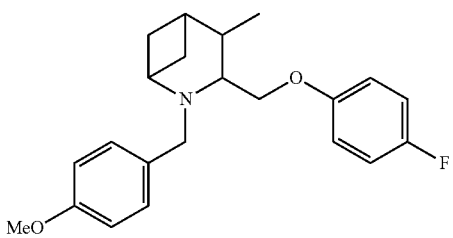 [SMILES: COc1ccc(CN2C3CC(C3)C(C)C2COc2ccc(F)cc2)cc1]

CIS/TRANS {2-[(4-methoxyphenyl)methyl]-4-methyl-2-azabicyclo[3.1.1]heptan-3-yl}methanol (p45, 400 mg, 1.53 mmol) was dissolved in anhydrous THF (8 mL). Then triphenylphosphine (600 mg, 2.3 mmol) was added, followed by 4-fluorophenol (257 mg, 2.3 mmol). The mixture was stirred at RT for 15 minutes, then cooled to 0° C. DIAD (0.453 mL, 2.3 mmol) was added dropwise and after 10 minutes the ice bath was removed, allowing the mixture to stir at RT for 30 minutes; then it was heated to 55° C. for 1.5 hours. The reaction was cooled down to RT and solvent removed under reduced pressure. The crude was then purified by FC on silica gel (eluent: Cy:AcOEt 8:2) affording CIS/TRANS 3-(4-fluorophenoxymethyl)-2-[(4-methoxyphenyl)methyl]-4-methyl-2-azabicyclo[3.1.1]heptane (p48, 492 mg, mixture of cis and trans diastereoisomers). Material used as crude in the next step.
MS (m/z): 356.1 [MH]$^+$.

Preparation 49: CIS/TRANS 3-(4-fluorophenoxymethyl)-4-methyl-2-azabicyclo[3.1.1]heptane

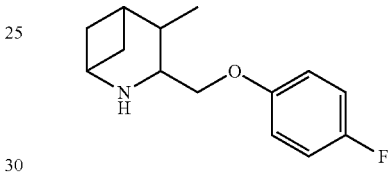

To a solution of CIS/TRANS 3-(4-fluorophenoxymethyl)-2-[(4-methoxyphenyl)methyl]-4-methyl-2-azabicyclo[3.1.1]heptane (p48, 492 mg, crude material: assumed 1.38 mmol) in MeOH (10 mL) ammonium formate (1.89 g, 30 mmol) and Pd(OH)$_2$ 20% (200 mg) were added. The mixture was stirred at 65° C. for 20 minutes, then cooled down to RT. The catalyst was filtered off, and the solvent was evaporated. Water was added, and pH was corrected at 7 with NaHCO$_3$, then the aqueous solution was extracted with AcOEt. The organic phase was washed with brine, dried over Na$_2$SO$_4$ and filtered. The solvent was evaporated and crude was purified by SCX first washing with MeOH, then eluting with NH$_3$ 1 M in MeOH affording CIS/TRANS 3-(4-fluorophenoxymethyl)-4-methyl-2-azabicyclo[3.1.1]heptane (p49, 181 mg, y=56%, mixture of cis and trans diastereoisomers).
MS (m/z): 236.0 [MH]$^+$.

Preparation 50: CIS-3-(4-fluorophenoxymethyl)-2-[(4-methoxyphenyl)methyl]-4-methyl-2-azabicyclo[3.1.1]heptane

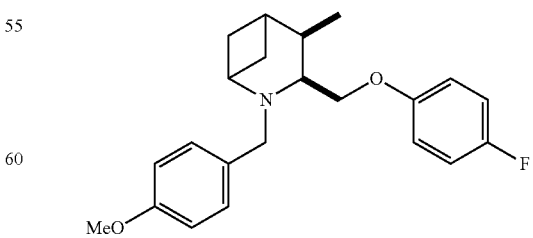

To an ice cooled solution of CIS-[4-[(4-methoxyphenyl)methyl]-2-methyl-4-azabicyclo[3.1.1]heptan-3-yl]methanol (p46, 500 mg, 1.91 mmol), 4-fluorophenol (0.25 mL, 2.87 mmol) and triphenylphosphine (752.67 mg, 2.87 mmol) in THF (12 mL), DIAD (0.57 mL, 2.87 mmol) was added. Reaction was left to warm to room temperature and then heated to 55° C. and stirred at the same temperature for 2 hrs. Further triphenylphosphine (752.67 mg, 2.87 mmol) and DIAD (0.57 mL, 2.87 mmol) were added and the reaction was heated at 55° C. for 1 h and then left at RT overnight. Solvent was removed under reduced pressure, crude was loaded on a SCX cartridge washing with MeOH and eluting with 1N ammonia solution in MeOH. Material obtained was purified by FC on silica gel (eluent: Cy to Cy/AcOEt 7:3) affording CIS-3-[(4-fluorophenoxy)methyl]-2-[(4-methoxyphenyl)methyl]-4-methyl-4-azabicyclo[3.1.1]heptane (p50, 400 mg, 1.125 mmol, y=59%) as a transparent oil.

MS (m/z): 356.4 [MH]$^+$.

Preparation 51: CIS-3-(4-fluorophenoxymethyl)-4-methyl-2-azabicyclo[3.1.1]heptane

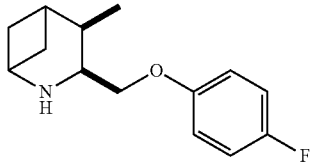 [SMILES: C[C@@H]1C2CC(C2)N[C@@H]1COc1ccc(F)cc1]

To a solution of CIS-3-[(4-fluorophenoxy)methyl]-2-[(4-methoxyphenyl)methyl]-4-methyl-4-azabicyclo[3.1.1]heptane (p50, 400 mg, 1.13 mmol) in Methanol (20 mL), ammonium formate (709.64 mg, 11.25 mmol) and palladium hydroxide (80.15 mg, 0.110 mmol) were added. Reaction was refluxed for 30 min then the mixture was cooled to room temperature and the catalyst was filtered out. Filtrate was evaporated under reduced pressure and crude obtained was loaded on a SCX cartridge, washing with MeOH and eluting with 1N ammonia solution in MeOH to afford CIS-3-[(4-fluorophenoxy)methyl]-4-methyl-2-azabicyclo[3.1.1]heptane (p51, 265 mg, y=quant).

MS (m/z): 236.4 [MH]$^+$.

Preparation 52: TRANS-3-(4-fluorophenoxymethyl)-2-[(4-methoxyphenyl)methyl]-4-methyl-2-azabicyclo[3.1.1]heptane

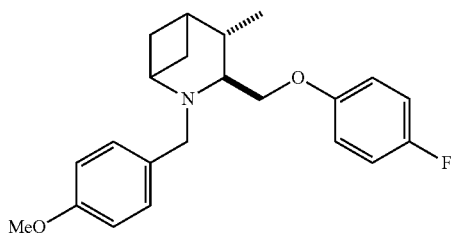 [SMILES: COc1ccc(CN2C3CC(C3)[C@H](C)[C@H]2COc2ccc(F)cc2)cc1]

To a solution of TRANS-[2-[(4-methoxyphenyl)methyl]-4-methyl-4-azabicyclo[3.1.1]heptan-3-yl]methanol (p47, 164 mg, 0.63 mmol) THF (5 mL) triphenylphosphine (246.88 mg, 0.94 mmol) and 4-fluorophenol (105.51 mg, 0.94 mmol) were added. The solution was cooled at 0° C. and DIAD (0.19 mL, 0.94 mmol) was added dropwise. The reaction was warmed to RT and after 5 min heated at 55° C. for 2 hrs. The reaction was concentrated under vacuum and the residue was purified by FC on silica gel (eluent: from cHex 100% to cHex/AcOEt 1:1) and then further purified by SCX washing with MeOH and then eluting with NH$_3$ 1 M in MeOH affording TRANS-3-[(4-fluorophenoxy)methyl]-2-[(4-methoxyphenyl)methyl]-4-methyl-4-azabicyclo[3.1.1]heptane (p52, 140 mg, y=63%) as yellow solid.

MS (m/z): 356.4 [MH]$^+$.

Preparation 53: TRANS-3-(4-fluorophenoxymethyl)-4-methyl-2-azabicyclo[3.1.1]heptane

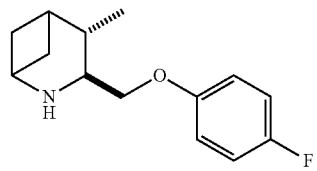 [SMILES: C[C@H]1C2CC(C2)N[C@@H]1COc1ccc(F)cc1]

To a solution of TRANS-3-[(4-fluorophenoxy)methyl]-2-[(4-methoxyphenyl)methyl]-4-methyl-4-azabicyclo[3.1.1]heptane (p52, 140 mg, 0.39 mmol) in Methanol (10 mL) ammonium formate (248.37 mg, 3.94 mmol) and palladium dihydroxide (27.66 mg, 0.04 mmol) were added. The reaction was stirred at 65° C. for 1 h. The mixture was cooled down then filtered over celite and concentrated under vacuum. The residue was purified by SCX cartridge first washing with MeOH and then eluting with NH$_3$ 1 M in MeOH affording TRANS-3-[(4-fluorophenoxy)methyl]-4-methyl-2-azabicyclo[3.1.1]heptane (p53, 92 mg, y=quant) as yellow oil. The product was used in the next step without further purification.

MS (m/z): 236.3 [MH]$^+$.

Preparation 54: CIS-{4-methyl-2-azabicyclo[3.1.1]heptan-3-yl}methanol

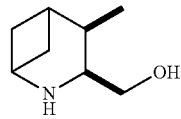

To a solution of CIS-[2-[(4-methoxyphenyl)methyl]-4-methyl-2-azabicyclo[3.1.1]heptan-3-yl]methanol (p46, 300 mg, 1.15 mmol) in Methanol (8.5 mL), ammonium formate (723.83 mg, 11.48 mmol) and palladium dihydroxide (81.76 mg, 0.110 mmol) were added. Reaction was heated to reflux and stirred at the same temperature for 30 min. Then it was cooled down to RT, the catalyst was filtered out and filtrate was evaporated to dryness. Crude was loaded on a SCX cartridge washing with MeOH and eluting with 1N ammonia solution in MeOH to afford CIS-(4-methyl-2-azabicyclo[3.1.1]heptan-3-yl)methanol (p54, 155 mg, y=95%).

MS (m/z): 142.2 [MH]$^+$.

Preparation 55: TRANS-{4-methyl-2-azabicyclo[3.1.1]heptan-3-yl}methanol

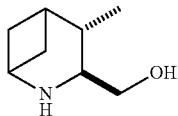

To a solution of TRANS-[2-[(4-methoxyphenyl)methyl]-4-methyl-2-azabicyclo[3.1.1]heptan-3-yl]methanol (p47, 600 mg, 2.3 mmol) in Methanol (50 mL) ammonium formate (1447.66 mg, 22.96 mmol) and palladium dihydroxide (161.19 mg, 0.23 mmol) were added. The reaction was left to stir at 60° C. for 1 h. The reaction was filtered over celite and concentrated under vacuum. The residue was purified by SCX cartridge first washing with MeOH and then eluting with NH$_3$ 1 M in MeOH affording TRANS-(4-methyl-2-azabicyclo[3.1.1]heptan-3-yl)methanol (p55, 311 mg, y=96%) as yellow oil. The product was used in the next step without further purifications.

MS (m/z): 142.1 [MH]$^+$.

Preparation 56: methyl 3-bromo-6-methylpyridine-2-carboxylate

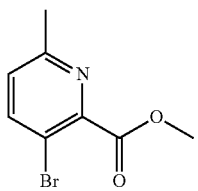

3-Bromo-6-methylpyridine-2-carboxylic acid (1.5 g, 6.94 mmol) was dissolved in MeOH (25 mL) and SOCl$_2$ (0.6 mL, 8.33 mmol) was added dropwise. The resulting solution was refluxed O/N. The day after volatiles were removed under vacuum, the residue was dissolved with water, the pH was adjusted to 7 with NaHCO$_3$, and the product was extracted with DCM (2×). The organic phase was dried and evaporated affording methyl 3-bromo-6-methylpyridine-2-carboxylate (p56, 1.35 g, y=84%) as yellow oil.

NMR ($^1$H, DMSO-d6): δ ppm 8.07-8.14 (m, 1H), 7.36-7.44 (m, 1H), 3.90 (s, 3H), 2.47 (s, 3H)

Preparation 57: methyl 6-methyl-3-(pyrimidin-2-yl)pyridine-2-carboxylate

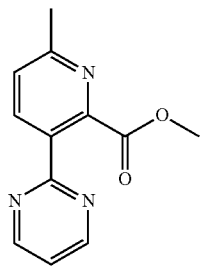 [SMILES: COC(=O)c1nc(C)ccc1-c1ncccn1]

methyl 3-bromo-6-methylpyridine-2-carboxylate (p56, 0.5 g, 2.17 mmol), 2-(Tributylstannyl)pyrimidine (0.76 mL, 2.39 mmol), Pd(PPh3)4 (250 mg, 0.22 mmol) were mixed in dioxane (10 mL) in a microwave vial. The solution was degassed for 2 min then irradiated for 1 h at 160° C. After cooling down the solution was filtered over Celite, rinsing with EtOAc. The solvent was removed under vacuum and the residue was purified by FC on silica gel (eluting from cHex to 40% AcOEt) to afford methyl 6-methyl-3-(pyrimidin-2-yl)pyridine-2-carboxylate (p57, 100 mg, y=20%).

MS (m/z): 230.0 [MH]$^+$.

Preparation 58: 6-methyl-3-(pyrimidin-2-yl)pyridine-2-carboxylic acid

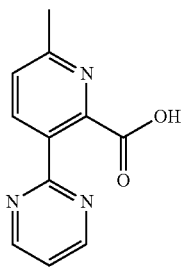 [SMILES: Cc1ccc(-c2ncccn2)c(C(=O)O)n1]

methyl 6-methyl-3-(pyrimidin-2-yl)pyridine-2-carboxylate (p57, 100 mg, 0.43 mmol) was dissolved in EtOH/H$_2$O (4/1 mL) then NaOH (86 mg, 2.15 mmol) was added. The resulting mixture was stirred at 100° C. for 3 hrs. Then the solution was cooled down, EtOH was removed under vacuum and the aqueous phase was acidified with 1N HCl until pH 2/3. Volatiles were removed under vacuum, the residue was purified by RP on C18 cartridge (from H$_2$O+0.1% HCOOH to 20% AcCN+0.1% HCOOH) to afford 6-methyl-3-(pyrimidin-2-yl)pyridine-2-carboxylic acid (p58, 80 mg, y=87%) as white solid.

MS (m/z): 216.1 [MH]$^+$.

Preparation 59: methyl 5-methyl-2-(tetramethyl-1,3,2-dioxaborolan-2-yl)benzoate

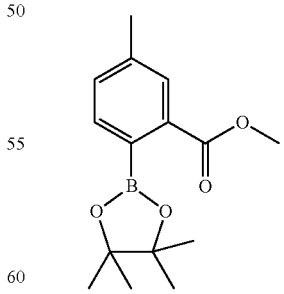

To a solution of methyl 2-iodo-5-methylbenzoate in 2-MeTHF (25 mL) triethylamine (3.0 mL, 21.7 mol) was added and the solution was degassed with N$_2$. Pinacol borane (1.56 mL, 10.8 mol) was added slowly (over 15 minutes) to the stirring solution while maintaining the purge.

The solution was further degassed for 10 minutes and Tri-o-tolylphosphine (110 mg, 0.36 mol) was added followed by Palladium (II) acetate (50 mg, 0.22 mol). This caused the reaction to turn black immediately with a slow exothermic from 11° C. to 25° C. At this point a delayed exothermic was observed and the reaction temperature increased to 60° C. (over 45 minutes). The reaction temperature was increased to 77° C. and aged for 2 hours. The heat source was removed and the reaction was cooled for 1 hour. A 26 w/w % ammonium chloride solution was added very slowly to control gas evolution and exothermic which caused a black precipitated to form. The supernatant was transferred to the extractor which already contained 43 mL of water. The remaining black slurry was filtered and washed with diethyl ether. The solution was transferred to a separatory funnel and the layers were separated. The crude was purified by FC on silica gel (eluent: Cy/EtoAc 8/2) affording methyl 5-methyl-2-(tetramethyl-1,3,2-dioxaborolan-2-yl)benzoate (p59, 1.51 g, y=76%).

MS (m/z): 276.0 [M]+.

Preparation 60: methyl 5-methyl-2-(pyrimidin-2-yl)benzoate

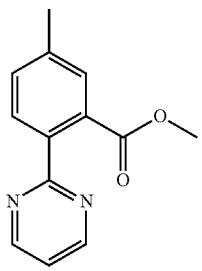

To a solution of methyl 5-methyl-2-(tetramethyl-1,3,2-dioxaborolan-2-yl)benzoate (p59, 1.51 g, 5.5 mmol) in 2-MeTHF (20 mL), 2-chloropyrimidine (0.756 g, 6.6 mmol) and Sodium carbonate (1.75 g, 16.5 mmol) were added. To this stirring suspension water (4 mL) was added. The thick slurry was degassed with nitrogen for 40 minutes, then PdCl$_2$(dppf)-CH$_2$Cl$_2$ adduct (0.163 g, 0.2 mmol) was added. The internal temperature was set to 74° C. and the mixture stirred for 16 hrs. The reaction was gone to completion therefore it was cooled to room temperature and treated with water (6 mL) and diethyl ether (12 mL) while maintaining stirring for 10 minutes. This solution was filtered washing with further diethyl ether (12 mL) and water (8 mL) then 12 mL of diethyl ether more. The layers was separated, organic one was dried and concentrated and the crude purified by FC on silica gel (eluent: Cy/EtoAc 7/3) affording methyl 5-methyl-2-(pyrimidin-2-yl)benzoate (p60, 231 mg, y=18%).

MS (m/z): 228.0 [MH]+.

Preparation 61: 5-methyl-2-(pyrimidin-2-yl)benzoic acid

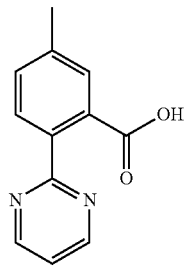 [SMILES: Cc1ccc(-c2ncccn2)c(C(=O)O)c1]

To a solution of methyl 5-methyl-2-(pyrimidin-2-yl)benzoate (p60, 231 mg, 1.01 mmol) in 2-Me-THF (4 mL) water (2.5 mL) and sodium hydroxide solution (10 N) (1.25 mL) were added.

The reaction turned red, the mixture was heated to 72° C. and stirred at that temperature overnight. The reaction was gone to completion; therefore it was cooled down to RT and transferred to an extractor washing with water and diethyl ether. The layers were separated and the aqueous phase was back-extracted twice with diethyl ether. The aqueous layer was acidified with HCl (12 N). A precipitated was formed, that was filtered washing with water and dried affording 5-methyl-2-(pyrimidin-2-yl)benzoic acid (p61, 140 mg, y=65%) as white solid.

MS (m/z): 214.0 [MH]+.

Preparation 62: 5-methyl-2-(2H-1,2,3-triazol-2-yl)-benzoic acid

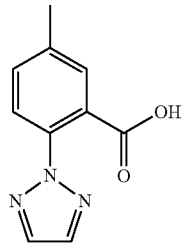

To a solution of methyl 2-iodo-5-methylbenzoate (1.00 g, 3.6 mmol) in DMF (3.5 mL), 1H-1,2,3-triazole (530 mg, 7.7 mmol), cesium carbonate (2.49 g, 7.6 mmol), copper (I) iodide (40 mg, 0.21 mmol) and (R,R)-(−)-N,N-Dimethyl-1,2-cyclohexanediamine (110 mg, 0.77 mmol) were added. The mixture was stirred at 120° C. microwave irradiation for 20 min, then an additional run of 10 min was performed. The mixture was diluted with water (50 mL) and washed with ethyl acetate (2×30 mL). The aqueous layer was acidified by adding of HCl 1N and extracted with ethyl acetate (3×25 mL). The combined organic layers were dried over anhydrous sodium sulphate, filtered and concentrated in vacuo. The residue was purified by FC on silica gel (eluting from DCM/MeOH 95:5 to 85:15) affording 5-methyl-2-(2H-1,2,3-triazol-2-yl)-benzoic acid (p62, 495 mg, y=51%) as pale orange solid.

MS (m/z): 204.0 [MH]+.

Preparation 63: methyl 3-amino-6-methylpyridine-2-carboxylate

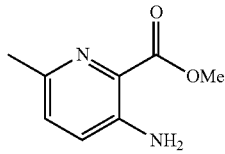

Step a:

6-methylpyridine-2,3-dicarboxylic acid (5.50 g, 30.36 mmol) was dissolved in Acetic anhydride (14.3 mL) and the mixture heated at 100° C. under nitrogen for 5 hours. Volatiles were removed under vacuum to give 2-methyl-5H, 7H-furo[3,4-b]pyridine-5,7-dione (Int. a, 4.97 g).

Step b:

2-methyl-5H,7H-furo[3,4-b]pyridine-5,7-dione (Int. a, 4.97 g, 30.47 mmol) was added portion wise over 5 minutes to MeOH (30 mL) at 0° C. under stirring. The mixture was stirred at 0° C. for 30 minutes, then at room temperature for other 2.5 hrs. The solution was evaporated under reduced pressure and the residue recrystallized from toluene (60 mL). Recrystallization was repeated three times affording a mixture of 2-(methoxycarbonyl)-6-methylpyridine-3-carboxylic acid and 3-(methoxycarbonyl)-6-methylpyridine-2-carboxylic acid (Int. b, 2.7 g) as yellow solid.

Step c:

Int. b (2.7 g, 13.85 mmol) was suspended in toluene (100 mL) and DIPEA (2.9 mL, 16.64 mmol) was added. The mixture was stirred 10 minutes at room temperature, then Diphenyl azidophospate (4.05 g, 14.7 mmol) was added in one portion and the mixture was heated to reflux and stirred at that temperature for 1 hour. The solution was cooled to room temperature and t-BuOH (5.82 mL, 61 mmol) was added in one portion. The mixture was then stirred at 70° C. for 1 hour and then cooled to room temperature. Et$_2$O was added and the resulting solution washed with NaHCO$_3$ satured solution. The water phases were combined and back-extracted with Et$_2$O. The combined organics were then dried over Na$_2$SO$_4$ and evaporated under reduced pressure. Crude was purified by FC on silica gel (eluent: Cy/EtOAc 7/3) affording methyl 3-{[(tert-butoxy)carbonyl]amino}-6-methylpyridine-2-carboxylate (Int. c, 2 g) as a white solid.

Step d:

Int. c (2 g, 7.5 mmol) was dissolved in DCM (50 mL) and then TFA (7.5 mL, 97.5 mmol) was added and the mixture stirred at RT overnight. Solvent was removed under reduced pressure and crude purified by SCX cartridge washing with MeOH and eluting with NH$_3$ 1 M in MeOH affording methyl 3-amino-6-methylpyridine-2-carboxylate (p63, 1.2 g, y=24% over 4 steps).

MS (m/z): 166.9 [MH]$^+$.

Preparation 64: methyl 3-iodo-6-methylpyridine-2-carboxylate

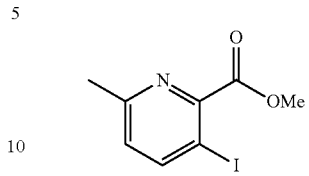

HCl 6N solution in water (30.75 mL, 41 mmol) was added to methyl 3-amino-6-methylpyridine-2-carboxylate (p63, 1.2 g, 7.22 mmol) and the resulting pale yellow mixture was diluted with water (2×10 mL) and then cooled to 0° C. (internal temperature).

A solution of sodium nitrite (0.730 g, 10.6 mmol) in water (5 mL) was dropped into the mixture over 1 minute. The mixture was stirred at 0° C. for 30 minutes, then a solution of KI (2.6 g, 15.5 mmol) in water (5 mL) was added over 1 minute and the mixture was left under stirring for 1 hour (temperature between 0° C. and +5° C.). AcOEt and water were added, phases were separated and the aqueous one was back-extracted with AcOEt. Combined organics were washed with NaHCO$_3$ saturated solution; aqueous solution from previous extraction was neutralised with NaHCO$_3$ satured solution and extracted with EtOAc. All the combined organic phases were dried over Na$_2$SO$_4$ and concentrated under reduced pressure. Crude was purified by FC on silica gel (eluent: Cy/EtOAc 7/3) affording methyl 3-iodo-6-methylpyridine-2-carboxylate (p64, 1.2 g, y=60%).

MS (m/z): 277.8 [M]$^+$.

Preparation 65: 6-methyl-3-(1,3-thiazol-2-yl)pyridine-2-carboxylic acid

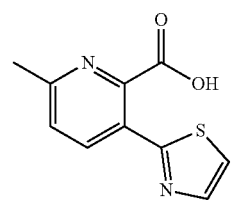

Step a:

A mixture of methyl 3-iodo-6-methylpyridine-2-carboxylate (p64, 1.2 g, 4.33 mmol), 2-(tributylstannyl)-1,3-thiazole (1.5 mL, 4.64 mmol) and Pd(Ph$_3$P)$_4$ (0.500 g, 0.433 mmol) in 1,4-Dioxane (10 mL) was stirred at RT overnight. The mixture was diluted with EtOAc and washed with NH$_4$Cl (saturated solution) and corrected with HCl 1N until pH about 5-6. The organic phase was separated and the aqueous phase was further extracted with EtOAc. The combined organics were washed, dried over Na$_2$SO$_4$, and filtered. The crude was purified by FC on silica gel (eluent: Cy/EtOAc 7/3) affording methyl 6-methyl-3-(1,3-thiazol-2-yl)pyridine-2-carboxylate (Int. a, 0.61 g).

Step b:

A mixture of Int. a (0.61 g, 2.60 mmol) and LiOH (0.164 g, 3.90 mmol) in THF (10 mL) and water (10 mL) was stirred at RT overnight. The mixture was diluted with EtOAc and washed with NH$_4$Cl (saturated solution) and pH adjusted to 5-6 with HCl. The organic phase was separated and the aqueous phase was back-extracted with EtOAc. The combined organics were washed, dried over Na₂SO₄, and filtered. The solvent was evaporated affording 6-methyl-3-(1,3-thiazol-2-yl)pyridine-2-carboxylic acid (p65, 0.6 g, y=63% over 2 steps) as a white solid.

MS (m/z): 176.9 [MH]⁺.

Preparation 66:
5-methyl-2-(1,3-thiazol-2-yl)benzoic acid

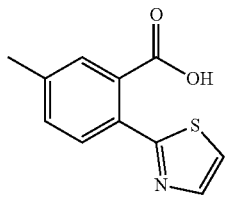

Step a:
2-(tributylstannyl)-1,3-thiazole (0.629 mL, 2 mmol) was dissolved in dioxane (4 mL) in a microwave tube, then methyl 2-iodo-5-ethylbenzoate (0.568 mL, 2.4 mmol) and Palladium Tetrakis (232 mg, 0.1 mmol) were added. Once the solid dissolved, the mixture was heated to 120° C. in a microwave reactor for 60 minutes. The mixture was then quenched with water and extracted with DCM. The organic phase was dried and concentrated under reduced pressure and the crude purified by FC on NH column (eluent: Cy:AcOEt 7:3) affording methyl 5-methyl-2-(1,3-thiazol-2-yl)benzoate (Int. a, 0.46 g).

Step b:
A mixture of Int. a (0.46 g, 1.97 mmol) and LiOH (0.124 g, 2.96 mmol) in THF (10 mL) and water (10 mL) was stirred at RT overnight. The mixture was diluted with EtOAc and washed with NH₄Cl (saturated solution) and pH adjusted to 5-6 with HCl 1N. The organic phase was separated and the aqueous phase was back-extracted with EtOAc. The combined organics were washed, dried over Na₂SO₄, and filtered. The solvent was evaporated affording 5-methyl-2-(1,3-thiazol-2-yl)benzoic acid (p66, 0.43 g, y=quant) as a white solid.

MS (m/z): 176.9 [MH]⁺.

Preparation 67: 6-methyl-3-(2H-1,2,3-triazol-2-yl)pyridine-2-carboxylic acid

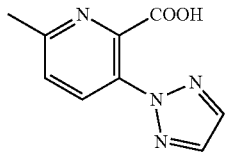

To a 3-necked, round-bottomed flask equipped with an overhead magnetic stirrer, reflux condenser, and nitrogen inlet were added 3-bromo-6-methylpyridine-2-carboxylic acid (5.0 g, 23.14 mmol), copper iodide (0.221 g, 1.16 mmol), and Cs₂CO₃ (15.08 g, 46.28 mmol). To these solids was added dioxane (25 mL), then water (1 mL), then 1H-1,2,3-triazole (2.7 mL, 46.28 mmol), and finally Trans-N,N'-dimethyl-cyclohexane-1,2-diamine (0.730 mL, 4.63 mmol). The mixture was then heated to 100° C. and stirred at that temperature overnight. The day after the mixture was cooled down to RT and MTBE and water were added. After vigorous mixing, the layers were separated and the bottom aqueous layer was acidified to pH 2 with 6N HCl. The resulting precipitate was removed by filtration affording a first crop of target compound (1 g). The mother-liquors were concentrated and purified by FC on C18 cartridge (eluent: from H₂O+0.1% formic acid to H₂O/ACN+0.1% formic acid 95:5). The fractions containing desired product were evaporated and combined with the previous crop affording 6-methyl-3-(2H-1,2,3-triazol-2-yl)pyridine-2-carboxylic acid (p67, 2.3 g, y=49%). Mixed fractions from FC were evaporated affording a less pure batch of target compound (1.2 g, 95% purity).

MS (m/z): 205.1 [M]⁺.

Preparation 68: ethyl 5-bromo-2-methyl-1,3-thiazole-4-carboxylate

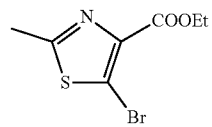

To a solution of 2-methyl-4-thiazolecarboxylic acid ethyl ester (3 g, 17.52 mmol) in MeCN (30 mL), 1-bromopyrrolidine-2,5-dione (6.24 g, 35.04 mmol) was added. Reaction was heated to reflux and stirred at the same temperature for 20 hrs. Then it was cooled down to RT and then cooled to 0° C. ss NaHCO₃(aq) was added and mixture was stirred for 15 min at the same temperature. MeCN was removed under reduced pressure and DCM was added. Aqueous layer was extracted several times with DCM, Combined organic layers were dried and concentrated under reduced pressure. Crude was purified by FC on silica gel (eluent: Cy/EtOAc from 100:0 to 70:30) to afford ethyl 5-bromo-2-methyl-1,3-thiazole-4-carboxylate (p68, 2.95 g, y=67%) as a pale orange solid.

MS (m/z): 249.8 [M]⁺.

Preparation 69: ethyl 2-methyl-5-pyrimidin-2-yl-1,3-thiazole-4-carboxylate

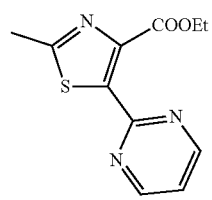 [SMILES: CCOC(=O)c1nc(C)sc1-c1ncccn1]

To a solution of ethyl 5-bromo-2-methyl-1,3-thiazole-4-carboxylate (p68, 250.11 mg, 1 mmol) in DMF (12 mL), cesium fluoride (305.82 mg, 2 mmol), Copper(I) iodide (19.05 mg, 0.100 mmol) and palladium triphenylphosphine (115.56 mg, 0.100 mmol) were added and mixture was degassed with nitrogen for 20 min. tributyl(2-pyrimidinyl)stannane (0.32 mL, 1 mmol) was added and the reaction was sealed and stirred under microwave irradiation at 130° C. for 30 min. Reaction was diluted with EtOAC and 1M KF aq.

solution was added. The two phases were stirred at room temperature for 1 h and then separated. Organic layer was dried over Na$_2$SO$_4$ and solvent was removed under reduced pressure. Crude was purified by FC on silica gel (eluent: Cy/EtOAc from 100:0 to 50:50) to afford ethyl 2-methyl-5-pyrimidin-2-yl-1,3-thiazole-4-carboxylate (p69, 92.5 mg, y=37%).

MS (m/z): 250.0 [MH]$^+$.

Preparation 70: 2-methyl-5-pyrimidin-2-yl-1,3-thiazole-4-carboxylic acid

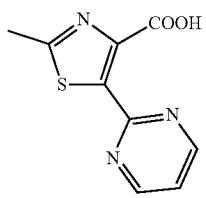

A solution of ethyl 2-methyl-5-pyrimidin-2-yl-1,3-thiazole-4-carboxylate (p69, 92.5 mg, 0.370 mmol) and 1M sodium hydroxide (1 mL, 1 mmol) in Ethanol (2.5 mL) was heated to 80° C. and stirred at that temperature for 30 min. The reaction was allowed to reach room temperature and then 2M HCl (aq.) was added until pH 4-5. The precipitate formed was filtered out, washed with water and dried under high vacuum to afford 2-methyl-5-pyrimidin-2-yl-1,3-thiazole-4-carboxylic acid (p70, 81.6 mg, y=quant).

MS (m/z): 221.9 [MH]$^+$.

Preparation 71: 5-(2-fluorophenyl)-2-methyl-1,3-thiazole-4-carboxylic acid

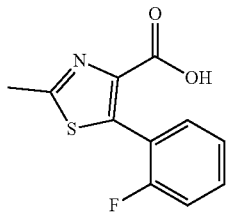 [SMILES: Cc1nc(C(=O)O)c(-c2ccccc2F)s1]

Step a:

A solution of 2-fluorobenzaldehyde (4.24 mL, 40.29 mmol) and methyl 2,2-dichloroacetate (4.17 mL, 40.29 mmol) in THF (15 mL) was added drop-wise to a stirred suspension of t-BuOK (4.52 g, 40.29 mmol) in THF (40 mL), at −60° C. and under a nitrogen atmosphere. The resulting reaction mixture was stirred 4 h at −60° C. then it was allowed to reach RT and stirred overnight. The mixture was concentrated in vacuo, DCM and ice-cold water were added, the organic phase was washed with water, dried over sodium sulfate and concentrated under reduced pressure. The crude material was purified by FC on silica gel (eluting with Cy/EA from 100/0 to 1/1) affording the product methyl 3-chloro-3-(2-fluorophenyl)-2-oxopropanoate (Int. a, 7.5 g) as brown oil. The product was used in the next step without further purifications.

Step b:

To a solution of Int. a (7.5 g, 32.52 mmol) in MeOH dry (60 mL) thioacetamide (2.44 g, 32.52 mmol) was added. The solution was stirred at 60° C. overnight. The reaction was concentrated under vacuum affording methyl 5-(2-fluorophenyl)-2-methyl-1,3-thiazole-4-carboxylate (Int. b, 9 g) as crude which was used in the next step without further purification.

Step c:

To a solution of Int. b (8.17 g, 32.52 mmol) in THF/H$_2$O/MeOH (50 mL/10 mL/50 mL) was added LiOH.H$_2$O (6.8 g, 162.6 mmol). The mixture was stirred overnight at RT then it was concentrated under reduced pressure, a s.s. of NaHCO$_3$ was added and the mixture diluted with DCM. Phases were separated and the aqueous phase was acified with HCl 1 N until pH=3 and extracted with AcOEt. The organic phase was washed with brine, dried over Na$_2$SO$_4$, filtered and concentrated under vacuum. The residue was purified by FC on C18 column (eluent: from 100% water+0.1% FA to 100% CH$_3$CN+0.1% FA) affording 5-(2-fluorophenyl)-2-methyl-1,3-thiazole-4-carboxylic acid (p71, 504 mg, y=6.5%) as yellow solid.

MS (m/z): 238.1 [MH]$^+$.

Preparation 72: 5-(4-fluorophenyl)-2-methyl-1,3-thiazole-4-carboxylic acid

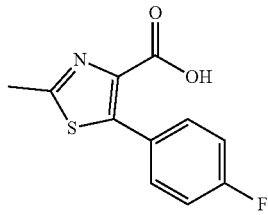 [SMILES: Cc1nc(C(=O)O)c(-c2ccc(F)cc2)s1]

Step a:

A solution of 4-fluorobenzaldehyde (3.46 mL, 32.25 mmol) and methyl 2,2-dichloroacetate (3.67 mL, 35.5 mmol) in THF (10 mL) was added by dropping funnel to a cooled suspension of t-ButOK (4.34 g, 38.7 mmol) in THF (40 mL) (T=−78° C.). After 4 hours at −78° C., the mixture was warmed to RT, and then stirred at that temperature overnight. The volatiles were then removed and the crude partitioned between water and DCM. Phases were separated and organic phase was dried and concentrated affording methyl 3-chloro-3-(4-fluorophenyl)-2-oxopropanoate (Int. a, 7.6 g) as crude material.

Step b:

Int. a (7.6 g, crude assumed 32.25 mmol) was dissolved in CH$_3$CN (60 mL) then

Thioacetamide (2.42 g, 32.25 mmol) and molecular sieves (4 Å) were added and the mixture stirred at RT overnight. Molecular sieves were removed and solvent evaporated. The residual yellow oil was dissolved in MeOH (50 mL) and the mixture heated at reflux for 4 hours. Then the mixture was cooled down to RT, 2 mL of HCl ~1.25 M solution in MeOH were added and the mixture was refluxed for further 2 hours. The mixture was then cooled down to RT, solvent eliminated under reduced pressure and the residue partitioned between water and DCM. Phases were separated and the organic one was dried and concentrated affording methyl 5-(4-fluorophenyl)-2-methyl-1,3-thiazole-4-carboxylate (Int. b, 1 g) that was used as crude in the next step.

Step c:

To a solution of Int. b (0.6 g, crude assumed 2.38 mmol) in THF (5 mL), water (5 mL) and lithium hydroxide (0.15 g, 3.57 mmol) were added and the solution was stirred overnight at RT. THF was eliminated under reduced pressure and the aqueous phase was acidified by addition of 6 N HCl. Water was removed under reduced pressure and the crude was purified by RP on C18 cartridge (from H₂O+0.1% HCOOH to 100% ACN +0.1% HCOOH) affording 5-(4-fluorophenyl)-2-methyl-1,3-thiazole-4-carboxylic acid (p72, 430 mg) as white solid.

MS (m/z): 238.1 [MH]⁺.

Preparation 73: methyl 2-amino-5-phenyl-1,3-thiazole-4-carboxylate

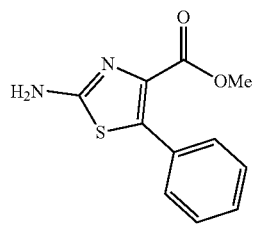 [SMILES: COC(=O)c1nc(N)sc1-c1ccccc1]

Step a:

A solution of benzaldehyde (9.6 mL, 94.23 mmol) and methyl 2,2-dichloroacetate (9.8 mL, 94.23 mL) in THF (30 mL) was added drop-wise to a stirred suspension of t-BuOK (10.57 g, 94.23 mmol) in THF (100 mL), at −60° C. and under a nitrogen atmosphere. The resulting reaction mixture was stirred 4 h at −60° C. then it was allowed to reach RT and stirred overnight. The mixture was concentrated in vacuo, DCM and ice-cold water were added, the organic phase was washed with water, dried over sodium sulfate and concentrated under reduced pressure.

The crude material was purified by FC on silica gel in portions (eluting with Cy/EA from 100/0 to 78/22) affording methyl 3-chloro-2-oxo-3-phenylpropanoate (Int. a, 5 g overall) as colourless oil.

Step b:

A solution of Int. a (1.01 g, 4.75 mmol) in acetone (6 mL) was added to a suspension of thiourea (0.36 g, 4.75 mmol) in acetone (10 mL) and the resulting reaction mixture was stirred overnight at 58° C. (external temperature). The mixture was filtered, the solid was washed with acetone and dried under vacuum affording methyl 2-amino-5-phenyl-1,3-thiazole-4-carboxylate (p73, 0.70 g, y=16% over 2 steps) as white solid.

MS (m/z): 235.0 [MH]⁺.

Preparation 74: methyl 2-chloro-5-phenyl-1,3-thiazole-4-carboxylate

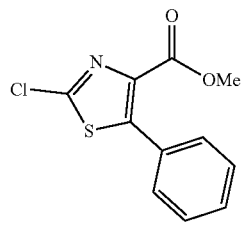 [SMILES: COC(=O)c1nc(Cl)sc1-c1ccccc1]

To a stirred mixture of methyl 2-amino-5-phenyl-1,3-thiazole-4-carboxylate (p73, 0.35 g, 1.49 mmol) in MeCN (6 mL), at RT and under a nitrogen atmosphere, CuCl₂ (260 mg, 1.94 mmol) was added followed by slow drop-wise addition of 3-methylbutyl nitrite (0.3 mL, 2.24 mmol) and the resulting reaction mixture was stirring at RT for 5 hrs. The mixture was filtered and the solution concentrated under reduced pressure. The residue was taken up with DCM and water, the organic phase was washed with water, dried over sodium sulfate and concentrated under vacuum. The crude material was purified by FC on silica gel (eluent: Cy/acetone from 100/0 to 85/15) affording methyl 2-chloro-5-phenyl-1,3-thiazole-4-carboxylate (p74, 195 mg, y=51%) as white solid.

MS (m/z): 254.0 [MH]⁺.

Preparation 75: 2-chloro-5-phenyl-1,3-thiazole-4-carboxylic acid

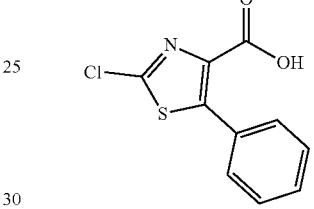

To a solution of methyl 2-chloro-5-phenyl-1,3-thiazole-4-carboxylate (p74, 310 mg, 1.22 mmol) in THF/MeOH (7/4 mL) was added a solution of LiOH.H₂O (513 mg, 12.22 mmol) in water (2 mL) and the resulting mixture was stirred overnight at RT. The mixture was concentrated under vacuum and the residue was taken up with DCM and aqueous 1N solution of HCl up to ~pH 5-6. The mixture was submitted to a phase separator cartridge and the solution was concentrated under vacuum affording 2-chloro-5-phenyl-1,3-thiazole-4-carboxylic acid (p75, 241 mg, y=82%) as white solid.

MS (m/z): 240.0 [MH]⁺.

Preparation 76: 2-methoxy-5-phenyl-1,3-thiazole-4-carboxylic acid

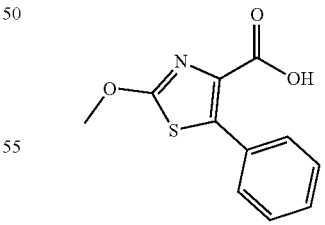

To a stirred solution of methyl 2-chloro-5-phenyl-1,3-thiazole-4-carboxylate (p75, 383 mg, 1.51 mmol) in MeOH (8 mL), at RT and under a nitrogen atmosphere, MeONa (163 mg, 3.02 mmol) was added portion-wise and the resulting reaction mixture was stirred overnight at 50° C. and then for 36 hrs at RT. The mixture was concentrated under reduced pressure and the residue taken up with DCM and water (aqueous 1 M HCl was added to the mixture up to pH ~6), the organic phase was dried over phase separator cartridge and concentrated under reduced pressure. Crude was first purified by FC on silica gel (eluent: DCM/MeOH from 100/0 to 98/2), then by RP on C18 cartridge (from H₂O+0.1% HCOOH to 100% ACN +0.1% HCOOH) affording 2-methoxy-5-phenyl-1,3-thiazole-4-carboxylic acid (p76, 100 mg, y=27%) as pale yellow solid.

MS (m/z): 236.1 [MH]⁺.

Preparation 77: 2-cyclopropyl-5-phenyl-1,3-thiazole-4-carboxylic acid

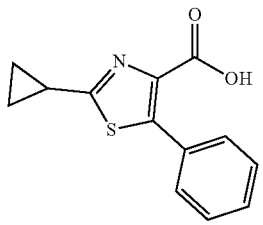 [SMILES: O=C(O)c1nc(C2CC2)sc1-c1ccccc1]

Step a:

A solution of benzaldehyde (9.6 mL, 94.23 mmol) and methyl 2,2-dichloroacetate (9.8 mL, 94.23 mL) in THF (30 mL) was added drop-wise to a stirred suspension of t-BuOK (10.57 g, 94.23 mmol) in THF (100 mL), at −60° C. and under a nitrogen atmosphere. The resulting reaction mixture was stirred 4 h at −60° C. then it was allowed to reach RT and stirred overnight. The mixture was concentrated in vacuo, DCM and ice-cold water were added, the organic phase was washed with water, dried over sodium sulfate and concentrated under reduced pressure.

The crude material was purified by FC on silica gel in portions (eluting with Cy/EA from 100/0 to 78/22) affording methyl 3-chloro-2-oxo-3-phenylpropanoate (Int. a, 5 g overall) as colourless oil.

Step b:

A solution of Int. a (360 mg, 1.69 mmol) in MeCN (4 mL), cyclopropanecarbothioamide (171 mg, 1.69 mmol) and molecular sieves (0.2 g) were added and the reaction mixture was shaken overnight at RT. No reaction was detected by UPLC analysis. The mixture was concentrated under reduced pressure, methanol (5 mL) was added and the mixture was shaken overnight at 60° C. The mixture was filtered and the filtrate concentrated under reduced pressure. The residue was purified by FC on silica gel (eluent: Cy/EA from 100/0 to 85/15) affording methyl 2-cyclopropyl-5-phenyl-1,3-thiazole-4-carboxylate (Int. b, 135 mg).

Step c:

To a solution of Int. b (135 mg, 0.52 mmol) in THF/H₂O/MeOH (2.5 mL/1 mL/0.5 mL) was added LiOH.H₂O (109 mg, 2.60 mmol). The mixture was stirred overnight at RT. The mixture was concentrated under reduced pressure, the residue was taken up with HCl 1 N aqueous solution and the resulting mixture was extracted with DCM. The organic phase was dried over a phase separator cartridge and the solution was concentrated under vacuum. Crude was purified by RP on C18 cartridge (from H₂O+0.1% HCOOH to 70% ACN +0.1% HCOOH) affording 2-cyclopropyl-5-phenyl-1,3-thiazole-4-carboxylic acid (p77, 53 mg) as white solid.

MS (m/z): 235.0 [MH]⁺.

Preparation 78: [2-(2-methyl-5-phenyl-1,3-thiazole-4-carbonyl)-2-azabicyclo[3.1.1]heptan-3-yl]methanol

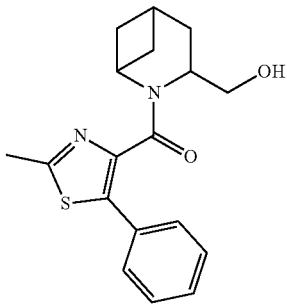 [SMILES: Cc1nc(C(=O)N2C(CO)CC3CC2C3)c(-c2ccccc2)s1]

2-methyl-5-phenyl-1,3-thiazole-4-carboxylic acid (235 mg, 1.07 mmol) was dissolved in DMF (5 mL), then HATU (479 mg, 1.26 mmol) was added followed by DIPEA (0.370 mL, 2.13 mmol). The resulting solution was stirred for 10 min then 2-azabicyclo[3.1.1]heptan-3-ylmethanol (p19, 123 mg, 0.97 mmol) in DMF (1 mL) was added and the mixture stirred for 1 hr. The mixture was diluted with NH₄Cl ss and DCM, the two phases were separated and the product was extracted twice with DCM. Combined organics were dried over phase separator and evaporated. The residue was purified by FC on NH column (eluent: from Cy to EtOAc 100%) affording [2-(2-methyl-5-phenyl-1,3-thiazole-4-carbonyl)-2-azabicyclo[3.1.1]heptan-3-yl]methanol (p78, 160 mg, y=50%) as pale yellow foam.

MS (m/z): 329.2 [MH]⁺.

Preparation 79: {2-[5-(4-fluorophenyl)-2-methyl-1,3-thiazole-4-carbonyl]-2-azabicyclo[3.1.1]heptan-3-yl}methanol

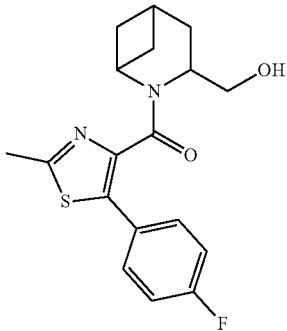 [SMILES: Cc1nc(C(=O)N2C(CO)CC3CC2C3)c(-c2ccc(F)cc2)s1]

To a solution of 5-(4-fluorophenyl)-2-methyl-1,3-thiazole-4-carboxylic acid (p72, 78.3 mg, 0.33 mmol) in DMF (2 mL) HATU (148 g, 0.39 mmol) and DIPEA (0.1 mL, 0.66 mmol) were added. The mixture was stirred at room temperature for 30 min and added to a solution of 2-azabicyclo[3.1.1]heptan-3-yl}methanol hydrochloride (p20, 50 mg, 0.30 mmol) and DIPEA (0.07 mL, 0.36 mmol) in DMF (1 mL). The reaction was stirred at room temperature for 1 h, water was added and the reaction was concentrated under vacuum. The residue was purified by FC C18 cartridge (eluent from 100% H₂O+0.1% FA to CH₃CN+0.1% 100%) affording {2-[5-(4-fluorophenyl)-2-methyl-1,3-thiazole-4-carbonyl]-2-azabicyclo[3.1.1]heptan-3-yl}methanol (p79, 0.076 g, y=73%) as yellow oil.

MS (m/z): 347.0 [MH]$^+$.

The following intermediates were prepared using an analogue procedure as in Preparation 79, reacting 2-azabicyclo[3.1.1]heptan-3-ylmethanol hydrochloride (p20) with the appropriate carboxylic acid (RCOOH) as reported in the table below.

| Prep. number | Structure | Name | RCOOH | MS (m/z): [MH]$^+$ | Y % |
|---|---|---|---|---|---|
| p80 | 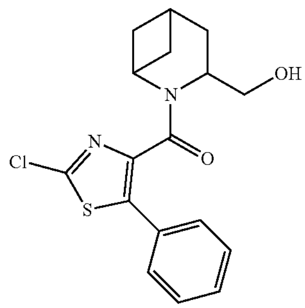 [SMILES: O=C(c1nc(Cl)sc1-c1ccccc1)N1C(CO)CC2CC1C2] | [2-(2-chloro-5-phenyl-1,3-thiazole-4-carbonyl)-2-azabicyclo[3.1.1]heptan-3-yl]methanol | p75 | 349.2 | 73 |
| p81 | 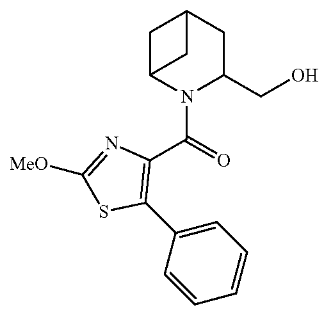 [SMILES: COc1nc(C(=O)N2C(CO)CC3CC2C3)c(-c2ccccc2)s1] | [2-(2-methoxy-5-phenyl-1,3-thiazole-4-carbonyl)-2-azabicyclo[3.1.1]heptan-3-yl]methanol | p76 | 345.2 | 60 |
| p82 | 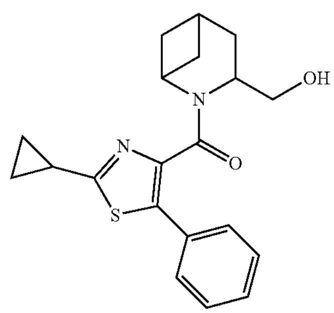 [SMILES: O=C(c1nc(C2CC2)sc1-c1ccccc1)N1C(CO)CC2CC1C2] | [2-(2-cyclopropyl-5-phenyl-1,3-thiazole-4-carbonyl)-2-azabicyclo[3.1.1]heptan-3-yl]methanol | p77 | 355.4 | 84 |

Preparation 83: CIS/TRANS [4-methyl-2-(2-methyl-5-phenyl-1,3-thiazole-4-carbonyl)-2-azabicyclo[3.1.1]heptan-3-yl]methanol

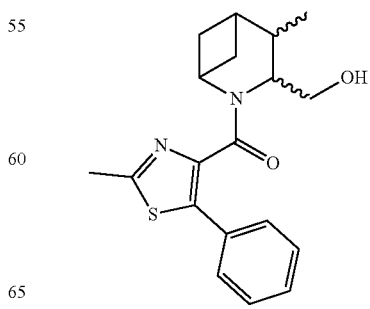

2-methyl-5-phenyl-1,3-thiazole-4-carboxylic acid (426 mg, 1.95 mmol) was dissolved in DMF (5 mL), then HATU (875 mg, 2.3 mmol) was added followed by DIPEA (0.4 mL, 2.3 mmol). The resulting solution was stirred for 30 min then it was added to a solution of CIS/TRANS {4-methyl-2-azabicyclo[3.1.1]heptan-3-yl}methanol (p39, 250 mg, 1.77 mmol) in DMF (2 mL) and stirred for 1 hr at RT. The mixture was diluted with s.s. of NaHCO$_3$ and extracted with AcOEt. The organic layer was washed with Brine, dried, filtered and concentrated under vacuum. The crude was purified by FC on silica gel (eluent: DCM to DCM/MeOH 8:2) and then by RP C18 cartridge (from Water/CH$_3$CN 95:5 with 0.1% of Formic acid to Water/CH$_3$CN 5:95 with 0.1% of Formic acid) affording CIS/TRANS [4-methyl-2-(2-methyl-5-phenyl-1,3-thiazole-4-carbonyl)-2-azabicyclo[3.1.1]heptan-3-yl]methanol (p83, 390 mg, y=64%, mixture of cis and trans diastereoisomers).

MS (m/z): 343.3 [MH]$^+$.

Preparation 84: CIS/TRANS {4-methyl-2-[6-methyl-3-(pyrimidin-2-yl)pyridine-2-carbonyl]-2-azabicyclo[3.1.1]heptan-3-yl}methanol

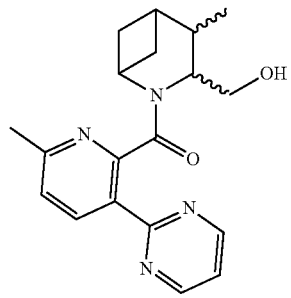 [SMILES: Cc1ccc(-c2ncccn2)c(C(=O)N2C3CC(C3)C(C)C2CO)n1]

To a solution of 6-methyl-3-(pyrimidin-2-yl)pyridine-2-carboxylic acid (p58, 703 mg, 3.27 mmol) in DMF (10 mL), HATU (1.24 g, 3.27 mmol) and DIPEA (1.14 mL, 6.53 mmol) were added. The mixture was stirred at room temperature for 30 min and then it was added to a solution of CIS/TRANS {4-methyl-2-azabicyclo[3.1.1]heptan-3-yl}methanol (p39, 419 mg, 2.97 mmol) in DMF (4 mL). The reaction was stirred at room temperature for 1 h. The reaction was concentrated under vacuum and the residue was purified by RP on C18 cartridge (eluent: from 100% H$_2$O+0.1% FA to CH$_3$CN+0.1% 100%) affording CIS/TRANS {4-methyl-2-[6-methyl-3-(pyrimidin-2-yl)pyridine-2-carbonyl]-2-azabicyclo[3.1.1]heptan-3-yl}methanol (p84, 230 mg, y=22%, mixture of cis and trans diastereoisomers).

MS (m/z): 339.1 [MH]$^+$.

Preparation 85: CIS-{4-methyl-2-[6-methyl-3-(2H-1,2,3-triazol-2-yl)pyridine-2-carbonyl]-2-azabicyclo[3.1.1]heptan-3-yl}methanol

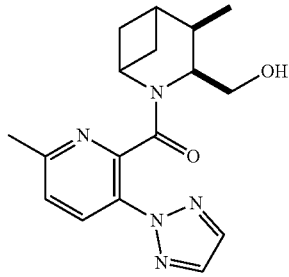 [SMILES: Cc1ccc(-n2nccn2)c(C(=O)N2C3CC(C3)[C@@H](C)[C@H]2CO)n1]

To a solution of 6-methyl-3-(triazol-2-yl)pyridine-2-carboxylic acid (p67, 478.05 mg, 2.34 mmol) and N,N-Diisopropylethylamine (0.39 mL, 2.34 mmol) in DMF (4 mL), HATU (890.19 mg, 2.34 mmol) was added. Mixture was stirred at room temperature for 30 min then it was added dropwise to a stirring solution of CIS-{4-methyl-2-azabicyclo[3.1.1]heptan-3-yl}methanol (p54, 290 mg, 1.95 mmol) in DMF (8 mL). The reaction was stirred at room temperature for 2 hrs. EtOAc was added and organic layer was washed with ss NaHCO$_3$, ss NH$_4$Cl and brine. Aqueous phases were back-extracted with EtOAc, organic layers were combined, dried and evaporated. Crude obtained was purified by FC on RP (eluent: H$_2$O+0.1% HCOOH/MeCN+0.1% HCOOH from 95:5 to 50:50) affording CIS-{4-methyl-2-[6-methyl-3-(2H-1,2,3-triazol-2-yl)pyridine-2-carbonyl]-2-azabicyclo[3.1.1]heptan-3-yl}methanol (p85, 353 mg, y=55%) as a white solid.

MS (m/z): 328.1 [MH]$^+$.

Preparation 86: TRANS-{4-methyl-2-[6-methyl-3-(2H-1,2,3-triazol-2-yl)pyridine-2-carbonyl]-2-azabicyclo[3.1.1]heptan-3-yl}methanol

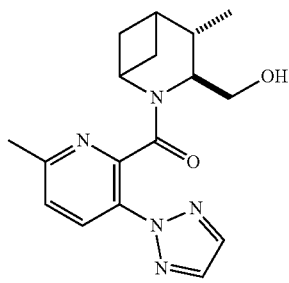 [SMILES: Cc1ccc(-n2nccn2)c(C(=O)N2C3CC(C3)[C@H](C)[C@H]2CO)n1]

To a solution of 6-methyl-3-(triazol-2-yl)pyridine-2-carboxylic acid (p67, 540 mg, 2.64 mmol) and HATU (1 g, 2.64 mmol) in DMF (12 mL) DIPEA (0.46 mL, 2.64 mmol) was added. The reaction was stirred at RT for 30 min and then added to a pre-cooled (0° C.) solution of TRANS-(2-methyl-4-azabicyclo[3.1.1]heptan-3-yl)methanol (p55, 311 mg, 2.2 mmol) in DMF (6 mL). The reaction was stirred at RT for 3 h, then s. s. solution of NaHCO$_3$ was added and the reaction was extracted with AcOEt. The organic phase was dried, filtered and concentrated under vacuum. The residue was purified by FC on silica gel (eluent: from cHex 100% to AcOEt 100%) TRANS-{4-methyl-2-[6-methyl-3-(2H-1,2, 3-triazol-2-yl)pyridine-2-carbonyl]-2-azabicyclo[3.1.1]heptan-3-yl}methanol (p86, 700 mg, y=97%) as yellow oil.
MS (m/z): 328.3 [MH]+.

Preparation 87: tert-butyl 3-{[(isoquinolin-3-yl)amino]methyl}-2-azabicyclo[3.1.1]heptane-2-carboxylate

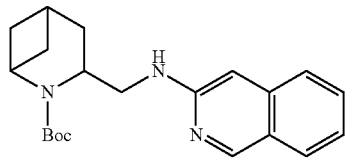 [SMILES: CC(C)(C)OC(=O)N1C(CNc2cc3ccccc3cn2)CC2CC1C2]

tert-butyl 3-formyl-2-azabicyclo[3.1.1]heptane-2-carboxylate (p30, 100 mg, 0.44 mmol) and isoquinolin-3-amine (63 mg, 0.44 mmol) were dissolved in DCM (3 mL), followed by AcOH (25 µL, 0.44 mmol). The mixture was stirred at RT for 15 min, then NaBH(OAc)₃ (131 mg, 0.62 mmol) was added and the reaction was shaken in a PLS apparatus at RT overnight. The reaction mixture was diluted with DCM, water was added and the two phases were separated. The organic one was concentrated and the crude was combined with crude from analogous preparation then purified by FC on NH column (eluent: Cy to EtOAc 30%) affording tert-butyl 3-{[(isoquinolin-3-yl)amino]methyl}-2-azabicyclo[3.1.1]heptane-2-carboxylate (p87, 94 mg) as green gum.
MS (m/z): 354.3 [MH]+.

The following intermediates were prepared using an analogue procedure as in Preparation 87, reacting tert-butyl 3-formyl-2-azabicyclo[3.1.1]heptane-2-carboxylate (p30) with the appropriate amine (R—NH₂) as reported in the table below.

Preparation 90: N-{2-azabicyclo[3.1.1]heptan-3-ylmethyl}isoquinolin-3-amine

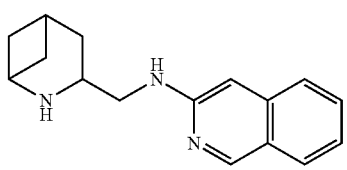

To a solution of tert-butyl 3-{[(isoquinolin-3-yl)amino]methyl}-2-azabicyclo[3.1.1]heptane-2-carboxylate (p87, 95 mg, 0.27 mmol) in DCM (3 mL), TFA (1 mL) was added and the reaction was stirred at RT for 2 h. Then it was concentrated under reduced pressure and the residue purified by SCX washing with MeOH and eluting with NH₃ 1 M in MeOH, affording N-{2-azabicyclo[3.1.1]heptan-3-ylmethyl}isoquinolin-3-amine (p90, 61.7 mg, y=88%) as green gum.
MS (m/z): 254.3 [MH]+.

The following intermediates were prepared using an analogue procedure as in Preparation 90, from the appropriate starting material as reported in the table below.

| Prep. | Structure | Name | RNH₂ | MS (m/z): [MH]+ | y % |
|---|---|---|---|---|---|
| p88 | 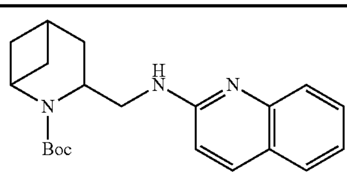 | tert-butyl 3-{[(quinolin-2-yl)amino]methyl}-2-azabicyclo[3.1.1]heptane-2-carboxylate | | 354.4 | 22 |
| p89 | 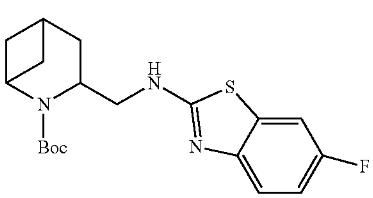 [SMILES: CC(C)(C)OC(=O)N1C(CNc2nc3ccc(F)cc3s2)CC2CC1C2] | Tert-butyl 3-{[(6-fluoro-1,3-benzothiazol-2-yl)amino]methyl}-2-azabicyclo[3.1.1]heptane-2-carboxylate | | 378.3 | 31 |

| Prep. | Structure | Name | SM | MS (m/z): [MH]+ | y % |
|---|---|---|---|---|---|
| p91 | 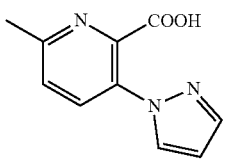 | N-{2-azabicyclo[3.1.1]heptan-3-ylmethyl}quinolin-2-amine | p88 | 254.3 | 89 |
| p92 | 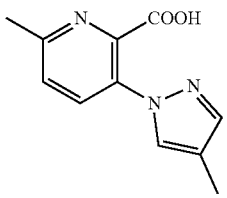 [SMILES: Cc1cnn(-c2ccc(C)nc2C(=O)O)c1] | N-{2-azabicyclo[3.1.1]heptan-3-ylmethyl}-6-fluoro-1,3-benzothiazol-2-amine | p89 | 278.2 | 90 |

Preparation 93: 6-methyl-3-pyrazol-1-ylpyridine-2-carboxylic acid

To a solution of 3-bromo-6-methylpyridine-2-carboxylic acid (500 mg, 2.31 mmol) in 1,4-Dioxane (2.5 mL)/Water (0.1 ml) 1H-pyrazole (157.57 mg, 2.31 mmol) was added, followed by CuI (22 mg, 0.12 mmol), (1R,2R)—N1,N2-dimethylcyclohexane-1,2-diamine (65.84 mg, 0.460 mmol) and cesium carbonate (1.52 g, 4.63 mmol). The reaction mixture was refluxed (100° C.) overnight. After cooling, MTBE and water were added. After vigorously stirring, the layers were separated and the bottom aqueous one was acidified to pH 2 with HCl 6N. It was extracted several times with EtOAc then combined organics were dried and concentrated to afford 6-methyl-3-pyrazol-1-ylpyridine-2-carboxylic acid (p93, 393 mg, y=84%).

MS (m/z): 204.1 [MH]+

Preparation 94: 6-methyl-3-(4-methyl-1H-pyrazol-1-yl)pyridine-2-carboxylic acid To a 2-necked, round-bottomed flask equipped with an overhead magnetic stirrer, reflux condenser, and nitrogen inlet were added 3-bromo-6-methylpyridine-2-carboxylic acid (0.50 g, 2.314 mmol), copper iodide (22 mg, 0.116 mmol), and Cs₂CO₃ (1.5 g, 4.63 mmol). To these solids were added dioxane (3 mL), then water (0.12 mL), then 4-methylpyrazole (0.38 mL, 4.63 mmol), and finally Trans-N,N'-dimethyl-cyclohexane-1,2-diamine (0.073 mL, 0.463 mmol). The mixture was then warmed to 105° C. for 6 hours. The mixture was cooled and then MTBE and water were added. After vigorous mixing, the layers were separated and the bottom aqueous layer was acidified to pH 2 with 6N HCl. The resulting precipitate was removed by filtration. The mother-liquors were concentrated and purified by RP on C18 column (eluent: from H₂O+0.1% formic acid to H₂O:MeCN+0.1% formic acid 75:25). The fractions containing desired product were evaporated to afford 6-methyl-3-(4-methyl-1H-pyrazol-1-yl)pyridine-2-carboxylic acid (p94, 454 mg, y=88%) as white solid.

MS (m/z): 218.2 [MH]+

Preparation 95 and 96: 6-methyl-3-(4-methyl-2H-1,2,3-triazol-2-yl)pyridine-2-carboxylic acid (p95) and 6-methyl-3-(4-methyl-1H-1,2,3-triazol-1-yl)pyridine-2-carboxylic acid (p96)

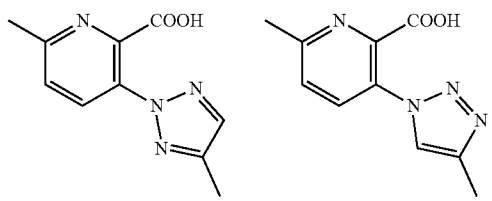 [SMILES: Cc1ccc(-n2ncc(C)n2)c(C(=O)O)n1 ; Cc1cn(-c2ccc(C)nc2C(=O)O)nn1]

3-bromo-6-methylpyridine-2-carboxylic acid (408 mg, 1.89 mmol) was dissolved in a mixture of 1,4-Dioxane (2 mL)\Water (0.200 mL), then 4-Methyl-1H-1,2,3-triazole (236 mg, 2.84 mmol), cesium carbonate (1.24 g, 3.78 mmol), CuI (18 mg, 0.09 mmol) and (1R,2R)—N1,N2-dimethylcyclohexane-1,2-diamine (54 mg, 0.38 mmol) were added. The mixture was stirred at 120° C. for 2 hrs. Reaction mixture was cooled to RT and then water and MTBE were added. After vigorously stirring, the layers were separated and the aqueous one was acidified to pH 2 with HCl 6N. The acidic solution was concentrated and purified by RP on C18 column [eluting H₂O (0.1% HCOOH)/CH₃CN from 100:0 to 60:40] affording 6-methyl-3-(4-methyl-2H-1,2,3-triazol-2-yl)pyridine-2-carboxylic acid (p95, 274 mg, y=66% yield) and 6-methyl-3-(4-methyl-1H-1,2,3-triazol-1-yl)pyridine-2-carboxylic acid (p96, 40 mg, y=10%) as a white solids.

P95

MS (m/z): 219.2 [MH]+

1H NMR (MeOD-d4) δ 8.17 (d, 1H), 7.72 (s, 1H), 7.54 (br. s., 1H), 2.62 (br. s., 3H), 2.38 (s, 3H)

P96

MS (m/z): 219.2 [MH]+

1H NMR (MeOD-d4) δ 8.05 (s, 1H), 7.94 (d, 1H), 7.62 (d, 1H), 2.67 (s, 3H), 2.40 (s, 3H)

Preparation 97: methyl 3-bromo-6-methylpyridine-2-carboxylate

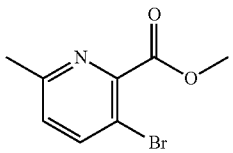

3-bromo-6-methylpyridine-2-carboxylic acid (1 g, 4.63 mmol) was dissolved in Methanol (16 mL) and thionyl chloride (0.41 mL, 5.55 mmol) was added dropwise. The resulting solution was refluxed overnight. Solvent was removed under vacuum. The residue was dissolved in water and pH was adjusted to 7 with NaHCO₃. The product was extracted twice with DCM. Combined organics were evaporated to afford methyl 3-bromo-6-methylpyridine-2-carboxylate (p97, 879 mg, y=82%).

MS (m/z): 232.1 [MH]+

Preparation 98: methyl 6'-methyl-[2,3'-bipyridine]-2'-carboxylate

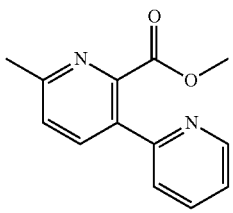

methyl 3-bromo-6-methylpyridine-2-carboxylate (p97, 879 mg, 3.82 mmol), CuI (36 mg, 0.19 mmol), Pd(PPh₃)₄ (221 mg, 0.19 mmol) and tributyl(2-pyridinyl)stannane (1.22 mL, 3.82 mmol) were mixed in 1,2-dimethoxyethane (20 mL). The solution was degassed with N₂ for 10 min and then it was stirred at 100° C. overnight. After cooling, the mixture was concentrated under vacuum. The residue was purified by FC on SiO₂ column (eluent from Cy to EtOAc 70%) to afford methyl 6'-methyl-[2,3'-bipyridine]-2'-carboxylate (p98, 700 mg, y=80%).

MS (m/z): 229.2 [MH]+

Preparation 99: 6'-methyl-[2,3'-bipyridine]-2'-carboxylic acid

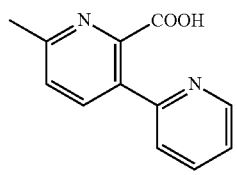 [SMILES: Cc1ccc(-c2ccccn2)c(C(=O)O)n1]

A mixture of methyl 6'-methyl-[2,3'-bipyridine]-2'-carboxylate (p98, 700 mg, 3.07 mmol) and lithium hydroxide hydrate (197.67 mg, 4.6 mmol) in THF (20 mL)/Water (20 mL) was stirred to RT overnight. THF was removed under vacuum and the aqueous residue was washed with DCM. Then it was acidified with HCl 6N to pH 3 and concentrated under vacuum. The residue was purified by RP on C18 column (eluent from water+0.1% formic ac. to MeCN+0.1% formic ac. 10%) to afford 6'-methyl-[2,3'-bipyridine]-2'-carboxylic acid (p99, 449 mg, y=68%).

MS (m/z): 215.2 [MH]+

Preparation 100: 3-(5-fluoropyrimidin-2-yl)-6-methylpyridine-2-carbonitrile

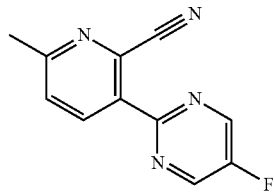 [SMILES: Cc1ccc(-c2ncc(F)cn2)c(C#N)n1]

Step a:

2,2,6,6-tetramethylpiperidine (8.72 mL, 51.7 mmol) was dissolved in dry THF (62 mL) under argon and stirred at −30° C.; n-Butyl lithium (21.33 mL, 53.32 mmol) 2.5 M in hexane was added over 5 m. The yellow solution was stirred at −30° C. for 20 min, then chilled at −78° C. and tripropan-2-yl borate (10.94 mL, 47.4 mmol) was added over 5 min. After 10 min at −78° C., 6-methyl-2-pyridinecarbonitrile (5000 mg, 42.32 mmol) dissolved in dry THF (35 mL) was added dropwise (over 20 min) maintaining internal temperature below −73° C. and the mixture became dark-brown. The mixture was stirred at −73° C. for 6 hrs. The mixture was quenched with acetic acid (5.94 mL, 103.75 mmol) dropwise at −73° C. (the temperature never exceeded −60° C.). The cooling bath was removed and the mixture left to reach the room temperature: during this period the mixture became thick and new THF (15 mL) had to be added in order to have a better stirring. The mixture was stirred 10 min at RT then 2,2-dimethylpropane-1,3-diol (6022.5 mg, 57.83 mmol) was added in one portion and the mixture stirred at RT overnight. The solvent was evaporated and the orange residue taken-up with DCM and 10% water solution of KH₂PO₄. The phases were separated and the water phase was back-extracted with DCM. The combined organic phases were washed with 10% water solution of KH₂PO₄ (50 ml). The DCM was evaporated. The residue was dissolved in Et₂O and extracted with NaOH 0.05 M (5×250 mL, boronic ester in water phase). The aqueous phases were joined together and the pH was adjusted between pH=4 and pH=5 with 10% water solution of KH$_2$PO$_4$ (50 mL). The so obtained yellow solution was extracted with EtOAc and DCM. All the organics joined together were dried (Na$_2$SO$_4$) and evaporated to afford 3-(5,5-dimethyl-1,3,2-dioxaborinan-2-yl)-6-methylpyridine-2-carbonitrile (Int a: 3.8 mg) which was used in the next step without purification.

Step b:

To a solution of 3-(5,5-dimethyl-1,3,2-dioxaborinan-2-yl)-6-methylpyridine-2-carbonitrile (250 mg, 0.65 mmol) and 2-bromo-5-fluoropyrimidine (115 mg, 0.65 mmol) in 1,4-Dioxane (2.6 mL) CsF (199.4 mg, 1.3 mmol), Pd(PPh$_3$)$_4$ (37.67 mg, 0.03 mmol) and CuI (22 mg, 0.11 mmol) were added. Mixture was degassed with nitrogen for 10 min, then sealed and shaken in a PLS apparatus at 65° C. overnight. Solvent was removed under reduced pressure and crude was purified by FC on SiO$_2$ (Cy/EtOAc from 100; 0 to 80:20) affording 3-(5-fluoropyrimidin-2-yl)-6-methylpyridine-2-carbonitrile (p100, 102 mg, y=73% yield) as a yellow solid.

MS (m/z): 215.0 [MH]$^+$

Preparation 101: 3-(5-fluoropyrimidin-2-yl)-6-methylpyridine-2-carboxylic acid

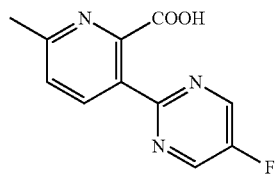 [SMILES: Cc1ccc(-c2ncc(F)cn2)c(C(=O)O)n1]

3-(5-fluoropyrimidin-2-yl)-6-methylpyridine-2-carbonitrile (p100, 102 mg, 0.48 mmol) was partially dissolved in HCl 6M in water (6 mL, 36 mmol), heated to 100° C. and stirred at the same temperature for 5 hrs. Solvent was removed under reduced pressure and crude was purified by RP on C18 column (H$_2$O+0.1% HCOOH/MeCN+0.1% HCOOH from 95:5 to 85:15) affording 3-(5-fluoropyrimidin-2-yl)-6-methylpyridine-2-carboxylic acid (p101, 74 mg, y=67%) as a pale yellow solid.

MS (m/z): 234.0 [MH]$^+$

Preparation 102: 6-methyl-3-(5-methylpyrimidin-2-yl)pyridine-2-carbonitrile

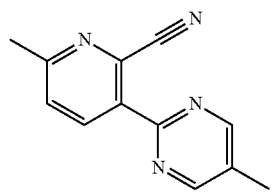

6-methyl-3-(5-methylpyrimidin-2-yl)pyridine-2-carbonitrile (p102, 63 mg, y=46%) was prepared using an analogue procedure as in Preparation 100, reacting 2-chloro-5-methylpyrimidine with the 3-(5,5-dimethyl-1,3,2-dioxaborinan-2-yl)-6-methylpyridine-2-carbonitrile (Int a of prep100).

MS (m/z): 211.0 [MH]$^+$

Preparation 103: 6-methyl-3-(5-methylpyrimidin-2-yl)pyridine-2-carboxylic acid

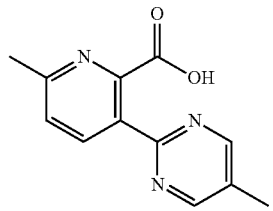

6-methyl-3-(5-methylpyrimidin-2-yl)pyridine-2-carbonitrile (p102, 63 mg, 0.3 mmol) was suspended in HCl 6M (4 mL, 24 mmol) in water and heated at 100° C. overnight. Mixture was left to cool to RT and NaHCO$_3$ was added to reach pH 4-5. Solvent was removed under reduced pressure and crude was purified by RP on C18 column (H$_2$O+0.1% HCOOH/MeCN+0.1% HCOOH from 95:5 to 85:15) affording 6-methyl-3-(5-methylpyrimidin-2-yl)pyridine-2-carboxylic acid (p103, 8.5 mg, y=12%).

MS (m/z): 230.0 [MH]$^+$

Preparation 104: 6-methyl-3-[5-(trifluoromethyl)pyrimidin-2-yl]pyridine-2-carbonitrile

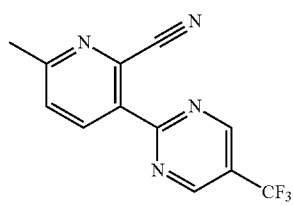 [SMILES: Cc1ccc(-c2ncc(C(F)(F)F)cn2)c(C#N)n1]

6-methyl-3-[5-(trifluoromethyl)pyrimidin-2-yl]pyridine-2-carbonitrile (p104, 111 mg, y=64%) was prepared using an analogue procedure as in Preparation 100, reacting 2-chloro-5-(trifluoromethyl)pyrimidine with the 3-(5,5-dimethyl-1,3,2-dioxaborinan-2-yl)-6-methylpyridine-2-carbonitrile (Int a of prep100).

MS (m/z): 265.0 [MH]$^+$

Preparation 105: 6-methyl-3-[5-(trifluoromethyl)pyrimidin-2-yl]pyridine-2-carboxylic acid

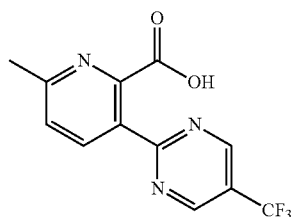

6-methyl-3-[5-(trifluoromethyl)pyrimidin-2-yl]pyridine-2-carbonitrile (p104, 111 mg, 0.42 mmol) was partially dissolved in HCl 6M (6 mL, 36 mmol). Reaction was heated at 100° C. and stirred at the same temperature for 3 hrs. Solvent was removed under reduced pressure and crude was purified by RP on C18 column (H₂O+0.1% HCOOH/MeCN+0.1% HCOOH from 95:5 to 75:25) to afford 6-methyl-3-[5-(trifluoromethyl)pyrimidin-2-yl]pyridine-2-carboxylic acid (p105, 58 mg, y=49%) as a pale yellow solid.

MS (m/z): 284.0 [MH]⁺

Preparation 106: ethyl 2-methyl-5-pyridin-2-yl-1,3-thiazole-4-carboxylate

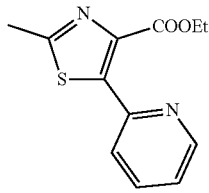 [SMILES: CCOC(=O)c1nc(C)sc1-c1ccccn1]

To a solution of ethyl 5-bromo-2-methyl-1,3-thiazole-4-carboxylate (p68, 1 g, 3.64 mmol) in DMF (50 mL), cesium fluoride (1.11 g, 7.28 mmol), CuI (69.29 mg, 0.360 mmol) and PPh₃ (420.44 mg, 0.360 mmol) were added and mixture was degassed with nitrogen for 20 min. tributyl(2-pyridinyl)stannane (1.18 mL, 3.64 mmol) was added and reaction was stirred at 100° C. overnight.

The reaction mixture was diluted with EtOAc and 1M KF aq. solution was added. The two phases were stirred at room temperature for 1 h and then separated. Organic layer was dried over Na₂SO₄ and solvent was removed under reduced pressure. Crude material was purified by FC on SiO₂ column (eluent from Cy to EtOAc 50%) to afford ethyl 2-methyl-5-pyridin-2-yl-1,3-thiazole-4-carboxylate (p106, 400 mg, y=44% yield).

MS (m/z): 249.0 [MH]⁺

Preparation 107: 2-methyl-5-pyridin-2-yl-1,3-thiazole-4-carboxylic acid

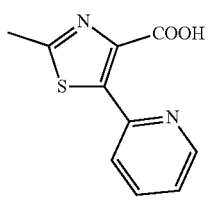

A solution of ethyl 2-methyl-5-pyridin-2-yl-1,3-thiazole-4-carboxylate (p106, 400 mg, 1.61 mmol) and 1M NaOH (4.82 mL, 4.82 mmol) in Ethanol (12.5 mL) was heated to 80° C. and stirred at that temperature for 30 min, then at RT overnight. Ethanol was removed under reduced pressure and 2M HCl was added dropwise until pH 4-5. Water was concentrated and the residue was dissolved in a mixture of DCM and MeOH. The suspension obtained was filtered and the solid discarded. Solvents were concentrated and the residue purified by FC on C18 column (eluent from water+0.1% formic ac. to MeCN+0.1% formic ac. 10%) to afford 2-methyl-5-pyridin-2-yl-1,3-thiazole-4-carboxylic acid (p107, 262 mg, y=74%) as white solid.

NMR (¹H, DMSO-d6): δ 13.67 (br. s., 1H) 8.61 (dt, 1H) 7.88-7.97 (m, 2H) 7.42 (ddd, 1H) 2.65-2.72 (m, 3H)

Preparation 108: ethyl 2-methyl-5-pyrazin-2-yl-1,3-thiazole-4-carboxylate

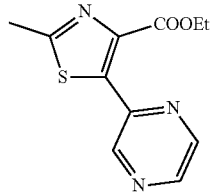 [SMILES: CCOC(=O)c1nc(C)sc1-c1cnccn1]

To a solution of ethyl 5-bromo-2-methyl-1,3-thiazole-4-carboxylate (p68, 1 g, 3.64 mmol) in DMF (50 mL), CuI (69.29 mg, 0.36 mmol), PPh₃ (420.44 mg, 0.36 mmol) and cesium fluoride (1.11 g, 7.28 mmol) were added and the mixture was degassed with nitrogen for 20 min. tributyl(2-pyrazinyl)stannane (1.15 mL, 3.64 mmol) was added and reaction was stirred at 100° C. overnight.

The reaction was cooled down to RT and diluted with EtOAc and then 1M KF aq. solution was added. The two phases were left stirring at RT for 1 h and then separated. Aqueous layer was extracted twice with EtOAc. Combined organics were dried over Na₂SO₄ and solvent was removed under reduced pressure. Crude was dissolved in DCM and the resulting suspension was filtered through a phase separator. The filtrate was concentrated under vacuum and the residue was purified by FC on SiO₂ column (eluent from Cy to EtOAc 30%) to afford ethyl 2-methyl-5-pyrazin-2-yl-1,3-thiazole-4-carboxylate (p108, 368 mg, y=41%) as yellow solid.

MS (m/z): 250.2 [MH]⁺

Preparation 109: 2-methyl-5-pyrazin-2-yl-1,3-thiazole-4-carboxylic acid

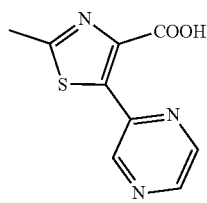

A solution of ethyl 2-methyl-5-pyrazin-2-yl-1,3-thiazole-4-carboxylate (p108, 368 mg, 1.48 mmol) and 1M sodium hydroxide (3.98 mL, 3.98 mmol) in Ethanol (12 mL) was stirred at RT overnight.

Ethanol was removed under reduced pressure and 2M HCl (aq.) was added until pH 4-5. Precipitate formation was observed. Precipitate was filtered out, washed with water and dried under high vacuum to afford a first crop of wanted product. Mother liquor were purified by RP on C18 column (eluent from water+0.1% formic ac. to MeCN+0.1% formic ac. 17%) to afford a second batch that was mixed with the previous one to afford 2-methyl-5-pyrazin-2-yl-1,3-thiazole-4-carboxylic acid (p109, 303.6 mg, y=93%) as white solid.

NMR (¹H, DMSO-d6): δ 13.34 (br. s., 1H) 9.13 (d, 1H) 8.68-8.71 (m, 1H) 8.63 (d, 1H) 2.72 (s, 3H)

Preparation 110: 5-bromo-2-methyl-1,3-thiazole-4-carboxylic acid

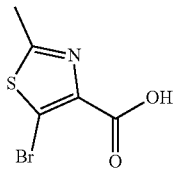

To a mixture of ethyl 5-bromo-2-methyl-1,3-thiazole-4-carboxylate (p68, 0.41 g, 1.64 mmol) in 3.3 mL of EtOH was added at RT an aqueous solution of NaOH (3.3 mL, 6.56 mmol, 2M). The resulting mixture was stirred at RT for 2 hours. Aqueous NH$_4$Cl ss and 1.3 mL of HCl 6N were added to the mixture and then was extracted with EtOAc (4×). The collected organic layers were dried over Na$_2$SO$_4$, filtered, concentrated under vacuum to give 5-bromo-2-methyl-1,3-thiazole-4-carboxylic acid (p110, 367 mg y=quant).

MS (m/z): 223.9 [MH]$^+$

Preparation 111: 2-methyl-5-(1H-1,2,3-triazol-1-yl)-1,3-thiazole-4-carboxylic acid and 2 methyl-5-(2H-1,2,3-triazol-2-yl)-1,3-thiazole-4-carboxylic acid

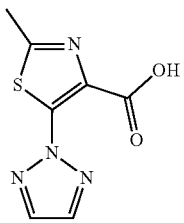 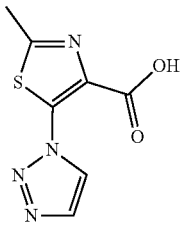

To a 2-necked, round-bottomed flask equipped with an overhead magnetic stirrer, reflux condenser, and nitrogen inlet were added 5-bromo-2-methyl-1,3-thiazole-4-carboxylic acid (p110, 0.100 g, 0.45 mmol), CuI (5 mg), and Cs$_2$CO$_3$ (0.295 g, 0.90 mmol). To these solids were added dioxane (1.5 mL), then water (0.06 mL), then 1 h-1,2,4-triazole (61 mg, 0.90 mmol), and finally Trans-N,N'-dimethyl-cyclohexane-1,2-diamine (0.02 mL). The mixture was then warmed to 100° C. for 18 hrs. The mixture was cooled and then MTBE and water were added. After vigorous mixing, the layers were separated and the bottom aqueous layer was acidified to pH 2 with 6N HCl. The resulting precipitate was removed by filtration. The mother-liquors were concentrated and purified by RP on C18 column (eluent: from H$_2$O+0.1% formic acid to H$_2$O:MeCN+0.1% formic acid 75:25). The fractions containing desired product were evaporated to afford a mixture of 2-methyl-5-(1H-1,2,3-triazol-1-yl)-1,3-thiazole-4-carboxylic acid and 2 methyl-5-(2H-1,2,3-triazol-2-yl)-1,3-thiazole-4-carboxylic acid (p111, 125 mg, y=50%).

MS (m/z): 210.9 [MH]$^+$

Preparation 112: ethyl 5-(5-chloropyridin-3-yl)-2-methyl-1,3-thiazole-4-carboxylate

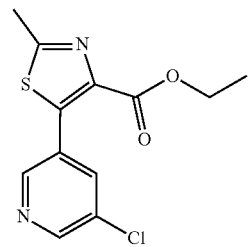 [SMILES: CCOC(=O)c1nc(C)sc1-c1cncc(Cl)c1]

To a mixture of potassium carbonate (218.8 mg, 1.58 mmol), ethyl 5-bromo-2-methyl-1,3-thiazole-4-carboxylate (p68, 200 mg, 0.72 mmol) and (5-chloro-3-pyridinyl)boronic acid (125 mg, 0.79 mmol) in DMF (2 mL), degassed under N$_2$, Pd(PPh$_3$)$_4$ (25 mg, 0.02 mmol) was added. The reaction mixture was degassed again under N$_2$ and stirred at 100° C. for 3.5 hrs. Starting material was still present, according by UPLC check. The mixture was cooled to RT and Pd(PPh$_3$)$_4$ (0.011 mmol, 12 mg), potassium carbonate (0.36 mmol, 50 mg) and (5-chloro-3-pyridinyl)boronic acid (0.36 mmol, 57 mg) were added. Then the reaction was stirred at 100° C. O/N. Starting material was still present, according by UPLC check. The mixture was cooled to RT and Pd(PPh$_3$)$_4$ (0.011 mmol, 12 mg), potassium carbonate (0.36 mmol, 50 mg) and (5-chloro-3-pyridinyl)boronic acid (0.36 mmol, 57 mg) were added. Then the reaction was stirred at 100° C. for further 4 hrs. After cooling to RT, solvent was removed under vacuum, then DCM and water were added and phases were separated. Aqueous one was extracted twice with DCM. Combined organics were dried and concentrated. The crude material was purified by FC on SiO$_2$ column (eluent from Cy to EtOAc 50%) to afford ethyl 5-(5-chloropyridin-3-yl)-2-methyl-1,3-thiazole-4-carboxylate (p112, 176.5 mg, y=87%) as yellow solid.

MS (m/z): 283.2 [MH]$^+$

Preparation 113: 5-(5-chloropyridin-3-yl)-2-methyl-1,3-thiazole-4-carboxylic acid

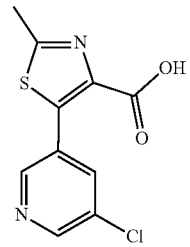 [SMILES: Cc1nc(C(=O)O)c(-c2cncc(Cl)c2)s1]

A solution of ethyl 5-(5-chloropyridin-3-yl)-2-methyl-1,3-thiazole-4-carboxylate (p112, 176 mg, 0.62 mmol) and 1M sodium hydroxide (1.68 mL, 1.68 mmol) in Ethanol (6 mL) was stirred at RT O/N. Ethanol was removed under reduced pressure and 2M HCl (aq.) was added until pH 4-5. Precipitate formation was observed. Precipitate was filtered out, washed with water and dried under high vacuum to afford 5-(5-chloropyridin-3-yl)-2-methyl-1,3-thiazole-4-carboxylic acid (p113, 134 mg, y=84%).

MS (m/z): 255.1 [MH]$^+$

Preparation 114: ethyl 2-methyl-5-(6-methylpyridin-2-yl)-1,3-thiazole-4-carboxylate

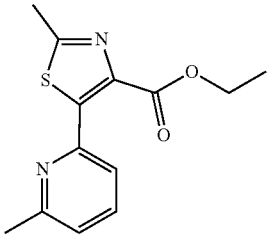 [SMILES: CCOC(=O)c1nc(C)sc1-c1cccc(C)n1]

To a solution of ethyl 5-bromo-2-methyl-1,3-thiazole-4-carboxylate (p68, 1 g, 3.64 mmol) in DMF (50 mL), CuI (70 mg, 0.36 mmol), Pd(PPh$_3$)$_4$ (420 mg, 0.36 mmol) and CsF (1.11 g, 7.28 mmol) were added and the mixture was degassed with nitrogen for 20 min. tributyl-(6-methyl-2-pyridinyl)stannane (1.23 mL, 3.64 mmol) was added and reaction was stirred at 100° C. overnight. Reaction was cooled to RT and diluted with EtOAc and 1M KF aq. solution was added. The two phases were stirred at room temperature for 4 hrs and then separated. Aqueous layer was extracted twice with EtOAc. Combined organics were dried over Na$_2$SO$_4$ and solvent was removed under reduced pressure. The crude material was dissolved in DCM and the resulting suspension was filtered. The filtrate was concentrated under vacuum and the residue was purified by FC on SiO$_2$ column (eluent from Cy to EtOAc 50%) to afford ethyl 2-methyl-5-(6-methylpyridin-2-yl)-1,3-thiazole-4-carboxylate (p114, 403 mg, y=42%) as orange oil.

MS (m/z): 263.2 [MH]$^+$

Preparation 115: 2-methyl-5-(6-methylpyridin-2-yl)-1,3-thiazole-4-carboxylic acid

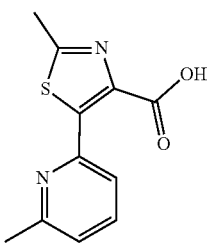 [SMILES: Cc1cccc(-c2sc(C)nc2C(=O)O)n1]

A solution of ethyl 2-methyl-5-(6-methylpyridin-2-yl)-1,3-thiazole-4-carboxylate (p114, 403 mg, 1.54 mmol) and 1M sodium hydroxide (4.14 mL, 4.14 mmol) in Ethanol (12 mL) was stirred at RT overnight. Ethanol was removed under reduced pressure and 2M HCl (aq.) was added until pH 4-5. Precipitate formation was observed. Precipitate was filtered out, washed with water and dried under high vacuum to afford 2-methyl-5-(6-methylpyridin-2-yl)-1,3-thiazole-4-carboxylic acid (p115, 291 mg, y=81%), as white solid.

MS (m/z): 235.2 [MH]$^+$

Preparation 116: ethyl 2-methyl-5-(6-methylpyridin-3-yl)-1,3-thiazole-4-carboxylate

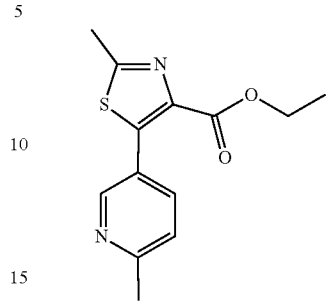

To a mixture of potassium carbonate (273.54 mg, 1.98 mmol), ethyl 5-bromo-2-methyl-1,3-thiazole-4-carboxylate (p68, 250 mg, 0.9 mmol) and Pd(PPh$_3$)$_4$ (3 mg, 0.03 mmol) in DMF (2 mL), degassed under N$_2$, (6-methyl-3-pyridinyl)boronic acid (135.51 mg, 0.99 mmol) was added. The reaction mixture was degassed again under N$_2$ and stirred at 100° C. for 6 hrs. Starting material was still present, according by UPLC check. The mixture was cooled to RT and Pd(PPh$_3$)$_4$ (0.014 mmol, 16 mg), potassium carbonate (0.45 mmol, 62 mg) and (6-methyl-3-pyridinyl)boronic acid (0.45 mmol, 62 mg) were added. Then the reaction was stirred at 100° C. O/N. The mixture was cooled to RT and Pd(PPh$_3$)$_4$ (0.014 mmol, 16 mg), potassium carbonate (0.45 mmol, 62 mg) and (6-methyl-3-pyridinyl)boronic acid (0.45 mmol, 62 mg) were added. Then the reaction was stirred at 100° C. for 5 hrs. The mixture was cooled to RT and Pd(PPh$_3$)$_4$ (0.014 mmol, 16 mg), potassium carbonate (0.45 mmol, 62 mg) and (6-methyl-3-pyridinyl)boronic acid (0.45 mmol, 62 mg) were added. Then the reaction was stirred at 100° C. O/N. Solvent was removed under vacuum, then DCM and water were added and phases were separated. Aqueous one was extracted twice with DCM. Combined organics were dried over a phase separator and concentrated. Crude material was purified RP on C18 column (eluent from water+0.1% HCOOH to MeCN+0.1% HCOOH 15%) to afford ethyl 2-methyl-5-(6-methylpyridin-3-yl)-1,3-thiazole-4-carboxylate (p116, 55 mg, y=23%) as yellow solid.

MS (m/z): 263.2 [MH]$^+$

Preparation 117: 2-methyl-5-(6-methylpyridin-3-yl)-1,3-thiazole-4-carboxylic acid

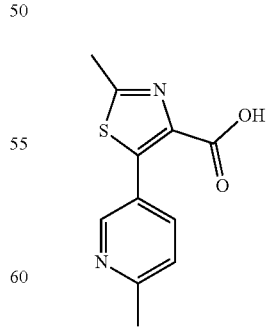

A solution of ethyl 2-methyl-5-(6-methylpyridin-3-yl)-1,3-thiazole-4-carboxylate (p116, 107 mg, 0.33 mmol) and 1M NaOH (0.88 mL, 0.88 mmol) in Ethanol (3 mL) was stirred at RT overnight. Ethanol was removed under reduced pressure and 2M HCl (aq.) was added until pH 4-5. Water was removed under reduced pressure and crude was purified by RP on C18 column (eluting H$_2$O+0.1% HCOOH/MeCN+0.1% HCOOH from 95:5 to 93:7) to afford 2-methyl-5-(6-methylpyridin-3-yl)-1,3-thiazole-4-carboxylic acid (p117, 96 mg, y=quant).

MS (m/z): 235.0 [MH]$^+$

Preparation 118: 2-methyl-5-(1H-pyrazol-1-yl)-1,3-thiazole-4-carboxylic acid

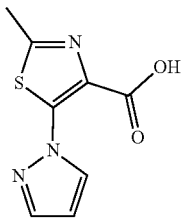

To a 2-necked, round-bottomed flask equipped with an overhead magnetic stirrer, reflux condenser, and nitrogen inlet were added 5-bromo-2-methyl-1,3-thiazole-4-carboxylic acid (p110, 0.100 g, 0.45 mmol), copper iodide (5 mg, 0.02 mmol), and Cs$_2$CO$_3$ (0.295 g, 0.900 mmol). To these solids were added dioxane (1.5 mL), water (0.06 mL), then 4-pyrazole (61 mg, 0.9 mmol), and finally Trans-N,N'-dimethyl-cyclohexane-1,2-diamine (0.02 mL, 0.09 mmol). The mixture was then warmed to 100° C. for 18 hours. The mixture was cooled and then MTBE and water were added. After vigorous mixing, the layers were separated and the bottom aqueous layer was acidified to pH 2 with 6N HCl. The aqueous solution was concentrated and purified by RP on C18 column (eluent: from H$_2$O+0.1% HCOOH to H$_2$O:MeCN+0.1% HCOOH 70:30). The fractions containing desired product were evaporated to afford 2-methyl-5-(1H-pyrazol-1-yl)-1,3-thiazole-4-carboxylic acid (p118, 88 mg, y=93%).

MS (m/z): 209.9 [MH]$^+$

Preparation 119: 5-fluoro-2-(2H-1,2,3-triazol-2-yl)benzoic acid

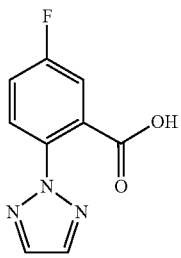 [SMILES: O=C(O)c1cc(F)ccc1-n1nccn1]

To a round-bottomed flask equipped with an overhead magnetic stirrer, reflux condenser, and nitrogen inlet were added 2-Bromo-5-fluorobenzoic acid (1 g, 4.57 mmol), copper iodide (0.045 g, 0.23 mmol), and Cs$_2$CO$_3$ (2.98 g, 9.13 mmol). To these solids were added dioxane (7 mL), water (0.035 ml), 1H-1,2,3-triazole (0.52 mL, 9.13 mmol), and finally trans-1,2-dimethylcyclohexane-1,2-diamine (0.145 mL, 0.91 mmol). The mixture was then warmed to 100° C. for 4 hrs. Then the mixture was cooled and MTBE and water were added. After vigorous mixing, the layers were separated and the bottom aqueous layer was acidified to pH 2 with 6N HCl. The aqueous phase was then extracted with DCM (3×). The combined organic layers were dried, and concentrated. The residue was purified by FC on SiO$_2$ column (eluting from DCM to DCM:MeOH 95:5) to afford 5-fluoro-2-(2H-1,2,3-triazol-2-yl)benzoic acid (p119, 0.52 g, y=55%) as white solid.

MS (m/z): 208.2 [MH]$^+$

Preparation 120: 5-chloro-2-(2H-1,2,3-triazol-2-yl)benzoic acid

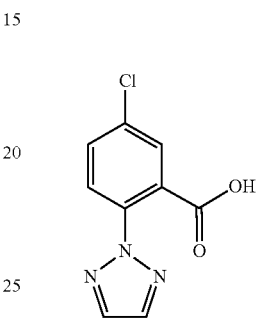

In a round-bottomed flask equipped with an overhead magnetic stirrer, reflux condenser, and nitrogen inlet were added 5-chloro-2-iodobenzoic acid (1.15 g, 4.07 mmol), copper iodide (0.04 g, 0.2 mmol), and Cs$_2$CO$_3$ (2.65 g, 8.14 mmol). To these solids were added dioxane (6 mL), water (0.05 mL), then 1H-1,2,3-triazole (0.47 mL, 8.14 mmol), and finally trans-1,2-dimethylcyclohexane-1,2-diamine (0.3 mL, 0.81 mmol). The mixture was then warmed to 100° C. for 4 hrs. Then the mixture was cooled and then MTBE and of water were added. After vigorous mixing, the layers were separated and the bottom aqueous layer was acidified to pH 2 with 6N HCl. The aqueous was then extracted twice with EtOAc. The combined organic layers were dried, filtered, and concentrated. The oil was stirred overnight in EtOAc (8 mL) and the resulting precipitate was removed by filtration affording a first crop of wanted product (100 mg). The mother-liquors were concentrated and purified by FC on SiO$_2$ column (eluting from DCM to DCM:MeOH: 90:10) to afford a second batch of the desired product that was mixed with the former to afford 5-chloro-2-(2H-1,2,3-triazol-2-yl)benzoic acid (p120, 620 mg, y=68%).

MS (m/z): 223.9 [MH]$^+$

Preparation 121: (3-ethoxy-6-methylpyridin-2-yl)methanol

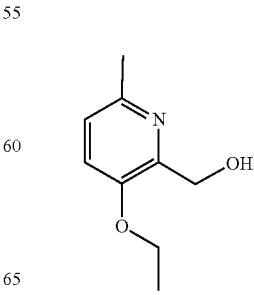

To a solution of 2-(hydroxymethyl)-6-methylpyridin-3-ol (2.0 g, 14.37 mmol) in DMF (20 mL) was added iodoethane (1.38 mL, 17.24 mmol) and potassium carbonate (9.92 g, 71.8 mmol). The reaction mixture was stirred at RT for 24 hrs then partitioned between diethyl ether and water. The organics were washed with brine, dried with $Na_2SO_4$, filtered and concentrated under vacuum to afford (3-ethoxy-6-methylpyridin-2-yl)methanol (p121, 1.05 g, 6.3 y=44%).

MS (m/z): 168.2 $[MH]^+$

Preparation 122:
3-ethoxy-6-methylpyridine-2-carboxylic acid

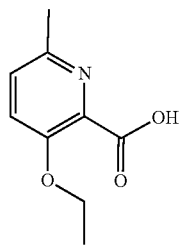

To a suspension of (3-ethoxy-6-methylpyridin-2-yl)methanol (p121, 1.05 g, 6.3 mmol) in water (5 mL) were added potassium hydroxide (0.353 g, 6.3 mmol) and $KMnO_4$ (2.0 g, 12.6 mmol) and the mixture was stirred at RT for 2 hrs. The reaction mixture was acidified to pH 4, filtered through pad of Celite® and concentrated under vacuum. The crude material was purified by RP on C18 column (eluting with Water+0.1% formic acid/MeCN+0.1% formic acid 90/10) to afford 3-ethoxy-6-methylpyridine-2-carboxylic acid (p122, 0.410 g, y=36%).

MS (m/z): 182.1 $[MH]^+$

Preparation 123: methyl
5-cyano-2-(2H-1,2,3-triazol-2-yl)benzoate

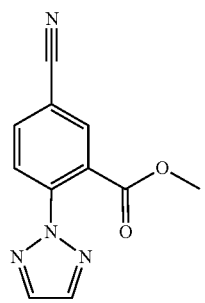 [SMILES: COC(=O)c1cc(C#N)ccc1-n1nccn1]

To a stirred solution of 1H-1,2,3-Triazole (0.26 mL, 4.52 mmol) in DMF (8 mL), at RT and under a nitrogen atmosphere, NaH 60% dispersion in oil (199 mg, 4.97 mmol) was added portion-wise. After 10 min, methyl 5-cyano-2-fluorobenzoate (890 mg, 4.97 mmol) was added portion-wise and the resulting reaction mixture was stirred at 85° C. for 4 hrs. After cooling at RT water and EA were added to the mixture, the organic phase was washed with water, dried over sodium sulphate and concentrated under reduced pressure. The crude material was purified by FC on $SiO_2$ column (eluting with Cy/EA from 100/0 to 75/25) methyl 5-cyano-2-(2H-1,2,3-triazol-2-yl)benzoate (p123, 360 mg, y=35% yield) as white solid.

MS (m/z): 229.0 $[MH]^+$

Preparation 124:
5-cyano-2-(2H-1,2,3-triazol-2-yl)benzoic acid

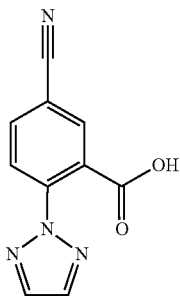 [SMILES: N#Cc1ccc(-n2nccn2)c(C(=O)O)c1]

methyl 5-cyano-2-(2H-1,2,3-triazol-2-yl)benzoate (p123, 412 mg, 1.32 mmol) was dissolved in THF (10 mL) and methanol (1 mL) then a solution of lithium hydroxide hydrate (68 mg, 1.58 mmol) in water (3 mL) was added and the reaction mixture was stirred O/N at RT. The mixture was concentrated under reduced pressure and the crude material was purified by RP on C18 column (eluting with MeCN/water (both added with 0.1% formic acid) from 0/100 to 20/80) to give 5-cyano-2-(2H-1,2,3-triazol-2-yl)benzoic acid (p124, 297 mg, y=quant) as white solid.

MS (m/z): 215.1 $[MH]^+$

Preparation 125: methyl
3-amino-6-methylpyrazine-2-carboxylate

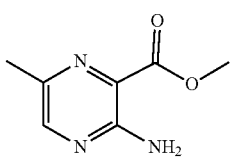

Methyl 3-amino-6-bromopyrazine-2-carboxylate (2 g, 8.62 mmol), $Pd_2(OAc)_3$ (0.2 g, 0.89 mmol) and Xantphos (0.79 g, 1.37 mmol) were placed in a closed vessel with toluene (30 mL) and water (1 mL). Methylboronic acid (0.78 g, 13.1 mmol) and potassium phosphate tribasic (3.42 g, 16.1 mmol) were added and the reaction mixture was heated to 115° C. for 1 h. The reaction mixture was allowed to reach RT, and then it was filtrate on Celite and washed with DCM. The filtrate was concentrate under vacuum and purified through FC on $SiO_2$ column (DCM:EtOAc from 98:2 to 85:15) affording methyl 3-amino-6-methylpyrazine-2-carboxylate (p125, 870 mg, y=60% yield) as a beige solid.

MS (m/z): 168.0 $[MH]^+$

Preparation 126: methyl
3-bromo-6-methylpyrazine-2-carboxylate

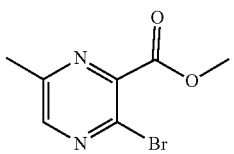

Br₂ (0.36 mL, 7.06 mmol) was added to a stirred mixture of methyl 3-amino-6-methylpyrazine-2-carboxylate (p125, 400 mg, 2.39 mmol) and HBr (2.82 mL, 11.96 mmol) at 0° C. A solution of sodium nitrite (412.75 mg, 5.98 mmol) in water (2.5 mL) was then added drop-wise at 0° C. The reaction mixture was stirred for 15 minutes at the same temperature. The reaction mixture was poured portion-wise into a mixture of aqueous saturated NaHCO₃ solution and ice and then extracted two times with DCM. The organic layer was washed with an aqueous 10% Na₂S₂O₃ solution, dried with Na₂SO₄, filtered and concentrated under vacuum. The crude material was purified by FC on SiO₂ (cHex/EtOAc from 90:10 to 70:30) to afford methyl 3-bromo-6-methylpyrazine-2-carboxylate (p126, 159 mg, y=29%) as a yellow oil.

MS (m/z): 232.9 [MH]⁺

Preparation 127: 6-methyl-3-(2H-1,2,3-triazol-2-yl)pyrazine-2-carboxylic acid

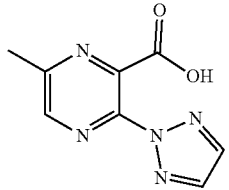

To a solution of methyl 3-bromo-6-methylpyrazine-2-carboxylate (p126, 281 mg, 1.22 mmol), 1H-1,2,3-Triazole (0.14 mL, 2.43 mmol) and (1R,2R)—N₁,N₂-dimethylcyclohexane-1,2-diamine (34.6 mg, 0.240 mmol) in 1,4-Dioxane (3.15 mL) and water (0.31 mL), cesium carbonate (792.5 mg, 2.43 mmol) and CuI (11.6 mg, 0.06 mmol) were added in a closed vessel. The blue suspension thus obtained was heated at 100° C. overnight, after that the mixture was concentrated under reduced pressure. The crude material was purified by RP on C18 (eluting H₂O:MeCN from 100:0 to 85:15) to give methyl 6-methyl-3-(2H-1,2,3-triazol-2-yl)pyrazine-2-carboxylate (p127, 105 mg, y=31%) as off-white solid.

MS (m/z): 206.0 [MH]⁺

Preparation 128: methyl 4-nitro-1H-pyrazole-3-carboxylate

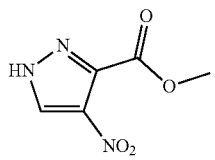

Thionyl chloride (6.28 mL, 86.07 mmol) was added to an ice cooled solution of 4-nitro-1H-pyrazole-3-carboxylic acid (10.4 g, 66.21 mmol) in methanol (150 mL). The resulting solution was stirred at RT O/N. The day after MeOH was removed under vacuum; toluene was added and dried again. The solid was suspended in pentane and filtered under vacuum to afford methyl 4-nitro-1H-pyrazole-3-carboxylate (p128, 11.15 g, y=98%) as creamy solid.

MS (m/z): 171.9 [MH]⁺

Preparation 129: methyl 1-methyl-4-nitro-1H-pyrazole-3-carboxylate

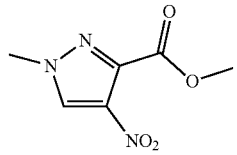

Step a

NaH 60% dispersion in oil (3.13 g, 78.2 mmol) was added portionwise to an ice cooled suspension of methyl 4-nitro-1H-pyrazole-3-carboxylate (p128, 11.15 g, 65.16 mmol) in THF (100 mL) and the resulting mixture was stirred for 30 min. Iodomethane (6.09 mL, 97.74 mmol) was added to the mixture and the reaction was stirred at RT O/N. The day after UPLC showed mainly hydrolysis of the methyl ester and presence of the corresponding carboxylic acid. The reaction was quenched with water and diluted with EtOAc, but no product was present in the organic phase so the organic phase was discarded. The water phase was acidified until pH 4 with 6N HCl, then extracted several times with EtOAc, but only traces of product were detected in organic phase. The water phase was then dried under vacuum, the orange residue was triturated with Et2O/MeOH 9/1 to afford 1-methyl-4-nitropyrazole-3-carboxylic acid (Int A, 20 g, 116.88 mmol) as pale yellow solid in mixture with inorganic salts that was used as such.

Step b 1-methyl-4-nitropyrazole-3-carboxylic acid (Int A, 20 g, 64.29 mmol) was suspended in methanol (200 mL), sulfuric acid (2.4 mL, 45 mmol) was added dropwise and the resulting suspension was refluxed O/N. The day after it was cooled, diluted with water, and then MeOH was removed under vacuum. The aqueous phase was extracted several times with EtOAc, the organic phase was dried and evaporated. The residue was triturated with pentane, and then with ether to afford methyl 1-methyl-4-nitro-1H-pyrazole-3-carboxylate (p129, 8.15 g, y=68%) as yellow-orange solid.

MS (m/z): 186.0 [MH]⁺

Preparation 130: methyl 4-amino-1-methyl-1H-pyrazole-3-carboxylate

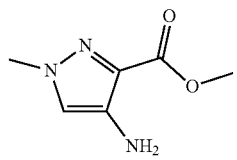

10% palladium/C (2.87 g, 2.7 mmol) was added to a stirred solution of methyl 1-methyl-4-nitro-1H-pyrazole-3-carboxylate (p129, 7.15 g, 38.6 mmol) in methanol (250 mL) and stirred at RT under H₂ atmosphere for 4 hrs. The catalyst was filtered off and the solvent was evaporated under vacuum to afford methyl 4-amino-1-methyl-1H-pyrazole-3-carboxylate (p130, 6 g, y=quant) as purple wax used as such in the next step.

MS (m/z): 156.1 [MH]⁺.

Preparation 131: methyl 4-bromo-1-methyl-1H-pyrazole-3-carboxylate

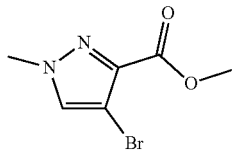

Isoamyl nitrite (1.3 mL, 9.67 mmol) was added drop-wise to a suspension of methyl 4-amino-1-methyl-1H-pyrazole-3-carboxylate (p130, 1 g, 6.45 mmol), CuBr$_2$ (1.44 g, 6.45 mmol) and CuBr (924 mg, 6.45 mmol) in MeCN (25 mL). The resulting mixture was stirred at 80° C. for 2 hrs. After cooling to RT the volatiles were evaporated under vacuum and the residue was purified by FC on SiO$_2$ column (eluting from cHex to 40% EtOAc) to afford methyl 4-bromo-1-methyl-1H-pyrazole-3-carboxylate (p131, 500 mg, y=35%) as brown solid.

MS (m/z): 220.9 [MH]$^+$

Preparation 132: methyl 1-methyl-4-phenyl-1H-pyrazole-3-carboxylate

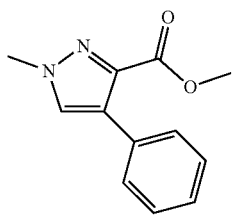

To a mixture of methyl 4-bromo-1-methyl-1H-pyrazole-3-carboxylate (p131, 80 mg, 0.37 mmol) and phenylboronic acid (57.9 mg, 0.47 mmol) in 1,4-Dioxane (2 mL) and Water (0.7 mL) potassium carbonate (151.44 mg, 1.1 mmol) was added. The mixture was degassed with N$_2$ and then Pd(Ph$_3$)$_4$ (42 mg, 0.04 mmol) was added. The reaction mixture was degassed again with N$_2$ and stirred at 120° C. for 3 hrs. It was cooled and diluted with EtOAc and water. Phases were separated and the aqueous one was extracted with EtOAc (2×). The organic phases were collected, dried and evaporated under vacuum. The crude material was purified by FC on SiO$_2$ column (eluting from cHex to 60% EtOAc) to afford methyl 1-methyl-4-phenyl-1H-pyrazole-3-carboxylate (p132, 50 mg, y=63%).

MS (m/z): 217.0 [MH]$^+$

Preparation 133: lithium 1-methyl-4-phenyl-1H-pyrazole-3-carboxylate

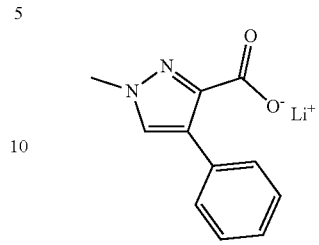

methyl 1-methyl-4-phenyl-1H-pyrazole-3-carboxylate (p132, 50 mg, 0.23 mmol) was dissolved in THF (3 mL) and Water (0.5 mL) then lithium hydroxide hydrate (11.9 mg, 0.28 mmol) was added and the reaction mixture was stirred at RT O/N. The day after volatiles were removed under vacuum to afford lithium 1-methyl-4-phenyl-1H-pyrazole-3-carboxylate (p133, 56 mg, y=quant) as white off solid used as such in the next step.

MS (m/z): 203.1 [MH]$^+$

Preparation 134: methyl 1-methyl-4-(pyrimidin-2-yl)-1H-pyrazole-3-carboxylate

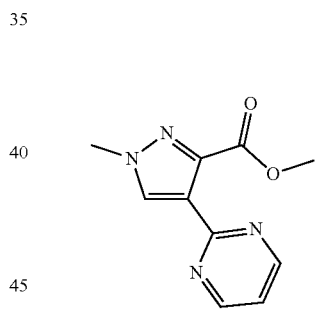

To a solution of methyl 4-bromo-1-methyl-1H-pyrazole-3-carboxylate (p131, 270 mg, 1.23 mmol) in DMF (8 mL), CuI (23.6 mg, 0.12 mmol) and Pd(Ph$_3$)$_4$ (142.4 mg, 0.12 mmol) were added and the mixture was degassed with nitrogen for 20 min before adding tributyl(2-pyrimidinyl)stannane (0.5 mL, 1.51 mmol). The reaction was stirred at 110° C. for 4 hrs. Reaction was cooled to RT and diluted with EtOAC and 1M KF aq. solution. Phases were stirred at RT for 1 h and then separated. Organic layer was dried and solvent was removed under reduced pressure. Crude material was purified by FC on NH column (eluting from Cy to 60% EtOAc) to afford methyl 1-methyl-4-(pyrimidin-2-yl)-1H-pyrazole-3-carboxylate (p134, 90 mg, y=33% yield) as white solid.

MS (m/z): 219.0 [MH]$^+$

Preparation 135: lithium 1-methyl-4-(pyrimidin-2-yl)-1H-pyrazole-3-carboxylate

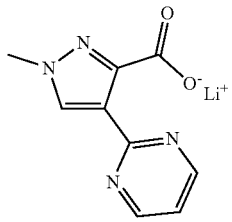

methyl 1-methyl-4-(pyrimidin-2-yl)-1H-pyrazole-3-carboxylate (p134, 90 mg, 0.41 mmol) was dissolved in THF (3 mL) and Water (1 mL) then lithium hydroxide hydrate (21 mg, 0.49 mmol) was added and the reaction mixture was stirred at RT O/N. The day after volatiles were removed under vacuum to afford lithium 1-methyl-4-(pyrimidin-2-yl)-1H-pyrazole-3-carboxylate (p135, 90 mg, y=quant) as white off solid used as such in the next step.

MS (m/z): 205.0 [MH]+

Preparation 136: 1H,2H-[1,3]thiazolo[5,4-b]pyridine-2-thione

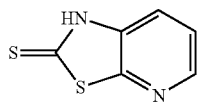

To a solution of 2-bromo-3-pyridinamine (700 mg, 4.05 mmol) in DMF (0.600 mL), potassium ethyl xanthogenate (1.3 g, 8.09 mmol) was added. The mixture was heated at 130° C. O/N. Water (100 mL) was added and the solution was treated with HCl 6N (2 mL). The precipitate was filtered, the solid was suspended in methanol and dried under reduced pressure to afford 1H-[1,3]thiazolo[5,4-b]pyridine-2-thione (p136, 674 mg, y=99%) as a beige solid.

MS (m/z): 169.0 [MH]+

Preparation 137: 2-chloro-[1,3]thiazolo[5,4-b]pyridine

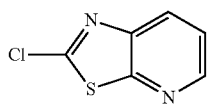

A solution of 1H-[1,3]thiazolo[5,4-b]pyridine-2-thione (p136, 670. mg, 3.98 mmol) and sulfuryl chloride (3.23 mL, 39.82 mmol) was stirred at RT for 2 hrs. Then it was poured onto ice, neutralized with Na2CO3 ss and extracted with EtOAc (×3). The combined organic extracts were washed with brine, dried and concentrated under reduced pressure. The crude mixture was purified by FC on SiO2 column (eluting with Cy/EtOAc 100 to 50:50) affording 2-chloro-[1,3]thiazolo[5,4-b]pyridine (p137, 267 mg, y=39%).

MS (m/z): 170.9 [MH]+

Preparation 138: 6,7-difluoroquinoxalin-2-ol

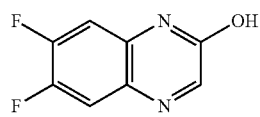

A solution of 4,5-difluorobenzene-1,2-diamine (500 mg, 3.47 mmol) and glyoxylic acid monohydrate (351.3 mg, 3.82 mmol) in Ethanol (20 mL) was refluxed for 2 hrs. Then it was cooled at 0° C. and filtrated. The solid obtained was suspended in DCM and dried under reduced pressure to afford 6,7-difluoroquinoxalin-2-ol (p138, 566 mg, y=89%) as a beige solid.

MS (m/z): 182.9 [MH]+

Preparation 139: 2-chloro-6,7-difluoroquinoxaline

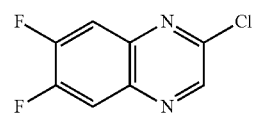 [SMILES: Fc1cc2ncc(Cl)nc2cc1F]

phosphorus oxychloride (0.86 mL, 9.17 mmol) was added to 6,7-difluoroquinoxalin-2-ol (p138, 167 mg, 0.92 mmol) and the mixture was refluxed for 1.5 h. Then it was cooled to RT and concentrated under reduced pressure. The residue was dissolved in DCM and cooled in an ice bath, before neutralizing with Na2CO3 5% aq. sol. The phases where separated and the organic phase was dried and concentrated under reduced pressure to afford 2-chloro-6,7-difluoroquinoxaline (p139,165 mg, y=90%).

MS (m/z): 200.9 [MH]+

Preparation 140: 2-amino-5-fluorophenol

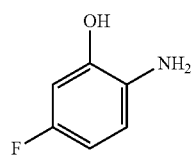

To a solution of 5-fluoro-2-nitrophenol (2 g, 12.73 mmol) and ammonium formate (4.01 g, 63.65 mmol) in methanol (20 mL), 20% Pd(OH)2 (0.91 g, 1.27 mmol) was added under nitrogen. Immediately after addition of 20% Pd(OH)2 the temperature of the solution increased and strong bubbling was observed for a few minutes. After 10 minutes the solution was filtered and evaporated under reduced pressure to get 2-amino-5-fluorophenol (p140, 1.7 g, y=quant) as a yellow oil.

MS (m/z): 128.2 [MH]+

Preparation 141: 6-fluoro-1,3-benzoxazole-2-thiol

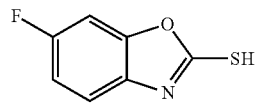 [SMILES: Fc1ccc2nc(S)oc2c1]

To a solution of 2-amino-5-fluorophenol (p140, 0.5 g, 3.54 mmol) in DMF (30 mL), in ethanol (15 mL), Potassium ethyl xanthogenate (567.46 mg, 3.54 mmol) was added. The resulting mixture was refluxed for 24 hrs. The mixture was cooled to RT, acidified with CH₃OH to pH 4, and then evaporated under reduced pressure. The crude material was purified by FC on SiO₂ column (eluting Cy/EtOAc 50:50) to afford 6-fluoro-1,3-benzoxazole-2-thiol (p141, 537 mg, y=90%) as a pink solid.

MS (m/z): 169.9 [MH]$^+$

Preparation 142: 2-chloro-[1,3]oxazolo[5,4-b]pyridine

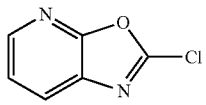

Step a

To a suspension of 3-aminopyridin-2-ol (128 mg, 1.16 mmol) in THF (3 mL), 1,1'-Thiocarbonyldiimidazole (310.7 mg, 1.74 mmol) was added. The resulting mixture was stirred at RT O/N. The solvent was removed under reduced pressure and residue was partitioned between HCl 1N (aq) and EtOAc. Layers were separated and aqueous phase was extracted several times with EtOAc. Organics were combined, dried and evaporated under reduced pressure to afford [1,3]oxazolo[5,4-b]pyridine-2-thiol (IntA, 148 mg, y=84%).

Step b

To a suspension of [1,3]oxazolo[5,4-b]pyridine-2-thiol (IntA, 90 mg, 0.59 mmol) in Toluene (2.5 mL) were added thionyl chloride (0.16 mL, 2.13 mmol) and a drop of DMF (0.02 mL). Reaction was heated at 110° C. for 2 hrs. Volatiles were carefully (sublimation observed) removed under reduced pressure to afford 2-chloro-[1,3]oxazolo[5,4-b]pyridine (p142, 95 mg, y=quant).

MS (m/z): 154.9 [MH]$^+$

Preparation 143: TRANS 3-{[(5-fluoropyridin-2-yl)oxy]methyl}-2-[(4-methoxyphenyl)methyl]-4-methyl-2-azabicyclo[3.1.1]heptane

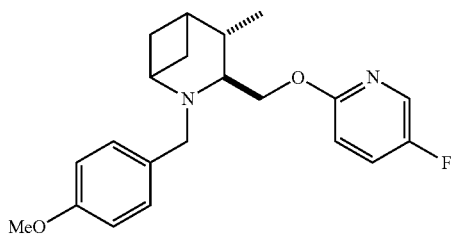 [SMILES: COc1ccc(CN2C3CC(C3)[C@H](C)[C@H]2COc2ccc(F)cn2)cc1]

To a solution of (TRANS)[2-[(4-methoxyphenyl)methyl]-4-methyl-4-azabicyclo[3.1.1]heptan-3-yl]methanol (p47, 430 mg, 1.65 mmol) in DMF (9 mL) 2,5-difluoropyridine (0.22 mL, 2.47 mmol) was added. The solution was cooled at 0° C. and NaH 60% dispersion in oil (98.7 mg, 2.47 mmol) was added. The reaction was warmed to RT and after 5 min heated to 60° C. for 24 hrs. Water was added and the reaction was extracted with AcOEt. The organic phase was washed with brine, dried and concentrated under vacuum. The residue was purified by FC on SiO₂ column (from cHex to 20% of AcOEt) affording TRANS 3-{[(5-fluoropyridin-2-yl)oxy]methyl}-2-[(4-methoxyphenyl)methyl]-4-methyl-2-azabicyclo[3.1.1]heptane (p143, 0.4 g, y=68%) as yellow oil.

MS (m/z): 357.3 [MH]$^+$

Preparation 144: TRANS 3-{[(5-fluoropyridin-2-yl)oxy]methyl}-4-methyl-2-azabicyclo[3.1.1]heptane

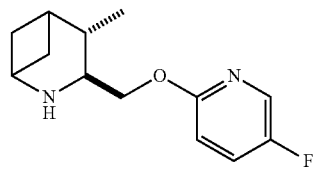 [SMILES: C[C@H]1C2CC(C2)N[C@@H]1COc1ccc(F)cn1]

To a solution of TRANS 3-{[(5-fluoropyridin-2-yl)oxy]methyl}-2-[(4-methoxyphenyl)methyl]-4-methyl-2-azabicyclo[3.1.1]heptane (p143, 400 mg, 1.12 mmol) in methanol (30 mL) 20% Pd(OH)₂ (15 mg, 0.02 mmol) and ammonium formate (708 mg, 11.22 mmol) were added. The reaction was stirred at 65° C. for 1 h and cooled to RT. The mixture was filtered over Celite and concentrated to dryness. The residue was purified by SCX first washing with MeOH and then with NH₃ 1 M in MeOH affording TRANS 3-{[(5-fluoropyridin-2-yl)oxy]methyl}-4-methyl-2-azabicyclo[3.1.1]heptane (p144, 241 mg, y=91%) as colourless oil.

MS (m/z): 237.2 [MH]$^+$

Preparation 145: TRANS 4-methyl-3-{[(methyldiphenylsilyl)oxy]methyl}-2-azabicyclo[3.1.1]heptane

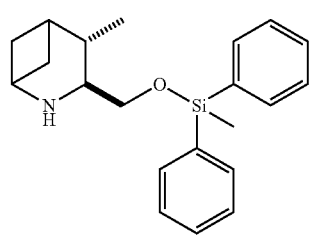 [SMILES: C[C@H]1C2CC(C2)N[C@@H]1CO[Si](C)(c1ccccc1)c1ccccc1]

(TRANS)(4-methyl-2-azabicyclo[3.1.1]heptan-3-yl)methanol (p55, 135 mg, 0.96 mmol) was dissolved in DMF (3 mL) then 1H-imidazole (228 mg, 3.35 mmol) and tert-butyl-chloro-diphenylsilane (0.27 mL, 1.05 mmol) were subsequently added and the resulting reaction mixture was stirred for 2 days at RT. The mixture was diluted with water and extracted with EA, the organic phase was washed with water, dried over sodium sulphate and concentrated under vacuum. The crude material was purified by FC on SiO₂ column (eluting with Cy/EA from 100/0 to 50/50) affording TRANS 4-methyl-3-{[(methyldiphenylsilyl)oxy]methyl}-2-azabicyclo[3.1.1]heptane (p145, 480 mg, y=quant) as yellow oil. The product was used in the next step without further purification.

MS (m/z): 380.5 [MH]$^+$

Preparation 146: TRANS 4-methyl-2-[6-methyl-3-(pyrimidin-2-yl)pyridine-2-carbonyl]-3-{[(methyldiphenylsilyl)oxy]methyl}-2-azabicyclo[3.1.1]heptane

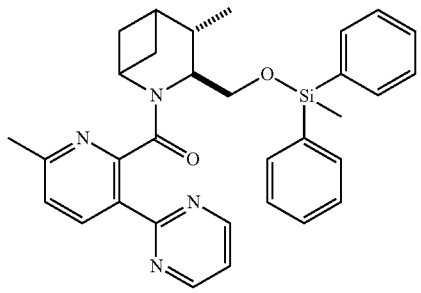 [SMILES: Cc1ccc(-c2ncccn2)c(C(=O)N2C3CC(C3)[C@H](C)[C@H]2CO[Si](C)(c2ccccc2)c2ccccc2)n1]

To a stirred mixture of 6-methyl-3-pyrimidin-2-ylpyridine-2-carboxylic acid (p58, 71.6 mg, 0.32 mmol), TRANS 4-methyl-3-{[(methyldiphenylsilyl)oxy]methyl}-2-azabicyclo[3.1.1]heptane (p145, 240 mg, 0.32 mmol) in DCM (3 mL), N,N-Diisopropylethylamine (0.16 mL, 0.95 mmol) and TBTU (111.6 mg, 0.35 mmol) were subsequently added and the mixture was stirred overnight at RT. The mixture was diluted with EA and washed with saturated sodium bicarbonate solution; the organic phase was dried over sodium sulphate and concentrated under vacuum. The crude material was purified by FC on NH column (eluting with Cy/EA from 100/0 to 75/25) affording TRANS 4-methyl-2-[6-methyl-3-(pyrimidin-2-yl)pyridine-2-carbonyl]-3 {[(methyldiphenylsilyl)oxy]methyl}-2-azabicyclo[3.1.1]heptane (p146, 154 mg, y=84%).

MS (m/z): 577.3 [MH]$^+$

Preparation 147: TRANS {4-methyl-2-[6-methyl-3-(pyrimidin-2-yl)pyridine-2-carbonyl]-2-azabicyclo[3.1.1]heptan-3-yl}methanol

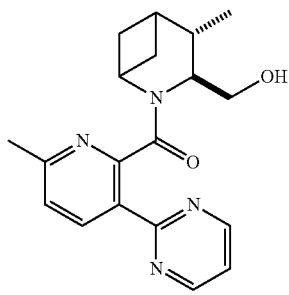 [SMILES: Cc1ccc(-c2ncccn2)c(C(=O)N2C3CC(C3)[C@H](C)[C@H]2CO)n1]

To a solution of TRANS 4-methyl-2-[6-methyl-3-(pyrimidin-2-yl)pyridine-2-carbonyl]-3 {[(methyldiphenylsilyl)oxy]methyl}-2-azabicyclo[3.1.1]heptane (p146, 146 mg, 0.25 mmol) in THF (2 mL), at RT, a 1M/THF solution of tetrabutylammonium fluoride (0.3 mL, 0.3 mmol) was added and the resulting reaction mixture was stirred overnight at RT. The mixture was concentrated under vacuum and the residue was purified by RP on C18 (from H$_2$O+0.1% FA to CH$_3$CN+0.1% FA) affording TRANS {4-methyl-2-[6-methyl-3-(pyrimidin-2-yl)pyridine-2-carbonyl]-2-azabicyclo[3.1.1]heptan-3-yl}methanol (p147, 85 mg, y=99%) as white foam.

MS (m/z): 339.2 [MH]$^+$

Preparation 148: CIS 3-{[(5-fluoropyridin-2-yl)oxy]methyl}-2-[(4-methoxyphenyl)methyl]-4-methyl-2-azabicyclo[3.1.1]heptane

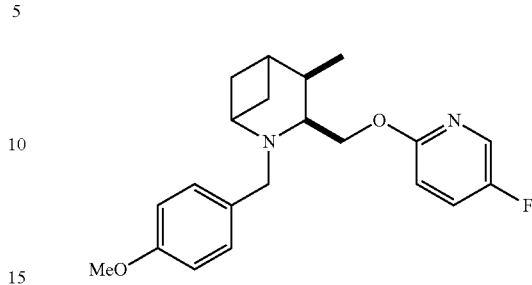

The intermediate p148 was prepared using an analogue procedure as in Preparation 143 reacting CIS [2-[(4-methoxyphenyl)methyl]-4-methyl-4-azabicyclo[3.1.1]heptan-3-yl]methanol (p46).

MS (m/z): 357.4 [MH]$^+$

Preparation 149: CIS 3-{[(5-fluoropyridin-2-yl)oxy]methyl}-4-methyl-2-azabicyclo[3.1.1]heptane

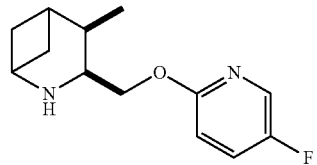 [SMILES: C[C@@H]1C2CC(C2)N[C@@H]1COc1ccc(F)cn1]

The intermediate p149 was prepared using an analogue procedure as in Preparation 144 reacting CIS 3-{[(5-fluoropyridin-2-yl)oxy]methyl}-2-[(4-methoxyphenyl)methyl]-4-methyl-2-azabicyclo[3.1.1]heptane (p148).

MS (m/z): 237.3 [MH]$^+$

Preparation 150: TRANS 2-({2-[(4-methoxyphenyl)methyl]-4-methyl-2-azabicyclo[3.1.1]heptan-3-yl}methyl)-2,3-dihydro-1H-isoindole-1,3-dione

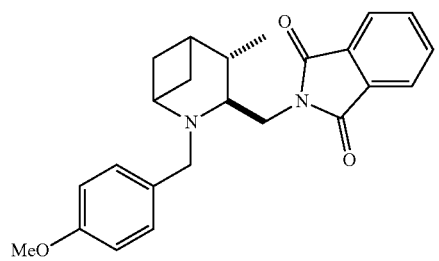 [SMILES: COc1ccc(CN2C3CC(C3)[C@H](C)[C@H]2CN2C(=O)c3ccccc3C2=O)cc1]

To a solution of TRANS-{2-[(4-methoxyphenyl)methyl]-4-methyl-2-azabicyclo[3.1.1]heptan-3-yl}methanol (p47, 1 g, 3.83 mmol) in THF (20 mL), PPh$_3$ (1.51 g, 5.74 mmol) and phthalimide (0.84 g, 5.74 mmol) were added. The mixture was cooled down to 0° C. and Diisopropyl azodicarboxylate (1.13 mL, 5.74 mmol) was added dropwise. The ice bath was removed and the reaction was stirred at RT for 5 min and at 55° C. for 3 hrs. The mixture was concentrated under vacuum and the residue was purified by FC on NH column (from cHex to cHex/AcOEt 1:1) affording TRANS 2-({2-[(4-methoxyphenyl)methyl]-4-methyl-2-azabicyclo[3.1.1]heptan-3-yl}methyl)-2,3-dihydro-1H-isoindole-1,3-dione (p150, 1.19 g, y=79%) as yellow oil.

MS (m/z): 391.4 [MH]+

Preparation 151: TRANS 2-({4-methyl-2-azabicyclo[3.1.1]heptan-3-yl}methyl)-2,3-dihydro-1H-isoindole-1,3-dione

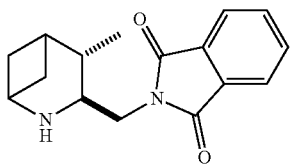 [SMILES: C[C@H]1C2CC(C2)N[C@@H]1CN1C(=O)c2ccccc2C1=O]

To a solution of TRANS 2-({2-[(4-methoxyphenyl)methyl]-4-methyl-2-azabicyclo[3.1.1]heptan-3-yl}methyl)-2,3-dihydro-1H-isoindole-1,3-dione (p150, 300 mg, 0.77 mmol) in methanol (10 mL), 20% Pd(OH)$_2$ (108 mg, 0.15 mmol) and ammonium formate (484 mg, 7.68 mmol) were added. The reaction was stirred at 65° C. for 1 h, cooled at RT. UPLC-MS analysis revealed still presence of SM therefore the reaction was cooled to RT and additional 0.2 eq of 20% Pd(OH)$_2$ (108 mg) and ammonium formate (484 mg) were added. The reaction was stirred at 65° C. for 2 hrs, then it was filtered over celite and concentrated under vacuum. The residue was purified by SCX first washing with MeOH and then with NH$_3$ 1 M in MeOH affording 2-({4-methyl-2-azabicyclo[3.1.1]heptan-3-yl}methyl)-2,3-dihydro-1H-isoindole-1,3-dione (p151, 184 mg, y=88%) as yellow oil.

MS (m/z): 271.3 [MH]+

Preparation 152: TRANS 2-({4-methyl-2-[6-methyl-3-(2H-1,2,3-triazol-2-yl)pyridine-2-carbonyl]-2-azabicyclo[3.1.1]heptan-3-yl}methyl)-2,3-dihydro-1H-isoindole-1,3-dione

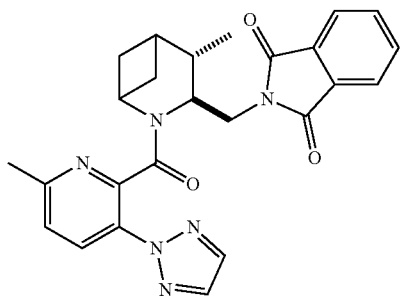 [SMILES: Cc1ccc(-n2nccn2)c(C(=O)N2C3CC(C3)[C@H](C)[C@H]2CN2C(=O)c3ccccc3C2=O)n1]

To a solution of 6-methyl-3-(2H-1,2,3-triazol-2-yl)pyridine-2-carboxylic acid (p67, 243 mg, 1.13 mmol) and HATU (380 mg, 1 mmol) in DMF (3 mL) was added N,N-Diisopropylethylamine (0.22 mL, 1.33 mmol). The reaction was stirred at RT for 30 min and then added to a solution of 2-({4-methyl-2-azabicyclo[3.1.1]heptan-3-yl}methyl)-2,3-dihydro-1H-isoindole-1,3-dione (p151, 180 mg, 0.67 mmol) in DMF (2 mL). The reaction was stirred O/N/RT. The day after s.s. of NaHCO$_3$ was added and the reaction was extracted with AcOEt (×3). The combined organic phases were washed with Brine, dried over Na$_2$SO$_4$, filtered and concentrated under vacuum. The residue was purified by FC on SiO$_2$ column (from cHex to cHex/AcOEt 1:1) affording TRANS 2-({4-methyl-2-[6-methyl-3-(2H-1,2,3-triazol-2-yl)pyridine-2-carbonyl]-2-azabicyclo[3.1.1]heptan-3-yl}methyl)-2,3-dihydro-1H-isoindole-1,3-dione (p152, 166 mg, y=55%) as yellow oil.

MS (m/z): 457.4 [MH]+

Preparation 153: TRANS {2-[(4-methoxyphenyl)methyl]-4-methyl-2-azabicyclo[3.1.1]heptan-3-yl}methanamine

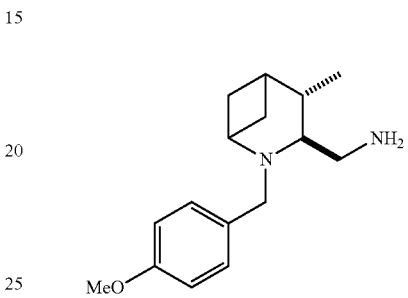

To a solution of TRANS 2-({2-[(4-methoxyphenyl)methyl]-4-methyl-2-azabicyclo[3.1.1]heptan-3-yl}methyl)-2,3-dihydro-1H-isoindole-1,3-dione (p150, 900 mg, 2.3 mmol) in ethanol (30 mL), hydrazine 64-65% in water (0.72 mL, 23.05 mmol) was added. Reaction mixture was stirred for 24 hrs at RT. A white solid was formed and it was filtered off. The clear solution was concentrated and purified by SCX eluting with MeOH and then 1 N NH$_3$ in MeOH to afford TRANS {2-[(4-methoxyphenyl)methyl]-4-methyl-2-azabicyclo[3.1.1]heptan-3-yl}methanamine (p153, 342 mg, y=57%) as light yellow oil.

MS (m/z): 261.1 [MH]+

Preparation 154: TRANS tert-butyl N-({2-[(4-methoxyphenyl)methyl]-4-methyl-2-azabicyclo[3.1.1]heptan-3-yl}methyl)carbamate

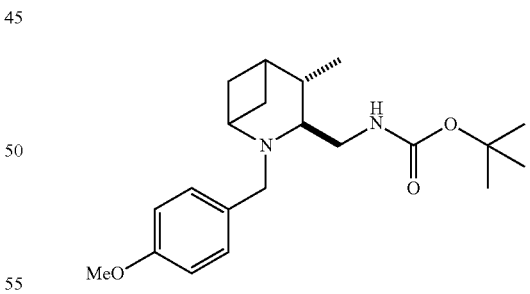

To a solution of TRANS {2-[(4-methoxyphenyl)methyl]-4-methyl-2-azabicyclo[3.1.1]heptan-3-yl}methanamine (p153, 342 mg, 1.31 mmol) in dry DCM (15 mL) was added Di-tert-butyl dicarbonate (315 mg, 1.44 mmol). Reaction mixture was stirred at RT overnight. The solvent was evaporated and then the residue was purified by SCX first washing with MeOH and then with 1M NH$_3$ in MeOH affording TRANS tert-butyl N-({2-[(4-methoxyphenyl)methyl]-4-methyl-2-azabicyclo[3.1.1]heptan-3-yl}methyl)carbamate (p154, 422 mg, y=89%) as yellow oil.

MS (m/z): 361.3 [MH]+

Preparation 155: TRANS tert-butyl N-({4-methyl-2-azabicyclo[3.1.1]heptan-3-yl}methyl)carbamate

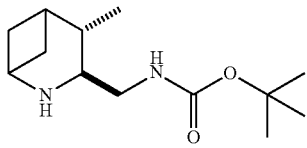 [SMILES: C[C@H]1C2CC(C2)N[C@@H]1CNC(=O)OC(C)(C)C]

To a degassed solution of TRANS tert-butyl N-({2-[(4-methoxyphenyl)methyl]-4-methyl-2-azabicyclo[3.1.1]heptan-3-yl}methyl)carbamate (p154, 422 mg, 0.9 mmol) in methanol (20 mL) were added 10% Pd/C (192 mg, 0.18 mmol) and ammonium formate (568 mg, 9.01 mmol). The mixture was stirred at reflux for 1 h. The mixture was then filtered over Celite® and evaporated affording TRANS tert-butyl N-({4-methyl-2-azabicyclo[3.1.1]heptan-3-yl}methyl)carbamate (p155, 216 mg, y=99%) as a grey oil.

MS (m/z): 241.1 [MH]$^+$

Preparation 156: TRANS tert-butyl N-({4-methyl-2-[6-methyl-3-(2H-1,2,3-triazol-2-yl)pyridine-2-carbonyl]-2-azabicyclo[3.1.1]heptan-3-yl}methyl)carbamate

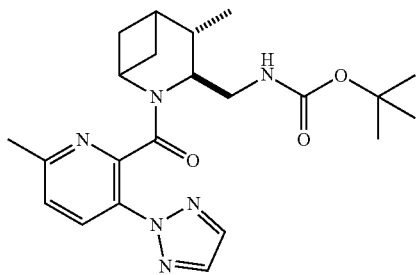 [SMILES: Cc1ccc(-n2nccn2)c(C(=O)N2C3CC(C3)[C@H](C)[C@H]2CNC(=O)OC(C)(C)C)n1]

A solution of 6-methyl-3-(2H-1,2,3-triazol-2-yl)pyridine-2-carboxylic acid (p67, 284 mg, 1.35 mmol), HATU (512 mg, 1.35 mmol) and N,N-Diisopropylethylamine (0.45 mL, 2.7 mmol) in dry DMF (4 mL) was stirred at RT for 1 h. Then, the previously prepared mixture was slowly added to a solution of TRANS tert-butyl N-({4-methyl-2-azabicyclo[3.1.1]heptan-3-yl}methyl)carbamate (p155, 216 mg, 0.9 mmol) in dry DMF (2 mL). Reaction mixture was stirred under N$_2$ at RT for 3 hrs. Water was added to reaction mixture and it was extracted with EtOAc. The combined organic layers were washed with Brine, dried, filtered and concentrated under vacuum. The crude material was purified by a FC on NH column (eluting from cHEx\EtOAc 80\20 to 60\40) affording TRANS tert-butyl N-({4-methyl-2-[6-methyl-3-(2H-1,2,3-triazol-2-yl)pyridine-2-carbonyl]-2-azabicyclo[3.1.1]heptan-3-yl}methyl)carbamate (p156, 396 mg, y=quant) as a colourless oil.

MS (m/z): 427.3 [MH]$^+$

Preparation 157: TRANS {4-methyl-2-[6-methyl-3-(2H-1,2,3-triazol-2-yl)pyridine-2-carbonyl]-2-azabicyclo[3.1.1]heptan-3-yl}methanamine

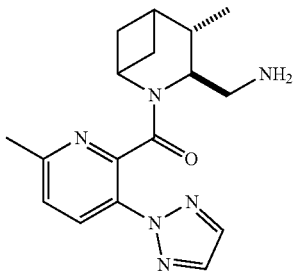 [SMILES: Cc1ccc(-n2nccn2)c(C(=O)N2C3CC(C3)[C@H](C)[C@H]2CN)n1]

Method A

To a solution of TRANS 2-({4-methyl-2-[6-methyl-3-(2H-1,2,3-triazol-2-yl)pyridine-2-carbonyl]-2-azabicyclo[3.1.1]heptan-3-yl}methyl)-2,3-dihydro-1H-isoindole-1,3-dione (p152, 166 mg, 0.36 mmol) in ethanol (7 mL), hydrazine 64-65% in water (0.11 mL, 3.64 mmol) was added. The reaction mixture was stirred for 24 hrs at RT. A white solid was formed and it was filtered under vacuum. The clear solution was concentrated and purified by SCX eluting with MeOH and then 1 N NH$_3$ in MeOH affording TRANS {4-methyl-2-[6-methyl-3-(2H-1,2,3-triazol-2*-yl)pyridine-2-carbonyl]-2-azabicyclo[3.1.1]heptan-3-yl}methanamine (p157, 106 mg, y=89%) as light yellow oil.

Method B

TRANS tert-butyl N-({4-methyl-2-[6-methyl-3-(2H-1,2,3-triazol-2-yl)pyridine-2-carbonyl]-2-azabicyclo[3.1.1]heptan-3-yl}methyl)carbamate (p156, 386 mg, 0.78 mmol) in DCM (20 mL) was added Trifluoroacetic acid (0.58 mL, 7.78 mmol) drop-wise. Reaction mixture was stirred at RT for 3 hrs. The volatiles were evaporated and the residue was purified by SCX eluting with MeOH and then 1M NH$_3$ in MeOH affording TRANS {4-methyl-2-[6-methyl-3-(2H-1,2,3-triazol-2-yl)pyridine-2-carbonyl]-2-azabicyclo[3.1.1]heptan-3-yl}methanamine (p157, 270 mg, y=quant) as light yellow oil.

MS (m/z): 327.4 [MH]$^+$

Preparation 158: CIS 2-({2-[(4-methoxyphenyl)methyl]-4-methyl-2-azabicyclo[3.1.1]heptan-3-yl}methyl)-2,3-dihydro-1H-isoindole-1,3-dione

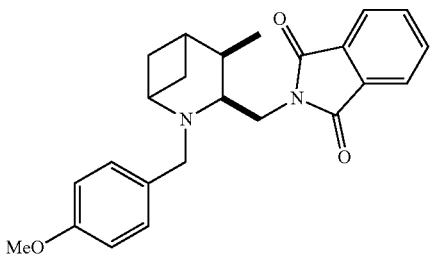 [SMILES: COc1ccc(CN2C3CC(C3)[C@@H](C)[C@H]2CN2C(=O)c3ccccc3C2=O)cc1]

To a solution of CIS-{2-[(4-methoxyphenyl)methyl]-4-methyl-2-azabicyclo[3.1.1]heptan-3-yl}methanol (p46, 1.9 g, 6.03 mmol) in THF (32 mL) PPh$_3$ (2.37 g, 9.05 mmol) and phthalimide (0.84 g, 5.74 mmol) were added. The mixture was cooled down to 0° C. and Diisopropyl azodicarboxylate (1.78 mL, 9.05 mmol) was added drop-wise. The ice bath was removed and the reaction was stirred at 55° C. for 2 hrs. The mixture was concentrated under vacuum and the residue was purified by FC on SiO$_2$ column (from cHex/AcOEt 80/20 to cHex/AcOEt to 50:50) affording CIS 2-({2-[(4-methoxyphenyl)methyl]-4-methyl-2-azabicyclo[3.1.1]heptan-3-yl}methyl)-2,3-dihydro-1H-isoindole-1,3-dione (p158, 1.95 g, y=83%) as yellow oil.

MS (m/z): 391.4 [MH]$^+$

Preparation 159: CIS {2-[(4-methoxyphenyl)methyl]-4-methyl-2-azabicyclo[3.1.1]heptan-3-yl}methanamine

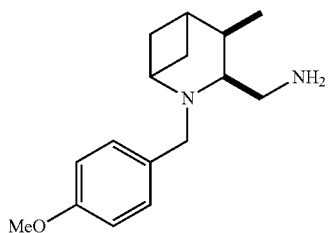 [SMILES: COc1ccc(CN2C3CC(C3)[C@@H](C)[C@H]2CN)cc1]

To a solution of CIS 2-({2-[(4-methoxyphenyl)methyl]-4-methyl-2-azabicyclo[3.1.1]heptan-3-yl}methyl)-2,3-dihydro-1H-isoindole-1,3-dione (p158, 1.95 g, 4.05 mmol) in ethanol (50 mL), hydrazine 64-65% in water (2.9 mL, 60.68 mmol) was added. Reaction mixture was stirred for O/N at RT. A white solid was formed and it was filtered off. The clear solution was concentrated and purified by SCX eluting with MeOH and then 1 N NH$_3$ in MeOH to afford CIS {2-[(4-methoxyphenyl)methyl]-4-methyl-2-azabicyclo[3.1.1]heptan-3-yl}methanamine (p159, 904 mg, y=86%).

MS (m/z): 261.1 [MH]$^+$

Preparation 160: CIS tert-butyl N-({2-[(4-methoxyphenyl)methyl]-4-methyl-2-azabicyclo[3.1.1]heptan-3-yl}methyl)carbamate

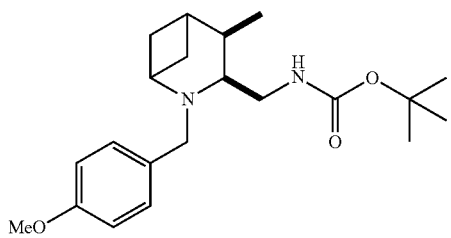 [SMILES: COc1ccc(CN2C3CC(C3)[C@@H](C)[C@H]2CNC(=O)OC(C)(C)C)cc1]

To a solution of CIS {2-[(4-methoxyphenyl)methyl]-4-methyl-2-azabicyclo[3.1.1]heptan-3-yl}methanamine (p159 1.25 g, 4.8 mmol) in dry DCM (35 mL) was added Di-tert-butyl dicarbonate (1.05 g, 4.8 mmol). Reaction mixture was stirred at RT overnight. The solvent was evaporated and then the residue was purified by FC on NH column (eluting from cHex to 10% EtOAc) affording CIS tert-butyl N-({2-[(4-methoxyphenyl)methyl]-4-methyl-2-azabicyclo[3.1.1]heptan-3-yl}methyl)carbamate (p160, 1.5 g, y=87%) as colorless oil.

MS (m/z): 361.2 [MH]$^+$

Preparation 161: CIS tert-butyl N-({4-methyl-2-azabicyclo[3.1.1]heptan-3-yl}methyl)carbamate

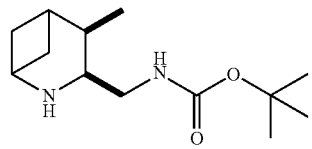 [SMILES: C[C@@H]1C2CC(C2)N[C@@H]1CNC(=O)OC(C)(C)C]

To a degassed solution of CIS tert-butyl N-({2-[(4-methoxyphenyl)methyl]-4-methyl-2-azabicyclo[3.1.1]heptan-3-yl}methyl)carbamate (p160, 1.5 g, 4.16 mmol) in methanol (40 mL) were added 10% Pd/C (0.89 g, 0.83 mmol) and ammonium formate (1.57 g, 24.97 mmol). The mixture was stirred at 65° C. for 1 h. After cooling at room temperature the mixture was filtered over Celite® and evaporated affording CIS tert-butyl N-({4-methyl-2-azabicyclo[3.1.1]heptan-3-yl}methyl)carbamate (p161, 915 mg, y=91%).

MS (m/z): 241.3 [MH]$^+$

Preparation 162: CIS tert-butyl N-({4-methyl-2-[6-methyl-3-(2H-1,2,3-triazol-2-yl)pyridine-2-carbonyl]-2-azabicyclo[3.1.1]heptan-3-yl}methyl)carbamate

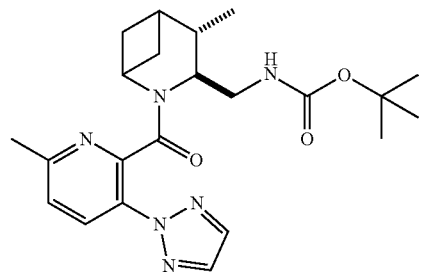 [SMILES: Cc1ccc(-n2nccn2)c(C(=O)N2C3CC(C3)[C@H](C)[C@H]2CNC(=O)OC(C)(C)C)n1]

A solution of 6-methyl-3-(2H-1,2,3-triazol-2-yl)pyridine-2-carboxylic acid (p67, 374 mg, 1.78 mmol), HATU (676 mg, 1.78 mmol) and N,N-Diisopropylethylamine (0.49 mL, 2.96 mmol) in dry DMF (5 mL) was stirred at RT for 1 h. Then, the previously prepared mixture was slowly added to a solution of CIS tert-butyl N-({4-methyl-2-azabicyclo[3.1.1]heptan-3-yl}methyl)carbamate (p161, 356 mg, 1.48 mmol) in dry DMF (5 mL). Reaction mixture was stirred under N$_2$ at RT for 3 hrs. Water was added to reaction mixture and it was extracted with EtOAc. The combined organic layers were washed with Brine and ss NH$_4$Cl, dried, filtered and concentrated under vacuum. The crude material was purified by a FC on NH column (eluting from cHEx\EtOAc 80\20 to 60\40) affording CIS tert-butyl N-({4-methyl-2-[6-methyl-3-(2H-1,2,3-triazol-2-yl)pyridine-2-carbonyl]-2-azabicyclo[3.1.1]heptan-3-yl}methyl)carbamate (p162, 525 mg, y=83%) as a colourless oil.

MS (m/z): 427.3 [MH]$^+$

The following intermediates were prepared using an analogue procedure as in Preparation 162, reacting CIS tert-butyl N-({4-methyl-2-azabicyclo[3.1.1]heptan-3-yl}methyl)carbamate (p161) with the appropriate carboxylic acid (R—COOH) as reported in the table below.

| Prep. | Structure | Name | RCOOH | MS (m/z): [MH]+ | y % |
|---|---|---|---|---|---|
| p163 | 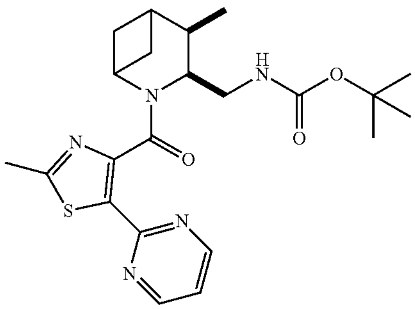 [SMILES: Cc1nc(C(=O)N2C3CC(C3)[C@@H](C)[C@H]2CNC(=O)OC(C)(C)C)c(-c2ncccn2)s1] | CIS tert-butyl N-({4-methyl-2-[2-methyl-5-(pyrimidin-2-yl)-1,3-thiazole-4-carbonyl]-2-azabicyclo[3.1.1]heptan-3-yl}methyl)carbamate | P70 | 444.1 | 32 |
| p164 | 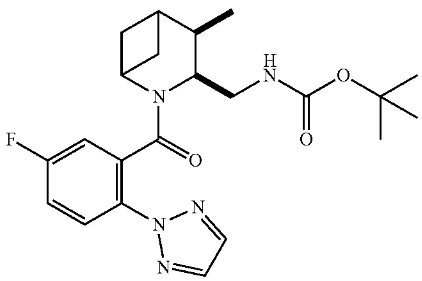 [SMILES: C[C@@H]1C2CC(C2)N(C(=O)c2cc(F)ccc2-n2nccn2)[C@@H]1CNC(=O)OC(C)(C)C] | CIS tert-butyl N-({2-[5-fluoro-2-(2H-1,2,3-triazol-2-yl)benzoyl]-4-methyl-2-azabicyclo[3.1.1]heptan-3-yl}methyl)carbamate | P119 | 430.4 | 52 |
| p165 | 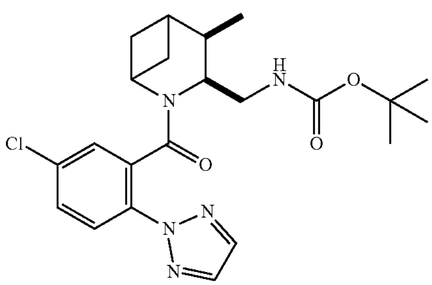 [SMILES: C[C@@H]1C2CC(C2)N(C(=O)c2cc(Cl)ccc2-n2nccn2)[C@@H]1CNC(=O)OC(C)(C)C] | CIS tert-butyl N-({2-[5-cloro-2-(2H-1,2,3-triazol-2-yl)benzoyl]-4-methyl-2-azabicyclo[3.1.1]heptan-3-yl}methyl)carbamate | P120 | 446.4 | 57 |
| p166 | 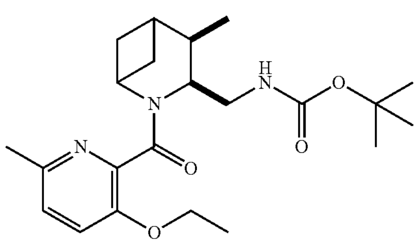 [SMILES: CCOc1ccc(C)nc1C(=O)N1C2CC(C2)[C@@H](C)[C@H]1CNC(=O)OC(C)(C)C] | CIS tert-butyl N-{[2-(3-ethoxy-6-methylpyridine-2-carbonyl)-4-methyl-2-azabicyclo[3.1.1]heptan-3-yl]methyl}carbamate | P122 | 404.3 | 79 |
| p167 | 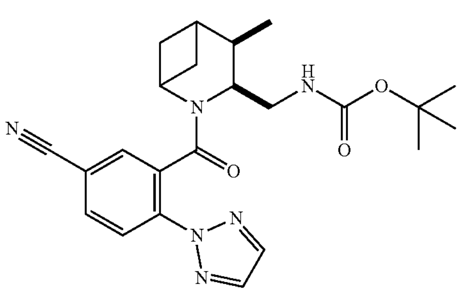 [SMILES: C[C@@H]1C2CC(C2)N(C(=O)c2cc(C#N)ccc2-n2nccn2)[C@@H]1CNC(=O)OC(C)(C)C] | CIS tert-butyl N-({2-[5-cyano-2-(2H-1,2,3-triazol-2-yl)benzoyl]-4-methyl-2-azabicyclo[3.1.1]heptan-3-yl}methyl)carbamate | P124 | 437.2 | 74 |

| Prep. | Structure | Name | RCOOH | MS (m/z): [MH]+ | y % |
|---|---|---|---|---|---|
| p168 | 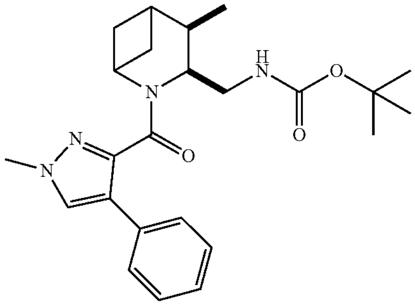 [SMILES: C[C@@H]1C2CC(C2)N(C(=O)c2nn(C)cc2-c2ccccc2)[C@@H]1CNC(=O)OC(C)(C)C] | CIS tert-butyl N-{[4-methyl-2-(1-methyl-4-phenyl-1H-pyrazole-3-carbonyl)-2-azabicyclo[3.1.1]heptan-3-yl]methyl}carbamate | P133 | 425.4 | quant |
| p169 | 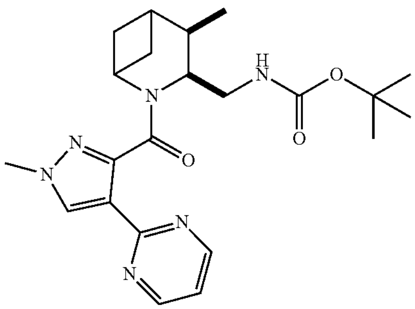 [SMILES: C[C@@H]1C2CC(C2)N(C(=O)c2nn(C)cc2-c2ncccn2)[C@@H]1CNC(=O)OC(C)(C)C] | CIS tert-butyl N-({4-methyl-2-[1-methyl-4-(pyrimidin-2-yl)-1H-pyrazole-3-carbonyl]-2-azabicyclo[3.1.1]heptan-3-yl}methyl)carbamate | P135 | 427.4 | quant |

Preparation 170: CIS {4-methyl-2-[6-methyl-3-(2H-1,2,3-triazol-2-yl)pyridine-2-carbonyl]-2-azabicyclo[3.1.1]heptan-3-yl}methanamine

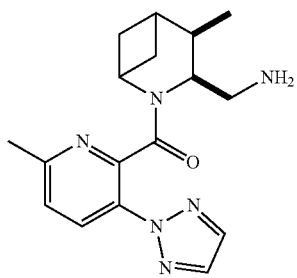 [SMILES: Cc1ccc(-n2nccn2)c(C(=O)N2C3CC(C3)[C@@H](C)[C@H]2CN)n1]

CIS tert-butyl N-({4-methyl-2-[6-methyl-3-(2H-1,2,3-triazol-2-yl)pyridine-2-carbonyl]-2-azabicyclo[3.1.1]heptan-3-yl}methyl)carbamate (p162, 520 mg, 1.22 mmol) in DCM (20 mL) was added Trifluoroacetic acid (0.58 mL, 7.78 mmol) drop-wise. Reaction mixture was stirred at RT for 3 hrs. The volatiles were evaporated and the residue was purified by SCX eluting with MeOH and then 1M NH$_3$ in MeOH affording CIS {4-methyl-2-[6-methyl-3-(2H-1,2,3-triazol-2-yl)pyridine-2-carbonyl]-2-azabicyclo[3.1.1]heptan-3-yl}methanamine (p170, 320 mg, y=80%) as orange oil.

MS (m/z): 327.4 [MH]+

The following intermediates were prepared using an analogue procedure as in Preparation 170, from the appropriate starting material as reported in the table below.

| Prep. | Structure | Name | SM | MS (m/z): [MH]+ | y % |
|---|---|---|---|---|---|
| P171 | 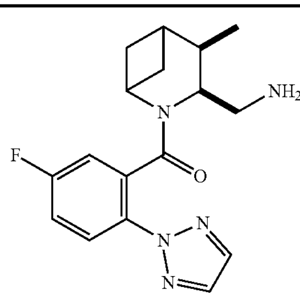 | CIS {2-[5-fluoro-2-(2H-1,2,3-triazol-2-yl)benzoyl]-4-methyl-2-azabicyclo[3.1.1]heptan-3-yl}methanamine | P164 | 330.4 | 93 |

-continued

| Prep. | Structure | Name | SM | MS (m/z): [MH]+ | y % |
|---|---|---|---|---|---|
| P172 | 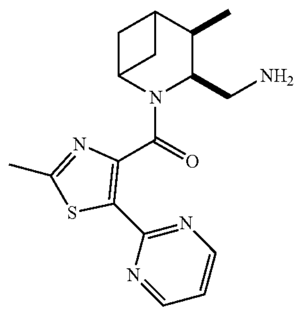 [SMILES: Cc1nc(C(=O)N2C3CC(C3)[C@@H](C)[C@H]2CN)c(-c2ncccn2)s1] | CIS {4-methyl-2-[2-methyl-5-(pyrimidin-2-yl)-1,3-thiazole-4-carbonyl]-2-azabicyclo[3.1.1]heptan-3-yl}methanamine | P163 | 344.3 | quant |
| P173 | 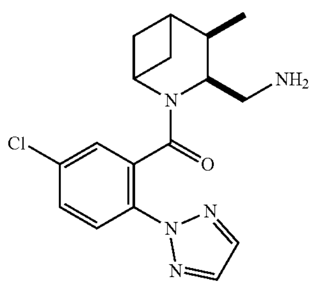 [SMILES: C[C@@H]1C2CC(C2)N(C(=O)c2cc(Cl)ccc2-n2nccn2)[C@@H]1CN] | CIS {2-[5-chloro-2-(2H-1,2,3-triazol-2-yl)benzoyl]-4-methyl-2-azabicyclo[3.1.1]heptan-3-yl}methanamine | P165 | 346.3 | 93 |
| P174 | 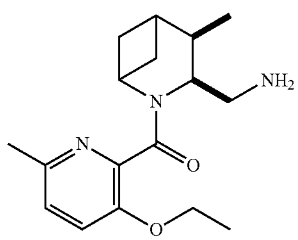 [SMILES: CCOc1ccc(C)nc1C(=O)N1C2CC(C2)[C@@H](C)[C@H]1CN] | CIS [2-(3-ethoxy-6-methylpyridine-2-carbonyl)-4-methyl-2-azabicyclo[3.1.1]heptan-3-yl]methanamine | P166 | 304.4 | 99 |
| P175 | 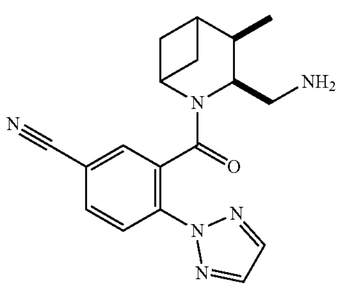 [SMILES: C[C@@H]1C2CC(C2)N(C(=O)c2cc(C#N)ccc2-n2nccn2)[C@@H]1CN] | CIS 3-[3-(aminomethyl)-4-methyl-2-azabicyclo[3.1.1]heptane-2-carbonyl]-4-(2H-1,2,3-triazol-2-yl)benzonitrile | P167 | 337.4 | 82 |
| P176 | 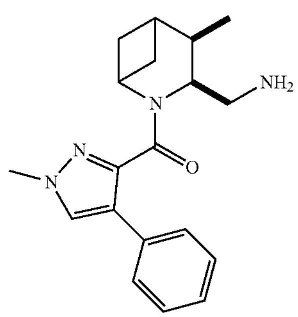 [SMILES: C[C@@H]1C2CC(C2)N(C(=O)c2nn(C)cc2-c2ccccc2)[C@@H]1CN] | CIS [4-methyl-2-(1-methyl-4-phenyl-1H-pyrazole-3-carbonyl)-2-azabicyclo[3.1.1]heptan-3-yl]methanamine | P168 | 325.4 | 87 |

| Prep. | Structure | Name | SM | MS (m/z): [MH]+ | y % |
|---|---|---|---|---|---|
| P177 | 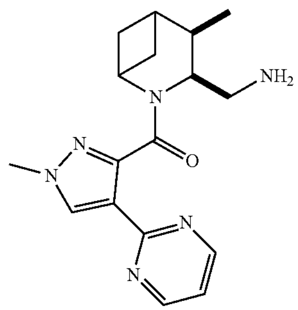 [SMILES: C[C@@H]1C2CC(C2)N(C(=O)c2nn(C)cc2-c2ncccn2)[C@@H]1CN] | CIS {4-methyl-2-[1-methyl-4-(pyrimidin-2-yl)-1H-pyrazole-3-carbonyl]-2-azabicyclo[3.1.1]heptan-3-yl}methanamine | P169 | 327.3 | 79 |

Preparation 178: CIS 4-fluoro-N-({2-[(4-methoxyphenyl)methyl]-4-methyl-2-azabicyclo[3.1.1]heptan-3-yl}methyl)aniline

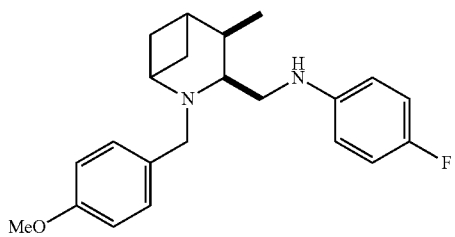 [SMILES: COc1ccc(CN2C3CC(C3)[C@@H](C)[C@H]2CNc2ccc(F)cc2)cc1]

CIS {2-[(4-methoxyphenyl)methyl]-4-methyl-2-azabicyclo[3.1.1]heptan-3-yl}methanamine (p159, 150 mg, 0.58 mmol) was dissolved in toluene (2.08 mL), then sodium tert-butoxide (110.7 mg, 1.15 mmol), 1-bromo-4-fluorobenzene (0.06 mL, 0.58 mmol) and BINAP (36 mg, 0.06 mmol) were added. The mixture was degassed under N₂ and then Pd₂(dba)₃ (15.8 mg, 0.02 mmol) was added. Reaction mixture was heated at 80° C. O/N. Water was added to the mixture and it was extracted with EtOAc. The crude material was purified by FC on NH column (eluted Cyclohexane/Ethyl Acetate from 100% to 50/50) affording CIS 4-fluoro-N-({2-[(4-methoxyphenyl)methyl]-4-methyl-2-azabicyclo[3.1.1]heptan-3-yl}methyl)aniline (p178, 85 mg, y=42%) as light yellow oil MS (m/z): 355.4 [MH]+.

Preparation 179: CIS 4-fluoro-N-({4-methyl-2-azabicyclo[3.1.1]heptan-3-yl}methyl)aniline

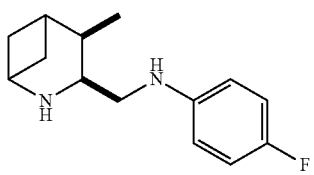 [SMILES: C[C@@H]1C2CC(C2)N[C@@H]1CNc1ccc(F)cc1]

CIS 4-fluoro-N-({2-[(4-methoxyphenyl)methyl]-4-methyl-2-azabicyclo[3.1.1]heptan-3-yl}methyl)aniline (p178, 85 mg, 0.24 mmol) was dissolved in Methanol (4.3 mL), then ammonium formate (151.2 mg, 2.4 mmol) and 10% Pd/C (51 mg, 0.05 mmol) were added. The resulting mixture was degassed and heated to reflux for 1.5 hrs. After this time, the mixture was filtered over Celite, evaporated and then purified by SCX eluted with MeOH and then 1 M NH₃\MeOH affording CIS 4-fluoro-N-({4-methyl-2-azabicyclo[3.1.1]heptan-3-yl}methyl)aniline (p179, y=68%).

MS (m/z): 355.4 [MH]+

Preparation 180: CIS N-({2-[(4-methoxyphenyl)methyl]-4-methyl-2-azabicyclo[3.1.1]heptan-3-yl}methyl)-5-(trifluoromethyl)pyrazin-2-amine

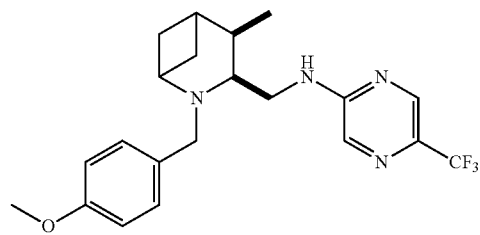 [SMILES: COc1ccc(CN2C3CC(C3)[C@@H](C)[C@H]2CNc2cnc(C(F)(F)F)cn2)cc1]

A solution of CIS {2-[(4-methoxyphenyl)methyl]-4-methyl-2-azabicyclo[3.1.1]heptan-3-yl}methanamine (p159, 300 mg, 1.15 mmol) N,N-Diisopropylethylamine (0.38 mL, 2.3 mmol) and 2-chloro-5-(trifluoromethyl)pyrazine (0.21 mL, 1.73 mmol) in DMSO (4 mL) was heated for 3 hrs at 80° C. The reaction was allowed to reach RT and partitioned between NaHCO₃ ss and EtOAc, and then the product was extracted several times with EtOAc. The combined organic layers were washed with Brine, dried over Na₂SO₄, filtered and concentrated under vacuum. The residue was then purified by FC on NH column (from cHex to AcOEt) affording CIS N-({2-[(4-methoxyphenyl)methyl]-4-methyl-2-azabicyclo[3.1.1]heptan-3-yl}methyl)-5-(trifluoromethyl)pyrazin-2-amine (p180, 216 mg, y=46%) as yellow oil MS (m/z): 407.1 [MH]+.

Preparation 181: CIS N-({4-methyl-2-azabicyclo[3.1.1]heptan-3-yl}methyl)-5-(trifluoromethyl)pyrazin-2-amine

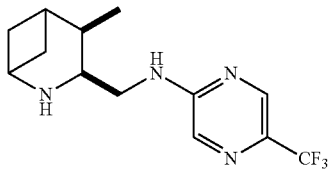 [SMILES: C[C@@H]1C2CC(C2)N[C@@H]1CNc1cnc(C(F)(F)F)cn1]

The intermediate p181 was prepared using an analogue procedure as in Preparation 144 reacting CIS N-({2-[(4-methoxyphenyl)methyl]-4-methyl-2-azabicyclo[3.1.1]heptan-3-yl}methyl)-5-(trifluoromethyl)pyrazin-2-amine (p180).
MS (m/z): 287.3 [MH]$^+$ Preparation 182:
4-chloro-2-(2H-1,2,3-triazol-2-yl)benzoic acid

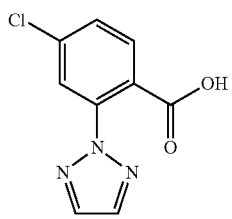 [SMILES: O=C(O)c1ccc(Cl)cc1-n1nccn1]

In a MW tube was added 4-chloro-2-iodobenzoic acid (260 mg, 0.92 mmol), 1H-1,2,3-Triazole (0.11 mL, 1.84 mmol) and (1R,2R)—N$_1$,N$_2$-dimethylcyclohexane-1,2-diamine (0.03 mL, 0.18 mmol). To these solids were added 1,4-Dioxane (1 mL) and Water (0.1 mL), then CuI (8.77 mg, 0.05 mmol) and finally Cs$_2$CO$_3$ (0.6 g, 1.84 mmol). The mixture was then warmed to 100° C. for 2.5 hrs and left at RT O/N. HCl 6 N was added until pH 2, then volatiles were removed under vacuum and the crude material was purified by RP on C18 column (from H$_2$O/CH$_3$CN 95:5+0.1% of FA to H$_2$O/CH$_3$CN 5:95+0.1% of FA) affording 4-chloro-2-(2H-1,2,3-triazol-2-yl)benzoic acid (p182, 120 mg, y=58%) as white solid.
MS (m/z): 223.9 [MH]$^+$ Preparation 183: CIS tert-butyl N-({4-methyl-2-[6-methyl-3-(pyrimidin-2-yl)pyridine-2-carbonyl]-2-azabicyclo[3.1.1]heptan-3-yl}methyl)carbamate

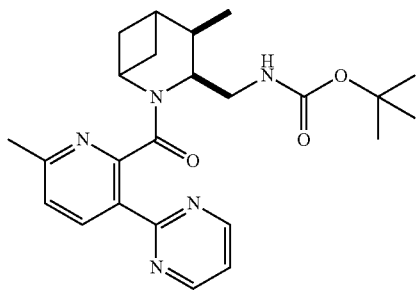 [SMILES: Cc1ccc(-c2ncccn2)c(C(=O)N2C3CC(C3)[C@@H](C)[C@H]2CNC(=O)OC(C)(C)C)n1]

To a solution of 6-methyl-3-(pyrimidin-2-yl)pyridine-2-carboxylic acid (p58, 103.68 mg, 0.46 mmol) and N,N-Diisopropylethylamine (0.21 mL, 1.25 mmol) in DMF (1.5 mL), TBTU (160.31 mg, 0.5 mmol) was added. The resulting mixture was stirred at RT for 30 min then a solution of CIS CIS tert-butyl N-({4-methyl-2-azabicyclo[3.1.1]heptan-3-yl}methyl)carbamate (p161, 100 mg, 0.42 mmol) in DMF (0.75 mL) was added drop-wise. The reaction mixture was stirred at RT for 3 hrs then partitioned between ss NaHCO$_3$ and EtOAc. Layers were separated and organic phase was washed with ss NH$_4$Cl. Aqueous phases were extracted with EtOAc, organics were combined, washed with brine, dried and evaporated under reduced pressure. The crude material was purified by FC on NH column (Cy/EtOAc from 100:0 to 80:20) to afford CIS tert-butyl N-({4-methyl-2-[6-methyl-3-(pyrimidin-2-yl)pyridine-2-carbonyl]-2-azabicyclo[3.1.1]heptan-3-yl}methyl)carbamate (p183, 84 mg, y=46%).
MS (m/z): 438.1 [MH]$^+$ Preparation 184: CIS {4-methyl-2-[6-methyl-3-(pyrimidin-2-yl)pyridine-2-carbonyl]-2-azabicyclo[3.1.1]heptan-3-yl}methanamine

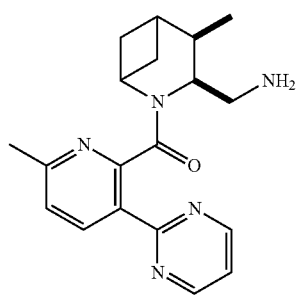 [SMILES: Cc1ccc(-c2ncccn2)c(C(=O)N2C3CC(C3)[C@@H](C)[C@H]2CN)n1]

The intermediate p184 was prepared using an analogue procedure as in Preparation 170 reacting CIS tert-butyl N-({4-methyl-2-[6-methyl-3-(pyrimidin-2-yl)pyridine-2-carbonyl]-2-azabicyclo[3.1.1]heptan-3-yl}methyl)carbamate (p183).
MS (m/z): 338.1 [MH]$^+$ Preparation 185:
4-fluoro-2-(2H-1,2,3-triazol-2-yl)benzoic acid

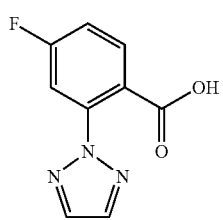 [SMILES: O=C(O)c1ccc(F)cc1-n1nccn1]

In a MW tube was added 4-fluoro-2-iodobenzoic acid (600 mg, 1.88 mmol), 1H-1,2,3-Triazole (0.22 mL, 3.76 mmol) and (1R,2R)—N$_1$,N$_2$-dimethylcyclohexane-1,2-diamine (0.06 mL, 0.38 mmol). To these solids were added 1,4-Dioxane (2 mL) and Water (0.2 mL), then CuI (18 mg, 0.09 mmol) and finally Cs$_2$CO$_3$ (1.22 g, 3.76 mmol). The mixture was then warmed to 100° C. for 2.5 hrs and left at RT O/N. HCl 6 N was added until pH 2, then volatiles were removed under vacuum and the crude material was purified by RP on C18 column (from H$_2$O/CH$_3$CN 95:5+0.1% of FA to H$_2$O/CH$_3$CN 5:95+0.1% of FA) affording 4-fluoro-2-(2H-1,2,3-triazol-2-yl)benzoic acid (p185, 250 mg, y=64%) as white solid.

MS (m/z): 206.3 [M−H]⁻

Preparation 186: 2-fluoro-6-(2H-1,2,3-triazol-2-yl)benzoic acid

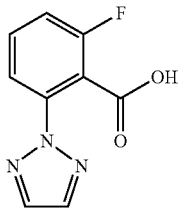

To a round-bottomed flask equipped with an overhead magnetic stirrer, reflux condenser, and nitrogen inlet were added 2-Fluoro-6-iodobenzoic acid (2.5 g, 9.4 mmol), CuI (0.09 g, 0.47 mmol), and 052003 (6.1 g, 18.8 mmol). To these solids were added dioxane (12.5 mL), water (0.05 mL), 1H-1,2,3-triazole (1.09 mL, 18.8 mmol), and finally (1R,2R)—N1,N2-dimethylcyclohexane-1,2-diamine (0.3 mL, 1.88 mmol). The mixture was then warmed to 100° C. ON. The day after the mixture was cooled and MTBE and water were added. After vigorous mixing, the layers were separated and the bottom aqueous layer was acidified to pH 2 with 6N HCl. The aqueous phase was then extracted with DCM (3×). The combined organic layers were dried, and concentrated. The residue was purified by FC on SiO$_2$ column (eluent: from DCM to DCM:MeOH 90:10) to afford 2-fluoro-6-(2H-1,2,3-triazol-2-yl)benzoic acid (p186, 1.1 g, y=56%).

MS (m/z): 208.0 [M+H]⁺

Preparation 187: 2-bromo-5-cyclopropylpyrazine

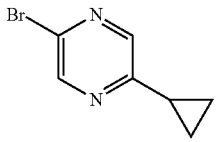

2,5-dibromopyrazine (1 g, 4.2 mmol) and 052003 (5.51 g, 16.82 mmol) were suspended in a Water (1.2 mL)/Toluene (22.8 mL) mixture. Suspension was degassed by bubbling nitrogen. Then [1,1'-Bis (diphenylphosphino)ferrocene]dichloropalladium (II) complex with DCM (86 mg, 0.11 mmol) and cyclopropylboronic acid (469.4 mg, 5.46 mmol) were added. The reaction mixture was refluxed for 2 hrs, then was cooled to room temperature and diluted with EtOAc; the organic layer was filtered, washed with water and brine. The organic phase was dried and evaporated under reduced pressure. The crude material was purified by FC on SiO$_2$ column (eluting with Cy) to afford 2-bromo-5-cyclopropylpyrazine (p187, 156 mg, y=19%).

MS (m/z): 202.0 [M+H]⁺

Preparation 188: 2-chloro-5-cyclopropylpyrimidine

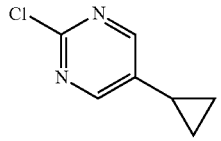

5-bromo-2-chloropyrimidine (1 g, 5.12 mmol) and Cs$_2$CO$_3$ (6.78 g, 20.68 mmol) were suspended in a Water (1.5 mL)/Toluene (28 mL) mixture. Suspension was degassed by bubbling nitrogen. Then [1,1'-Bis (diphenylphosphino)ferrocene]dichloropalladium (II) complex with DCM (106 mg, 0.13 mmol) and cyclopropylboronic acid (577.3 mg, 6.72 mmol) were added. The reaction mixture was refluxed for 2 hrs, then was cooled to room temperature and diluted with EtOAc; the organic layer was filtered, washed with water and brine. The organic phase was dried and evaporated under reduced pressure. The crude material was purified by FC on SiO$_2$ column (eluting with Cy/EtOAc from 100:0 to 85:15) to afford 2-chloro-5-cyclopropylpyrimidine (p188, 630 mg, y=79%) as a white solid.

MS (m/z): 155.2 [M+H]⁺

EXAMPLES

The following examples were synthesised following one of the general procedures reported below as indicated in the table.

General Procedure a:

A mixture of 2-azabicyclo[3.1.1]heptanes (p17-18, p21-22, p28-29, p35 as reported; 1 eq), carboxylic acid (p58, 61, 62, 65-67, 71 or commercially available if not specified in the table; 1.2 eq), DIPEA (3 eq), and T3P (3 eq) in DMF dry (33 vol) was stirred at 90° C. for 40 minutes then left stirring at RT for 1 h. The solvent was evaporated and crude material purified by FC on C18 cartridge (eluent: water+0.1% HCOOH/acetonitrile+0.1% HCOOH) then the compound was dissolved in 3-5 mL NaHCO$_3$ saturated aqueous solution and extracted with DCM. Organic layers were dried and solvent removed under reduced pressure to give the title compound.

General Procedure B:

A mixture of 2-azabicyclo[3.1.1]heptanes (p17-18, p21-22, p28-29, p35 as reported; 1 eq), carboxylic acid (p58, 61, 62, 65-67, 71 or commercially available if not specified in the table; 1.1 eq), DIPEA (4 eq), and T3P (3 eq) in DMF dry (33 vol) was stirred at 90-95° C. for 20-45 minutes. The solvent was evaporated and crude material purified by FC either on silica gel or aminic silica using Cy/AcOEt as eluting mixture. Then the product was triturated with Et$_2$O to give the target compound General Procedure C:

A mixture of 2-azabicyclo[3.1.1]heptanes (p17-18, p21-22, p28-29, p35 as reported; 1 eq), carboxylic acid (p58, 61, 62, 65-67, 71 or commercially available if not specified in the table; 0.9 eq), DIPEA (4 eq), and T3P (3 eq) in DMF dry (33 vol) was stirred at 90° C. for 15 minutes. The reaction mixture was partitioned between AcOEt and a NaOH solution (0.5N). The aqueous phase was extracted with AcOEt, and the combined organics were washed with brine, dried over Na$_2$SO$_4$, and filtered. The solvent was evaporated and crude material purified by FC on silica gel using Cy/AcOEt as eluting mixture. Then the product was triturated with Et$_2$O to give the target compound.

General Procedure D:

A mixture of 2-azabicyclo[3.1.1]heptanes (p17-18, p21-22, p28-29, p35 as reported; 1 eq), carboxylic acid (p58, 61, 62, 65-67, 71 or commercially available if not specified in the table; 1.2 eq), DIPEA (2 eq), and T3P (1 eq) in DMF dry (100 vol) was stirred at 80° C. for 18 hrs. The mixture was concentrated under reduced pressure and extracted with DCM and iced water. The organic phase washed with Brine, then it was concentrated under reduced pressure and the crude was purified by FC on aminic silica using Cy/AcOEt as eluting mixture. Then the product further purified by FC on C18 cartridge (eluent: water+0.1% HCOOH/acetonitrile+0.1% HCOOH) to give the target compound General Procedure E:

A mixture of 2-azabicyclo[3.1.1]heptanes (p17-18, p21-22, p28-29, p35 as reported; 1 eq), carboxylic acid (p58, 61, 62, 65-67, 71 or commercially available if not specified in the table; 1.2 eq), DIPEA (1.5 eq), and T3P (3 eq) in DMF dry (100 vol) was stirred at 50° C. for 1 hr. The mixture was treated with 1N NaOH, and then extracted with AcOEt, the extract was dried over Na$_2$SO$_4$, evaporated and purified by FC on silica gel using Cy/AcOEt as eluting mixture. Then the product further purified by FC on C18 cartridge (eluent: water+0.1% HCOOH/acetonitrile+0.1% HCOOH) to give the target compound.

General Procedure F:

To a solution of carboxylic acid (p58, 61, 62, 65-67, 71 or commercially available if not specified in the table; 1.1 eq) in DMF (40 vol), HATU (1.3 eq) and DIPEA (2.2 eq) were added. Mixture was stirred at RT for 30 min and then added dropwise to a solution of 2-azabicyclo[3.1.1]heptanes (p17-18, p21-22, p28-29, p35 as reported; 1 eq) in DMF (20 vol) and DIPEA (1.1 eq). The reaction was stirred at room temperature for 1 h, then solvent was removed under reduced pressure and crude purified by FC on either C18, NH or silica column with the appropriate eluent mixture to give the title compound.

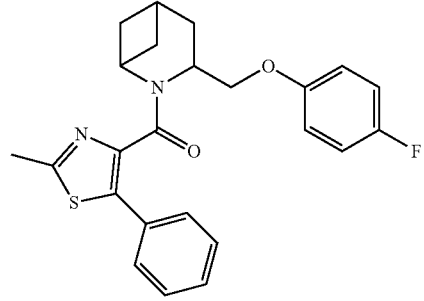

| Example | Starting materials | Gen. procedure | Yield (%) |
|---|---|---|---|
| 1 | p28 | B | 50 |

MS (m/z): 423.0 [MH]$^+$.
NMR ($^1$H, DMSO-d6): δ 7.26-7.47 (m, 5 H), 6.96-7.22 (m, 4 H), 4.63 (d, 1 H), 4.09-4.28 (m, 2 H), 3.88-3.96 (m, 1 H), 2.67 (s, 3H), 2.39-2.46 (m, 1 H), 2.31 (d, 1 H), 2.02-2.21 (m, 3 H), 1.69 (t, 1 H), 1.03 (t, 1 H)

3-[(4-fluorophenoxy)methyl]-2-(2-methyl-5-phenyl-1,3-thiazole-4-carbonyl)-2-azabicyclo[3.1.1]heptane The racemic mixture was separated into the single enantiomers by preparative chiral HPLC

| Preparative chiral chromatography protocol: | Column | Chiralpak IC (25 × 2.0 cm), 5 μ |
|---|---|---|
| | Mobile phase | n-Hexane/Ethanol 60/40% v/v |
| | Flow rate (ml/min) | 15 ml/min |
| | DAD detection | 220 nm |
| | Loop | 2500 μl |
| | Injection | 30 mg (each injection) |
| 2 | Enantiomer 1 | Rt: 8.9 min    100% ee |

MS (m/z): 423.1 [MH]$^+$.
(3R or 3S) 3-[(4-fluorophenoxy)methyl]-2-(2-methyl-5-phenyl-1,3-thiazole-4-carbonyl)-2-azabicyclo[3.1.1]heptane 3R or 3S enantiomer -continued

| Example | Starting materials | Gen. procedure | Yield (%) |
|---|---|---|---|
| 3 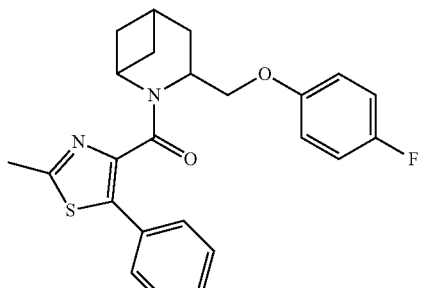 3S or 3R enantiomer | Enantiomer 2 Rt: 13.9 min 100% ee  MS (m/z): 423.1 [MH]⁺. (3S or 3R) 3-[(4-fluorophenoxy)methyl]-2-(2-methyl-5-phenyl-1,3-thiazole-4-carbonyl)-2-azabicyclo[3.1.1]heptane | | |
| 4 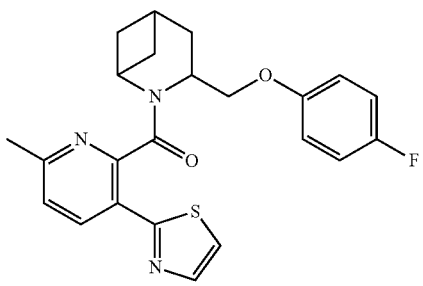 3-(4-fluorophenoxymethyl)-2-{[6-methyl-3-(1,3-thiazol-2-yl)pyridin-2-yl]carbonyl}-2-azabicyclo[3.1.1]heptane | p28 + p65 | B | 71 |

MS (m/z): 424.0 [MH]⁺.
NMR (¹H, DMSO-d6): δ 8.19 (d, 1 H), 7.92 (d, 1 H), 7.80 (d, 1 H), 7.44 (d, 1 H), 6.95-7.20 (m, 4 H), 4.56-4.65 (m, 1 H), 4.40 (dd, 1 H), 4.17 (t, 1 H), 3.77 (q, 1 H), 2.53 (s, 3 H), 2.42-2.48 (m, 1 H), 2.32-2.39 (m, 1 H), 2.22 (d, J = 13.7 Hz, 1 H), 2.14 (dt, 1 H), 2.02-2.08 (m, 1 H), 1.80 (t, 1 H), 1.15-1.27 (m, 1 H)

The racemic mixture was separated into the single enantiomers by preparative chiral HPLC

| Preparative chiral chromatography protocol: | Column | Chiralpak AD-H (25 × 2.0 cm), 5 μ |
|---|---|---|
| | Mobile phase | n-Hexane/(Ethanol/Methanol + 0.1% ipa) 85/15% v/v |
| | Flow rate (ml/min) | 14 ml/min |
| | DAD detection | 220 nm |
| | Loop | 2500 μl |
| | Injection | 23 mg (each injection) |

| 5 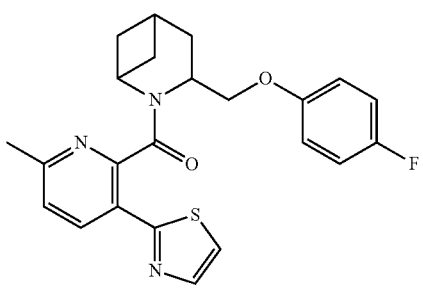 3R or 3S enantiomer | Enantiomer 1 Rt: 8.1 min 99% ee  MS (m/z): 424.3 [MH]⁺. (3R or 3S) 3-(4-fluorophenoxymethyl)-2-{[6-methyl-3-(1,3-thiazol-2-yl)pyridin-2-yl]carbonyl}-2-azabicyclo[3.1.1]heptane | | |

| Example | Starting materials | Gen. procedure | Yield (%) |
|---------|-------------------|----------------|-----------|
| 6 | Enantiomer 2 | Rt: 10.3 min | 99% ee |

MS (m/z): 424.3 [MH]⁺.
(3S or 3R) 3-(4-fluorophenoxymethyl)-2-{[6-methyl-3-(1,3-thiazol-2-yl)pyridin-2-yl]carbonyl}-2-azabicyclo[3.1.1]heptane 3S or 3R enantiomer

| 7 | p28 + p66 | B | 57 |

MS (m/z): 423.0 [MH]⁺.
NMR (¹H, DMSO-d6): δ 7.88 (d, 1 H), 7.77 (d, 1 H), 7.72 (d, 1 H), 7.31-7.37 (m, 1 H), 7.04-7.19 (m, 4 H), 7.02 (s, 1 H), 4.53-4.61 (m, 1 H), 4.48 (dd, 1 H), 4.00 (t, 1 H), 3.82 (m, 1 H), 2.37-2.42 (m, 1 H), 2.35-2.36 (m, 3 H), 2.11-2.33 (m, 3 H), 1.84-1.92 (m, 1 H), 1.57 (t, 1 H), 0.85 (t, 1 H)

3-(4-fluorophenoxymethyl)-2-{[5-methyl-2-(1,3-thiazol-2-yl)phenyl]carbonyl}-2-azabicyclo[3.1.1]heptane The racemic mixture was separated into the single enantiomers by preparative chiral HPLC

| Preparative chiral chromatography protocol: | Column | Chiralpak AD-H (25 × 2.0 cm), 5 µ |
|---|---|---|
| | Mobile phase | n-Hexane/(Ethanol/Methanol + 0.1% ipa) 80/20% v/v |
| | Flow rate (ml/min) | 18 ml/min |
| | DAD detection | 220 nm |
| | Loop | 2700 µl |
| | Injection | 32 mg (each injection) |

| 8 | Enantiomer 1 | Rt: 7.3 min | 99% ee |

MS (m/z): 423.3 [MH]⁺.
(3R or 3S) 3-(4-fluorophenoxymethyl)-2-{[5-methyl-2-(1,3-thiazol-2-yl)phenyl]carbonyl}-2-azabicyclo[3.1.1]heptane 3R or 3S enantiomer

| Example | Starting materials | Gen. procedure | Yield (%) |
|---|---|---|---|
| 9 | Enantiomer 2 | Rt: 12.0 min | 99% ee |

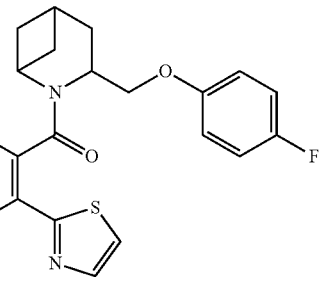

3S or 3R enantiomer

MS (m/z): 423.3 [MH]+.
(3S or 3R) 3-(4-fluorophenoxymethyl)-2-{[5-methyl-2-(1,3-thiazol-2-yl)phenyl]carbonyl}-2-azabicyclo[3.1.1]heptane

| | | | |
|---|---|---|---|
| 10 | p28 + p62 | B | 37 |

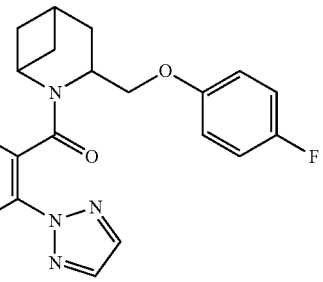

3-(4-fluorophenoxymethyl)-2-{[5-methyl-2-(2H-1,2,3-triazol-2-yl)phenyl]carbonyl}-2-azabicyclo[3.1.1]heptane MS (m/z): 407.0 [MH]+.
NMR ($^1$H, DMSO-d6): δ 7.98-8.08 (m, 2 H), 7.71 (d, 1 H), 7.34-7.45 (m, 1 H), 7.24 (s, 1 H), 7.03-7.20 (m, 4 H), 4.60 (t, 1 H), 4.37 (dd, 1 H), 3.88 (t, 1 H), 3.82 (q, 1 H), 2.42-2.47 (m, 1 H), 2.35-2.38 (m, 3 H), 2.10-2.33 (m, 2 H), 1.91-2.07 (m, 2 H), 1.44-1.49 (m, 1 H), 1.14 (t, 1 H).

The racemic mixture was separated into the sinqle enantiomers by preparative chiral HPLC

| Preparative chiral chromatography protocol: | Column | Chiralpak AD-H (25 × 2.0 cm), 5 μ |
|---|---|---|
| | Mobile phase | n-Hexane/(Ethanol/Methanol + 0.1% ipa) 80/20% v/v |
| | Flow rate (ml/min) | 14 ml/min |
| | DAD detection | 220 nm |
| | Loop | 750 μl |
| | Injection | 30 mg (each injection) |
| 11 | Enantiomer 1 | Rt: 7.6 min | 99% ee |

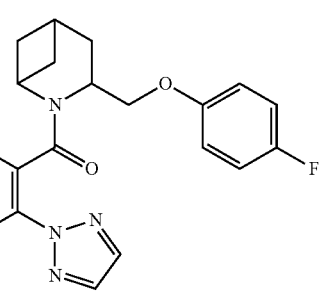

3R or 3S enantiomer

MS (m/z): 407.4 [MH]+.
(3R or 3S) 3-(4-fluorophenoxymethyl)-2-{[5-methyl-2-(2H-1,2,3-triazol-2-yl)phenyl]carbonyl}-2-azabicyclo[3.1.1]heptane -continued

| Example | Starting materials | Gen. procedure | Yield (%) |
|---|---|---|---|
| 12 | Enantiomer 2 | Rt: 13.6 min | 99% ee |

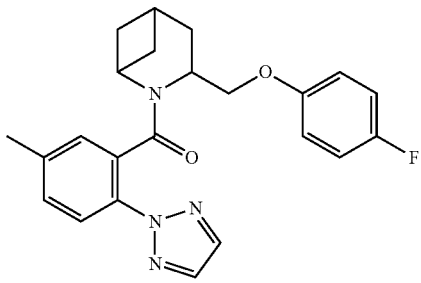

3S or 3R enantiomer

MS (m/z): 407.3 [MH]⁺.
(3S or 3R) 3-(4-fluorophenoxymethyl)-2-{[5-methyl-2-(2H-1,2,3-triazol-2-yl)phenyl]carbonyl}-2-azabicyclo[3.1.1]heptane

| | | | |
|---|---|---|---|
| 13 | p28 + p58 | B | 52 |

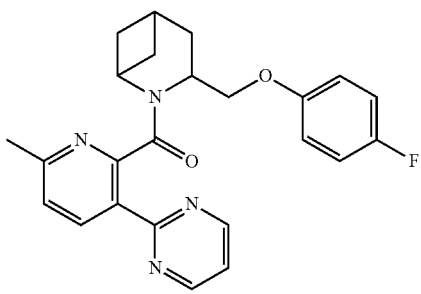

3-(4-fluorophenoxymethyl)-2-{[6-methyl-3-(pyrimidin-2-yl)pyridin-2-yl]carbonyl}-2-azabicyclo[3.1.1]heptane MS (m/z): 419.0 [MH]⁺.
NMR ($^1$H, DMSO-d6): δ 8.84-8.92 (m, 2 H), 8.46 (d, 1 H), 7.42-7.49 (m, 2 H), 7.07-7.18 (m, 4 H), 4.56-4.63 (m, 1 H), 4.43 (dd, 1 H), 4.17 (t, 1 H), 3.88 (q, 1 H), 2.54 (s, 3 H), 2.50 (m, 1 H), 2.39-2.46 (m, 1 H), 2.20-2.27 (m, 1 H), 2.13-2.19 (m, 1 H), 2.05-2.13 (m, 1 H), 1.79-1.86 (m, 1 H), 1.48 (t, 1 H)

The racemic mixture was separated into the single enantiomers by preparative chiral HPLC

| Preparative chiral chromatography protocol: | Column | Chiralpak AD-H (25 × 2.0 cm), 5 μ |
|---|---|---|
| | Mobile phase | n-Hexane/(Ethanol/Methanol 1.1 + 0.1% ipa) 85/15% v/v |
| | Flow rate (ml/min) | 14 ml/min |
| | DAD detection | 220 nm |
| | Loop | 2000 μl |
| | Injection | 10 mg (each injection) |

| 14 | Enantiomer 1 | Rt: 7.6 min | 100% ee |
|---|---|---|---|

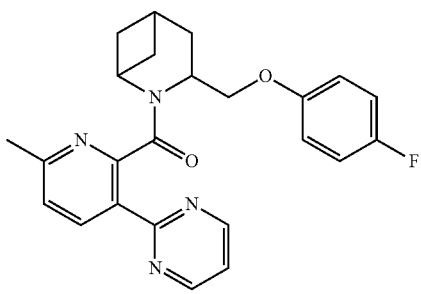

3R or 3S enantiomer

MS (m/z): 419.1 [MH]⁺.
(3R or 3S) 3-(4-fluorophenoxymethyl)-2-{[6-methyl-3-(pyrimidin-2-yl)pyridin-2-yl]carbonyl}-2-azabicyclo[3.1.1]heptane

| Example | Starting materials | Gen. procedure | Yield (%) |
|---|---|---|---|
| 15 | Enantiomer 2 | Rt: 9.4 min | 97.8% ee |

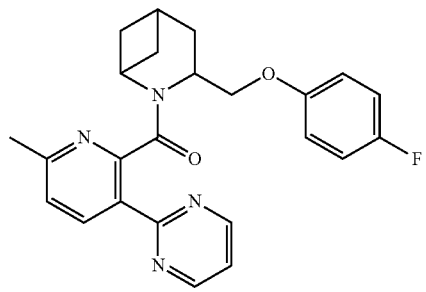

MS (m/z): 419.1 [MH]$^+$.
(3S or 3R) 3-(4-fluorophenoxymethyl)-2-{[6-methyl-3-(pyrimidin-2-yl)pyridin-2-yl]carbonyl}-2-azabicyclo[3.1.1]heptane 3S or 3R enantiomer

| | | | |
|---|---|---|---|
| 16 | p28 + p61 | B | 26 |

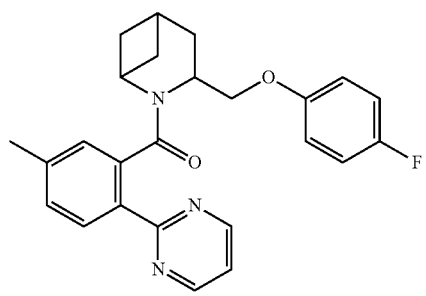

MS (m/z): 418.1 [MH]$^+$.
NMR ($^1$H, DMSO-d6): δ 8.79-8.87 (m, 1 H), 8.06 (d, 1 H), 7.40 (t, 2 H), 7.33-7.37 (m, 1 H), 7.05-7.20 (m, 5 H), 4.61 (d, 1 H), 4.49-4.56 (m, 1 H), 4.01-4.08 (m, 1 H), 3.87 (d, 1 H), 2.44-2.54 (m, 1 H), 2.36 (s, 3 H), 2.29-2.43 (m, 1 H), 2.12-2.27 (m, 2 H), 1.93-2.05 (m, 1 H), 1.74-1.81 (m, 1 H), 1.28-1.36 (m, 1 H)

3-(4-fluorophenoxymethyl)-2-{[5-methyl-2-(pyrimidin-2-yl)phenyl]carbonyl}-2-azabicyclo[3.1.1]heptane The racemic mixture was separated into the sinqle enantiomers by preparative chiral HPLC

| Preparative chiral chromatography protocol: | Column | Chiralpak IC (25 × 2.0 cm), 5 μ |
|---|---|---|
| | Mobile phase | n-Hexane/Ethanol 70/30% v/v |
| | Flow rate (ml/min) | 15 ml/min |
| | DAD detection | 220 nm |
| | Loop | 2500 μL |
| | Injection | 7.5 mg/injection |

| 17 | Enantiomer 1 | Rt: 11.2 min | 99% ee |
|---|---|---|---|

MS (m/z): 418.1 [MH]$^+$.
(3S or 3R) 3-(4-fluorophenoxymethyl)-2-{[5-methyl-2-(pyrimidin-2-yl)phenyl]carbonyl}-2-azabicyclo[3.1.1]heptane 3S or 3R enantiomer -continued

| Example | Starting materials | Gen. procedure | Yield (%) |
|---------|-------------------|----------------|-----------|
| 18 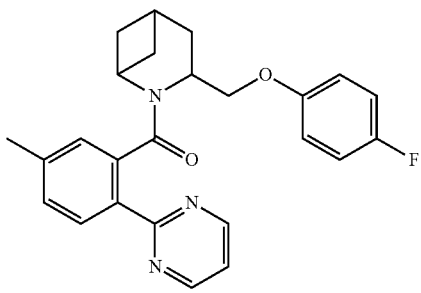<br>3R or 3S enantiomer | Enantiomer 2<br><br>MS (m/z): 418.1 [MH]⁺.<br>(3R or 3S) 3-(4-fluorophenoxymethyl)-2-{[5-methyl-2-(pyrimidin-2-yl)phenyl]carbonyl}-2-azabicyclo[3.1.1]heptane | Rt: 18.8 min | 99% ee |
| 19 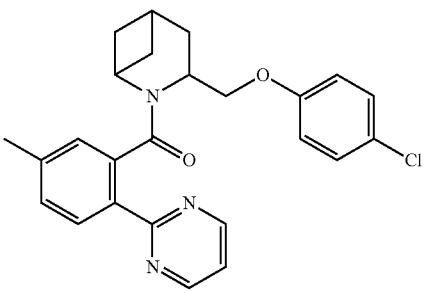<br>3-(4-chlorophenoxymethyl)-2-{[5-methyl-2-(pyrimidin-2-yl)phenyl]carbonyl}-2-azabicyclo[3.1.1]heptane | p29 + p61<br><br>MS (m/z): 434.3 [MH]⁺.<br>NMR (¹H, DMSO-d6): δ 8.83 (d, 2 H), 8.11 (d, 1 H), 7.40 (t, 2 H), 6.94 (s, 5 H), 4.49-4.66 (m, 2 H), 4.05-4.11 (m, 1 H), 3.93 (q, 1 H), 2.34 (br. s., 3 H), 2.29-2.47 (m, 2 H), 2.13-2.24 (m, 2 H), 1.93-2.00 (m, 1 H), 1.57 (t, 1 H), 1.32 (t, 1 H) | A | 33 |
| 20 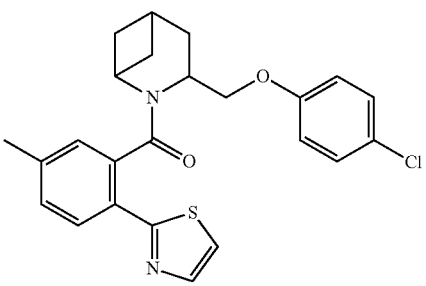<br>3-(4-chlorophenoxymethyl)-2-{[5-methyl-2-(1,3-thiazol-2-yl)phenyl]carbonyl}-2-azabicyclo[3.1.1]heptane | p29 + p66<br><br>MS (m/z): 439.2 [MH]⁺.<br>NMR (¹H, DMSO-d6): δ 7.86 (dd, 1H), 7.65-7.79 (m, 2H), 7.26-7.41 (m, 3H), 6.95-7.24 (m, 3H), 4.53-4.72 (m, 1H), 4.32-4.52 (m, 1H), 3.99-4.29 (m, 1H), 3.74-3.97 (m, 1H), 2.38-2.48 (m, 1H), 2.36 (d, 3H), 2.10-2.33 (m, 3H), 1.84-2.08 (m, 1H), 1.52-1.80 (m, 1H), 0.77-1.49 (m, 2H) | B | 33 |

| Example | Starting materials | Gen. procedure | Yield (%) |
|---|---|---|---|
| 21 | p21 + p58 | B | 37 |

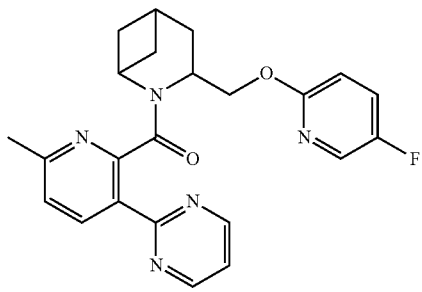

3-{[(5-fluoropyridin-2-yl)oxy]methyl}-2-{[6-methyl-3-(pyrimidin-2-yl)pyridin-2-yl]carbonyl}-2-azabicyclo[3.1.1]heptane MS (m/z): 420.1 [MH]$^+$.
NMR ($^1$H, DMSO-d6): δ 8.89 (d, 2 H), 8.44-8.50 (m, 1 H), 8.19 (d, 1 H), 7.67-7.78 (m, 1 H), 7.46-7.51 (m, 1 H), 7.44 (d, 1 H), 6.97 (d, 1 H), 4.60-4.72 (m, 2 H), 4.38 (t, 1 H), 3.87 (q, 1 H), 2.56 (br. s., 3 H), 2.46-2.51 (m, 2 H), 2.07-2.27 (m, 3 H), 1.76 (t, 1 H), 1.49 (t, 1 H)

The racemic mixture was separated into the single enantiomers by preparative chiral HPLC

| Preparative chiral chromatography protocol: | | |
|---|---|---|
| | Column | Chiralpak AS-H (25 × 2.0 cm), 5 μ |
| | Mobile phase | n-Hexane/Ethanol 50/50% v/v |
| | Flow rate (ml/min) | 14 ml/min |
| | DAD detection | 220 nm |
| | Loop | 1000 μl |
| | Injection | 20 mg (each injection) |

| 22 | Enantiomer 1 | Rt: 5.2 min | 100% ee |

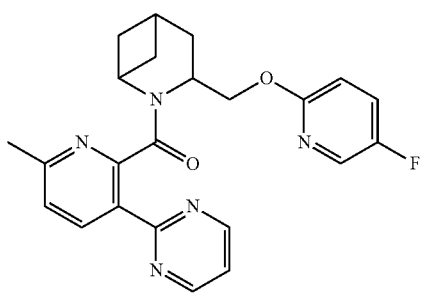

3S or 3R enantiomer

MS (m/z): 420.3 [MH]$^+$.
(3S or 3R) 3-{[(5-fluoropyridin-2-yl)oxy]methyl}-2-{[6-methyl-3-(pyrimidin-2-yl)pyridin-2-yl]carbonyl}-2-azabicyclo[3.1.1]heptane

| 23 | Enantiomer 2 | Rt: 8.8 min | 100% ee |

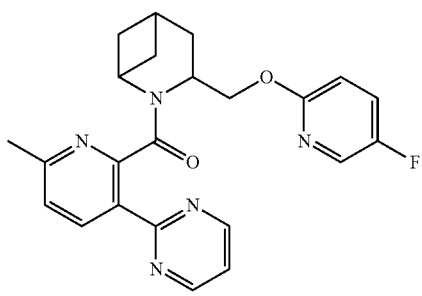

3R or 3S enantiomer

MS (m/z): 420.3 [MH]$^+$.
(3R or 3S) 3-{[(5-fluoropyridin-2-yl)oxy]methyl}-2-{[6-methyl-3-(pyrimidin-2-yl)pyridin-2-yl]carbonyl}-2-azabicyclo[3.1.1]heptane -continued

| Example | Starting materials | Gen. procedure | Yield (%) |
|---|---|---|---|
| 24 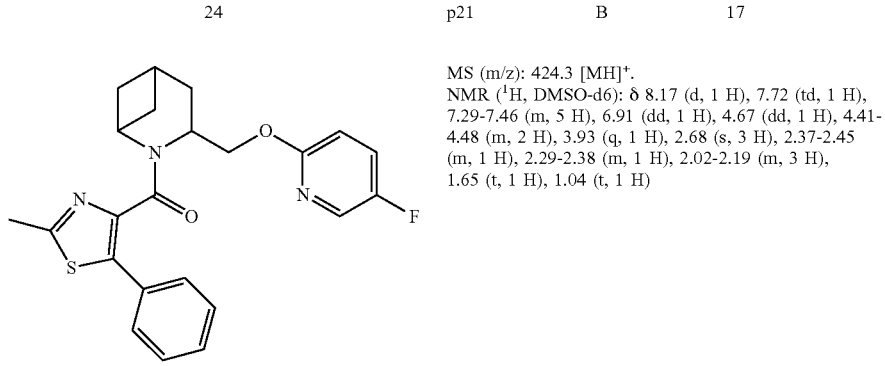 3-{[(5-fluoropyridin-2-yl)oxy]methyl}-2-[(2-methyl-5-phenyl-1,3-thiazol-4-yl)carbonyl]-2-azabicyclo[3.1.1]heptane | p21 | B | 17 |

MS (m/z): 424.3 [MH]$^+$.
NMR ($^1$H, DMSO-d6): δ 8.17 (d, 1 H), 7.72 (td, 1 H), 7.29-7.46 (m, 5 H), 6.91 (dd, 1 H), 4.67 (dd, 1 H), 4.41-4.48 (m, 2 H), 3.93 (q, 1 H), 2.68 (s, 3 H), 2.37-2.45 (m, 1 H), 2.29-2.38 (m, 1 H), 2.02-2.19 (m, 3 H), 1.65 (t, 1 H), 1.04 (t, 1 H)

| Example | Starting materials | Gen. procedure | Yield (%) |
|---|---|---|---|
| 25 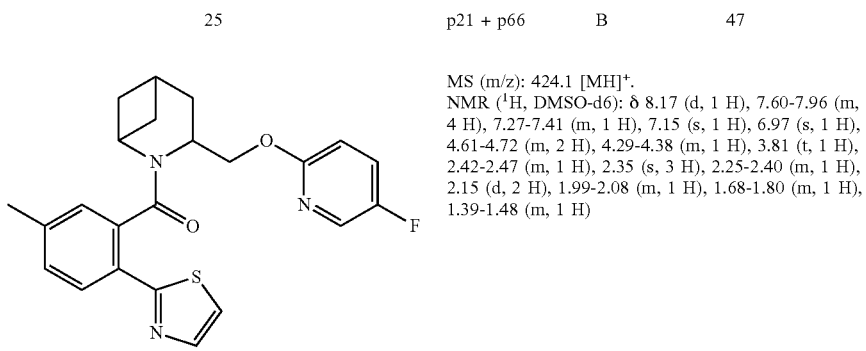 3-{[(5-fluoropyridin-2-yl)oxy]methyl}-2-{[5-methyl-2-(1,3-thiazol-2-yl)phenyl]carbonyl}-2-azabicyclo[3.1.1]heptane | p21 + p66 | B | 47 |

MS (m/z): 424.1 [MH]$^+$.
NMR ($^1$H, DMSO-d6): δ 8.17 (d, 1 H), 7.60-7.96 (m, 4 H), 7.27-7.41 (m, 1 H), 7.15 (s, 1 H), 6.97 (s, 1 H), 4.61-4.72 (m, 2 H), 4.29-4.38 (m, 1 H), 3.81 (t, 1 H), 2.42-2.47 (m, 1 H), 2.35 (s, 3 H), 2.25-2.40 (m, 1 H), 2.15 (d, 2 H), 1.99-2.08 (m, 1 H), 1.68-1.80 (m, 1 H), 1.39-1.48 (m, 1 H)

The racemic mixture was separated into the sinqle enantiomers by preparative chiral HPLC

| Preparative chiral chromatography protocol: | Column | Chiralpak IC (25 × 2.0 cm), 5 μ |
|---|---|---|
| | Mobile phase | n-Hexane/Ethanol 60/40% v/v |
| | Flow rate (ml/min) | 14 ml/min |
| | DAD detection | 220 nm |
| | Loop | 1000 μl |
| | Injection | 53 mg (each injection) |

| 26 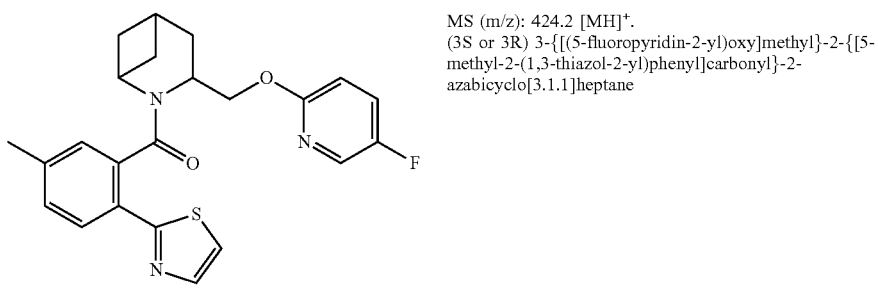 3S or 3R enantiomer | Enantiomer 1 | Rt: 11.6 min | 100% ee |

MS (m/z): 424.2 [MH]$^+$.
(3S or 3R) 3-{[(5-fluoropyridin-2-yl)oxy]methyl}-2-{[5-methyl-2-(1,3-thiazol-2-yl)phenyl]carbonyl}-2-azabicyclo[3.1.1]heptane

| Example | Starting materials | Gen. procedure | Yield (%) |
|---|---|---|---|
| 27 | Enantiomer 2 | Rt: 14.6 min | 100% ee |

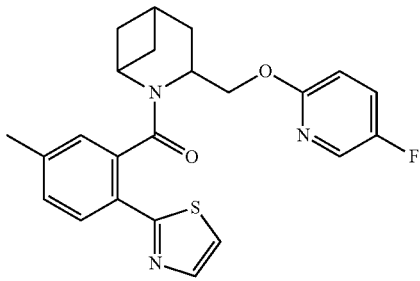

3R or 3S enantiomer

MS (m/z): 424.2 [MH]⁺.
(3R or 3S) 3-{[(5-fluoropyridin-2-yl)oxy]methyl}-2-{[5-methyl-2-(1,3-thiazol-2-yl)phenyl]carbonyl}-2-azabicyclo[3.1.1]heptane

| | | | |
|---|---|---|---|
| 28 | p21 + p62 | B | 52 |

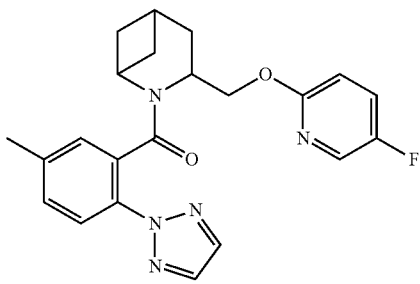

3-{[(5-fluoropyridin-2-yl)oxy]methyl}-2-{[5-methyl-2-(2H-1,2,3-triazol-2-yl)phenyl]carbonyl}-2-azabicyclo[3.1.1]heptane MS (m/z): 408.3 [MH]⁺.
NMR (¹H, DMSO-d6): δ 8.16 (d, 1 H), 7.93 (s, 2 H), 7.77 (d, 1 H), 7.68-7.74 (m, 1 H), 7.39 (dd, 1 H), 7.23 (d, 1 H), 6.94 (td, 1 H), 4.59-4.68 (m, 1 H), 4.56 (d, 1 H), 4.22 (t, 1 H), 3.83 (q, 1 H), 2.41-2.48 (m, 1 H), 2.35 (s, 3 H), 2.32 (m, 1 H), 2.10-2.23 (m, 2 H), 1.93-2.05 (m, 1 H), 1.77 (t, 1 H), 1.40-1.48 (m, 1 H)

The racemic mixture was separated into the single enantiomers by preparative chiral HPLC

| Preparative chiral chromatography protocol: | Column | Chiralpak IC (25 × 2.0 cm), 5 μ |
|---|---|---|
| | Mobile phase | n-Hexane/Ethanol 60/40% v/v |
| | Flow rate (ml/min) | 14 ml/min |
| | DAD detection | 220 nm |
| | Loop | 1000 μl |
| | Injection | 53 mg (each injection) |

| | | | |
|---|---|---|---|
| 29 | Enantiomer 1 | Rt: 9.9 min | 100% ee |

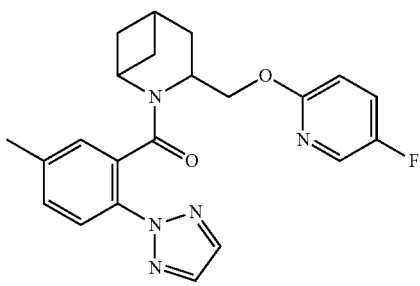

3S or 3R enantiomer

MS (m/z): 408.2 [MH]⁺.
(3S or 3R) 3-{[(5-fluoropyridin-2-yl)oxy]methyl}-2-{[5-methyl-2-(2H-1,2,3-triazol-2-yl)phenyl]carbonyl}-2-azabicyclo[3.1.1]heptane

| Example | Starting materials | Gen. procedure | Yield (%) |
|---|---|---|---|
| 30 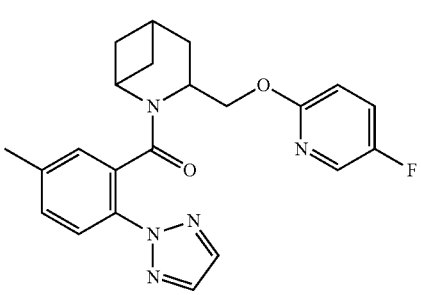 3S or 3R enantiomer | Enantiomer 2 Rt: 12.2 min 100% ee MS (m/z): 408.2 [MH]⁺. (3R or 3S) 3-{[(5-fluoropyridin-2-yl)oxy]methyl}-2-{[5-methyl-2-(2H-1,2,3-triazol-2-yl)phenyl]carbonyl}-2-azabicyclo[3.1.1]heptane | | |
| 31 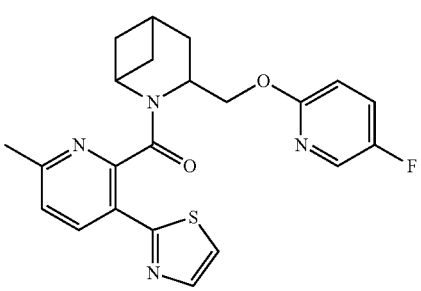 3-{[(5-fluoropyridin-2-yl)oxy]methyl}-2-{[6-methyl-3-(1,3-thiazol-2-yl)pyridin-2-yl]carbonyl}-2-azabicyclo[3.1.1]heptane | p21 + p65 MS (m/z): 425.0 [MH]⁺. NMR (¹H, DMSO-d6): δ 8.14-8.23 (m, 2 H), 7.90 (d, 1 H), 7.81 (d, 1 H), 7.72 (td, 1 H), 7.41-7.45 (m, 1H), 6.95 (dd, 1 H), 4.57-4.69 (m, 2 H), 4.40-4.49 (m, 1 H), 3.76 (q, 1 H), 2.52 (s, 3 H), 2.31-2.47 (m, 2 H), 2.00-2.22 (m, 3 H), 1.77 (t, 1 H), 1.18-1.27 (m, 1 H) | A | 46 |
| 32 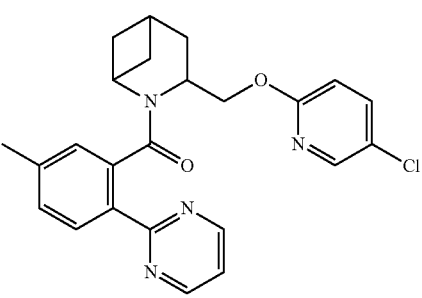 3-{[(5-chloropyridin-2-yl)oxy]methyl}-2-{[5-methyl-2-(pyrimidin-2-yl)phenyl]carbonyl}-2-azabicyclo[3.1.1]heptane | p22 + p61 MS (m/z): 435.3 [MH]⁺. NMR (¹H, DMSO-d6): δ 8.85 (m, 2 H), 8.23 (d, 1 H), 8.09 (d, 1 H), 7.84 (d, 1 H), 7.40 (t, 1 H), 7.33 (d, 1 H), 6.96 (d, 1 H), 6.86 (s, 1 H), 4.81 (dd, 1 H), 4.61-4.70 (m, 1 H), 4.26 (t, 1 H), 3.93 (q, 1 H), 2.41-2.46 (m, 1 H), 2.38 (s, 3 H), 2.33-2.36 (m, 1 H), 2.17 (d, 2 H), 1.93-2.02 (m, 1 H), 1.75 (t, 1 H), 1.40-1.51 (m, 1 H) | B | 55 |

The racemic mixture was separated into the sinqle enantiomers by preparative chiral HPLC

| Preparative chiral chromatography protocol: | Column | Chiralpak IC (25 × 2.0 cm), 5 μ |
|---|---|---|
| | Mobile phase | n-Hexane/Ethanol 50/50% v/v |
| | Flow rate (ml/min) | 18 ml/min |
| | DAD detection | 220 nm |
| | Loop | 3300 μl |
| | Injection | 30 mg (each injection) |

| Example | Starting materials | Gen. procedure | Yield (%) |
|---------|-------------------|----------------|-----------|
| 33 | Enantiomer 1 | Rt: 8.4 min | 100% ee |

MS (m/z): 424.2 [MH]⁺.
(3S or 3R) 3-{[(5-chloropyridin-2-yl)oxy]methyl}-2-{[5-methyl-2-(pyrimidin-2-yl)phenyl]carbonyl}-2-azabicyclo[3.1.1]heptane 3S or 3R enantiomer

| | | | |
|---|---|---|---|
| 34 | Enantiomer 2 | Rt: 13.8 min | 100% ee |

MS (m/z): 424.2 [MH]⁺.
(3R or 3S) 3-{[(5-chloropyridin-2-yl)oxy]methyl}-2-{[5-methyl-2-(pyrimidin-2-yl)phenyl]carbonyl}-2-azabicyclo[3.1.1]heptane 3R or 3S enantiomer

| | | | |
|---|---|---|---|
| 35 | p17 + p61 | C | 36 |

MS (m/z): 469.3 [MH]⁺.
NMR (¹H, DMSO-d6): δ 8.84 (d, 2 H), 8.61 (s, 1 H), 8.05-8.16 (m, 2 H), 7.40 (t, 1 H), 7.33 (d, 1 H), 7.10 (d, 1 H), 6.87 (s, 1 H), 4.92 (dd, 1 H), 4.64-4.70 (m, 1 H), 4.33-4.39 (m, 1 H), 3.94 (q, 1 H), 2.42-2.48 (m, 1 H), 2.34 (s, 3H), 2.31-2.42 (m, 1 H), 2.14-2.22 (m, 2 H), 1.95-2.03 (m, 1 H), 1.76 (t, 1 H), 1.41-1.51 (m, 1 H)

2-{[5-methyl-2-(pyrimidin-2-yl)phenyl]carbonyl}-3-({[5-(trifluoromethyl)pyridin-2-yl]oxy}methyl)-2-azabicyclo[3.1.1]heptane The racemic mixture was separated into the sinqle enantiomers by preparative chiral SFC

| Preparative chiral chromatography protocol: | | |
|---|---|---|
| | Column | Chiralpak OD-H (25 × 2.0 cm), 5 μ |
| | Modifier | Methanol 17% |
| | Flow rate (ml/min) | 46 |
| | Pressure (bar) | 120 |
| | Temperature (° C.) | 38 |
| | UV detection | 220 nm |
| | Loop | 650 μL |
| | Injection | 9.75 mg |

-continued

| Example | Starting materials | Gen. procedure | Yield (%) |
|---|---|---|---|
| 36 | Enantiomer 1 | Rt: 3.7 min | 99% ee |

MS (m/z): 469.3 [MH]⁺.
(3S or 3R) 2-{[5-methyl-2-(pyrimidin-2-yl)phenyl]carbonyl}-3-({[5-(trifluoromethyl)pyridin-2-yl]oxy}methyl)-2-azabicyclo[3.1.1]heptane 3S or 3R enantiomer

| 37 | Enantiomer 2 | Rt: 5.4 min | 99% ee |
|---|---|---|---|

MS (m/z): 469.3 [MH]⁺.
(3R or 3S) 2-{[5-methyl-2-(pyrimidin-2-yl)phenyl]carbonyl}-3-({[5-(trifluoromethyl)pyridin-2-yl]oxy}methyl)-2-azabicyclo[3.1.1]heptane 3R or 3S enantiomer

| 38 | p18 | D | 37 |
|---|---|---|---|

MS (m/z): 456.1 [MH]⁺.
NMR (¹H, DMSO-d6): δ 8.82-9.16 (m, 1 H), 8.04 (d, 1 H), 7.83 (d, 1 H), 7.61-7.71 (m, 1 H), 7.42-7.47 (m, 1 H), 7.26-7.42 (m, 5 H), 7.24 (s, 1 H), 4.67-5.03 (m, 1 H), 4.53 (d, 2 H), 3.94 (q, 1 H), 2.66 (s, 3 H), 2.26-2.45 (m, 2 H), 2.17-2.25 (m, 1 H), 2.02-2.16 (m, 2 H), 1.00-1.90 (m, 2 H)

3-{[2-(2-methyl-5-phenyl-1,3-thiazole-4-carbonyl)-2-azabicyclo[3.1.1]heptan-3-yl]methoxy}isoquinoline

| 39 | p28 + p67 | F | 6 |
|---|---|---|---|

MS (m/z): [MH]⁺.
NMR (¹H, DMSO-d6): δ 8.17 (d, 1H), 7.69 (s, 2H), 7.30 (d, 1H), 7.06-6.96 (m, 4H), 4.85-4.79 (m, 1H), 4.58 (dd, 1H), 4.19 (dd, 1H), 3.94 (q, 1H), 2.63 (s, 3H), 2.56-2.52 (m, 1H), 2.40-2.38 (m, 2H), 2.16-2.07 (m, 2H), 1.89-1.85 (m, 1H), 1.45 (t, 1H).

3-[(4-fluorophenoxy)methyl]-2-[6-methyl-3-(2H-1,2,3-triazol-2-yl)pyridine-2-carbonyl]-2-azabicyclo[3.1.1]heptane -continued

| Example | Starting materials | Gen. procedure | Yield (%) |
|---------|-------------------|----------------|-----------|
| 40 3-[(4-fluorophenoxy)methyl]-2-[5-(2-fluorophenyl)-2-methyl-1,3-thiazole-4-carbonyl]-2-azabicyclo[3.1.1]heptane | p28 + p71 | F | 56 |

MS (m/z): 441.1 [MH]+.
NMR (1H, Chloroform-d): δ 7.45-7.41 (m, 1H), 7.33-7.27 (m, 1H), 7.09-7.02 (m, 2H), 6.99-6.92 (m, 4H), 4.77-4.71 (m, 1H), 4.38 (dd, 1H), 4.16 (q, 1H), 4.03 (dd, 1H), 2.74 (s, 3H), 2.46-2.44 (m, 1H), 2.29-2.26 (m, 2H), 2.07 (dt, 2H), 1.58-1.53 (m, 1H), 1.07-1.02 (m, 1H).

| Example | Starting materials | Gen. procedure | Yield (%) |
|---------|-------------------|----------------|-----------|
| 41 3-[2-(4-fluorophenoxy)ethyl]-2-[5-methyl-2-(pyrimidin-2-yl)benzoyl]-2-azabicyclo[3.1.1]heptane | p35 + p61 | E | 36 |

MS (m/z): 432.2 [MH]+.
NMR (1H, DMSO-d6): δ 8.74 (d, 2 H), 8.18 (d, 1 H), 7.30 (d, 1 H), 7.15 (t, 1 H), 7.11 (d, 1 H), 6.84-7.00 (m, 4 H), 4.51-4.65 (m, 1 H), 4.13-4.34 (m, 2 H), 4.03-4.09 (m, 1 H), 2.83-2.93 (m, 1 H), 2.43-2.58 (m, 2 H), 2.41 (s, 3 H), 2.08-2.28 (m, 3 H), 1.88-1.96 (m, 1 H), 1.79 (t, 1 H), 1.11 (t, 1 H)

The racemic mixture was separated into the sinqle enantiomers by preparative chiral HPLC

| Preparative chiral chromatography protocol: | Column | Chiralpak IC (25 × 2.0 cm), 5 μ |
|---|---|---|
| | Mobile phase | n-Hexane/Ethanol 40/60% v/v |
| | Flow rate (ml/min) | 14 ml/min |
| | DAD detection | 220 nm |
| | Loop | 3000 μl |
| | Injection | 40 mg (each injection) |

| Example | Starting materials | Gen. procedure | Yield (%) |
|---|---|---|---|
| 42 | Enantiomer 1 | Rt: 10 min | 100% ee |

MS (m/z): 432.2 [MH]+.
(3S or 3R) 3-[2-(4-fluorophenoxy)ethyl]-2-[5-methyl-2-(pyrimidin-2-yl)benzoyl]-2-azabicyclo[3.1.1]heptane 3S or 3R enantiomer

| | | | |
|---|---|---|---|
| 43 | Enantiomer 2 | Rt: 16.3 min | 100% ee |

MS (m/z): 432.2 [MH]+.
(3R or 3S) 3-[2-(4-fluorophenoxy)ethyl]-2-[5-methyl-2-(pyrimidin-2-yl)benzoyl]-2-azabicyclo[3.1.1]heptane 3R or 3S enantiomer The following examples were synthesised following one of the general procedures reported below as indicated in the table.

General Procedure G:

To a stirred suspension of NaH 60% w/w (1.3 eq) in dry DMF (~30 vol), the desired alcohol intermediate (p78-82 as reported on the table, 1 eq) was added at RT. After 30', the corresponding aryl chloride (1.1 eq) was added and the reaction mixture was stirred at room temperature for 2 hrs. The reaction was quenched adding iced water and the mixture was extracted with dichloromethane. Combined organics were dried and concentrated. The crude was purified by FC on silica gel and/or NH column (eluting mixture Cy/AcOEt) and/or C18 cartridge (eluent from water+0.1% formic acid/MeCN+0.1% formic acid) and/or preparative HPLC to afford the title compound.

General Procedure H:

The desired alcohol intermediate (p78-82 as reported in the table, 1 eq) was dissolved in THF (~40 vol). PPh$_3$ (1.5 eq) was added, followed by the desired phenol (commercially available, 1.5 eq). The mixture was stirred at RT for 15', then cooled to 0° C. DIAD (1.5 eq) was added dropwise and, after 10', the ice bath was removed and the mixture was allowed to reach RT and stirred for at that temperature for 1.5-2.5 hrs. The mixture was concentrated and the crude obtained was purified by FC on silica gel and/or NH column (eluting mixture Cy/AcOEt) and/or C18 cartridge (eluent from water+0.1% formic acid/MeCN+0.1% formic acid) to afford the title compound.

General Procedure I:

The desired alcohol intermediate (p78-82 as reported in the table, 1 eq) was dissolved in THF (~40 vol). PPh$_3$ (1.5 eq) was added, followed by the desired phenol (commercially available, 1.5 eq). The mixture was stirred at RT for 15', then cooled to 0° C. DIAD (1.5 eq) was added dropwise and, after 10', the ice bath was removed and the mixture was heated to 55° C. and stirred for 1.5-2.5 hrs. The mixture was concentrated and the crude obtained was purified by FC on silica gel and/or NH column (eluting mixture Cy/AcOEt) and/or C18 cartridge (eluent from water+0.1% formic acid/MeCN+0.1% formic acid) to afford the title compound.

General Procedure L:

To a stirred suspension of NaH 60% w/w (1.3 eq) in dry DMF (~30 vol), the desired alcohol intermediate (p78-82 as reported on the table, 1 eq) was added at RT. After 30', the corresponding aryl fluoride (1.1 eq) was added and the reaction mixture was stirred at room temperature for 2 hrs. The reaction was quenched adding iced water and the mixture was extracted with dichloromethane. Combined organics were dried and concentrated. The crude was purified by FC on silica gel and/or NH column (eluting mixture Cy/AcOEt) and/or C18 cartridge (eluent from water+0.1% formic acid/MeCN+0.1% formic acid) and/or preparative HPLC to afford the title compound.

| Example number | Intermediate | Gen. procedure | Yield (%) |
|---|---|---|---|
| 44 | p78 | G | 50 |

3-(3-fluorophenoxymethyl)-2-(2-methyl-5-phenyl-1,3-thiazole-4-carbonyl)-2-azabicyclo[3.1.1]heptane MS (m/z): 423.0 [MH]+.
NMR (1H, CHLOROFORM-d): δ 0.97 (t, 1 H) 1.27 (br. s., 1 H) 1.57-1.65 (m, 1 H) 1.96-2.08 (m, 2 H) 2.25-2.33 (m, 2 H) 2.44 (dd, 1 H) 2.73 (s, 3 H) 4.04 (q, 1 H) 4.10-4.20 (m, 1 H) 4.45 (dd, 1 H) 4.74-4.86 (m, 1 H) 6.68 (td, 1 H) 6.75 (dt, 1 H) 6.83 (dd, 1 H) 7.20-7.33 (m, 4 H) 7.42 (dd, 2 H)

| 45 | p78 | G | 39 |
|---|---|---|---|

3-(2-fluorophenoxymethyl)-2-(2-methyl-5-phenyl-1,3-thiazole-4-carbonyl)-2-azabicyclo[3.1.1]heptane MS (m/z): 423.0 [MH]+.
NMR (1H, DMSO-d6): δ 7.41-7.45 (m, 1H), 7.22-7.33 (m, 5H), 7.05-7.14 (m, 2H), 6.89-6.96 (m, 1H), 4.78-4.90 (m, 1H), 4.46-4.54 (m, 1H), 4.27-4.37 (m, 1H), 4.06 (d, 1H), 2.74 (s, 3H), 2.27-2.52 (m, 3H), 2.03 (br. s., 2H), 1.73 (s, 1H), 1.02 (d, 1H)

| 46 | p78 | H | 34 |
|---|---|---|---|

3-(4-bromophenoxymethyl)-2-(2-methyl-5-phenyl-1,3-thiazole-4-carbonyl)-2-azabicyclo[3.1.1]heptane MS (m/z): 483.2 [M]+.
NMR (1H, CHLOROFORM-d) δ 7.38-7.46 (m, 4 H) 7.26-7.34 (m, 3 H) 6.93-6.98 (m, 2 H) 4.75-4.83 (m, 1 H) 4.47 (dd, 1 H) 4.13 (dd, 1 H) 4.05 (q, 1 H) 2.75 (s, 3 H) 2.41-2.48 (m, 1 H) 2.26-2.31 (m, 2 H) 1.96-2.08 (m, 2 H) 1.60 (dd, 1 H) 0.92-0.99 (m, 1 H)

-continued

| Example number | Intermediate | Gen. procedure | Yield (%) |
|---|---|---|---|
| 47 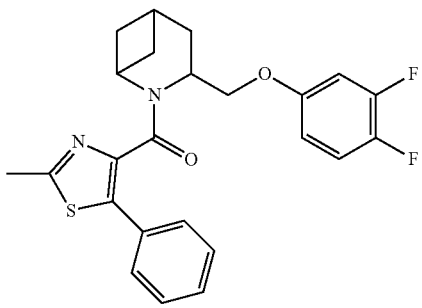 3-(3,4-difluorophenoxymethyl)-2-(2-methyl-5-phenyl-1,3-thiazole-4-carbonyl)-2-azabicyclo[3.1.1]heptane | p78 | H | 55 |

MS (m/z): 441.3 [MH]+.
NMR (1H, CHLOROFORM-d) δ 7.41-7.46 (m, 2 H) 7.27-7.34 (m, 3 H) 7.09 (q, 1 H) 6.89 (ddd, 1 H) 6.76-6.82 (m, 1 H) 4.73-4.82 (m, 1 H) 4.45 (dd, 1 H) 4.02-4.13 (m, 2 H) 2.75 (s, 3 H) 2.42-2.49 (m, 1 H) 2.26-2.32 (m, 2 H) 1.97-2.09 (m, 2 H) 1.53-1.61 (m, 1 H) 0.92-0.99 (m, 1 H)

| Example number | Intermediate | Gen. procedure | Yield (%) |
|---|---|---|---|
| 48 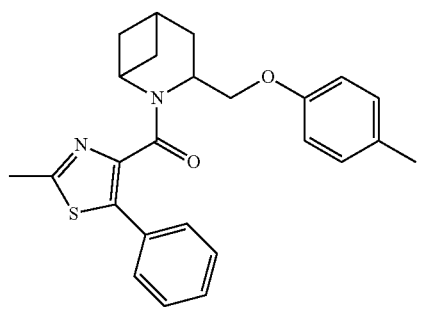 2-(2-methyl-5-phenyl-1,3-thiazole-4-carbonyl)-3-(4-methylphenoxymethyl)-2-azabicyclo[3.1.1]heptane | p78 | H | 55 |

MS (m/z): 419.3 [MH]+.
NMR (1H, CHLOROFORM-d) δ 7.42-7.47 (m, 2 H) 7.26-7.32 (m, 3 H) 7.09-7.15 (m, 2 H) 6.92-6.98 (m, 2 H) 4.78-4.86 (m, 1 H) 4.47 (dd, 1 H) 4.10-4.16 (m, 1 H) 4.05 (q, 1 H) 2.74 (s, 3 H) 2.40-2.48 (m, 1 H) 2.24-2.37 (m, 5 H) 1.96-2.06 (m, 2 H) 1.61-1.69 (m, 1 H) 0.98 (t, 1 H)

| Example number | Intermediate | Gen. procedure | Yield (%) |
|---|---|---|---|
| 49 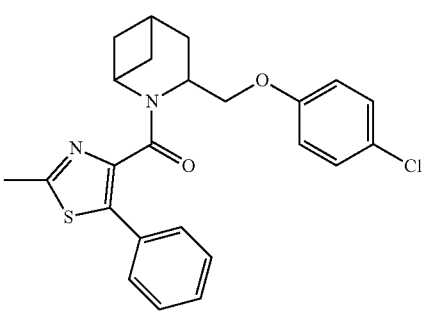 3-(4-chlorophenoxymethyl)-2-(2-methyl-5-phenyl-1,3-thiazole-4-carbonyl)-2-azabicyclo[3.1.1]heptane | p78 | H | 70 |

MS (m/z): 439.2 [MH]+.
NMR (1H, CHLOROFORM-d) δ 7.40-7.50 (m, 2 H) 7.23-7.36 (m, 5 H) 6.97-7.07 (m, 2 H) 4.75-4.85 (m, 1 H) 4.44-4.53 (m, 1 H) 4.09-4.19 (m, 1 H) 4.01-4.09 (m, 1 H) 2.74 (s, 3 H) 2.41-2.51 (m, 1 H) 2.26-2.36 (m, 2 H) 1.96-2.10 (m, 2 H) 1.53-1.67 (m, 1 H) 0.92-1.03 (m, 1 H)

| Example number | Intermediate | Gen. procedure | Yield (%) |
|---|---|---|---|
| 50 | p79 | H | 63 |

3-(4-fluorophenoxymethyl)-2-[5-(4-fluorophenyl)-2-methyl-1,3-thiazole-4-carbonyl]-2-azabicyclo[3.1.1]heptane MS (m/z): 441.0 [MH]$^+$.
NMR ($^1$H, CHLOROFORM-d) δ 7.37-7.47 (m, 2H), 6.88-7.07 (m, 5H), 4.74-4.86 (m, 1H), 4.37 (d, 1H), 4.15-4.24 (m, 1H), 4.05 (d, 1H), 2.74 (s, 3H), 2.45-2.53 (m, 1H), 2.33 (br. s., 2H), 2.00-2.13 (m, 2H), 1.63-1.75 (m, 1H), 0.99-1.11 (m, 1H)

| Example number | Intermediate | Gen. procedure | Yield (%) |
|---|---|---|---|
| 51 | p80 | H | 17 |

2-(2-chloro-5-phenyl-1,3-thiazole-4-carbonyl)-3-[(4-fluorophenoxy)methyl]-2-azabicyclo[3.1.1]heptane MS (m/z): 443.3 [MH]$^+$.
NMR ($^1$H, CHLOROFORM-d) δ 7.42 (d, 2H), 7.28 (s, 4H), 6.90-7.06 (m, 3H), 4.73-4.85 (m, 1H), 4.37 (dd, 1H), 4.16 (dd, 1H), 4.08 (d, 1H), 2.44-2.58 (m, 1H), 2.29-2.38 (m, 2H), 2.00-2.18 (m, 2H), 1.65-1.78 (m, 1H), 0.98-1.12 (m, 1H)

| Example number | Intermediate | Gen. procedure | Yield (%) |
|---|---|---|---|
| 52 | p81 | H | 48 |

3-[(4-fluorophenoxy)methyl]-2-(2-methoxy-5-phenyl-1,3-thiazole-4-carbonyl)-2-azabicyclo[3.1.1]heptane MS (m/z): 439.3 [MH]$^+$.
NMR ($^1$H, CHLOROFORM-d) δ 7.34-7.46 (m, 2H), 7.19-7.30 (m, 4H), 6.96-7.06 (m, 3H), 4.73-4.84 (m, 1H), 4.38-4.50 (m, 1H), 4.07-4.20 (m, 5H), 2.43-2.53 (m, 1H), 2.24-2.37 (m, 2H), 1.99-2.13 (m, 2H), 1.52-1.63 (m, 1H), 1.02-1.13 (m, 1H)

-continued

| Example number | Intermediate | Gen. procedure | Yield (%) |
|---|---|---|---|
| 53 | p82 | H | 42 |

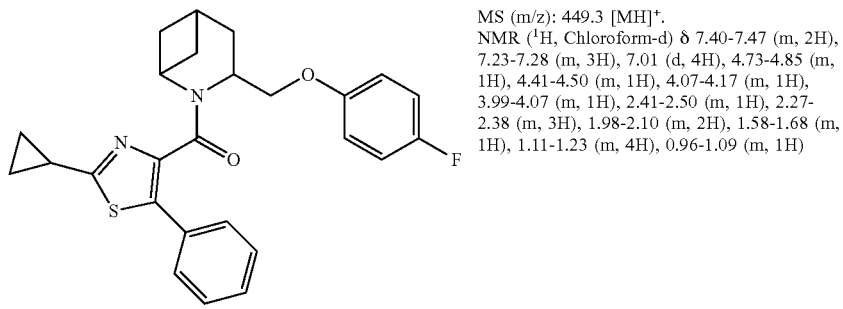

2-(2-cyclopropyl-5-phenyl-1,3-thiazole-4-
carbonyl)-3-[(4-fluorophenoxy)methyl]-2-
azabicyclo[3.1.1]heptane MS (m/z): 449.3 [MH]+.
NMR (¹H, Chloroform-d) δ 7.40-7.47 (m, 2H), 7.23-7.28 (m, 3H), 7.01 (d, 4H), 4.73-4.85 (m, 1H), 4.41-4.50 (m, 1H), 4.07-4.17 (m, 1H), 3.99-4.07 (m, 1H), 2.41-2.50 (m, 1H), 2.27-2.38 (m, 3H), 1.98-2.10 (m, 2H), 1.58-1.68 (m, 1H), 1.11-1.23 (m, 4H), 0.96-1.09 (m, 1H)

| 54 | p78 | I | 15 |
|---|---|---|---|

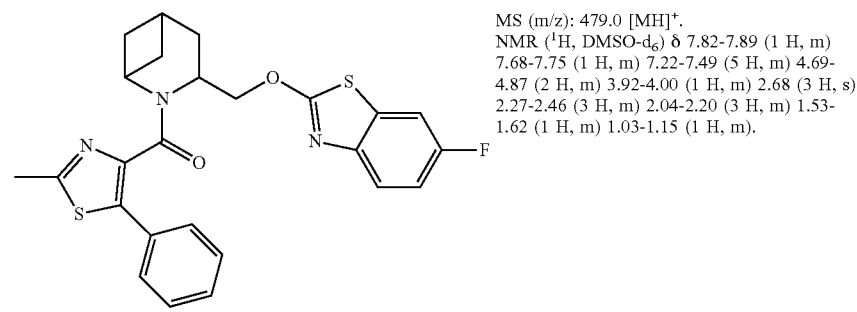

6-fluoro-2-{[2-(2-methyl-5-phenyl-1,3-thiazole-4-
carbonyl)-2-azabicyclo[3.1.1]heptan-3-
yl]methoxy}-1,3-benzothiazole MS (m/z): 479.0 [MH]+.
NMR (¹H, DMSO-d₆) δ 7.82-7.89 (1 H, m) 7.68-7.75 (1 H, m) 7.22-7.49 (5 H, m) 4.69-4.87 (2 H, m) 3.92-4.00 (1 H, m) 2.68 (3 H, s) 2.27-2.46 (3 H, m) 2.04-2.20 (3 H, m) 1.53-1.62 (1 H, m) 1.03-1.15 (1 H, m).

| 55 | p78 | L | 15 |
|---|---|---|---|

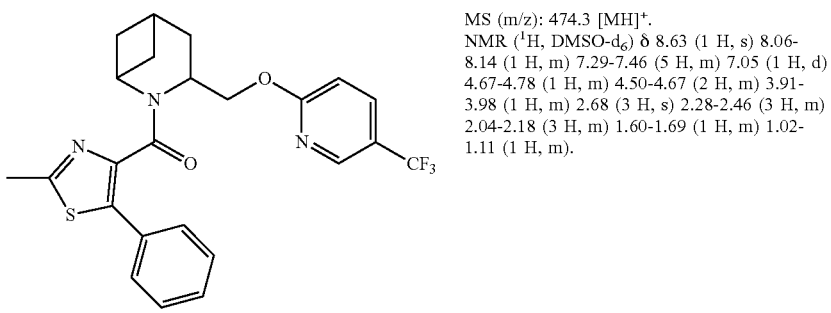

2-(2-methyl-5-phenyl-1,3-thiazole-4-carbonyl)-
3-({[5-(trifluoromethyl)pyridin-2-yl]oxy}
methyl)-2-azabicyclo[3.1.1]heptane MS (m/z): 474.3 [MH]+.
NMR (¹H, DMSO-d₆) δ 8.63 (1 H, s) 8.06-8.14 (1 H, m) 7.29-7.46 (5 H, m) 7.05 (1 H, d) 4.67-4.78 (1 H, m) 4.50-4.67 (2 H, m) 3.91-3.98 (1 H, m) 2.68 (3 H, s) 2.28-2.46 (3 H, m) 2.04-2.18 (3 H, m) 1.60-1.69 (1 H, m) 1.02-1.11 (1 H, m).

| Example number | Intermediate | Gen. procedure | Yield (%) |
|---|---|---|---|
| 56<br><br>2-{[2-(2-methyl-5-phenyl-1,3-thiazole-4-carbonyl)-2-azabicyclo[3.1.1]heptan-3-yl]methoxy}quinoline | p78 | H | 29 |

MS (m/z): 456.3 [MH]+.
NMR (¹H, CHLOROFORM-d) δ 8.01 (d, 1 H) 7.88 (d, 1 H) 7.74 (d, 1 H) 7.65 (t, 1 H) 7.50 (d, 2 H) 7.40 (t, 1 H) 7.30-7.36 (m, 3 H) 6.93 (d, 1 H) 4.83-5.01 (m, 2 H) 4.69-4.76 (m, 1 H) 4.07 (q, 1 H) 2.75 (s, 3 H) 2.41-2.48 (br. s., 1 H) 2.23-2.41 (m, 2 H) 2.00-2.1 (br. s., 2 H) 1.67-1.76 (m, 1 H) 1.06 (t, 1 H)

| Example number | Intermediate | Gen. procedure | Yield (%) |
|---|---|---|---|
| 57<br><br>2-(2-methyl-5-phenyl-1,3-thiazole-4-carbonyl)-3-[({7-methyl-7H-pyrrolo[2,3-d]pyrimidin-2-yl}oxy)methyl]-2-azabicyclo[3.1.1]heptane | p78 | H | 8 |

MS (m/z): 460.3 [MH]+.
NMR (¹H, CHLOROFORM-d) δ 8.72 (s, 1 H) 7.49 (dd, 2 H) 7.29-7.38 (m, 3 H) 7.00 (d, 1 H) 6.46-6.49 (m, 1 H) 4.90-4.99 (m, 2 H) 4.54-4.61 (m, 1 H) 4.06 (q, 1 H) 3.82 (s, 3 H) 2.74 (s, 3 H) 2.30-2.48 (m, 3 H) 1.96-2.09 (m, 2 H) 1.73-1.80 (m, 1 H) 0.98 (t, 1 H)

| Example number | Intermediate | Gen. procedure | Yield (%) |
|---|---|---|---|
| 58<br><br>2-{[2-(2-methyl-5-phenyl-1,3-thiazole-4-carbonyl)-2-azabicyclo[3.1.1]heptan-3-yl]methoxy}quinoxaline | p78 | H | 54 |

MS (m/z): 457.3 [M]+.
NMR (¹H, CHLOROFORM-d) δ 8.43 (s, 1H), 8.02 (dd, 1H), 7.85 (dd, 1H), 7.72-7.64 (m, 1H), 7.63-7.51 (m, 1H). 7.50-7.38 (m, 2H), 7.32-7.27 (m, 3H), 4.97-4.90 (m, 1H), 4.84 (dd, 1H), 4.70 (dd, 1H), 4.06 (q, 1H), 2.72 (s, 3H), 2.59-2.18 (m, 3H), 2.13-1.95 (m, 2H), 1.73-1.51 (m, 2H), 1.02 (t, 1H).

The following examples were synthesised following the general procedure reported below as indicated in the table.
General Procedure M:

2-methyl-5-phenyl-1,3-thiazole-4-carboxylic acid (1.1 eq) was dissolved in DMF (~25 vol), then HATU (1.3 eq) was added followed by DIPEA (2.2 eq). The resulting solution was stirred for 10 min at RT then desired intermediate (p90-92 as reported in the table, 1 eq) in DMF (~25 vol) was added and stirred at RT for 1 hr. The mixture was diluted with iced NH₄Cl ss and DCM, the two phases were separated and aqueous phase was back-extracted twice with DCM. Combined organics were dried and concentrated under reduced pressure. The residue was purified by FC on C18 cartridge (eluent from water+0.1% formic ac./MeCN+0.1% formic ac. 40%) to afford the title compound.

| Example number | Intermediate | General procedure | Yield (%) |
|---|---|---|---|
| 59 | p90 | M | 87 |

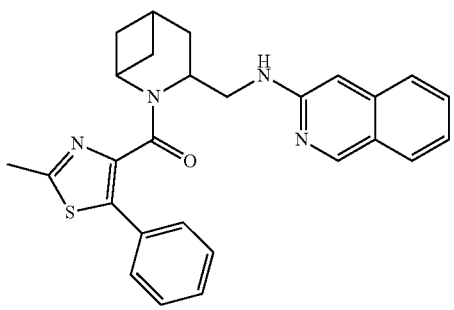 [SMILES: Cc1nc(C(=O)N2C(CNc3cc4ccccc4cn3)CC3CC2C3)c(-c2ccccc2)s1]

MS (m/z): 455.3 [MH]⁺.
NMR (¹H, CHLOROFORM-d): δ 8.83 (s, 1 H) 7.76 (d, 1 H) 7.70 (d, 1 H) 7.54 (t, 1 H) 7.43-7.50 (m, 2 H) 7.33-7.41 (m, 3 H) 7.21-7.31 (m, 2 H) 5.65-5.96 (m, 1 H) 4.64-4.77 (m, 1 H) 4.03-4.13 (m, 2 H) 3.38-3.51 (m, 1 H) 2.77 (s, 3 H) 2.43-2.52 (m, 1 H) 2.26-2.37 (m, 1 H) 2.14-2.24 (m, 1 H) 2.02-2.11 (m, 1 H) 1.94-2.02 (m, 1 H) 1.44-1.53 (m, 1 H) 0.89 (t, 1 H)

N-[[2-(2-methyl-5-phenyl-1,3-thiazole-4-carbonyl)-2-azabicyclo[3.1.1]heptan-3-yl]methyl}isoquinolin-3-amine

| 60 | p91 | M | 48 |
|---|---|---|---|

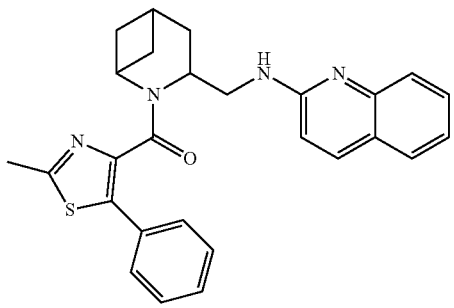 [SMILES: Cc1nc(C(=O)N2C(CNc3ccc4ccccc4n3)CC3CC2C3)c(-c2ccccc2)s1]

MS (m/z): 435.3 [MH]⁺.
NMR (¹H, DMSO-d6): δ 9.99 (br. s., 1 H), 7.31-8.52 (m, 5 H), 7.26-7.60 (m, 5 H), 6.97-7.27 (m, 1 H), 4.59 (t, 1 H), 3.99-4.15 (m, 1 H), 3.62-3.97 (m, 2 H), 2.71 (s, 3 H), 2.43-2.49 (m, 1 H), 2.27-2.40 (m, 1 H), 2.13-2.25 (m, 1 H), 2.00-2.12 (m, 2 H), 1.58-1.69 (m, 1 H), 0.86 (br. s., 1 H)

N-{[2-(2-methyl-5-phenyl-1,3-thiazole-4-carbonyl)-2-azabicyclo[3.1.1]heptan-3-yl]methyl}quinolin-2-amine

| 61 | p92 | M | 34 |
|---|---|---|---|

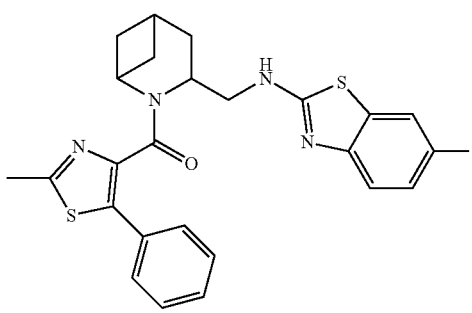

MS (m/z): 479.3 [M]⁺.
NMR (¹H, CHLOROFORM-d) δ 7.42-7.51 (m, 3 H) 7.26-7.34 (m, 3 H) 6.98-7.07 (m, 2 H) 4.86-4.94 (m, 1 H) 4.10 (d, 1 H) 3.90-3.99 (m, 1 H) 3.78-3.86 (m, 1 H) 2.74 (s, 3 H) 2.41-2.51 (m, 2 H) 2.04-2.13 (m, 2 H) 1.96-2.04 (m, 1 H) 1.58-1.63 (m, 1 H) 1.11 (t, 1 H)

6-fluoro-N-{[2-(2-methyl-5-phenyl-1,3-thiazole-4-carbonyl)-2-azabicyclo[3.1.1]heptan-3-yl]methyl}-1,3-benzothiazol-2-amine Example 62 and 63: (3S,4R or 3R,4S)-4-fluoro-3-{[(5-fluoropyridin-2-yl)oxy]methyl}-2-(2-methyl-5-phenyl-1,3-thiazole-4-carbonyl)-2-azabicyclo[3.1.1]heptane (E62) and (3R,4S or 3S,4R)-4-fluoro-3-{[(5-fluoropyridin-2-yl)oxy]methyl}-2-(2-methyl-5-phenyl-1,3-thiazole-4-carbonyl)-2-azabicyclo[3.1.1]heptane (E63)

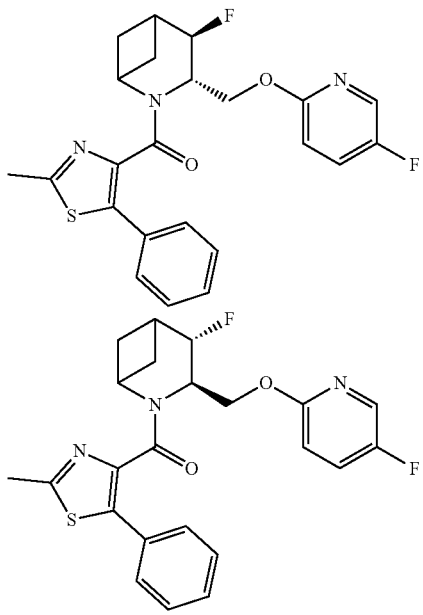

Step a.

2-methyl-5-phenyl-1,3-thiazole-4-carboxylic acid (1.18 g, 5.38 mmol) was dissolved in DMF (5 mL), then HATU (2.4 g, 6.36 mmol) was added followed by DIPEA (1.87 mL, 10.76 mmol). The resulting solution was stirred for 10 min cis/trans 3-(hydroxymethyl)-2-azabicyclo[3.1.1]heptan-4-ol (p9, 700 mg, 4.89 mmol) in DMF (0.5 mL) was added and stirred for 1 hr. The mixture was diluted with NH₄Clss and DCM, the two phases were separated and the product was extracted several times with DCM. The combined organic phases were dried and evaporated. The residue was purified by FC on silica gel (from DCM to 10% MeOH) to afford CIS-3-(hydroxymethyl)-2-(2-methyl-5-phenyl-1,3-thiazole-4-carbonyl)-2-azabicyclo[3.1.1]heptan-4-ol (Int. a, 900 mg) and TRANS-3-(hydroxymethyl)-2-(2-methyl-5-phenyl-1,3-thiazole-4-carbonyl)-2-azabicyclo[3.1.1]heptan-4-ol (100 mg).

Step b:

Int. a (850 mg, 2.47 mmol) and imidazole (670 mg, 9.88 mmol) were dissolved in DMF (5 mL). A solution of tert-Butyldimethylsilyl chloride (744 mg, 4.93 mmol) in DMF (3 mL) was added dropwise and the mixture was stirred at RT for 30 min until completion. Reaction was quenched with water and extracted with DCM. Organic layers were dried and solvent was removed under reduced pressure. The residue was purified by FC on silica gel (eluting from cHex to 60% EtOAc) to afford 3-{[(tert-butyldimethylsilyl)oxy]methyl}-2-(2-methyl-5-phenyl-1,3-thiazole-4-carbonyl)-2-azabicyclo[3.1.1]heptan-4-ol (Int. b, 600 mg).

Step c:

Int. b (250 mg, 0.54 mmol) was dissolved in DCM (8 mL) and cooled with an ice bath. DAST (0.144 mL, 1.09 mmol) was added dropwise and mixture was stirred at RT 1 h. Reaction was quenched carefully with water and extracted with DCM. Organic layers were dried and solvent was removed under reduced pressure. The residue was dissolved in DCM (8 mL) and HCl 1.25M in MeOH (1.25 mL, 1.25 mmol) was added dropwise. The mixture was stirred at RT 2 hrs. Solvent was removed under vacuum and the residue was purified by FC on silica gel (from DCM to 10% MeOH) to afford [4-fluoro-2-(2-methyl-5-phenyl-1,3-thiazole-4-carbonyl)-2-azabicyclo[3.1.1]heptan-3-yl]methanol (Int. c, 120 mg) as mixture of target intermediate and by-products due to carbocation rearrangement during the fluorination step.

Step d:

Int. c (120 mg, 0.346 mmol) was dissolved in DMF (3 mL) and cooled with an ice bath. NaH 60% w/w dispersion in mineral oil (21 mg, 0.52 mmol) was added and mixture was stirred 10 min before adding 2,5-difluoropyridine (0.05 mL, 0.52 mmol). The mixture was stirred at RT for 3 hrs. The mixture was diluted with water and extracted several times with DCM. Organic layers were dried and solvent was removed under reduced pressure to afford crude which was purified by FC on silica gel (eluting from DCM to 5% MeOH) then further purified by chiral prep HPLC:

| Column | Chiralpak AD-H (25 × 2.0 cm), 5µ |
|---|---|
| Mobile phase | n-Hexane/(2-propanol + 0.1% isopropylamine) 83/17% v/v |
| Flow rate (ml/min) | 17 ml/min |
| DAD detection | 220 nm |
| Loop | 400 µL |
| Injection | 7.8 mg/injection | affording:

(3S,4R or 3R,4S)-4-fluoro-3-{[(5-fluoropyridin-2-yl)oxy]methyl}-2-(2-methyl-5-phenyl-1,3-thiazole-4-carbonyl)-2-azabicyclo[3.1.1]heptane (E62)

Enantiomer 1, Rt=24.7 min, 100% ee
MS (m/z): 442.0 [MH]⁺.
NMR (¹H, CHLOROFORM-d): δ 1.35-1.78 (m, 2H), 1.81-2.32 (m, 1H), 2.12 (dd, 1H), 2.61-2.91 (m, 4H), 4.09 (q, 1H), 4.49-4.77 (m, 2H), 4.78-4.94 (m, 1H), 5.01-5.39 (m, 1H), 6.75 (dd, 1H), 7.28-7.49 (m, 6H), 8.01 (d, 1H)

(3R,4S or 3S,4R)-4-fluoro-3-{[(5-fluoropyridin-2-yl)oxy]methyl}-2-(2-methyl-5-phenyl-1,3-thiazole-4-carbonyl)-2-azabicyclo[3.1.1]heptane (E63)

Enantiomer 2, Rt=32.7 min, 100% ee
MS (m/z): 442.0 [MH]⁺.
NMR (¹H, CHLOROFORM-d): δ 1.36-1.71 (m, 1H), 1.49-1.79 (m, 1H), 1.81-2.28 (m, 1H), 2.12 (dq, 1H), 2.61-2.87 (m, 4H), 3.96-4.15 (m, 1H), 4.42-4.77 (m, 2H), 4.77-4.95 (m, 1H), 4.99-5.43 (m, 1H), 6.75 (dd, 1H), 7.28-7.57 (m, 5H), 7.33-7.40 (m, 1H), 8.01 (d, 1H)

The following examples were synthesised following one of the general procedures reported below as indicated in the table.

General Procedure N:

4-methyl-2-azabicyclo[3.1.1]heptane (p40-42, p49, 51, 53 as reported; 1 eq) was dissolved in DMF (~50 vol), then the carboxylic acid (p58, p61-62, p65-67, p70 or commercially available if not specified in the table; 1.2 eq) was added followed by T3P (2 eq) and DIPEA (2 eq). The mixture was heated at 90° C. and left stirring at the same temperature 1-18 hrs, then the solvent was evaporated and the crude material purified by FC either on silica gel or aminic silica using Cy/AcOEt as eluting mixture to give the title compound.

General Procedure O:

A mixture of 4-methyl-2-azabicyclo[3.1.1]heptane (p40-42, p49, 51, 53 as reported; 1 eq), carboxylic acid (p58, p61-62, p65-67, p70 or commercially available if not specified in the table; 1.2 eq), DIPEA (3 eq), and T3P (3 eq) in DMF dry (~33 vol) was stirred at 90° C. for 40 minutes then left stirring at RT for 1 h. The solvent was evaporated and crude material purified by FC either on silica gel or aminic silica using Cy/AcOEt as eluting mixture to give the title compound.

General Procedure P:

A mixture of 2-azabicyclo[3.1.1]heptanes (p40-42, p49, 51, 53 as reported; 1 eq), carboxylic acid (p58, p61-62, p65-67, p70 or commercially available if not specified in the table; 1.2 eq), DIPEA (1.5 eq), and T3P (3 eq) in DMF dry (100 vol) was stirred at 50° C. for 1 hr. The mixture was treated with 1N NaOH, and then extracted with AcOEt, the extract was dried over $Na_2SO_4$, evaporated and purified by FC on silica gel using Cy/AcOEt as eluting mixture. Then the product further purified by FC on C18 cartridge (eluent: water+0.1% HCOOH/acetonitrile+0.1% HCOOH) to give the target compound.

General Procedure Q:

To a stirred solution of carboxylic acid (1.2 eq) and HATU (1.2 eq) in DMF (2 mL) dipea (2 eq) was added. The reaction was stirred at RT for 30 min-1 h and then added to a solution of azabicyclo[3.1.1]heptane (1 eq) in DMF (1 mL). The reaction was stirred for 3 h at RT. A saturated aqueous solution of $NaHCO_3$ was added and the reaction was extracted with AcOEt. The combined organic phases were washed with a saturated solution of $NH_4Cl$ and Brine. The organic phase was dried, filtered and concentrated under vacuum. The residue crude material was purified by FC either on silica gel or aminic silica or C18 column using the appropriate eluents.

General Procedure R:

The desired alcohol intermediate (p83-86 as reported in the table, 1 eq) was dissolved in THF (~40 vol). $PPh_3$ (1.5 eq) was added, followed by the desired phenol (commercially available, 1.5 eq). The mixture was stirred at RT for 15', then cooled to 0° C. DIAD (1.5 eq) was added dropwise and, after 10', the ice bath was removed and the mixture was allowed to reach RT and stirred for at that temperature for 1.5-2.5 hrs. The mixture was concentrated and the crude obtained was purified by FC on silica gel and/or NH column (eluting mixture Cy/AcOEt) and/or C18 cartridge (eluent from water+0.1% formic acid/MeCN+0.1% formic acid) to afford the title compound.

General Procedure S:

To a solution of aryl halide (1.5 eq), NaH 60% dispersion in mineral oil (1.5 eq) and desired alcohol intermediate (p83-86 as reported in the table, 1 eq) were added. The reaction was stirred at 60° C. O/N. the reaction mixture was cooled down to RT, quenched with water and extracted with AcOEt. The organic phase was washed with Brine, dried and concentrated under vacuum. The residue was purified by FC on silica gel and/or NH column (eluting mixture Cy/AcOEt) and/or C18 cartridge (eluent from water+0.1% formic acid/MeCN+0.1% formic acid) to afford the title compound

| Example | Starting materials | Gen. procedure | Yield (%) |
| --- | --- | --- | --- |
| 64 | p49 | N | 82 |

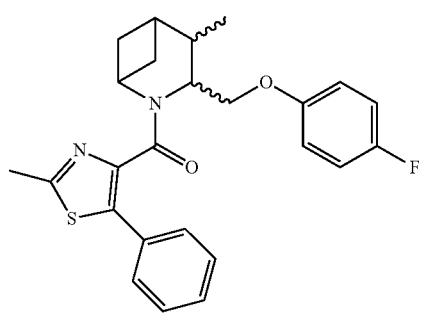 [SMILES: Cc1nc(C(=O)N2C3CC(C3)C(C)C2COc2ccc(F)cc2)c(-c2ccccc2)s1]

MS (m/z): 437.0 [MH]⁺.
NMR ($^1$H, DMSO-d6): δ 7.26-7.48 (m, 5 H), 6.95-7.20 (m, 4 H), 4.74-4.81 (m, 1 H), 4.33-4.39 (m, 1 H), 3.98-4.03 (m, 1 H), 3.87-3.95 (m, 1 H), 2.65-2.70 (m, 3 H), 2.60-2.65 (m, 1 H), 2.17-2.24 (m, 1 H), 2.02-2.16 (m, 1 H), 1.82-1.95 (m, 1 H), 1.03-1.13 (m, 4 H), 0.95-1.01 (m, 1 H)

CIS/TRANS 3-(4-fluorophenoxymethyl)-4-methyl-2-(2-methyl-5-phenyl-1,3-thiazole-4-carbonyl)-2-azabicyclo[3.1.1]heptane The diastereomeric mixture was separated into the single enantiomers for each diastereomer by preparative chiral HPLC

| Preparative chiral chromatography protocol: | Column | Chiralpak IC (25 × 2.0 cm), 5µ |
| --- | --- | --- |
| | Mobile phase | N-Hexane/Ethanol 75/25% v/v |
| | Flow rate (ml/min) | 14 ml/min |
| | DAD detection | 220 nm |
| | Loop | 1000 µL |
| | Injection | 9.6 mg/injection |

-continued

| Example | Starting materials | Gen. procedure | Yield (%) |
|---|---|---|---|
| 65 | TRANS<br>Enantiomer 1<br>MS (m/z): 437.0 [MH]$^+$.<br>NMR ($^1$H, DMSO-d6): δ 7.29-7.46 (m, 5 H), 7.11-7.19 (m, 2 H), 7.00-7.07 (m, 2 H), 4.25-4.29 (m, 1 H), 4.17-4.23 (m, 1 H), 4.02-4.09 (m, 1 H), 3.92 (d, 1 H), 2.67 (s, 3 H), 2.38-2.47 (m, 1 H), 2.20 (dd, 1 H), 2.09-2.17 (m, 1 H), 1.85-1.94 (m, 1 H), 1.63 (t, 1 H), 1.07-1.12 (m, 1 H), 1.06 (d, 3 H) | Rt: 1.07 min | 100% ee |
| | or | | |
| | (3R,4R or 3S,4S) 3-(4-fluorophenoxymethyl)-4-methyl-2-(2-methyl-5-phenyl-1,3-thiazole-4-carbonyl)-2-azabicyclo[3.1.1]heptane | | |
| 66 | CIS<br>Enantiomer 1<br>MS (m/z): 437.0 [MH]$^+$.<br>NMR ($^1$H, DMSO-d6): δ 7.27-7.45 (m, 5 H), 7.15 (t, 2 H), 6.98-7.04 (m, 2 H), 4.78 (t, 1 H), 4.33-4.40 (m, 1 H), 4.01 (dd, 1 H), 3.90 (q, 1 H), 2.65-2.70 (m, 3 H), 2.60-2.66 (m, 1 H), 2.02-2.15 (m, 3 H), 1.86 (t, 1 H), 1.09 (d, 3H), 0.98 (t, 1 H) | Rt: 11.7 min | 98.4% ee |
| | or | | |
| | (3R,4S or 3S,4R) 3-(4-fluorophenoxymethyl)-4-methyl-2-(2-methyl-5-phenyl-1,3-thiazole-4-carbonyl)-2-azabicyclo[3.1.1]heptane | | |

-continued

| Example | Starting materials | Gen. procedure | Yield (%) |
|---|---|---|---|
| 67 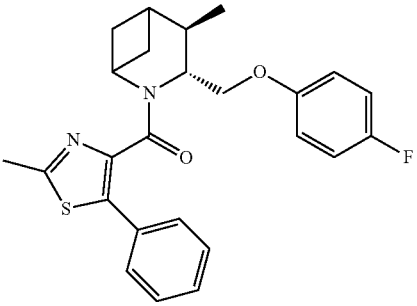 [SMILES: Cc1nc(C(=O)N2C3CC(C3)[C@@H](C)[C@@H]2COc2ccc(F)cc2)c(-c2ccccc2)s1] 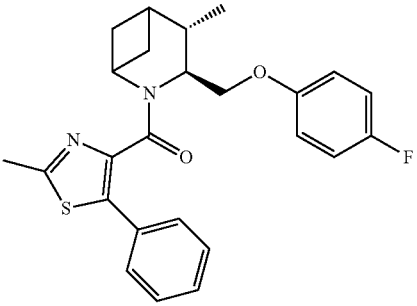 [SMILES: Cc1nc(C(=O)N2C3CC(C3)[C@H](C)[C@H]2COc2ccc(F)cc2)c(-c2ccccc2)s1] (3S,4S or 3R,4R) 3-(4-fluorophenoxymethyl)-4-methyl-2-(2-methyl-5-phenyl-1,3-thiazole-4-carbonyl)-2-azabicyclo[3.1.1]heptane | TRANS Enantiomer 2 MS (m/z): 437.0 [MH]+. NMR (1H, DMSO-d6): δ 7.29-7.46 (m, 5 H), 7.11-7.19 (m, 2 H), 7.00-7.07 (m, 2 H), 4.25-4.29 (m, 1 H), 4.17-4.23 (m, 1 H), 4.02-4.09 (m, 1 H), 3.92 (d, 1 H), 2.67 (s, 3 H), 2.38-2.47 (m, 1 H), 2.20 (dd, 1 H), 2.09-2.17 (m, 1 H), 1.85-1.94 (m, 1 H), 1.63 (t, 1 H), 1.07-1.12 (m, 1 H), 1.06(d, 3 H) | Rt: 13.5 min | 100% ee |
| 68 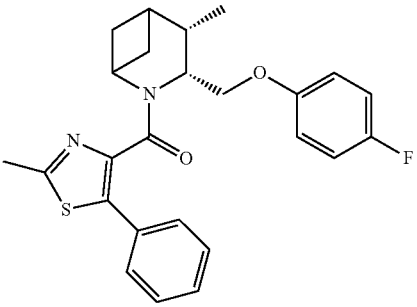 [SMILES: Cc1nc(C(=O)N2C3CC(C3)[C@H](C)[C@@H]2COc2ccc(F)cc2)c(-c2ccccc2)s1] 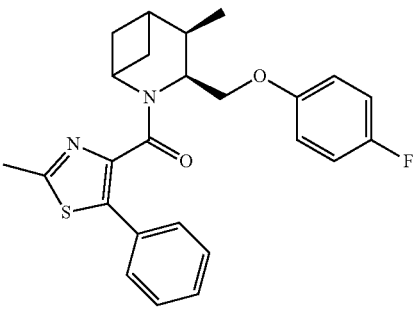 [SMILES: Cc1nc(C(=O)N2C3CC(C3)[C@@H](C)[C@H]2COc2ccc(F)cc2)c(-c2ccccc2)s1] (3S,4R or 3R,4S) 3-(4-fluorophenoxymethyl)-4-methyl-2-(2-methyl-5-phenyl-1,3-thiazole-4-carbonyl)-2-azabicyclo[3.1.1]heptane | CIS Enantiomer 2 MS (m/z): 437.0 [MH]+. NMR (1H, DMSO-d6): δ 7.27-7.45 (m, 5 H), 7.15 (t, 2 H), 6.98-7.04 (m, 2 H), 4.78 (t, 1 H), 4.33-4.40 (m, 1 H), 4.01 (dd, 1 H), 3.90 (q, 1 H), 2.65-2.70 (m, 3 H), 2.60-2.66 (m, 1 H), 2.02-2.15 (m, 3 H), 1.86 (t,, 1 H), 1.09 (d, 3H), 0.98 (t, 1 H) | Rt: 22.1 min | 100% ee | or or

| Example | Starting materials | Gen. procedure | Yield (%) |
|---|---|---|---|
| 69 | p49 + p61 | N | 76 |

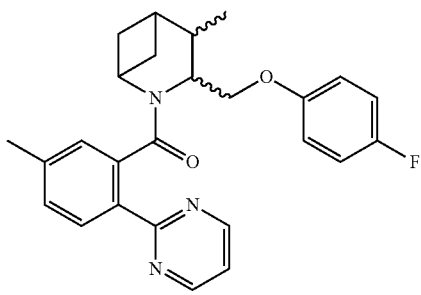 [SMILES: Cc1ccc(-c2ncccn2)c(C(=O)N2C3CC(C3)C(C)C2COc2ccc(F)cc2)c1]

MS (m/z): 432.1 [MH]$^+$.
NMR ($^1$H, DMSO-d6): δ 8.68-8.97 (m, 1 H), 8.03-8.20 (m, 1 H), 7.38-7.43 (m, 1 H), 7.30-7.37 (m, 1 H), 6.85-7.22 (m, 6 H), 4.68-4.80 (m, 1 H), 4.22-4.42 (m, 2 H), 3.81-3.97 (m, 1 H), 2.64-2.72 (m, 1 H), 2.36 (br. s., 3 H), 1.40-2.25 (m, 5 H), 1.09-1.18 (m, 3 H)

CIS/TRANS 3-(4-fluorophenoxymethyl)-4-methyl-2-[5-methyl-2-(pyrimidin-2-yl)benzoyl]-2-azabicyclo[3.1.1]heptane The diastereomeric mixture was separated into the single enantiomers for each diastereomer by preparative chiral HPLC

| Preparative chiral chromatography protocol: | Column | Chiralpak IC (25 × 2.0 cm), 5µ |
|---|---|---|
| | Mobile phase | n-Hexane/Ethanol 70/30% v/v |
| | Flow rate (ml/min) | 14 ml/min |
| | DAD detection | 220 nm |
| | Loop | 1000 µL |
| | Injection | 9.5 mg/injection |
| 70 | TRANS | Rt: 10.1 min    100% ee |
| | Enantiomer 1 | |

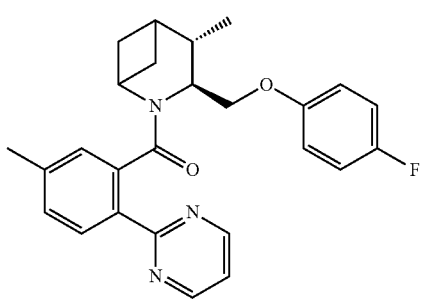 [SMILES: Cc1ccc(-c2ncccn2)c(C(=O)N2C3CC(C3)[C@H](C)[C@H]2COc2ccc(F)cc2)c1]

MS (m/z): 432.1 [MH]$^+$.
NMR ($^1$H, Acetone): δ 1.16-1.25 (m, 3 H), 1.46-1.88 (m, 3 H), 1.94-2.01 (m, 1 H), 2.11-2.14 (m, 1 H), 2.25-2.46 (m, 4 H), 2.54-2.70 (m, 1 H), 3.94-4.13 (m, 1 H), 4.14-4.29 (m, 1 H), 4.33-4.89 (m, 2 H), 6.94-7.00 (m, 1 H), 7.03-7.25 (m, 4 H), 7.30-7.44 (m, 2 H), 8.12-8.26 (m, 1 H), 8.73-8.91 (m, 2 H)

or

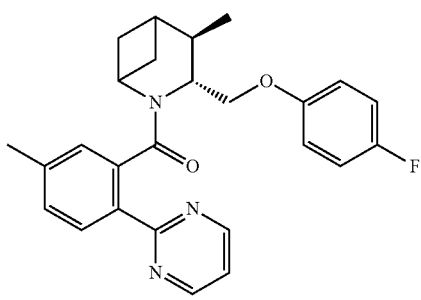 [SMILES: Cc1ccc(-c2ncccn2)c(C(=O)N2C3CC(C3)[C@@H](C)[C@@H]2COc2ccc(F)cc2)c1]

(3S,4S or 3R,4R) 3-(4-fluorophenoxymethyl)-4-methyl-2-[5-methyl-2-(pyrimidin-2-yl)benzoyl]-2-azabicyclo[3.1.1]heptane -continued

| Example | Starting materials | Gen. procedure | Yield (%) |
|---|---|---|---|
| 71 | CIS Enantiomer 1 | Rt: 12.0 min | 100% ee |

MS (m/z): 432.1 [MH]+.
NMR (¹H, Acetone): δ 1.21-1.27 (m, 3 H), 1.40-2.01 (m, 2 H), 2.11-2.35 (m, 3 H), 2.36-2.42 (m, 3 H), 3.92-4.13 (m, 1 H), 4.29-4.60 (m, 2 H), 4.81-5.00 (m, 1 H), 6.92-7.18 (m, 5 H), 7.33 (d, 2 H), 8.19 (s, 1 H), 8.72-8.91 (m, 2 H)

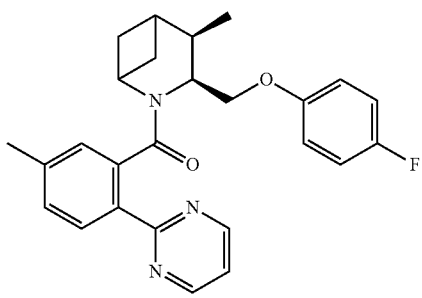 [SMILES: Cc1ccc(-c2ncccn2)c(C(=O)N2C3CC(C3)[C@@H](C)[C@H]2COc2ccc(F)cc2)c1]

or

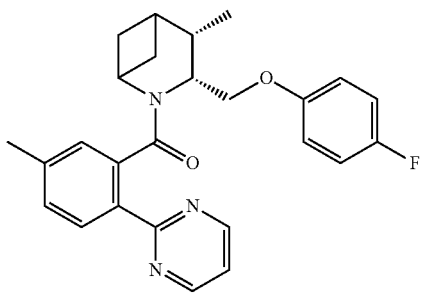 [SMILES: Cc1ccc(-c2ncccn2)c(C(=O)N2C3CC(C3)[C@H](C)[C@@H]2COc2ccc(F)cc2)c1]

(3S,4R or 3R,4S) 3-(4-fluorophenoxymethyl)-4-methyl-2-[5-methyl-2-(pyrimidin-2-yl)benzoyl]-2-azabicyclo[3.1.1]heptane

| | | | |
|---|---|---|---|
| 72 | TRANS Enantiomer 2 | Rt: 13.7 min | 95.2% ee |

MS (m/z): 432.1 [MH]+.
NMR (¹H, Acetone): δ 1.23 (d, 3 H), 1.53-2.00 (m, 3 H), 2.09-2.28 (m, 2 H), 2.29-2.36 (m, 1 H), 2.37-2.45 (m, 3 H), 2.54-2.68 (m, 1 H), 3.95-4.14 (m, 1 H), 4.14-4.31 (m, 1 H), 4.33-4.86 (m, 2 H), 6.92-7.00 (m, 1 H), 7.08 (s, 4 H), 7.28-7.42 (m, 2 H), 8.09-8.26 (m, 1 H), 8.84 (d, 1 H)

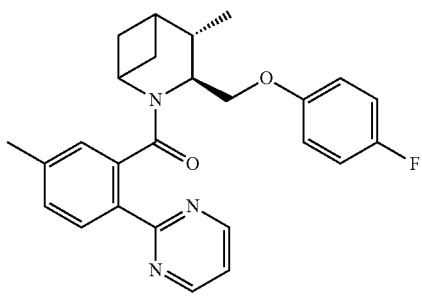 [SMILES: Cc1ccc(-c2ncccn2)c(C(=O)N2C3CC(C3)[C@H](C)[C@H]2COc2ccc(F)cc2)c1]

or

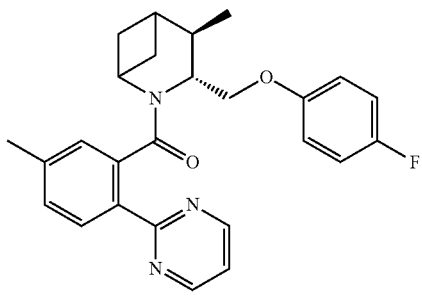 [SMILES: Cc1ccc(-c2ncccn2)c(C(=O)N2C3CC(C3)[C@@H](C)[C@@H]2COc2ccc(F)cc2)c1]

(3R,4R or 3S,4S) 3-(4-fluorophenoxymethyl)-4-methyl-2-[5-methyl-2-(pyrimidin-2-yl)benzoyl]-2-azabicyclo[3.1.1]heptane -continued

| Example | Starting materials | Gen. procedure | Yield (%) |
|---|---|---|---|
| 73 | CIS<br>Enantiomer 2 | Rt: 22.5 min | 100% ee |

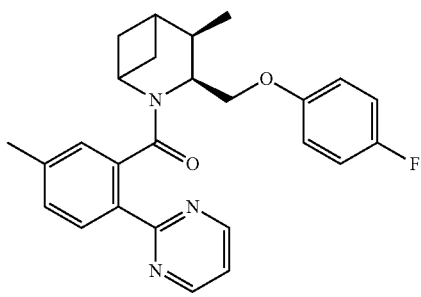 [SMILES: Cc1ccc(-c2ncccn2)c(C(=O)N2C3CC(C3)[C@@H](C)[C@H]2COc2ccc(F)cc2)c1]

MS (m/z): 432.1 [MH]$^+$.
NMR ($^1$H, Acetone): δ 1.24 (d, J = 7.34 Hz, 3 H), 1.41-2.03 (m, 3 H), 2.11-2.35 (m, 4 H), 2.36-2.45 (m, 3 H), 3.96-4.13 (m, 1 H), 4.27-4.61 (m, 2 H), 4.78-5.04 (m, 1 H), 6.88-7.19 (m, 5 H), 7.25-7.45 (m, 2 H), 8.11-8.30 (m, 1 H), 8.81 (d, 1 H)

or

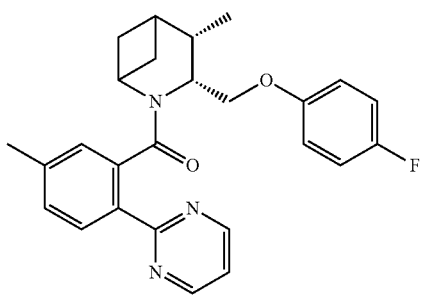 [SMILES: Cc1ccc(-c2ncccn2)c(C(=O)N2C3CC(C3)[C@H](C)[C@@H]2COc2ccc(F)cc2)c1]

(3R,4S or 3S,4R) 3-(4-fluorophenoxymethyl)-4-methyl-2-[5-methyl-2-(pyrimidin-2-yl)benzoyl]-2-azabicyclo[3.1.1]heptane

| 74 | p40 + p61 | N | 58 |

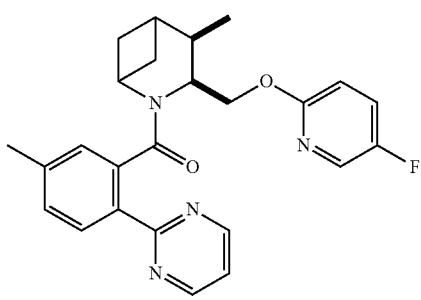

MS (m/z): 433.1 [MH]$^+$.
NMR ($^1$H, DMSO-d6): δ 8.78-8.93 (m, 2 H), 8.25 (d, 1 H), 8.05-8.19 (m, 1 H), 7.71 (td, 1 H), 7.45 (t, 1H), 7.35 (d, 1 H), 7.11 (s, 1 H), 6.93 (dd, 1 H), 4.79 (t, 1 H), 4.65 (d, 1 H), 4.50 (t, 1 H), 3.86 (d, 1 H), 2.66-2.77 (m, 1 H), 2.35-2.42 (m, 3 H), 2.13-2.25 (m, 1 H), 1.96-2.03 (m, 1 H), 1.90-1.97 (m, 1 H), 1.57 (t, 1 H), 1.16-1.23 (m, 1 H), 1.08-1.15 (m, 3 H)

mixture of cis-isomers
Racemic mixture of cis-3-{[(5-fluoropyridin-2-yl)oxy]methyl}-4-methyl-2-[4-methyl-2-(pyrimidin-2-yl)benzoyl]-2-azabicyclo[3.1.1]heptane
The racemic mixture was separated into the single enantiomers by preparative chiral HPLC

| Preparative chiral chromatography protocol: | Column | Chiralpak IC (25 × 2.0 cm), 5μ |
|---|---|---|
| | Mobile phase | n-Hexane/Ethanol 50/50% v/v |
| | Flow rate (ml/min) | 14 ml/min |
| | DAD detection | 220 nm |
| | Loop | 500 μl |
| | Injection | 14.5 mg (each injection) |

| Example | Starting materials | Gen. procedure | Yield (%) |
|---|---|---|---|
| 75 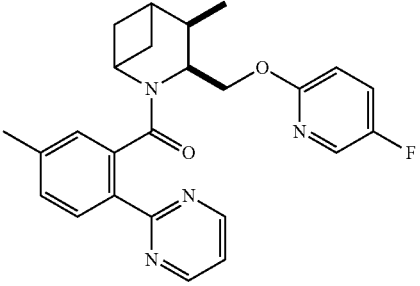<br>(3S,4R) or (3R,4S) enantiomer | Enantiomer 1<br>MS (m/z): 433.1 [MH]⁺.<br>(3S,4R or 3R,4S) 3-{[(5-fluoropyridin-2-yl)oxy]methyl}-4-methyl-2-[5-methyl-2-(pyrimidin-2-yl)benzoyl]-2-azabicyclo[3.1.1]heptane | RT: 10.1 min | 100 ee % |
| 76 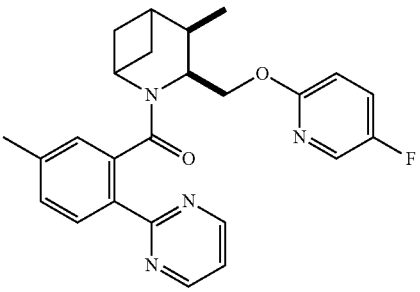<br>(3R,4S) or (3S,4R) enantiomer | Enantiomer 2<br>MS (m/z): 433.1 [MH]⁺.<br>(3R,4S or 3S,4R) 3-{[(5-fluoropyridin-2-yl)oxy]methyl}-4-methyl-2-[5-methyl-2-(pyrimidin-2-yl)benzoyl]-2-azabicyclo[3.1.1]heptane | Rt: 15.7 min | 100 ee % |
| 77 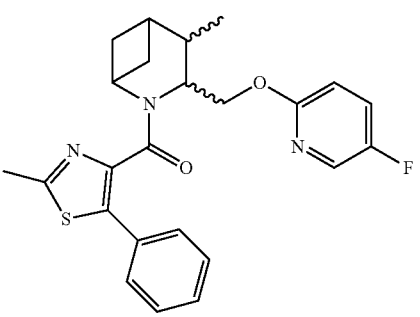 [SMILES: Cc1nc(C(=O)N2C3CC(C3)C(C)C2COc2ccc(F)cn2)c(-c2ccccc2)s1]<br>CIS/TRANS 3-{[(5-fluoropyridin-2-yl)oxy]methyl}-4-methyl-2-(2-methyl-5-phenyl-1,3-thiazole-4-carbonyl)-2-azabicyclo[3.1.1]heptane | p40<br>MS (m/z): 438.1 [MH]⁺.<br>NMR (¹H, DMSO-d6): δ 8.17 (s, 1H), 7.60-7.76 (m, 1H), 7.25-7.47 (m, 5H), 6.85-6.95 (m, 1H), 3.85-5.07 (m, 4H), 2.65-2.65 (m, 3H), 1.53-2.72 (m, 6H), 1.04-1.13 ppm (m, 3H) | N | 40 |
| 78 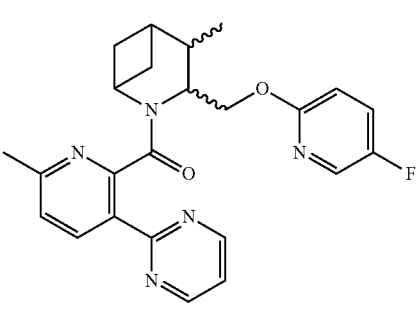 [SMILES: Cc1ccc(-c2ncccn2)c(C(=O)N2C3CC(C3)C(C)C2COc2ccc(F)cn2)n1]<br>CIS/TRANS 3-{[(5-fluoropyridin-2-yl)oxy]methyl}-4-methyl-2-[6-methyl-3-(pyrimidin-2-yl)pyridine-2-carbonyl]-2-azabicyclo[3.1.1]heptane<br>The diastereomeric mixture was separated into the single enantiomers for each diastereomer by preparative chiral HPLC | p40 + p58<br>MS (m/z): 434.4 [MH]⁺.<br>NMR (¹H, DMSO-d6): δ 8.79-8.97 (m, 1 H), 8.34-8.53 (m, 1 H), 7.82-8.26 (m, 1 H), 7.55-7.76 (m, 1 H), 7.29-7.53 (m, 2 H), 6.54-7.03 (m, 1 H), 3.78-4.99 (m, 4 H), 2.64-2.81 (m, 1 H), 2.53 (s, 3 H), 2.02-2.39 (m, 3 H), 1.40-1.98 (m, 2 H), 0.89-1.29 (m, 3 H) | N | 98 |

| Example | Starting materials | Gen. procedure | Yield (%) |
|---|---|---|---|
| Preparative chiral chromatography protocol: | Column | Chiralpak AD-H (25 × 2.0 cm), 5µ | |
| | Mobile phase | n-Hexane/(2-Propanol/Methanol 1/1) 90/10% v/v | |
| | Flow rate (ml/min) | 15 ml/min | |
| | DAD detection | 220 nm | |
| | Loop | 1500 µl | |
| | Injection | 35 mg (each injection) | |
| 79 | CIS Enantiomer 1 | Rt: 14.4 min | 100% ee |

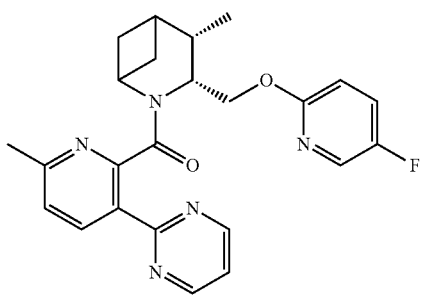 [SMILES: Cc1ccc(-c2ncccn2)c(C(=O)N2C3CC(C3)[C@H](C)[C@@H]2COc2ccc(F)cn2)n1]

MS (m/z): 434.4 [MH]⁺.
NMR (¹H, DMSO-d6): δ 8.82-8.96 (m, 2 H), 8.47 (d, 1 H), 8.21 (d, 1 H), 7.67-7.76 (m, 1 H), 7.46-7.52 (m, 1 H), 7.44 (d, 1 H), 6.94 (dd, 1 H), 4.74-4.83 (m, 1 H), 4.49-4.63 (m, 2 H), 3.85 (q, 1 H), 2.72-2.80 (m, 1 H), 2.53 (s, 3 H), 1.99-2.41 (m, 3 H), 1.41-1.83 (m, 2 H), 1.13 (d, 3 H)

or

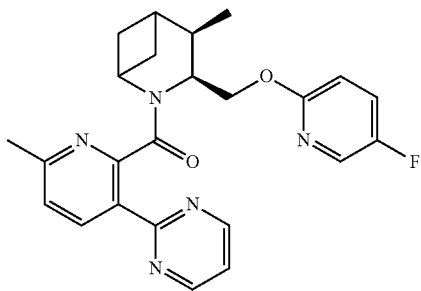 [SMILES: Cc1ccc(-c2ncccn2)c(C(=O)N2C3CC(C3)[C@@H](C)[C@H]2COc2ccc(F)cn2)n1]

(3R,4S or 3S,4R) 3-{[(5-fluoropyridin-2-yl)oxy]methyl}-4-methyl-2-[6-methyl-3-(pyrimidin-2-yl)pyridine-2-carbonyl]-2-azabicyclo[3.1.1]heptane

| 80 | TRANS Enantiomer 1 | Rt: 19.3 min | 100% ee |
|---|---|---|---|

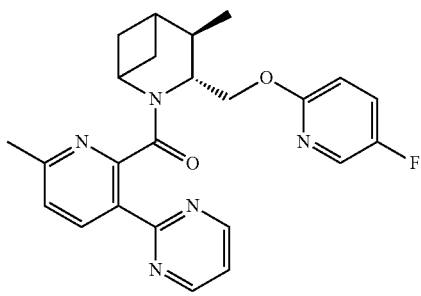 [SMILES: Cc1ccc(-c2ncccn2)c(C(=O)N2C3CC(C3)[C@@H](C)[C@@H]2COc2ccc(F)cn2)n1]

MS (m/z): 434.4 [MH]⁺.
NMR (¹H, DMSO-d6): δ 8.88 (d, 2 H), 8.46 (d, 1 H), 8.18 (d, 1 H), 7.72 (td, 1 H), 7.39-7.50 (m, 2 H), 6.96 (dd, 1 H), 4.66 (dd, 1 H), 4.41 (t, 1 H), 4.03-4.13 (m, 1 H), 3.88 (q, 1 H), 2.54 (s, 3 H), 2.48 (br. s., 1 H), 2.24-2.32 (m, 1 H), 2.14-2.22 (m, 1 H), 1.94 (dt, 1 H), 1.68-1.75 (m, 1 H), 1.59-1.66 (m, 1 H), 1.22 (d, 3 H)

or

| Example | Starting materials | Gen. procedure | Yield (%) |
|---|---|---|---|

(3R,4R or 3S,4S) 3-{[(5-fluoropyridin-2-yl)oxy]methyl}-4-methyl-2-[6-methyl-3-(pyrimidin-2-yl)pyridine-2-carbonyl]-2-azabicyclo[3.1.1]heptane

| | | | |
|---|---|---|---|
| 81 | CIS<br>Enantiomer 2 | Rt: 24.2 min | 100% ee |

MS (m/z): 434.4 [MH]⁺.
NMR (¹H, DMSO-d6): δ 8.82-8.96 (m, 2 H), 8.47 (d, 1 H), 8.21 (d, 1 H), 7.67-7.76 (m, 1 H), 7.46-7.52 (m, 1 H), 7.44 (d, 1 H), 6.94 (dd, 1 H), 4.74-4.83 (m, 1 H), 4.49-4.463 (m, 2 H), 3.85 (q, 1 H), 2.72-2.80 (m, 1 H), 2.53 (s, 3 H), 1.99-2.41 (m, 3 H), 1.41-1.83 (m, 2 H), 1.13 (d, 3 H)

or (3S,4R or 3R,4S) 3-{[(5-fluoropyridin-2-yl)oxy]methyl}-4-methyl-2-[6-methyl-3-(pyrimidin-2-yl)pyridine-2-carbonyl]-2-azabicyclo[3.1.1]heptane

| | | | |
|---|---|---|---|
| 82 | TRANS<br>Enantiomer 2 | Rt: 37.4 min | 100% ee |

MS (m/z): 434.4 [MH]⁺.
NMR (¹H, DMSO-d6): δ 8.88 (d, 2 H), 8.46 (d, 1 H), 8.18 (d, 1 H), 7.72 (td, 1 H), 7.39-7.50 (m, 2 H), 6.96 (dd, 1 H), 4.66 (dd, 1 H), 4.41 (t, 1 H), 4.03-4.13 (m, 1 H), 3.88 (q, 1 H), 2.54 (s, 3 H), 2.48 (br. s., 1 H), 2.24-2.32 (m, 1 H), 2.14-2.22 (m, 1 H), 1.94 (dt, 1 H), 1.68-1.75 (m, 1 H), 1.59-1.66 (m, 1 H), 1.22 (d, 3 H)

or

-continued

| Example | Starting materials | Gen. procedure | Yield (%) |
|---|---|---|---|
| 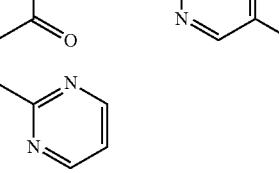<br>(3S,4S or 3R,4R) 3-{[(5-fluoropyridin-2-yl)oxy]methyl}-4-methyl-2-[6-methyl-3-(pyrimidin-2-yl)pyridin-2-carbonyl]-2-azabicyclo[3.1.1]heptane<br>83 | p41 | O | 76 |
| 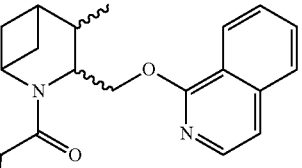<br>CIS/TRANS 1-{[4-methyl-2-(4-methyl-5-phenyl-1,3-thiazole-4-carbonyl)-2-azabicyclo[3.1.1]heptan-3-yl]methoxy}isoquinoline<br>84 | MS (m/z): 470.1 [MH]$^+$.<br>NMR ($^1$H, CHLOROFORM-d): δ 0.94-1.41 (m, 5 H) 1.64-2.62 (m, 6 H) 3.89-5.44 (m, 1 H) 7.07-7.26 (m, 4 H) 7.41-8.39 (m, 7 H)<br>p42 | P | 57 |
| 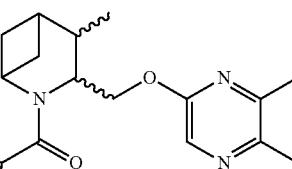<br>CIS/TRANS 7-chloro-2-{[4-methyl-2-(2-methyl-5-phenyl-1,3-thiazole-4-carbonyl)-2-azabicyclo[3.1.1]heptan-3-yl]methoxy}quinoxaline<br>85 | MS (m/z): 505.1 [MH]$^+$.<br>NMR ($^1$H, DMSO-d6): δ 8.26-8.67 (m, 1 H), 8.06 (d, 1 H), 7.95 (d, 1 H), 7.70 (dd, 1 H), 7.18-7.51 (m, 5H), 3.77-5.12 (m, 4 H), 2.44-2.76 (m, 4 H), 1.54-2.40 (m, 4 H), 0.83-1.22 (m, 4 H)<br>p83 | R | 85 |
| 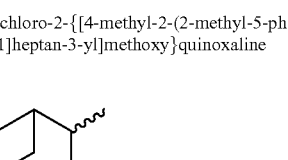<br>CIS/TRANS 3-{[4-methyl-2-(2-methyl-5-phenyl-1,3-thiazole-4-carbonyl)-2-azabicyclo[3.1.1]heptan-3-yl]methoxy}isoquinoline<br>The diastereomeric mixture was separated into the single enantiomers for each diastereomer by preparative chiral HPLC | MS (m/): 470.3 [MH]$^+$.<br>NMR ($^1$H, DMSO-d6): δ 9.09 (s, 1H), 8.10-7.99 (m, 1H), 7.90-7.79 (m, 1H), 7.71-7.61 (m, 1H), 7.50-7.33 (m, 4H), 7.32-7.20 (m, 3H), 4.79-4.53 (m, 1H), 4.95-4.18 (m, 1H), 4.45-4.09 (m, 1H), 5.10-3.85 (m, 1H), 2.77-2.43 (m, 1H), 2.74-2.27 (m, 3H), 2.27-2.04 (m, 1H), 1.16-1.08 (m, 3H), 2.30-0.91 (m, 4H) | | |

-continued

| Example | Starting materials | Gen. procedure | Yield (%) |
|---------|-------------------|----------------|-----------|
| Preparative chiral chromatography protocol: | Column | Chiralpak AD-H (25 × 2.0 cm), 5µ | |
| | Mobile phase | n-Hexane/(2-Propanol/Methanol 1/1) 90/10% v/v | |
| | Flow rate (ml/min) | 15 ml/min | |
| | DAD detection | 220 nm | |
| | Loop | 1500 µl | |
| | Injection | 35 mg (each injection) | |
| 86 | TRANS Enantiomer 1 | Rt: 15.9 min | 100% ee |

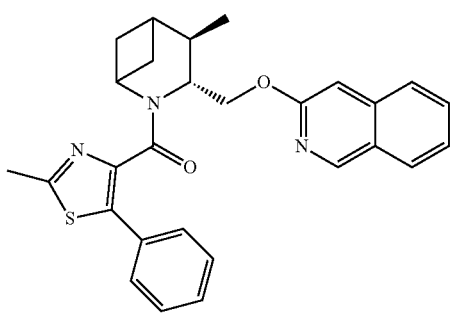 [SMILES: Cc1nc(C(=O)N2C3CC(C3)[C@@H](C)[C@@H]2COc2cc3ccccc3cn2)c(-c2ccccc2)s1]

MS (m/z): 470.3 [MH]⁺.
NMR (¹H, DMSO-d6): δ 9.09 (s, 1 H), 8.06 (d, 1 H), 7.86 (d, 1 H), 7.68 (t, 1 H), 7.18-7.50 (m, 7 H), 4.55-4.65 (m, 2 H), 4.09-4.16 (m, 1 H), 3.94 (d, 1 H), 2.67 (s, 3 H), 2.45-.53 (m, 1 H), 2.10-2.25 (m, 2 H), 1.86-1.96 (m, 1 H), 1.73 (t, 1H), 1.12 (d, 3 H), 1.08-1.16 (m, 1 H)

or

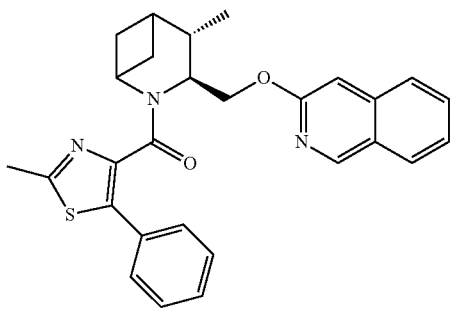 [SMILES: Cc1nc(C(=O)N2C3CC(C3)[C@H](C)[C@H]2COc2cc3ccccc3cn2)c(-c2ccccc2)s1]

3-{[(3R,4R or 3S,4S)-4-methyl-2-(2-methyl-5-phenyl-1,3-thiazole-4-carbonyl)-2-azabicyclo[3.1.1]heptan-3-yl]methoxy}isoquinoline

| 87 | CIS Enantiomer 1 | Rt: 18.0 min | 98.6% ee |

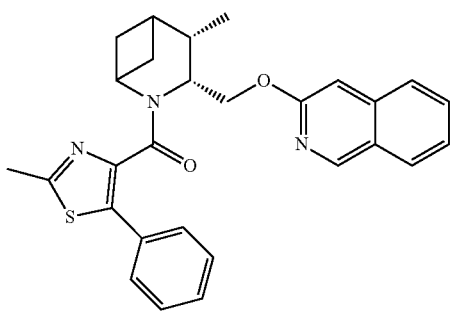 [SMILES: Cc1nc(C(=O)N2C3CC(C3)[C@H](C)[C@@H]2COc2cc3ccccc3cn2)c(-c2ccccc2)s1]

MS (m/z): 470.3 [MH]⁺.
NMR (¹H, CHLOROFORM-d): δ 0.87-1.39 (m, 1 H), 0.99-1.24 (m, 3 H), 1.70-2.31 (m, 2 H), 1.92-2.45 (m, 1 H), 2.10-2.74 (m, 1 H), 2.10-2.20 (m, 1 H), 2.39-2.75 (m, 3 H), 3.96-5.16 (m, 1 H), 4.14-4.57 (m, 1 H), 4.22-5.16 (m, 1 H), 4.56-4.86 (m, 1 H), 6.77-7.15 (m, 1 H), 7.17-7.33 (m, 3 H), 7.38 (t, 1 H), 7.43-7.51 (m, 2 H), 7.58 (t, 1 H), 7.63-7.75 (m, 1 H), 7.89 (d, 1 H), 8.82-9.01 (m, 1 H)

or

| Example | Starting materials | Gen. procedure | Yield (%) |
|---|---|---|---|

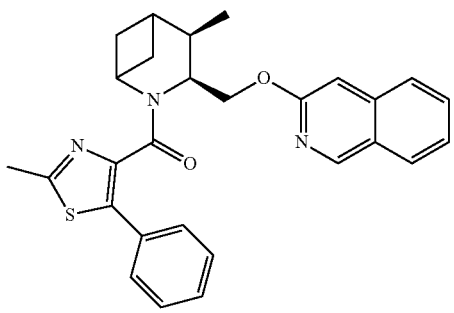 [SMILES: Cc1nc(C(=O)N2C3CC(C3)[C@@H](C)[C@H]2COc2cc3ccccc3cn2)c(-c2ccccc2)s1]

3-{[(3R,4S or 3S,4R)-4-methyl-2-(2-methyl-5-phenyl-1,3-thiazole-4-carbonyl)-2-azabicyclo[3.1.1]heptan-3-yl]methoxy}isoquinoline

| 88 | TRANS Enantiomer 2 | Rt: 22.0 min | 100% ee |

MS (m/z): 470.3 [MH]+.
NMR ($^1$H, DMSO-d6): δ 9.09 (s, 1 H), 8.06 (d, 1 H), 7.86 (d, 1 H), 7.68 (t, 1 H), 7.18-7.50 (m, 7 H), 4.55-4.65 (m, 2 H), 4.09-4.16 (m, 1 H), 3.94 (d, 1 H), 2.67 (s, 3 H), 2.45-2.53 (m, 1 H), 2.10-2.25 (m, 2 H), 1.86-1.96 (m, 1 H), 1.73 (t, 1 H), 1.12 (d, 3 H), 1.08-1.16 (m, 1 H)

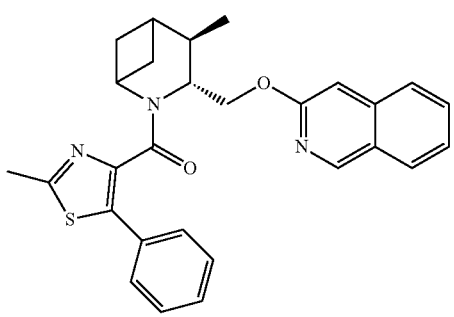 [SMILES: Cc1nc(C(=O)N2C3CC(C3)[C@@H](C)[C@@H]2COc2cc3ccccc3cn2)c(-c2ccccc2)s1]

or

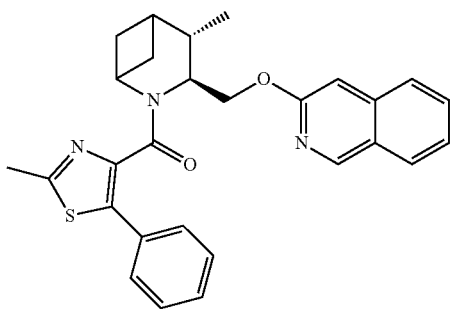 [SMILES: Cc1nc(C(=O)N2C3CC(C3)[C@H](C)[C@H]2COc2cc3ccccc3cn2)c(-c2ccccc2)s1]

3-{[(3S,4S or 3R,4R)-4-methyl-2-(2-methyl-5-phenyl-1,3-thiazole-4-carbonyl)-2-azabicyclo[3.1.1]heptan-3-yl]methoxy}isoquinoline

| 89 | CIS Enantiomer 2 | Rt: 30.0 min | 100% ee |

MS (m/z): 470.3 [MH]+.
NMR ($^1$H, CHLOROFORM-d): δ 0.87-1.39 (m, 1 H), 0.99-1.24 (m, 3 H), 1.70-2.31 (m, 2 H), 1.92-2.45 (m, 1 H), 2.10-2.74 (m, 1 H), 2.10-2.20 (m, 1 H), 2.39-2.75 (m, 3 H), 3.96-5.16 (m, 1 H), 4.14-4.57 (m, 1 H), 4.22-5.16 (m, 1 H), 4.56-4.86 (m, 1 H), 6.77-7.15 (m, 1 H), 7.17-7.33 (m, 3 H), 7.38 (t, 1H), 7.43-7.51 (m, 2 H), 7.58 (t, 1 H), 7.63-7.75 (m, 1 H), 7.89 (d, 1 H), 8.82-9.01 (m, 1 H)

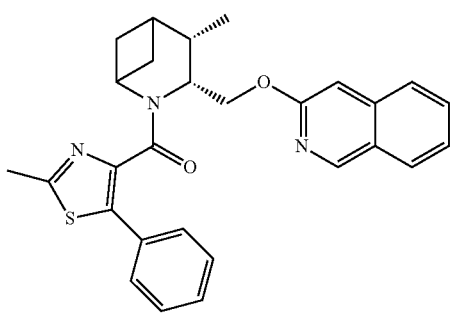 [SMILES: Cc1nc(C(=O)N2C3CC(C3)[C@H](C)[C@@H]2COc2cc3ccccc3cn2)c(-c2ccccc2)s1]

or

| Example | Starting materials | Gen. procedure | Yield (%) |
|---|---|---|---|
| | 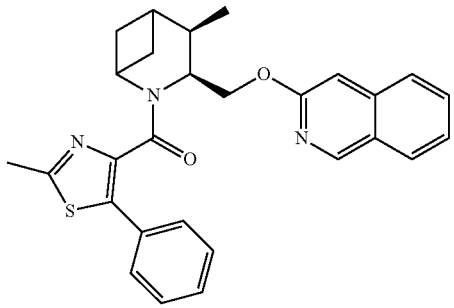 [SMILES: Cc1nc(C(=O)N2C3CC(C3)[C@@H](C)[C@H]2COc2cc3ccccc3cn2)c(-c2ccccc2)s1]<br>3-{[(3S,4R or 3R,4S)-4-methyl-2-(2-methyl-5-phenyl-1,3-thiazole-4-carbonyl)-2-azabicyclo[3.1.1]heptan-3-yl]methoxy}isoquinoline | p84 R | 46 |

MS (m/z): 433.3 [MH]$^+$.
NMR ($^1$H, DMSO-d6): δ 8.82-8.97 (m, 2H), 8.38-8.49 (m, 1H), 7.29-7.55 (m, 2H), 6.62-7.18 (m, 4H), 3.81-4.84 (m, 4H), 2.52-2.56 (m, 3H), 1.39-2.85 (m, 6H), 0.95-1.20 ppm (m, 3H)

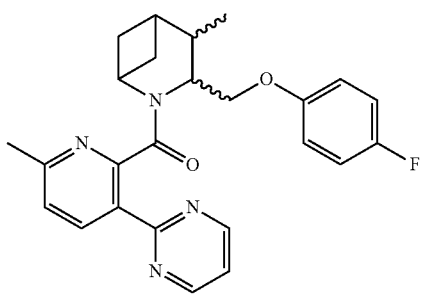 [SMILES: Cc1ccc(-c2ncccn2)c(C(=O)N2C3CC(C3)C(C)C2COc2ccc(F)cc2)n1]

CIS/TRANS 3-[(4-fluorophenoxy)methyl]-4-methyl-2-[6-methyl-3-(pyrimidin-2-yl)pyridine-2-carbonyl]-2-azabicyclo[3.1.1]heptane The diastereomeric mixture was separated into the single enantiomers for each diastereomer by preparative chiral HPLC

| Preparative chiral chromatography protocol: | Column | Chiralpak IC (25 × 3.0 cm), 5μ |
|---|---|---|
| | Mobile phase | n-Hexane/(Ethanol + 0.1% isopropylamine) 70/30% v/v |
| | Flow rate (ml/min) | 40 ml/min |
| | DAD detection | 220 nm |
| | Loop | 1300 μL |
| | Injection | 25.4 mg/injection |
| 90 | CIS<br>Enantiomer 1 | Rt: 5.9 min 100% ee |

MS (m/z): 433.3 [MH]$^+$.
NMR ($^1$H, CHLOROFORM-d): δ 1.01-1.27 (m, 3 H), 1.49-1.92 (m, 1 H), 1.69-2.08 (m, 1 H), 1.98-2.41 (m, 1 H), 2.20 (s, 1 H), 2.16-2.65 (m, 3 H), 2.21-2.33 (m, 1 H), 2.65-2.87 (m, 1 H), 3.88-5.08 (m, 1 H), 4.45 (s, 1 H), 4.23-4.64 (m, 2 H), 6.59-7.07 (m, 4 H), 7.08-7.25 (m, 1 H), 7.14-7.35 (m, 1 H), 8.47-8.58 (m, 1 H), 8.58-8.88 (m, 2 H)

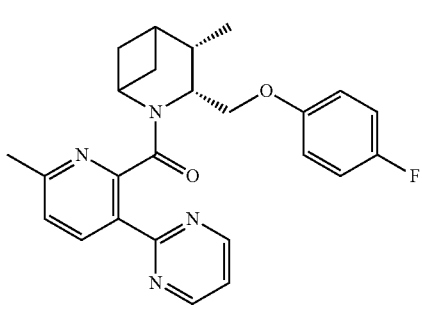 [SMILES: Cc1ccc(-c2ncccn2)c(C(=O)N2C3CC(C3)[C@H](C)[C@@H]2COc2ccc(F)cc2)n1]

or

-continued

| Example | Starting materials | Gen. procedure | Yield (%) |
|---|---|---|---|

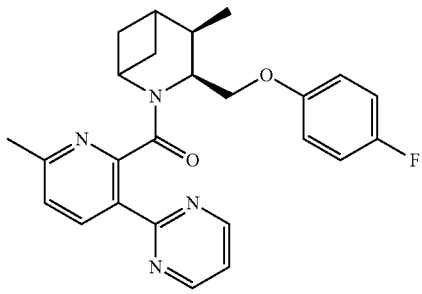 [SMILES: Cc1ccc(-c2ncccn2)c(C(=O)N2C3CC(C3)[C@@H](C)[C@H]2COc2ccc(F)cc2)n1]

(3R,4S or 3S,4R)-3-(4-fluorophenoxymethyl)-4-methyl-2-[6-methyl-3-(pyrimidin-2-yl)pyridine-2-carbonyl]-2-azabicyclo[3.1.1]heptane

| 91 | | CIS<br>Enantiomer 2 | Rt: 6.8 min | 97.6% ee |
|---|---|---|---|---|

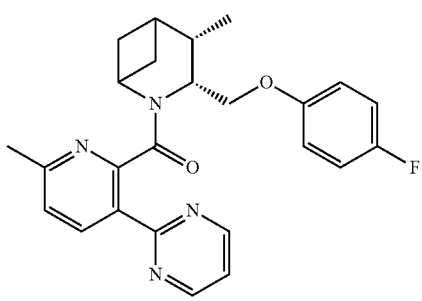 [SMILES: Cc1ccc(-c2ncccn2)c(C(=O)N2C3CC(C3)[C@H](C)[C@@H]2COc2ccc(F)cc2)n1]

MS (m/z): 433.3 [MH]⁺.
NMR ($^1$H, CHLOROFORM-d): δ 0.98-1.34 (m, 3 H), 1.46-1.93 (m, 1 H), 1.69-2.07 (m, 1 H), 1.97-2.41 (m, 1 H), 2.07-2.51 (m, 1 H), 2.17-2.65 (m, 3 H), 2.21-2.32 (m, 1 H), 2.66-2.86 (m, 1 H), 3.81-5.05 (m, 1 H), 4.07-5.18 (m, 1 H), 4.23-4.64 (m, 2 H), 6.57-7.06 (m, 4 H), 7.07-7.25 (m, 1 H), 7.13-7.35 (m, 1 H), 8.49-8.57 (m, 1 H), 8.58-8.87 (m, 2 H)

or

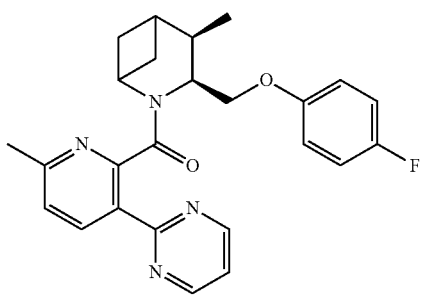 [SMILES: Cc1ccc(-c2ncccn2)c(C(=O)N2C3CC(C3)[C@@H](C)[C@H]2COc2ccc(F)cc2)n1]

(3S,4R or 3R,4S)-3-(4-fluorophenoxymethyl)-4-methyl-2-[6-methyl-3-(pyrimidin-2-yl)pyridine-2-carbonyl]-2-azabicyclo[3.1.1]heptane

| 92 | | TRANS<br>Enantiomer 1 | Rt: 7.6 min | 100% ee |
|---|---|---|---|---|

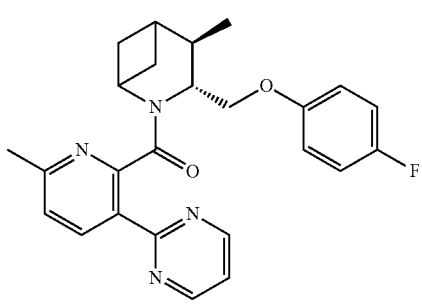 [SMILES: Cc1ccc(-c2ncccn2)c(C(=O)N2C3CC(C3)[C@@H](C)[C@@H]2COc2ccc(F)cc2)n1]

MS (m/z): 433.3 [MH]⁺.
NMR ($^1$H, CHLOROFORM-d): δ 1.02-1.24 (m, 3 H), 1.60-1.96 (m, 2 H), 1.73-2.22 (m, 2 H), 2.25-2.37 (m, 1 H), 2.46-2.68 (m, 3 H), 2.58-2.74 (m, 1 H), 3.89-3.98 (m, 1 H), 4.18-4.77 (m, 2 H), 4.29-4.40 (m, 1 H), 6.53-7.11 (m, 2 H), 6.82-7.04 (m, 2 H), 7.15 (t, 1 H), 7.26-7.32 (m, 1 H), 8.48-8.63 (m, 1 H), 8.64-8.87 (m, 2 H)

or

-continued

| Example | Starting materials | Gen. procedure | Yield (%) |
|---|---|---|---|

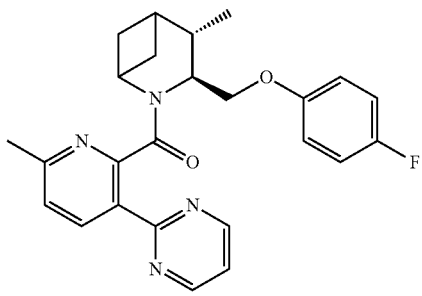 [SMILES: Cc1ccc(-c2ncccn2)c(C(=O)N2C3CC(C3)[C@H](C)[C@H]2COc2ccc(F)cc2)n1]

(3R,4R or 3S,4S)-3-(4-fluorophenoxymethyl)-4-methyl-2-[6-methyl-3-(pyrimidin-2-yl)pyridine-2-carbonyl]-2-azabicyclo[3.1.1]heptane

| 93 | TRANS Enantiomer 2 | | Rt: 8.2 min 98.4% ee |

MS (m/z): 433.3 [MH]$^+$.
NMR ($^1$H, CHLOROFORM-d): δ 0.98-1.24 (m, 3 H), 1.63-2.22 (m, 5 H), 2.31 (dd, 1 H), 2.41-2.73 (m, 4 H), 3.79-4.78 (m, 4 H), 6.51-7.11 (m, 4 H), 7.15 (t, 1 H), 8.53 (d, 1 H), 8.64-8.86 (m, 2 H)

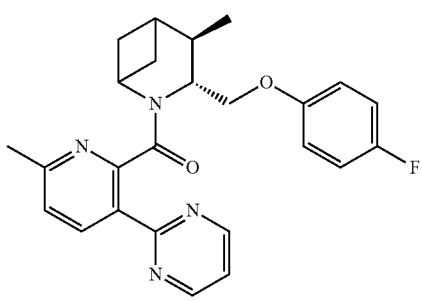 [SMILES: Cc1ccc(-c2ncccn2)c(C(=O)N2C3CC(C3)[C@@H](C)[C@@H]2COc2ccc(F)cc2)n1]

or

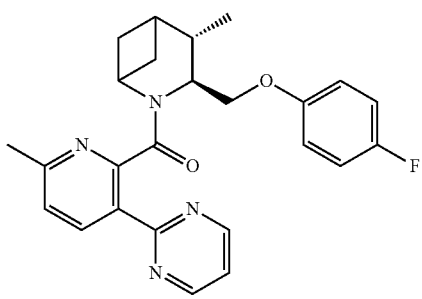 [SMILES: Cc1ccc(-c2ncccn2)c(C(=O)N2C3CC(C3)[C@H](C)[C@H]2COc2ccc(F)cc2)n1]

(3S,4S or 3R,4R)-3-(4-fluorophenoxymethyl)-4-methyl-2-[6-methyl-3-(pyrimidin-2-yl)pyridine-2-carbonyl]-2-azabicyclo[3.1.1]heptane

| 94 | p51 + p70 | Q | 54 |

MS (m/z): 439.1 [MH]$^+$.
NMR ($^1$H, CHLOROFORM-d): δ 8.53 (d, 2H), 6.67-7.15 (m, 5H), 3.97-5.18 (m, 4H), 2.34-2.86 (m, 2H), 2.76 (s, 3H), 1.65-2.21 (m, 4H), 1.28 (d, 3H)

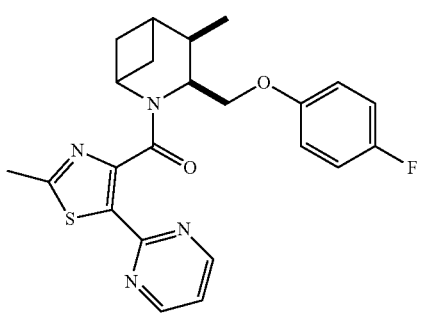

mixture of cis-isomers
Racemic mixture of cis-3-[(4-fluorophenoxy)methyl]-4-methyl-2-[2-methyl-5-(pyrimidin-2-yl)-1,3-thiazole-4-carbonyl]-2-azabicyclo[3.1.1]heptane -continued

| Example | Starting materials | Gen. procedure | Yield (%) |
|---|---|---|---|
| 95 | p51 + p67 | Q | 18 |

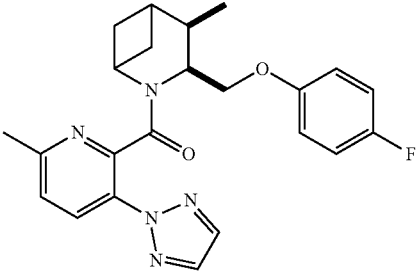

MS (m/z): 422.1 [MH]$^+$.
NMR ($^1$H, CHLOROFORM-d): δ 1.00-1.31 (m, 3 H), 1.45-1.54 (m, 1 H) 1.69-2.11 (m, 2 H) 2.11-2.66 (m, 5 H) 2.67-2.84 (m, 1 H) 3.91-4.17 (m, 1 H) 4.24-4.39 (m, 1 H) 4.41-4.55 (m, 1 H) 4.87-5.04 (m, 1 H) 6.60-7.05 (m, 4 H) 7.19-7.31 (m, 1 H) 7.55-7.88 (m, 2 H) 8.10-8.26 (m, 1 H)

mixture of cis-isomers
Racemic mixture of cis-3-[(4-fluorophenoxy)methyl]-4-methyl-2-[6-methyl-3-(2H-1,2,3-triazol-2-yl)pyridine-2-carbonyl]-2-azabicyclo[3.1.1]heptane

| 96 | p51 + p65 | Q | 3 |
|---|---|---|---|

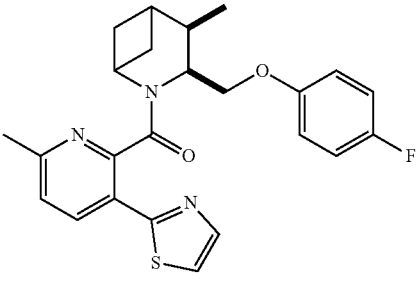

MS (m/z): 438.1 [MH]$^+$.
NMR ($^1$H, CHLOROFORM-d): δ 0.96-1.45 (m, 4 H) 1.65-1.84 (m, 1 H) 2.00-2.15 (m, 2 H) 2.14-2.64 (m, 4 H) 2.63-2.80 (m, 1 H) 3.80-4.15 (m, 1 H) 4.20-4.38 (m, 1 H) 4.38-4.52 (m, 1 H) 4.92-5.07 (m, 1 H) 6.59-7.19 (m, 4 H) 7.27 (s, 1 H) 7.71-7.89 (m, 1 H) 7.98-8.15 (m, 1 H)

Racemic mixture of cis-3-[(4-fluorophenoxy)methyl]-4-methyl-2-[6-methyl-3-(1,3-thiazol-2-yl)pyridine-2-carbonyl]-2-azabicyclo[3.1.1]heptane

| 97 | p51 + p62 | Q | 17 |
|---|---|---|---|

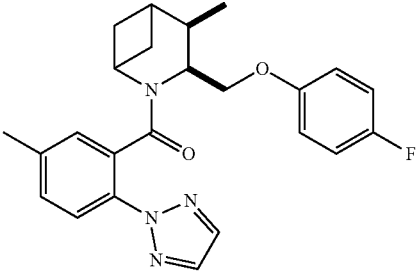

MS (m/z): 421.1 [MH]$^+$.
NMR ($^1$H, CHLOROFORM-d): δ 1.22 (dd, 3 H) 1.39-1.48 (m, 1 H) 1.64-2.27 (m, 4 H) 2.39 (m, 3 H) 2.51-2.78 (m, 1 H) 3.85-4.62 (m, 3 H) 4.87-5.04 (m, 1 H) 6.54-7.22 (m, 5 H) 7.28-7.33 (m, 1 H) 7.50 (s, 1 H) 7.67-7.88 (m, 2 H)

mixture of cis-isomers
Racemic mixture of cis-3-[(4-fluorophenoxy)methyl]-4-methyl-2-[5-methyl-2-(2H-1,2,3-triazol-2-yl)benzoyl]-2-azabicyclo[3.1.1]heptane

| 98 | p51 + p66 | Q | 4 |
|---|---|---|---|

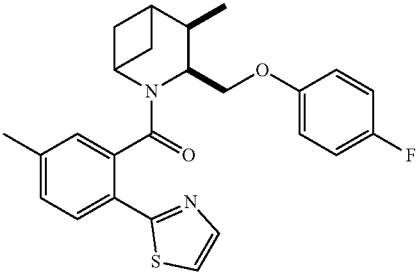

MS (m/z): 437.3 [MH]$^+$.
NMR ($^1$H, CHLOROFORM-d): δ 7.72 (s, 2H), 7.32-7.63 (m, 1H), 7.10-7.27 (m, 2H), 6.94-7.08 (m, 4H), 3.84-5.06 (m, 4H), 2.59-2.82 (m, 2H), 2.40 (d, 3H), 1.83-2.31 (m, 4H), 0.97-1.49 (m, 3H)

mixture of cis-isomers
Racemic mixture of cis-3-[(4-fluorophenoxy)methyl]-4-methyl-2-[5-methyl-2-(1,3-thiazol-2-yl)benzoyl]-2-azabicyclo[3.1.1]heptane -continued

| Example | Starting materials | Gen. procedure | Yield (%) |
|---|---|---|---|
| 99 | p85 | S | 34 |

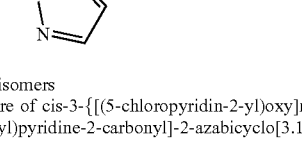

MS (m/z): 439.1 [MH]⁺.
NMR (¹H, CHLOROFORM-d): δ 8.16-8.25 (m, 1H), 8.06-8.15 (m, 1H), 7.72-7.85 (m, 2H), 7.44-7.58 (m, 1H), 7.20-7.33 (m, 1H), 6.38-6.82 (m, 1H), 4.54-5.09 (m, 4H), 2.27-2.83 (m, 5H), 1.80-2.26 (m, 4H), 1.00-1.20 (m, 3H)

mixture of cis-isomers
Racemic mixture of cis-3-{[(5-chloropyridin-2-yl)oxy]methyl}-4-methyl-2-[6-methyl-3-(2H-1,2,3-triazol-2-yl)pyridine-2-carbonyl]-2-azabicyclo[3.1.1]heptane

| 100 | p85 | S | 28 |
|---|---|---|---|

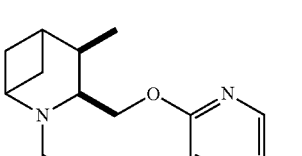

MS (m/z): 419.1 [MH]⁺.
NMR (¹H, CHLOROFORM-d): δ 8.17 (d, 1H), 7.93-8.03 (m, 1H), 7.70-7.86 (m, 2H), 7.32-7.43 (m, 1H), 7.19-7.32 (m, 1H), 6.75 (d, 1H), 3.93-5.10 (m, 4H), 2.27-2.83 (m, 2H), 2.62 (s, 3H), 1.84-2.26 (m, 4H), 1.01-1.22 (m, 3H)

mixture of cis-isomers
Racemic mixture of cis-4-methyl-2-[6-methyl-3-(2H-1,2,3-triazol-2-yl)pyridine-2-carbonyl]-3-{[(5-methylpyridin-2-yl)oxy]methyl}-2-azabicyclo[3.1.1]heptane

| 101 | p52 + p66 | Q | 19 |
|---|---|---|---|

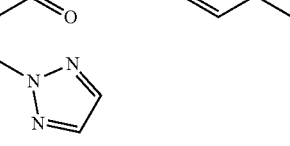

MS (m/z): 437.4 [MH]⁺.
NMR (¹H, CHLOROFORM-d): δ 8.10-8.36 (m, 2H), 7.77 (s, 2H), 7.51-7.61 (m, 1H), 7.27-7.37 (m, 3H), 6.76-6.86 (m, 1H), 4.76 (d, 1H), 4.56-4.64 (m, 1H), 4.31-4.37 (m, 1H), 3.93-4.01 (m, 1H), 2.51-2.69 (m, 4H), 2.28-2.36 (m, 1H), 2.13-2.24 (m, 1H), 1.89-1.98 (m, 1H), 1.85 (t, 1H), 1.64 (d, 1H), 1.24 (d, 3H)

mixture of trans-isomers
Racemic mixture of trans-3-[(4-fluorophenoxy)methyl]-4-methyl-2-[5-methyl-2-(1,3-thiazol-2-yl)benzoyl]-2-azabicyclo[3.1.1]heptane

| 102 | p86 | S | 6 |
|---|---|---|---|

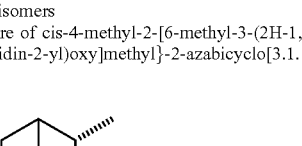

MS (m/z): 439.4 [MH]⁺.
NMR (¹H, CHLOROFORM-d): δ 8.13-8.32 (m, 2H), 7.77 (s, 2H), 7.54-7.60 (m, 1H), 7.30-7.34 (m, 1H), 6.80-6.87 (m, 1H), 4.74-4.81 (m, 1H), 4.57-4.68 (m, 1H), 4.32-4.39 (m, 1H), 3.93-4.04 (m, 1H), 2.64 (s, 4H), 2.26-2.34 (m, 1H), 2.11-2.23 (m, 1H), 1.80-1.98 (m, 2H), 1.60-1.68 (m, 1H), 1.24 (d, 3H)

mixture of trans-isomers
Racemic mixture of trans-3-{[(5-chloropyridin-2-yl)oxy]methyl}-4-methyl-2-[6-methyl-3-(2H-1,2,3-triazol-2-yl)pryidine-2-carbonyl]-2-azabicyclo[3.1.1]heptane

| Example | Starting materials | Gen. procedure | Yield (%) |
|---|---|---|---|
| 103 | p52 + p67 | Q | 32 |

MS (m/z): 422.3 [MH]+.
NMR (1H, CHLOROFORM-d): δ 8.17 (d, 1H), 7.67 (s, 2H), 7.29 (d, 1H), 7.07-6.94 (m, 4H), 4.57 (dd, 1H), 4.29 (dt, 1H), 4.23 (dd, 1H), 3.93 (q, 1H), 2.62 (s, 4H), 2.35-2.26 (m, 1H), 2.16 (dt, 1H), 1.92 (dt, 1H), 1.80 (dd, 1H), 1.27-1.12 (m, 4H).

mixture of trans-isomers
Racemic mixture of trans-3-[(4-fluorophenoxy)methyl]-4-methyl-2-[6-methyl-3-(2H-1,2,3-triazol-2-yl)pyridine-2-carbonyl]-2-azabicyclo[3.1.1]heptane
The racemic mixture was separated into the single enantiomers by preparative chiral HPLC

| Preparative chiral chromatography protocol: | Column | Chiralpak IA (25 × 2.0 cm), 5μ |
|---|---|---|
| | Mobile phase | n-Hexane/2-Propanol 60/40% v/v |
| | Flow rate (ml/min) | 17 ml/min |
| | DAD detection | 220 nm |
| | Loop | 1000 μL |
| | Injection | 11.5 mg/injection |
| 104 | Enantiomer 1 | Rt: 6.2 min    100 ee % |

MS (m/z): 422.4 [MH]+.
(3R,4R or 3S,4S)-3-[(4-fluorophenoxy)methyl]-4-methyl-2-[6-methyl-3-(2H-1,2,3-triazol-2-yl)pyridine-2-carbonyl]-2-azabicyclo[3.1.1]heptane 3R,4R or 3S,4S enantiomer

| 105 | Enantiomer 2 | Rt: 8.9 min    96 ee % |
|---|---|---|

MS (m/z): 422.4 [MH]+.
(3S,4S or 3R,4R)-3-[(4-fluorophenoxy)methyl]-4-methyl-2-[6-methyl-3-(2H-1,2,3-triazol-2-yl)pyridine-2-carbonyl]-2-azabicyclo[3.1.1]heptane 3S,4S or 3R,4R enantiomer

| 106 | p52 + p65 | Q | 62 |

MS (m/z): 438.3 [MH]+.
NMR (1H, CHLOROFORM-d): δ 8.09 (d, 1 H), 7.71-7.93 (m, 1 H), 7.16-7.48 (m, 2 H), 6.90-7.09 (m, 4 H), 4.55 (d, 1 H), 4.20-4.35 (m, 2 H), 3.84 (d, 1 H), 2.55-2.67 (m, 4 H), 2.22-2.35 (m, 1 H), 1.27-2.21 (m, 4 H), 1.15 (d, 3 H)

| Example | Starting materials | Gen. procedure | Yield (%) |
|---|---|---|---| mixture of trans-isomers
Racemic mixture of trans-3-[(4-fluorophenoxy)methyl]-4-methyl-2-[6-methyl-3-(1,3-thiazol-2-yl)pyridine-2-carbonyl]-2-azabicyclo[3.1.1]heptane
The racemic mixture was separated into the single enantiomers by preparative chiral HPLC

| Preparative chiral chromatography protocol: | Column | Chiralpak IA (25 × 2.0 cm), 5µ |
|---|---|---|
| | Mobile phase | n-Hexane/2-Propanol 60/40% v/v |
| | Flow rate (ml/min) | 17 ml/min |
| | DAD detection | 220 nm |
| | Loop | 500 µL |
| | Injection | 10 mg/injection |

107

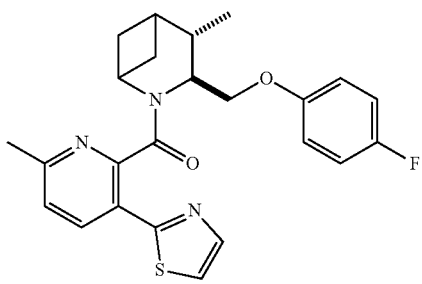

3R,4R or 3S,4S enantiomer

Enantiomer 1

MS (m/z): 438.4 [MH]⁺.
(3R,4R or 3S,4S)-3-[(4-fluorophenoxy)methyl]-4-methyl-2-[6-methyl-3-(1,3-thiazol-2-yl)pyridine-2-carbonyl]-2-azabicyclo[3.1.1]heptane Rt: 7.3 min    100 ee %

108

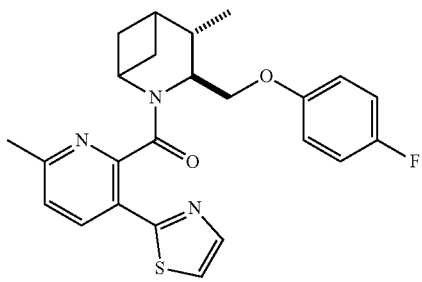

3S,4S or 3R,4R enantiomer

Enantiomer 2

MS (m/z): 438.4 [MH]⁺.
(3S,4S or 3R,4R)-3-[(4-fluorophenoxy)methyl]-4-methyl-2-[6-methyl-3-(1,3-thiazol-2-yl)pyridine-2-carbonyl]-2-azabicyclo[3.1.1]heptane Rt: 10.5 min    94.6 ee %

109

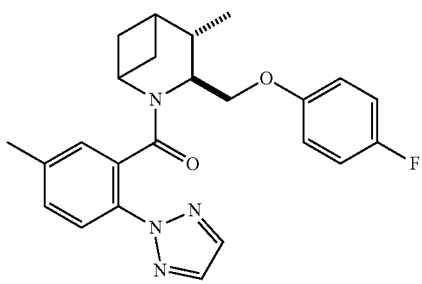

mixture of trans-isomers
Racemic mixture of trans-3-[(4-fluorophenoxy)methyl]-4-methyl-2-[5-methyl-2-(2H-1,2,3-triazol-2-yl)benzoyl]-2-azabicyclo[3.1.1]heptane p52 + p62

MS (m/z): 421.1 [MH]⁺.
NMR (¹H, CHLOROFORM-d): δ 7.49-7.95 (m, 3 H), 6.83-7.37 (m, 6 H), 3.83-4.64 (m, 4 H), 2.35-2.46 (m, 3 H), 2.21-2.68 (m, 2 H), 1.40-2.21 (m, 4 H), 1.09-1.19 (m, 3 H)

Q    18

| Example | Starting materials | Gen. procedure | Yield (%) |
|---|---|---|---|
| 110 | p86 | S | 24 |

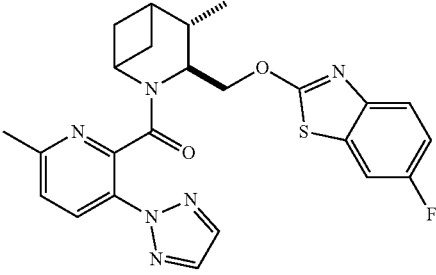

MS (m/z): 479.1 [MH]⁺.
NMR (¹H, CHLOROFORM-d): δ 8.17 (d, 1H), 7.76 (s, 2H), 7.63 (dd, 1 H), 7.36 (dd, 1H), 7.29 (d, 1H), 7.09 (td, 1H), 5.14-4.82 (m, 2H), 4.36 (dt, 1H), 3.98 (q, 1H), 2.61 (s, 3H), 2.38-2.26 (m, 1H), 2.19 (dt, 1H), 1.94 (dd, 1H), 1.84-1.74 (m, 1H), 1.63 (t, 1H), 1.25 (d, 3H).

mixture of trans-isomers
Racemic mixture of trans-6-fluoro-2-({4-methyl-2-[6-methyl-3-(2H-1,2,3-triazol-2-yl)pyridine-2-carbonyl]-2-azabicyclo[3.1.1]heptan-3-yl}methoxy)-1,3-benzothiazole

| 111 | p86 | R | 18 |
|---|---|---|---|

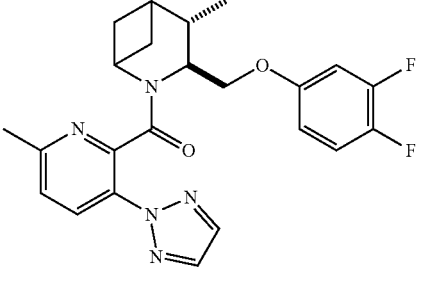

MS (m/z): 440.4 [MH]⁺.
NMR (¹H, CHLOROFRM-d): δ 8.17 (d, 1H), 7.71 (s, 2 H), 7.30 (d, 1H), 7.07 (q, 1H), 6.95-6.89 (m, 1H), 6.86-6.79 (m, 1H), 4.57 (dd, 1H), 4.30-4.25 (m, 1H), 4.21 (dd, 1H), 3.93 (q, 1H), 2.62 (s, 3H), 2.33-2.28 (m, 1H), 2.17 (dt, 1H), 1.92 (dt, 1H), 1.80-1.71 (m, 1H), 1.17 (d, 3H).

mixture of trans-isomers
Racemic mixture of trans-3-[(3,4-difluorophenoxy)methyl]-4-methyl-2-[6-methyl-3-(2H-1,2,3-triazol-2-yl)pyridine-2-carbonyl]-2-azabicyclo[3.1.1]heptane

| 112 | p86 | R | 17 |
|---|---|---|---|

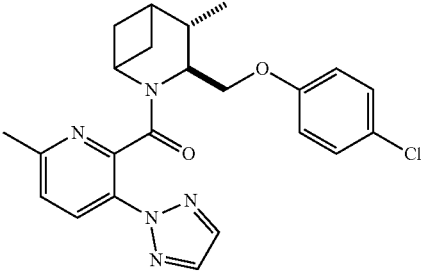

MS (m/z): 438.3 [MH]⁺.
NMR (¹H, CHLOROFORM-d): δ 8.17 (d, 1H), 7.67 (s, 3H), 7.31-7.23 (m, 2H), 7.05-7.02 (m, 2H), 4.59 (dd, 1H), 4.30-4.22 (m, 2H), 3.93 (q, 1H), 2.62 (s, 4H), 2.31-2.29 (m, 1H), 2.19-2.13 (m, 1H), 1.95-1.91 (m, 1H), 1.81-1.7 7(m, 1H), 1.16 (d, 3H).

mixture of trans-isomers
Racemic mixture of trans-3-[(4-chlorophenoxy)methyl]-4-methyl-2-[6-methyl-3-(2H-1,2,3-triazol-2-yl)pyridine-2-carbonyl]-2-azabicyclo[3.1.1]heptane General Procedure T:
To a solution of 2-azabicyclo[3.1.1]heptane (e.g. p157, p170-175; 1 eq) in DMSO (15-40 vol) the appropriate aryl halide (1-1.2 eq) and DIPEA (2-10 eq) were added. The reaction mixture was stirred at 90-100° C. from 1 h to O/N. The reaction mixture was cooled down to RT, diluted with water and extracted with AcOEt. The organic phase was washed with Brine, dried and concentrated under vacuum. The residue was purified by FC on silica gel and/or NH column (eluting mixture Cy/AcOEt) and/or C18 column (eluent from water+0.1% formic acid/MeCN+0.1% formic acid) to afford the title compound.

General Procedure U:
To a solution of 2-azabicyclo[3.1.1]heptane (e.g. p176-177; 1 eq) in DMF (15-20 vol) the appropriate aryl halide (1.2 eq) and $K_2CO_3$ (1.4 eq) were added. The reaction mixture was stirred at 90-100° C. from 1 h to O/N. The reaction mixture was cooled down to RT, diluted with water and extracted with AcOEt. The organic phase was washed with Brine, dried and concentrated under vacuum. The residue was purified by FC on silica gel and/or NH column (eluting mixture Cy/AcOEt) and/or C18 column (eluent from water+0.1% formic acid/MeCN+0.1% formic acid) to afford the title compound.

General Procedure V:
To a solution of the appropriate carboxylic acid (e.g. p105; 1-1.1 eq) and DIPEA (1.6 eq) in DMF (15-30 vol), TBTU (1.5 eq) was added. Mixture was stirred at RT for 30 min-1 h. Then 2-azabicyclo[3.1.1]heptane (e.g. p51; 1 eq)

dissolved in DMF (15-30 vol) was added drop-wise and reaction was stirred at RT from 1 h to O/N. It was then diluted with EtOAc, washed with ss NaHCO₃ and ss NH₄Cl. Aqueous layers were back extracted with EtOAc, organic phases were reunited, dried using a phase separator and evaporated under reduced pressure. The residue was purified by FC on silica gel and/or NH column (eluting mixture Cy/AcOEt) and/or C18 column (eluent from water+0.1% formic acid/MeCN+0.1% formic acid) to afford the title compound.

General Procedure W:

A suspension of 2-azabicyclo[3.1.1]heptane (e.g. p170; 1 eq), sodium tert-butoxide (2 eq), BINAP (0.1 eq) and appropriate aryl halide (1.2 eq) in Toluene (~15 vol) was degassed with N₂/vacuum cycles. Pd₂(dba)₃ (0.03 eq) was added and reaction was heated at 100° C. O/N. Mixture was left to cool RT and diluted with water. Aqueous phase was extracted with EtOAc, layers were separated, and the organic phase was dried and concentrated under reduced pressure. The residue was purified by FC on silica gel and/or NH column (eluting mixture Cy/AcOEt) and/or C18 column (eluent from water+0.1% formic acid/MeCN+0.1% formic acid) to afford the title compound.

General Procedure X:

To a suspension of 2-azabicyclo[3.1.1]heptane (e.g. p170; 1 eq), and appropriate aryl halide (1 eq) in 1,4 dioxane (~60 vol) potassium tert-butoxide (2 eq), DavePhos (0.1 eq) and Pd₂(dba)₃ (0.5 eq) were added and reaction was heated at 90° C. O/N. Mixture was left to cool RT and diluted with water. Aqueous phase was extracted with EtOAc, layers were separated, and the organic phase was dried and concentrated under reduced pressure. The residue was purified by FC on silica gel and/or NH column (eluting mixture Cy/AcOEt) and/or C18 column (eluent from water+0.1% formic acid/MeCN+0.1% formic acid) to afford the title compound.

General Procedure Z:

The desired alcohol intermediate (e.g. p86; 1 eq) was dissolved in THF (~40 vol). PPh₃ (1.5 eq) was added, followed by the desired phenol (1.5 eq). The mixture was stirred 15 min at RT, then cooled to 0° C. DIAD (1.5 eq) was added drop-wise and, the mixture was allowed to reach RT, and then was heated at 55° C. from 1 to 3 hrs. The mixture was concentrated and the crude material was purified by FC on silica gel and/or NH column (eluting mixture Cy/AcOEt) and/or C18 column (eluent from water+0.1% formic acid/ MeCN+0.1% formic acid) to afford the title compound.

General Procedure A1:

To a suspension of thiol intermediate (p141 or commercially available if not specified in the table; 1.3 eq) and oxalyl dichloride (1.6 eq) in DCM (~20 vol) was added drop wise a solution of 2-azabicyclo[3.1.1]heptane (p170, 1 eq) and triethylamine (2 eq) in DMF (~15 vol). Bubbling was observed. Reaction was stirred for 5 min at RT then heated at 85° C. and stirred from 5 to 12 hrs. Mixture was left to cool to RT, diluted with water and ss NaHCO₃(aq) and extracted with DCM. Solvent was evaporated under reduced pressure and the crude material was purified by FC on silica gel and/or NH column (eluting mixture Cy/AcOEt) and/or C18 column (eluent from water+0.1% formic acid/MeCN+ 0.1% formic acid) to afford the title compound.

General Procedure B1:

To a solution of 2-azabicyclo[3.1.1]heptane (e.g. p171, p175 or p177; 1 eq) in DMF (10-20 vol) the appropriate aryl halide (1-1.2 eq) and DIPEA (1.5 eq) were added. The reaction mixture was stirred at 90° C. O/N. The reaction mixture was cooled down to RT, diluted with water and extracted with AcOEt. The organic phase was washed with Brine, dried and concentrated under vacuum. The residue was purified by FC on silica gel and/or NH column (eluting mixture Cy/AcOEt) and/or C18 column (eluent from water+ 0.1% formic acid/MeCN+0.1% formic acid) to afford the title compound.

| Example | Starting materials | Gen. procedure | Yield (%) |
| --- | --- | --- | --- |
| 113 | p53 + P70 | Q | 49 |

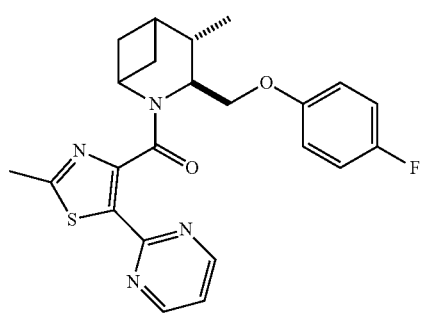

MS (m/z): 439.1 [MH]⁺
NMR (¹H, CDCl₃-d) δ: 8.57 (d, 2H), 6.85-7.18 (m, 5H), 4.59-4.73 (m, 1H), 4.39-4.46 (m, 1H), 4.25-4.33 (m, 1H), 3.98-4.05 (m, 1H), 2.77 (s, 4H), 2.31-2.40 (m, 1H), 2.16-2.26 (m, 1H), 1.96-2.05 (m, 1H), 1.84-1.94 (m, 1H), 1.65-1.75 (m, 1H), 1.22 (d, 3H)

Racemic mixture of trans-3-[(4-fluorophenoxy)methyl]-4-methyl-2-[2-methyl-5-(pyrimidin-2-yl)-1,3-thiazole-4-carbonyl]-2-azabicyclo[3.1.1]heptane

| Preparative chiral chromatography protocol: | Column | Chiralpak AD-H (25 × 0.46 cm), 5 u |
| --- | --- | --- |
| | Mobile phase | n-Hexane/Ethanol 60/40% v/v |
| | Flow rate (ml/min) | 17 ml/min |
| | DAD detection | 220 nm |
| | Loop | 1500 μl |
| | Injection | 23 mg (each injection) |

| Example | Starting materials | Gen. procedure | Yield (%) |
|---|---|---|---|
| 114 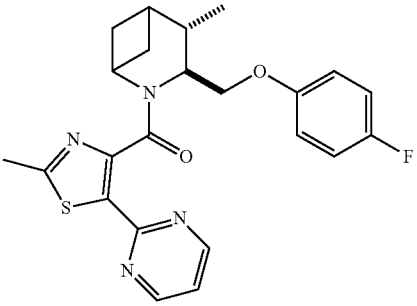 3S,4S or 3R,4R enantiomer | Enantiomer 1 | Rt: 7.1 min | 100% ee |

MS (m/z): 439.1 [MH]$^+$
(3S,4S) or (3R,4R)-3-[(4-fluorophenoxy)methyl]-4-methyl-2-[2-methyl-5-(pyrimidin-2-yl)-1,3-thiazole-4-carbonyl]-2-azabicyclo[3.1.1]heptane

| | | | |
|---|---|---|---|
| 115 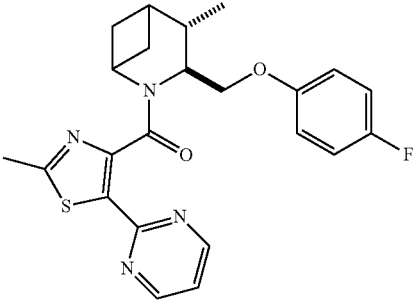 3R,4R or 3S,4S enantiomer | Enantiomer 2 | Rt: 10.4 min | 100% ee |

MS (m/z): 439.1 [MH]$^+$
(3R,4R) or (3S,4S)-3-[(4-fluorophenoxy)methyl]-4-methyl-2-[2-methyl-5-(pyrimidin-2-yl)-1,3-thiazole-4-carbonyl]-2-azabicyclo[3.1.1]heptane

| | | | |
|---|---|---|---|
| 116 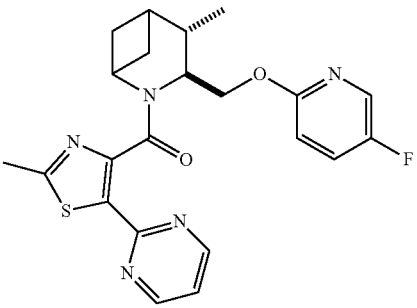 | P144 + P70 | Q | 6 |

MS (m/z): [MH]$^+$
NMR ($^1$H, CDCl$_3$-d) δ: 8.62-8.76 (m, 2H), 8.04 (d, 1H), 7.37 (ddd, 1H), 7.08-7.16 (m, 1H), 6.85 (dd, 1H), 4.88 (dd, 1H), 4.61 (dd, 1H), 4.44-4.51 (m, 1H), 4.02 (q, 1H), 2.70-2.81 (m, 3H), 2.60 (td, 1H), 2.35 (dd, 1H), 2.21 (td, 1H), 2.00 (d, 1H), 1.84-1.92 (m, 1H), 1.74 (d, 1H), 1.27 (d, 3H)

Racemic mixture of trans-3-{[(5-fluoropyridin-2-yl)oxy]methyl}-4-methyl-2-[2-methyl-5-(pyrimidin-2-yl)-1,3-thiazole-4-carbonyl]-2-azabicyclo[3.1.1]heptane

| | | | |
|---|---|---|---|
| 117 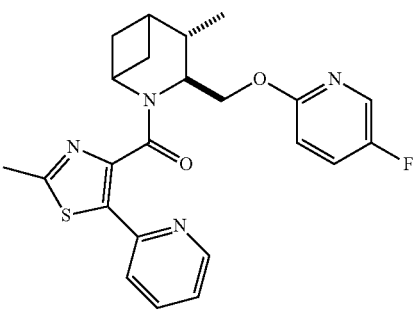 | P144 | Q | 52 |

MS (m/z): 439.4 [MH]$^+$
NMR ($^1$H, CDCl$_3$-d) δ: 8.51-8.60 (m, 1H), 8.04 (d, 1H), 7.65-7.68 (m, 1H), 7.42-7.50 (m, 1H), 7.34-7.42 (m, 1H), 7.12-7.18 (m, 1H), 6.78 (dd, 1H), 4.73-4.82 (m, 1H), 4.61-4.70 (m, 1H), 4.34-4.43 (m, 1H), 4.02-4.10 (m, 1H), 2.74 (s, 3H), 2.49-2.58 (m, 1H), 2.26-2.34 (m, 1H), 2.12-2.21 (m, 1H), 1.97-2.05 (m, 1H), 1.76-1.85 (m, 1H), 1.44-1.54 (m, 1H), 1.21 (d, 3H)

Racemic mixture of trans-3-{[(5-fluoropyridin-2-yl)oxy]methyl}-4-methyl-2-[2-methyl-5-(pyridin-2-yl)-1,3-thiazole-4-carbonyl]-2-azabicyclo[3.1.1]heptane

| Example | Starting materials | Gen. procedure | Yield (%) |
|---|---|---|---|
| 118 | P147 | S | 52 |

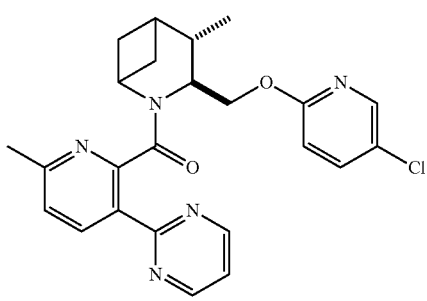

MS (m/z): 439.4 [MH]$^+$
NMR ($^1$H, CDCl$_3$-d) δ: 8.79 (d, 2H), 8.52-8.59 (m, 1H), 8.12-8.18 (m, 1H), 7.52-7.60 (m, 1H), 7.29-7.32 (m, 1H), 7.18-7.25 (m, 1H), 6.82-6.89 (m, 1H), 4.87-4.96 (m, 1H), 4.51-4.62 (m, 1H), 4.36-4.44 (m, 1H), 3.39-4.03 (m, 1H), 2.64 (s, 3H), 2.52-2.61 (s, 1H), 2.27-2.37 (m, 1H), 2.12-2.21 (m, 1H), 1.90-2.01 (m, 1H), 1.67-1.85 (m, 2H), 1.27 (d, 3H)

Racemic mixture of trans-3-{[(5-chloropyridin-2-yl)oxy]methyl}-4-methyl-2-[6-methyl-3-(pyrimidin-2-yl)pyridine-2-carbonyl]-2-azabicyclo[3.1.1]heptane

112

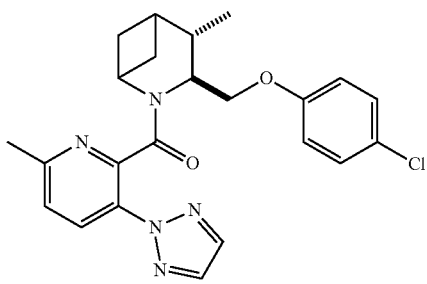

Racemic mixture of trans-3-[(4-chlorophenoxy)methyl]-4-methyl-2-[6-methyl-3-(2H-1,2,3-triazol-2-yl)pyridine-2-carbonyl]-2-azabicyclo[3.1.1]heptane

| Preparative chiral chromatography protocol: | Column | Chiralpak AD-H (25 × 2.0 cm), 5μ |
|---|---|---|
| | Mobile phase | n-Hexane/Ethanol 50/50% v/v |
| | Flow rate (ml/min) | 17 ml/min |
| | DAD detection | 220 nm |
| | Loop | 500 μl |
| | Injection | 7.5 mg (each injection) |
| 119 | Enantiomer 1 | Rt: 5.8 min    100% ee |

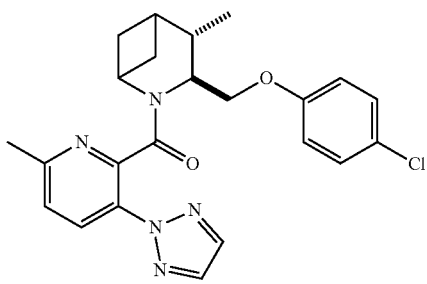

MS (m/z): 438.3 [MH]$^+$
(3S,4S) or (3R,4R)-3-[(4-chlorophenoxy)methyl]-4-methyl-2-[6-methyl-3-(2H-1,2,3-triazol-2-yl)pyridin-2-carbonyl]-2-azabicyclo[3.1.1]heptane 3S,4S or 3R,4R enantiomer -continued

| Example | | Starting materials | Gen. procedure | Yield (%) |
|---|---|---|---|---|
| 120 | 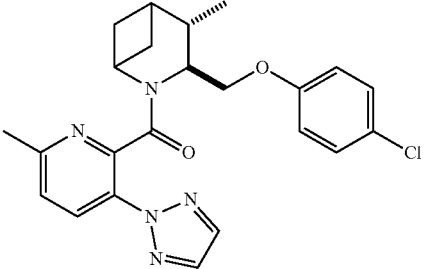 3R,4R or 3S,4S enantiomer | Enantiomer 2 | Rt: 6.8 min | 96.8% ee |
| | | MS (m/z): 438.3 [MH]+ (3R,4R) or (3S,4S)-3-[(4-chlorophenoxy)methyl]-4-methyl-2-[6-methyl-3-(2H-1,2,3-triazol-2-yl)pyridine-2-carbonyl]-2-azabicyclo[3.1.1]heptane | | |
| 121 | 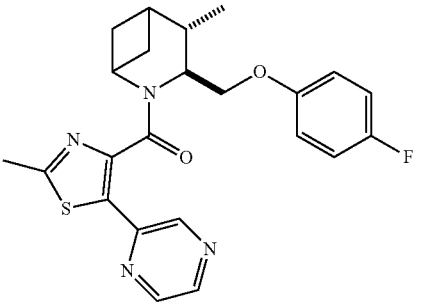 Racemic mixture of trans-3-[(4-fluorophenoxy)methyl]-4-methyl-2-[2-methyl-5-(pyrazin-2-yl)-1,3-thiazole-4-carbonyl]-2-azabicyclo[3.1.1]heptane | P53 + P109 | Q | 53 |
| | | MS (m/z): 439.4 [MH]+ NMR (1H, CDCl3-d) δ: 8.91 (d, 1H), 8.43-8.50 (m, 2H), 6.97-7.09 (m, 4H), 4.46-4.54 (m, 1H), 4.31-4.40 (m, 2H), 4.07-4.13 (m, 1H), 2.77 (s, 3H), 2.62-2.69 (m, 1H), 2.31-2.38 (m, 1H), 2.17-2.25 (m, 1H), 1.99-2.07 (m, 1H), 1.76-1.85 (m, 1H), 1.49-1.57 (m, 1H), 1.20 (d, 3H) | | |
| 122 | 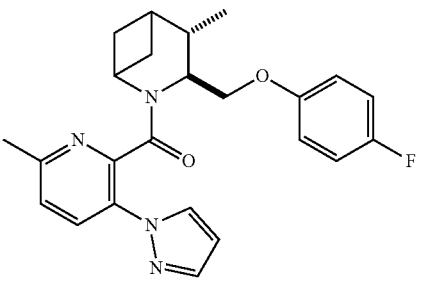 Racemic mixture of trans-3-[(4-fluorophenoxy)methyl]-4-methyl-2-[6-methyl-3-(1H-pyrazol-1-yl)pyridine-2-carbonyl]-2-azabicyclo[3.1.1]heptane | P53 + P93 | Q | 24 |
| | | MS (m/z): 421.5 [MH]+ NMR (1H, CDCl3-d) δ: 7.82-7.90 (m, 2H), 7.66-7.69 (m, 1H), 7.30-7.34 (m, 1H), 6.95-7.05 (m, 4H), 6.28-6.34 (m, 1H), 4.42-4.49 (m, 1H), 4.16-4.23 (m, 1H), 4.06-4.15 (m, 1H), 3.79-3.86 (m, 1H), 2.65 (s, 3H), 2.52-2.60 (m, 1H), 2.20-2.28 (m, 1H), 2.07-2.16 (m, 1H), 1.84-1.91 (m, 1H), 1.62-1.72 (m, 1H), 1.54-1.60 (m, 1H), 1.10 (d, 3H) | | |
| 123 | 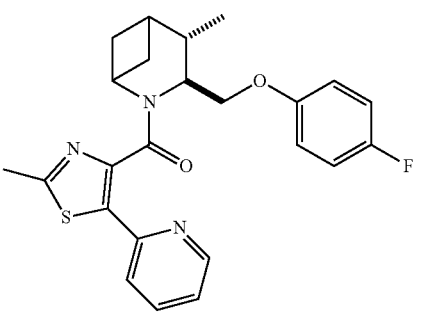 Racemic mixture of trans-3-[(4-fluorophenoxy)methyl]-4-methyl-2-[2-methyl-5-(pyridin-2-yl)-1,3-thiazole-4-carbonyl]-2-azabicyclo[3.1.1]heptane | P53 + P107 | Q | 60 |
| | | MS (m/z): 438.4 [MH]+ NMR (1H, CDCl3-d) δ: 8.50-8.56 (m, 1H), 7.55-7.61 (m, 1H), 7.29-7.33 (m, 1H), 7.08-7.14 (m, 1H), 6.95-7.07 (m, 4H), 4.48-4.58 (m, 1H), 4.29-4.42 (m, 2H), 4.04-4.12 (m, 1H), 2.74 (s, 3H), 2.60-2.70 (m, 1H), 2.26-2.35 (m, 1H), 2.14-2.21 (m, 1H), 1.98-2.08 (m, 1H), 1.84 (s, 1H), 1.45-1.54 (m, 1H), 1.13-1.22 (m, 3H) | | |

-continued

| Example | Starting materials | Gen. procedure | Yield (%) |
|---|---|---|---|
| Preparative chiral chromatography protocol: | Column<br>Mobile phase<br>Flow rate (ml/min)<br>DAD dettection<br>Loop<br>Injection | Chiralpak IC (25 × 2.0 cm), 5 u<br>n-Hexane/Ethanol 55/45% v/v<br>17 ml/min<br>22 nm<br>1000 μl<br>11 mg (each injection) | |
| 124 | Enantiomer 1 | Rt: 9.3 min | 100% ee |

MS (m/z): 438.4 [MH]+
(3S,4S) or (3R,4R)-3-[(4-fluorophenoxy)methyl]-4-methyl-2-[2-methyl-5-(pyridin-2-yl)-1,3-thiazole-4-carbonyl]-2-azabicyclo[3.1.1]heptane 3S,4S or 3R,4R enantiomer

| | | | |
|---|---|---|---|
| 125 | Enantiomer 2 | Rt: 14.9 min | 100% ee |

MS (m/z): 438.4 [MH]+.
(3R,4R) or (3S,4S)-3-[(4-fluorophenoxy)methyl]-4-methyl-2-[2-methyl-5-(pyridin-2-yl)-1,3-thiazole-4-carbonyl]-2-azabicyclo[3.1.1]heptane 3R,4R or 3S,4S enantiomer

| | | | |
|---|---|---|---|
| 126 | P53 + P111 | Q | 42 |

MS (m/z): 428.4 [MH]+
NMR (1H, CDCl$_3$-d) δ: 7.66 (s, 2H), 6.96-7.09 (m, 4H), 4.49-4.57 (m, 1H), 4.30-4.39 (m, 1H), 4.20-4.30 (m, 1H), 4.09-4.16 (m, 1H), 2.74 (s, 3H), 2.63-2.71 (m, 1H), 2.31-2.38 (m, 1H), 2.17-2.25 (m, 1H), 1.97-2.06 (m, 1H), 1.80-1.87 (m, 1H), 1.59-1.64 (m, 1H), 1.19 (d, 3H)

Racemic mixture of trans-3-[(4-fluorophenoxy)methyl]-4-methyl-2-[2-methyl-5-(2H-1,2,3-triazol-2-yl)-1,3-thiazole-4-carbonyl]-2-azabicyclo[3.1.1]heptane

| Example | Starting materials | Gen. procedure | Yield (%) |
|---|---|---|---|
| 127 | P53 + P95 | Q | 32 |

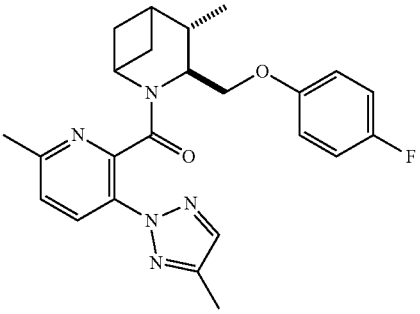

MS (m/z): 436.2 [MH]+
NMR (1H, CDCl3-d) δ: 8.15 (d, 1H), 7.48 (s, 1H), 7.24-7.32 (m, 1H), 6.95-7.12 (m, 4H), 4.68 (dd, 1H), 4.26-4.37 (m, 1H), 4.13-4.24 (m, 1H), 3.97 (q, 1H), 2.60-2.71 (m, 4H), 2.28-2.38 (m, 4H), 2.15-2.25 (m, 1H), 1.90-1.98 (m, 1H), 1.77-1.85 (m, 1H), 1.60-1.68 (m, 1H), 1.20 (d, 3H)

Racemic mixture of trans-3-[(4-fluorophenoxy)methyl]-4-methyl-2-[6-methyl-3-(4-methyl-2H-1,2,3-triazol-2-yl)pyridine-2-carbonyl]-2-azabicyclo[3.1.1]heptane

| 128 | P53 + P119 | Q | 91 |
|---|---|---|---|

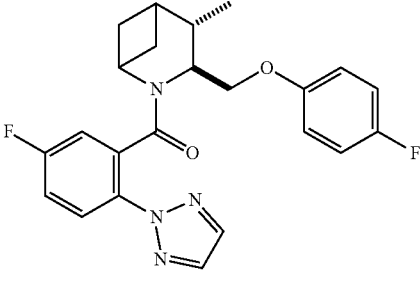

MS (m/z): 425.1 [MH]+
NMR (1H, CDCl3-d) δ: 7.83-8.01 (m, 1H), 7.81 (s, 1H), 7.56 (s, 1H), 6.90-7.27 (m, 6H), 4.44-4.55 (m, 1H), 4.25-4.35 (m, 1H), 4.10-4.20 (m, 1H), 3.88-4.09 (m, 1H), 2.59-2.68 (m, 1H), 2.18-2.36 (m, 2H), 2.02-2.12 (m, 1H), 1.84-1.93 (m, 1H), 1.33-1.56 (m, 2H), 1.17 (dd, 3H)

Racemic mixture of trans-2-[5-fluoro-2-(2H-1,2,3-triazol-2-yl)benzoyl]-3-{(4-fluorophenoxy)methyl]-4-methyl-2-azabicyclo[3.1.1]heptane

| 129 | P85 | S | 30 |
|---|---|---|---|

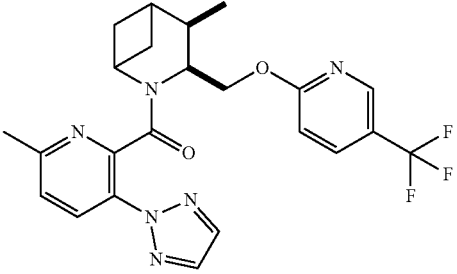

MS (m/z): 473.1 [MH]+
NMR (1H, CDCl3-d) δ: 8.37-8.51 (m, 1H), 8.14-8.24 (m, 1H), 7.68-7.87 (m, 3H), 7.19-7.33 (m, 1H), 6.49-6.94 (m, 1H), 4.95-5.11 (m, 1H), 4.81-4.93 (m, 1H), 4.61-4.79 (m, 1H), 3.94-4.25 (m, 1H), 2.68-2.83 (m, 1H,) 2.05-2.65 (m, 6H), 1.77-1.98 (m, 1H), 1.50-1.60 (m, 1H), 0.99-1.21 (m, 3H)

Racemic mixture of cis-4-methyl-2-[6-methyl-3-(2H-1,2,3-triazol-2-yl)pyridine-2-carbonyl]-3-({[5-(trifluoromethyl)pyridin-2-yl]oxy}methyl)-2-azabicyclo[3.1.1]heptane

| 130 | P149 + P67 | Q | 9 |
|---|---|---|---|

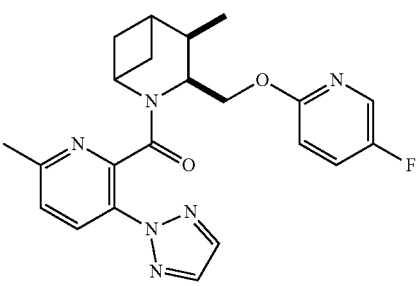

MS (m/z): 423.4 [MH]+
NMR (1H, CDCl3-d) δ: 0.99-1.22 (m, 3 H) 1.47-1.55 (m, 1 H) 1.80-2.00 (m, 1H) 2.04-2.64 (m, 4H) 2.20-2.26 (m, 1 H) 2.65-2.82 (m, 1 H) 3.93-4.20 (m, 1 H) 4.51-4.82 (m, 2 H) 4.93-5.08 (m, 1 H) 6.35-6.82 (m, 1 H) 7.16-7.38 (m, 2 H) 7.71-7.84 (m, 2 H) 7.93-8.04 (m, 1 H) 8.14-8.23 (m, 1 H)

Racemic mixture of cis-3-{[(5-fluoropyridin-2-yl)oxy]methyl}-4-methyl-2-[6-methyl-3-(2H-1,2,3-triazol-2-yl)pyridine-2-carbonyl]-2-azabicyclo[3.1.1]heptane -continued

| Example | Starting materials | Gen. procedure | Yield (%) |
|---|---|---|---|
| 131 | P149 + P99 | Q | 10 |

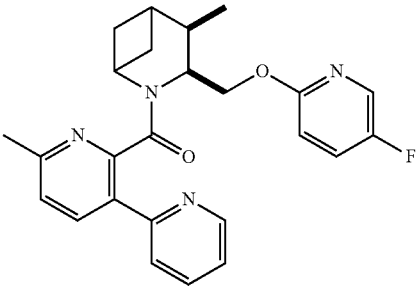

MS (m/z): 433.4 [MH]⁺
NMR (¹H, CDCl₃-d) δ: 0.92-1.15 (m, 3 H) 1.32-1.65 (m, 1 H) 1.67-1.84 (m, 1 H) 1.91-2.70 (m, 7 H) 3.80 (q, 1 H) 4.09-4.45 (m, 1 H) 4.50-4.72 (m, 1 H) 4.87-5.01 (m, 1 H) 6.37-6.78 (m, 1 H) 7.12-7.22 (m, 1 H) 7.23-7.38 (m, 2 H) 7.55-7.80 (m, 2 H) 7.85-8.06 (m, 2 H) 8.66 (d, 1 H)

Racemic mixture of cis-2'-(3-{[(-fluoropyridin-2-yl)oxy]methyl}-4-methyl-2-azabicyclo[3.1.1]heptane-2-carbonyl)-6'-methyl-2,3'-bipyridine

| 132 | P51 + P107 | Q | 71 |

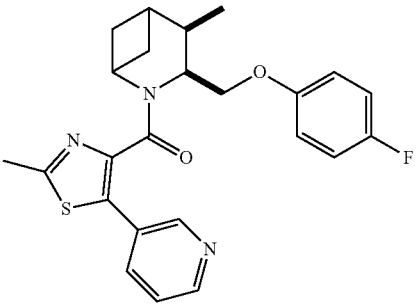

MS (m/z): 438.1 [MH]⁺
NMR (¹H, CDCl₃-d) δ: 0.99-1.40 (m, 4 H) 1.49-2.37 (m, 6 H) 2.39-2.83 (m, 4 H) 3.95-4.31 (m, 2 H) 4.56 (dd, 1 H) 4.99-5.18 (m, 1 H) 6.58-7.04 (m, 4 H) 7.05-7.18 (m, 1 H) 7.23 (td, 1 H) 7.55-7.67 (m, 1 H) 8.46-8.57 (m, 1 H)

Racemic mixture of cis-3-[(4-fluorophenoxy)methyl]-4-methyl-2-[2-methyl-5-(pyridin-2-yl)-1,3-thiazole-4-carbonyl]-2-azabicyclo[3.1.1]heptane

| 133 | P51 + P105 | V | 60 |

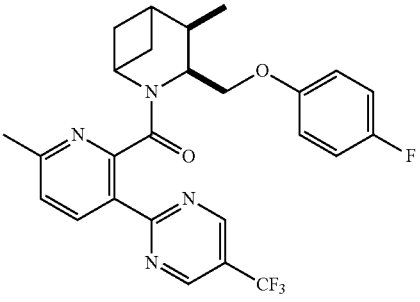

MS (m/z): 501.4 [MH]⁺
NMR (¹H, CDCl₃-d) δ: 1.03-1.34 (m, 3 H) 1.51-1.88 (m, 2H) 2.03-2.66 (m, 6 H) 2.68-2.90 (m, 1 H) 3.92-4.19 (m, 1 H) 4.25-4.42 (m, 1 H) 4.52-4.66 (m, 1 H) 4.93-5.09 (m, 1 H) 6.60-7.13 (m, 4 H) 7.17-7.35 (m, 1 H) 8.59 (d, 1 H) 8.71-9.05 (m, 2 H)

Racemic mixture of cis-3-[(4-fluorophenoxy)methyl]-4-methyl-2-{6-methyl-3-[5-(trifluoromethyl)pyrimidin-2-yl]pyridine-2-carbonyl}-2-azabicyclo[3.1.1]heptane

| 134 | P51 + P101 | V | 70 |

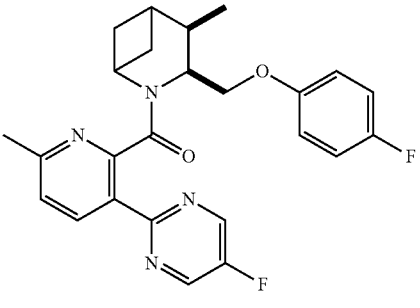

MS (m/z): 451.4 [MH]⁺
NMR (¹H, CDCl₃-d) δ: 0.97-1.33 (m, 3 H) 1.60-1.83 (m, 2 H) 2.02-2.10 (m, 1 H) 2.12-2.65 (m, 5 H) 2.67-2.87 (m, 1 H) 3.90-4.17 (m, 1 H) 4.23-4.43 (m, 1 H) 4.44-4.66 (m, 1 H) 4.90-5.06 (m, 1 H) 6.62-7.08 (m, 4 H) 7.15-7.30 (m, 1 H) 8.32-8.71 (m, 3 H)

Racemic mixture of cis-3-[(4-fluorophenoxy)methyl]-2-[3-(5-fluropyrimidin-2-yl)-6-methylpyridine-2-carbonyl]-4-methyl-2-azabicyclo[3.1.1]heptane -continued

| Example | Starting materials | Gen. procedure | Yield (%) |
|---|---|---|---|
| 135 | P51 + P94 | V | 26 |

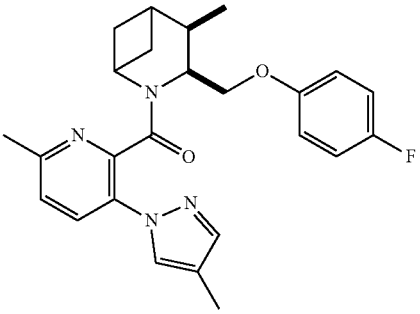

MS (m/z): 435.24 [MH]+
NMR (1H, DMSO-d6) δ: 7.90-7.97 (m, 1 H) 7.80-8.01 (m, 1 H) 7.48-7.58 (m, 1 H) 7.29-7.46 (m, 1 H) 6.73-7.18 (m, 4 H) 4.23-4.38 (m, 1 H) 4.01-4.33 (m, 1 H) 3.97-4.75 (m, 1 H) 3.73-4.66 (m, 1 H) 2.52-2.70 (m, 1 H) 1.96-2.57 (m, 3 H) 1.95-2.11 (m, 3 H) 1.91-2.30 (m, 4 H) 1.48-1.87 (m, 1 H) 0.91-1.14 (m, 3 H)

Racemic mixture of cis-3-[(4-fluorophenoxy)methyl]-4-methyl-2-[6-methyl-3-(4-methyl-1H-pyrazol-1-yl)pyridine-2-carbonyl]-2-azabicyclo[3.1.1]heptane

| 136 | P51 + P109 | V | 3 |
|---|---|---|---|

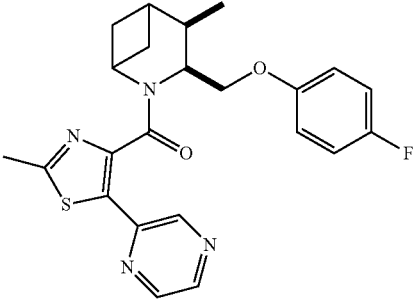

MS (m/z): [MH]+
NMR (1H, CDCl3-d) δ: 8.92 (s, 1H), 8.38-8.54 (m, 2H), 6.95-7.05 (m, 4H), 5.01-5.08 (m, 1H), 4.47 (dd, 1H), 4.31 (dd, 1H), 4.07 (q, 1H), 2.73-2.85 (m, 4H), 1.96-2.34 (m, 4H), 1.35 (t, 1H), 1.18-1.29 (m, 3H)

Racemic mixture of cis-3-[(4-fluorophenoxy)methyl]-4-methyl-2-[2-methyl-5-(pyrazin-2-yl)-1,3-thiazole-4-carbonyl]-2-azabicyclo[3.1.1]heptane

| 137 | P51 + P115 | V | 64 |
|---|---|---|---|

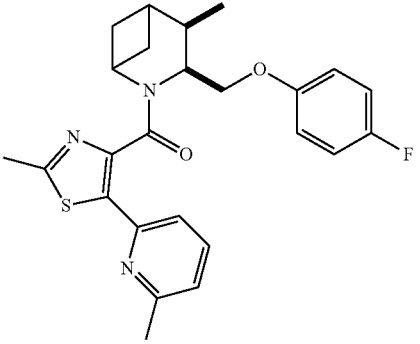

MS (m/z): 452.1 [MH]+
NMR (1H, CDCl3-d) δ: 1.21 (m, 4 H) 1.49-1.74 (m, 1 H) 2.00-2.24 (m, 3 H) 2.24-2.80 (m, 7 H) 3.99-4.57 (m, 3 H) 4.99-5.16 (m, 1 H) 6.56-7.05 (m, 5 H) 7.16 (t, 1 H) 7.37 (d, 1 H)

Racemic mixture of cis-3-[(4-fluorophenoxy)methyl]-4-methyl-2-[2-methyl-5-(6-methylpyridin-2-yl)-1,3-thiazole-4-carbonyl]-2-azabicyclo[3.1.1]heptane

| 138 | P51 + P103 | V | 18 |
|---|---|---|---|

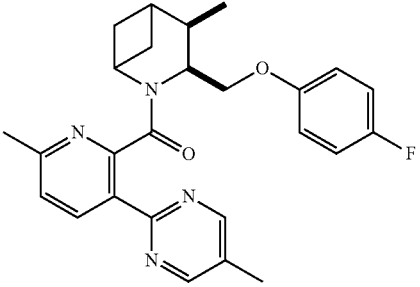

MS (m/z): 447.2 [MH]+
NMR (1H, CDCl3-d) δ: 1.02-1.30 (m, 3 H) 1.49-1.92 (m, 2 H) 2.01-2.85 (m, 10 H) 3.85-4.61 (m, 3 H) 4.92-5.06 (m, 1 H) 6.60-7.10 (m, 4 H) 7.14-7.34 (m, 1 H) 8.36-8.63 (m, 3 H)

| Example | Starting materials | Gen. procedure | Yield (%) |
|---|---|---|---|
| Racemic mixture of cis-3-[(4-fluorophenoxy)methyl]-4-methyl-2-[6-methyl-3-(5-methylpyrimidin-2-yl)pyridine-2-carbonyl]-2-azabicyclo[3.1.1]heptane | | | |
| 139 | P51 + P113 | V | 29 |

MS (m/z): 472.1 [MH]+
NMR ($^1$H, CDCl$_3$-d) δ: 1.00-1.45 (m, 4 H) 1.91 (t, 1 H) 2.04-2.79 (m, 7 H) 3.98-4.38 (m, 3 H) 4.96 (t, 1 H) 6.59-7.02 (m, 4 H) 7.84 (s, 1 H) 8.48 (d, 1 H) 8.56 (s, 1 H)

| | | | |
|---|---|---|---|
| Racemic mixture of cis-2-[5-(5-chloropyridin-3-yl)-2-methyl-1,3-thiazole-4-carbonyl]-3-[(4-fluorophenoxy)methyl]-4-methyl-2-azabicyclo[3.1.1]heptane | | | |
| 140 | P51 + P111 | V | 52 |

MS (m/z): 428.3 [MH]+
NMR ($^1$H, DMSO-d$_6$) δ: 8.10 (s, 2H), 7.10-7.18 (m, 2H), 7.00-7.08 (m, 3H), 4.74-4.84 (m, 1H), 4.29-4.39 (m, 1H), 4.05-4.17 (m, 1H), 3.93-4.02 (m, 1H), 2.62-2.74 (s, 4H), 2.04-2.31 (m, 3H), 1.83 (t, 1H), 1.29 (t, 1H), 1.14 (d, 3H)

| | | | |
|---|---|---|---|
| Racemic mixture of cis-3-[(4-flurophenoxy)methyl]-4-methyl-2-[2-methyl-5-(2H-1,2,3-triazol-2-yl)-1,3-thiazole-4-carbonyl]-2-azabicyclo[3.1.1]heptane | | | |
| 141 | P51 + P118 | V | 40 |

MS (m/z): 427.8 [MH]+
NMR ($^1$H, DMSO-d$_6$) δ: 7.93-7.98 (m, 1H), 7.71-7.75 (m, 1H), 7.09-7.18 (m, 2H), 6.97-7.07 (m, 2H), 6.36-6.44 (m, 1H), 4.77-4.86 (m, 1H), 4.31-4.41 (m, 1H), 4.01-4.10 (m, 2H), 2.68-2.74 (m, 1H), 2.64 (s, 3H), 2.07-2.25 (m, 3H), 1.85-1.93 (m, 1H), 1.18-1.25 (m, 1H), 1.11 (d, 3H).

| | | | |
|---|---|---|---|
| Racemic mixture of cis-3-[(4-fluorophenoxy)methyl]-4-methyl-2-[2-methyl-5-(1H-pyrazol-1-yl)-1,3-thiazole-4-carbonyl]-2-azabicyclo[3.1.1]heptane | | | |
| 142 | P51 + P124 | V | 65 |

MS (m/z): 432.1 [MH]+
NMR ($^1$H, CDCl$_3$-d) δ: 8.17-8.23 (m, 1H), 7.88 (s, 1H), 7.76-7.82 (m, 1H), 7.45-7.65 (m, 2H), 6.94-7.07 (m, 4H), 4.93-5.02 (m ,1H), 4.48-4.61 (m, 1H), 4.19-4.39 (m, 1H), 3.87-4.02 (m, 1H), 2.74-2.88 (m, 1H), 1.99-2.38 (m, 4H), 1.48-1.56 (m, 1H), 1.27 (d, 3H)

-continued

| Example | Starting materials | Gen. procedure | Yield (%) |
|---|---|---|---|
| Racemic mixture of cis-3-{3-[(4-fluorophenoxy)methyl]-4-methyl-2-azabicyclo[3.1.1]heptane-2-carbonyl}-4-(2H-1,2,3-triazol-2-yl)benzonitrile | | | |
| 143 | P51 + P117 | V | 33 |

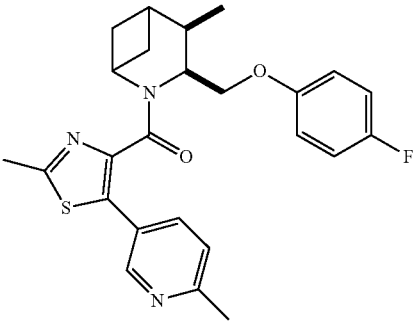

MS (m/z): 452.2 [MH]$^+$
NMR ($^1$H, CDCl$_3$-d) δ: 8.54 (s, 1H), 7.68 (dd, 1H), 6.82-7.05 (m, 5H), 4.96 (t, 1H), 4.36-4.45 (m, 1H), 4.17 (d, 1H), 4.05 (q, 1H), 2.65-2.84 (m, 4H), 2.45-2.61 (m, 4H), 2.12-2.25 (m, 2H), 2.02-2.10 (m, 1H), 1.92-2.00 (m, 1H), 1.19 (d, 3H)

Racemic mixture of cis-3-[(4-fluorophenoxy)methyl]-4-methyl-2-[2-methyl-5-(6-methylpyridin-3-yl)-1,3-thiazole-4-carbonyl]-2-azabicylco[3.1.1]heptane
144    P51 + P95    Q    51

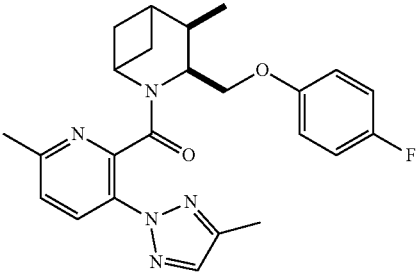

MS (m/z): 436.3 [MH]$^+$
NMR ($^1$H, CDCl$_3$-d) δ: 8.11-8.20 (m, 1H), 7.39-7.59 (m, 1H), 7.13-7.28 (m, 1H), 6.89-7.06 (m, 3H), 6.63-6.70 (m, 1H), 4.95-5.04 (m, 1H), 3.91-4.55 (m, 3H), 2.69-2.83 (m, 1H), 1.96-2.62 (m, 9H), 1.67-1.95 (m, 1H), 1.47-1.58 (m, 1H), 1.02-1.30 (m, 3H)

Racemic mixture of cis-3-[(4-fluorophenoxy)methyl]-4-methyl-2-[6-methyl-3-(4-methyl-2H-1,2,3-triazol-2-yl)pyridine-2-carbonyl]-2-azabicyclo[3.1.1]heptane
145    P51 + P127    Q    39

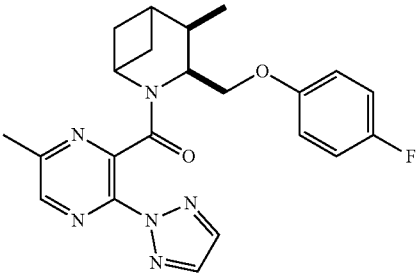

MS (m/z): 423.2 [MH]$^+$
NMR ($^1$H, MeOD-d$_4$) δ: 8.47-8.61 (m, 1H), 7.92-8.14 (m, 2H), 6.69-7.14 (m, 4H), 4.91 (ddd, 1H), 4.02-4.53 (m, 3H), 2.75-2.91 (m, 1H), 2.05-2.73 (m, 7H), 1.57-1.94 (m, 1H), 1.06-1.35 (m, 3H)

Racemic mixture of cis-3-[(4-fluorophenoxy)methyl]-4-methyl-2-[6-methyl-3-(2H-1,2,3-triazol-2-yl)pyrazine-2-carbonyl]-2-azabicyclo[3.1.1]heptane
146    P51 + P96    Q    15

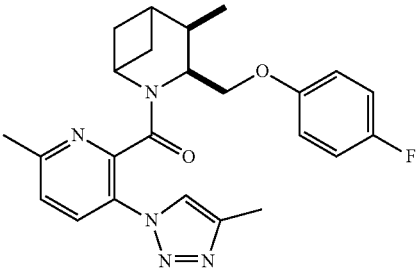

MS (m/z): 436.1 [MH]$^+$
NMR ($^1$H, CDCl$_3$-d) δ: 7.74-7.90 (m, 2H), 7.21-7.39 (m, 1H), 6.65-7.05 (m, 4H), 4.84-4.93 (m, 1H), 3.81-4.37 (m, 3H), 2.54-2.73 (m, 4H), 2.03-2.46 (m, 7H), 1.62-1.94 (m, 1H), 1.00-1.21 (m, 3H)

| Example | Starting materials | Gen. procedure | Yield (%) |
|---|---|---|---|

Racemic mixture of cis-3-[(4-fluorophenoxy)methyl]-4-methyl-2-[6-methyl-3-(4-methyl-1H-1,2,3-triazol-1-yl)pyridine-2-carbonyl]-2-azabicyclo[3.1.1]heptane

| 147 | P157 | T | 17 |

MS (m/z): 478.2 [MH]+
NMR (¹H, CDCl₃-d) δ: 8.23-8.29 (m, 1H), 7.85 (s, 2H), 7.45-7.52 (m, 1H), 7.32-7.37 (m, 1H), 7.25-7.31 (m, 1H), 7.19-7.25 (m, 1H), 6.98-7.06 (m, 1H), 3.84-4.32 (m, 4H), 2.65 (s, 3H), 2.27-2.38 (m, 2H), 2.14-2.25 (m, 1H), 1.94-2.04 (m, 1H), 1.69-1.76 (m, 2H), 1.27 (d, 3H)

| 148 | P157 | T | 15 |

MS (m/z): 438.2 [MH]+
NMR (¹H, CDCl₃-d) δ: 8.22 (d, 1H), 8.04 (d, 1H), 7.78 (s, 2H), 7.30-7.40 (m, 2H), 6.64 (d, 1H), 5.98 (br. s., 1H), 4.19-4.27 (m, 1H), 3.96-4.03 (m, 1H), 3.85-3.95 (m, 1H), 3.70-3.81 (m, 1H), 2.65 (s, 3H), 2.27-2.39 (m, 2H), 2.18 (dt, 1H), 1.88-1.96 (m, 1H), 1.68-1.79 (m, 1H), 1.6-1.67 (m, 1H), 1.21 (d, 3H)

Racemic mixture of trans-5-chloro-N-({4-methyl-2-[6-methyl-3-(2H-1,2,3-triazol-2-yl)pyridine-2-carbonyl]-2-azabicyclo[3.1.1]heptan-3-yl}methyl)pyridin-2-amine

| 149 | P157 | T | 19 |

MS (m/z): 455.3 [MH]+
NMR (¹H, CDCl₃-d) δ: 9.00 (s, 1H), 8.26 (d, 1H), 7.99 (s, 2H), 7.60-7.71 (m, 3), 7.32 (d, 1H), 7.21-7.26 (m, 1H), 6.52 (br. s., 1H), 4.33-4.45 (m, 1H), 4.12-4.27 (m, 2H), 4.04 (q, 1H), 2.64 (s, 3H), 2.45 (br. s., 1H), 2.08-2.26 (m, 2H), 1.96-2.03 (m, 1H), 1.72-1.78 (m, 2H), 1.22-1.27 (d, 3H)

Racemic mixture of trans-N-({4-methyl-2-[6-methyl-3-(2H-,2,3-triazol-2-yl)pyridine-2-carbonyl]-2-azabicyclo[3.1.1]heptan-3-yl}methyl)quinazolin-2-amine

| 150 | P157 | T | 12 |

MS (m/z): 460.2 [MH]+
NMR (¹H, CDCl₃-d) δ: 8.26 (d, 1H), 7.86 (s, 2H), 7.58 (d, 2H), 7.30-7.36 (m, 2H), 7.19 (br. s., 1H), 7.05-7.12 (m, 1H), 4.19-4.31 (m, 2H), 4.04 (q, 1H), 3.86-3.95 (m, 1H), 2.65 (s, 3H), 2.27-2.39 (m, 2H), 2.15-2.22 (m, 1H), 1.99 (br. s., 1H), 1.70-1.76 (m, 2H), 1.27 (d, 3H)

Racemic mixture of trans-N-({4-methyl-2-[6-methyl-3-(2H-1,2,3-triazol-2-yl)pyridine-2-carbonyl]-2-azabicyclo[3.1.1]heptan-3-yl}methyl)-1,3-benzothiazol-2-amine

| Example | Starting materials | Gen. procedure | Yield (%) |
|---|---|---|---|
| 151 | P170 | W | 11 |

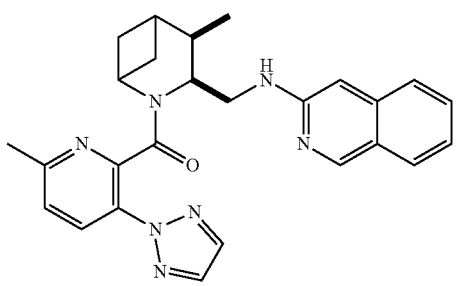

MS (m/z): 454.6 [MH]⁺
NMR (¹H, CDCl₃-d) δ: 8.70-8.91 (m, 1H), 8.02-8.26 (m, 1H), 7.68-7.89 (m, 3H), 7.41-7.58 (m, 2H), 7.31 (d, 1H), 7.18 (t, 1H), 6.75 (s, 1H), 5.89 (br. s., 1H), 4.93-5.15 (m, 1H), 3.72-4.08 (m, 3H), 2.80 (quin, 1H), 2.44-2.65 (m, 3H), 1.87-2.43 (m, 5H), 1.16-1.32 (m, 3H)

Racemic mixture of cis-N-({4-methyl-2-[6-methyl-3-(2H-1,2,3-triazol-2-yl)pyridine-2-carbonyl]-2-azabicyclo[3.1.1]heptan-3-yl}methyl)isoquinolin-3-amine

| | | | |
|---|---|---|---|
| 152 | P170 | T | 38 |

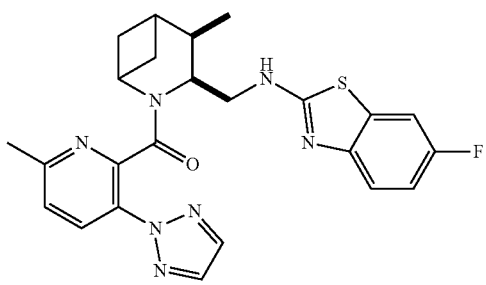

MS (m/z): 478.4 [MH]⁺
NMR (¹H, CDCl₃-d) δ: 8.08-8.31 (m, 1 H), 7.63-7.90 (m, 2 H), 7.37-7.57 (m, 1 H), 7.14-7.35 (m, 2 H), 6.91-7.06 (m, 1 H), 4.42-5.23 (m, 1 H), 4.00-4.24 (m, 1 H), 3.99 (d, 1 H), 3.60-3.94 (m, 1 H), 2.73-2.97 (m, 1 H), 2.57-2.69 (m, 3 H), 2.22-2.38 (m, 1 H), 1.96-2.32 (m, 2 H), 1.51-2.45 (m, 2 H), 1.06-1.34 (m, 3 H)

Racemic mixture of cis-6-fluoro-N-({4-methyl-2-[6-methyl-3-(2H-1,2,3-triazol-2-yl)pyridine-2-carbonyl]-2-azabicyclo[3.1.1]heptan-3-yl}methyl)-1,3-benzothiazol-2-amine The racemic mixture was separated into the single enantiomers by preparative chiral HPLC

| Preparative chiral chromatography protocol: | Column | Chiralpak AD-H (25 × 0.46 cm), 5 u |
|---|---|---|
| | Mobile phase | n-Hexane/Ethanol 40/60% v/v |
| | Flow rate (ml/min) | 17 ml/min |
| | DAD detection | 220 nm |
| | Loop | 1000 µl |
| | Injection | 13 mg (each injection) |
| 153 | Enantiomer 1 | Rt: 8.7 min          100% ee |

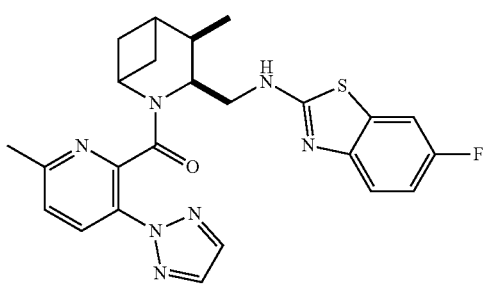

MS (m/z): 478.4 [MH]⁺
6-fluoro-N-{[(3S,4R) or (3R,4S)-4-methyl-2-[6-methyl-3-(2H-1,2,3-triazol-2-yl)pyridine-2-carbonyl]-2-azabicyclo[3.1.1]heptan-3-yl]methyl}-1,3-benzothiazol-2-amine 3S,4R or 3R,4S enantiomer -continued

| Example | Starting materials | Gen. procedure | Yield (%) |
|---|---|---|---|
| 154 | Enantiomer 2 | Rt: 12.7 min | 100% ee |

MS (m/z): 478.4 [MH]⁺
6-fluoro-N-{[(3R,4S) or (3S,4R)-4-methyl-2-[6-methyl-3-(2H-1,2,3-triazol-2-yl)pyridine-2-carbonyl]-2-azabicyclo[3.1.1]heptan-3-yl]methyl}-1,3-benzothiazol-2-amine

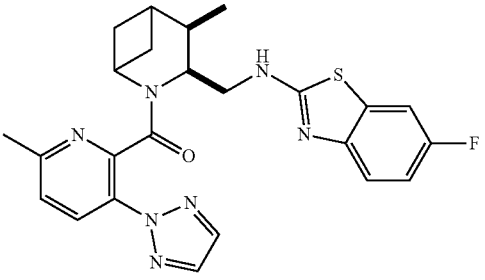

3R,4S or 3S,4R enantiomer

| | | | |
|---|---|---|---|
| 155 | | P170 | T | 34 |

MS (m/z): 455.5 [MH]⁺
NMR (¹H, CDCl₃-d) δ: 8.80-9.03 (m, 1H), 8.02-8.26 (m, 1H), 7.78-7.92 (m, 2H), 7.47-7.73 (m, 3H), 7.30 (d, 1H), 7.18-7.24 (m, 1H), 6.78 (br.s., 1H), 4.89-5.14 (m, 1H), 4.26-4.54 (m, 1H), 3.80-4.20 (m, 2H), 2.74-2.88 (m, 1H), 2.59 (s, 3H), 2.03-2.44 (m, 4H), 1.67-1.94 (m, 1H), 1.18-1.32 (m, 3H)

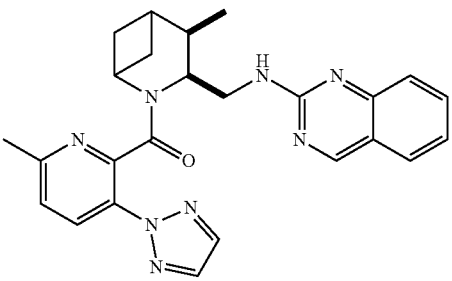

Racemic mixture of cis-N-({4-methyl-2-[6-methyl-3-(2H-1,2,3-triazol-2-yl)pyridin-2-carbonyl]-2-azabicyclo[3.1.1]heptan-3-yl}methyl)quinazolin-2-amine

| | | | |
|---|---|---|---|
| 156 | | P170 | T | 9 |

MS (m/z): 438.4 [MH]⁺
NMR (¹H, CDCl₃-d) δ: 8.23 (d, 1H), 8.06 (d, 1H), 7.65 (s, 2H), 7.28-7.35 (m, 2H), 6.38-6.48 (m, 1H), 6.30 (br. s., 1H), 5.03 (td, 1H), 3.93-4.06 (m, 2H), 3.70 (ddd, 1H), 2.71-2.84 (m, 1H), 2.63 (s, 3H), 1.97-2.31 (m, 4H), 1.53-1.61 (m, 1H), 1.09-1.25 (m, 3H)

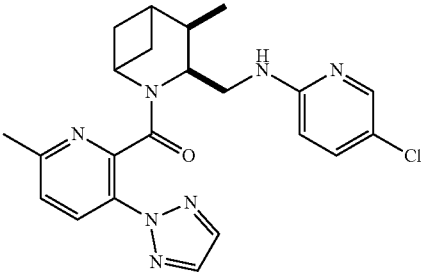

Racemic mixture of cis-5-chloro-N-({4-methyl-2-[6-methyl-3-(2H-1,2,3-triazol-2-yl)pyridine-2-carbonyl]-2-azabicyclo[3.1.1]heptan-3-yl}methyl)pyridin-2-amine

| | | | |
|---|---|---|---|
| 157 | | P170 | T | 64 |

MS (m/z): 478.3 [MH]⁺
NMR (¹H, CDCl₃-d) δ: 8.15-8.30 (m, 1H), 7.65-7.93 (m, 2H), 7.29-7.48 (m, 4H), 6.74-6.87 (m, 1H), 5.01-5.16 (m, 1H), 3.80-4.23 (m, 3H), 2.75-2.91 (m, 1H), 2.62 (s, 3H), 1.90-2.33 (m, 4H), 1.67-1.76 (m, 1H), 1.15-1.29 (m, 3H)

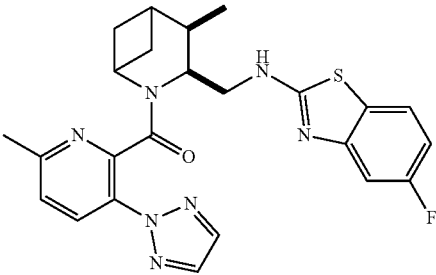

Racemic mixture of cis-5-fluoro-N-({4-methyl-2-[6-methyl-3-(2H-1,2,3-triazol-2-yl)pyridine-2-carbonyl]-2-azabicyclo[3.1.1]heptan-3-yl}methyl)-1,3-benzothiazol-2-amine

| Example | Starting materials | Gen. procedure | Yield (%) |
|---|---|---|---|
| 158 | P170 | T | 69 |

MS (m/z): 455.2 [MH]+
NMR ($^1$H, CDCl$_3$-d) δ: 8.18-8.28 (m, 1H), 8.02-8.09 (m, 1H), 7.85-7.93 (m, 1H), 7.68-7.78 (m, 1H), 7.49-7.64 (m, 3H), 7.31-7.42 (m, 2H), 7.22 (br.s., 1H), 5.09-5.23 (m, 1H), 3.85-4.24 (m, 3H), 2.77-2.91 (m, 1H), 2.61 (s, 3H), 2.05-2.35 (m, 4H), 1.64-1.75 (m, 1H), 1.22-1.33 (m, 3H)

Racemic mixture of cis-N-({4-methyl-2-[6-methyl-3-(2H-1,2,3-triazol-2-yl)pyridine-2-carbonyl]-2-azabicyclo[3.1.1]heptan-3-yl}methyl)quinoxalin-2-amine
The racemic mixture was separated into the single enantiomers by preparative chiral HPLC

| Preparative chiral chromatography protocol: | Column | Chiralpak AD-H (25 × 2.0 cm), 5μ |
|---|---|---|
| | Mobile phase | n-Hexane/(Ethanol + 0.1% IPA) 50/50% v/v |
| | Flow rate (ml/min) | 17 ml/min |
| | DAD detection | 220 nm |
| | Loop | 1000 μl |
| | Injection | 9.35 mg (each injection) |
| 159 | Enantiomer 1 | Rt: 10.4 min    97.8% ee |

MS (m/z): 455.2 [MH]+
N-{[(3S,4R) or (3R,4S)-4-methyl-2-[6-methyl-3-(2H-1,2,3-triazol-2-yl)pyridine-2-carbonyl]-2-azabicyclo[3.1.1]heptan-3-yl]methyl}quinoxalin-2-amine 3S,4R or 3R,4S enantiomer

| 160 | Enantiomer 2 | Rt: 12.9 min    100% ee |
|---|---|---|

MS (m/z): 455.2 [MH]+
N-{[(3R,4S) or (3S,4R)-4-methyl-2-[6-methyl-3-(2H-1,2,3-triazol-2-yl)pyridine-2-carbonyl]-2-azabicyclo[3.1.1]heptan-3-yl]methyl}quinoxalin-2-amine 3R,4S or 3S,4R enantiomer

| 161 | P170 | W | 16 |

MS (m/z): 454.2 [MH]+
NMR ($^1$H, CDCl$_3$-d) δ: 8.22 (d, 1H), 7.47-7.93 (m, 6H), 7.32 (d, 1H), 7.20 (t, 1H), 6.55-6.73 (m, 2H), 5.06-5.17 (m, 1H), 4.21-4.35 (m, 1H), 3.82-4.02 (m, 2H), 2.72-2.89 (m, 1H), 2.62 (s, 3H), 1.99-2.33 (m, 4H), 161-1.68 (m, 1H), 1.18-1.34 (m, 3H)

| Example | Starting materials | Gen. procedure | Yield (%) |
|---|---|---|---|
| Racemic mixture of cis-N-({4-methyl-2-[6-methyl-3-(2H-1,2,3-triazol-2-yl)pyridine-2-carbonyl]-2-azabicyclo[3.1.1]heptan-3-yl}methyl)quinolin-2-amine | | | |
| 162 | P172 | T | 14 |

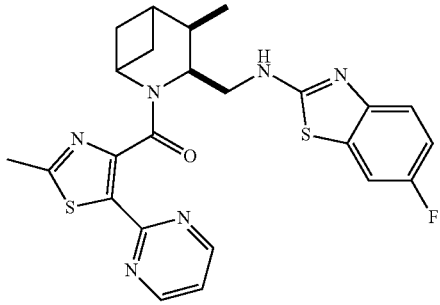

MS (m/z): 495.1 [MH]$^+$
NMR ($^1$H, CDCl$_3$-D) δ: 8.56-8.79 (m, 2H), 7.46-7.52 (m, 1H), 7.38-7.44 (m, 1H), 7.17-7.27 (m, 1H), 6.94-7.09 (m, 2H), 5.01-5.25 (m, 1H), 3.82-4.31 (m, 3H), 2.71-2.83 (m, 4H), 1.95-2.33 (m, 4H), 1.61-1.67 (m, 1H), 1.10-1.32 (m, 4H)

Racemic mixture of cis-6-fluoro-N-({4-methyl-2-[2-methyl-5-(pyrimidin-2-yl)-1,3-thiazole-4-carbonyl]-2-azabicyclo[3.1.1]heptan-3-yl}methyl)-1,3-benzothiazol-2-amine
The racemic mixture was separated into the single enantiomers by preparative chiral HPLC

| Preparative chiral chromatography protocol: | Column | Chiralpak AS-H (25 × 2.0 cm), 5µ |
|---|---|---|
| | Modifier | Ethanol 20% |
| | Flow rate (ml/min) | 45 ml/min |
| | Pressure (bar) | 120 |
| | Temperature (° C.) | 38 |
| | UV detection | 220 nm |
| | Loop | 900 µl |
| | Injection | 6 mg (each injection) |
| 163 | Enantiomer 1 | Rt: 5.4 min 100% ee |

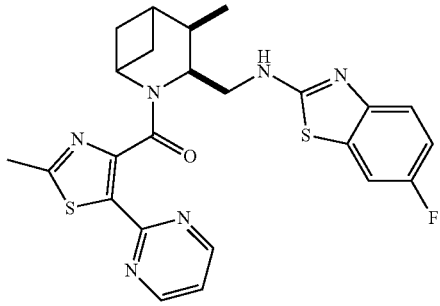

MS (m/z): 495.1 [MH]$^+$
6-fluoro-N-({(3S,4R) or (3R,4S)4-methyl-2-[2-methyl-5-(pyrimidin-2-yl)-1,3-thiazole-4-carbonyl]-2-azabicyclo[3.1.1]heptan-3-yl}methyl)-1,3-benzothiazol-2-amine 3S,4R or 3R,4S enantiomer

| 164 | Enantiomer 2 | Rt: 7.5 min 98.2% ee |

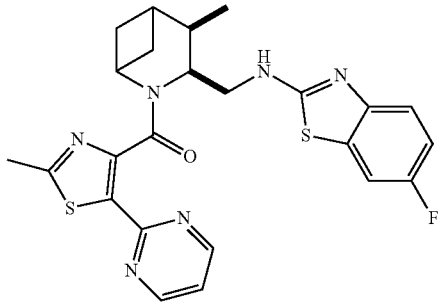

MS (m/z): 495.1 [MH]$^+$
6-fluoro-N-({(3R,4S) or (3S,4R)4-methyl-2-[2-methyl-5-(pyrimidin-2-yl)-1,3-thiazole-4-carbonyl]-2-azabicyclo[3.1.1]heptan-3-yl}methyl)-1,3-benzothiazol-2-amine 3R,4S or 3S,4R enantiomer

| Example | Starting materials | Gen. procedure | Yield (%) |
|---|---|---|---|
| 165 | P170 | T | 63 |

MS (m/z): 473.4 [MH]+
NMR (¹H, CDCl₃-d) δ: 8.31-83.8 (m, 1H), 8.25 (d, 1H), 7.76-7.91 (m, 1H), 7.64 (s, 2H), 73.1-7.42 (m, 2H), 5.07-5.18 (m, 1H), 3.98-4.11 (m, 2H), 3.77-3.8 7(m, 1H), 2.76-2.88 (m, 1H), 2.62 (s, 3H), 2.25-2.33 (m, 1H), 2.08-2.22 (m, 2H), 1.98-2.06 (m, 1H), 1.63-1.72 (m, 1H), 1.24 (d, 3H)

Racemic mixture of cis-N-({4-methyl-2-[6-methyl-3-(2H-1,2,3-triazol-2-yl)pyridine-2-carbonyl]-2-azabicyclo[3.1.1]heptan-3-yl}methyl)-5-(trifluoromethyl)pyrazin-2-amine
The racemic mixture was separated into the single enantiomers by preparative chiral HPLC

| Preparative chiral chromatography protocol: | Column | Chiralpak AD-H (25 × 2.0 cm), 5μ |
|---|---|---|
| | Mobile phase | n-Hexane (Ethanol/Methanol 1/1 + 0.1 ipa) 65/35% v/v |
| | Flow rate (ml/min) | 17 ml/min |
| | DAD detection | 220 nm |
| | Loop | 600 μl |
| | Injection | 9.9 mg (each injection) |
| 166 | Enantiomer 1 | Rt: 6.2 min | 90% ee |

MS (m/z): 473.4 [MH]+
N-{[(3S,4R) or (3R,4S)-4-methyl-2-[6-methyl-3-(2H-1,2,3-triazol-2-yl)pyridine-2-carbonyl]-2-azabicyclo[3.1.1]heptan-3-yl]methyl}-5-(trifluoromethyl)pyrazin-2-amine 3S,4R or 3R,4S enantiomer

| 167 | Enantiomer 2 | Rt: 8.6 min | 100% ee |

MS (m/z): 473.4 [MH]+
N-{[(3R,4S) or (3S,4R)-4-methyl-2-[6-methyl-3-(2H-1,2,3-triazol-2-yl)pyridine-2-carbonyl]-2-azabicyclo[3.1.1]heptan-3-yl]methyl}-5-(trifluoromethyl)pyrazin-2-amine 3R,4S or 3S,4R enantiomer

| 168 | P171 | T | 27 |

MS (m/z): 481.2 [MH]+
NMR (¹H, CDCl₃-d) δ: 7.94-8.04 (m, 1H), 7.62-7.87 (m, 2H), 7.45-7.58 (m, 2H), 7.27-7.37 (m, 2H), 6.67-7.15 (m, 2H), 5.02-5.15 (m, 1H), 3.74-4.27 (m, 3H), 2.59-2.84 (m, 1H), 2.30 (s, 4H), 1.45-1.55 (m, 1H), 1.17-1.31 (m, 3H)

| Example | Starting materials | Gen. procedure | Yield (%) |
|---|---|---|---|

Racemic mixture of cis-6-fluoro-N-({2-[5-fluoro-2-(2H-1,2,3-triazol-2-yl)benzoyl]-4-methyl-2-azabicyclo[3.1.1]heptan-3-yl}methyl)-1,3-benzothiazol-2-amine
The racemic mixture was separated into the single enantiomers by preparative chiral HPLC

| | | | |
|---|---|---|---|
| Preparative chiral chromatography protocol: | | Column | Chiralpak AD-H (25 × 2.0 cm), 5µ |
| | | Mobile phase | n-Hexane/Ethanol 20/80% v/v |
| | | Flow rate (ml/min) | 17 ml/min |
| | | DAD detection | 220 nm |
| | | Loop | 750 µl |
| | | Injection | 12 mg (each injection) |
| 169 | | Enantiomer 1 | Rt: 8.0 min 100% ee |

MS (m/z): 481.2 [MH]⁺
6-fluoro-N-({(3S,4R) or (3R,4S)2-[5-fluoro-2-(2H-1,2,3-triazol-2-yl)benzoyl]-4-methyl-2-azabicyclo[3.1.1]heptan-3-yl}methyl)-1,3-benzothiazol-2-amine 3S,4R or 3R,4S enantiomer

| 170 | | Enantiomer 2 | Rt: 15.7 min 100% ee |

MS (m/z): 481.2 [MH]⁺
6-fluoro-N-({(3R,4S) or (3S,4R)2-[5-fluoro-2-(2H-1,2,3-triazol-2-yl)benzoyl]-4-methyl-2-azabicyclo[3.1.1]heptan-3-yl}methyl)-1,3-benzothiazol-2-amine 3R,4S or 3S,4R enantiomer

| 171 | | P173 | T | 24 |

MS (m/z): 497.1 [MH]⁺
NMR (¹H, CDCl₃-d) δ: 7.94-8.06 (m, 1H), 7.58-7.85 (m, 2H), 7.45-7.57 (m, 2H), 7.14-7.35 (m, 2H), 6.79-7.14 (m, 2H), 5.01-5.15 (m, 1H), 3.76-4.27 (m, 3H), 2.59-2.86 (m, 1H), 1.85-2.36 (m, 4H), 1.47-1.55 (m, 1H), 1.20-1.29 (m, 3H)

Racemic mixture of cis-N-({2-[5-chloro-2-(2H-1,2,3-triazol-2-yl)benzoyl]-4-methyl-2-azabicyclo[3.1.1]heptan-3-yl}methyl)-6-fluoro-1,3-benzothiazol-2-amine
The racemic mixture was separated into the single enantiomers by preparative chiral HPLC

| | | | |
|---|---|---|---|
| Preparative chiral chromatography protocol: | | Column | Chiralpak AD-H (25 × 2.0 cm), 5µ |
| | | Mobile phase | n-Hexan/Ethanol 35/65% v/v |
| | | Flow rate (ml/min) | 17 ml/min |
| | | DAD detection | 220 nm |
| | | Loop | 1500 µl |
| | | Injection | 18.5 mg (each injection) |

| Example | Starting materials | Gen. procedure | Yield (%) |
|---|---|---|---|
| 172 | Enantiomer 1 | Rt: 11.5 min | 100% ee |

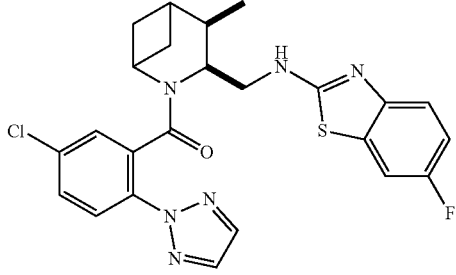

3S,4R or 3R,4S enantiomer

MS (m/z): 497.1 [MH]+
N-({(3S,4R) or (3R,4S)2-[5-chloro-2-(2H-1,2,3-triazol-2-yl)benzoyl]-4-methyl-2-azabicyclo[3.1.1]heptan-3-yl}methyl)-6-fluoro-1,3-benzothiazol-2-amine

| 173 | Enantiomer 2 | Rt: 18.0 min | 100% ee |
|---|---|---|---|

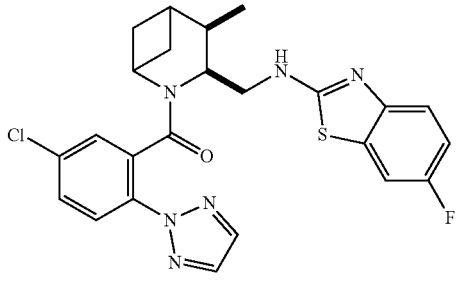

3R,4S or 3S,4R enantiomer

MS (m/z): 497.1 [MH]+
N-({(3R,4S) or (3S,4R)2-[5-chloro-2-(2H-1,2,3-triazol-2-yl)benzoyl]-4-methyl-2-azabicyclo[3.1.1]heptan-3-yl}methyl)-6-fluoro-1,3-benzothiazol-2-amine

| 174 | P174 | T | 20 |
|---|---|---|---|

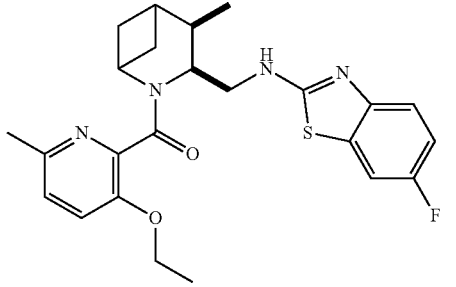

Racemic mixture of cis-N-{[2-(3-ethoxy-6-methylpyridine-2-carbonyl)-4-methyl-2-azabicyclo[3.1.1]heptan-3-yl]methyl}-6-fluoro-1,3-benzothiazol-2-amine MS (m/z): 455.4 [MH]+
NMR (1H, DMSO-d6) δ: 7.58-8.11 (m, 1 H), 7.52-7.64 (m, 1 H), 7.21-7.44 (m, 2 H), 6.98-7.10 (m, 1 H), 6.88-7.23 (m, 1 H), 3.95-4.78 (m, 1 H), 3.94-4.11 (m, 2 H), 3.67-4.12 (m, 1 H), 3.67-4.88 (m, 1 H), 3.40-3.60 (m, 1 H), 2.54-2.70 (m, 1 H), 2.18-2.41 (m, 3 H), 2.08-2.28 (m, 3 H), 1.67-1.96 (m, 1 H), 1.34-1.77 (m, 1 H), 1.19-1.33 (m, 3 H), 0.98-1.16 (m, 3 H)

| 175 | P175 | T | 79 |
|---|---|---|---|

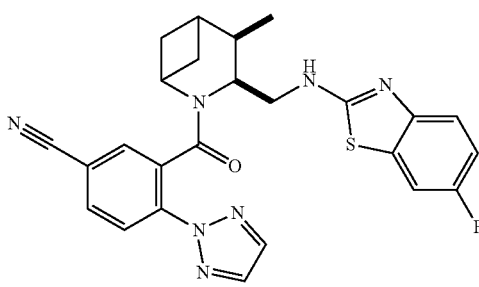

Racemic mixture of cis-3-(3-{[(6-fluoro-1,3-benzothiazol-2-yl)amino]methyl}-4-methyl-2-azabicyclo[3.1.1]heptane-2-carbonyl)-4-(2H-1,2,3-triazol-2-yl)benzonitrile MS (m/z): 488.1 [MH]+
NMR (1H, CDCl3-d) δ: 8.19-8.32 (m, 1H), 7.76-7.86 (m, 1H), 7.68-7.90 (s, 2H), 7.45-7.64 (m, 2H), 7.24-7.34 (m, 1H), 6.64-7.14 (m, 2H), 5.04-5.18 (m, 1H), 3.81-4.28 (m, 3H), 2.62-2.88 (m, 1H), 1.91-2.38 (m, 4H), 1.49-1.58 (m, 1H), 1.18-1.33 (m, 3H)

| Example | Starting materials | Gen. procedure | Yield (%) |
|---|---|---|---|
| The racemic mixture was separated into the single enantiomers by preparative chiral HPLC | | | |
| Preparative chiral chromatography protocol: | Column | Whelk O1 (R,R) (25 × 2. cm), 10μ | |
| | Mobile phase | n-Hexane/Ethanol 50/50% v/v | |
| | Flow rate (ml/min) | 17 ml/min | |
| | DAD detection | 220 nm | |
| | Loop | 850 μl | |
| | Injection | 15.5 mg (each injection) | |
| 176 | Enantiomer 1 | Rt: 11.6 min | 100% ee |

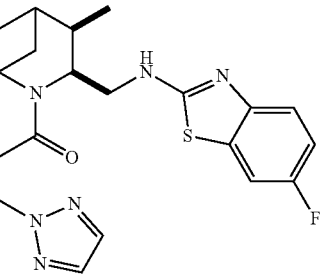

MS (m/z): 488.1 [MH]+
3-[(3S,4R) or (3R,4S)-3-{[(6-fluoro-1,3-benzothiazol-2-yl)amino]methyl}-4-methyl-2-azabicyclo[3.1.1]heptane-2-carbonyl]-4-(2H-1,2,3-triazol-2-yl)benzonitrile 3S,4R or 3R,4S enantiomer

| 177 | | Enantiomer 2 | Rt: 15.5 min | 100% ee |
|---|---|---|---|---|

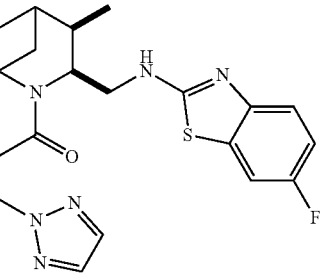

MS (m/z): 488.1 [MH]+
3-[(3R,4S) or (3S,4R)-3-{[(6-fluoro-1,3-benzothiazol-2-yl)amino]methyl}-4-methyl-2-azabicyclo[3.1.1]heptane-2-carbonyl]-4-(2H-1,2,3-triazol-2-yl)benzonitrile 3R,4S or 3S,4R enantiomer

| 178 | | P170 | T | 43 |
|---|---|---|---|---|

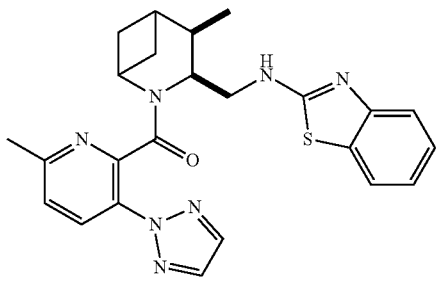

MS (m/z): 460.4 [MH]+
NMR (1H, CDCl3-d) δ: 8.12-8.31 (m, 1H), 7.66-7.94 (m, 2H), 7.45-7.63 (m, 2H), 7.29-7.36 (m, 2H), 7.01-7.12 (m, 1H), 5.12 (td, 1H), 3.86-4.27 (m, 3H), 2.76-2.94 (m, 1H), 2.58-2.73 (m, 3H), 1.95-2.34 (m, 4H), 1.71 (t, 1H), 1.15-1.28 (m, 3H)

Racemic mixture of cis-N-({4-methyl-2-[6-methyl-3-(2H-1,2,3-triazol-2-yl)pyridine-2-carbonyl]-2-azabicyclo[3.1.1]heptan-3-yl}methyl)-1,3-benzothiazol-2-amine
The racemic mixture was separated into the single enantiomers by preparative chiral HPLC

| Preparative chiral chromatography protocol: | Column | Chiralpak AD-H (25 × 2.0 cm), 5μ |
|---|---|---|
| | Mobile phase | n-Hexane/(Ethanol + 0.1% IPA) 40/60% v/v |
| | Flow rate (ml/min) | 17 ml/min |
| | DAD detection | 220 nm |
| | Loop | 750 μl |
| | Injection | 12.3 mg (each injection) |

| Example | Starting materials | Gen. procedure | Yield (%) |
|---------|-------------------|----------------|-----------|
| 179 | Enantiomer 1 | Rt: 9.1 min | 100% ee |

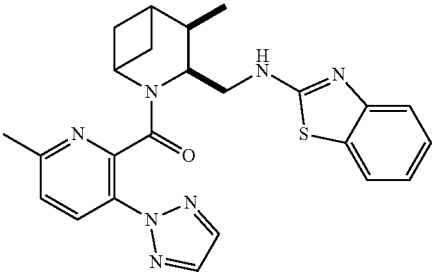

MS (m/z): 460.4 [MH]⁺
N-{[(3S,4R) or (3R,4S)-4-methyl-2-[6-methyl-3-(2H-1,2,3-triazol-2-yl)pyridine-2-carbonyl]-2-azabicyclo[3.1.1]heptan-3-yl]methyl}-1,3-benzothiazol-2-amine 3S,4R or 3R,4S enantiomer

| | | | |
|---|---|---|---|
| 180 | Enantiomer 2 | Rt: 12.9 min | 100% ee |

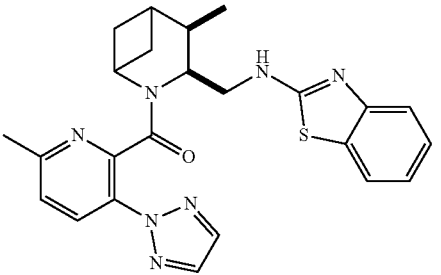

MS (m/z): 460.4 [MH]⁺
N-{[(3R,4S) or (3S,4R)-4-methyl-2-[6-methyl-3-(2H-1,2,3-triazol-2-yl)pyridine-2-carbonyl]-2-azabicyclo[3.1.1]heptan-3-yl]methyl}-1,3-benzothiazol-2-amine 3R,4S or 3S,4R enantiomer

| | | | |
|---|---|---|---|
| 181 | P170 | T | 90 |

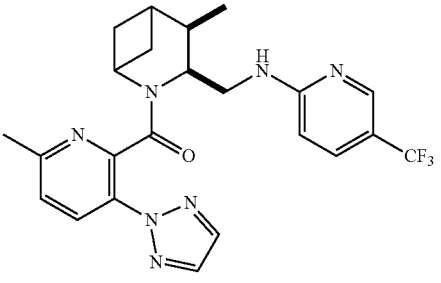

MS (m/z): 472.4 [MH]⁺
NMR (¹H, CDCl₃-d) δ: 8.31-8.40 (m, 1H), 8.06-8.26 (m, 1H), 7.59-7.91 (m, 2H), 7.39-7.51 (m, 1H), 7.33 (d, 1H), 6.68-6.86 (m, 1H), 6.39-6.57 (m, 1H), 4.87-5.10 (m, 1H), 3.94-4.13 (m, 2H), 3.78 (ddd, 1H), .279 (quin, 1H), 2.55-2.65 (m, 3H), 1.94-2.30 (m, 4H), 1.63 (t, 1H), 1.12-1.29 (m, 3H)

Racemic mixture of cis-N-({4-methyl-2-[6-methyl-3-(2H-1,2,3-triazol-2-yl)pyridine-2-carbonyl]-2-azabicyclo[3.1.1]heptan-3-yl}methyl)-5-(trifluoromethyl)pyridin-2-amine
The racemic mixture was separated into the single enantiomers by preparative chiral HPLC

| Preparative chiral chromatography protocol: | Column | Chiralpak AD-H (25 × 2.0 cm), 5μ |
|---|---|---|
| | Mobile phase | n-Hexane/(Ethanol + 0.1% isopropylamine) 20/80% v/v |
| | Flow rate (ml/min) | 17 ml/min |
| | DAD detection | 220 nm |
| | Loop | 1000 μl |
| | Injection | 10 mg (each injection) |

| Example | Starting materials | Gen. procedure | Yield (%) |
|---|---|---|---|
| 182 | Enantiomer 1 | Rt: 5.7 min | 89.2% ee |

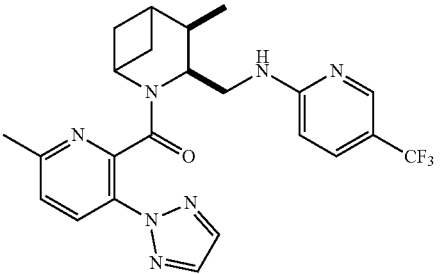

MS (m/z): 472.4 [MH]+
N-{[(3S,4R) or (3R,4S)-4-methyl-2-[6-methyl-3-(2H-1,2,3-triazol-2-yl)pyridine-2-carbonyl]-2-azabicyclo[3.1.1]heptan-3-yl]methyl}-5-(trifluoromethyl)pyridin-2-amine 3S,4R or 3R,4S enantiomer

| | | | |
|---|---|---|---|
| 183 | Enantiomer 2 | Rt: 7.3 min | 100% ee |

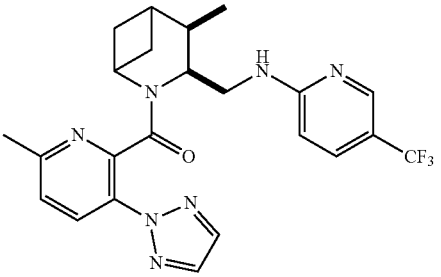

MS (m/z): 472.4 [MH]+
N-{[(3R,4S) or (3S,4R)-4-methyl-2-[6-methyl-3-(2H-1,2,3-triazol-2-yl)pyridine-2-carbonyl]-2-azabicyclo[3.1.1]heptan-3-yl]methyl}-5-(trifluoromethyl)pyridin2-amine 3R,4S or 3S,4R enantiomer

| | | | |
|---|---|---|---|
| 184 | P170 + P137 | T | 85 |

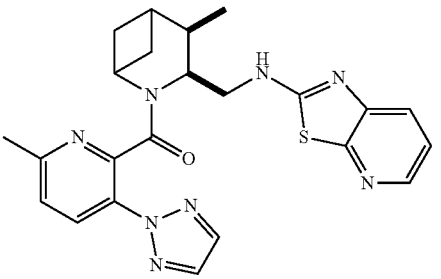

MS (m/z): 461.2 [MH]+
NMR (1H, MeOD-d4) δ: 8.16-8.40 (m, 1H), 8.08-8.16 (m, 1H), 7.92-8.04 (m, 2H), 7.64-7.80 (m, 1H), 7.54 (d, 1H), 7.26-7.39 (m, 1H), 4.90-5.01 (m, 1H), 4.24-4.31 (m, 1H), 3.97-4.08 (m, 1H), 3.87 (dd, 1H), 2.75-2.85 (m, 1H), 2.43-2.64 (m, 3H), 1.85-2.40 (m, 4H), 1.54-1.68 (m, 1H), 1.09-1.28 (m, 3H)

Racemic mixture of cis-N-({4-methyl-2-[6-methyl-3-(2H-1,2,3-triaozl-2-yl)pyridine-2-carbonyl]-2-azabicyclo[3.1.1]heptan-3-yl}methyl)-[1,3]thiazolo[5,4-b]pyridin-2-amine The racemic mixture was separated into the single enantiomers by preparative chiral HPLC

| Preparative chiral chromatography protocol: | Column | Chiralpak AD-H (25 × 2.0 cm), 5μ |
|---|---|---|
| | Modifier | Methanol 30% |
| | Flow rate (ml/min) | 45 |
| | Pressure (bar) | 120 |
| | Temperature (° C.) | 38 |
| | UV detection | 210 nm |
| | Loop | 650 μl |
| | Injection | 7.5 mg (each injection) |

| Example | Starting materials | Gen. procedure | Yield (%) |
|---|---|---|---|
| 185 | Enantiomer 1 | Rt: 6.9 min | 100% ee |

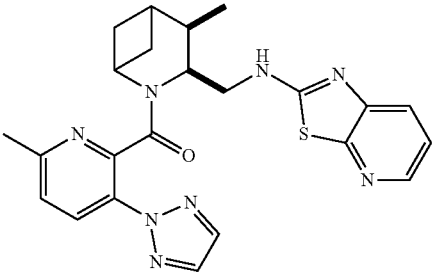

MS (m/z): 461.2 [MH]+
N-({(3S,4R) or (3R,4S)4-methyl-2-[6-methyl-3-(2H-1,2,3-triazol-2-yl)pyridine-2-carbonyl]-2-azabicyclo[3.1.1]heptan-3-yl}methyl)-[1,3]thiazolo[5,4-b]pyridin-2-amine 3S,4R or 3R,4S enantiomer

| | | | |
|---|---|---|---|
| 186 | Enantiomer 2 | Rt: 9.1 min | 96% ee |

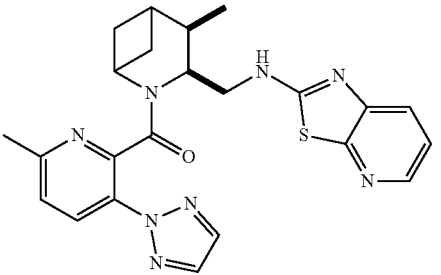

MS (m/z): 461.2 [MH]+
N-({(3R,4S) or (3S,4R)-4-methyl-2-[6-methyl-3-(2H-1,2,3-triazol-2-yl)pyridine-2-carbonyl]-2-azabicyclo[3.1.1]heptan-3-yl}methyl)-[1,3]thiazolo[5,4-b]pyridin-2-amine 3R,4S or 3S,4R enantiomer

| | | | |
|---|---|---|---|
| 187 | P171 | W | 48 |

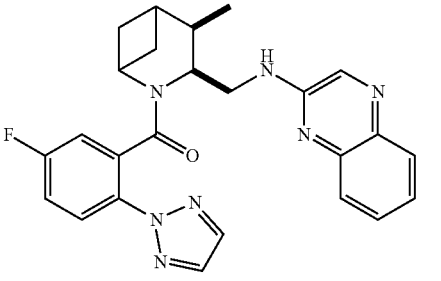

MS (m/z): 458.4 [MH]+
NMR (1H, CDCl3-d) δ: 8.03-8.27 (m, 1H), 7.99 (dd, 1H), 7.89 (d, 1H), 7.67-7.77 (m, 1H), 7.54-7.63 (m, 1H), 7.44-7.84 (m, 2H), 7.34-7.41 (m, 1H), 7.17-7.28 (m, 1H), 6.77-7.12 (m, 2H), 5.06-5.18 (m, 1H), 3.69-4.35 (m, 3H), 2.61-2.86 (m, 1H), 1.88-2.37 (m, 4H), 1.51 (t, 1H), 1.21-1.34 (m, 3H)

Racemic mixture of cis-N-({2-[5-fluoro-2-(2H-1,2,3-triazol-2-yl)benzoyl]-4-methyl-2-azabicyclo[3.1.1]heptan-3-yl}methyl)quinoxalin-2-amine
The racemic mixture was separated into the single enantiomers by preparative chiral HPLC

| Preparative chiral chromatography protocol: | Column | Chiralpak AD-H (25 × 2.0 cm), 5μ |
|---|---|---|
| | Mobile phase | n-Hexane/(Ethanol + Methanol 1/1) 20/80% v/v |
| | Flow rate (ml/min) | 17 ml/min |
| | DAD detection | 220 nm |
| | Loop | 1000 μl |
| | Injection | 37.5 mg (each injection) |

| Example | Starting materials | Gen. procedure | Yield (%) |
|---|---|---|---|
| 188 | Enantiomer 1 | Rt: 7.7 min | 100% ee |

MS (m/z): 458.4 [MH]⁺
N-({(3S,4R) or (3R,4S)2-[5-fluoro-2-(2H-1,2,3-triazol-2-yl)benzoyl]-4-methyl-2-azabicyclo[3.1.1]heptan-3-yl}methyl)quinoxalin-2-amine 3S,4R or 3R,4S enantiomer

| | | | |
|---|---|---|---|
| 189 | Enantiomer 2 | Rt: 17.7 min | 100% ee |

MS (m/z): 458.4 [MH]⁺
N-({(3R,4S) or (3S,4R)2-[5-fluoro-2-(2H-1,2,3-triazol-2-yl)benozyl]-4-methyl-2-azabicyclo[3.1.1]heptan-3-yl}methyl)quinoxalin-2-amine 3R,4S or 3S,4R enantiomer

| | | | |
|---|---|---|---|
| 190 | P171 | T | 35 |

MS (m/z): 475.4 [MH]⁺
NMR ($^1$H, CDCl$_3$-d) δ: 8.33-8.41 (m, 1H), 7.98 (dd, 1H), 7.52-7.85 (m, 2H), 7.47-7.57 (m, 1H), 7.25 (ddd, 1H), 6.78-7.10 (m, 1H), 6.24-6.63 (br. s., 1H), 6.40-6.54 (m, 1H), 4.97-5.09 (m, 1H), 3.54-4.23 (m, 3H), 2.59-2.80 (m, 1H), 1.80-2.33 (m, 4H), 1.41-1.52 (m, 1H), 1.18-1.25 (m, 3H)

Racemic mixture of cis-N-({2-[5-fluoro-2-(2H-1,2,3-triazol-2-yl)benzoyl]-4-methyl-2-azabicyclo[3.1.1]heptan-3-yl}methyl)-5-(trifluoromethyl)pyridin-2-amine
The racemic mixture was separated into the single enantiomers by preparative chiral HPLC

| Preparative chiral chromatography protocol: | Column | Chiralpak AD-H (25 × 2.0 cm), 5µ |
|---|---|---|
| | Mobile phase | n-Hexane/(Ethanol + Methanol 1/1) 20/80% v/v |
| | Flow rate (ml/min) | 14 ml/min |
| | DAD detection | 220 nm |
| | Loop | 1000 µl |
| | Injection | 27.5 mg (each injection) |

| Example | Starting materials | Gen. procedure | Yield (%) |
|---|---|---|---|
| 191 | Enantiomer 1 | Rt: 5.3 min | 100% ee |

MS (m/z): 475.4 [MH]+.
N-({(3S,4R) or (3R,4S)2-[5-fluoro-2-(2H-1,2,3-triazol-2-yl)benzoyl]-4-methyl-2-azabicyclo[3.1.1]heptan-3-yl}methyl)-5-(trifluoromethyl)pyridin-2-amine 3S,4R or 3R,4S enantiomer

| 192 | Enantiomer 2 | Rt: 7.8 nin | 99.2% ee |

MS (m/z): 475.4 [MH]+.
N-({(3R,4S) or (3S,4R)2-[5-fluoro-2-(2H-1,2,3-triazol-2-yl)benzoyl]-4-methyl-2-azabicyclo[3.1.1]heptan-3-yl}methyl)-5-(trifluoromethyl)pyridin-2-amine 3R,4S or 3S,4R enantiomer

| 193 | P170 | T | 32 |

MS (m/z): 473.3 [MH]+
NMR ($^1$H, CDCl$_3$-d) δ: 8.31-8.58 (m, 2H), 8.08-8.29 (m, 1H), 7.78-7.89 (m, 2H), 7.22-7.34 (m, 1H), 7.18 (br. s., 1H), 4.88-5.14 (m, 1H), 3.78-4.28 (m, 3H), 2.74-2.87 (m, 1H), 2.59-2.68 (m, 3H), 1.87-2.37 (m, 4H), 1.64-1.75 (m, 1H), 1.22 (d, 3H)

Racemic mixture of cis-N-({4-methyl-2-[6-methyl-3-(2H-1,2,3-triazol-2-yl)pyridine-2-carbonyl]-2-azabicyclo[3.1.1]heptan-3-yl}methyl)-5-(trifluoromethyl)pyrimidin-2-amine
The racemic mixture was separated into the single enantiomers by preparative chiral HPLC

| Preparative chiral chromatography protocol: | | |
|---|---|---|
| | Column | Chiralpak AS-H (25 × 2.0 cm), 5μ |
| | Mobile phase | n-Hexane/Ethanol 65/35% v/v |
| | Flow rate (ml/min) | 17 ml/min |
| | DAD detection | 220 nm |
| | Loop | 1000 μl |
| | Injection | 9 mg (each injection) |

-continued

| Example | Starting materials | Gen. procedure | Yield (%) |
|---|---|---|---|
| 194 | Enantiomer 1 | Rt: 4.1 min | 98.2% ee |

MS (m/z): 473.3 [MH
N-{[(3S,4R) or (3R,4S)-4-methyl-2-[6-methyl-3-(2H-1,2,3-triazol-2-yl)pyridine-2-carbonyl]-2-azabicyclo[3.1.1]heptan-3-yl]methyl}-5-(trifluoromethyl)pyrimidin-2-amine 3S,4R or 3R,4S enantiomer

| 195 | Enantiomer 2 | Rt: 6.9 min | 98.4% ee |

MS (m/z): 473.3 [MH
N-{[(3R,4S) or (3S,4R)-4-methyl-2-[6-methyl-3-(2H-1,2,3-triazol-2-yl)pyridin-2-carbonyl]-2-azabicyclo[3.1.1]heptan-3-yl]methyl}-5-(trifluoromethyl)pyrimidin-2-amine 3R,4S or 3S,4R enantiomer

| 196 | P170 | W | 29 |

MS (m/z): 436.3 [MH]$^+$
NMR ($^1$H, CDCl$_3$-d) δ: 8.02-8.27 (m, 1H), 7.67-7.91 (m, 2H), 7.16-7.34 (m, 1H), 6.91-7.12 (m, 1H), 6.39-6.53 (m, 1H), 5.69-5.98 (m, 1H), 4.89-5.01 (m, 1H), 3.92-4.06 (m, 2H), 3.58-3.80 (m, 2H), 2.70-2.81 (m, 1H), 2.53-2.63 (m, 3H), 2.82-2.42 (m, 3H), 1.91-2.30 (m, 3H), 1.53-1.63 (m, 1H), 1.10-1.30 (m, 3H)

Racemic mixture of cis-5-fluoro-6-methyl-N-({4-methyl-2-[6-methyl-3-(2H-1,2,3-triazol-2-yl)pyridine-2-carbonyl]-2-azabicyclo[3.1.1]heptan-3-yl}methyl)pyridin-2-amine

| 197 | P170 | T | 14 |

MS (m/z): 472.3 [MH]$^+$
NMR ($^1$H, CDCl$_3$-d) δ: 7.78-8.26 (m, 1H), 7.66-7.91 (m, 2H), 7.28-7.46 (m, 2H), 6.58-6.89 (m, 2H), 6.24 (br.s., 1H), 4.88-5.05 (m, 1H), 4.07-4.19 (m, 1H), 3.92-4.00 (m, 1H), 3.69-3.85 (m, 1H), 2.68-2.82 (m, 1H), 2.62 (s, 3H), 1.95-2.45 (m, 5H), 1.21-1.32 (m, 3H)

Racemic mixture of cis-N-({4-methyl-2-[6-methyl-3-(2H-1,2,3-triazol-2-yl)pyridine-2-carbonyl]-2-azabicyclo[3.1.1]heptan-3-yl}methyl)-6-(trifluoromethyl)pyridin-2-amine

| Example | Starting materials | Gen. procedure | Yield (%) |
|---|---|---|---|
| 198 | P170 | T | 18 |

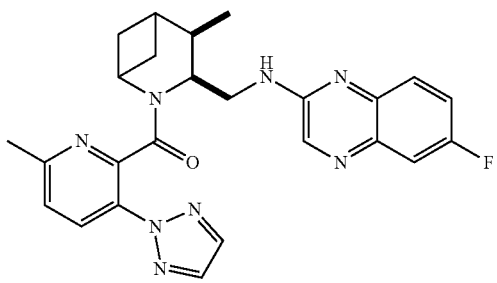

MS (m/z): 473.4 [MH]+
NMR (1H, CDCl3-d) δ: 8.24 (d, 1H), 8.08 (s, 1H), 7.66-7.72 (m, 1H), 7.59 (s, 2H), 7.51-7.56 (m, 1H), 7.31-7.38 (m, 2H), 7.19 (br.s., 1H), 5.12-5.20 (m, 1H), 3.83-4.23 (m, 3H), 2.77-2.93 (m, 1H), 2.61 (s, 3H), 2.04-2.50 (m, 5H), 1.29 (d, 3H)

Racemic mixture of cis-6-fluoro-N-({4-methyl-2-[6-methyl-3-(2H-1,2,3-triazol-2-yl)pyridine-2-carbonyl]-2-azabicyclo[3.1.1]heptan-3-yl}methyl)quinoxalin-2-amine The racemic mixture was separated into the single enantiomers by preparative chiral HPLC

| Preparative chiral chromatography protocol: | Column | Chiralpak AD-H (25 × 2.0 cm), 5μ |
|---|---|---|
| | Modifier | Methanol 35% |
| | Flow rate (ml/min) | 45 |
| | Pressure (bar) | 120 |
| | Temperature (° C.) | 38 |
| | UV detection | 220 nm |
| | Loop | 600 μl |
| | Injection | 8.4 mg (each injection) |
| 199 | Enantiomer 1    Rt: 6.5 min    100% ee | |

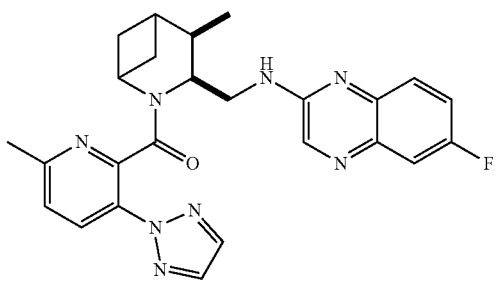

MS (m/z): 473.4 [MH]+
6-fluoro-N-{[(3S,4R) or (3R,4S)-4-methyl-2-[6-methyl-3-(2H-1,2,3-triazol-2-yl)pyridine-2-carbonyl]-2-azabicyclo[3.1.1]heptan-3-yl]methyl}quinoxalin-2-amine 3S,4R or 3R,4S enantiomer

| 200 | Enantiomer 2 | Rt: 9.4 min | 100% ee |
|---|---|---|---|

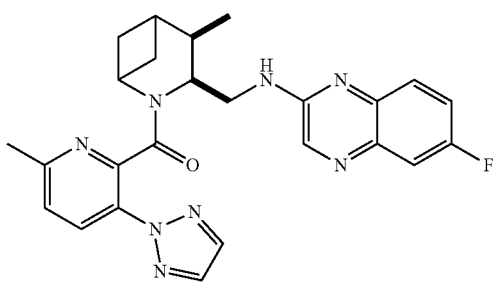

MS (m/z): 473.4 [MH]+.
6-fluoro-N-{[(3R,4S) or (3S,4R)-4-methyl-2-[6-methyl-3-(2H-1,2,3-triazol-2-yl)pyridine-2-carbonyl]-2-azabicyclo[3.1.1]heptan-3-yl]methyl}quinoxalin-2-amine 3R,4S or 3S,4R enantiomer

| Example | Starting materials | Gen. procedure | Yield (%) |
|---------|-------------------|----------------|-----------|
| 201 | P170 + P139 | T | 41 |

MS (m/z): 491.4 [MH]+
NMR (¹H, CDCl₃-d) δ: 8.24 (d, 1H), 8.03 (s, 1H), 7.58-7.66 (m, 3H), 7.42-7.49 (m, 1H), 7.33 (d, 1H), 5.10-5.20 (m, 1H), 4.10-4.20 (m, 1H), 3.97-4.05 (m, 1H), 3.84-3.94 (m, 1H), 2.80-2.88 (m, 1H), 2.61 (s, 3H), 2.05-2.33 (m, 4H), 1.63-1.70 (m, 1H), 1.29 (d, 3H)

Racemic mixture of cis-6,7-difluoro-N-({4-methyl-2-[6-methyl-3-(2H-1,2,3-triazol-2-yl)pyridine-2-carbonyl]-2-azabicyclo[3.1.1]heptan-3-yl}methyl)quinoxalin-2-amine

| | | | |
|---|---|---|---|
| 202 | P179 + p66 | Q | 47 |

MS (m/z): 436.2 [MH]+
NMR (¹H, CDCl₃-d) δ: 7.32-7.89 (m, 3H), 7.07-7.27 (m, 2H), 6.86-6.97 (m, 2H), 6.56-6.73 (m, 2H), 4.99-5.12 (m, 1H), 3.85-4.02 (m, 1H), 3.29-3.76 (m, 2H), 2.51-2.79 (m, 1H), 2.32-2.45 (m, 3H), 1.73-2.25 (m, 4H), 1.42-1.49 (m, 1H), 1.14-1.24 (m, 3H)

Racemic mixture of cis-4-fluoro-N-({4-methyl-2-[5-methyl-2-(1,3-thiazol-2-yl)benzoyl]-2-azabicyclo[3.1.1]heptan-3-yl}methyl)aniline

| | | | |
|---|---|---|---|
| 203 | P173 | T | 44 |

MS (m/z): 492.1 [MH]+
NMR (¹H, CDCl₃-d) δ: 8.31-8.39 (m, 1H), 8.00 (d, 1H), 7.80-7.96 (m, 1H), 7.32-7.79 (m, 3H), 7.08-7.25 (m, 1H), 5.01-5.13 (m, 1H), 3.96-4.24 (m, 2H), 3.59-3.89 (m, 1H), 2.61-2.85 (m, 1H), 1.81-2.37 (m, 4H), 1.46-1.55 (m, 1H), 1.16-1.27 (m, 3H)

Racemic mixture of cis-N-({2-[5-chloro-2-(2H-1,2,3-triazol-2-yl)benzoyl]-4-methyl-2-azabicyclo[3.1.1]heptan-3-yl}methyl)-5-(trifluoromethyl)pyrazin-2-amine The racemic mixture was separated into the single enantiomers by preparative chiral HPLC

| Preparative chiral chromatography protocol: | | |
|---|---|---|
| | Column | Chiralpak AD-H (25 × 2.0 cm), 5μ |
| | Mobile phase | n-Hexane/(Ethanol + Methanol 1/1) 20/80% v/v |
| | Flow rate (ml/min) | 17 ml/min |
| | DAD detection | 220 nm |
| | Loop | 1000 μl |
| | Injection | 15 mg (each injection) |

| Example | Starting materials | Gen. procedure | Yield (%) |
|---|---|---|---|
| 204 | Enantiomer 1 | Rt: 4.7 min | 100% ee |

MS (m/z): 492.1 [MH]⁺
N-({(3S,4R) of (3R,4S)2-[5-chloro-2-(2H-1,2,3-triazol-2-yl)benzoyl]-4-methyl-2-azabicyclo[3.1.1]heptan-3-yl}methyl)-5-(trifluoromethyl)pyrazin-2-amine

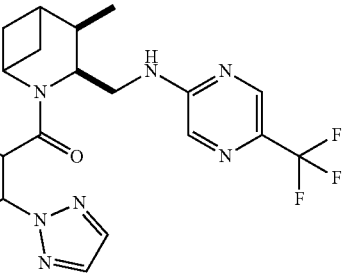

3S,4R or 3R,4S enantiomer

| 205 | Enantiomer 2 | Rt: 8.4 min | 100% ee |
|---|---|---|---|

MS (m/z): 492.1 [MH]⁺
N-({(3R,4S) or (3S,4R)2-[5-chloro-2-(2H-1,2,3-triazol-2-yl)benozyl]-4-methyl-2-azabicyclo[3.1.1]heptan-3-yl}methyl)-5-(trifluoromethyl)pyrazin-2-amine

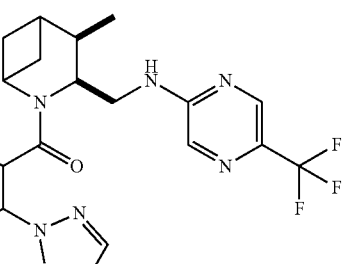

3R,4S or 3S,4R enantiomer

| 206 | P173 | T | 47 |
|---|---|---|---|

MS (m/z): 475.4 [MH]⁺
NMR (¹H, CDCl₃-d) δ: 8.71-8.76 (m, 1H), 8.23-8.44 (m, 1H), 7.97-8.09 (m, 2H), 7.46-7.85 (m, 4H), 7.18-7.43 (m, 1H), 7.10-7.36 (m, 1H), 5.08-5.19 (m, 1H), 4.09-4.33 (m, 1H), 4.01-4.06 (m, 1H), 3.73-3.95 (m, 1H), 2.64-2.87 (m, 1H), 1.90-2.39 (m, 4H), 1.50-1.56 (m, 1H), 1.23-1.34 (m, 3H)

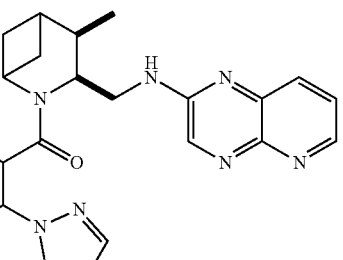

Racemic mixture of cis-N-({2-[5-chloro-2-(2H-1,2,3-triazol-2-yl)benzoyl]-4-methyl-2-azabicyclo[3.1.1]heptan-3-yl}methyl)pyrido[2,3-b]pyrazin-2-amine

| 207 | P173 | T | 35 |
|---|---|---|---|

MS (m/z): 492.4 [MH]⁺
NMR (¹H, CDCl₃-d) δ: 8.04-8.25 (m, 1H), 7.94-8.0 (m, 1H), 7.64-7.73 (m, 1H), 7.45-7.82 (m, 4H), 6.99-7.40 (m, 2H), 6.67-7.07 (br. s., 1H), 5.07-5.16 (m, 1H), 3.67-4.32 (m, 3H), 2.62-2.85 (m, 1H), 2.04-2.36 (m, 3H), 1.89-2.00 (m, 1H), 1.47-1.56 (m, 1H), 1.22-1.33 (m, 3H)

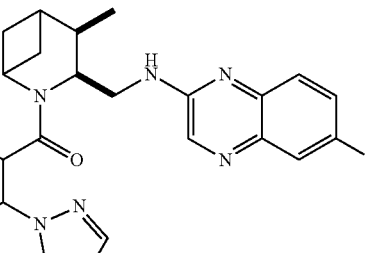

Racemic mixture of cis-N-({2-[5-chloro-2-(2H-1,2,3-triazol-2-yl)benzoyl]-4-methyl-2-azabicyclo[3.1.1]heptan-3-yl}methyl)-6-fluoroquinoxalin-2-amine
The racemic mixture was separated into the single enantiomers by preparative chiral HPLC

| Preparative chiral chromatography protocol: | Column | Chiralpak AD-H (25 × 3.0 cm), 5μ |
|---|---|---|
| | Mobile phase | n-Hexane/(Ethanol + Methanol 1/1) 20/80% v/v |
| | Flow rate (ml/min) | 40 ml/min |

| Example | Starting materials | Gen. procedure | Yield (%) |
|---|---|---|---|
| | DAD detection | 220 nm | |
| | Loop | 2500 µl | |
| | Injection | 24 mg (each injection) | |
| 208 | Enantiomer 1 | Rt: 7.0 min | 100% ee |

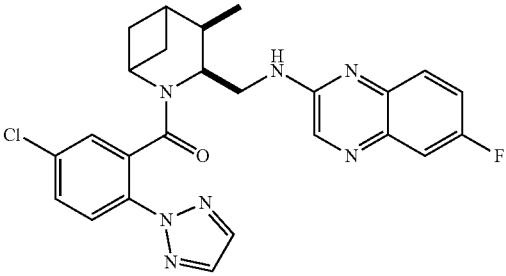

3S,4R or 3R,4S enantiomer

MS (m/z): 492.4 [MH]+
N-{[(3S,4R) or (3r,4R)-2-[5-chloro-2-(2H-1,2,3-triazol-2-yl)benzoyl]-4-methyl-2-azabicyclo[3.1.1]heptan-3-yl]methyl}-6-fluoroquinoxalin-2-amine

| | | | |
|---|---|---|---|
| 209 | Enantiomer 2 | Rt: 17.6 min | 100% ee |

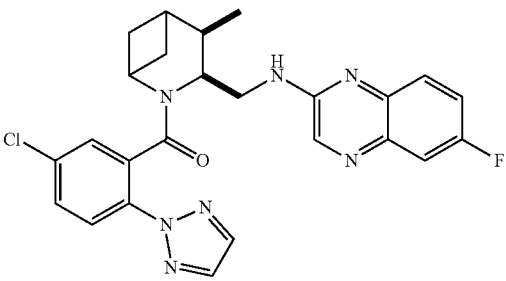

3R,4S or 3S,4R enantiomer

MS (m/z): 492.4 [MH]+
N-{[(3R,4R) or (3S,4R)-2-[5-chloro-2-(2H-1,2,3-triazol-2-yl)benzoyl]-4-methyl-2-azabicyclo[3.1.1]heptan-3-yl]methyl}-6-fluoroquinoxalin-2-amine

| | | | |
|---|---|---|---|
| 210 | P176 | U | 54 |

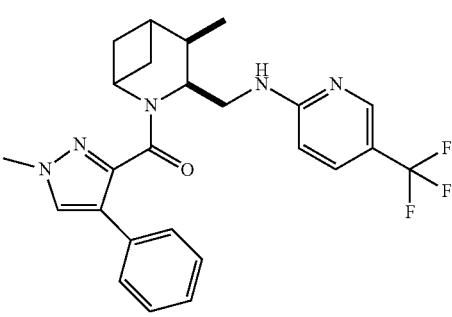

MS (m/z): 470.4 [MH]+
NMR (1H, CDCl3-d) δ: 8.26-8.41 (m, 1H), 7.43-7.55 (m, 2H), 7.32-7.41 (m, 2H), 7.14-7.23 (m, 3H), 6.78 (br. s., 1H), 6.47 (d, 1H), 5.12 (dt, 1H), 4.20 (q, 1H), 3.85-3.99 (m, 4H), 3.67-3.82 (m, 1H), 2.67 (quin, 1H), 2.15-2.24 (m, 1H), 2.06-2.15 (m, 1H), 2.01 (td, 1H), 1.87 (t, 1H), 1.14-1.28 (m, 4H)

Racemic mixture of cis-N-{[4-methyl-2-(1-methyl-4-phenyl-1H-pyrazole-3-carbonyl)-2-azabicyclo[3.1.1]heptan-3-yl]methyl}-5-(trifluoromethyl)pyridin-2-amine
The racemic mixture was separated into the single enantiomers by preparative chiral HPLC

| Preparative chiral chromatography protocol: | Column | Chiralpak AD-H (25 × 2.0 cm), 5µ |
|---|---|---|
| | Modifier | Methanol 20% |
| | Flow rate (ml/min) | 45 |
| | Pressure (bar) | 120 |
| | Temperature (° C.) | 38 |
| | UV detection | 220 nm |
| | Loop | 500 µl |
| | Injection | 27 mg (each injection) |

| Example | Starting materials | Gen. procedure | Yield (%) |
|---|---|---|---|
| 211 | Enantiomer 1 | Rt: 9.3 min | 100% |

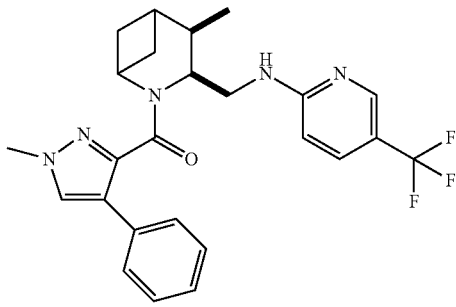

MS (m/z): 470.4 [MH]+
N-{[(3S,4R) or (3R,4R)-4-methyl-2-(1-methyl-4-phenyl-1H-pyrazole-3-carbonyl)-2-azabicyclo[3.1.1]heptan-3-yl]methyl}-5-(trifluoromethyl)pyridin-2-amine 3S,4R or 3R,4S enantiomer

| 212 | Enantiomer 2 | Rt: 11.6 min | 99% ee |
|---|---|---|---|

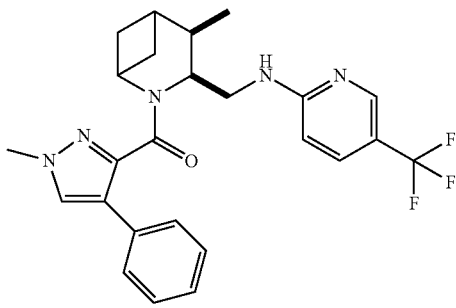

MS (m/z): 470.4 [MH]+
N-{[(3R,4S) or (3S,4R)-4-methyl-2-(1-methyl-4-phenyl-1H-pyrazole-3-carbonyl)-2-azabicyclo[3.1.1]heptan-3-yl]methyl}-5-(trifluoromethyl)pyridin-2-amine 3R,4S or 3S,4R enantiomer

| 213 | | P177 | U | 21 |
|---|---|---|---|---|

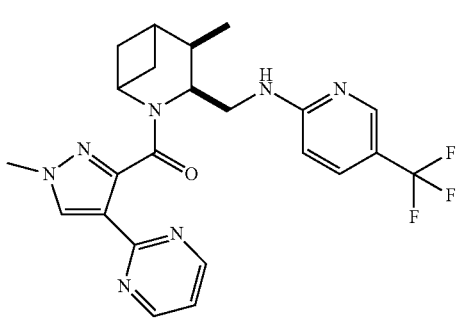

MS (m/z): 472.4 [MH]+
NMR ($^1$H, CDCl$_3$-d) δ: 8.48-8.70 (m, 2H), 8.24-8.40 (m, 1H), 7.97-8.14 (m, 1H), 7.46 (dd, 1H), 6.97-7.13 (m, 1H), 6.92 (br. s., 1H), 6.28-6.54 (m, 1H), 5.02-5.23 (m, 1H), 4.10-4.39 (m, 2H), 3.86-4.02 (m, 3H), 3.68-3.82 (m, 1H), 2.65-2.85 (m, 1H), 1.93-2.53 (m, 4H), 1.57 (t, 1H), 1.06-1.27 (m, 3H)

Racemic mixture of cis-N-({4-methyl-2-[1-methyl-4-(pyrimidin-2-yl)-1H-pyrazole-3-carbonyl]-2-azabicyclo[3.1.1]heptan-3-yl}methyl)-5-(trifluoromethyl)pyridin-2-amine
The racemic mixture was separated into the single enantiomers by preparative chiral HPLC

| Preparative chiral chromatography protocol: | Column | Chiralpak AD-H (25 × 2.0 cm), 5µ |
|---|---|---|
| | Modifier | Methanol 20% |
| | Flow rate (ml/min) | 45 |
| | Pressure (bar) | 120 |
| | Temperature (° C.) | 38 |
| | UV detection | 220 nm |
| | Loop | 700 µl |
| | Injection | 21.5 mg (each injection) |

-continued

| Example | Starting materials | Gen. procedure | Yield (%) |
|---|---|---|---|
| 214 | Enantiomer 1 | Rt: 7.3 min | 100% ee |

MS (m/z): 472.4 [MH]+
N-{[(3S,4R) or (3R,4S)-4-methyl-2-[1-methyl-4-(pyrimidin-2-yl)-1H-pyrazole-3-carbonyl]-2-azabicyclo[3.1.1]heptan-3-yl]methyl}-5-(trifluoromethyl)pyridin-2-amine 3S,4R or 3R,4S enantiomer

| 215 | Enantiomer 2 | Rt: 14.1 min | 100% ee |

MS (m/z): 472.4 [MH]+
N-{[(3R,4S) or (3S,4R)-4-methyl-2-{1-methyl-4-(pyrimidin-2-yl)-1H-pyrazole-3-carbonyl]-2-azabicyclo[3.1.1]heptan-3-yl]methyl}-5-(trifluoromethyl)pyridin-2-amine 3R,4S or 3S,4R enantiomer

| 216 | P170 | X | 15 |

MS (m/z): 419.2 [MH]+
NMR (¹H, CDCl₃-d) δ: 8.23 (d, 1H), 7.88 (s, 1H), 7.73-7.78 (m, 1H), 7.64 (s, 2H), 7.32 (d, 1H), 6.44 (br. s., 1H), 5.02-5.14 (m, 1H), 3.96-4.07 (m, 2H), 3.64-3.76 (m, 1H), 2.73-2.85 (m, 1H), 2.57-2.69 (m, 3H), 2.39 (s, 3H), 1.98-2.30 (m, 4H), 1.66-1.73 (m, 1H), 1.13-1.26 (m, 3H)

Racemic mixture of cis-5-methyl-N-({4-methyl-2-[6-methyl-3-(2H-1,2,3-triazol-2-yl)pyridine-2-carbonyl]-2-azabicyclo[3.1.1]heptan-3-yl}methyl)pyrazin-2-amine

| 217 | P170 | T | 35 |

MS (m/z): 473.1 [MH]+
NMR (¹H, CDCl₃-d) δ: 8.24 (d, 1H), 8.08 (s, 1H), 7.89-7.95 (m, 1H), 7.68 (s, 2H), 7.33 (d, 1H), 6.93 (br. s., 1H), 5.06 (td, 1H), 3.74-4.12 (m, 3H), 2.79 (dt, 1H), 2.53-2.63 (m, 3H), 2.24-2.32 (m, 1H), 1.99-2.19 (m, 3H), 1.59-1.65 (m, 1H), 1.15-1.27 (m, 3H)

Racemic mixture of cis-N-({4-methyl-2-[6-methyl-3-(2H-1,2,3-triazol-2-yl)pyridine-2-carbonyl]-2-azabicyclo[3.1.1]heptan-3-yl}methyl)-6-(trifluoromethyl)pyrazin-2-amine -continued

| Example | Starting materials | Gen. procedure | Yield (%) |
|---|---|---|---|
| 218 | P170 | A1 | 32 |

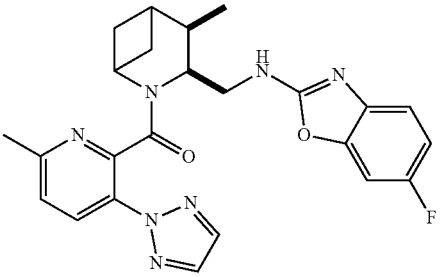

MS (m/z): 462.3 [MH]⁺
NMR (¹H, CDCl₃-d) δ: 8.14-8.31 (m, 1H), 7.68-7.78 (m, 2H), 7.21-7.35 (m, 2H), 7.07-7.15 (m, 1H), 6.85-7.03 (m, 2H), 4.86-5.19 (m, 1H), 3.67-4.14 (m, 3H), 2.47-2.95 (m, 1H), 2.60-2.72 (m, 3H), 1.97-2.47 (m, 4H), 1.65-1.77 (m, 1H), 1.24 (d, 3H)

Racemic mixture of cis-6-fluoro-N-({4-methyl-2-[6-methyl-3-(2H-1,2,3-triazol-2-yl)pyridine-2-carbonyl]-2-azabicyclo[3.1.1]heptan-3-yl}methyl)-1,3-benzoxazol-2-amine
The racemic mixture was separated into the single enantiomers by preparative chiral HPLC Preparative chiral chromatography protocol:
- Column: Chiralpak AD-H (25 × 2.0 cm), 5μ
- Mobile phase: n-Hexane/(Ethanol + Methanol 1/1) 90/10% v/v
- Flow rate (ml/min): 17 ml/min
- DAD detection: 220 nm
- Loop: 500 μl
- Injection: 10.8 mg (each injection)

| 219 | Enantiomer 1 | Rt: 9.2 min | 100% ee |
|---|---|---|---|

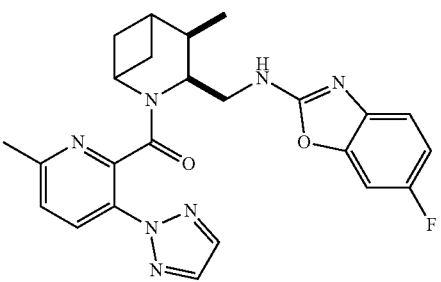

MS (m/z): 462.3 [MH]⁺
6-fluoro-N-{[(3S,4R) or (3R,4S)-4-methyl-2-[6-methyl-3-(2H-1,2,3-triazol-2-yl)pyridine-2-carbonyl]-2-azabicyclo[3.1.1]heptan-3-yl]methyl}-1,3-benzoxazol-2-amine 3S,4R or 3R,4S enantiomer

| 220 | Enantiomer 2 | Rt: 12.9 min | 100% ee |
|---|---|---|---|

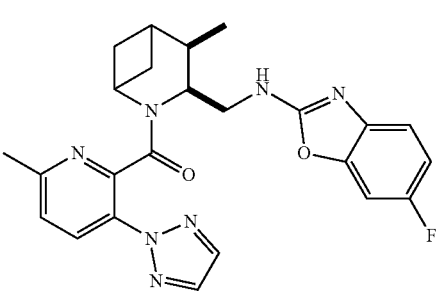

MS (m/z): 462.3 [MH]⁺
6-fluoro-N-{[(3R,4S) or (3S,4R)-4-methyl-2-[6-methyl-3-(2H-1,2,3-triazol-2-yl)pyridine-2-carbonyl]-2-azabicyclo[3.1.1]heptan-3-yl]methyl}-1,3-benzoxazol-2-amine 3R,4S or 3S,4R enantiomer

| 221 | P171 | T | 69 |
|---|---|---|---|

MS (m/z): 476.3 [MH]⁺
NMR (¹H, CDCl₃-d) δ: 8.32-8.37 (m, 1H), 8.00 (dd, 1H), 7.49-7.96 (m, 3H), 6.82-7.27 (m, 3H), 5.00-5.12 (m, 1H), 3.57-4.21 (m, 3H), 2.57-2.83 (m, 1H), 1.80-2.37 (m, 4H), 1.15-1.26 (m, 3H), 0.72-1.54 (m, 1H).

| Example | Starting materials | Gen. procedure | Yield (%) |
|---|---|---|---|

Racemic mixture of cis-N-({2-[5-fluoro-2-(2H-1,2,3-triazol-2-yl)benzoyl]-4-methyl-2-azabicyclo[3.1.1]heptan-3-yl}methyl)-5-(trifluoromethyl)pyrazin-2-amine The racemic mixture was separated into the single enantiomers by preparative chiral HPLC Preparative chiral chromatography protocol:

| | |
|---|---|
| Column | Chiralpak AD-H (25 × 04.6 cm), 5μ |
| Mobile phase | n-Hexane/(Ethanol + Methanol 1/1) 40/60% v/v |
| Flow rate (ml/min) | 17 ml/min |
| DAD detection | 220 nm |
| Loop | 700 μl |
| Injection | 25 mg (each injection) |

222

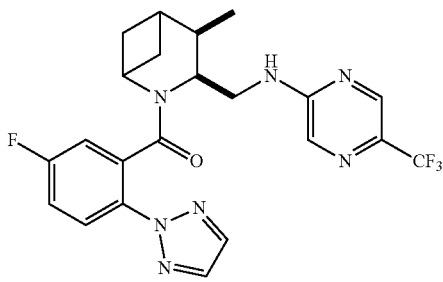

3S,4R or 3R,4S enantiomer

Enantiomer 1    Rt: 4.7 min    100% ee

MS (m/z): 476.3 [MH]+
N-{[(3S,4R) of (3R,4S)-2-[5-fluoro-2-(2H-1,2,3-triazol-2-yl)benzoyl]-4-methyl-2-azabicyclo[3.1.1]heptan-3-yl]methyl}-5-(trifluoromethyl)pyrazin-2-amine

223

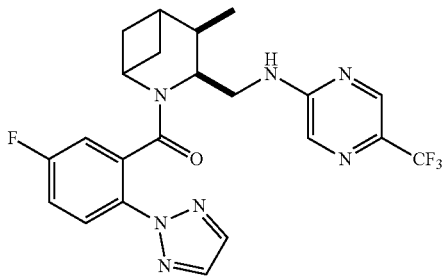

3R,4S or 3S,4R enantiomer

Enantiomer 2    Rt: 8.3 min    100% ee

MS (m/z): 476.3 [MH]+
N-{[(3R,4S) or (3S,4R)-2-[5-fluoro-2-(2H-1,2,3-triazol-2-yl)benzoyl]-4-methyl-2-azabicyclo[3.1.1]heptan-3-yl]methyl}-5-(trifluoromethyl)pyrazin-2-amine

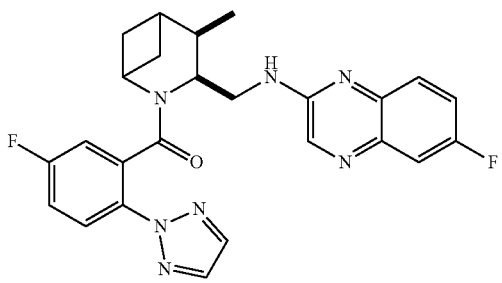

MS (m/z): 476.4 [MH]+
NMR ($^1$H, CDCl$_3$-d) δ: 8.04-8.26 (m, 1H), 7.99 (dd, 1H), 7.51-7.76 (m, 2H), 7.41-7.88 (m, 2H), 7.17-7.38 (m, 2H), 6.77-7.10 (m, 2H), 5.11 (td, 1H), 3.62-4.32 (m, 3H), 2.60-2.85 (m, 1H), 1.90-2.38 (m, 4H), 1.22-1.32 (m, 3H), 0.76-1.54 (m, 1H)

Racemic mixture of cis-6-fluoro-N-({2-[5-fluoro-2-(2H-1,2,3-triazol-2-yl)benzoyl]-4-methyl-2-azabicyclo[3.1.1]heptan-3-yl}methyl)quinoxalin-2-amine

| Example | Starting materials | Gen. procedure | Yield (%) |
|---|---|---|---|
| 224 | P170 | T | 82 |

MS (m/z): 444.5 [MH]+
NMR (1H, CDCl3-d) δ: 8.13-8.30 (m, 1H), 7.67-7.89 (m, 2H), 7.30-7.44 (m, 2H), 6.99-7.27 (m, 4H), 4.87-5.19 (m, 1H), 3.69-4.17 (m, 3H), 2.76-2.95 (m, 1H), 2.59-2.72 (m, 3H), 1.97-2.46 (m, 4H), 1.73 (t, 1H), 1.14-1.27 (m, 3H)

Racemic mixture of cis-N-({4-methyl-2-[6-methyl-3-(2H-1,2,3-triazol-2-yl)pyridine-2-carbonyl]-2-azabicyclo[3.1.1]heptan-3-yl}methyl)-1,3-benzoxazol-2-amine
The racemic mixture was separated into the single enantiomers by preparative chiral HPLC Preparative chiral chromatography protocol:
Column: Whelk O1 (R,R) (25 × 2.0 cm), 10µ
Modifier: Methanol 25%
Flow rate (ml/min): 45
Pressure (bar): 120
Temperature (° C.): 38
UV detection: 220 nm
Loop: 500 µl
Injection: 13.8 mg (each injection)

| | | | |
|---|---|---|---|
| 226 | Enantiomer 1 | Rt: 9.7 min | 100% ee |

MS (m/z): 444.5 [MH]+
N-{[(3S,4R) or (3R,3S)-4-methyl-2-[6-methyl-3-(2H-1,2,3-triazol-2-yl)pyridine-2-carbonyl]-2-azabicyclo[3.1.1]heptan-3-yl]methyl}-1,3-benzoxazol-2-amine 3S,4R or 3R,4S enantiomer

| | | | |
|---|---|---|---|
| 227 | Enantiomer 2 | Rt: 12 min | 92.8% ee |

MS (m/z): 444.5 [MH]+
N-{[(3R,4S) or (3S,4R)-4-methyl-2-[6-methyl-3-(2H-1,2,3-triazol-2-yl)pyridine-2-carbonyl]-2-azabicyclo[3.1.1]heptan-3-yl]methyl}-1,3-benzoxazol-2-amine 3R,4S or 3S,4R enantiomer

| | | | |
|---|---|---|---|
| 228 | P171 | T | 68 |

MS (m/z): 464.3 [MH]+
NMR (1H, CDCl3-d) δ: 8.18-8.23 (m, 1H), 7.95-8.05 (m, 1H), 7.70-7.78 (m, 1H), 7.61-7.84 (m, 2H), 7.35-7.42 (m, 1H), 7.18-7.27 (m, 2H), 6.96-7.10 (m, 1H), 5.04-5.14 (m, 1H), 3.75-4.30 (m, 3H), 2.58-2.85 (m, 1H), 1.84-2.37 (m, 4H), 0.71-1.56 (m, 1H), 1.19-1.29 (m, 3H)

| Example | Starting materials | Gen. procedure | Yield (%) |
|---|---|---|---|

Racemic mixture of cis-N-({2-[5-fluoro-2-(2H-1,2,3-triazol-2-yl)benzoyl]-4-methyl-2-azabicyclo[3.1.1]heptan-3-yl}methyl)-[1,3]thiazolo[5,4-b]pyridin-2-amine
The racemic mixture was separated into the single enantiomers by preparative chiral HPLC Preparative chiral chromatography protocol:

| | Column | Chiralpak AD-H (25 × 2.0 cm), 5μ |
|---|---|---|
| | Mobile phase | n-Hexane/(Ethanol + Methanol 1/1) 70/30% v/v |
| | Flow rate (ml/min) | 17 ml/min |
| | DAD detection | 220 nm |
| | Loop | 12500 μl |
| | Injection | 45 mg (each injection) |

229 Enantiomer 1   Rt: 8.2 min   100% ee

MS (m/z): 464.3 [MH]+
N-{[(3S,4R) or (3R,4S)-2-[5-fluoro-2-(2H-1,2,3-triazol-2-yl)benzoyl]-4-methyl-2-azabicylco[3.1.1]heptan-3-yl]methyl}-[1,3]thiazolo[4,3-b]pyridin-2-amine 3S,4R or 3R,4S enantiomer 230 Enantiomer 2   Rt: 18 min   100% ee MS (m/z): 464.3 [MH]+
N-{[(3R,4S) or (3S,4R)-2-[5-fluoro-2-(2H-1,2,3-triazol-2-yl)benzoyl]-4-methyl-2-azabicyclo[3.1.1]heptan-3-yl]methyl}-[1,3]thiazolo[5,4-b]pyridin-2-amine 3R,4S or 3S,4R enantiomer

231   P175   T   47

MS (m/z): 471.4 [MH]+
NMR (1H, CDCl3-d) δ: 8.18-8.31 (m, 2H), 7.73-7.87 (m, 2H), 7.71-7.92 (m, 2H), 7.47-7.64 (m, 1H), 7.01-7.40 (br. s., 1H), 7.19-7.27 (m, 1H), 5.08-5.16 (m, 1H), 3.85-4.34 (m, 3H), 2.66-2.91 (m, 1H), 1.92-2.51 (m, 4H), 1.08-1.57 (m, 1H), 1.21-1.31 (m, 3H)

Racemic mixture of cis-3-{4-methyl-3-[({[1,3]thiazolo[5,4-b]pyridin-2-yl}amino)methyl]-2-azabicyclo[3.1.1]heptane-2-carbonyl}-4-(2H-1,2,3-triazol-2-yl)benzonitrile
The racemic mixture was separated into the single enantiomers by preparative chiral HPLC Preparative chiral chromatography protocol:

| | Column | Chiralpak AD-H (25 × 2.0 cm), 5μ |
|---|---|---|
| | Mobile phase | n-Hexane/(Ethanol + Methanol 1/1) 70/30% v/v |
| | Flow rate (ml/min) | 17 ml/min |
| | DAD detection | 220 nm |
| | Loop | 1000 μl |
| | Injection | 25 mg (each injection) |

| Example | Starting materials | Gen. procedure | Yield (%) |
|---|---|---|---|
| 232 | Enantiomer 1 | Rt: 11.4 min | 100% ee |

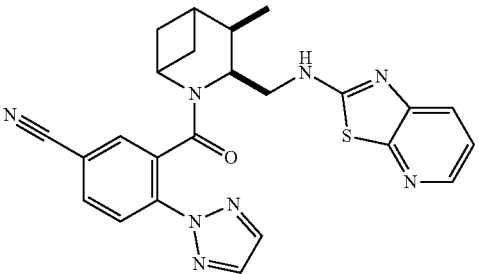

MS (m/z): 471.4 [MH]$^+$
3-[(3S,4R) or (3R,4S)-4-methyl-3-[({[1,3]thiazolo[5,4-b]pyridin-2-yl}amino)methyl]-2-azabicyclo[3.1.1]heptane-2-carbonyl]-4-(2H-1,2,3-triazol-2-yl)benzonitrile 3S,4R or 3R,4S enantiomer

| | | | |
|---|---|---|---|
| 233 | Enantiomer 2 | Rt: 17.7 min | 100% ee |

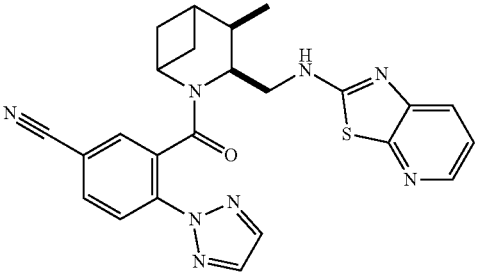

MS (m/z): 471.4 [MH]$^+$
3-[(3R,4S) or (3S,4R)-4-methyl-3-[({[1,3]thiazolo[5,4-b]pyridin-2-yl}amino)methyl]-2-azabicyclo[3.1.1]heptane-2-carbonyl]-4-(2H-1,2,3-triazol-2-yl)benzonitrile 3R,4S or 3S,4R enantiomer

| | | | |
|---|---|---|---|
| 234 | P173 | T | 84 |

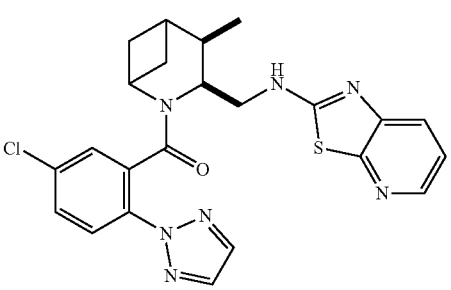

MS (m/z): 480.3 [MH]$^+$
NMR ($^1$H, CDCl$_3$-d) δ: 8.18-8.22 (m, 1H), 7.96-8.04 (m, 1H), 7.72-7.77 (m, 1H), 7.64-7.86 (m, 2H), 7.46-7.55 (m, 1H), 7.19-7.33 (m, 2H), 7.18-7.45 (br. s., 1H), 5.10 (m, 1H), 3.79-4.32 (m, 3H), 2.61-2.84 (m, 1H), 1.98-2.37 (m, 3H), 1.87-1.95 (m, 1H), 0.8-1.56 (m, 1H), 1.19-1.30 (m, 3H).

Racemic mixture of cis-N-({2-[5-chloro-2-(2H-1,2,3-triazol-2-yl)benzoyl]-4-methyl-2-azabicyclo[3.1.1]heptan-3-yl}methyl)-[1,3]thiazolo[5,4-b]pyridin-2-amine
The racemic mixture was separated into the single enantiomers by preparative chiral HPLC

| Preparative chiral chromatography protocol: | Column | Chiralpak AD-H (25 × 2.0 cm), 5μ |
|---|---|---|
| | Mobile phase | n-Hexane/(Ethanol + Methanol 1/1) 70/30% v/v |
| | Flow rate (ml/min) | 17 ml/min |
| | DAD detection | 220 nm |
| | Loop | 1250 μl |
| | Injection | 25 mg (each injection) |

-continued

| Example | Starting materials | Gen. procedure | Yield (%) |
|---|---|---|---|
| 235 | Enantiomer 1 | Rt: 9.9 min | 100% ee |

MS (m/z): 480.3 [MH]⁺
N-{[(3S,4R) or (3R,4S)-2-[5-chloro-2-(2H-1,2,3-triazol-2-yl)benzoyl]-4-methyl-2-azabicyclo[3.1.1]heptan-3-yl]methyl}-[1,3]thiazolo[5,4-b]pyridin-2-amine 3S,4R or 3R,4S enantiomer

| | | | |
|---|---|---|---|
| 236 | Enantiomer 2 | Rt: 17 min | 100% ee |

MS (m/z): 480.3 [MH]⁺
N-{[(3R,4S) or (3S,4R)-2-[5-chloro-2-(2H-1,2,3-triazol-2-yl)benzoyl]-4-methyl-2-azabicyclo[3.1.1]heptan-3-yl]methyl}-[1,3]thiazolo[5,4-b]pyridin-2-amine 3R,4S or 3S,4R enantiomer

| | | | |
|---|---|---|---|
| 237 | P175 | T | 40 |

MS (m/z): 483.4 [MH]⁺
NMR (¹H, CDCl₃-d) δ: 8.24-8.38 (m, 2H), 7.49-7.97 (m, 5H), 7.03-7.22 (br.s., 1H), 5.03-5.12 (m, 1H), 3.67-4.25 (m, 3H), 2.67-2.88 (m, 1H), 1.87-2.40 (m, 4H), 0.98-1.57 (m, 1H), 1.19-1.29 (m, 3H)

Racemic mixture of cis-3-[4-methyl-3-({[5-(trifluoromethyl)pyrazin-2-yl]amino}methyl)-2-azabicyclo[3.1.1]heptane-2-carbonyl]-4-(2H-1,2,3-triazol-2-yl)benzonitrile

| | | | |
|---|---|---|---|
| 238 | P175 | B1 | 20 |

MS (m/z): 483.4 [MH]⁺
NMR (¹H, CDCl₃-d) δ: 8.17-8.29 (m, 1H), 8.03-8.22 (m, 1H), 7.75-7.86 (m, 1H), 7.64-7.73 (m, 1H), 7.52-7.91 (m, 2 H), 7.49-7.58 (m, 1H), 7.30-7.41 (m, 1 H), 6.53-7.08 (m, 1 H), 5.06-5.16 (m, 1H), 4.05-4.35 (m, 1H), 3.90-4.00 (m, 1H), 3.73-3.99 (m, 1H), 2.67-2.88 (m, 1H), 1.91-2.41 (m, 4H), 1.27-1.33 (m, 3H), 0.96-1.57 (m, 1H)

Racemic mixture of cis-3-(3-{[(6-fluoroquinoxalin-2-yl)amino]methyl}-4-methyl-2-azabicyclo[3.1.1]heptane-2-carobnyl)-4-(2H-1,2,3-triazol-2-yl)benzonitrile -continued

| Example | Starting materials | Gen. procedure | Yield (%) |
|---|---|---|---|
| 239 | P173 | T | 65 |

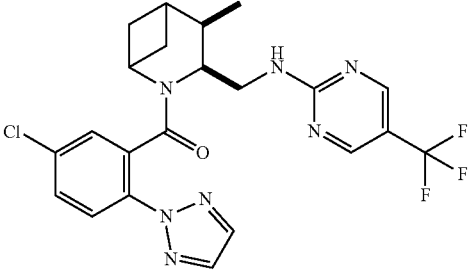

MS (m/z): 492.0 [MH]+
NMR (¹H, CDCl₃-d) δ: 8.40-8.62 (m, 2H), 7.92-8.09 (m, 1H), 7.73-7.85 (m, 2H), 7.43-7.55 (m, 1H), 7.07-7.34 (m, 1H), 6.76-7.16 (br.s., 1H), 4.94-5.13 (m, 1H), 3.68-4.35 (m, 3H), 2.56-2.82 (m, 1H), 1.79-12.38 (m, 4H), 0.82-1.55 (m, 1H), 1.16-1.25 (m, 3H)

Racemic mixture of cis-N-({2-[5-chloro-2-(2H-1,2,3-triazol-2-yl)benzoyl]-4-methyl-2-azabicyclo[3.1.1]heptan-3-yl}methyl)-5-(trifluoromethyl)pyrimidin-2-amine
The racemic mixture was separated into the single enantiomers by preparative chiral HPLC

| Preparative chiral chromatography protocol: | Column | Chiralpak AD-H (25 × 2.0 cm), 5μ |
|---|---|---|
| | Mobile phase | n-Hexane/(Ethanol + Methanol 1/1) 30/70% v/v |
| | Flow rate (ml/min) | 17 ml/min |
| | DAD detection | 220 nm |
| | Loop | 1900 μl |
| | Injection | 20.3 mg (each injection) |
| 240 | Enantiomer 1 | Rt: 5.9 min          100% ee |

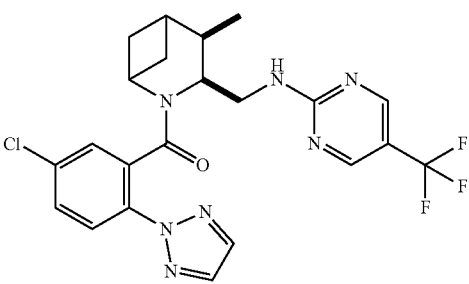

MS (m/z): 492.0 [MH]+
N-{[(3S,4R) or (3R,4S)-2-[5-chloro-2-(2H-1,2,3-triazol-2-yl)benzoyl]-4-methyl-2-azabicyclo[3.1.1]heptan-3-yl]methyl}-5-(trifluoromethyl)pyrimidin-2-amine 3S,4R or 3R,4S enantiomer

| 241 | Enantiomer 2 | Rt: 8.2 min          100% ee |
|---|---|---|

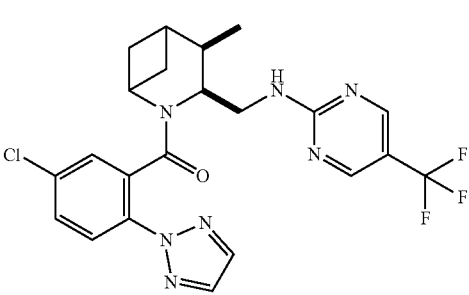

MS (m/z): 492.0 [MH]+
N-{[(3R,4S) or (3S,4R)-2-[5-chloro-2-(2H-1,2,3-triazol-2-yl)benzoyl]-4-methyl-2-azabicyclo[3.1.1]heptan-3-yl]methyl}-5-(trifluoromethyl)pyrimidin-2-amine 3R,4S or 3S,4R enantiomer

| 242 | P173 + P142 | T | 86 |

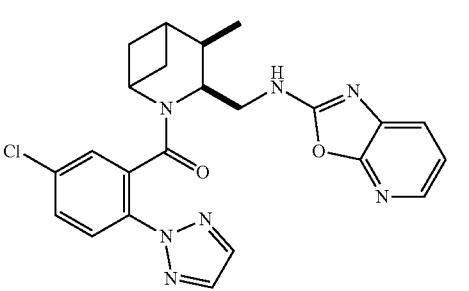

MS (m/z): 464.0 [MH]+
NMR (¹H, CDCl₃-d) δ: 7.94-8.07 (m, 2H), 7.73-7.85 (m, 2H), 7.59-7.64 (m, 1H), 7.47-7.55 (m, 1H), 7.25-7.33 (m, 1H), 7.05-7.18 (m, 2H), 5.03-5.15 (m, 1H), 3.80-4.26 (m, 3H), 2.59-2.88 (m, 1H), 1.85-2.38 (m, 4H), 0.67-1.58 (m, 1H), 1.16-1.29 (m, 3H)

| Example | Starting materials | Gen. procedure | Yield (%) |
|---|---|---|---|

Racemic mixture of cis-N-({2-[5-chloro-2-(2H-1,2,3-triazol-2-yl)benzoyl]-4-methyl-2-azabicyclo[3.1.1]heptan-3-yl}methyl)-[1,3]oxazolo[5,4-b]pyridin-2-amine The racemic mixture was separated into the single enantiomers by preparative chiral HPLC

| Preparative chiral chromatography protocol | | Column | Chiralpak AD-H (25 × 2.0 cm), 5µ |
|---|---|---|---|
| | | Mobile phase | n-Hexane/(Ethanol + Methanol 1/1) 60/40% v/v |
| | | Flow rate (ml/min) | 17 ml/min |
| | | DAD detection | 220 nm |
| | | Loop | 2000 µl |
| | | Injection | 34.4 mg (each injection) |
| 243 | | Enantiomer 1 | Rt: 9.0 min    100% ee |

MS (m/z): 464.0 [MH]+
N-{[(3S,4R) or (3R,4S)-2-[5-chloro-2-(2H-1,2,3-triazol-2-yl)benzoyl]-4-methyl-2-azabicyclo[3.1.1]heptan-3-yl]methyl}-[1,3]oxazolo[5,4-b]pyridin-2-amine 3S,4R or 3R,4S enantiomer

| 244 | | Enantiomer 2 | Rt: 14.3 min    100% ee |
|---|---|---|---|

MS (m/z): 464.0 [MH]+
N-{[(3R,4S) or (3S,4R)-2-[5-chloro-2-(2H-1,2,3-triazol-2-yl)benzoyl]-4-methyl-2-azabicyclo[3.1.1]heptan-3-yl]methyl}-[1,3]oxazolo[5,4-b]pyridin-2-amine 3R,4S or 3S,4R enantiomer

| 245 | | P177 | B1 | 44 |
|---|---|---|---|---|

MS (m/z): 473.1 [MH]+
NMR (1H, CDCl3-d) δ: 8.47-8.71 (m, 2H), 8.21-8.36 (m, 1H), 7.93-8.17 (m, 1H), 7.75-7.90 (m, 1H), 6.75-7.61 (br. s., 1H), 6.99-7.15 (m, 1H), 5.04-5.30 (m, 1H), 4.12-4.48 (m, 2H), 3.86-4.02 (m, 3H), 3.70-3.85 (m, 1H), 2.69-2.85 (m, 1H), 1.90-2.54 (m, 4H), 1.55-1.61 (m, 1H), 1.06-1.30 (m, 3H).

Racemic mixture of cis-N-({4-methyl-2-[1-methyl-4-(pyrimidin-2-yl)-1H-pyrazole-3-carbonyl]-2-azabicyclo[3.1.1]heptan-3-yl}methyl)-5-(trifluoromethyl)pyrazin-2-amine The racemic mixture was separated into the single enantiomers by preparative chiral HPLC

| Example | Starting materials | Gen. procedure | Yield (%) |
|---|---|---|---|
| 246 | P181 + P182 | Q | 65 |

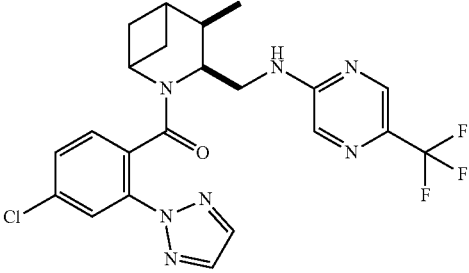

MS (m/z): 492.0 [MH]+
NMR (1H, CDCl3-d) δ: 8.28-8.40 (m, 1H), 8.04-8.13 (m, 1H), 7.74-7.94 (m, 1H,) 7.53-7.86 (m, 2H), 7.33-7.45 (m, 1H), 7.10-7.31 (m, 1H), 6.98-7.31 (m, 1H), 5.01-5.15 (m, 1H), 3.44-4.21 (m, 3H), 2.60-2.84 (m, 1H), 1.82-2.36 (m, 4H), 1.16-1.25 (m, 3H), 0.74-1.52 (m, 1H)

Racemic mixture of cis-N-({2-[4-chloro-2-(2H-1,2,3-triazol-2-yl)benzoyl]-4-methyl-2-azabicyclo[3.1.1]heptan-3-yl}methyl)-5-(trifluoromethyl)pyrazin-2-amine

| 247 | P173 | T | 65 |
|---|---|---|---|

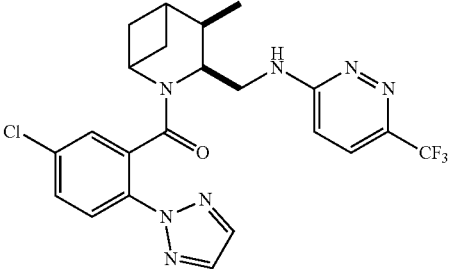

MS (m/z): 492.1 [MH]+
NMR (1H, CDCl3-d) δ: 7.93-8.02 (m, 1H), 7.53-7.85 (m, 2H), 7.46-7.53 (m, 1H), 7.33-7.43 (m, 1 H), 7.03-7.33 (m, 1H), 6.72-6.98 (m, 1H), 6.63-6.85 (m, 1H), 4.99-5.14 (m, 1H), 3.69-4.43 (m, 3H), 2.59-2.84 (m, 1H), 1.78-2.36 (m, 4H) 1.16-1.29 (m, 3H) 0.78-1.52 (m, 1H)

Racemic mixture of cis-N-({2-[5-chloro-2-(2H-1,2,3-triazol-2-yl)benzoyl]-4-methyl-2-azabicyclo[3.1.1]heptan-3-yl}methyl)-6-(trifluoromethyl)pyridazin-3-amine

| 248 | P184 | T | 20 |
|---|---|---|---|

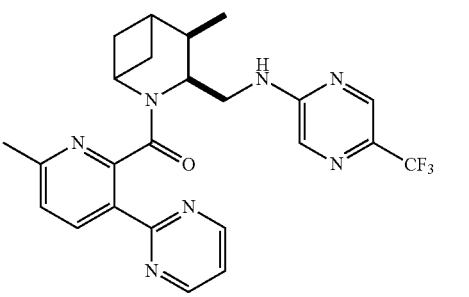

MS (m/z): 484.1 [MH]+
NMR (1H, CDCl3-d) δ: 8.50-8.84 (m, 2H), 8.39-8.60 (m, 1H), 8.20-8.36 (m, 1H), 7.71-7.88 (m, 1 H), 7.66-7.87 (m, 1H), 7.21-7.36 (m, 1H), 7.05-7.31 (m, 1H), 4.85-5.20 (m, 1H), 3.53-4.19 (m, 3H), 2.71-2.98 (m, 1H), 2.55-2.68 (m, 3H), 1.87-2.49 (m, 4H), 1.18-1.81 (m,1 H), 1.13-1.28 (m, 3 H)

Racemic mixture of cis-N-({4-methyl-2-[6-methyl-3-(pyrimidin-2-yl)pyridine-2-carbonyl]-2-azabicyclo[3.1.1]heptan-3-yl}methyl)-5-(trifluoromethyl)pyrazin-2-amine General Procedure C1:

To a solution of 2-azabicyclo[3.1.1]heptane (e.g. p171 and p173, 1 eq) in 1,4-Dioxane (~10 vol) was added the appropriate aryl halide (e.g. p187, 1.1 eq), Pd2(dba)3 (0.1 eq), dicyclohexyl-[2-[2,4,6-tri(propan-2-yl)phenyl]phenyl] phosphine (0.2 eq), and sodium tert-butoxide (1.1 eq). The mixture was heated at 110° C. O/N. The mixture was left to cool to room temperature, diluted with EtOAc and washed with water. The organic layer was dried and evaporated under reduced pressure. The residue was purified by FC on silica gel and/or NH column (eluting mixture Cy/AcOEt) and/or C18 column (eluent from water+0.1% formic acid/ MeCN+0.1% formic acid) to afford the title compound.

| Example | Starting materials | Gen. procedure | Yield (%) |
|---------|-------------------|----------------|-----------|

The racemic mixture of Example 248 was separated into the single enantiomers by preparative chiral HPLC Preparative chiral chromatography protocol:
- Column: Chiralpak AS-H (25 × 2.0 cm), 5 µ
- Modifier: (Mehanol + 0.1% isopropylamine) 20%
- Flow rate (ml/min): 45 ml/min
- Pressure (bar): 120
- Temperature (° C.): 38
- UV detection: 220 nm
- Loop: 700 µl
- Injection: 9 mg (each injection)

249    Enantiomer 1    Rt: 6.2 min    100% ee

MS (m/z): 484.1 [MH]$^+$
N-{[(3S,4R) or (3R,4S)-4-methyl-2-[6-methyl-3-(pyrimidin-2-yl)pyridine-2-carbonyl]-2-azabicyclo[3.1.1]heptan-3-yl]methyl}-5-(trifluoromethyl)pyrazin-2-amine 3S,4R or 3R,4S enantiomer 250    Enantiomer 2    Rt: 10.4 min    100% ee MS (m/z): 484.1 [MH]$^+$
N-{[(3R,4S) or (3S,4R)-4-methyl-2-[6-methyl-3-(pyrimidin-2-yl)pyridine-2-carbonyl]-2-azabicyclo[3.1.1]heptan-3-yl]methyl}-5-(trifluoromethyl)pyrazin-2-amine 3R,4S or 3S,4R enantiomer

251    P171    T    76

MS (m/z): 476.1 [MH]$^+$
NMR ($^1$H, CDCl$_3$-d) δ: 8.45-8.59 (m, 2H), 7.94-8.05 (m, 1H), 7.72-7.83 (m, 2H), 7.17-7.27 (m, 1H), 6.81-7.12 (m, 2H), 4.93-5.12 (m, 1H), 3.64-4.34 (m, 3H), 2.56-2.81 (m, 1H), 1.74-2.33 (m, 4H), 1.13-1.23 (m, 3H), 0.70-1.53 (m, 1H)

Racemic mixture of cis N-({2-[5-fluoro-2-(2H-1,2,3-triazol-2-yl)benzoyl]-4-methyl-2-azabicyclo[3.1.1]heptan-3-yl}methyl)-5-(trifluoromethyl)pyrimidin-2-amine -continued

| Example | Starting materials | Gen. procedure | Yield (%) |
|---|---|---|---|
| 252 | P181 + P185 | Q | 60 |

MS (m/z): 476.1 [MH]+
NMR (¹H, CDCl₃-d) δ: 8.30-8.38 (m, 1H), 7.75-7.95 (m, 2H), 7.51-7.85 (m, 2H), 7.07-7.38 (m, 3H), 5.04-5.17 (m, 1H), 3.63-4.21 (m, 3H), 2.62-2.85 (m, 1H), 1.84-2.36 (m, 4H), 1.16-1.27 (m, 3H), 0.75-1.50 (m, 1H)

Racemic mixture of cis N-({2-[4-fluoro-2-(2H-1,2,3-triazol-2-yl)benzoyl]-4-methyl-2-azabicyclo[3.1.1]heptan-3-yl}methyl)-5-(trifluoromethyl)pyrazin-2-amine

| | | | |
|---|---|---|---|
| 253 | P181 + P186 | Q | 72 |

MS (m/z): 476.1 [MH]+
NMR (¹H, CDCl₃-d) δ: 6.69-8.43 (m, 8 H), 3.37-5.35 (m, 4 H), 2.56-2.94 (m, 1 H), 1.27-2.52 (m, 5 H), 0.97-1.26 (m, 3 H)

Racemic mixture of cis N-({2-[2-fluoro-6-(2H-1,2,3-triazol-2-yl)benzoyl]-4-methyl-2-azabicyclo[3.1.1]heptan-3-yl}methyl)-5-(trifluoromethyl)pyrazin-2-amine

| | | | |
|---|---|---|---|
| 254 | P181 + P62 | Q | 83 |

MS (m/z): 472.1 [MH]+
NMR (¹H, CDCl₃-d) δ: 8.29-8.36 (m, 1H), 7.79-7.96 (m, 2H), 7.46-7.78 (m, 2H), 7.29-7.38 (m, 2H), 6.85-7.18 (m, 1H), 5.04-5.12 (m, 1H), 3.54-4.19 (m, 3H), 2.56-2.83 (m, 1H), 2.34-2.46 (m, 3H), 1.77-2.32 (m, 4H), .15-1.24 (m, 3H), 0.64-1.48 (m, 1H)

Racemic mixture of cis N-({4-methyl-2-[5-methyl-2-(2H-1,2,3-triazol-2-yl)benzoyl]-2-azabicyclo[3.1.1]heptan-3-yl}methyl)-5-(trifluoromethyl)pyrazin-2-amine The racemic mixture was separated into the single enantiomers by preparative chiral HPLC

| Preparative chiral chromatography protocol: | | |
|---|---|---|
| | Column | Chiralpak AD-H (25 × 2.0 cm), 5 μ |
| | Mobile phase | n-Hexane/(Ethanol + Methanol 1/1) 55/45% v/v |
| | Flow rate (ml/min) | 17 ml/min |
| | DAD detection | 220 nm |
| | Loop | 2000 μl |
| | Injection | 31 mg (each injection) |

-continued

| Example | Starting materials | Gen. procedure | Yield (%) |
|---|---|---|---|
| 255 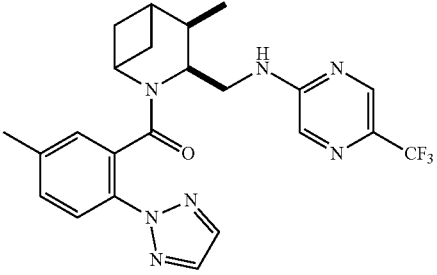<br>3S,4R or 3R,4S enantiomer | Enantiomer 1 | Rt: 5.9 min | 100% ee |
| | MS (m/z): 472.1 [MH]+<br>N-{[(3S,4R) or (3R,4S)-4-methyl-2-[5-methyl-2-(2H-1,2,3-triazol-2-yl)benzoyl]-2-azabicyclo[3.1.1]heptan-3-yl]methyl}-5-(trifluoromethyl)pyrazin-2-amine | | |
| 256 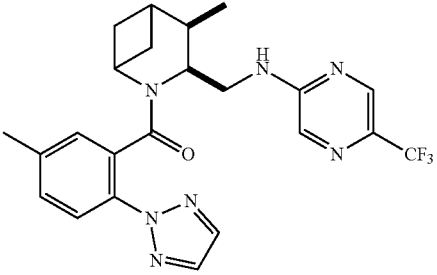<br>3R,4S or 3S,4R enantiomer | Enantiomer 2 | Rt: 11.7 min | 100% ee |
| | MS (m/z): 472.1 [MH]+<br>N-{[(3R,4S) or (3S,4R)-4-methyl-2-[5-methyl-2-(2H-1,2,3-triazol-2-yl)benzoyl]-2-azabicyclo[3.1.1]heptan-3-yl]methyl}-5-(trifluoromethyl)pyrazin-2-amine | | |
| 257 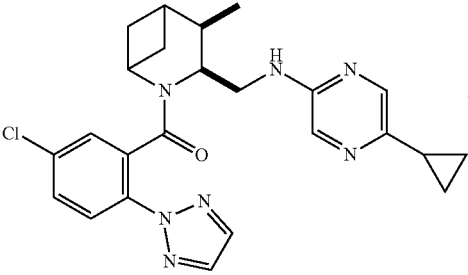<br>Racemic mixture of cis N-({2-[5-chloro-2-(2H-1,2,3-triazol-2-yl)benzoyl]-4-methyl-2-azabicyclo[3.1.1]heptan-3-yl}methyl)-5-cyclopropylpyrazin-2-amine | P173 + P187 | C1 | 11 |
| | MS (m/z): 464.1 [MH]+<br>NMR (1H, CDCl3-d) δ: 7.89-8.00 (m, 2H), 7.71-7.85 (m, 1H), 7.54-7.83 (m, 2H), 7.42-7.53 (m, 1H), 7.01-7.34 (m, 1H), 5.85-6.22 (m, 1H), 4.94-5.11 (m, 1H), 3.51-4.15 (m, 3H), 2.58-2.80 (m, 1H), 1.83-2.33 (m, 5H), 1.15-1.25 (m, 3H), 0.87-0.95 (m, 4H), 0.80-1.54 (m, 1H) | | |
| 258 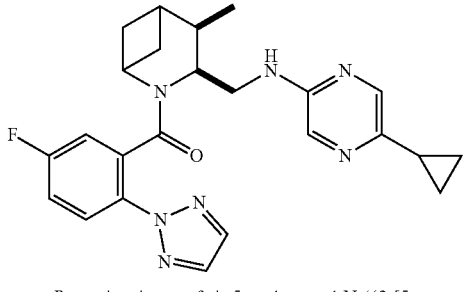<br>Racemic mixture of cis 5-cyclopropyl-N-({2-[5-fluoro-2-(2H-1,2,3-triazol-2-yl)benzoyl]-4-methyl-2-azabicyclo[3.1.1]heptan-3-yl}methyl)pyrazin-2-amine | P171 + P187 | C1 | 19 |
| | MS (m/z): 448.1 [MH]+<br>NMR (1H, CDCl3-d) δ: 7.53-8.00 (m, 5H), 7.42-7.53 (m, 1H), 7.01-7.34 (m, 1H), 5.85-6.19 (m, 1H), 4.95-5.08 (m, 1H), 3.51-4.14 (m, 3H), 2.56-2.81 (m, 1H), 1.83-2.33 (m, 5H), 1.17-1.25 (m, 3H), 0.87-0.96 (m, 4H), 0.8-1.53 (m, 1H). | | |

| Example | Starting materials | Gen. procedure | Yield (%) |
|---|---|---|---|
| 259 | P173 + P188 | T | 38 |

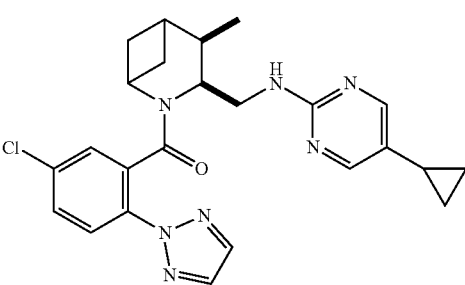

MS (m/z): 464.1 [MH]+
NMR (1H, CDCl3-d) δ: 8.13 (s, 2H), 7.89-8.03 (m, 1H), 7.77-7.82 (m, 2H), 7.42-7.51 (m, 1H), 7.05-7.34 (m, 1H), 5.88-6.33 (m, 1H), 4.88-5.09 (m, 1H), 3.63-4.25 (m, 3H), 2.57-2.79 (m, 1H), 1.69-2.31 (m, 5H), 1.17-1.24 (m, 3H), 0.89-0.96 (m, 2H), 0.81-1.52 (m, 1H), 0.58-0.66 (m, 2H)

Racemic mixture of cis N-({2-[5-chloro-2-(2H-1,2,3-triazol-2-yl)benzoyl]-4-methyl-2-azabicyclo[3.1.1]heptan-3-yl}methyl)-5-cyclopropylpyrimidin-2-amine

| | | | |
|---|---|---|---|
| 260 | P171 + P188 | T | 35 |

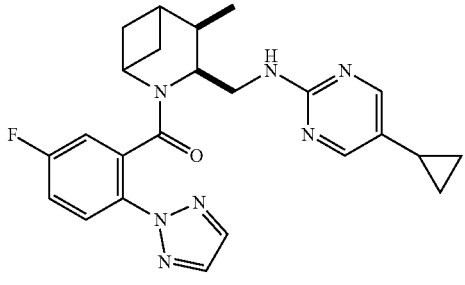

MS (m/z): 448.1 [MH]+
NMR (1H, CDCl3-d) δ: 8.08-8.18 (m, 2H), 7.89-8.03 (m, 1H), 7.70-7.84 (m, 2H), 7.13-7.26 (m, 1H), 6.68-7.09 (m, 1H), 5.91-6.32 (m, 1H), 4.88-5.06 (m, 1H), 3.59-4.25 (m, 3H), 2.54-2.78 (m, 1H), 1.68-2.28 (m, 5H), 1.14-1.24 (m, 3H), 0.87-0.96 (m, 2H), 0.76-1.50 (m, 1H), 0.58-0.64 (m, 2H)

Racemic mixture of cis 5-cyclopropyl-N-({2-[5-fluoro-2-(2H-1,2,3-triazol-2-yl)benzoyl]-4-methyl-2-azabicyclo[3.1.1]heptan-3-yl}methyl)pyrimidin-2-amine

Example 261

Compounds of the examples were assayed for their Orexin type 1 and type 2 receptor binding activity using the Scintillation Proximity Assay and Intracellular Calcium Measurement methods described above. Results are shown in Table 1.

TABLE 1

| | $OX_1$ and $OX_2$ binding and functional antagonist values for representative examples. | | | |
|---|---|---|---|---|
| Example | OX1 pKi (SPA binding) | OX2 pKi (SPA binding) | OX1 fpKi (FLIPR) | OX2 fpKi (FLIPR) |
| 1 | 8.14 | 6.97 | 8.20 | 6.53 |
| 3 | | | 8.63 | 7.09 |
| 4 | | | 8.24 | 6.79 |
| 6 | | | 8.29 | 7.03 |
| 7 | | | 8.15 | 6.85 |
| 9 | | | 8.4 | 7.1 |
| 10 | | | 7.83 | 6.46 |
| 12 | | | 7.56 | 5.98 |
| 13 | | | 8.11 | 6.77 |
| 15 | | | 8.39 | 7.28 |
| 16 | | | 7.54 | 6.27 |
| 17 | | | 7.82 | 6.45 |
| 19 | | | 7.04 | 6.01 |
| 20 | | | 7.64 | 6.41 |
| 22 | | | 7.46 | 6.76 |

TABLE 1-continued

| | $OX_1$ and $OX_2$ binding and functional antagonist values for representative examples. | | | |
|---|---|---|---|---|
| Example | OX1 pKi (SPA binding) | OX2 pKi (SPA binding) | OX1 fpKi (FLIPR) | OX2 fpKi (FLIPR) |
| 24 | | | 7.33 | 6.12 |
| 25 | | | 7.52 | 6.68 |
| 26 | | | 7.74 | 6.74 |
| 29 | | | 7.33 | 6.21 |
| 31 | | | 7.01 | 6.11 |
| 32 | | | 7.14 | 6.29 |
| 33 | | | 7.62 | 6.96 |
| 35 | | | 7.13 | 6.2 |
| 36 | | | 7.17 | 6.7 |
| 38 | 7.61 | 6.9 | | |
| 39 | 7.64 | 6.19 | | |
| 40 | 7.33 | 6.19 | | |
| 41 | | | 7.65 | 6.65 |
| 42 | | | 7.74 | 6.97 |
| 44 | 7.15 | 6.38 | | |
| 45 | 7.22 | 7.12 | | |
| 46 | 7.62 | 6.51 | | |
| 47 | 7.61 | 6.91 | | |
| 48 | 7.45 | 6.53 | | |
| 49 | 7.88 | 6.81 | | |
| 50 | 7.66 | 6.52 | | |
| 51 | 7.22 | ND | | |
| 52 | 7.71 | 6.79 | | |
| 53 | 7.58 | 7.13 | | |
| 54 | 7.77 | 7.03 | | |

TABLE 1-continued

OX$_1$ and OX$_2$ binding and functional antagonist values for representative examples.

| Example | OX1 pKi (SPA binding) | OX2 pKi (SPA binding) | OX1 fpKi (FLIPR) | OX2 fpKi (FLIPR) |
|---|---|---|---|---|
| 55 | 7.38 | 6.49 | | |
| 56 | 7.98 | 7.12 | | |
| 57 | 7.35 | 6.86 | | |
| 58 | 7.4 | 6.76 | | |
| 59 | 8.1 | 7.46 | | |
| 60 | 8.27 | 7.39 | | |
| 61 | 9.12 | 8.03 | | |
| 63 | 8.06 | 6.37 | | |
| 64 | | | 8.5 | 6.55 |
| 67 | | | 8.86 | 6.25 |
| 68 | | | 9.13 | 6.86 |
| 69 | | | 7.89 | 6.53 |
| 70 | | | 7.87 | 5.61 |
| 71 | | | 8.47 | 7.05 |
| 74 | | | 7.54 | 6.23 |
| 75 | | | 7.98 | 6.98 |
| 77 | | | 7.66 | <6 |
| 78 | | | 7.45 | 6.63 |
| 81 | | | 8.01 | 7.23 |
| 82 | | | 8 | 5.65 |
| 83 | | | 8.46 | 7.33 |
| 84 | | | 7.12 | 5.73 |
| 85 | | | 8.2 | 5.98 |
| 86 | 7.05 | 5.89 | | |
| 88 | 7.92 | 6.56 | | |
| 89 | 8.86 | 6 | | |
| 91 | 8.46 | 7.45 | | |
| 93 | 8.71 | 6.39 | | |
| 94 | 8.04 | 6.35 | | |
| 95 | 8.09 | 6.6 | | |
| 96 | 8.18 | 6.88 | | |
| 97 | 7.74 | 6.51 | | |
| 98 | 7.86 | 6.75 | | |
| 99 | 7.37 | 6.18 | | |
| 100 | 7.03 | 5.96 | | |
| 101 | 8.02 | 6.15 | | |
| 102 | 7.23 | 5.71 | | |
| 103 | 8 | 5.6 | | |
| 105 | 8.2 | 5.88 | | |
| 106 | 8.16 | 6.12 | | |
| 108 | 8.49 | 6.39 | | |
| 109 | 7.51 | 5.89 | | |
| 110 | 7 | 6.06 | | |
| 111 | 7.53 | 5.99 | | |
| 112 | 7.83 | 5.92 | | |

ND: Not determined

Example 262

Compounds of the examples were assayed for their Orexin type 1 and type 2 receptor binding using the Scintillation Proximity Assay described above. Results are shown in Table 2.

TABLE 2

OX$_1$ and OX$_2$ binding values for representative examples.

| Example | OX1 pKi (SPA binding) | OX2 pKi (SPA binding) |
|---|---|---|
| 113 | 8.21 | 5.72 |
| 115 | 8.5 | 5.93 |
| 116 | 7.32 | 5.26 |
| 117 | 7.13 | 5.47 |
| 118 | 7.39 | 5.75 |
| 119 | 7.08 | 5.77 |
| 120 | 8 | 5.98 |
| 121 | 7.36 | 5.54 |
| 122 | 7.22 | 5.4 |
| 123 | 8.02 | 6.12 |
| 124 | 8.43 | 6.3 |
| 126 | 7.39 | 5.7 |
| 127 | 7.91 | 6.1 |
| 128 | 6.85 | 5.61 |
| 129 | 6.81 | 5.14 |
| 130 | 6.9 | 6.08 |
| 131 | 7.02 | 6.1 |
| 132 | 7.97 | 6.72 |
| 133 | 7.25 | 6.79 |
| 134 | 7.85 | 7.03 |
| 135 | 7.78 | 6.39 |
| 136 | 7.26 | 5.92 |
| 137 | 7.97 | 6.34 |
| 138 | 8.08 | 7.05 |
| 139 | 7.85 | 6.18 |
| 140 | 7.49 | 6.22 |
| 141 | 6.91 | 6.45 |
| 142 | 7 | 6.33 |
| 143 | 7.14 | 5.93 |
| 144 | 7.96 | 6.83 |
| 145 | 7.03 | 5.62 |
| 146 | 6.88 | 5.53 |
| 147 | 7.57 | 6.66 |
| 148 | 6.85 | 5.62 |
| 149 | 6.82 | 5.72 |
| 150 | 7.5 | 6.14 |
| 151 | 7.59 | 5.42 |
| 152 | 8.68 | 6.1 |
| 154 | 9.06 | 6.23 |
| 155 | 7.71 | 5.49 |
| 156 | 7.53 | 5.35 |
| 157 | 7.84 | 5.63 |
| 158 | 8.4 | 5.74 |
| 159 | 6.84 | 4.59 |
| 160 | 8.68 | 5.98 |
| 161 | 7.32 | 5.2 |
| 162 | 8.83 | 5.59 |
| 164 | 8.93 | 5.68 |
| 165 | 7.63 | 4.83 |
| 166 | 6.99 | 4.29 |
| 167 | 8.12 | 5.13 |
| 168 | 8.46 | 5.88 |
| 170 | 8.86 | 5.99 |
| 171 | 8.9 | 6.32 |
| 173 | 9.36 | 6.53 |
| 174 | 8.82 | 7.06 |
| 175 | 8.41 | 6.02 |
| 177 | 8.95 | 6.46 |
| 178 | 8.52 | 5.63 |
| 180 | 8.78 | 5.58 |
| 181 | 8.09 | 5.09 |
| 183 | 8.31 | 5.26 |
| 184 | 8.08 | 5.07 |
| 186 | 8.42 | 5.36 |
| 187 | 8.19 | 5.63 |
| 189 | 8.51 | 5.92 |
| 190 | 7.8 | 4.98 |
| 192 | 8.13 | 5.19 |
| 193 | 7.57 | 4.64 |
| 194 | 7.51 | 4.66 |
| 196 | 7.65 | 5.74 |
| 197 | 6.99 | 5.76 |
| 198 | 8.07 | 6.27 |
| 200 | 8.24 | 6.37 |
| 201 | 7.97 | 6.55 |
| 202 | 6.71 | 6.02 |
| 203 | 8.17 | 5.05 |
| 205 | 8.59 | 5.34 |
| 206 | 7.79 | 5.06 |
| 207 | 8.46 | 6.44 |
| 209 | 8.74 | 6.8 |
| 210 | 8.69 | 5.84 |
| 211 | 8.91 | 6.25 |
| 213 | 7.91 | 4.39 |

TABLE 2-continued

OX₁ and OX₂ binding values for representative examples.

| Example | OX1 pKi (SPA binding) | OX2 pKi (SPA binding) |
|---|---|---|
| 215 | 8.15 | 4.79 |
| 216 | 6.94 | 4.62 |
| 217 | 6.85 | 5.29 |
| 218 | 8.33 | 5.47 |
| 219 | 8.71 | 5.79 |
| 221 | 7.73 | 4.94 |
| 223 | 8.13 | 4.98 |
| 224 | 8.04 | 6.19 |
| 225 | 8.32 | 5.22 |
| 226 | 8.46 | 5.39 |
| 227 | 7.11 | 4.9 |
| 228 | 7.94 | 5.04 |
| 230 | 8.46 | 5.32 |
| 231 | 8.2 | 5.21 |
| 233 | 8.41 | 5.11 |
| 234 | 8.45 | 5.46 |
| 236 | 8.99 | 5.7 |
| 237 | 7.33 | 4.82 |
| 238 | 7.98 | 6.32 |
| 239 | 8.04 | 5.51 |
| 241 | 8.27 | 5.59 |
| 242 | 8.1 | 5.14 |
| 244 | 8.25 | 5.18 |
| 245 | 7.55 | 4.49 |
| 246 | 7.57 | 5.61 |
| 247 | 6.74 | 4.88 |
| 248 | 7.76 | 4.58 |
| 249 | 5.12 | <4.5 |
| 250 | 7.9 | 4.85 |
| 251 | 7.65 | 4.69 |
| 252 | 7.19 | 4.95 |
| 253 | 7.88 | 5 |
| 254 | 8.37 | 5.12 |
| 256 | 8.75 | 5.18 |
| 257 | 7.58 | 5.41 |
| 258 | 7.07 | 5.35 |
| 259 | 7.66 | 5.32 |
| 260 | 7.45 | 4.89 |

Example 263—Fraction Unbound

Measurement of Brain Fraction Unbound (Equilibrium Dialysis)

Brain fractions unbound were determined using equilibrium dialysis in a 96-well format as described in Kalvass and Maurer, 2002. Brain homogenates were prepared using 2 ml/g CSF surrogate (7.30 g/l NaCl, 186.4 mg/l KCl, 239.9 mg/l $MgCl_2$, 185.2 mg/l $CaCl_2$, and 536.0 mg/l $Na_2HPO_4.7H_2O$, pH 7.4). Dialysis membranes (12-14-kDA cutoff) obtained from Spectrum Laboratories Inc. (Rancho Dominguez, Calif.) were conditioned in water (HPLC grade) for 60 min, followed by 20 min in 20% ethanol, and 15 min in CSF surrogate.

Assay compound concentrations were 5 µM. Diluted brain homogenate was spiked with the compound of interest, and 150-µl aliquots were loaded into the 96-well equilibrium dialysis apparatus and dialyzed against an equal volume of CSF surrogate. Equilibrium was achieved by incubating the 96-well equilibrium dialysis apparatus in a temperature-controlled incubator at 37° C. for 5 h, using an orbital shaker at 125 rpm. At the end of the incubation period, 50-µl aliquots of brain homogenate and buffer were transferred to a 96-well plate, and the composition in each tube was balanced with control fluid to equalize the brain and buffer volumes. Sample extraction was performed by addition of 400 µl of acetonitrile containing internal standard (rolipram). The samples were then vortex-mixed and centrifuged, and 100 µl of supernatants was transferred into a 96-well plate, diluted with 200 µl of 16% acetonitrile/water, and analyzed by liquid chromatography-tandem mass spectrometry (LC-MS/MS).

The brain unbound fraction (FU brain) was calculated from the ratio of analyte/internal standard peak area ratios determined in buffer versus brain homogenate samples using equation (1), which accounts for the effect of tissue dilution on unbound fraction (Kalvass and Maurer, 2002):

$$f_{u-diluted} = \frac{1/D}{(1/f_{u-diluted} - 1) + 1/D} \quad (1)$$

where D is the dilution factor in brain homogenate and fu-diluted is the measured free fraction of diluted brain tissue.

Results

Brain fraction unbound data are reported in Table 3:

TABLE 3

| Example compound | FU brain (%, rat) |
|---|---|
| 230 | 4.38 |
| 233 | 6.6 |
| 186 | 14.7 |
| 213 | 8.76 |
| 183 | 2.56 |
| 167 | 5.93 |
| 215 | 7.61 |
| 223 | 2.20 |
| 165 | 4.77 |
| 205 | 0.89 |
| 115 | 1.51 |
| 105 | 1.16 |
| 93 | 2.58 |

These results demonstrate that the compounds of the invention show adequate free fraction in brain.

The invention claimed is:
1. A compound of formula I,

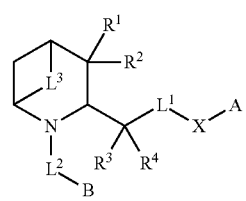

wherein:
$L^1$ represents a direct bond or —[$CR^5R^6$]—;
X represents a direct bond, —O—, —N($R^x$)—, —$CH_2$— or —S—;
A represents an aryl, heteroaryl, cycloalkyl or heterocycloalkyl group, each of which is optionally substituted with one or more $Q^1$ groups;
$L^2$ represents a direct bond or —C(=O)—;
B represents an aryl, heteroaryl, cycloalkyl or heterocycloalkyl group, each of which is optionally substituted with one or more $Q^2$ groups;
$L^3$ represents —$CH_2$— or —$CH_2CH_2$—;
$R^1$ and $R^2$ independently represent hydrogen, halogen, —$OR^7$, —$NR^8R^9$, $C_{1-12}$ alkyl, $C_{2-12}$ alkenyl, $C_{2-12}$ alkynyl or $C_{3-12}$ cycloalkyl (which latter four groups are optionally substituted by one or more $E^1$ substituents); or $R^1$ and $R^2$ together with the carbon atom to which they are bound form C=O, C=C($R^{10}$)$R^{11}$ or a $C_{3-6}$ cycloalkyl group optionally substituted by one or more $E^2$ substituents;

$R^3$, $R^4$, $R^5$ and $R^6$ independently represent hydrogen, halogen, $C_{1-12}$ alkyl, $C_{2-12}$ alkenyl, $C_{2-12}$ alkynyl or $C_{3-6}$ cycloalkyl (which latter four groups are optionally substituted by one or more $E^3$ substituents); or any relevant pair of $R^3$, $R^4$, $R^5$ and $R^6$ form, together with the carbon atom to which they are bound, C=O or a $C_{3-6}$ cycloalkyl group optionally substituted by one or more $E^4$ substituents;

$R^7$, $R^8$, $R^9$, $R^{10}$ and $R^{11}$ independently represent hydrogen or a $C_{1-6}$ alkyl group optionally substituted by one or more halo atoms;

$R^x$ represents hydrogen, $C_{1-6}$ alkyl, or $C_{3-6}$ cycloalkyl (which latter two groups are optionally substituted by one or more halo atoms);

$Q^1$ and $Q^2$ independently represent halogen, —CN, —NHCOR$^{12}$, $C_{1-6}$ alkyl, $C_{3-6}$ cycloalkyl, —O—$C_{1-6}$ alkyl, aryl or heteroaryl (which latter five groups are optionally substituted by one or more substituents selected from halogen, methyl and halomethyl);

$E^1$, $E^2$, $E^3$ and $E^4$ independently represent halogen or a $C_{1-6}$ alkyl group optionally substituted by one or more halo atoms;

$R^{12}$ represents $C_{1-6}$ alkyl or phenyl;

or a pharmaceutically acceptable ester, amide, salt, or solvate thereof.

2. A compound as claimed in claim 1, wherein X represents —O—, —N($R^x$)— or —CH$_2$—.

3. A compound as claimed in claim 2, wherein the —[CR$^3$R$^4$]—L$^1$—X— linker has one of the following structures:

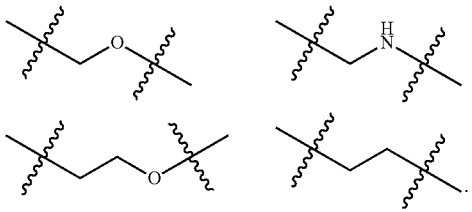

4. A compound as claimed in claim 1, wherein L$^2$ represents —C(=O)—.

5. A compound as claimed in claim 1, wherein $R^1$ and $R^2$ independently represent hydrogen, halogen, —OR$^7$, or $C_{1-4}$ alkyl optionally substituted by one or more halo atoms.

6. A compound as claimed in claim 1, wherein A represents an aryl or heteroaryl group, each of which is optionally substituted by one or more $Q^1$ groups.

7. A compound as claimed in claim 1, wherein B represents an aryl or heteroaryl group, each of which is optionally substituted by one or more $Q^2$ substituents.

8. A compound as claimed in claim 1, wherein the compound is an antagonist of OX1R and/or OX1R/OX2R selected from the group consisting of:

3-[(4-fluorophenoxy)methyl]-2-(2-methyl-5-phenyl-1,3-thiazole-4-carbonyl)-2-azabicyclo[3.1.1]heptane;
(3R)-3-[(4-fluorophenoxy)methyl]-2-(2-methyl-5-phenyl-1,3-thiazole-4-carbonyl)-2-azabicyclo[3.1.1]heptane;
(3S)-3-[(4-fluorophenoxy)methyl]-2-(2-methyl-5-phenyl-1,3-thiazole-4-carbonyl)-2-azabicyclo[3.1.1]heptane;
3-(4-fluorophenoxymethyl)-2-{[6-methyl-3-(1,3-thiazol-2-yl)pyridin-2-yl]carbonyl}-2-azabicyclo[3.1.1]heptane;
(3R)-3-(4-fluorophenoxymethyl)-2-{[6-methyl-3-(1,3-thiazol-2-yl)pyridin-2-yl]carbonyl}-2-azabicyclo[3.1.1]heptane;
(3S)-3-(4-fluorophenoxymethyl)-2-{[6-methyl-3-(1,3-thiazol-2-yl)pyridin-2-yl]carbonyl}-2-azabicyclo[3.1.1]heptane;
3-(4-fluorophenoxymethyl)-2-{[5-methyl-2-(1,3-thiazol-2-yl)phenyl]carbonyl}-2-azabicyclo[3.1.1]heptane;
(3R)-3-(4-fluorophenoxymethyl)-2-{[5-methyl-2-(1,3-thiazol-2-yl)phenyl]carbonyl}-2-azabicyclo[3.1.1]heptane;
(3S)-3-(4-fluorophenoxymethyl)-2-{[5-methyl-2-(1,3-thiazol-2-yl)phenyl]carbonyl}-2-azabicyclo[3.1.1]heptane;
3-(4-fluorophenoxymethyl)-2-{[5-methyl-2-(2H-1,2,3-triazol-2-yl)phenyl]carbonyl}-2-azabicyclo[3.1.1]heptane;
(3R)-3-(4-fluorophenoxymethyl)-2-{[5-methyl-2-(2H-1,2,3-triazol-2-yl)phenyl]carbonyl}-2-azabicyclo[3.1.1]heptane;
(3S)-3-(4-fluorophenoxymethyl)-2-{[5-methyl-2-(2H-1,2,3-triazol-2-yl)phenyl]carbonyl}-2-azabicyclo[3.1.1]heptane;
3-(4-fluorophenoxymethyl)-2-{[6-methyl-3-(pyrimidin-2-yl)pyridin-2-yl]carbonyl}-2-azabicyclo[3.1.1]heptane;
(3R)-3-(4-fluorophenoxymethyl)-2-{[6-methyl-3-(pyrimidin-2-yl)pyridin-2-yl]carbonyl}-2-azabicyclo[3.1.1]heptane;
(3S)-3-(4-fluorophenoxymethyl)-2-{[6-methyl-3-(pyrimidin-2-yl)pyridin-2-yl]carbonyl}-2-azabicyclo[3.1.1]heptane;
3-(4-fluorophenoxymethyl)-2-{[5-methyl-2-(pyrimidin-2-yl)phenyl]carbonyl}-2-azabicyclo[3.1.1]heptane;
(3S)-3-(4-fluorophenoxymethyl)-2-{[5-methyl-2-(pyrimidin-2-yl)phenyl]carbonyl}-2-azabicyclo [3.1.1]heptane;
(3R)-3-(4-fluorophenoxymethyl)-2-{[5-methyl-2-(pyrimidin-2-yl)phenyl]carbonyl}-2-azabicyclo[3.1.1]heptane;
3-(4-chlorophenoxymethyl)-2-{[5-methyl-2-(pyrimidin-2-yl)phenyl]carbonyl}-2-azabicyclo [3.1.1]heptane;
3-(4-chlorophenoxymethyl)-2-{[5-methyl-2-(1,3-thiazol-2-yl)phenyl]carbonyl}-2-azabicyclo [3.1.1]heptane;
3-{[(5-fluoropyridin-2-yl)oxy]methyl}-2-{[6-methyl-3-(pyrimidin-2-yl)pyridin-2-yl]carbonyl}-2-azabicyclo [3.1.1]heptane;
(3S)-3-{[(5-fluoropyridin-2-yl)oxy]methyl}-2-{[6-methyl-3-(pyrimidin-2-yl)pyridin-2-yl]carbonyl}-2-azabicyclo[3.1.1]heptane;
(3R)-3-{[(5-fluoropyridin-2-yl)oxy]methyl}-2-{[6-methyl-3-(pyrimidin-2-yl)pyridin-2-yl]carbonyl}-2-azabicyclo[3.1.1]heptane;
3-{[(5-fluoropyridin-2-yl)oxy]methyl}-2-[(2-methyl-5-phenyl-1,3-thiazol-4-yl)carbonyl]-2-azabicyclo [3.1.1] heptane;
3-{[(5-fluoropyridin-2-yl)oxy]methyl}-2-{[5-methyl-2-(1,3-thiazol-2-yl)phenyl]carbonyl}-2-azabicyclo [3.1.1]heptane;

(3S)-3-{[(5-fluoropyridin-2-yl)oxy]methyl}-2-{[5-methyl-2-(1,3-thiazol-2-yl)phenyl]carbonyl}-2-azabicyclo[3.1.1]heptane;

(3R)-3-{[(5-fluoropyridin-2-yl)oxy]methyl}-2-{[5-methyl-2-(1,3-thiazol-2-yl)phenyl]carbonyl}-2-azabicyclo[3.1.1]heptane;

3-{[(5-fluoropyridin-2-yl)oxy]methyl}-2-{[5-methyl-2-(2H-1,2,3-triazol-2-yl)phenyl]carbonyl}-2-azabicyclo[3.1.1]heptane;

(3S)-3-{[(5-fluoropyridin-2-yl)oxy]methyl}-2-{[5-methyl-2-(2H-1,2,3-triazol-2-yl)phenyl]carbonyl}-2-azabicyclo[3.1.1]heptane;

(3R)-3-{[(5-fluoropyridin-2-yl)oxy]methyl}-2-{[5-methyl-2-(2H-1,2,3-triazol-2-yl)phenyl]carbonyl}-2-azabicyclo[3.1.1]heptane;

3-{[(5-fluoropyridin-2-yl)oxy]methyl}-2-{[6-methyl-3-(1,3-thiazol-2-yl)pyridin-2-yl]carbonyl}-2-azabicyclo[3.1.1]heptane;

3-{[(5-chloropyridin-2-yl)oxy]methyl}-2-{[5-methyl-2-(pyrimidin-2-yl)phenyl]carbonyl}-2-azabicyclo[3.1.1]heptane;

(3S)-3-{[(5-chloropyridin-2-yl)oxy]methyl}-2-{[5-methyl-2-(pyrimidin-2-yl)phenyl]carbonyl}-2-azabicyclo[3.1.1]heptane;

(3R)-3-{[(5-chloropyridin-2-yl)oxy]methyl}-2-{[5-methyl-2-(pyrimidin-2-yl)phenyl]carbonyl}-2-azabicyclo[3.1.1]heptane;

2-{[5-methyl-2-(pyrimidin-2-yl)phenyl]carbonyl}-3-({[5-(trifluoromethyl)pyridin-2-yl]oxy}methyl)-2-azabicyclo[3.1.1]heptane;

(3S)-2-{[5-methyl-2-(pyrimidin-2-yl)phenyl]carbonyl}-3-({[5-(trifluoromethyl)pyridin-2-yl]oxy}methyl)-2-azabicyclo [3.1.1]heptane;

(3R)-2-{[5-methyl-2-(pyrimidin-2-yl)phenyl]carbonyl}-3-({[5-(trifluoromethyl)pyridin-2-yl]oxy}methyl)-2-azabicyclo[3.1.1]heptane;

3-{[2-(2-methyl-5-phenyl-1,3-thiazole-4-carbonyl)-2-azabicyclo[3.1.1]heptan-3-yl]methoxy}isoquinoline;

3-[(4-fluorophenoxy)methyl]-2-[6-methyl-3-(2H-1,2,3-triazol-2-yl)pyridine-2-carbonyl]-2-azabicyclo[3.1.1]heptane;

3-[(4-fluorophenoxy)methyl]-2-[5-(2-fluorophenyl)-2-methyl-1,3-thiazole-4-carbonyl]-2-azabicyclo[3.1.1]heptane;

3-[2-(4-fluorophenoxy)ethyl]-2-[5-methyl-2-(pyrimidin-2-yl)benzoyl]-2-azabicyclo[3.1.1]heptane;

(3S)-3-[2-(4-fluorophenoxy)ethyl]-2-[5-methyl-2-(pyrimidin-2-yl)benzoyl]-2-azabicyclo[3.1.1]heptane;

(3R)-3-[2-(4-fluorophenoxy)ethyl]-2-[5-methyl-2-(pyrimidin-2-yl)benzoyl]-2-azabicyclo[3.1.1]heptane;

3-(3-fluorophenoxymethyl)-2-(2-methyl-5-phenyl-1,3-thiazole-4-carbonyl)-2-azabicyclo[3.1.1]heptane;

3-(2-fluorophenoxymethyl)-2-(2-methyl-5-phenyl-1,3-thiazole-4-carbonyl)-2-azabicyclo[3.1.1]heptane;

3-(4-bromophenoxymethyl)-2-(2-methyl-5-phenyl-1,3-thiazole-4-carbonyl)-2-azabicyclo[3.1.1]heptane;

3-(3,4-difluorophenoxymethyl)-2-(2-methyl-5-phenyl-1,3-thiazole-4-carbonyl)-2-azabicyclo[3.1.1]heptane;

2-(2-methyl-5-phenyl-1,3-thiazole-4-carbonyl)-3-(4-methylphenoxymethyl)-2-azabicyclo[3.1.1]heptane;

3-(4-chlorophenoxymethyl)-2-(2-methyl-5-phenyl-1,3-thiazole-4-carbonyl)-2-azabicyclo[3.1.1]heptane;

3-(4-fluorophenoxymethyl)-2-[5-(4-fluorophenyl)-2-methyl-1,3-thiazole-4-carbonyl]-2-azabicyclo [3.1.1]heptane;

2-(2-chloro-5-phenyl-1,3-thiazole-4-carbonyl)-3-[(4-fluorophenoxy)methyl]-2-azabicyclo[3.1.1]heptane;

3-[(4-fluorophenoxy)methyl]-2-(2-methoxy-5-phenyl-1,3-thiazole-4-carbonyl)-2-azabicyclo[3.1.1]heptane;

2-(2-cyclopropyl-5-phenyl-1,3-thiazole-4-carbonyl)-3-[(4-fluorophenoxy)methyl]-2-azabicyclo[3.1.1]heptane;

6-fluoro-2-{[2-(2-methyl-5-phenyl-1,3-thiazole-4-carbonyl)-2-azabicyclo [3.1.1]heptan-3-yl]methoxy}-1,3-benzothiazole;

2-(2-methyl-5-phenyl-1,3-thiazole-4-carbonyl)-3-({[5-(trifluoromethyl)pyridin-2-yl]oxy}methyl)-2-azabicyclo[3.1.1]heptane;

2-{[2-(2-methyl-5-phenyl-1,3-thiazole-4-carbonyl)-2-azabicyclo[3.1.1]heptan-3-yl]methoxy}quinoline;

2-(2-methyl-5-phenyl-1,3-thiazole-4-carbonyl)-3-[({7-methyl-7H-pyrrolo [2,3-d]pyrimidin-2-yl}oxy)methyl]-2-azabicyclo[3.1.1]heptane;

2-{[2-(2-methyl-5-phenyl-1,3-thiazole-4-carbonyl)-2-azabicyclo[3.1.1]heptan-3-yl]methoxy}quinoxaline;

N-{[2-(2-methyl-5-phenyl-1,3-thiazole-4-carbonyl)-2-azabicyclo[3.1.1]heptan-3-yl]methyl}isoquinolin-3-amine;

N-{[2-(2-methyl-5-phenyl-1,3-thiazole-4-carbonyl)-2-azabicyclo[3.1.1]heptan-3-yl]methyl}quinolin-2-amine;

6-fluoro-N-{[2-(2-methyl-5-phenyl-1,3-thiazole-4-carbonyl)-2-azabicyclo[3.1.1]heptan-3-yl]methyl}-1,3-benzothiazol-2-amine;

(3S,4R)-4-fluoro-3-{[(5-fluoropyridin-2-yl)oxy]methyl}-2-(2-methyl-5-phenyl-1,3-thiazole-4-carbonyl)-2-azabicyclo[3.1.1]heptane;

(3R,4S)-4-fluoro-3-{[(5-fluoropyridin-2-yl)oxy]methyl}-2-(2-methyl-5-phenyl-1,3-thiazole-4-carbonyl)-2-azabicyclo[3.1.1]heptane;

3-(4-fluorophenoxymethyl)-4-methyl-2-(2-methyl-5-phenyl-1,3-thiazole-4-carbonyl)-2-azabicyclo[3.1.1]heptane;

(3R,4R)-3-(4-fluorophenoxymethyl)-4-methyl-2-(2-methyl-5-phenyl-1,3-thiazole-4-carbonyl)-2-azabicyclo[3.1.1]heptane;

(3R,4S)-3-(4-fluorophenoxymethyl)-4-methyl-2-(2-methyl-5-phenyl-1,3-thiazole-4-carbonyl)-2-azabicyclo[3.1.1]heptane;

(3S,4S)-3-(4-fluorophenoxymethyl)-4-methyl-2-(2-methyl-5-phenyl-1,3-thiazole-4-carbonyl)-2-azabicyclo[3.1.1]heptane;

(3S,4R)-3-(4-fluorophenoxymethyl)-4-methyl-2-(2-methyl-5-phenyl-1,3-thiazole-4-carbonyl)-2-azabicyclo[3.1.1]heptane;

3-(4-fluorophenoxymethyl)-4-methyl-2-[5-methyl-2-(pyrimidin-2-yl)benzoyl]-2-azabicyclo[3.1.1]heptane;

(3S,4S)-3-(4-fluorophenoxymethyl)-4-methyl-2-[5-methyl-2-(pyrimidin-2-yl)benzoyl]-2-azabicyclo [3.1.1]heptane;

(3R,4S)-3-(4-fluorophenoxymethyl)-4-methyl-2-[5-methyl-2-(pyrimidin-2-yl)benzoyl]-2-azabicyclo [3.1.1]heptane;

(3R,4R)-3-(4-fluorophenoxymethyl)-4-methyl-2-[5-methyl-2-(pyrimidin-2-yl)benzoyl]-2-azabicyclo [3.1.1]heptane;

(3S,4R)-3-(4-fluorophenoxymethyl)-4-methyl-2-[5-methyl-2-(pyrimidin-2-yl)benzoyl]-2-azabicyclo [3.1.1]heptane;

Racemic mixture of cis-3-{[(5-fluoropyridin-2-yl)oxy]methyl}-4-methyl-2-[5-methyl-2-(pyrimidin-2-yl)benzoyl]-2-azabicyclo[3.1.1]heptane;

(3S,4R)-3-{[(5-fluoropyridin-2-yl)oxy]methyl}-4-methyl-2-[5-methyl-2-(pyrimidin-2-yl)benzoyl]-2-azabicyclo [3.1.1]heptane;

(3R,4S)-3-{[(5-fluoropyridin-2-yl)oxy]methyl}-4-methyl-2-[5-methyl-2-(pyrimidin-2-yl)benzoyl]-2-azabicyclo [3.1.1]heptane;

3-{[(5-fluoropyridin-2-yl)oxy]methyl}-4-methyl-2-(2-methyl-5-phenyl-1,3-thiazole-4-carbonyl)-2-azabicyclo[3.1.1]heptane;

3-{[(5-fluoropyridin-2-yl)oxy]methyl}-4-methyl-2-[6-methyl-3-(pyrimidin-2-yl)pyridine-2-carbonyl]-2-azabicyclo[3.1.1]heptane;

(3R,4S)-3-{[(5-fluoropyridin-2-yl)oxy]methyl}-4-methyl-2-[6-methyl-3-(pyrimidin-2-yl)pyridine-2-carbonyl]-2-azabicyclo[3.1.1]heptane;

(3R,4R)-3-{[(5-fluoropyridin-2-yl)oxy]methyl}-4-methyl-2-[6-methyl-3-(pyrimidin-2-yl)pyridine-2-carbonyl]-2-azabicyclo[3.1.1]heptane;

(3S,4R)-3-{[(5-fluoropyridin-2-yl)oxy]methyl}-4-methyl-2-[6-methyl-3-(pyrimidin-2-yl)pyridine-2-carbonyl]-2-azabicyclo[3.1.1]heptane;

(3S,4S)-3-{[(5-fluoropyridin-2-yl)oxy]methyl}-4-methyl-2-[6-methyl-3-(pyrimidin-2-yl)pyridine-2-carbonyl]-2-azabicyclo[3.1.1]heptane;

1-{[4-methyl-2-(2-methyl-5-phenyl-1,3-thiazole-4-carbonyl)-2-azabicyclo [3.1.1]heptan-3-yl]methoxy}isoquinoline;

7-chloro-2-{[4-methyl-2-(2-methyl-5-phenyl-1,3-thiazole-4-carbonyl)-2-azabicyclo[3.1.1]heptan-3-yl]methoxy}quinoxaline;

3-{[4-methyl-2-(2-methyl-5-phenyl-1,3-thiazole-4-carbonyl)-2-azabicyclo [3.1.1]heptan-3-yl]methoxy}isoquinoline;

3-{[(3R,4R)-4-methyl-2-(2-methyl-5-phenyl-1,3-thiazole-4-carbonyl)-2-azabicyclo[3.1.1]heptan-3-yl]methoxy}isoquinoline;

3-{[(3R,4S)-4-methyl-2-(2-methyl-5-phenyl-1,3-thiazole-4-carbonyl)-2-azabicyclo[3.1.1]heptan-3-yl]methoxy}isoquinoline;

3-{[(3S,4S)-4-methyl-2-(2-methyl-5-phenyl-1,3-thiazole-4-carbonyl)-2-azabicyclo [3.1.1]heptan-3-yl]methoxy}isoquinoline;

3-{[(3S,4R)-4-methyl-2-(2-methyl-5-phenyl-1,3-thiazole-4-carbonyl)-2-azabicyclo [3.1.1]heptan-3-yl]methoxy}isoquinoline;

(3R,4S)-3-(4-fluorophenoxymethyl)-4-methyl-2-[6-methyl-3-(pyrimidin-2-yl)pyridine-2-carbonyl]-2-azabicyclo[3.1.1]heptane;

(3S,4R)-3-(4-fluorophenoxymethyl)-4-methyl-2-[6-methyl-3-(pyrimidin-2-yl)pyridine-2-carbonyl]-2-azabicyclo[3.1.1]heptane;

(3R,4R)-3-(4-fluorophenoxymethyl)-4-methyl-2-[6-methyl-3-(pyrimidin-2-yl)pyridine-2-carbonyl]-2-azabicyclo[3.1.1]heptane;

(3S,4S)-3-(4-fluorophenoxymethyl)-4-methyl-2-[6-methyl-3-(pyrimidin-2-yl)pyridine-2-carbonyl]-2-azabicyclo[3.1.1]heptane;

Racemic mixture of cis-3-[(4-fluorophenoxy)methyl]-4-methyl-2-[2-methyl-5-(pyrimidin-2-yl)-1,3-thiazole-4-carbonyl]-2-azabicyclo[3.1.1]heptane;

Racemic mixture of cis-3-[(4-fluorophenoxy)methyl]-4-methyl-2-[6-methyl-3-(2H-1,2,3-triazol-2-yl)pyridine-2-carbonyl]-2-azabicyclo[3.1.1]heptane;

Racemic mixture of cis-3-[(4-fluorophenoxy)methyl]-4-methyl-2-[6-methyl-3-(1,3-thiazol-2-yl)pyridine-2-carbonyl]-2-azabicyclo[3.1.1]heptane;

Racemic mixture of cis-3-[(4-fluorophenoxy)methyl]-4-methyl-2-[5-methyl-2-(2H-1,2,3-triazol-2-yl)benzoyl]-2-azabicyclo[3.1.1]heptane;

Racemic mixture of cis-3-[(4-fluorophenoxy)methyl]-4-methyl-2-[5-methyl-2-(1,3-thiazol-2-yl)benzoyl]-2-azabicyclo[3.1.1]heptane;

Racemic mixture of cis-3-{[(5-chloropyridin-2-yl)oxy]methyl}-4-methyl-2-[6-methyl-3-(2H-1,2,3-triazol-2-yl)pyridine-2-carbonyl]-2-azabicyclo[3.1.1]heptane;

Racemic mixture of cis-4-methyl-2-[6-methyl-3-(2H-1,2,3-triazol-2-yl)pyridine-2-carbonyl]-3-{[(5-methylpyridin-2-yl)oxy]methyl}-2-azabicyclo [3.1.1]heptane;

Racemic mixture of trans-3-[(4-fluorophenoxy)methyl]-4-methyl-2-[5-methyl-2-(1,3-thiazol-2-yl)benzoyl]-2-azabicyclo[3.1.1]heptane;

Racemic mixture of trans-3-{[(5-chloropyridin-2-yl)oxy]methyl}-4-methyl-2-[6-methyl-3-(2H-1,2,3-triazol-2-yl)pyridine-2-carbonyl]-2-azabicyclo[3.1.1]heptane;

Racemic mixture of trans-3-[(4-fluorophenoxy)methyl]-4-methyl-2-[6-methyl-3-(2H-1,2,3-triazol-2-yl)pyridine-2-carbonyl]-2-azabicyclo[3.1.1]heptane;

(3R,4R)-3-[(4-fluorophenoxy)methyl]-4-methyl-2-[6-methyl-3-(2H-1,2,3-triazol-2-yl)pyridine-2-carbonyl]-2-azabicyclo[3.1.1]heptane;

(3S,4S)-3-[(4-fluorophenoxy)methyl]-4-methyl-2-[6-methyl-3-(2H-1,2,3-triazol-2-yl)pyridine-2-carbonyl]-2-azabicyclo[3.1.1]heptane;

Racemic mixture of trans-3-[(4-fluorophenoxy)methyl]-4-methyl-2-[6-methyl-3-(1,3-thiazol-2-yl)pyridine-2-carbonyl]-2-azabicyclo[3.1.1]heptane;

(3R,4R)-3-[(4-fluorophenoxy)methyl]-4-methyl-2-[6-methyl-3-(1,3-thiazol-2-yl)pyridine-2-carbonyl]-2-azabicyclo[3.1.1]heptane;

(3S,4S)-3-[(4-fluorophenoxy)methyl]-4-methyl-2-[6-methyl-3-(1,3-thiazol-2-yl)pyridine-2-carbonyl]-2-azabicyclo[3.1.1]heptane;

Racemic mixture of trans-3-[(4-fluorophenoxy)methyl]-4-methyl-2-[5-methyl-2-(2H-1,2,3-triazol-2-yl)benzoyl]-2-azabicyclo[3.1.1]heptane;

Racemic mixture of trans-6-fluoro-2-({4-methyl-2-[6-methyl-3-(2H-1,2,3-triazol-2-yl)pyridine-2-carbonyl]-2-azabicyclo[3.1.1]heptan-3-yl}methoxy)-1,3-benzothiazole;

Racemic mixture of trans-3-[(3,4-difluorophenoxy)methyl]-4-methyl-2-[6-methyl-3-(2H-1,2,3-triazol-2-yl)pyridine-2-carbonyl]-2-azabicyclo[3.1.1]heptane;

Racemic mixture of trans-3-[(4-fluorophenoxy)methyl]-4-methyl-2-[2-methyl-5-(pyrimidin-2-yl)-1,3-thiazole-4-carbonyl]-2-azabicyclo[3.1.1]heptane;

Racemic mixture of trans-3-{[(5-fluoropyridin-2-yl)oxy]methyl}-4-methyl-2-[2-methyl-5-(pyrimidin-2-yl)-1,3-thiazole-4-carbonyl]-2-azabicyclo[3.1.1]heptane;

Racemic mixture of trans-3-{[(5-fluoropyridin-2-yl)oxy]methyl}-4-methyl-2-[2-methyl-5-(pyridin-2-yl)-1,3-thiazole-4-carbonyl]-2-azabicyclo[3.1.1]heptane;

Racemic mixture of cis-2'-(3-{[(5-fluoropyridin-2-yl)oxy]methyl}-4-methyl-2-azabicyclo[3.1.1]heptane-2-carbonyl)-6'-methyl-2,3'-bipyridine;

Racemic mixture of cis-3-[(4-fluorophenoxy)methyl]-4-methyl-2-[2-methyl-5-(pyridin-2-yl)-1,3-thiazole-4-carbonyl]-2-azabicyclo[3.1.1]heptane;

Racemic mixture of cis-3-[(4-fluorophenoxy)methyl]-4-methyl-2-{6-methyl-3-[5-(trifluoromethyl)pyrimidin-2-yl]pyridine-2-carbonyl}-2-azabicyclo[3.1.1]heptane;

Racemic mixture of trans-3-[(4-chlorophenoxy)methyl]-4-methyl-2-[6-methyl-3-(2H-1,2,3-triazol-2-yl)pyridine-2-carbonyl]-2-azabicyclo[3.1.1]heptane;

(3S,4S)-3-[(4-chlorophenoxy)methyl]-4-methyl-2-[6-methyl-3-(2H-1,2,3-triazol-2-yl)pyridine-2-carbonyl]-2-azabicyclo[3.1.1]heptane;
(3R,4R)-3-[(4-chlorophenoxy)methyl]-4-methyl-2-[6-methyl-3-(2H-1,2,3-triazol-2-yl)pyridine-2-carbonyl]-2-azabicyclo[3.1.1]heptane;
Racemic mixture of cis-3-[(4-fluorophenoxy)methyl]-2-[3-(5-fluoropyrimidin-2-yl)-6-methylpyridine-2-carbonyl]-4-methyl-2-azabicyclo[3.1.1]heptane;
(3S,4S)-3-[(4-fluorophenoxy)methyl]-4-methyl-2-[2-methyl-5-(pyrimidin-2-yl)-1,3-thiazole-4-carbonyl]-2-azabicyclo[3.1.1]heptane;
(3R,4R)-3-[(4-fluorophenoxy)methyl]-4-methyl-2-[2-methyl-5-(pyrimidin-2-yl)-1,3-thiazole-4-carbonyl]-2-azabicyclo[3.1.1]heptane;
Racemic mixture of trans-3-[(4-fluorophenoxy)methyl]-4-methyl-2-[2-methyl-5-(pyrazin-2-yl)-1,3-thiazole-4-carbonyl]-2-azabicyclo[3.1.1]heptane;
Racemic mixture of trans-3-[(4-fluorophenoxy)methyl]-4-methyl-2-[6-methyl-3-(1H-pyrazol-1-yl)pyridine-2-carbonyl]-2-azabicyclo[3.1.1]heptane;
Racemic mixture of cis-N-({4-methyl-2-[6-methyl-3-(2H-1,2,3-triazol-2-yl)pyridine-2-carbonyl]-2-azabicyclo[3.1.1]heptan-3-yl}methyl)isoquinolin-3-amine;
Racemic mixture of cis-6-fluoro-N-({4-methyl-2-[6-methyl-3-(2H-1,2,3-triazol-2-yl)pyridine-2-carbonyl]-2-azabicyclo[3.1.1]heptan-3-yl}methyl)-1,3-benzothiazol-2-amine;
Racemic mixture of cis-3-[(4-fluorophenoxy)methyl]-4-methyl-2-[6-methyl-3-(4-methyl-1H-pyrazol-1-yl)pyridine-2-carbonyl]-2-azabicyclo[3.1.1]heptane;
Racemic mixture of cis-3-[(4-fluorophenoxy)methyl]-4-methyl-2-[2-methyl-5-(pyrazin-2-yl)-1,3-thiazole-4-carbonyl]-2-azabicyclo[3.1.1]heptane;
Racemic mixture of cis-N-({4-methyl-2-[6-methyl-3-(2H-1,2,3-triazol-2-yl)pyridine-2-carbonyl]-2-azabicyclo[3.1.1]heptan-3-yl}methyl)quinazolin-2-amine;
Racemic mixture of cis-3-[(4-fluorophenoxy)methyl]-4-methyl-2-[2-methyl-5-(6-methylpyridin-2-yl)-1,3-thiazole-4-carbonyl]-2-azabicyclo [3.1.1]heptane;
Racemic mixture of cis-3-[(4-fluorophenoxy)methyl]-4-methyl-2-[6-methyl-3-(5-methylpyrimidin-2-yl)pyridine-2-carbonyl]-2-azabicyclo[3.1.1]heptane;
Racemic mixture of cis-2-[5-(5-chloropyridin-3-yl)-2-methyl-1,3-thiazole-4-carbonyl]-3-[(4-fluorophenoxy)methyl]-4-methyl-2-azabicyclo[3.1.1]heptane;
Racemic mixture of cis-3-[(4-fluorophenoxy)methyl]-4-methyl-2-[2-methyl-5-(2H-1,2,3-triazol-2-yl)-1,3-thiazole-4-carbonyl]-2-azabicyclo [3.1.1]heptane;
Racemic mixture of cis-3-[(4-fluorophenoxy)methyl]-4-methyl-2-[2-methyl-5-(1H-pyrazol-1-yl)-1,3-thiazole-4-carbonyl]-2-azabicyclo [3.1.1]heptane;
Racemic mixture of trans-3-{[(5-chloropyridin-2-yl)oxy]methyl}-4-methyl-2-[6-methyl-3-(pyrimidin-2-yl)pyridine-2-carbonyl]-2-azabicyclo[3.1.1]heptane;
Racemic mixture of trans-3-[(4-fluorophenoxy)methyl]-4-methyl-2-[2-methyl-5-(pyridin-2-yl)-1,3-thiazole-4-carbonyl]-2-azabicyclo[3.1.1]heptane;
(3S,4S)-3-[(4-fluorophenoxy)methyl]-4-methyl-2-[2-methyl-5-(pyridin-2-yl)-1,3-thiazole-4-carbonyl]-2-azabicyclo[3.1.1]heptane;
(3R,4R)-3-[(4-fluorophenoxy)methyl]-4-methyl-2-[2-methyl-5-(pyridin-2-yl)-1,3-thiazole-4-carbonyl]-2-azabicyclo[3.1.1]heptane;
Racemic mixture of trans-3-[(4-fluorophenoxy)methyl]-4-methyl-2-[2-methyl-5-(2H-1,2,3-triazol-2-yl)-1,3-thiazole-4-carbonyl]-2-azabicyclo[3.1.1]heptane;
Racemic mixture of trans-3-[(4-fluorophenoxy)methyl]-4-methyl-2-[6-methyl-3-(4-methyl-2H-1,2,3-triazol-2-yl)pyridine-2-carbonyl]-2-azabicyclo[3.1.1]heptane;
Racemic mixture of trans-2-[5-fluoro-2-(2H-1,2,3-triazol-2-yl)benzoyl]-3-[(4-fluorophenoxy)methyl]-4-methyl-2-azabicyclo[3.1.1]heptane;
Racemic mixture of cis-4-methyl-2-[6-methyl-3-(2H-1,2,3-triazol-2-yl)pyridine-2-carbonyl]-3-({[5-(trifluoromethyl)pyridin-2-yl]oxy}methyl)-2-azabicyclo[3.1.1]heptane;
Racemic mixture of cis-3-{[(5-fluoropyridin-2-yl)oxy]methyl}-4-methyl-2-[6-methyl-3-(2H-1,2,3-triazol-2-yl)pyridine-2-carbonyl]-2-azabicyclo[3.1.1]heptane;
Racemic mixture of cis-3-{3-[(4-fluorophenoxy)methyl]-4-methyl-2-azabicyclo[3.1.1]heptane-2-carbonyl}-4-(2H-1,2,3-triazol-2-yl)benzonitrile;
Racemic mixture of cis-3-[(4-fluorophenoxy)methyl]-4-methyl-2-[2-methyl-5-(6-methylpyridin-3-yl)-1,3-thiazole-4-carbonyl]-2-azabicyclo[3.1.1]heptane;
Racemic mixture of cis-3-[(4-fluorophenoxy)methyl]-4-methyl-2-[6-methyl-3-(4-methyl-2H-1,2,3-triazol-2-yl)pyridine-2-carbonyl]-2-azabicyclo[3.1.1]heptane;
Racemic mixture of cis-3-[(4-fluorophenoxy)methyl]-4-methyl-2-[6-methyl-3-(2H-1,2,3-triazol-2-yl)pyrazine-2-carbonyl]-2-azabicyclo[3.1.1]heptane;
Racemic mixture of cis-3-[(4-fluorophenoxy)methyl]-4-methyl-2-[6-methyl-3-(4-methyl-1H-1,2,3-triazol-1-yl)pyridine-2-carbonyl]-2-azabicyclo [3.1.1]heptane;
Racemic mixture of trans-6-fluoro-N-({4-methyl-2-[6-methyl-3-(2H-1,2,3-triazol-2-yl)pyridine-2-carbonyl]-2-azabicyclo[3.1.1]heptan-3-yl}methyl)-1,3-benzothiazol-2-amine;
Racemic mixture of trans-5-chloro-N-({4-methyl-2-[6-methyl-3-(2H-1,2,3-triazol-2-yl)pyridine-2-carbonyl]-2-azabicyclo[3.1.1]heptan-3-yl}methyl)pyridin-2-amine;
Racemic mixture of trans-N-({4-methyl-2-[6-methyl-3-(2H-1,2,3-triazol-2-yl)pyridine-2-carbonyl]-2-azabicyclo[3.1.1]heptan-3-yl}methyl)quinazolin-2-amine;
Racemic mixture of trans-N-({4-methyl-2-[6-methyl-3-(2H-1,2,3-triazol-2-yl)pyridine-2-carbonyl]-2-azabicyclo [3.1.1]heptan-3-yl}methyl)-1,3-benzothiazol-2-amine;
6-fluoro-N-{[(3R,4S)-4-methyl-2-[6-methyl-3-(2H-1,2,3-triazol-2-yl)pyridine-2-carbonyl]-2-azabicyclo [3.1.1]heptan-3-yl]methyl}-1,3-benzothiazol-2-amine;
6-fluoro-N-{[(3S,4R)-4-methyl-2-[6-methyl-3-(2H-1,2,3-triazol-2-yl)pyridine-2-carbonyl]-2-azabicyclo [3.1.1]heptan-3-yl]methyl}-1,3-benzothiazol-2-amine;
Racemic mixture of cis-5-chloro-N-({4-methyl-2-[6-methyl-3-(2H-1,2,3-triazol-2-yl)pyridine-2-carbonyl]-2-azabicyclo[3.1.1]heptan-3-yl}methyl)pyridin-2-amine;
Racemic mixture of cis-5-fluoro-N-({4-methyl-2-[6-methyl-3-(2H-1,2,3-triazol-2-yl)pyridine-2-carbonyl]-2-azabicyclo[3.1.1]heptan-3-yl}methyl)-1,3-benzothiazol-2-amine;
Racemic mixture of cis-N-({4-methyl-2-[6-methyl-3-(2H-1,2,3-triazol-2-yl)pyridine-2-carbonyl]-2-azabicyclo[3.1.1]heptan-3-yl}methyl)quinoxalin-2-amine;
N-{[(3S,4R)-4-methyl-2-[6-methyl-3-(2H-1,2,3-triazol-2-yl)pyridine-2-carbonyl]-2-azabicyclo[3.1.1]heptan-3-yl]methyl}quinoxalin-2-amine;
N-{[(3R,4S)-4-methyl-2-[6-methyl-3-(2H-1,2,3-triazol-2-yl)pyridine-2-carbonyl]-2-azabicyclo[3.1.1]heptan-3-yl]methyl}quinoxalin-2-amine;

Racemic mixture of cis-N-({4-methyl-2-[6-methyl-3-(2H-1,2,3-triazol-2-yl)pyridine-2-carbonyl]-2-azabicyclo[3.1.1]heptan-3-yl}methyl)quinolin-2-amine;

Racemic mixture of cis-6-fluoro-N-({4-methyl-2-[2-methyl-5-(pyrimidin-2-yl)-1,3-thiazole-4-carbonyl]-2-azabicyclo[3.1.1]heptan-3-yl}methyl)-1,3-benzothiazol-2-amine;

6-fluoro-N-({(3R,4S)-4-methyl-2-[2-methyl-5-(pyrimidin-2-yl)-1,3-thiazole-4-carbonyl]-2-azabicyclo[3.1.1]heptan-3-yl}methyl)-1,3-benzothiazol-2-amine;

6-fluoro-N-({(3S,4R)-4-methyl-2-[2-methyl-5-(pyrimidin-2-yl)-1,3-thiazole-4-carbonyl]-2-azabicyclo[3.1.1]heptan-3-yl}methyl)-1,3-benzothiazol-2-amine;

Racemic mixture of cis-N-({4-methyl-2-[6-methyl-3-(2H-1,2,3-triazol-2-yl)pyridine-2-carbonyl]-2-azabicyclo[3.1.1]heptan-3-yl}methyl)-5-(trifluoromethyl)pyrazin-2-amine;

N-{[(3 S,4R)-4-methyl-2-[6-methyl-3-(2H-1,2,3-triazol-2-yl)pyridine-2-carbonyl]-2-azabicyclo[3.1.1]heptan-3-yl]methyl}-5-(trifluoromethyl)pyrazin-2-amine;

N-{[(3R,4S)-4-methyl-2-[6-methyl-3-(2H-1,2,3-triazol-2-yl)pyridine-2-carbonyl]-2-azabicyclo[3.1.1]heptan-3-yl]methyl}-5-(trifluoromethyl)pyrazin-2-amine;

Racemic mixture of cis-6-fluoro-N-({2-[5-fluoro-2-(2H-1,2,3-triazol-2-yl)benzoyl]-4-methyl-2-azabicyclo[3.1.1]heptan-3-yl}methyl)-1,3-benzothiazol-2-amine;

6-fluoro-N-({(3R,4S)-2-[5-fluoro-2-(2H-1,2,3-triazol-2-yl)benzoyl]-4-methyl-2-azabicyclo[3.1.1]heptan-3-yl}methyl)-1,3-benzothiazol-2-amine;

6-fluoro-N-({(3S,4R)-2-[5-fluoro-2-(2H-1,2,3-triazol-2-yl)benzoyl]-4-methyl-2-azabicyclo [3.1.1]heptan-3-yl}methyl)-1,3-benzothiazol-2-amine;

Racemic mixture of cis-N-({2-[5-chloro-2-(2H-1,2,3-triazol-2-yl)benzoyl]-4-methyl-2-azabicyclo[3.1.1]heptan-3-yl}methyl)-6-fluoro-1,3-benzothiazol-2-amine;

N-({(3S,4R)-2-[5-chloro-2-(2H-1,2,3-triazol-2-yl)benzoyl]-4-methyl-2-azabicyclo [3.1.1]heptan-3-yl}methyl)-6-fluoro-1,3-benzothiazol-2-amine;

N-({(3R,4S)-2-[5-chloro-2-(2H-1,2,3-triazol-2-yl)benzoyl]-4-methyl-2-azabicyclo [3.1.1]heptan-3-yl}methyl)-6-fluoro-1,3-benzothiazol-2-amine;

Racemic mixture of cis-N-{[2-(3-ethoxy-6-methylpyridine-2-carbonyl)-4-methyl-2-azabicyclo[3.1.1]heptan-3-yl]methyl}-6-fluoro-1,3-benzothiazol-2-amine;

Racemic mixture of cis-3-(3-{[(6-fluoro-1,3-benzothiazol-2-yl)amino]methyl}-4-methyl-2-azabicyclo[3.1.1]heptane-2-carbonyl)-4-(2H-1,2,3-triazol-2-yl)benzonitrile;

3-[(3S,4R)-3-{[(6-fluoro-1,3-benzothiazol-2-yl)amino]methyl}-4-methyl-2-azabicyclo[3.1.1]heptane-2-carbonyl]-4-(2H-1,2,3-triazol-2-yl)benzonitrile;

3-[(3R,4S)-3-{[(6-fluoro-1,3-benzothiazol-2-yl)amino]methyl}-4-methyl-2-azabicyclo [3.1.1]heptane-2-carbonyl]-4-(2H-1,2,3-triazol-2-yl)benzonitrile;

Racemic mixture of cis-N-({4-methyl-2-[6-methyl-3-(2H-1,2,3-triazol-2-yl)pyridine-2-carbonyl]-2-azabicyclo[3.1.1]heptan-3-yl}methyl)-1,3-benzothiazol-2-amine;

N-{[(3 S,4R)-4-methyl-2-[6-methyl-3-(2H-1,2,3-triazol-2-yl)pyridine-2-carbonyl]-2-azabicyclo [3.1.1]heptan-3-yl]methyl}-1,3-benzothiazol-2-amine;

N-{[(3R,4S)-4-methyl-2-[6-methyl-3-(2H-1,2,3-triazol-2-yl)pyridine-2-carbonyl]-2-azabicyclo[3.1.1]heptan-3-yl]methyl}-1,3-benzothiazol-2-amine;

Racemic mixture of cis-N-({4-methyl-2-[6-methyl-3-(2H-1,2,3-triazol-2-yl)pyridine-2-carbonyl]-2-azabicyclo[3.1.1]heptan-3-yl}methyl)-5-(trifluoromethyl)pyridin-2-amine;

N-{[(3S,4R)-4-methyl-2-[6-methyl-3-(2H-1,2,3-triazol-2-yl)pyridine-2-carbonyl]-2-azabicyclo [3.1.1]heptan-3-yl]methyl}-5-(trifluoromethyl)pyridin-2-amine;

N-{[(3R,4S)-4-methyl-2-[6-methyl-3-(2H-1,2,3-triazol-2-yl)pyridine-2-carbonyl]-2-azabicyclo[3.1.1]heptan-3-yl]methyl}-5-(trifluoromethyl)pyridin-2-amine;

Racemic mixture of cis-N-({4-methyl-2-[6-methyl-3-(2H-1,2,3-triazol-2-yl)pyridine-2-carbonyl]-2-azabicyclo[3.1.1]heptan-3-yl}methyl)-[1,3]thiazolo [5,4-b]pyridin-2-amine;

N-({(3 S,4R)-4-methyl-2-[6-methyl-3-(2H-1,2,3-triazol-2-yl)pyridine-2-carbonyl]-2-azabicyclo[3.1.1]heptan-3-yl}-methyl)-[1,3]thiazolo [5,4-b]pyridin-2-amine;

N-({(3R,4S)-4-methyl-2-[6-methyl-3-(2H-1,2,3-triazol-2-yl)pyridine-2-carbonyl]-2-azabicyclo [3.1.1]heptan-3-yl}-methyl)-[1,3]thiazolo [5,4-b]pyridin-2-amine;

Racemic mixture of cis-N-({2-[5-fluoro-2-(2H-1,2,3-triazol-2-yl)benzoyl]-4-methyl-2-azabicyclo [3.1.1]heptan-3-yl}-methyl)quinoxalin-2-amine;

N-({(3 S,4R)-2-[5-fluoro-2-(2H-1,2,3-triazol-2-yl)benzoyl]-4-methyl-2-azabicyclo[3.1.1]heptan-3-yl}methyl)quinoxalin-2-amine;

N-({(3R,4S)-2-[5-fluoro-2-(2H-1,2,3-triazol-2-yl)benzoyl]-4-methyl-2-azabicyclo[3.1.1]heptan-3-yl}methyl)quinoxalin-2-amine;

Racemic mixture of cis-N-({2-[5-fluoro-2-(2H-1,2,3-triazol-2-yl)benzoyl]-4-methyl-2-azabicyclo[3.1.1]heptan-3-yl}methyl)-5-(trifluoromethyl)pyridin-2-amine;

N-({(3 S,4R)-2-[5-fluoro-2-(2H-1,2,3-triazol-2-yl)benzoyl]-4-methyl-2-azabicyclo[3.1.1]heptan-3-yl}methyl)-5-(trifluoromethyl)pyridin-2-amine;

N-({(3R,4S)-2-[5-fluoro-2-(2H-1,2,3-triazol-2-yl)benzoyl]-4-methyl-2-azabicyclo[3.1.1]heptan-3-yl}methyl)-5-(trifluoromethyl)pyridin-2-amine;

Racemic mixture of cis-N-({4-methyl-2-[6-methyl-3-(2H-1,2,3-triazol-2-yl)pyridine-2-carbonyl]-2-azabicyclo[3.1.1]heptan-3-yl}methyl)-5-(trifluoromethyl)pyrimidin-2-amine;

N-{[(3S,4R)-4-methyl-2-[6-methyl-3-(2H-1,2,3-triazol-2-yl)pyridine-2-carbonyl]-2-azabicyclo[3.1.1]heptan-3-yl]methyl}-5-(trifluoromethyl)pyrimidin-2-amine;

N-{[(3R,4S)-4-methyl-2-[6-methyl-3-(2H-1,2,3-triazol-2-yl)pyridine-2-carbonyl]-2-azabicyclo[3.1.1]heptan-3-yl]methyl}-5-(trifluoromethyl)pyrimidin-2-amine;

Racemic mixture of cis-5-fluoro-6-methyl-N-({4-methyl-2-[6-methyl-3-(2H-1,2,3-triazol-2-yl)pyridine-2-carbonyl]-2-azabicyclo[3.1.1]heptan-3-yl}methyl)pyridin-2-amine;

Racemic mixture of cis-N-({4-methyl-2-[6-methyl-3-(2H-1,2,3-triazol-2-yl)pyridine-2-carbonyl]-2-azabicyclo[3.1.1]heptan-3-yl}methyl)-6-(trifluoromethyl)pyridin-2-amine;

Racemic mixture of cis-6-fluoro-N-({4-methyl-2-[6-methyl-3-(2H-1,2,3-triazol-2-yl)pyridine-2-carbonyl]-2-azabicyclo[3.1.1]heptan-3-yl}methyl)quinoxalin-2-amine;

6-fluoro-N-{[(3 S,4R)-4-methyl-2-[6-methyl-3-(2H-1,2,3-triazol-2-yl)pyridine-2-carbonyl]-2-azabicyclo [3.1.1]heptan-3-yl]methyl}quinoxalin-2-amine;

6-fluoro-N-{[(3R,4S)-4-methyl-2-[6-methyl-3-(2H-1,2,3-triazol-2-yl)pyridine-2-carbonyl]-2-azabicyclo [3.1.1]heptan-3-yl]methyl}quinoxalin-2-amine;

Racemic mixture of cis-6,7-difluoro-N-({4-methyl-2-[6-methyl-3-(2H-1,2,3-triazol-2-yl)pyridine-2-carbonyl]-2-azabicyclo [3.1.1]heptan-3-yl}methyl)quinoxalin-2-amine;

Racemic mixture of cis-4-fluoro-N-({4-methyl-2-[5-methyl-2-(1,3-thiazol-2-yl)benzoyl]-2-azabicyclo[3.1.1]heptan-3-yl}methyl)aniline;

Racemic mixture of cis-N-({2-[5-chloro-2-(2H-1,2,3-triazol-2-yl)benzoyl]-4-methyl-2-azabicyclo[3.1.1]heptan-3-yl}methyl)-5-(trifluoromethyl)pyrazin-2-amine;

N-({(3 S,4R)-2-[5-chloro-2-(2H-1,2,3-triazol-2-yl)benzoyl]-4-methyl-2-azabicyclo [3.1.1]heptan-3-yl}methyl)-5-(trifluoromethyl)pyrazin-2-amine;

N-({(3R,4S)-2-[5-chloro-2-(2H-1,2,3-triazol-2-yl)benzoyl]-4-methyl-2-azabicyclo [3.1.1]heptan-3-yl}methyl)-5-(trifluoromethyl)pyrazin-2-amine;

Racemic mixture of cis-N-({2-[5-chloro-2-(2H-1,2,3-triazol-2-yl)benzoyl]-4-methyl-2-azabicyclo[3.1.1]heptan-3-yl}methyl)pyrido [2,3-b]pyrazin-2-amine;

Racemic mixture of cis-N-({2-[5-chloro-2-(2H-1,2,3-triazol-2-yl)benzoyl]-4-methyl-2-azabicyclo[3.1.1]heptan-3-yl}methyl)-6-fluoroquinoxalin-2-amine;

N-{[(3S,4R)-2-[5-chloro-2-(2H-1,2,3-triazol-2-yl)benzoyl]-4-methyl-2-azabicyclo [3.1.1]heptan-3-yl] methyl}-6-fluoroquinoxalin-2-amine;

N-{[(3R,4R)-2-[5-chloro-2-(2H-1,2,3-triazol-2-yl)benzoyl]-4-methyl-2-azabicyclo[3.1.1]heptan-3-yl] methyl}-6-fluoroquinoxalin-2-amine;

Racemic mixture of cis-N-{[4-methyl-2-(1-methyl-4-phenyl-1H-pyrazole-3-carbonyl)-2-azabicyclo[3.1.1]heptan-3-yl]methyl}-5-(trifluoromethyl)pyridin-2-amine;

N-{[(3 S,4R)-4-methyl-2-(1-methyl-4-phenyl-1H-pyrazole-3-carbonyl)-2-azabicyclo[3.1.1]heptan-3-yl]methyl}-5-(trifluoromethyl)pyridin-2-amine;

N-{[(3R,4S)-4-methyl-2-(1-methyl-4-phenyl-1H-pyrazole-3-carbonyl)-2-azabicyclo[3.1.1]heptan-3-yl]methyl}-5-(trifluoromethyl)pyridin-2-amine;

Racemic mixture of cis-N-({4-methyl-2-[1-methyl-4-(pyrimidin-2-yl)-1H-pyrazole-3-carbonyl]-2-azabicyclo[3.1.1]heptan-3-yl}methyl)-5-(trifluoromethyl)pyridin-2-amine;

N-{[(3S,4R)-4-methyl-2-[1-methyl-4-(pyrimidin-2-yl)-1H-pyrazole-3-carbonyl]-2-azabicyclo[3.1.1]heptan-3-yl]methyl}-5-(trifluoromethyl)pyridin-2-amine;

N-{[(3R,4S)-4-methyl-2-[1-methyl-4-(pyrimidin-2-yl)-1H-pyrazole-3-carbonyl]-2-azabicyclo[3.1.1]heptan-3-yl]methyl}-5-(trifluoromethyl)pyridin-2-amine;

Racemic mixture of cis-5-methyl-N-({4-methyl-2-[6-methyl-3-(2H-1,2,3-triazol-2-yl)pyridine-2-carbonyl]-2-azabicyclo[3.1.1]heptan-3-yl}methyl)pyrazin-2-amine;

Racemic mixture of cis-N-({4-methyl-2-[6-methyl-3-(2H-1,2,3-triazol-2-yl)pyridine-2-carbonyl]-2-azabicyclo[3.1.1]heptan-3-yl}methyl)-6-(trifluoromethyl)pyrazin-2-amine;

Racemic mixture of cis-6-fluoro-N-({4-methyl-2-[6-methyl-3-(2H-1,2,3-triazol-2-yl)pyridine-2-carbonyl]-2-azabicyclo[3.1.1]heptan-3-yl}methyl)-1,3-benzoxazol-2-amine;

6-fluoro-N-{[(3 S,4R)-4-methyl-2-[6-methyl-3-(2H-1,2,3-triazol-2-yl)pyridine-2-carbonyl]-2-azabicyclo [3.1.1]heptan-3-yl]methyl}-1,3-benzoxazol-2-amine;

6-fluoro-N-{[(3R,4S)-4-methyl-2-[6-methyl-3-(2H-1,2,3-triazol-2-yl)pyridine-2-carbonyl]-2-azabicyclo [3.1.1]heptan-3-yl]methyl}-1,3-benzoxazol-2-amine;

Racemic mixture of cis-N-({2-[5-fluoro-2-(2H-1,2,3-triazol-2-yl)benzoyl]-4-methyl-2-azabicyclo[3.1.1]heptan-3-yl}methyl)-5-(trifluoromethyl)pyrazin-2-amine;

N-{[(3 S,4R)-2-[5-fluoro-2-(2H-1,2,3-triazol-2-yl)benzoyl]-4-methyl-2-azabicyclo[3.1.1]heptan-3-yl] methyl}-5-(trifluoromethyl)pyrazin-2-amine;

N-{[(3R,4S)-2-[5-fluoro-2-(2H-1,2,3-triazol-2-yl)benzoyl]-4-methyl-2-azabicyclo[3.1.1]heptan-3-yl] methyl}-5-(trifluoromethyl)pyrazin-2-amine;

Racemic mixture of cis-6-fluoro-N-({2-[5-fluoro-2-(2H-1,2,3-triazol-2-yl)benzoyl]-4-methyl-2-azabicyclo [3.1.1]heptan-3-yl}methyl)quinoxalin-2-amine;

Racemic mixture of cis-N-({4-methyl-2-[6-methyl-3-(2H-1,2,3-triazol-2-yl)pyridine-2-carbonyl]-2-azabicyclo[3.1.1]heptan-3-yl}methyl)-1,3-benzoxazol-2-amine;

N-{[(3S,4R)-4-methyl-2-[6-methyl-3-(2H-1,2,3-triazol-2-yl)pyridine-2-carbonyl]-2-azabicyclo[3.1.1]heptan-3-yl]methyl}-1,3-benzoxazol-2-amine;

N-{[(3R,4S)-4-methyl-2-[6-methyl-3-(2H-1,2,3-triazol-2-yl)pyridine-2-carbonyl]-2-azabicyclo[3.1.1]heptan-3-yl]methyl}-1,3-benzoxazol-2-amine;

Racemic mixture of cis-N-({2-[5-fluoro-2-(2H-1,2,3-triazol-2-yl)benzoyl]-4-methyl-2-azabicyclo[3.1.1]heptan-3-yl}methyl)-[1,3]thiazolo [5,4-b]pyridin-2-amine;

N-{[(3S,4R)-2-[5-fluoro-2-(2H-1,2,3-triazol-2-yl)benzoyl]-4-methyl-2-azabicyclo[3.1.1]heptan-3-yl] methyl}-[1,3]thiazolo[5,4-b]pyridin-2-amine;

N-{[(3R,4S)-2-[5-fluoro-2-(2H-1,2,3-triazol-2-yl)benzoyl]-4-methyl-2-azabicyclo[3.1.1]heptan-3-yl] methyl}-[1,3]thiazolo[5,4-b]pyridin-2-amine;

Racemic mixture of cis-3-{4-methyl-3-[({[1,3]thiazolo[5,4-b]pyridin-2-yl}amino)methyl]-2-azabicyclo[3.1.1] heptane-2-carbonyl}-4-(2H-1,2,3-triazol-2-yl)benzonitrile;

3-[(3S,4R)-4-methyl-3-[({[1,3]thiazolo[5,4-b]pyridin-2-yl}amino)methyl]-2-azabicyclo[3.1.1]heptane-2-carbonyl]-4-(2H-1,2,3-triazol-2-yl)benzonitrile;

3-[(3R,4S)-4-methyl-3-[({[1,3]thiazolo [5,4-b]pyridin-2-yl}amino)methyl]-2-azabicyclo[3.1.1]heptane-2-carbonyl]-4-(2H-1,2,3-triazol-2-yl)benzonitrile;

Racemic mixture of cis-N-({2-[5-chloro-2-(2H-1,2,3-triazol-2-yl)benzoyl]-4-methyl-2-azabicyclo[3.1.1]heptan-3-yl}methyl)-[1,3]thiazolo [5,4-b]pyridin-2-amine;

N-{[(3 S,4R)-2-[5-chloro-2-(2H-1,2,3-triazol-2-yl)benzoyl]-4-methyl-2-azabicyclo[3.1.1]heptan-3-yl] methyl}-[1,3]thiazolo[5,4-b]pyridin-2-amine;

N-{[(3R,4S)-2-[5-chloro-2-(2H-1,2,3-triazol-2-yl)benzoyl]-4-methyl-2-azabicyclo[3.1.1]heptan-3-yl] methyl}-[1,3]thiazolo[5,4-b]pyridin-2-amine;

Racemic mixture of cis-3-[4-methyl-3-({[5-(trifluoromethyl)pyrazin-2-yl]amino}methyl)-2-azabicyclo[3.1.1] heptane-2-carbonyl]-4-(2H-1,2,3-triazol-2-yl)benzonitrile;

Racemic mixture of cis-3-(3-{[(6-fluoroquinoxalin-2-yl)amino]methyl}-4-methyl-2-azabicyclo[3.1.1]heptane-2-carbonyl)-4-(2H-1,2,3-triazol-2-yl)benzonitrile;

Racemic mixture of cis-N-({2-[5-chloro-2-(2H-1,2,3-triazol-2-yl)benzoyl]-4-methyl-2-azabicyclo[3.1.1]heptan-3-yl}methyl)-5-(trifluoromethyl)pyrimidin-2-amine;

N-{[(3S,4R)-2-[5-chloro-2-(2H-1,2,3-triazol-2-yl)benzoyl]-4-methyl-2-azabicyclo[3.1.1]heptan-3-yl] methyl}-5-(trifluoromethyl)pyrimidin-2-amine;

N-{[(3R,4S)-2-[5-chloro-2-(2H-1,2,3-triazol-2-yl)benzoyl]-4-methyl-2-azabicyclo[3.1.1]heptan-3-yl] methyl}-5-(trifluoromethyl)pyrimidin-2-amine;

Racemic mixture of cis-N-({2-[5-chloro-2-(2H-1,2,3-triazol-2-yl)benzoyl]-4-methyl-2-azabicyclo[3.1.1]heptan-3-yl}methyl)[1,3]oxazolo[5,4-b]pyridin-2-amine;

N-{[(3S,4R)-2-[5-chloro-2-(2H-1,2,3-triazol-2-yl)benzoyl]-4-methyl-2-azabicyclo[3.1.1]heptan-3-yl]methyl}[1,3]oxazolo[5,4-b]pyridin-2-amine;

N-{[(3R,4S)-2-[5-chloro-2-(2H-1,2,3-triazol-2-yl)benzoyl]-4-methyl-2-azabicyclo[3.1.1]heptan-3-yl]methyl}[1,3]oxazolo[5,4-b]pyridin-2-amine;

Racemic mixture of cis-N-({4-methyl-2-[1-methyl-4-(pyrimidin-2-yl)-1H-pyrazole-3-carbonyl]-2-azabicyclo[3.1.1]heptan-3-yl}methyl)-5-(trifluoromethyl)pyrazin-2-amine;

Racemic mixture of cis-N-({2-[4-chloro-2-(2H-1,2,3-triazol-2-yl)benzoyl]-4-methyl-2-azabicyclo[3.1.1]heptan-3-yl}methyl)-5-(trifluoromethyl)pyrazin-2-amine;

Racemic mixture of cis-N-({2-[5-chloro-2-(2H-1,2,3-triazol-2-yl)benzoyl]-4-methyl-2-azabicyclo[3.1.1]heptan-3-yl}methyl)-6-(trifluoromethyl)pyridazin-3-amine;

Racemic mixture of cis-N-({4-methyl-2-[6-methyl-3-(pyrimidin-2-yl)pyridine-2-carbonyl]-2-azabicyclo[3.1.1]heptan-3-yl}methyl)-5-(trifluoromethyl)pyrazin-2-amine;

N-{[(3S,4R) or (3R,4S)-4-methyl-2-[6-methyl-3-(pyrimidin-2-yl)pyridine-2-carbonyl]-2-azabicyclo[3.1.1]heptan-3-yl]methyl}-5-(trifluoromethyl)pyrazin-2-amine;

N-{[(3R,4S) or (3S,4R)-4-methyl-2-[6-methyl-3-(pyrimidin-2-yl)pyridine-2-carbonyl]-2-azabicyclo[3.1.1]heptan-3-yl]methyl}-5-(trifluoromethyl)pyrazin-2-amine;

Racemic mixture of cis-N-({2-[4-fluoro-2-(2H-1,2,3-triazol-2-yl)benzoyl]-4-methyl-2-azabicyclo[3.1.1]heptan-3-yl}methyl)-5-(trifluoromethyl)pyrazin-2-amine;

Racemic mixture of cis-N-({2-[5-fluoro-2-(2H-1,2,3-triazol-2-yl)benzoyl]-4-methyl-2-azabicyclo[3.1.1]heptan-3-yl}methyl)-5-(trifluoromethyl)pyrimidin-2-amine;

Racemic mixture of cis-N-({2-[2-fluoro-6-(2H-1,2,3-triazol-2-yl)benzoyl]-4-methyl-2-azabicyclo[3.1.1]heptan-3-yl}methyl)-5-(trifluoromethyl)pyrazin-2-amine;

Racemic mixture of cis-N-({4-methyl-2-[5-methyl-2-(2H-1,2,3-triazol-2-yl)benzoyl]-2-azabicyclo[3.1.1]heptan-3-yl}methyl)-5-(trifluoromethyl)pyrazin-2-amine;

N-{[(3S,4R) or (3R,4S)-4-methyl-2-[5-methyl-2-(2H-1,2,3-triazol-2-yl)benzoyl]-2-azabicyclo[3.1.1]heptan-3-yl]methyl}-5-(trifluoromethyl)pyrazin-2-amine;

N-{[(3R,4S) or (3S,4R)-4-methyl-2-[5-methyl-2-(2H-1,2,3-triazol-2-yl)benzoyl]-2-azabicyclo[3.1.1]heptan-3-yl]methyl}-5-(trifluoromethyl)pyrazin-2-amine;

Racemic mixture of cis-N-({2-[5-chloro-2-(2H-1,2,3-triazol-2-yl)benzoyl]-4-methyl-2-azabicyclo[3.1.1]heptan-3-yl}methyl)-5-cyclopropylpyrazin-2-amine;

Racemic mixture of cis-5-cyclopropyl-N-({2-[5-fluoro-2-(2H-1,2,3-triazol-2-yl)benzoyl]-4-methyl-2-azabicyclo[3.1.1]heptan-3-yl}methyl)pyrazin-2-amine;

Racemic mixture of cis-N-({2-[5-chloro-2-(2H-1,2,3-triazol-2-yl)benzoyl]-4-methyl-2-azabicyclo[3.1.1]heptan-3-yl}methyl)-5-cyclopropylpyrimidin-2-amine; and Racemic mixture of cis 5-cyclopropyl-N-({2-[5-fluoro-2-(2H-1,2,3-triazol-2-yl)benzoyl]-4-methyl-2-azabicyclo[3.1.1]heptan-3-yl}methyl)pyrimidin-2-amine.

9. A compound as claimed in claim 1, wherein A represents an aryl, heteroaryl, cycloalkyl or heterocycloalkyl group, each of which is substituted with one or more $Q^1$ groups.

10. A compound as claimed in claim 1, wherein B represents an aryl, heteroaryl, cycloalkyl or heterocycloalkyl group, each of which is substituted with one or more $Q^2$ groups.

11. A compound of claim 1, wherein $R^1$ and $R^2$ independently represent hydrogen, halogen, —$OR^7$, —$NR^8R^9$, $C_{1-12}$ alkyl, $C_{2-12}$ alkenyl, $C_{2-12}$ alkynyl or $C_{3-12}$ cycloalkyl, which latter four groups are substituted by one or more $E^1$ substituents; or $R^1$ and $R^2$ together with the carbon atom to which they are bound form C=O, C=C($R^{10}$)$R^{11}$ or a $C_{3-6}$ cycloalkyl group optionally by one or more $E^2$ substituents.

12. A compound as claimed in claim 1, wherein $R^3$, $R^4$, $R^5$ and $R^6$ independently represent hydrogen, halogen, $C_{1-12}$ alkyl, $C_{2-12}$ alkenyl, $C_{2-12}$ alkynyl or $C_{3-6}$ cycloalkyl, which latter four groups are substituted by one or more $E^3$ substituents; or any relevant pair of $R^3$, $R^4$, $R^5$ and $R^6$ form, together with the carbon atom to which they are bound, C=O or a $C_{3-6}$ cycloalkyl group substituted by one or more $E^4$ substituents.

13. A compound as claimed in claim 1, wherein $R^7$, $R^8$, $R^9$, $R^{10}$ and $R^{11}$ independently represent hydrogen or a $C_{1-6}$ alkyl group substituted by one or more halo atoms.

14. A compound as claimed in claim 1, wherein $Q^1$ and $Q^2$ independently represent halogen, —CN, —$NHCOR^{12}$, $C_{1-6}$ alkyl, $C_{3-6}$ cycloalkyl, —O—$C_{1-6}$ alkyl, aryl or heteroaryl, which latter five groups are substituted by one or more substituents selected from halogen, methyl and halomethyl.

15. A compound as claimed in claim 1, wherein $E^1$, $E^2$, $E^3$ and $E^4$ independently represent halogen or a $C_{1-6}$ alkyl group substituted by one or more halo atoms; $R^{12}$ represents $C_{1-6}$ alkyl or phenyl.

16. A compound as claimed in claim 14, wherein $Q^1$ and $Q^2$ independently represent halogen, —CN, —$NHCOR^{12}$, $C_{1-6}$ alkyl, $C_{3-6}$cycloalkyl, —O—$C_{1-6}$, aryl or heteroaryl, which latter five groups are substituted by one or more substituents selected from halogen, methyl and trifluoromethyl.

17. A pharmaceutical formulation comprising a compound of formula I, as defined in claim 1, or a pharmaceutically acceptable ester, amide, salt, or solvate thereof, in admixture with a pharmaceutically acceptable adjuvant, diluent or carrier.

18. The pharmaceutical formulation as claimed in claim 17, further comprising a second therapeutic agent that is useful in the treatment of a disease or disorder in which antagonism of the orexin-1 and/or orexin-2 receptors is desired and/or required in admixture with a second pharmaceutically-acceptable adjuvant, diluent or carrier.

19. A method of treating a disease or disorder selected from the group consisting of substance dependence, addiction, an anxiety disorder, a panic disorder, binge eating, a compulsive disorder, an impulse control disorder, cognitive impairment, and Alzheimer's disease, comprising administering a therapeutically effective amount of a compound of formula I as defined in claim 1, or a pharmaceutically-acceptable ester, amide, salt, or solvate thereof, to a patient suffering from, or susceptible to, such a condition.

20. The method, as claimed in claim 19, wherein the disease or disorder is binge eating, alcohol addiction, nicotine addiction, or cocaine addiction.

* * * * *